United States Patent
Chuah et al.

(10) Patent No.: US 11,007,280 B2
(45) Date of Patent: May 18, 2021

(54) OPTIMIZED LIVER-SPECIFIC EXPRESSION SYSTEMS FOR FVIII AND FIX

(71) Applicant: Vrije Universiteit Brussel, Brussels (BE)

(72) Inventors: Marinee Chuah, Bierbeek (BE); Thierry Vandendriessche, Bierbeek (BE)

(73) Assignee: Vrije Universiteit Brussel, Brussels (BE)

( * ) Notice: Subject to any disclaimer, the term of this patent is extended or adjusted under 35 U.S.C. 154(b) by 234 days.

(21) Appl. No.: 15/558,725

(22) PCT Filed: Mar. 17, 2016

(86) PCT No.: PCT/EP2016/055825
§ 371 (c)(1),
(2) Date: Sep. 15, 2017

(87) PCT Pub. No.: WO2016/146757
PCT Pub. Date: Sep. 22, 2016

(65) Prior Publication Data
US 2018/0071406 A1    Mar. 15, 2018

(30) Foreign Application Priority Data
Mar. 17, 2015 (EP) .................................. 15159395

(51) Int. Cl.
| | | |
|---|---|---|
| A61K 48/00 | (2006.01) | |
| C12N 15/86 | (2006.01) | |
| C07K 14/755 | (2006.01) | |
| C12N 9/64 | (2006.01) | |
| C07K 14/745 | (2006.01) | |
| C12N 15/85 | (2006.01) | |
| A61K 38/37 | (2006.01) | |
| A61K 38/48 | (2006.01) | |
| A61K 38/00 | (2006.01) | |

(52) U.S. Cl.
CPC .......... *A61K 48/0058* (2013.01); *A61K 38/37* (2013.01); *A61K 38/4846* (2013.01); *A61K 48/0066* (2013.01); *C07K 14/745* (2013.01); *C07K 14/755* (2013.01); *C12N 9/644* (2013.01); *C12N 15/85* (2013.01); *C12N 15/86* (2013.01); *A61K 38/00* (2013.01); *C12N 2750/14141* (2013.01); *C12N 2750/14143* (2013.01); *C12N 2750/14343* (2013.01); *C12N 2830/008* (2013.01); *C12N 2830/15* (2013.01); *C12N 2830/36* (2013.01); *C12N 2830/42* (2013.01); *C12N 2830/85* (2013.01)

(58) Field of Classification Search
None
See application file for complete search history.

(56) References Cited

U.S. PATENT DOCUMENTS

| | | | | |
|---|---|---|---|---|
| 2002/0076798 A1* | 6/2002 | Miao | ........................ | A61K 48/00 435/226 |
| 2006/0189561 A1* | 8/2006 | Roelvink | .............. | C12N 15/111 514/44 R |
| 2007/0243168 A1* | 10/2007 | Kay | ................... | A61K 48/0058 424/93.2 |
| 2013/0024960 A1* | 1/2013 | Nathwani | ............ | C07K 14/755 800/16 |
| 2015/0071883 A1 | 3/2015 | Colosi | | |

FOREIGN PATENT DOCUMENTS

| | | |
|---|---|---|
| WO | 2001/098482 A1 | 12/2001 |
| WO | 2007/149852 A2 | 12/2007 |
| WO | 2009/130208 A1 | 10/2009 |
| WO | 2011/005968 A1 | 1/2011 |
| WO | 2014/063753 A1 | 5/2014 |
| WO | 2014/064277 A1 | 5/2014 |

OTHER PUBLICATIONS

International Search Report PCT/EP2016/055825, dated Jun. 9, 2016.
Di Matteo, et al., "Hyperactive PiggyBac Transposons for Sustained and Robust Liver-targeted Gene Therapy," Molecular Therapy,vol. 22, No. 9, Jul. 18, 2014 (Jul. 18, 2014), pp. 1614-1624.
Miao, et al.(2000). Inclusion of the hepatic locus control region, an intron, and untranslated region increases and stabilizes hepatic factor IX gene expression in vivo but not in vitro. Mol Ther. 1, 522-32.
Zhang, et al., "Optimized human factor IX expression cassettes for hepatic-directed gene therapy of hemophilia B," Frontiers of Medicine, vol. 9, No. 1, Feb. 7, 2015 (Feb. 7, 2015), pp. 90-99.
Wu, et al.,"Optimization of Self-complementary AAV Vectors for Liver-directed Expression Results in Sustained Correction of Hemophilia B at Low Vector Dose," Molecular Therapy, vol. 16, No. 2, Feb. 1, 2008 '(Feb. 1, 2008), pp. 280-289.
Zhong, et al. (2008). Next generation of adenoassociated virus 2 vectors: point mutations in tyrosines lead to high-efficiency transduction at lower doses. Proc Natl Acad Sci USA 105,7827-32.
Arruda, et al., (2010). Peripheral transvenular delivery of adena-associated viral vectors to skeletal muscle as a novel therapy for hemophilia B. Blood 115, 4678-88.

(Continued)

*Primary Examiner* — Christopher M Babic
*Assistant Examiner* — Kimberly A. Aron
(74) *Attorney, Agent, or Firm* — McDonnell Boehnen Hulbert & Bergnoff LLP

(57) ABSTRACT

The present invention relates to nucleic acid expression cassettes and vectors containing liver-specific regulatory elements and codon-optimized factor IX or factor VIII transgenes, methods employing these expression cassettes and vectors and uses thereof. The present invention is particularly useful for applications using liver-directed gene therapy, in particular for the treatment of hemophilia A and B.

19 Claims, 89 Drawing Sheets
Specification includes a Sequence Listing.

(56) References Cited

OTHER PUBLICATIONS

Axelrod, et al. (1990). Phenotypic correction of factor IX deficiency in skin fibroblasts of hemophilic dogs. Proc Natl Acad Sci USA; 87, 5173-7.

Bainbridge, et al. (2008) Effect of Gene Therapy on Visual Function in Leber's Congenital Amaurosis. N Engl J Med. 358, 2231-2239.

Brown, et al. (2004). Helper-dependent adenoviral vectors mediate therapeutic factor VIII expression for several months with minimal accompanying toxicity in a canine model of severe hemophilia A. Blood 103, 804-10.

Brown, et al. (2007). A microRNA-regulated lentiviral vector mediates stable correction of hemophilia B mice. Blood 110, 4144-52.

Brunetti-Pierri, et al. Bioengineered factor IX molecules with increased catalytic activity improve the therapeutic index of gene therapy vectors for hemophilia B. Hum Gene Ther. May 2009;20(5):479-85.

Buchlis, et al. (2012). Factor IX expression in skeletal muscle of a severe hemophilia B patient 1 0 years after AA V-mediated gene transfer. Blood 119, 3038-41.

Budker, et al. Naked DNA delivered intraportally expresses efficiently in hepatocytes. (1996) Gene Ther. Jul;3 (7):593-8.

Cantore, et al. Hyper-functional coagulation factor IX improves the efficacy of gene therapy in hemophilic mice. Blood. Oct. 4, 2012.

Chang, et al. (1998). Changing residue 338 in human factor IX from arginine to alanine causes an increase in catalytic activity. J Bioi Chem 273(20): 12089-12094.

Chowdhury, et al. (1991) Long-term improvement of hypercholesterolemia after ex vivo gene therapy in LDLR-deficient rabbits. Science. Dec. 20;254(5039): 1802-5.

Chuah, et al. (2003). Therapeutic factor VIII levels and negligible toxicity in mouse and dog models of hemophilia A following gene therapy with high-capacity adenoviral vectors. Blood 101, 1734-43.

Chuah, et al. Recent progress in gene therapy for hemophilia. Hum Gene Ther. Jun. 2012;23(6):557-65.

Chuah, et al. Platelet-directed gene therapy overcomes inhibitory antibodies to factor VIII. J Thromb Haemost. Aug. 2012;10(8):1566-9.

Donsante, et al.(2007). AAV vector integration sites in mouse hepatocellular carcinoma. Science 317, 477.

Dobrzynski, et al. (2006) Prevention of cytotoxic T lymphocyte responses to factor IX-expressing hepatocytes by gene transfer-induced regulatory T cells. Proc Natl Acad Sci USA 103, 4592-4597.

Ehrhardt, et al. (2002). A new adenoviral helper-dependent vector results in long-term therapeutic levels of human coagulation factor IX at low doses in vivo. Blood 99, 3923-30.

Fields, et al. (2001). Risk and prevention of anti-factor IX formation in AAV mediated gene transfer in the context of a large deletion of F9. Mol. Ther. 4, 201-210.

Follenzi, et al. (2004 ). Targeting lentiviral vector expression to hepatocytes limits transgene-specific immune response and establishes long-term expression of human antihemophilic factor IX in mice. Blood 103, 3700-9.

Gao, et al. (2002). Novel adenaassociated viruses from rhesus monkeys as vectors for human gene therapy. Proc Natl Acad Sci USA 99, 11854-9.

Gao, et al.(2004 ). Clades of Adeno-associated viruses are widely disseminated in human tissues. J. Viro 178, 6381-6388.

Herzog, et al.(1999). Long-term correction of canine hemophilia B by gene transfer of blood coagulation factor IX mediated by adena-associated viral vector. Nat Med. 5, 56-63.

Herzog, et al. (2001). Muscledirected gene transfer and transient immune suppression result in sustained partial correction of canine hemophilia B caused by a null mutation. Mol Ther. 4, 192-200.

Herzog, et al. (1997) Stable gene transfer and expression of human blood coagulation factor IX after intramuscular injection of recombinant adeno-associated virus. Proc Natl Acad Sci USA. 94, 5804-5809.

Herzog, et al. (2002) Influence of vector dose on factor IX-specific T and B cell responses in muscle-directed gene therapy. Hum Gene Ther 13, 1281-1291.

High, et al. (2001). Gene Transfer as an approach to treating Hemophilia. Circ Res. 88, 137-144.

High, et al. (2011) Gene therapy for hemophilia: a long and winding road. J Thromb Haemost. 9 Suppl. 1: 2-11.

Jiang H, et al. (2006). Multiyear therapeutic benefit of AAV serotypes 2, 6, and 8 delivering factor VIII to hemophilia A mice and dogs. Blood. 108, 20 107-15.

Kao, et al. (2010). Fix-Triple, a gain-of-function factor IX variant, improves haemostasis in mouse models without increased risk of thrombosis. Thromb Haemost 104(2): 355-365.

Kay, et al. (1992) Expression of human alpha 1-antitrypsin in dogs after autologous transplantation of retroviral transduced hepatocytes. Proc Natl Acad Sci U SA. Jan. 1 ;89(1 ):89-93.

Kay MA, et al. (2000). Evidence for gene transfer and expression of factor IX in hemophilia B patients treated with an AAV vector. Nat Genet. 24, 257-61.

Kistner, et al. (1996) Doxycycline-mediated quantitative and tissue-specific control of gene expression in transgenic mice. Proc Natl Acad Sci U S A. Oct. 1; 93(20): 10933-8.

Kren, et al.(2009). Nanocapsule-delivered Sleeping Beauty mediates therapeutic Factor VIII expression in liver sinusoidal endothelial cells of hemophilia A mice. J Clin Invest. 19, 2086-99.

Kuriyama, et al. (1991) A potential approach for gene therapy targeting hepatoma using a liver-specific promoter on a retroviral vector Cell Struct Funct. Dec; 16(6):503-10.

Li, et al. (2011 ). Assessing the potential for AAV vector genotoxicity in a murine model. Blood. 117, 3311-9.

Lin, et al.(2010). Generation of a novel factor IX with augmented clotting activities in vitro and in vivo. J Thromb Haemost 8(8): 1773-1783.

Liu, et al.(1999) Hydrodynamics-based transfection in animals by systemic administration of plasmid DNA. Gene Ther. Jul;6(7): 1258-66.

Manno, et al. (2006). Successful transduction of liver in hemophilia by AAV-Factor IX and limitations imposed by the host immune response. Nat Med. 12, 342-7.

Mates, et al. (2009). Molecular evolution of a novel hyperactive Sleeping Beauty transposase enables robust stable gene transfer in vertebrates. Nat Genet. 41, 753-6.

Matrai, et al. (2010). Pre clinical and clinical progress in hemophilia gene therapy. Curr Opin Hematol. 17, 387-92.

Matrai, et al. (2010). Recent advances in lentiviral vector development and applications. Mol Ther. 18, 477-90.

Matrai, et al. (2011). Hepatocyte-targeted expression by integrase-defective lentiviral vectors induces antigen-specific tolerance in mice with low genotoxic risk. Hepatology 53, 1696-707.

Matsui, et al. (2009). A murine model for induction of long-term immunologic tolerance to factor VIII does not require persistent detectable levels of plasma factor VIII and involves contributions from Foxp3+ T regulatory cells. Blood. 114, 677-85.

Matsui, et al. (2011 ). A microRNA-regulated and GP64-pseudotyped lentiviral vector mediates stable expression of FVIII in a murine model of Hemophilia A. Mol Ther. 19, 723-30.

McCarty, et al. (2001 ). Self-complementary recombinant adena-associated virus (scAAV) vectors promote efficient transduction independently of DNA synthesis. Gene Ther. 8, 1248-54.

McCarty, et al. (2003). Adena-associated virus terminal repeat (TR) mutant generates self-complementary vectors to overcome the rate-limiting step to transduction in vivo. Gene Ther. 10, 2112-8.

Mcintosh, et al. (2013) Therapeutic levels of FVIII following a single peripheral vein administration of rAAV vector encoding a novel human factor VIII variant. Blood. ??

Miao, et al. (2004). Bioengineering of coagulation factor VIII for improved secretion. Blood 103(9):3412-3419.

Milanov, et al. ( 2012) Engineered factor IX variants bypass FVIII and correct hemophilia A phenotype in mice Blood 119:602-611.

Miller (1990) Retrovirus packaging cells. Hum Gene Ther. Spring;1 (1 ):5-14.

Mingozzi, et al. (2003). Induction of immune tolerance to coagulation factor IX antigen by in vivo hepatic gene transfer. J Clin Invest. 111, 1347-56.

(56) References Cited

OTHER PUBLICATIONS

Mingozzi, et al. (2007). CD8(+) Tcell responses to adeno-associated virus capsid in humans. Nat Med. 13, 419-22.
Mount, et al. (2002) Sustained phenotypic correction of hemophilia B dogs with a factor IX null mutation by liver directed gene therapy. Blood 99, 2670-6.
Nair, et al. (2014). Computationally designed liver-specific transcriptional modules and hyperactive factor IX improve hepatic gene therapy. Blood 123,3195-9.
Naldini, et al. (1996) In vivo gene delivery and stable transduction of nondividing cells by a lentiviral vector. Science. Apr. 12;272(5259):263-7.
Nathwani, et al. (2002). Sustained high-level expression of human factor IX (hFIX) after liver targeted delivery of recombinant adeno-associated virus encoding the hFIX gene in rhesus macaques. Blood 100, 1662-1669.
Nathwani, et al. (2006).Self-complementary adeno-associated virus vectors containing a novel liver-specific human factor IX expression cassette enable highly efficient transduction of murine and nonhuman primate liver. Blood 107, 2653-61.
Nathwani, et al. (2011 ). Adenovirus-associated virus vector-mediated gene transfer in hemophilia B. N Engl J Med. 365, 2357-2365.
Ohlfest, et al. (2004). Phenotypic correction and long-term expression of factor VIII in hemophilic mice by immunotolerization and nonviral gene transfer using the Sleeping Beauty transposon system. Blood 105,2691-8.
Petrus, et al.(2001) Gene therapy strategies for hemophilia: benefits versus risks. J Gene Med 12, 797-809.
Sandberg H, et al. (2001 ). Structural and functional characteristics of the B domain-deleted recombinant factor VIII proteint, r-VIII SQ. Thromb Haemost. 85(1): 93-100.
Schuettrumpf, et al. (2005). Factor IX variants improve gene therapy efficacy for hemophilia B. Blood 1 05(6): 2316-2323.
Simioni, et al. (2009). X-linked thrombophilia with a mutant factor IX (factor IX Padua). N Engl J Med 361(17): 1671-1675.
Snyder, et al. (1997). Persistent and therapeutic concentrations of human factor IX in mice after hepatic gene transfer of recombinant AA V vectors. Nat Genet. 16, 270-276.
Snyder, et al. (1999). Correction of hemophilia Bin canine and murine models using recombinant adeno-associated viral vectors. Nat Med. 5, 64-70.
Trapnell. (1993) Adenoviral vectors for gene transfer. Adv. Drug Del. Rev. 12: 185-199.
Vandenberghe, et al. (2006). Heparin binding directs activation of T cells against adeno-associated virus serotype 2 capsid. Nat Med. 12, 967-71.
Vandendriessche, et al. (1999). Long-term expression of human coagulation factor VIII and correction of hemophilia A after in vivo retroviral gene transfer in factor VIII-deficient mice. Proc Natl Acad Sci USA. 96, 10379-84.
Vandendriessche, et al. (2002). Lentiviral vectors containing the human immunodeficiency virus type-1 central polypurine tract can efficiently transduce nondividing hepatocytes and antigen-presenting cells in vivo. Blood 100, 813-22.
Vandendriessche, et al. (2007). Efficacy and safety of adeno-associated viral vectors based on serotype 8 and 9 vs. lentiviral vectors for hemophilia B gene therapy. J Thromb Haemost. 5, 16-24.
Vandendriessche, et al. (2009). Emerging potential of transposons for gene therapy and generation of induced pluripotent stem cells. Blood 114, 1461-8.
Vandendriessche, et al. (2012). Clinical progress in gene therapy: sustained partial correction of the bleeding disorder in patients suffering from severe hemophilia B. Hum Gene Ther. 23, 4-6.
Wang, et al. (1999). Sustained correction of bleeding disorder in hemophilia B mice by gene therapy. Proc Natl Acad Sci USA 96, 3906-3910.
Wang, et al. (2000). Sustained expression of therapeutic level of factor IX in hemophilia B dogs by AA V-mediated gene therapy in liver. Mol Ther. 1, 154-158.
Wang, et al. (2005) Major role of local immune responses in antibody formation to factor IX in AAV gene transfer. Gene Ther 12, 1453-464.
Ward, et al. (2010) Codon optimization of human factor VIII cDNAs leads to high-level expression. Blood 117, 798-807.
Yusa, et al. (2011) A hyperactive piggyBac transposase for mammalian applications. Proc Natl Acad Sci USA;108 (4):1531-6.
Zhang, et al. (1999) High levels of foreign gene expression in hepatocytes after tail vein injections of naked plasmid DNA. Hum Gene Ther. Jul. 1 ;10(10)1735-7.
Xu, et al. (2003). Neonatal or hepatocyte growth factor-potentiated adult gene therapy with a retroviral vector results in therapeutic levels of canine factor IX for hemophilia B. Blood 101, 3924-3932.
Xu, et al. (2005). Absence of a desmopressin response after therapeutic expression of factor VIII in hemophilia A dogs with liver-directed neonatal gene therapy. Proc Natl Acad Sci USA 102, 6080-6085.
Yamada, et al. (2003) Nanoparticles for the delivery of genes and drugs to human hepatocytes. Nat Biotechnol. Aug;21 (8):885-90.
Yant, et al. (2000). Somatic integration and long-term transgene expression in normal and haemophilic mice using a DNA transposon system. Nat Genet. 25, 35-41.

\* cited by examiner

Figure 13

SEQ ID NO.1: pAAVsc-SerpEnh-TTRm-MVM-co-FIX-R338L-BGHpA

AGCTGGCGTAATAGCGAAGAGGCCCGCACCGATCGCCCTTCCCAACAGTTGCGCAGCCTGAATGGCGAATG
GCGATTCCGTTGCAATGGCTGGCGGTAATATTGTTCTGGATATTACCAGCAAGGCCGATAGTTTGAGTTCT
TCTACTCAGGCAAGTGATGTTATTACTAATCAAAGAAGTATTGCGACAACGGTTAATTTGCGTGATGGACA
GACTCTTTTACTCGGTGGCCTCACTGATTATAAAAACACTTCTCAGGATTCTGGCGTACCGTTCCTGTCTA
AAATCCCTTTAATCGGCCTCCTGTTTAGCTCCCGCTCTGATTCTAACGAGGAAAGCACGTTATACGTGCTC
GTCAAAGCAACCATAGTACGCGCCCTGTAGCGGCGCATTAAGCGCGGCGGGTGTGGTGGTTACGCGCAGCG
TGACCGCTACACTTGCCAGCGCCCTAGCGCCCGCTCCTTTCGCTTTCTTCCCTTCCTTTCTCGCCACGTTC
GCCGGCTTTCCCCGTCAAGCTCTAAATCGGGGGCTCCCTTTAGGGTTCCGATTTAGTGCTTTACGGCACCT
CGACCCCAAAAAACTTGATTAGGGTGATGGTTCACGTAGTGGGCCATCGCCCTGATAGACGGTTTTTCGCC
CTTTGACGTTGGAGTCCACGTTCTTTAATAGTGGACTCTTGTTCCAAACTGGAACAACACTCAACCCTATC
TCGGTCTATTCTTTTGATTTATAAGGGATTTTGCCGATTTCGGCCTATTGGTTAAAAAATGAGCTGATTTA
ACAAAAATTTAACGCGAACTTTAACAAAATATTAACGTTTACAATTTAAATATTTGCTTATACAATCTTCC
TGTTTTTGGGGCTTTTCTGATTATCAACCGGGGTACATATGATTGACATGCTAGTTTTACGATTACCGTTC
ATCGCCCTGCGCGCTCGCTCGCTCACTGAGGCCGCCCGGGCAAAGCCCGGGCGTCGGGCGACCTTTGGTCG
CCCGGCCTCAGTGAGCGAGCGAGCGCGCAGAGAGGGAGTGGAATTCACGCGTGGATCTGAATTCAATTCAC
GCGTGGTACGGCCGCGGTACCGGCGCGCCGGGGGAGGCTGCTGGTGAATATTAACCAAGGTCACCCCAGTT
ATCGGAGGAGCAAACAGGGGCTAAGTCCACACGCGTGGTACCGTCTGTCTGCACATTTCGTAGAGCGAGTG
TTCCGATACTCTAATCTCCCTAGGCAAGGTTCATATTTGTGTAGGTTACTTATTCTCCTTTTGTTGACTAA
GTCAATAATCAGAATCAGCAGGTTTGGAGTCAGCTTGGCAGGGATCAGCAGCCTGGGTTGGAAGGAGGGGG
TATAAAAGCCCCTTCACCAGGAGAAGCCGTCACACAGATCCACAAGCTCCTGAAGAGGTAAGGGTTTAAGG
GATGGTTGGTTGGTGGGGTATTAATGTTTAATTACCTGGAGCACCTGCCTGAAATCACTTTTTTTCAGGTT
GGCTAGCCCACCATGCAGCGCGTGAACATGATCATGGCCGAGAGCCCCGGCCTGATCACCATCTGCCTGCT
GGGCTACCTGCTGAGCGCCGAGTGCACCGTGTTCCTGGACCACGAGAACGCCAACAAGATCCTGAACCGCC
CCAAGCGCTACAACAGCGGCAAGCTGGAGGAGTTCGTGCAGGGCAACCTGGAGCGCGAGTGCATGGAGGAG
AAGTGCAGCTTCGAGGAGGCCCGCGAGGTGTTCGAGAACACCGAGCGCACCACCGAGTTCTGGAAGCAGTA
CGTGGACGGCGACCAGTGCGAGAGCAACCCCTGCCTGAACGGCGGCAGCTGCAAGGACGACATCAACAGCT
ACGAGTGCTGGTGCCCCTTCGGCTTCGAGGGCAAGAACTGCGAGCTGGACGTGACCTGCAACATCAAGAAC
GGCCGCTGCGAGCAGTTCTGCAAGAACAGCGCCGACAACAAGGTGGTGTGCAGCTGCACCGAGGGCTACCG
CCTGGCCGAGAACCAGAAGAGCTGCGAGCCCGCCGTGCCCTTCCCCTGCGGCCGCGTGAGCGTGAGCCAGA
CCAGCAAGCTGACCCGCGCCGAGGCCGTGTTCCCCGACGTGGACTACGTGAACAGCACCGAGGCCGAGACC
ATCCTGGACAACATCACCCAGAGCACCCAGAGCTTCAACGACTTCACCCGCGTGGTGGGCGGCGAGGACGC
CAAGCCCGGCCAGTTCCCCTGGCAGGTGGTGCTGAACGGCAAGGTGGACGCCTTCTGCGGCGGCAGCATCG
TGAACGAGAAGTGGATCGTGACCGCCGCCCACTGCGTGGAGACCGGCGTGAAGATCACCGTGGTGGCCGGC
GAGCACAACATCGAGGAGACCGAGCACACCGAGCAGAAGCGCAACGTGATCCGCATCATCCCCCACCACAA
CTACAACGCCGCCATCAACAAGTACAACCACGACATCGCCCTGCTGGAGCTGGACGAGCCCCTGGTGCTGA
ACAGCTACGTGACCCCCATCTGCATCGCCGACAAGGAGTACACCAACATCTTCCTGAAGTTCGGCAGCGGC
TACGTGAGCGGCTGGGGCCGCGTGTTCCACAAGGGCCGCAGCGCCCTGGTGCTGCAGTACCTGCGCGTGCC
CCTGGTGGACCGCGCCACCTGCCTGCTGAGCACCAAGTTCACCATCTACAACAACATGTTCTGCGCCGGCT
TCCACGAGGGCGGCCGCGACAGCTGCCAGGGCGACAGCGGCGGCCCCCACGTGACCGAGGTGGAGGGCACC
AGCTTCCTGACCGGCATCATCAGCTGGGGCGAGGAGTGCGCCATGAAGGGCAAGTACGGCATCTACACCAA
GGTGAGCCGCTACGTGAACTGGATCAAGGAGAAGACCAAGCTGACCTAATGAAAGATGGATTTCCAAGGTT
AATTCATTGGAATTGAAATTAACAGCCCCCCCCCCCCCCCTGCAGATCTGAGCCGAATTCCTGCAGC
CCGGGGGATCAGCCTCGACTGTGCCTTCTAGTTGCCAGCCATCTGTTGTTTGCCCCTCCCCCGTGCCTTCC
TTGACCCTGGAAGGTGCCACTCCCACTGTCCTTTCCTAATAAAATGAGGAAATTGCATCGCATTGTCTGAG
TAGGTGTCATTCTATTCTGGGGGGTGGGGTGGGCAGGACAGCAAGGGGGAGGATTGGGAAGACAATAGCA
GGCATGCTGGGGATGCGGTGGGCTCTATGGCTTCTGAGGCGGAAAGAACCAGCTGGGGACCGGTGGATCTC
GATAGCAGGCATGCTGGGGAGAGATCGATCTGAGGAACCCCTAGTGATGGAGTTGGCCACTCCCTCTCTGC
GCGCTCGCTCGCTCACTGAGGCCGCCCGGGCAAAGCCCGGGCGTCGGGCGACCTTTGGTCGCCCGGCCTCA
GTGAGCGAGCGAGCGCGCAGAGAGGGAGTGGCCAACCCCCCCCCCCCCCCCCGGCGATTCTCTTGTTT
GCTCCAGACTCTCAGGCAATGACCTGATAGCCTTTGTAGAGACCTCTCAAAAATAGCTACCCTCTCCGGCA
TGAATTTATCAGCTAGAACGGTTGAATATCATATTGATGGTGATTTGACTGTCTCCGGCCTTTCTCACCCG

Figure 13 (continued)

```
TTTGAATCTTTACCTACACATTACTCAGGCATTGCATTTAAAATATATGAGGGTTCTAAAAATTTTTATCC
TTGCGTTGAAATAAAGGCTTCTCCCGCAAAAGTATTACAGGGTCATAATGTTTTTGGTACAACCGATTTAG
CTTTATGCTCTGAGGCTTTATTGCTTAATTTTGCTAATTCTTTGCCTTGCCTGTATGATTTATTGGATGTT
GGAATCGCCTGATGCGGTATTTTCTCCTTACGCATCTGTGCGGTATTTCACACCGCATATGGTGCACTCTC
AGTACAATCTGCTCTGATGCCGCATAGTTATATGGTGCACTCTCAGTACAATCTGCTCTGATGCCGCATAG
TTAAGCCAGCCCCGACACCCGCCAACACAGCCAGCCCCGACACCCGCCAACACCCGCTGACGCGCCCTGAC
GGGCTTGTCTGCTCCCGGCATCCGCTTACAGACAAGCTGTGACCGTCTCCGGGAGCTGCATGTGTCAGAGG
TTTTCACCGTCATCACCGAAACGCGCGAGACGAAAGGGCCTCGTGATACGCCTATTTTTATAGGTTAATGT
CATGATAATAATGGTTTCTTAGACGTCAGGTGGCACTTTTCGGGGAAATGTGCGCGGAACCCCTATTTGTT
TATTTTTCTAAATACATTCAAATATGTATCCGCTCATGAGACAATAACCCTGATAAATGCTCAATAATATT
GAAAAAGGAAGAGTATGAGTATTCAACATTTCCGTGTCGCCCTTATTCCCTTTTTTGCGGCATTTTGCCTT
CCTGTTTTTGCTCACCCAGAAACGCTGGTGAAAGTAAAAGATGCTGAAGATCAGTTGGGTGCACGAGTGGG
TTACATCGAACTGGATCTCAACAGCGGTAAGATCCTTGAGAGTTTTCGCCCCGAAGAACGTTTTCCAATGA
TGAGCACTTTTAAAGTTCTGCTATGTGGCGCGGTATTATCCCGTATTGACGCCGGGCAAGAGCAACTCGGT
CGCCGCATACACTATTCTCAGAATGACTTGGTTGAGTACTCACCAGTCACAGAAAAGCATCTTACGGATGG
CATGACAGTAAGAGAATTATGCAGTGCTGCCATAACCATGAGTGATAACACTGCGGCCAACTTACTTCTGA
CAACGATCGGAGGACCGAAGGAGCTAACCGCTTTTTGCACAACATGGGGGATCATGTAACTCGCCTTGAT
CGTTGGGAACCGGAGCTGAATGAAGCCATACCAAACGACGAGCGTGACACCACGATGCCTGTAGCAATGGC
AACAACGTTGCGCAAACTATTAACTGGCGAACTACTTACTCTAGCTTCCCGGCAACAATTAATAGACTGGA
TGGAGGCGGATAAAGTTGCAGGACCACTTCTGCGCTCGGCCCTTCCGGCTGGCTGGTTTATTGCTGATAAA
TCTGGAGCCGGTGAGCGTGGGTCTCGCGGTATCATTGCAGCACTGGGGCCAGATGGTAAGCCCTCCCGTAT
CGTAGTTATCTACACGACGGGGAGTCAGGCAACTATGGATGAACGAAATAGACAGATCGCTGAGATAGGTG
CCTCACTGATTAAGCATTGGTAACTGTCAGACCAAGTTTACTCATATATACTTTAGATTGATTTAAAACTT
CATTTTTAATTTAAAAGGATCTAGGTGAAGATCCTTTTTGATAATCTCATGACCAAAATCCCTTAACGTGA
GTTTTCGTTCCACTGAGCGTCAGACCCCGTAGAAAAGATCAAAGGATCTTCTTGAGATCCTTTTTTTCTGC
GCGTAATCTGCTGCTTGCAAACAAAAAAACCACCGCTACCAGCGGTGGTTTGTTTGCCGGATCAAGAGCTA
CCAACTCTTTTTCCGAAGGTAACTGGCTTCAGCAGAGCGCAGATACCAAATACTGTCCTTCTAGTGTAGCC
GTAGTTAGGCCACCACTTCAAGAACTCTGTAGCACCGCCTACATACCTCGCTCTGCTAATCCTGTTACCAG
TGGCTGCTGCCAGTGGCGATAAGTCGTGTCTTACCGGGTTGGACTCAAGACGATAGTTACCGGATAAGGCG
CAGCGGTCGGGCTGAACGGGGGGTTCGTGCACACAGCCCAGCTTGGAGCGAACGACCTACACCGAACTGAG
ATACCTACAGCGTGAGCTATGAGAAAGCGCCACGCTTCCCGAAGGGAGAAAGGCGGACAGGTATCCGGTAA
GCGGCAGGGTCGGAACAGGAGAGCGCACGAGGGAGCTTCCAGGGGGAAACGCCTGGTATCTTTATAGTCCT
GTCGGGTTTCGCCACCTCTGACTTGAGCGTCGATTTTTGTGATGCTCGTCAGGGGGCGGAGCCTATGGAA
AAACGCCAGCAACGCGGCCTTTTTACGGTTCCTGGCCTTTTGCTGGCCTTTTGCTCACATGTTCTTTCCTG
CGTTATCCCCTGATTCTGTGGATAACCGTATTACCGCCTTTGAGTGAGCTGATACCGCTCGCCGCAGCCGA
ACGACCGAGCGCAGCGAGTCAGTGAGCGAGGAAGCGGAAGAGCGCCCAATACGCAAACCGCCTCTCCCCGC
GCGTTGGCCGATTCATTAATG

SEQ ID NO.2: pAAVsc-3xSerpEnh-TTRm-MVM-co-FIX-R338L-BGHpA

AGCTGGCGTAATAGCGAAGAGGCCCGCACCGATCGCCCTTCCCAACAGTTGCGCAGCCTGAATGGCGAATG
GCGATTCCGTTGCAATGGCTGGCGGTAATATTGTTCTGGATATTACCAGCAAGGCCGATAGTTTGAGTTCT
TCTACTCAGGCAAGTGATGTTATTACTAATCAAAGAAGTATTGCGACAACGGTTAATTTGCGTGATGGACA
GACTCTTTTACTCGGTGGCCTCACTGATTATAAAAACACTTCTCAGGATTCTGGCGTACCGTTCCTGTCTA
AAATCCCTTTAATCGGCCTCCTGTTTAGCTCCCGCTCTGATTCTAACGAGGAAAGCACGTTATACGTGCTC
GTCAAAGCAACCATAGTACGCGCCCTGTAGCGGCGCATTAAGCGCGGCGGGTGTGGTGGTTACGCGCAGCG
TGACCGCTACACTTGCCAGCGCCCTAGCGCCCGCTCCTTTCGCTTTCTTCCCTTCCTTTCTCGCCACGTTC
GCCGGCTTTCCCCGTCAAGCTCTAAATCGGGGGCTCCCTTTAGGGTTCCGATTTAGTGCTTTACGGCACCT
CGACCCCAAAAAACTTGATTAGGGTGATGGTTCACGTAGTGGGCCATCGCCCTGATAGACGGTTTTTCGCC
CTTTGACGTTGGAGTCCACGTTCTTTAATAGTGGACTCTTGTTCCAAACTGGAACAACACTCAACCCTATC
TCGGTCTATTCTTTTGATTTATAAGGGATTTTGCCGATTTCGGCCTATTGGTTAAAAAATGAGCTGATTTA
ACAAAAATTTAACGCGAACTTTAACAAAATATTAACGTTTACAATTTAAATATTTGCTTATACAATCTTCC
TGTTTTTGGGGCTTTTCTGATTATCAACCGGGGTACATATGATTGACATGCTAGTTTTACGATTACCGTTC
ATCGCCCTGCGCGCTCGCTCGCTCACTGAGGCCGCCCGGGCAAAGCCCGGGCGTCGGGCGACCTTTGGTCG
CCCGGCCTCAGTGAGCGAGCGAGCGCGCAGAGAGGGAGTGGAATTCACGCGTGGATCTGAATTCAATTCAC
```

Figure 13 (continued)

```
GCGTGGTACGGCCGCGGTACCGGCGCGCCCGTACGCGGGGGAGGCTGCTGGTGAATATTAACCAAGGTCAC
CCCAGTTATCGGAGGAGCAAACAGGGGCTAAGTCCACCGGGGGAGGCTGCTGGTGAATATTAACCAAGGTC
ACCCCAGTTATCGGAGGAGCAAACAGGGGCTAAGTCCACCGGGGGAGGCTGCTGGTGAATATTAACCAAGG
TCACCCCAGTTATCGGAGGAGCAAACAGGGGCTAAGTCCACTGTACAACGCGTGAATTCGCTAGCGTCTGT
CTGCACATTTCGTAGAGCGAGTGTTCCGATACTCTAATCTCCCTAGGCAAGGTTCATATTTGTGTAGGTTA
CTTATTCTCCTTTTGTTGACTAAGTCAATAATCAGAATCAGCAGGTTTGGAGTCAGCTTGGCAGGGATCAG
CAGCCTGGGTTGGAAGGAGGGGTATAAAAGCCCCTTCACCAGGAGAAGCCGTCACACAGATCCACAAGCT
CCTGTCTAGAAAGAGGTAAGGGTTTAAGGGATGGTTGGTTGGTGGGTATTAATGTTTAATTACCTGGAGC
ACCTGCCTGAAATCACTTTTTTTCAGGTTGGGCTAGCCCACCATGCAGCGCGTGAACATGATCATGGCCGA
GAGCCCCGGCCTGATCACCATCTGCCTGCTGGGCTACCTGCTGAGCGCCGAGTGCACCGTGTTCCTGGACC
ACGAGAACGCCAACAAGATCCTGAACCGCCCCAAGCGCTACAACAGCGGCAAGCTGGAGGAGTTCGTGCAG
GGCAACCTGGAGCGCGAGTGCATGGAGGAGAAGTGCAGCTTCGAGGAGGCCCGCGAGGTGTTCGAGAACAC
CGAGCGCACCACCGAGTTCTGGAAGCAGTACGTGGACGGCGACCAGTGCGAGAGCAACCCCTGCCTGAACG
GCGGCAGCTGCAAGGACGACATCAACAGCTACGAGTGCTGGTGCCCCTTCGGCTTCGAGGGCAAGAACTGC
GAGCTGGACGTGACCTGCAACATCAAGAACGGCCGCTGCGAGCAGTTCTGCAAGAACAGCGCCGACAACAA
GGTGGTGTGCAGCTGCACCGAGGGCTACCGCCTGGCCGAGAACCAGAAGAGCTGCGAGCCCGCCGTGCCCT
TCCCCTGCGGCCGCGTGAGCGTGAGCCAGACCAGCAAGCTGACCCGCGCCGAGGCCGTGTTCCCCGACGTG
GACTACGTGAACAGCACCGAGGCCGAGACCATCCTGGACAACATCACCCAGAGCACCCAGAGCTTCAACGA
CTTCACCCGCGTGGTGGGCGGCGAGGACGCCAAGCCCGGCCAGTTCCCCTGGCAGGTGGTGCTGAACGGCA
AGGTGGACGCCTTCTGCGGCGGCAGCATCGTGAACGAGAAGTGGATCGTGACCGCCGCCCACTGCGTGGAG
ACCGGCGTGAAGATCACCGTGGTGGCCGGCGAGCACAACATCGAGGAGACCGAGCACACCGAGCAGAAGCG
CAACGTGATCCGCATCATCCCCCACCACAACTACAACGCCGCCATCAACAAGTACAACCACGACATCGCCC
TGCTGGAGCTGGACGAGCCCCTGGTGCTGAACAGCTACGTGACCCCCATCTGCATCGCCGACAAGGAGTAC
ACCAACATCTTCCTGAAGTTCGGCAGCGGCTACGTGAGCGGCTGGGGCCGCGTGTTCCACAAGGGCCGCAG
CGCCCTGGTGCTGCAGTACCTGCGCGTGCCCCTGGTGGACCGCGCCACCTGCCTGCTGAGCACCAAGTTCA
CCATCTACAACAACATGTTCTGCGCCGGCTTCCACGAGGGCGGCCGCGACAGCTGCCAGGGCGACAGCGGC
GGCCCCCACGTGACCGAGGTGGAGGGCACCAGCTTCCTGACCGGCATCATCAGCTGGGGCGAGGAGTGCGC
CATGAAGGGCAAGTACGGCATCTACACCAAGGTGAGCCGCTACGTGAACTGGATCAAGGAGAAGACCAAGC
TGACCTAATGAAAGATGGATTTCCAAGGTTAATTCATTGGAATTGAAAATTAACAGCCCCCCCCCCCCCC
CCCTGCAGATCTGAGCCGAATTCCTGCAGCCCGGGGATCAGCCTCGACTGTGCCTTCTAGTTGCCAGCCA
TCTGTTGTTTGCCCCTCCCCCGTGCCTTCCTTGACCCTGGAAGGTGCCACTCCCACTGTCCTTTCCTAATA
AAATGAGGAAATTGCATCGCATTGTCTGAGTAGGTGTCATTCTATTCTGGGGGGTGGGGTGGGGCAGGACA
GCAAGGGGGAGGATTGGGAAGACAATAGCAGGCATGCTGGGGATGCGGTGGGCTCTATGGCTTCTGAGGCG
GAAAGAACCAGCTGGGGACCGGTGGATCTCGATAGCAGGCATGCTGGGGAGAGATCGATCTGAGGAACCCC
TAGTGATGGAGTTGGCCACTCCCTCTCTGCGCGCTCGCTCGCTCACTGAGGCCGCCCGGGCAAAGCCCGGG
CGTCGGGCGACCTTTGGTCGCCCGGCCTCAGTGAGCGAGCGAGCGCGCAGAGAGGGAGTGGCCAACCCCCC
CCCCCCCCCCCCCCGGCGATTCTCTTGTTTGCTCCAGACTCTCAGGCAATGACCTGATAGCCTTTGTAGAG
ACCTCTCAAAAATAGCTACCCTCTCCGGCATGAATTTATCAGCTAGAACGGTTGAATATCATATTGATGGT
GATTTGACTGTCTCCGGCCTTTCTCACCCGTTTGAATCTTTACCTACACATTACTCAGGCATTGCATTTAA
AATATATGAGGGTTCTAAAAATTTTTATCCTTGCGTTGAAATAAAGGCTTCTCCCGCAAAAGTATTACAGG
GTCATAATGTTTTGGTACAACCGATTTAGCTTTATGCTCTGAGGCTTTATTGCTTAATTTTGCTAATTCT
TTGCCTTGCCTGTATGATTTATTGGATGTTGGAATCGCCTGATGCGGTATTTTCTCCTTACGCATCTGTGC
GGTATTTCACACCGCATATGGTGCACTCTCAGTACAATCTGCTCTGATGCCGCATAGTTATATGGTGCACT
CTCAGTACAATCTGCTCTGATGCCGCATAGTTAAGCCAGCCCCGACACCCGCCAACACAGCCAGCCCCGAC
ACCCGCCAACACCCGCTGACGCGCCCTGACGGGCTTGTCTGCTCCCGGCATCCGCTTACAGACAAGCTGTG
ACCGTCTCCGGGAGCTGCATGTGTCAGAGGTTTTCACCGTCATCACCGAAACGCGCGAGACGAAAGGGCCT
CGTGATACGCCTATTTTTATAGGTTAATGTCATGATAATAATGGTTTCTTAGACGTCAGGTGGCACTTTTC
GGGGAAATGTGCGCGGAACCCCTATTTGTTTATTTTTCTAAATACATTCAAATATGTATCCGCTCATGAGA
CAATAACCCTGATAAATGCTCAATAATATTGAAAAAGGAAGAGTATGAGTATTCAACATTTCCGTGTCGCC
CTTATTCCCTTTTTTGCGGCATTTTGCCTTCCTGTTTTTGCTCACCCAGAAACGCTGGTGAAAGTAAAAGA
TGCTGAAGATCAGTTGGGTGCACGAGTGGGTTACATCGAACTGGATCTCAACAGCGGTAAGATCCTTGAGA
GTTTTCGCCCCGAAGAACGTTTTCCAATGATGAGCACTTTTAAAGTTCTGCTATGTGGCGCGGTATTATCC
CGTATTGACGCCGGGCAAGAGCAACTCGGTCGCCGCATACACTATTCTCAGAATGACTTGGTTGAGTACTC
ACCAGTCACAGAAAAGCATCTTACGGATGGCATGACAGTAAGAGAATTATGCAGTGCTGCCATAACCATGA
GTGATAACACTGCGGCCAACTTACTTCTGACAACGATCGGAGGACCGAAGGAGCTAACCGCTTTTTTGCAC
```

Figure 13 (continued)

```
AACATGGGGGATCATGTAACTCGCCTTGATCGTTGGGAACCGGAGCTGAATGAAGCCATACCAAACGACGA
GCGTGACACCACGATGCCTGTAGCAATGGCAACAACGTTGCGCAAACTATTAACTGGCGAACTACTTACTC
TAGCTTCCCGGCAACAATTAATAGACTGGATGGAGGCGGATAAAGTTGCAGGACCACTTCTGCGCTCGGCC
CTTCCGGCTGGCTGGTTTATTGCTGATAAATCTGGAGCCGGTGAGCGTGGGTCTCGCGGTATCATTGCAGC
ACTGGGGCCAGATGGTAAGCCCTCCCGTATCGTAGTTATCTACACGACGGGGAGTCAGGCAACTATGGATG
AACGAAATAGACAGATCGCTGAGATAGGTGCCTCACTGATTAAGCATTGGTAACTGTCAGACCAAGTTTAC
TCATATATACTTTAGATTGATTTAAAACTTCATTTTTAATTTAAAAGGATCTAGGTGAAGATCCTTTTTGA
TAATCTCATGACCAAAATCCCTTAACGTGAGTTTTCGTTCCACTGAGCGTCAGACCCCGTAGAAAAGATCA
AAGGATCTTCTTGAGATCCTTTTTTTCTGCGCGTAATCTGCTGCTTGCAAACAAAAAAACCACCGCTACCA
GCGGTGGTTTGTTTGCCGGATCAAGAGCTACCAACTCTTTTTCCGAAGGTAACTGGCTTCAGCAGAGCGCA
GATACCAAATACTGTCCTTCTAGTGTAGCCGTAGTTAGGCCACCACTTCAAGAACTCTGTAGCACCGCCTA
CATACCTCGCTCTGCTAATCCTGTTACCAGTGGCTGCTGCCAGTGGCGATAAGTCGTGTCTTACCGGGTTG
GACTCAAGACGATAGTTACCGGATAAGGCGCAGCGGTCGGGCTGAACGGGGGGTTCGTGCACACAGCCCAG
CTTGGAGCGAACGACCTACACCGAACTGAGATACCTACAGCGTGAGCTATGAGAAAGCGCCACGCTTCCCG
AAGGGAGAAAGGCGGACAGGTATCCGGTAAGCGGCAGGGTCGGAACAGGAGAGCGCACGAGGGAGCTTCCA
GGGGGAAACGCCTGGTATCTTTATAGTCCTGTCGGGTTTCGCCACCTCTGACTTGAGCGTCGATTTTTGTG
ATGCTCGTCAGGGGGCGGAGCCTATGGAAAAACGCCAGCAACGCGGCCTTTTTACGGTTCCTGGCCTTTT
GCTGGCCTTTTGCTCACATGTTCTTTCCTGCGTTATCCCCTGATTCTGTGGATAACCGTATTACCGCCTTT
GAGTGAGCTGATACCGCTCGCCGCAGCCGAACGACCGAGCGCAGCGAGTCAGTGAGCGAGGAAGCGGAAGA
GCGCCCAATACGCAAACCGCCTCTCCCCGCGCGTTGGCCGATTCATTAATG

SEQ ID NO.3: pAAVsc-TTRe-TTRm-MVM-co-FIX-R338L-BGHpA

AGCTGGCGTAATAGCGAAGAGGCCCGCACCGATCGCCCTTCCCAACAGTTGCGCAGCCTGAATGGCGAATG
GCGATTCCGTTGCAATGGCTGGCGGTAATATTGTTCTGGATATTACCAGCAAGGCCGATAGTTTGAGTTCT
TCTACTCAGGCAAGTGATGTTATTACTAATCAAAGAAGTATTGCGACAACGGTTAATTTGCGTGATGGACA
GACTCTTTTACTCGGTGGCCTCACTGATTATAAAAACACTTCTCAGGATTCTGGCGTACCGTTCCTGTCTA
AAATCCCTTTAATCGGCCTCCTGTTTAGCTCCCGCTCTGATTCTAACGAGGAAAGCACGTTATACGTGCTC
GTCAAAGCAACCATAGTACGCGCCCTGTAGCGGCGCATTAAGCGCGGCGGGTGTGGTGGTTACGCGCAGCG
TGACCGCTACACTTGCCAGCGCCCTAGCGCCCGCTCCTTTCGCTTTCTTCCCTTCCTTTCTCGCCACGTTC
GCCGGCTTTCCCCGTCAAGCTCTAAATCGGGGGCTCCCTTTAGGGTTCCGATTTAGTGCTTTACGGCACCT
CGACCCCAAAAAACTTGATTAGGGTGATGGTTCACGTAGTGGGCCATCGCCCTGATAGACGGTTTTTCGCC
CTTTGACGTTGGAGTCCACGTTCTTTAATAGTGGACTCTTGTTCCAAACTGGAACAACACTCAACCCTATC
TCGGTCTATTCTTTTGATTTATAAGGGATTTTGCCGATTTCGGCCTATTGGTTAAAAAATGAGCTGATTTA
ACAAAAATTTAACGCGAACTTTAACAAAATATTAACGTTTACAATTTAAATATTTGCTTATACAATCTTCC
TGTTTTTGGGGCTTTTCTGATTATCAACCGGGGTACATATGATTGACATGCTAGTTTTACGATTACCGTTC
ATCGCCCTGCGCGCTCGCTCGCTCACTGAGGCCGCCCGGGCAAAGCCCGGGCGTCGGGCGACCTTTGGTCG
CCCGGCCTCAGTGAGCGAGCGAGCGCGCAGAGAGGGAGTGGAATTCACGCGTGGATCTGAATTCAATTCAC
GCGTGGTACGGCCGCGGTACCCACTGGGAGGATGTTGAGTAAGATGGAAAACTACTGATGACCCTTGCAGA
GACAGAGTATTAGGACATGTTTGAACAGGGGCCGGGCGATCAGCAGGTAGCTCTAGAGGATCCCCGTCTGT
CTGCACATTTCGTAGAGCGAGTGTTCCGATACTCTAATCTCCCTAGGCAAGGTTCATATTTGTGTAGGTTA
CTTATTCTCCTTTTGTTGACTAAGTCAATAATCAGAATCAGCAGGTTTGGAGTCAGCTTGGCAGGGATCAG
CAGCCTGGGTTGGAAGGAGGGGGTATAAAAGCCCCTTCACCAGGAGAAGCCGTCACACAGATCCACAAGCT
CCTGGCTAGAAAGAGGTAAGGGTTTAAGGGATGGTTGGTTGGTGGGGTATTAATGTTTAATTACCTGGAGC
ACCTGCCTGAAATCACTTTTTTTCAGGTTGGGCTAGCCCACCATGCAGCGCGTGAACATGATCATGGCCGA
GAGCCCCGGCCTGATCACCATCTGCCTGCTGGGCTACCTGCTGAGCGCCGAGTGCACCGTGTTCCTGGACC
ACGAGAACGCCAACAAGATCCTGAACCGCCCCAAGCGCTACAACAGCGGCAAGCTGGAGGAGTTCGTGCAG
GGCAACCTGGAGCGCGAGTGCATGGAGGAGAAGTGCAGCTTCGAGGAGGCCCGCGAGGTGTTCGAGAACAC
CGAGCGCACCACCGAGTTCTGGAAGCAGTACGTGGACGGCGACCAGTGCGAGAGCAACCCCTGCCTGAACG
GCGGCAGCTGCAAGGACGACATCAACAGCTACGAGTGCTGGTGCCCCTTCGGCTTCGAGGGCAAGAACTGC
GAGCTGGACGTGACCTGCAACATCAAGAACGGCCGCTGCGAGCAGTTCTGCAAGAACAGCGCCGACAACAA
GGTGGTGTGCAGCTGCACCGAGGGCTACCGCCTGGCCGAGAACCAGAAGAGCTGCGAGCCCGCCGTGCCCT
TCCCCTGCGGCCGCGTGAGCGTGAGCCAGACCAGCAAGCTGACCCGCGCCGAGGCCGTGTTCCCCGACGTG
GACTACGTGAACAGCACCGAGGCCGAGACCATCCTGGACAACATCACCCAGAGCACCCAGAGCTTCAACGA
CTTCACCCGCGTGGTGGGCGGCGAGGACGCCAAGCCCGGCCAGTTCCCCTGGCAGGTGGTGCTGAACGGCA
```

Figure 13 (continued)

```
AGGTGGACGCCTTCTGCGGCGGCAGCATCGTGAACGAGAAGTGGATCGTGACCGCCGCCCACTGCGTGGAG
ACCGGCGTGAAGATCACCGTGGTGGCCGGCGAGCACAACATCGAGGAGACCGAGCACACCGAGCAGAAGCG
CAACGTGATCCGCATCATCCCCCACCACAACTACAACGCCGCCATCAACAAGTACAACCACGACATCGCCC
TGCTGGAGCTGGACGAGCCCCTGGTGCTGAACAGCTACGTGACCCCCATCTGCATCGCCGACAAGGAGTAC
ACCAACATCTTCCTGAAGTTCGGCAGCGGCTACGTGAGCGGCTGGGGCCGCGTGTTCCACAAGGGCCGCAG
CGCCCTGGTGCTGCAGTACCTGCGCGTGCCCCTGGTGGACCGCGCCACCTGCCTGCTGAGCACCAAGTTCA
CCATCTACAACAACATGTTCTGCGCCGGCTTCCACGAGGGCGGCCGCGACAGCTGCCAGGGCGACAGCGGC
GGCCCCCACGTGACCGAGGTGGAGGGCACCAGCTTCCTGACCGGCATCATCAGCTGGGGCGAGGAGTGCGC
CATGAAGGGCAAGTACGGCATCTACACCAAGGTGAGCCGCTACGTGAACTGGATCAAGGAGAAGACCAAGC
TGACCTAATGAAAGATGGATTTCCAAGGTTAATTCATTGGAATTGAAAATTAACAGCCCCCCCCCCCCCC
CCCTGCAGATCTGAGCCGAATTCCTGCAGCCCGGGGATCAGCCTCGACTGTGCCTTCTAGTTGCCAGCCA
TCTGTTGTTTGCCCCTCCCCCGTGCCTTCCTTGACCCTGGAAGGTGCCACTCCCACTGTCCTTTCCTAATA
AAATGAGGAAATTGCATCGCATTGTCTGAGTAGGTGTCATTCTATTCTGGGGGGTGGGGTGGGGCAGGACA
GCAAGGGGGAGGATTGGGAAGACAATAGCAGGCATGCTGGGGATGCGGTGGGCTCTATGGCTTCTGAGGCG
GAAAGAACCAGCTGGGGACCGGTGGATCTCGATAGCAGGCATGCTGGGGAGAGATCGATCTGAGGAACCCC
TAGTGATGGAGTTGGCCACTCCCTCTCTGCGCGCTCGCTCGCTCACTGAGGCCGCCCGGGCAAAGCCCGGG
CGTCGGGCGACCTTTGGTCGCCCGGCCTCAGTGAGCGAGCGAGCGCGCAGAGAGGGAGTGGCCAACCCCCC
CCCCCCCCCCCCCGGCGATTCTCTTGTTTGCTCCAGACTCTCAGGCAATGACCTGATAGCCTTTGTAGAG
ACCTCTCAAAAATAGCTACCCTCTCCGGCATGAATTTATCAGCTAGAACGGTTGAATATCATATTGATGGT
GATTTGACTGTCTCCGGCCTTTCTCACCCGTTTGAATCTTTACCTACACATTACTCAGGCATTGCATTTAA
AATATATGAGGGTTCTAAAAATTTTTATCCTTGCGTTGAAATAAAGGCTTCTCCCGCAAAAGTATTACAGG
GTCATAATGTTTTTGGTACAACCGATTTAGCTTTATGCTCTGAGGCTTTATTGCTTAATTTTGCTAATTCT
TTGCCTTGCCTGTATGATTTATTGGATGTTGGAATCGCCTGATGCGGTATTTTCTCCTTACGCATCTGTGC
GGTATTTCACACCGCATATGGTGCACTCTCAGTACAATCTGCTCTGATGCCGCATAGTTATATGGTGCACT
CTCAGTACAATCTGCTCTGATGCCGCATAGTTAAGCCAGCCCCGACACCCGCCAACACAGCCAGCCCCGAC
ACCCGCCAACACCCGCTGACGCGCCCTGACGGGCTTGTCTGCTCCCGGCATCCGCTTACAGACAAGCTGTG
ACCGTCTCCGGGAGCTGCATGTGTCAGAGGTTTTCACCGTCATCACCGAAACGCGCGAGACGAAAGGGCCT
CGTGATACGCCTATTTTTATAGGTTAATGTCATGATAATAATGGTTTCTTAGACGTCAGGTGGCACTTTTC
GGGGAAATGTGCGCGGAACCCCTATTTGTTTATTTTTCTAAATACATTCAAATATGTATCCGCTCATGAGA
CAATAACCCTGATAAATGCTCAATAATATTGAAAAAGGAAGAGTATGAGTATTCAACATTTCCGTGTCGCC
CTTATTCCCTTTTTTGCGGCATTTTGCCTTCCTGTTTTTGCTCACCCAGAAACGCTGGTGAAAGTAAAAGA
TGCTGAAGATCAGTTGGGTGCACGAGTGGGTTACATCGAACTGGATCTCAACAGCGGTAAGATCCTTGAGA
GTTTTCGCCCCGAAGAACGTTTTCCAATGATGAGCACTTTTAAAGTTCTGCTATGTGGCGCGGTATTATCC
CGTATTGACGCCGGGCAAGAGCAACTCGGTCGCCGCATACACTATTCTCAGAATGACTTGGTTGAGTACTC
ACCAGTCACAGAAAAGCATCTTACGGATGGCATGACAGTAAGAGAATTATGCAGTGCTGCCATAACCATGA
GTGATAACACTGCGGCCAACTTACTTCTGACAACGATCGGAGGACCGAAGGAGCTAACCGCTTTTTTGCAC
AACATGGGGGATCATGTAACTCGCCTTGATCGTTGGGAACCGGAGCTGAATGAAGCCATACCAAACGACGA
GCGTGACACCACGATGCCTGTAGCAATGGCAACAACGTTGCGCAAACTATTAACTGGCGAACTACTTACTC
TAGCTTCCCGGCAACAATTAATAGACTGGATGGAGGCGGATAAAGTTGCAGGACCACTTCTGCGCTCGGCC
CTTCCGGCTGGCTGGTTTATTGCTGATAAATCTGGAGCCGGTGAGCGTGGGTCTCGCGGTATCATTGCAGC
ACTGGGGCCAGATGGTAAGCCCTCCCGTATCGTAGTTATCTACACGACGGGGAGTCAGGCAACTATGGATG
AACGAAATAGACAGATCGCTGAGATAGGTGCCTCACTGATTAAGCATTGGTAACTGTCAGACCAAGTTTAC
TCATATATACTTTAGATTGATTTAAAACTTCATTTTTAATTTAAAAGGATCTAGGTGAAGATCCTTTTTGA
TAATCTCATGACCAAAATCCCTTAACGTGAGTTTTCGTTCCACTGAGCGTCAGACCCCGTAGAAAAGATCA
AAGGATCTTCTTGAGATCCTTTTTTTCTGCGCGTAATCTGCTGCTTGCAAACAAAAAAACCACCGCTACCA
GCGGTGGTTTGTTTGCCGGATCAAGAGCTACCAACTCTTTTTCCGAAGGTAACTGGCTTCAGCAGAGCGCA
GATACCAAATACTGTCCTTCTAGTGTAGCCGTAGTTAGGCCACCACTTCAAGAACTCTGTAGCACCGCCTA
CATACCTCGCTCTGCTAATCCTGTTACCAGTGGCTGCTGCCAGTGGCGATAAGTCGTGTCTTACCGGGTTG
GACTCAAGACGATAGTTACCGGATAAGGCGCAGCGGTCGGGCTGAACGGGGGGTTCGTGCACACAGCCCAG
CTTGGAGCGAACGACCTACACCGAACTGAGATACCTACAGCGTGAGCTATGAGAAAGCGCCACGCTTCCCG
AAGGGAGAAAGGCGGACAGGTATCCGGTAAGCGGCAGGGTCGGAACAGGAGAGCGCACGAGGGAGCTTCCA
GGGGGAAACGCCTGGTATCTTTATAGTCCTGTCGGGTTTCGCCACCTCTGACTTGAGCGTCGATTTTTGTG
ATGCTCGTCAGGGGGCGGAGCCTATGGAAAAACGCCAGCAACGCGGCCTTTTTACGGTTCCTGGCCTTTT
GCTGGCCTTTTGCTCACATGTTCTTTCCTGCGTTATCCCCTGATTCTGTGGATAACCGTATTACCGCCTTT
```

Figure 13 (continued)

```
GAGTGAGCTGATACCGCTCGCCGCAGCCGAACGACCGAGCGCAGCGAGTCAGTGAGCGAGGAAGCGGAAGA
GCGCCCAATACGCAAACCGCCTCTCCCCGCGCGTTGGCCGATTCATTAATG

SEQ ID NO.4: pAAVsc-3xSerpEnh-TTRe-TTRm-MVM-co-FIX-R338L-BGHpA

AGCTGGCGTAATAGCGAAGAGGCCCGCACCGATCGCCCTTCCCAACAGTTGCGCAGCCTGAATGGCGAATG
GCGATTCCGTTGCAATGGCTGGCGGTAATATTGTTCTGGATATTACCAGCAAGGCCGATAGTTTGAGTTCT
TCTACTCAGGCAAGTGATGTTATTACTAATCAAAGAAGTATTGCGACAACGGTTAATTTGCGTGATGGACA
GACTCTTTTACTCGGTGGCCTCACTGATTATAAAAACACTTCTCAGGATTCTGGCGTACCGTTCCTGTCTA
AAATCCCTTTAATCGGCCTCCTGTTTAGCTCCCGCTCTGATTCTAACGAGGAAAGCACGTTATACGTGCTC
GTCAAAGCAACCATAGTACGCGCCCTGTAGCGGCGCATTAAGCGCGGCGGGTGTGGTGGTTACGCGCAGCG
TGACCGCTACACTTGCCAGCGCCCTAGCGCCCGCTCCTTTCGCTTTCTTCCCTTCCTTTCTCGCCACGTTC
GCCGGCTTTCCCCGTCAAGCTCTAAATCGGGGGCTCCCTTTAGGGTTCCGATTTAGTGCTTTACGGCACCT
CGACCCCAAAAAACTTGATTAGGGTGATGGTTCACGTAGTGGGCCATCGCCCTGATAGACGGTTTTTCGCC
CTTTGACGTTGGAGTCCACGTTCTTTAATAGTGGACTCTTGTTCCAAACTGGAACAACACTCAACCCTATC
TCGGTCTATTCTTTTGATTTATAAGGGATTTTGCCGATTTCGGCCTATTGGTTAAAAAATGAGCTGATTTA
ACAAAAATTTAACGCGAACTTTAACAAAATATTAACGTTTACAATTTAAATATTTGCTTATACAATCTTCC
TGTTTTTGGGGCTTTTCTGATTATCAACCGGGGTACATATGATTGACATGCTAGTTTTACGATTACCGTTC
ATCGCCCTGCGCGCTCGCTCGCTCACTGAGGCCGCCCGGGCAAAGCCCGGGCGTCGGGCGACCTTTGGTCG
CCCGGCCTCAGTGAGCGAGCGAGCGCGCAGAGAGGGAGTGGAATTCACGCGTGGATCTGAATTCAATTCAC
GCGTGGTACGGCCGCGGGGGGGAGGCTGCTGGTGAATATTAACCAAGGTCACCCCAGTTATCGGAGGAGCA
AACAGGGGCTAAGTCCACCGGGGGAGGCTGCTGGTGAATATTAACCAAGGTCACCCCAGTTATCGGAGGAG
CAAACAGGGGCTAAGTCCACCGGGGGAGGCTGCTGGTGAATATTAACCAAGGTCACCCCAGTTATCGGAGG
AGCAAACAGGGGCTAAGTCCACGGTACCCACTGGGAGGATGTTGAGTAAGATGGAAAACTACTGATGACCC
TTGCAGAGACAGAGTATTAGGACATGTTTGAACAGGGGCCGGGCGATCAGCAGGTAGCTCTAGAGGATCCC
CGTCTGTCTGCACATTTCGTAGAGCGAGTGTTCCGATACTCTAATCTCCCTAGGCAAGGTTCATATTTGTG
TAGGTTACTTATTCTCCTTTTGTTGACTAAGTCAATAATCAGAATCAGCAGGTTTGGAGTCAGCTTGGCAG
GGATCAGCAGCCTGGGTTGGAAGGAGGGGGTATAAAAGCCCCTTCACCAGGAGAAGCCGTCACACAGATCC
ACAAGCTCCTGGCTAGAAAGAGGTAAGGGTTTAAGGGATGGTTGGTTGGTGGGGTATTAATGTTTAATTAC
CTGGAGCACCTGCCTGAAATCACTTTTTTTCAGGTTGGGCTAGCCCACCATGCAGCGCGTGAACATGATCA
TGGCCGAGAGCCCCGGCCTGATCACCATCTGCCTGCTGGGCTACCTGCTGAGCGCCGAGTGCACCGTGTTC
CTGGACCACGAGAACGCCAACAAGATCCTGAACCGCCCCAAGCGCTACAACAGCGGCAAGCTGGAGGAGTT
CGTGCAGGGCAACCTGGAGCGCGAGTGCATGGAGGAGAAGTGCAGCTTCGAGGAGGCCCGCGAGGTGTTCG
AGAACACCGAGCGCACCACCGAGTTCTGGAAGCAGTACGTGGACGGCGACCAGTGCGAGAGCAACCCCTGC
CTGAACGGCGGCAGCTGCAAGGACGACATCAACAGCTACGAGTGCTGGTGCCCCTTCGGCTTCGAGGGCAA
GAACTGCGAGCTGGACGTGACCTGCAACATCAAGAACGGCCGCTGCGAGCAGTTCTGCAAGAACAGCGCCG
ACAACAAGGTGGTGTGCAGCTGCACCGAGGGCTACCGCCTGGCCGAGAACCAGAAGAGCTGCGAGCCCGCC
GTGCCCTTCCCCTGCGGCCGCGTGAGCGTGAGCCAGACCAGCAAGCTGACCCGCGCCGAGGCCGTGTTCCC
CGACGTGGACTACGTGAACAGCACCGAGGCCGAGACCATCCTGGACAACATCACCCAGAGCACCCAGAGCT
TCAACGACTTCACCCGCGTGGTGGGCGGCGAGGACGCCAAGCCCGGCCAGTTCCCCTGGCAGGTGGTGCTG
AACGGCAAGGTGGACGCCTTCTGCGGCGGCAGCATCGTGAACGAGAAGTGGATCGTGACCGCCGCCCACTG
CGTGGAGACCGGCGTGAAGATCACCGTGGTGGCCGGCGAGCACAACATCGAGGAGACCGAGCACACCGAGC
AGAAGCGCAACGTGATCCGCATCATCCCCCACCACAACTACAACGCCGCCATCAACAAGTACAACCACGAC
ATCGCCCTGCTGGAGCTGGACGAGCCCCTGGTGCTGAACAGCTACGTGACCCCCATCTGCATCGCCGACAA
GGAGTACACCAACATCTTCCTGAAGTTCGGCAGCGGCTACGTGAGCGGCTGGGGCCGCGTGTTCCACAAGG
GCCGCAGCGCCCTGGTGCTGCAGTACCTGCGCGTGCCCCTGGTGGACCGCGCCACCTGCCTGCTGAGCACC
AAGTTCACCATCTACAACAACATGTTCTGCGCCGGCTTCCACGAGGGCGGCCGCGACAGCTGCCAGGGCGA
CAGCGGCGGCCCCCACGTGACCGAGGTGGAGGGCACCAGCTTCCTGACCGGCATCATCAGCTGGGGCGAGG
AGTGCGCCATGAAGGGCAAGTACGGCATCTACACCAAGGTGAGCCGCTACGTGAACTGGATCAAGGAGAAG
ACCAAGCTGACCTAATGAAAGATGGATTTCCAAGGTTAATTCATTGGAATTGAAAATTAACAGCCCCCCCC
CCCCCCCCCCTGCAGATCTGAGCCGAATTCCTGCAGCCCGGGGGATCAGCCTCGACTGTGCCTTCTAGTTG
CCAGCCATCTGTTGTTTGCCCCTCCCCCGTGCCTTCCTTGACCCTGGAAGGTGCCACTCCCACTGTCCTTT
CCTAATAAAATGAGGAAATTGCATCGCATTGTCTGAGTAGGTGTCATTCTATTCTGGGGGGTGGGGTGGGG
CAGGACAGCAAGGGGGAGGATTGGGAAGACAATAGCAGGCATGCTGGGGATGCGGTGGGCTCTATGGCTTC
TGAGGCGGAAAGAACCAGCTGGGGACCGGTGGATCTCGATAGCAGGCATGCTGGGGAGAGATCGATCTGAG
```

Figure 13 (continued)

```
GAACCCCTAGTGATGGAGTTGGCCACTCCCTCTCTGCGCGCTCGCTCGCTCACTGAGGCCGCCCGGGCAAA
GCCCGGGCGTCGGGCGACCTTTGGTCGCCCGGCCTCAGTGAGCGAGCGAGCGCGCAGAGAGGGAGTGGCCA
ACCCCCCCCCCCCCCCCCCCGGCGATTCTCTTGTTTGCTCCAGACTCTCAGGCAATGACCTGATAGCCTT
TGTAGAGACCTCTCAAAAATAGCTACCCTCTCCGGCATGAATTTATCAGCTAGAACGGTTGAATATCATAT
TGATGGTGATTTGACTGTCTCCGGCCTTTCTCACCCGTTTGAATCTTTACCTACACATTACTCAGGCATTG
CATTTAAAATATATGAGGGTTCTAAAAATTTTTATCCTTGCGTTGAAATAAAGGCTTCTCCCGCAAAAGTA
TTACAGGGTCATAATGTTTTTGGTACAACCGATTTAGCTTTATGCTCTGAGGCTTTATTGCTTAATTTTGC
TAATTCTTTGCCTTGCCTGTATGATTTATTGGATGTTGGAATCGCCTGATGCGGTATTTTCTCCTTACGCA
TCTGTGCGGTATTTCACACCGCATATGGTGCACTCTCAGTACAATCTGCTCTGATGCCGCATAGTTATATG
GTGCACTCTCAGTACAATCTGCTCTGATGCCGCATAGTTAAGCCAGCCCCGACACCCGCCAACACAGCCAG
CCCCGACACCCGCCAACACCCGCTGACGCGCCCTGACGGGCTTGTCTGCTCCCGGCATCCGCTTACAGACA
AGCTGTGACCGTCTCCGGGAGCTGCATGTGTCAGAGGTTTTCACCGTCATCACCGAAACGCGCGAGACGAA
AGGGCCTCGTGATACGCCTATTTTTATAGGTTAATGTCATGATAATAATGGTTTCTTAGACGTCAGGTGGC
ACTTTTCGGGGAAATGTGCGCGGAACCCCTATTTGTTTATTTTTCTAAATACATTCAAATATGTATCCGCT
CATGAGACAATAACCCTGATAAATGCTCAATAATATTGAAAAAGGAAGAGTATGAGTATTCAACATTTCCG
TGTCGCCCTTATTCCCTTTTTTGCGGCATTTTGCCTTCCTGTTTTTGCTCACCCAGAAACGCTGGTGAAAG
TAAAAGATGCTGAAGATCAGTTGGGTGCACGAGTGGGTTACATCGAACTGGATCTCAACAGCGGTAAGATC
CTTGAGAGTTTTCGCCCCGAAGAACGTTTTCCAATGATGAGCACTTTTAAAGTTCTGCTATGTGGCGCGGT
ATTATCCCGTATTGACGCCGGGCAAGAGCAACTCGGTCGCCGCATACACTATTCTCAGAATGACTTGGTTG
AGTACTCACCAGTCACAGAAAAGCATCTTACGGATGGCATGACAGTAAGAGAATTATGCAGTGCTGCCATA
ACCATGAGTGATAACACTGCGGCCAACTTACTTCTGACAACGATCGGAGGACCGAAGGAGCTAACCGCTTT
TTTGCACAACATGGGGGATCATGTAACTCGCCTTGATCGTTGGGAACCGGAGCTGAATGAAGCCATACCAA
ACGACGAGCGTGACACCACGATGCCTGTAGCAATGGCAACAACGTTGCGCAAACTATTAACTGGCGAACTA
CTTACTCTAGCTTCCCGGCAACAATTAATAGACTGGATGGAGGCGGATAAAGTTGCAGGACCACTTCTGCG
CTCGGCCCTTCCGGCTGGCTGGTTTATTGCTGATAAATCTGGAGCCGGTGAGCGTGGGTCTCGCGGTATCA
TTGCAGCACTGGGGCCAGATGGTAAGCCCTCCCGTATCGTAGTTATCTACACGACGGGGAGTCAGGCAACT
ATGGATGAACGAAATAGACAGATCGCTGAGATAGGTGCCTCACTGATTAAGCATTGGTAACTGTCAGACCA
AGTTTACTCATATATACTTTAGATTGATTTAAAACTTCATTTTTAATTTAAAAGGATCTAGGTGAAGATCC
TTTTTGATAATCTCATGACCAAAATCCCTTAACGTGAGTTTTCGTTCCACTGAGCGTCAGACCCCGTAGAA
AAGATCAAAGGATCTTCTTGAGATCCTTTTTTTCTGCGCGTAATCTGCTGCTTGCAAACAAAAAAACCACC
GCTACCAGCGGTGGTTTGTTTGCCGGATCAAGAGCTACCAACTCTTTTTCCGAAGGTAACTGGCTTCAGCA
GAGCGCAGATACCAAATACTGTCCTTCTAGTGTAGCCGTAGTTAGGCCACCACTTCAAGAACTCTGTAGCA
CCGCCTACATACCTCGCTCTGCTAATCCTGTTACCAGTGGCTGCTGCCAGTGGCGATAAGTCGTGTCTTAC
CGGGTTGGACTCAAGACGATAGTTACCGGATAAGGCGCAGCGGTCGGGCTGAACGGGGGGTTCGTGCACAC
AGCCCAGCTTGGAGCGAACGACCTACACCGAACTGAGATACCTACAGCGTGAGCTATGAGAAAGCGCCACG
CTTCCCGAAGGGAGAAAGGCGGACAGGTATCCGGTAAGCGGCAGGGTCGGAACAGGAGAGCGCACGAGGGA
GCTTCCAGGGGGAAACGCCTGGTATCTTTATAGTCCTGTCGGGTTTCGCCACCTCTGACTTGAGCGTCGAT
TTTTGTGATGCTCGTCAGGGGGCGGAGCCTATGGAAAAACGCCAGCAACGCGGCCTTTTTACGGTTCCTG
GCCTTTTGCTGGCCTTTTGCTCACATGTTCTTTCCTGCGTTATCCCCTGATTCTGTGGATAACCGTATTAC
CGCCTTTGAGTGAGCTGATACCGCTCGCCGCAGCCGAACGACCGAGCGCAGCGAGTCAGTGAGCGAGGAAG
CGGAAGAGCGCCCAATACGCAAACCGCCTCTCCCCGCGCGTTGGCCGATTCATTAATG
```

SEQ ID NO.5: SerpEnh

```
GGGGGAGGCTGCTGGTGAATATTAACCAAGGTCACCCCAGTTATCGGAGGAGCAAACAGGGGCTAAGTCCA
C
```

SEQ ID NO.6: TTRm (TTR minimal promotor)

```
GTCTGTCTGCACATTTCGTAGAGCGAGTGTTCCGATACTCTAATCTCCCTAGGCAAGGTTCATATTTGTGT
AGGTTACTTATTCTCCTTTTGTTGACTAAGTCAATAATCAGAATCAGCAGGTTTGGAGTCAGCTTGGCAGG
GATCAGCAGCCTGGGTTGGAAGGAGGGGGTATAAAAGCCCCTTCACCAGGAGAAGCCGTC
```

SEQ ID NO.7: TTRm5'UTR
ACACAGATCCACAAGCTCCTG

Figure 13 (continued)

SEQ ID NO.8: MVM intron

AAGAGGTAAGGGTTTAAGGGATGGTTGGTTGGTGGGGTATTAATGTTTAATTACCTGGAGCACCTGCCTGA
AATCACTTTTTTTCAGGTTGG

SEQ ID NO.9: Co-FIX-R338L

ATGCAGCGCGTGAACATGATCATGGCCGAGAGCCCCGGCCTGATCACCATCTGCCTGCTGGGCTACCTGCT
GAGCGCCGAGTGCACCGTGTTCCTGGACCACGAGAACGCCAACAAGATCCTGAACCGCCCCAAGCGCTACA
ACAGCGGCAAGCTGGAGGAGTTCGTGCAGGGCAACCTGGAGCGCGAGTGCATGGAGGAGAAGTGCAGCTTC
GAGGAGGCCCGCGAGGTGTTCGAGAACACCGAGCGCACCACCGAGTTCTGGAAGCAGTACGTGGACGGCGA
CCAGTGCGAGAGCAACCCCTGCCTGAACGGCGGCAGCTGCAAGGACGACATCAACAGCTACGAGTGCTGGT
GCCCCTTCGGCTTCGAGGGCAAGAACTGCGAGCTGGACGTGACCTGCAACATCAAGAACGGCCGCTGCGAG
CAGTTCTGCAAGAACAGCGCCGACAACAAGGTGGTGTGCAGCTGCACCGAGGGCTACCGCCTGGCCGAGAA
CCAGAAGAGCTGCGAGCCCGCCGTGCCCTTCCCCTGCGGCCGCGTGAGCGTGAGCCAGACCAGCAAGCTGA
CCCGCGCCGAGGCCGTGTTCCCCGACGTGGACTACGTGAACAGCACCGAGGCCGAGACCATCCTGGACAAC
ATCACCCAGAGCACCCAGAGCTTCAACGACTTCACCCGCGTGGTGGGCGGCGAGGACGCCAAGCCCGGCCA
GTTCCCCTGGCAGGTGGTGCTGAACGGCAAGGTGGACGCCTTCTGCGGCGGCAGCATCGTGAACGAGAAGT
GGATCGTGACCGCCGCCCACTGCGTGGAGACCGGCGTGAAGATCACCGTGGTGGCCGGCGAGCACAACATC
GAGGAGACCGAGCACACCGAGCAGAAGCGCAACGTGATCCGCATCATCCCCCACCACAACTACAACGCCGC
CATCAACAAGTACAACCACGACATCGCCCTGCTGGAGCTGGACGAGCCCCTGGTGCTGAACAGCTACGTGA
CCCCCATCTGCATCGCCGACAAGGAGTACACCAACATCTTCCTGAAGTTCGGCAGCGGCTACGTGAGCGGC
TGGGGCCGCGTGTTCCACAAGGGCCGCAGCGCCCTGGTGCTGCAGTACCTGCGCGTGCCCCTGGTGGACCG
CGCCACCTGCCTGCTGAGCACCAAGTTCACCATCTACAACAACATGTTCTGCGCCGGCTTCCACGAGGGCG
GCCGCGACAGCTGCCAGGGCGACAGCGGCGGCCCCCACGTGACCGAGGTGGAGGGCACCAGCTTCCTGACC
GGCATCATCAGCTGGGGCGAGGAGTGCGCCATGAAGGGCAAGTACGGCATCTACACCAAGGTGAGCCGCTA
CGTGAACTGGATCAAGGAGAAGACCAAGCTGACCTAATGA

SEQ ID NO.10: BGHpolyA

GATCTGAGCCGAATTCCTGCAGCCCGGGGGATCAGCCTCGACTGTGCCTTCTAGTTGCCAGCCATCTGTTG
TTTGCCCCTCCCCCGTGCCTTCCTTGACCCTGGAAGGTGCCACTCCCACTGTCCTTTCCTAATAAAATGAG
GAAATTGCATCGCATTGTCTGAGTAGGTGTCATTCTATTCTGGGGGGTGGGGTGGGGCAGGACAGCAAGGG
GGAGGATTGGGAAGACAATAGCAGGCATGCTGGGGATGCGGTGGGCTCTATGGCTTCTGAGGCGGAAAGAA
CCAGCTGGGGA

SEQ ID NO.11: <u>3xSERP</u>
<u>GGGGGAGGCTGCTGGTGAATATTAACCAAGGTCACCCCAGTTATCGGAGGAGCAAACAGGGGCTAAGTCCA</u>
<u>CCGGGGGAGGCTGCTGGTGAATATTAACCAAGGTCACCCCAGTTATCGGAGGAGCAAACAGGGGCTAAGTC</u>
<u>CACCGGGGGAGGCTGCTGGTGAATATTAACCAAGGTCACCCCAGTTATCGGAGGAGCAAACAGGGGCTAAG</u>
<u>TCCAC</u>

SEQ ID NO.12: TTRe (TTR Enhancer)

CACTGGGAGGATGTTGAGTAAGATGGAAAACTACTGATGACCCTTGCAGAGACAGAGTATTAGGACATGTT
TGAACAGGGGCCGGGCGATCAGCAGGTAG

SEQ ID NO.13: <u>3xSERP</u>-Flank-*TTRe*

<u>GGGGGAGGCTGCTGGTGAATATTAACCAAGGTCACCCCAGTTATCGGAGGAGCAAACAGGGGCTAAGTCCA</u>
<u>CCGGGGGAGGCTGCTGGTGAATATTAACCAAGGTCACCCCAGTTATCGGAGGAGCAAACAGGGGCTAAGTC</u>
<u>CACCGGGGGAGGCTGCTGGTGAATATTAACCAAGGTCACCCCAGTTATCGGAGGAGCAAACAGGGGCTAAG</u>
<u>TCCAC</u>GGTACC<i>CACTGGGAGGATGTTGAGTAAGATGGAAAACTACTGATGACCCTTGCAGAGACAGAGTAT</i>
<i>TAGGACATGTTTGAACAGGGGCCGGGCGATCAGCAGGTAG</i>

Figure 13 (continued)

SEQ ID NO.25: pAAVsc-3xSerpEnh-TTREnh-TTRm-MVM-co-FIX-R338L-Synt.pA

```
AGCTGGCGTAATAGCGAAGAGGCCCGCACCGATCGCCCTTCCCAACAGTTGCGCAGCCTGAATGGCGAATG
GCGATTCCGTTGCAATGGCTGGCGGTAATATTGTTCTGGATATTACCAGCAAGGCCGATAGTTTGAGTTCT
TCTACTCAGGCAAGTGATGTTATTACTAATCAAAGAAGTATTGCGACAACGGTTAATTTGCGTGATGGACA
GACTCTTTTACTCGGTGGCCTCACTGATTATAAAAACACTTCTCAGGATTCTGGCGTACCGTTCCTGTCTA
AAATCCCTTTAATCGGCCTCCTGTTTAGCTCCCGCTCTGATTCTAACGAGGAAAGCACGTTATACGTGCTC
GTCAAAGCAACCATAGTACGCGCCCTGTAGCGGCGCATTAAGCGCGGCGGGTGTGGTGGTTACGCGCAGCG
TGACCGCTACACTTGCCAGCGCCCTAGCGCCCGCTCCTTTCGCTTTCTTCCCTTCCTTTCTCGCCACGTTC
GCCGGCTTTCCCCGTCAAGCTCTAAATCGGGGGCTCCCTTTAGGGTTCCGATTTAGTGCTTTACGGCACCT
CGACCCCAAAAAACTTGATTAGGGTGATGGTTCACGTAGTGGGCCATCGCCCTGATAGACGGTTTTTCGCC
CTTTGACGTTGGAGTCCACGTTCTTTAATAGTGGACTCTTGTTCCAAACTGGAACAACACTCAACCCTATC
TCGGTCTATTCTTTTGATTTATAAGGGATTTTGCCGATTTCGGCCTATTGGTTAAAAAATGAGCTGATTTA
ACAAAAATTTAACGCGAACTTTAACAAAATATTAACGTTTACAATTTAAATATTTGCTTATACAATCTTCC
TGTTTTTGGGGCTTTTCTGATTATCAACCGGGGTACATATGATTGACATGCTAGTTTTACGATTACCGTTC
ATCGCCCTGCGCGCTCGCTCGCTCACTGAGGCCGCCCGGGCAAAGCCCGGGCGTCGGGCGACCTTTGGTCG
CCCGGCCTCAGTGAGCGAGCGAGCGCGCAGAGAGGGAGTGGAATTCACGCGTGGATCTGAATTCAATTCAC
GCGTGGTACGGCCGCGGGGGGAGGCTGCTGGTGAATATTAACCAAGGTCACCCCAGTTATCGGAGGAGCA
AACAGGGGCTAAGTCCACCGGGGGAGGCTGCTGGTGAATATTAACCAAGGTCACCCCAGTTATCGGAGGAG
CAAACAGGGGCTAAGTCCACCGGGGGAGGCTGCTGGTGAATATTAACCAAGGTCACCCCAGTTATCGGAGG
AGCAAACAGGGGCTAAGTCCACGGTACCCACTGGGAGGATGTTGAGTAAGATGGAAAACTACTGATGACCC
TTGCAGAGACAGAGTATTAGGACATGTTTGAACAGGGGCCGGGCGATCAGCAGGTAGCTCTAGAGGATCCC
CGTCTGTCTGCACATTTCGTAGAGCGAGTGTTCCGATACTCTAATCTCCCTAGGCAAGGTTCATATTTGTG
TAGGTTACTTATTCTCCTTTTGTTGACTAAGTCAATAATCAGAATCAGCAGGTTTGGAGTCAGCTTGGCAG
GGATCAGCAGCCTGGGTTGGAAGGAGGGGGTATAAAAGCCCCTTCACCAGGAGAAGCCGTCACACAGATCC
ACAAGCTCCTGGCTAGAAAGAGGTAAGGGTTTAAGGGATGGTTGGTTGGTGGGTATTAATGTTTAATTAC
CTGGAGCACCTGCCTGAAATCACTTTTTTTCAGGTTGGGCTAGCCCACCATGCAGCGCGTGAACATGATCA
TGGCCGAGAGCCCCGGCCTGATCACCATCTGCCTGCTGGGCTACCTGCTGAGCGCCGAGTGCACCGTGTTC
CTGGACCACGAGAACGCCAACAAGATCCTGAACCGCCCCAAGCGCTACAACAGCGGCAAGCTGGAGGAGTT
CGTGCAGGGCAACCTGGAGCGCGAGTGCATGGAGGAGAAGTGCAGCTTCGAGGAGGCCCGCGAGGTGTTCG
AGAACACCGAGCGCACCACCGAGTTCTGGAAGCAGTACGTGGACGGCGACCAGTGCGAGAGCAACCCCTGC
CTGAACGGCGGCAGCTGCAAGGACGACATCAACAGCTACGAGTGCTGGTGCCCCTTCGGCTTCGAGGGCAA
GAACTGCGAGCTGGACGTGACCTGCAACATCAAGAACGGCCGCTGCGAGCAGTTCTGCAAGAACAGCGCCG
ACAACAAGGTGGTGTGCAGCTGCACCGAGGGCTACCGCCTGGCCGAGAACCAGAAGAGCTGCGAGCCCGCC
GTGCCCTTCCCCTGCGGCCGCGTGAGCGTGAGCCAGACCAGCAAGCTGACCCGCGCCGAGGCCGTGTTCCC
CGACGTGGACTACGTGAACAGCACCGAGGCCGAGACCATCCTGGACAACATCACCCAGAGCACCCAGAGCT
TCAACGACTTCACCCGCGTGGTGGGCGGCGAGGACGCCAAGCCCGGCCAGTTCCCCTGGCAGGTGGTGCTG
AACGGCAAGGTGGACGCCTTCTGCGGCGGCAGCATCGTGAACGAGAAGTGGATCGTGACCGCCGCCCACTG
CGTGGAGACCGGCGTGAAGATCACCGTGGTGGCCGGCGAGCACAACATCGAGGAGACCGAGCACACCGAGC
AGAAGCGCAACGTGATCCGCATCATCCCCCACCACAACTACAACGCCGCCATCAACAAGTACAACCACGAC
ATCGCCCTGCTGGAGCTGGACGAGCCCCTGGTGCTGAACAGCTACGTGACCCCCATCTGCATCGCCGACAA
GGAGTACACCAACATCTTCCTGAAGTTCGGCAGCGGCTACGTGAGCGGCTGGGGCCGCGTGTTCCACAAGG
GCCGCAGCGCCCTGGTGCTGCAGTACCTGCGCGTGCCCCTGGTGGACCGCGCCACCTGCCTGCTGAGCACC
AAGTTCACCATCTACAACAACATGTTCTGCGCCGGCTTCCACGAGGGCGGCCGCGACAGCTGCCAGGGCGA
CAGCGGCGGCCCCCACGTGACCGAGGTGGAGGGCACCAGCTTCCTGACCGGCATCATCAGCTGGGGCGAGG
AGTGCGCCATGAAGGGCAAGTACGGCATCTACACCAAGGTGAGCCGCTACGTGAACTGGATCAAGGAGAAG
ACCAAGCTGACCTAATGAAAGATGGATTTCCAAGGTTAATTCATTGGAATTGAAAATTAACAGCCCCCCC
CCCCCCCCCCTGCAGATCTAATAAAAGATCTTTATTTTCATTAGATCTGTGTGTTGGTTTTTTGTGTGCCG
GTGGATCTCGATAGCAGGCATGCTGGGAGAGATCGATCTGAGGAACCCCTAGTGATGGAGTTGGCCACTC
CCTCTCTGCGCGCTCGCTCGCTCACTGAGGCCGCCCGGGCAAAGCCCGGGCGTCGGGCGACCTTTGGTCGC
CCGGCCTCAGTGAGCGAGCGAGCGCGCAGAGAGGGAGTGGCCAACCCCCCCCCCCCCCCCCCGGCGATT
CTCTTGTTTGCTCCAGACTCTCAGGCAATGACCTGATAGCCTTTGTAGAGACCTCTCAAAAATAGCTACCC
TCTCCGGCATGAATTTATCAGCTAGAACGGTTGAATATCATATTGATGGTGATTTGACTGTCTCCGGCCTT
TCTCACCCGTTTGAATCTTTACCTACACATTACTCAGGCATTGCATTTAAAATATATGAGGGTTCTAAAAA
```

Figure 13 (continued)

```
TTTTTATCCTTGCGTTGAAATAAAGGCTTCTCCCGCAAAAGTATTACAGGGTCATAATGTTTTTGGTACAA
CCGATTTAGCTTTATGCTCTGAGGCTTTATTGCTTAATTTTGCTAATTCTTTGCCTTGCCTGTATGATTTA
TTGGATGTTGGAATCGCCTGATGCGGTATTTTCTCCTTACGCATCTGTGCGGTATTTCACACCGCATATGG
TGCACTCTCAGTACAATCTGCTCTGATGCCGCATAGTTATATGGTGCACTCTCAGTACAATCTGCTCTGAT
GCCGCATAGTTAAGCCAGCCCCGACACCCGCCAACACAGCCAGCCCCGACACCCGCCAACACCCGCTGACG
CGCCCTGACGGGCTTGTCTGCTCCCGGCATCCGCTTACAGACAAGCTGTGACCGTCTCCGGGAGCTGCATG
TGTCAGAGGTTTTCACCGTCATCACCGAAACGCGCGAGACGAAAGGGCCTCGTGATACGCCTATTTTTATA
GGTTAATGTCATGATAATAATGGTTTCTTAGACGTCAGGTGGCACTTTTCGGGGAAATGTGCGCGGAACCC
CTATTTGTTTATTTTTCTAAATACATTCAAATATGTATCCGCTCATGAGACAATAACCCTGATAAATGCTC
AATAATATTGAAAAAGGAAGAGTATGAGTATTCAACATTTCCGTGTCGCCCTTATTCCCTTTTTTGCGGCA
TTTTGCCTTCCTGTTTTTGCTCACCCAGAAACGCTGGTGAAAGTAAAAGATGCTGAAGATCAGTTGGGTGC
ACGAGTGGGTTACATCGAACTGGATCTCAACAGCGGTAAGATCCTTGAGAGTTTTCGCCCCGAAGAACGTT
TTCCAATGATGAGCACTTTTAAAGTTCTGCTATGTGGCGCGGTATTATCCCGTATTGACGCCGGGCAAGAG
CAACTCGGTCGCCGCATACACTATTCTCAGAATGACTTGGTTGAGTACTCACCAGTCACAGAAAAGCATCT
TACGGATGGCATGACAGTAAGAGAATTATGCAGTGCTGCCATAACCATGAGTGATAACACTGCGGCCAACT
TACTTCTGACAACGATCGGAGGACCGAAGGAGCTAACCGCTTTTTTGCACAACATGGGGGATCATGTAACT
CGCCTTGATCGTTGGGAACCGGAGCTGAATGAAGCCATACCAAACGACGAGCGTGACACCACGATGCCTGT
AGCAATGGCAACAACGTTGCGCAAACTATTAACTGGCGAACTACTTACTCTAGCTTCCCGGCAACAATTAA
TAGACTGGATGGAGGCGGATAAAGTTGCAGGACCACTTCTGCGCTCGGCCCTTCCGGCTGGCTGGTTTATT
GCTGATAAATCTGGAGCCGGTGAGCGTGGGTCTCGCGGTATCATTGCAGCACTGGGGCCAGATGGTAAGCC
CTCCCGTATCGTAGTTATCTACACGACGGGGAGTCAGGCAACTATGGATGAACGAAATAGACAGATCGCTG
AGATAGGTGCCTCACTGATTAAGCATTGGTAACTGTCAGACCAAGTTTACTCATATATACTTTAGATTGAT
TTAAAACTTCATTTTTAATTTAAAAGGATCTAGGTGAAGATCCTTTTTGATAATCTCATGACCAAAATCCC
TTAACGTGAGTTTTCGTTCCACTGAGCGTCAGACCCCGTAGAAAAGATCAAAGGATCTTCTTGAGATCCTT
TTTTTCTGCGCGTAATCTGCTGCTTGCAAACAAAAAAACCACCGCTACCAGCGGTGGTTTGTTTGCCGGAT
CAAGAGCTACCAACTCTTTTTCCGAAGGTAACTGGCTTCAGCAGAGCGCAGATACCAAATACTGTCCTTCT
AGTGTAGCCGTAGTTAGGCCACCACTTCAAGAACTCTGTAGCACCGCCTACATACCTCGCTCTGCTAATCC
TGTTACCAGTGGCTGCTGCCAGTGGCGATAAGTCGTGTCTTACCGGGTTGGACTCAAGACGATAGTTACCG
GATAAGGCGCAGCGGTCGGGCTGAACGGGGGGTTCGTGCACACAGCCCAGCTTGGAGCGAACGACCTACAC
CGAACTGAGATACCTACAGCGTGAGCTATGAGAAAGCGCCACGCTTCCCGAAGGGAGAAAGGCGGACAGGT
ATCCGGTAAGCGGCAGGGTCGGAACAGGAGAGCGCACGAGGGAGCTTCCAGGGGAAACGCCTGGTATCTT
TATAGTCCTGTCGGGTTTCGCCACCTCTGACTTGAGCGTCGATTTTTGTGATGCTCGTCAGGGGGGCGGAG
CCTATGGAAAAACGCCAGCAACGCGGCCTTTTTACGGTTCCTGGCCTTTTGCTGGCCTTTTGCTCACATGT
TCTTTCCTGCGTTATCCCCTGATTCTGTGGATAACCGTATTACCGCCTTTGAGTGAGCTGATACCGCTCGC
CGCAGCCGAACGACCGAGCGCAGCGAGTCAGTGAGCGAGGAAGCGGAAGAGCGCCCAATACGCAAACCGCC
TCTCCCCGCGCGTTGGCCGATTCATTAATG
```

SEQ ID NO.26: Flank-<u>3xSERP</u>-Flank-*TTRe*

AATTCACGCGTGGATCTGAATTCAATTCACGCGTGGTACGGCCGCGG<u>GGGGGAGGCTGCTGGTGAATATTA
ACCAAGGTCACCCCAGTTATCGGAGGAGCAAACAGGGGCTAAGTCCACCGGGGGAGGCTGCTGGTGAATAT
TAACCAAGGTCACCCCAGTTATCGGAGGAGCAAACAGGGGCTAAGTCCACCGGGGGAGGCTGCTGGTGAAT
ATTAACCAAGGTCACCCCAGTTATCGGAGGAGCAAACAGGGGCTAAGTCCAC</u>GGTACC*CACTGGGAGGATG*
*TTGAGTAAGATGGAAAACTACTGATGACCCTTGCAGAGACAGAGTATTAGGACATGTTTGAACAGGGGCCG*
*GGCGATCAGCAGGTAG*

SEQ ID NO.27: Flank-<u>3xSERP</u>-Flank-*TTRe*-Flank

AATTCACGCGTGGATCTGAATTCAATTCACGCGTGGTACGGCCGCGG<u>GGGGGAGGCTGCTGGTGAATATTA
ACCAAGGTCACCCCAGTTATCGGAGGAGCAAACAGGGGCTAAGTCCACCGGGGGAGGCTGCTGGTGAATAT
TAACCAAGGTCACCCCAGTTATCGGAGGAGCAAACAGGGGCTAAGTCCACCGGGGGAGGCTGCTGGTGAAT
ATTAACCAAGGTCACCCCAGTTATCGGAGGAGCAAACAGGGGCTAAGTCCAC</u>GGTACC*CACTGGGAGGATG*
*TTGAGTAAGATGGAAAACTACTGATGACCCTTGCAGAGACAGAGTATTAGGACATGTTTGAACAGGGGCCG*
*GGCGATCAGCAGGTAG*CTCTAGAGGATCCCC

Figure 13 (continued)

SEQ ID NO.28: Flank-<u>3xSERP</u>-Flank-*TTRe*-Flank-TTRm

AATTCACGCGTGGATCTGAATTCAATTCACGCGTGGTACGGCCGCGGGGGGGAGGCTGCTGGTGAATATTA
<u>ACCAAGGTCACCCCAGTTATCGGAGGAGCAAACAGGGGCTAAGTCCACCGGGGGAGGCTGCTGGTGAATAT</u>
<u>TAACCAAGGTCACCCCAGTTATCGGAGGAGCAAACAGGGGCTAAGTCCACCGGGGGAGGCTGCTGGTGAAT</u>
<u>ATTAACCAAGGTCACCCCAGTTATCGGAGGAGCAAACAGGGGCTAAGTCCAC</u>GGTACC*CACTGGGAGGATG*
*TTGAGTAAGATGGAAAACTACTGATGACCCTTGCAGAGACAGAGTATTAGGACATGTTTGAACAGGGGCCG*
*GGCGATCAGCAGGTAG*CTCTAGAGGATCCCCGTCTGTCTGCACATTTCGTAGAGCGAGTGTTCCGATACTC
TAATCTCCCTAGGCAAGGTTCATATTTGTGTAGGTTACTTATTCTCCTTTTGTTGACTAAGTCAATAATCA
GAATCAGCAGGTTTGGAGTCAGCTTGGCAGGGATCAGCAGCCTGGGTTGGAAGGAGGGGGTATAAAAGCCC
CTTCACCAGGAGAAGCCGTC

SEQ ID NO.29: Flank-<u>3xSERP</u>-Flank-*TTRe*-Flank-TTRm-Flank

AATTCACGCGTGGATCTGAATTCAATTCACGCGTGGTACGGCCGCGGGGGGGAGGCTGCTGGTGAATATTA
<u>ACCAAGGTCACCCCAGTTATCGGAGGAGCAAACAGGGGCTAAGTCCACCGGGGGAGGCTGCTGGTGAATAT</u>
<u>TAACCAAGGTCACCCCAGTTATCGGAGGAGCAAACAGGGGCTAAGTCCACCGGGGGAGGCTGCTGGTGAAT</u>
<u>ATTAACCAAGGTCACCCCAGTTATCGGAGGAGCAAACAGGGGCTAAGTCCAC</u>GGTACC*CACTGGGAGGATG*
*TTGAGTAAGATGGAAAACTACTGATGACCCTTGCAGAGACAGAGTATTAGGACATGTTTGAACAGGGGCCG*
*GGCGATCAGCAGGTAG*CTCTAGAGGATCCCCGTCTGTCTGCACATTTCGTAGAGCGAGTGTTCCGATACTC
TAATCTCCCTAGGCAAGGTTCATATTTGTGTAGGTTACTTATTCTCCTTTTGTTGACTAAGTCAATAATCA
GAATCAGCAGGTTTGGAGTCAGCTTGGCAGGGATCAGCAGCCTGGGTTGGAAGGAGGGGGTATAAAAGCCC
CTTCACCAGGAGAAGCCGTCACACAGATCCACAAGCTCCTGGCTAGA

SEQ ID NO.30: Flank-<u>3xSERP</u>-Flank-*TTRe*-Flank-TTRm-Flank-*MVM*

AATTCACGCGTGGATCTGAATTCAATTCACGCGTGGTACGGCCGCGGGGGGGAGGCTGCTGGTGAATATTA
<u>ACCAAGGTCACCCCAGTTATCGGAGGAGCAAACAGGGGCTAAGTCCACCGGGGGAGGCTGCTGGTGAATAT</u>
<u>TAACCAAGGTCACCCCAGTTATCGGAGGAGCAAACAGGGGCTAAGTCCACCGGGGGAGGCTGCTGGTGAAT</u>
<u>ATTAACCAAGGTCACCCCAGTTATCGGAGGAGCAAACAGGGGCTAAGTCCAC</u>GGTACC*CACTGGGAGGATG*
*TTGAGTAAGATGGAAAACTACTGATGACCCTTGCAGAGACAGAGTATTAGGACATGTTTGAACAGGGGCCG*
*GGCGATCAGCAGGTAG*CTCTAGAGGATCCCCGTCTGTCTGCACATTTCGTAGAGCGAGTGTTCCGATACTC
TAATCTCCCTAGGCAAGGTTCATATTTGTGTAGGTTACTTATTCTCCTTTTGTTGACTAAGTCAATAATCA
GAATCAGCAGGTTTGGAGTCAGCTTGGCAGGGATCAGCAGCCTGGGTTGGAAGGAGGGGGTATAAAAGCCC
CTTCACCAGGAGAAGCCGTCACACAGATCCACAAGCTCCTGGCTAGA*AAGAGGTAAGGGTTTAAGGGATGG*
*TTGGTTGGTGGGGTATTAATGTTTAATTACCTGGAGCACCTGCCTGAAATCACTTTTTTTCAGGTTGG*

SEQ ID NO.31: Flank-<u>3xSERP</u>-Flank-*TTRe*-Flank-TTRm-Flank-*MVM*-Flank

AATTCACGCGTGGATCTGAATTCAATTCACGCGTGGTACGGCCGCGGGGGGGAGGCTGCTGGTGAATATTA
<u>ACCAAGGTCACCCCAGTTATCGGAGGAGCAAACAGGGGCTAAGTCCACCGGGGGAGGCTGCTGGTGAATAT</u>
<u>TAACCAAGGTCACCCCAGTTATCGGAGGAGCAAACAGGGGCTAAGTCCACCGGGGGAGGCTGCTGGTGAAT</u>
<u>ATTAACCAAGGTCACCCCAGTTATCGGAGGAGCAAACAGGGGCTAAGTCCAC</u>GGTACC*CACTGGGAGGATG*
*TTGAGTAAGATGGAAAACTACTGATGACCCTTGCAGAGACAGAGTATTAGGACATGTTTGAACAGGGGCCG*
*GGCGATCAGCAGGTAG*CTCTAGAGGATCCCCGTCTGTCTGCACATTTCGTAGAGCGAGTGTTCCGATACTC
TAATCTCCCTAGGCAAGGTTCATATTTGTGTAGGTTACTTATTCTCCTTTTGTTGACTAAGTCAATAATCA
GAATCAGCAGGTTTGGAGTCAGCTTGGCAGGGATCAGCAGCCTGGGTTGGAAGGAGGGGGTATAAAAGCCC
CTTCACCAGGAGAAGCCGTCACACAGATCCACAAGCTCCTGGCTAGA*AAGAGGTAAGGGTTTAAGGGATGG*
*TTGGTTGGTGGGGTATTAATGTTTAATTACCTGGAGCACCTGCCTGAAATCACTTTTTTTCAGGTTGG***GCT
AGCCCACC**

SEQ ID NO.32: Flank-<u>3xSERP</u>-Flank-*TTRe*-Flank-TTRm-Flank-*MVM*-Flank-<u>co-FIX-R338L</u>

Figure 13 (continued)

AATTCACGCGTGGATCTGAATTCAATTCACGCGTGGTACGGCCGCGGGGGGGAGGCTGCTGGTGAATATTA
ACCAAGGTCACCCCAGTTATCGGAGGAGCAAACAGGGGCTAAGTCCACCGGGGGAGGCTGCTGGTGAATAT
TAACCAAGGTCACCCCAGTTATCGGAGGAGCAAACAGGGGCTAAGTCCACCGGGGGAGGCTGCTGGTGAAT
ATTAACCAAGGTCACCCCAGTTATCGGAGGAGCAAACAGGGGCTAAGTCCACGGTACC*CACTGGGAGGATG*
*TTGAGTAAGATGGAAAACTACTGATGACCCTTGCAGAGACAGAGTATTAGGACATGTTTGAACAGGGGCCG*
*GGCGATCAGCAGGTAG*CTCTAGAGGATCCCCGTCTGTCTGCACATTTCGTAGAGCGAGTGTTCCGATACTC
TAATCTCCCTAGGCAAGGTTCATATTTGTGTAGGTTACTTATTCTCCTTTTGTTGACTAAGTCAATAATCA
GAATCAGCAGGTTTGGAGTCAGCTTGGCAGGGATCAGCAGCCTGGGTTGGAAGGAGGGGTATAAAAGCCC
CTTCACCAGGAGAAGCCGTCACACAGATCCACAAGCTCCTGGCTAGA*AAGAGGTAAGGGTTTAAGGGATGG*
*TTGGTTGGTGGGGTATTAATGTTTAATTACCTGGAGCACCTGCCTGAAATCACTTTTTTTCAGGTTGG*GCT
AGCCCACCATGCAGCGCGTGAACATGATCATGGCCGAGAGCCCCGGCCTGATCACCATCTGCCTGCTGGGC
TACCTGCTGAGCGCCGAGTGCACCGTGTTCCTGGACCACGAGAACGCCAACAAGATCCTGAACCGCCCCAA
GCGCTACAACAGCGGCAAGCTGGAGGAGTTCGTGCAGGGCAACCTGGAGCGCGAGTGCATGGAGGAGAAGT
GCAGCTTCGAGGAGGCCCGCGAGGTGTTCGAGAACACCGAGCGCACCACCGAGTTCTGGAAGCAGTACGTG
GACGGCGACCAGTGCGAGAGCAACCCCTGCCTGAACGGCGGCAGCTGCAAGGACGACATCAACAGCTACGA
GTGCTGGTGCCCCTTCGGCTTCGAGGGCAAGAACTGCGAGCTGGACGTGACCTGCAACATCAAGAACGGCC
GCTGCGAGCAGTTCTGCAAGAACAGCGCCGACAACAAGGTGGTGTGCAGCTGCACCGAGGGCTACCGCCTG
GCCGAGAACCAGAAGAGCTGCGAGCCCGCCGTGCCCTTCCCCTGCGGCCGCGTGAGCGTGAGCCAGACCAG
CAAGCTGACCCGCGCCGAGGCCGTGTTCCCCGACGTGGACTACGTGAACAGCACCGAGGCCGAGACCATCC
TGGACAACATCACCCAGAGCACCCAGAGCTTCAACGACTTCACCCGCGTGGTGGGCGGCGAGGACGCCAAG
CCCGGCCAGTTCCCCTGGCAGGTGGTGCTGAACGGCAAGGTGGACGCCTTCTGCGGCGGCAGCATCGTGAA
CGAGAAGTGGATCGTGACCGCCGCCCACTGCGTGGAGACCGGCGTGAAGATCACCGTGGTGGCCGGCGAGC
ACAACATCGAGGAGACCGAGCACACCGAGCAGAAGCGCAACGTGATCCGCATCATCCCCCACCACAACTAC
AACGCCGCCATCAACAAGTACAACCACGACATCGCCCTGCTGGAGCTGGACGAGCCCCTGGTGCTGAACAG
CTACGTGACCCCCATCTGCATCGCCGACAAGGAGTACACCAACATCTTCCTGAAGTTCGGCAGCGGCTACG
TGAGCGGCTGGGGCCGCGTGTTCCACAAGGGCCGCAGCGCCCTGGTGCTGCAGTACCTGCGCGTGCCCCTG
GTGGACCGCGCCACCTGCCTGCTGAGCACCAAGTTCACCATCTACAACAACATGTTCTGCGCCGGCTTCCA
CGAGGGCGGCCGCGACAGCTGCCAGGGCGACAGCGGCGGCCCCCACGTGACCGAGGTGGAGGGCACCAGCT
TCCTGACCGGCATCATCAGCTGGGGCGAGGAGTGCGCCATGAAGGGCAAGTACGGCATCTACACCAAGGTG
AGCCGCTACGTGAACTGGATCAAGGAGAAGACCAAGCTGACCTAATGA

SEQ ID NO.33: Flank-<u>3xSERP</u>-Flank-*TTRe*-Flank-TTRm-Flank-*MVM*-Flank-<u>co-FIX-R338L</u>-Flank

AATTCACGCGTGGATCTGAATTCAATTCACGCGTGGTACGGCCGCGGGGGGGAGGCTGCTGGTGAATATTA
ACCAAGGTCACCCCAGTTATCGGAGGAGCAAACAGGGGCTAAGTCCACCGGGGGAGGCTGCTGGTGAATAT
TAACCAAGGTCACCCCAGTTATCGGAGGAGCAAACAGGGGCTAAGTCCACCGGGGGAGGCTGCTGGTGAAT
ATTAACCAAGGTCACCCCAGTTATCGGAGGAGCAAACAGGGGCTAAGTCCACGGTACC*CACTGGGAGGATG*
*TTGAGTAAGATGGAAAACTACTGATGACCCTTGCAGAGACAGAGTATTAGGACATGTTTGAACAGGGGCCG*
*GGCGATCAGCAGGTAG*CTCTAGAGGATCCCCGTCTGTCTGCACATTTCGTAGAGCGAGTGTTCCGATACTC
TAATCTCCCTAGGCAAGGTTCATATTTGTGTAGGTTACTTATTCTCCTTTTGTTGACTAAGTCAATAATCA
GAATCAGCAGGTTTGGAGTCAGCTTGGCAGGGATCAGCAGCCTGGGTTGGAAGGAGGGGTATAAAAGCCC
CTTCACCAGGAGAAGCCGTCACACAGATCCACAAGCTCCTGGCTAGA*AAGAGGTAAGGGTTTAAGGGATGG*
*TTGGTTGGTGGGGTATTAATGTTTAATTACCTGGAGCACCTGCCTGAAATCACTTTTTTTCAGGTTGG*GCT
AGCCCACCATGCAGCGCGTGAACATGATCATGGCCGAGAGCCCCGGCCTGATCACCATCTGCCTGCTGGGC
TACCTGCTGAGCGCCGAGTGCACCGTGTTCCTGGACCACGAGAACGCCAACAAGATCCTGAACCGCCCCAA
GCGCTACAACAGCGGCAAGCTGGAGGAGTTCGTGCAGGGCAACCTGGAGCGCGAGTGCATGGAGGAGAAGT
GCAGCTTCGAGGAGGCCCGCGAGGTGTTCGAGAACACCGAGCGCACCACCGAGTTCTGGAAGCAGTACGTG
GACGGCGACCAGTGCGAGAGCAACCCCTGCCTGAACGGCGGCAGCTGCAAGGACGACATCAACAGCTACGA
GTGCTGGTGCCCCTTCGGCTTCGAGGGCAAGAACTGCGAGCTGGACGTGACCTGCAACATCAAGAACGGCC
GCTGCGAGCAGTTCTGCAAGAACAGCGCCGACAACAAGGTGGTGTGCAGCTGCACCGAGGGCTACCGCCTG
GCCGAGAACCAGAAGAGCTGCGAGCCCGCCGTGCCCTTCCCCTGCGGCCGCGTGAGCGTGAGCCAGACCAG
CAAGCTGACCCGCGCCGAGGCCGTGTTCCCCGACGTGGACTACGTGAACAGCACCGAGGCCGAGACCATCC
TGGACAACATCACCCAGAGCACCCAGAGCTTCAACGACTTCACCCGCGTGGTGGGCGGCGAGGACGCCAAG
CCCGGCCAGTTCCCCTGGCAGGTGGTGCTGAACGGCAAGGTGGACGCCTTCTGCGGCGGCAGCATCGTGAA

Figure 13 (continued)

CGAGAAGTGGATCGTGACCGCCGCCCACTGCGTGGAGACCGGCGTGAAGATCACCGTGGTGGCCGGCGAGC
ACAACATCGAGGAGACCGAGCACACCGAGCAGAAGCGCAACGTGATCCGCATCATCCCCCACCACAACTAC
AACGCCGCCATCAACAAGTACAACCACGACATCGCCCTGCTGGAGCTGGACGAGCCCCTGGTGCTGAACAG
CTACGTGACCCCCATCTGCATCGCCGACAAGGAGTACACCAACATCTTCCTGAAGTTCGGCAGCGGCTACG
TGAGCGGCTGGGGCCGCGTGTTCCACAAGGGCCGCAGCGCCCTGGTGCTGCAGTACCTGCGCGTGCCCCTG
GTGGACCGCGCCACCTGCCTGCTGAGCACCAAGTTCACCATCTACAACAACATGTTCTGCGCCGGCTTCCA
CGAGGGCGGCCGCGACAGCTGCCAGGGCGACAGCGGCGGCCCCCACGTGACCGAGGTGGAGGGCACCAGCT
TCCTGACCGGCATCATCAGCTGGGGCGAGGAGTGCGCCATGAAGGGCAAGTACGGCATCTACACCAAGGTG
AGCCGCTACGTGAACTGGATCAAGGAGAAGACCAAGCTGACCTAATGAAAGATGGATTTCCAAGGTTAATT
CATTGGAATTGAAAATTAACAGCCCCCCCCCCCCCCCCTGCA

SEQ ID NO.34: Flank-<u>3xSERP</u>-Flank-*TTRe*-Flank-TTRm-Flank-*MVM*-Flank-<u>co-FIX-R338L</u>-Flank-BGHpA

AATTCACGCGTGGATCTGAATTCAATTCACGCGTGGTACGGCCGCGG<u>GGGGGAGGCTGCTGGTGAATATTA
ACCAAGGTCACCCCAGTTATCGGAGGAGCAAACAGGGGCTAAGTCCACCGGGGGAGGCTGCTGGTGAATAT
TAACCAAGGTCACCCCAGTTATCGGAGGAGCAAACAGGGGCTAAGTCCACCGGGGGAGGCTGCTGGTGAAT
ATTAACCAAGGTCACCCCAGTTATCGGAGGAGCAAACAGGGGCTAAGTCCAC</u>GGTACC*CACTGGGAGGATG
TTGAGTAAGATGGAAAACTACTGATGACCCTTGCAGAGACAGAGTATTAGGACATGTTTGAACAGGGGCCG
GGCGATCAGCAGGTAG*CTCTAGAGGATCCCCGTCTGTCTGCACATTTCGTAGAGCGAGTGTTCCGATACTC
TAATCTCCCTAGGCAAGGTTCATATTTGTGTAGGTTACTTATTCTCCTTTTGTTGACTAAGTCAATAATCA
GAATCAGCAGGTTTGGAGTCAGCTTGGCAGGGATCAGCAGCCTGGGTTGGAAGGAGGGGTATAAAAGCCC
CTTCACCAGGAGAAGCCGTCACACAGATCCACAAGCTCCTGGCTAGA*AAGAGGTAAGGGTTTAAGGGATGG
TTGGTTGGTGGGGTATTAATGTTTAATTACCTGGAGCACCTGCCTGAAATCACTTTTTTTCAGGTTGG***GCT
AGCCCACCATGCAGCGCGTGAACATGATCATGGCCGAGAGCCCCGGCCTGATCACCATCTGCCTGCTGGGC
TACCTGCTGAGCGCCGAGTGCACCGTGTTCCTGGACCACGAGAACGCCAACAAGATCCTGAACCGCCCCAA
GCGCTACAACAGCGGCAAGCTGGAGGAGTTCGTGCAGGGCAACCTGGAGCGCGAGTGCATGGAGGAGAAGT
GCAGCTTCGAGGAGGCCCGCGAGGTGTTCGAGAACACCGAGCGCACCACCGAGTTCTGGAAGCAGTACGTG
GACGGCGACCAGTGCGAGAGCAACCCCTGCCTGAACGGCGGCAGCTGCAAGGACGACATCAACAGCTACGA
GTGCTGGTGCCCCTTCGGCTTCGAGGGCAAGAACTGCGAGCTGGACGTGACCTGCAACATCAAGAACGGCC
GCTGCGAGCAGTTCTGCAAGAACAGCGCCGACAACAAGGTGGTGTGCAGCTGCACCGAGGGCTACCGCCTG
GCCGAGAACCAGAAGAGCTGCGAGCCCGCCGTGCCCTTCCCCTGCGGCCGCGTGAGCGTGAGCCAGACCAG
CAAGCTGACCCGCGCCGAGGCCGTGTTCCCCGACGTGGACTACGTGAACAGCACCGAGGCCGAGACCATCC
TGGACAACATCACCCAGAGCACCCAGAGCTTCAACGACTTCACCCGCGTGGTGGGCGGCGAGGACGCCAAG
CCCGGCCAGTTCCCCTGGCAGGTGGTGCTGAACGGCAAGGTGGACGCCTTCTGCGGCGGCAGCATCGTGAA
CGAGAAGTGGATCGTGACCGCCGCCCACTGCGTGGAGACCGGCGTGAAGATCACCGTGGTGGCCGGCGAGC
ACAACATCGAGGAGACCGAGCACACCGAGCAGAAGCGCAACGTGATCCGCATCATCCCCCACCACAACTAC
AACGCCGCCATCAACAAGTACAACCACGACATCGCCCTGCTGGAGCTGGACGAGCCCCTGGTGCTGAACAG
CTACGTGACCCCCATCTGCATCGCCGACAAGGAGTACACCAACATCTTCCTGAAGTTCGGCAGCGGCTACG
TGAGCGGCTGGGGCCGCGTGTTCCACAAGGGCCGCAGCGCCCTGGTGCTGCAGTACCTGCGCGTGCCCCTG
GTGGACCGCGCCACCTGCCTGCTGAGCACCAAGTTCACCATCTACAACAACATGTTCTGCGCCGGCTTCCA
CGAGGGCGGCCGCGACAGCTGCCAGGGCGACAGCGGCGGCCCCCACGTGACCGAGGTGGAGGGCACCAGCT
TCCTGACCGGCATCATCAGCTGGGGCGAGGAGTGCGCCATGAAGGGCAAGTACGGCATCTACACCAAGGTG
AGCCGCTACGTGAACTGGATCAAGGAGAAGACCAAGCTGACCTAATGAAAGATGGATTTCCAAGGTTAATT
CATTGGAATTGAAAATTAACAGCCCCCCCCCCCCCCCCTGCA**GATCTGAGCCGAATTCCTGCAGCCCGG
GGGATCAGCCTCGACTGTGCCTTCTAGTTGCCAGCCATCTGTTGTTTGCCCCTCCCCGTGCCTTCCTTGA
CCCTGGAAGGTGCCACTCCCACTGTCCTTTCCTAATAAAATGAGGAAATTGCATCGCATTGTCTGAGTAGG
TGTCATTCTATTCTGGGGGGTGGGGTGGGGCAGGACAGCAAGGGGGAGGATTGGGAAGACAATAGCAGGCA
TGCTGGGGATGCGGTGGGCTCTATGGCTTCTGAGGCGGAAAGAACCAGCTGGGGA

SEQ ID NO.35: Flank-<u>3xSERP</u>-Flank-*TTRe*-Flank-TTRm-Flank-*MVM*-Flank-<u>co-FIX-R338L</u>-Flank-BGHpA-Flank

AATTCACGCGTGGATCTGAATTCAATTCACGCGTGGTACGGCCGCGG<u>GGGGGAGGCTGCTGGTGAATATTA
ACCAAGGTCACCCCAGTTATCGGAGGAGCAAACAGGGGCTAAGTCCACCGGGGGAGGCTGCTGGTGAATAT</u>

Figure 13 (continued)

```
TAACCAAGGTCACCCCAGTTATCGGAGGAGCAAACAGGGGCTAAGTCCACCGGGGGAGGCTGCTGGTGAAT
ATTAACCAAGGTCACCCCAGTTATCGGAGGAGCAAACAGGGGCTAAGTCCACGGTACCCACTGGGAGGATG
TTGAGTAAGATGGAAAACTACTGATGACCCTTGCAGAGACAGAGTATTAGGACATGTTTGAACAGGGGCCG
GGCGATCAGCAGGTAGCTCTAGAGGATCCCCGTCTGTCTGCACATTTCGTAGAGCGAGTGTTCCGATACTC
TAATCTCCCTAGGCAAGGTTCATATTTGTGTAGGTTACTTATTCTCCTTTTGTTGACTAAGTCAATAATCA
GAATCAGCAGGTTTGGAGTCAGCTTGGCAGGGATCAGCAGCCTGGGTTGGAAGGAGGGGTATAAAAGCCC
CTTCACCAGGAGAAGCCGTCACACAGATCCACAAGCTCCTGGCTAGAAAGAGGTAAGGGTTTAAGGGATGG
TTGGTTGGTGGGGTATTAATGTTTAATTACCTGGAGCACCTGCCTGAAATCACTTTTTTTCAGGTTGGGCT
AGCCCACCATGCAGCGCGTGAACATGATCATGGCCGAGAGCCCCGGCCTGATCACCATCTGCCTGCTGGGC
TACCTGCTGAGCGCCGAGTGCACCGTGTTCCTGGACCACGAGAACGCCAACAAGATCCTGAACCGCCCCAA
GCGCTACAACAGCGGCAAGCTGGAGGAGTTCGTGCAGGGCAACCTGGAGCGCGAGTGCATGGAGGAGAAGT
GCAGCTTCGAGGAGGCCCGCGAGGTGTTCGAGAACACCGAGCGCACCACCGAGTTCTGGAAGCAGTACGTG
GACGGCGACCAGTGCGAGAGCAACCCCTGCCTGAACGGCGGCAGCTGCAAGGACGACATCAACAGCTACGA
GTGCTGGTGCCCCTTCGGCTTCGAGGGCAAGAACTGCGAGCTGGACGTGACCTGCAACATCAAGAACGGCC
GCTGCGAGCAGTTCTGCAAGAACAGCGCCGACAACAAGGTGGTGTGCAGCTGCACCGAGGGCTACCGCCTG
GCCGAGAACCAGAAGAGCTGCGAGCCCGCCGTGCCCTTCCCCTGCGGCCGCGTGAGCGTGAGCCAGACCAG
CAAGCTGACCCGCGCCGAGGCCGTGTTCCCCGACGTGGACTACGTGAACAGCACCGAGGCCGAGACCATCC
TGGACAACATCACCCAGAGCACCCAGAGCTTCAACGACTTCACCCGCGTGGTGGGCGGCGAGGACGCCAAG
CCCGGCCAGTTCCCCTGGCAGGTGGTGCTGAACGGCAAGGTGGACGCCTTCTGCGGCGGCAGCATCGTGAA
CGAGAAGTGGATCGTGACCGCCGCCCACTGCGTGGAGACCGGCGTGAAGATCACCGTGGTGGCCGGCGAGC
ACAACATCGAGGAGACCGAGCACACCGAGCAGAAGCGCAACGTGATCCGCATCATCCCCCACCACAACTAC
AACGCCGCCATCAACAAGTACAACCACGACATCGCCCTGCTGGAGCTGGACGAGCCCCTGGTGCTGAACAG
CTACGTGACCCCCATCTGCATCGCCGACAAGGAGTACACCAACATCTTCCTGAAGTTCGGCAGCGGCTACG
TGAGCGGCTGGGGCCGCGTGTTCCACAAGGGCCGCAGCGCCCTGGTGCTGCAGTACCTGCGCGTGCCCCTG
GTGGACCGCGCCACCTGCCTGCTGAGCACCAAGTTCACCATCTACAACAACATGTTCTGCGCCGGCTTCCA
CGAGGGCGGCCGCGACAGCTGCCAGGGCGACAGCGGCGGCCCCCACGTGACCGAGGTGGAGGGCACCAGCT
TCCTGACCGGCATCATCAGCTGGGGCGAGGAGTGCGCCATGAAGGGCAAGTACGGCATCTACACCAAGGTG
AGCCGCTACGTGAACTGGATCAAGGAGAAGACCAAGCTGACCTAATGAAAGATGGATTTCCAAGGTTAATT
CATTGGAATTGAAAATTAACAGCCCCCCCCCCCCCCCCTGCAGATCTGAGCCGAATTCCTGCAGCCCGG
GGGATCAGCCTCGACTGTGCCTTCTAGTTGCCAGCCATCTGTTGTTTGCCCCTCCCCCGTGCCTTCCTTGA
CCCTGGAAGGTGCCACTCCCACTGTCCTTTCCTAATAAAATGAGGAAATTGCATCGCATTGTCTGAGTAGG
TGTCATTCTATTCTGGGGGGTGGGGTGGGGCAGGACAGCAAGGGGGAGGATTGGGAAGACAATAGCAGGCA
TGCTGGGGATGCGGTGGGCTCTATGGCTTCTGAGGCGGAAAGAACCAGCTGGGACCGGTGGATCTCGATA
GCAGGCATGCTGGGGAGAGATCG
```

SEQ ID NO.36: Flank-<u>3xSERP</u>-Flank-*TTRe*-Flank-TTRm-Flank-*MVM*-Flank-<u>co-FIX-R338L</u>-Flank-Synt.pA

```
AATTCACGCGTGGATCTGAATTCAATTCACGCGTGGTACGGCCGCGGGGGGGAGGCTGCTGGTGAATATTA
ACCAAGGTCACCCCAGTTATCGGAGGAGCAAACAGGGGCTAAGTCCACCGGGGGAGGCTGCTGGTGAATAT
TAACCAAGGTCACCCCAGTTATCGGAGGAGCAAACAGGGGCTAAGTCCACCGGGGGAGGCTGCTGGTGAAT
ATTAACCAAGGTCACCCCAGTTATCGGAGGAGCAAACAGGGGCTAAGTCCACGGTACCCACTGGGAGGATG
TTGAGTAAGATGGAAAACTACTGATGACCCTTGCAGAGACAGAGTATTAGGACATGTTTGAACAGGGGCCG
GGCGATCAGCAGGTAGCTCTAGAGGATCCCCGTCTGTCTGCACATTTCGTAGAGCGAGTGTTCCGATACTC
TAATCTCCCTAGGCAAGGTTCATATTTGTGTAGGTTACTTATTCTCCTTTTGTTGACTAAGTCAATAATCA
GAATCAGCAGGTTTGGAGTCAGCTTGGCAGGGATCAGCAGCCTGGGTTGGAAGGAGGGGTATAAAAGCCC
CTTCACCAGGAGAAGCCGTCACACAGATCCACAAGCTCCTGGCTAGAAAGAGGTAAGGGTTTAAGGGATGG
TTGGTTGGTGGGGTATTAATGTTTAATTACCTGGAGCACCTGCCTGAAATCACTTTTTTTCAGGTTGGGCT
AGCCCACCATGCAGCGCGTGAACATGATCATGGCCGAGAGCCCCGGCCTGATCACCATCTGCCTGCTGGGC
TACCTGCTGAGCGCCGAGTGCACCGTGTTCCTGGACCACGAGAACGCCAACAAGATCCTGAACCGCCCCAA
GCGCTACAACAGCGGCAAGCTGGAGGAGTTCGTGCAGGGCAACCTGGAGCGCGAGTGCATGGAGGAGAAGT
GCAGCTTCGAGGAGGCCCGCGAGGTGTTCGAGAACACCGAGCGCACCACCGAGTTCTGGAAGCAGTACGTG
GACGGCGACCAGTGCGAGAGCAACCCCTGCCTGAACGGCGGCAGCTGCAAGGACGACATCAACAGCTACGA
GTGCTGGTGCCCCTTCGGCTTCGAGGGCAAGAACTGCGAGCTGGACGTGACCTGCAACATCAAGAACGGCC
GCTGCGAGCAGTTCTGCAAGAACAGCGCCGACAACAAGGTGGTGTGCAGCTGCACCGAGGGCTACCGCCTG
```

Figure 13 (continued)

GCCGAGAACCAGAAGAGCTGCGAGCCCGCCGTGCCCTTCCCCTGCGGCCGCGTGAGCGTGAGCCAGACCAG
CAAGCTGACCCGCGCCGAGGCCGTGTTCCCCGACGTGGACTACGTGAACAGCACCGAGGCCGAGACCATCC
TGGACAACATCACCCAGAGCACCCAGAGCTTCAACGACTTCACCCGCGTGGTGGGCGGCGAGGACGCCAAG
CCCGGCCAGTTCCCCTGGCAGGTGGTGCTGAACGGCAAGGTGGACGCCTTCTGCGGCGGCAGCATCGTGAA
CGAGAAGTGGATCGTGACCGCCGCCCACTGCGTGGAGACCGGCGTGAAGATCACCGTGGTGGCCGGCGAGC
ACAACATCGAGGAGACCGAGCACACCGAGCAGAAGCGCAACGTGATCCGCATCATCCCCCACCACAACTAC
AACGCCGCCATCAACAAGTACAACCACGACATCGCCCTGCTGGAGCTGGACGAGCCCCTGGTGCTGAACAG
CTACGTGACCCCCATCTGCATCGCCGACAAGGAGTACACCAACATCTTCCTGAAGTTCGGCAGCGGCTACG
TGAGCGGCTGGGGCCGCGTGTTCCACAAGGGCCGCAGCGCCCTGGTGCTGCAGTACCTGCGCGTGCCCCTG
GTGGACCGCGCCACCTGCCTGCTGAGCACCAAGTTCACCATCTACAACAACATGTTCTGCGCCGGCTTCCA
CGAGGGCGGCCGCGACAGCTGCCAGGGCGACAGCGGCGGCCCCCACGTGACCGAGGTGGAGGGCACCAGCT
TCCTGACCGGCATCATCAGCTGGGGCGAGGAGTGCGCCATGAAGGGCAAGTACGGCATCTACACCAAGGTG
AGCCGCTACGTGAACTGGATCAAGGAGAAGACCAAGCTGACCTAATGAAAGATGGATTTCCAAGGTTAATT
CATTGGAATTGAAAATTAACAGCCCCCCCCCCCCCCCCCTGCAAATAAAGATCTTTATTTTCATTAGAT
CTGTGTGTTGGTTTTTTGTGTG

SEQ ID NO.37: Flank-3xSERP-Flank-*TTRe*-Flank-TTRm-Flank-*MVM*-Flank-<u>co-</u>
<u>FIX-R338L</u>-Flank-Synt.pA-Flank

AATTCACGCGTGGATCTGAATTCAATTCACGCGTGGTACGGCCGCGGGGGGGAGGCTGCTGGTGAATATTA
ACCAAGGTCACCCCAGTTATCGGAGGAGCAAACAGGGGCTAAGTCCACCGGGGGAGGCTGCTGGTGAATAT
TAACCAAGGTCACCCCAGTTATCGGAGGAGCAAACAGGGGCTAAGTCCACCGGGGGAGGCTGCTGGTGAAT
ATTAACCAAGGTCACCCCAGTTATCGGAGGAGCAAACAGGGGCTAAGTCCACGGTACC*CACTGGGAGGATG*
*TTGAGTAAGATGGAAAACTACTGATGACCCTTGCAGAGACAGAGTATTAGGACATGTTTGAACAGGGGCCG*
*GGCGATCAGCAGGTAG*CTCTAGAGGATCCCCGTCTGTCTGCACATTTCGTAGAGCGAGTGTTCCGATACTC
TAATCTCCCTAGGCAAGGTTCATATTTGTGTAGGTTACTTATTCTCCTTTTGTTGACTAAGTCAATAATCA
GAATCAGCAGGTTTGGAGTCAGCTTGGCAGGGATCAGCAGCCTGGGTTGGAAGGAGGGGGTATAAAAGCCC
CTTCACCAGGAGAAGCCGTCACACAGATCCACAAGCTCCTGGCTAGA*AAGAGGTAAGGGTTTAAGGGATGG*
*TTGGTTGGTGGGGTATTAATGTTTAATTACCTGGAGCACCTGCCTGAAATCACTTTTTTTCAGGTTGG*GCT
AGCCCACCATGCAGCGCGTGAACATGATCATGGCCGAGAGCCCCGGCCTGATCACCATCTGCCTGCTGGGC
TACCTGCTGAGCGCCGAGTGCACCGTGTTCCTGGACCACGAGAACGCCAACAAGATCCTGAACCGCCCCAA
GCGCTACAACAGCGGCAAGCTGGAGGAGTTCGTGCAGGGCAACCTGGAGCGCGAGTGCATGGAGGAGAAGT
GCAGCTTCGAGGAGGCCCGCGAGGTGTTCGAGAACACCGAGCGCACCACCGAGTTCTGGAAGCAGTACGTG
GACGGCGACCAGTGCGAGAGCAACCCCTGCCTGAACGGCGGCAGCTGCAAGGACGACATCAACAGCTACGA
GTGCTGGTGCCCCTTCGGCTTCGAGGGCAAGAACTGCGAGCTGGACGTGACCTGCAACATCAAGAACGGCC
GCTGCGAGCAGTTCTGCAAGAACAGCGCCGACAACAAGGTGGTGTGCAGCTGCACCGAGGGCTACCGCCTG
GCCGAGAACCAGAAGAGCTGCGAGCCCGCCGTGCCCTTCCCCTGCGGCCGCGTGAGCGTGAGCCAGACCAG
CAAGCTGACCCGCGCCGAGGCCGTGTTCCCCGACGTGGACTACGTGAACAGCACCGAGGCCGAGACCATCC
TGGACAACATCACCCAGAGCACCCAGAGCTTCAACGACTTCACCCGCGTGGTGGGCGGCGAGGACGCCAAG
CCCGGCCAGTTCCCCTGGCAGGTGGTGCTGAACGGCAAGGTGGACGCCTTCTGCGGCGGCAGCATCGTGAA
CGAGAAGTGGATCGTGACCGCCGCCCACTGCGTGGAGACCGGCGTGAAGATCACCGTGGTGGCCGGCGAGC
ACAACATCGAGGAGACCGAGCACACCGAGCAGAAGCGCAACGTGATCCGCATCATCCCCCACCACAACTAC
AACGCCGCCATCAACAAGTACAACCACGACATCGCCCTGCTGGAGCTGGACGAGCCCCTGGTGCTGAACAG
CTACGTGACCCCCATCTGCATCGCCGACAAGGAGTACACCAACATCTTCCTGAAGTTCGGCAGCGGCTACG
TGAGCGGCTGGGGCCGCGTGTTCCACAAGGGCCGCAGCGCCCTGGTGCTGCAGTACCTGCGCGTGCCCCTG
GTGGACCGCGCCACCTGCCTGCTGAGCACCAAGTTCACCATCTACAACAACATGTTCTGCGCCGGCTTCCA
CGAGGGCGGCCGCGACAGCTGCCAGGGCGACAGCGGCGGCCCCCACGTGACCGAGGTGGAGGGCACCAGCT
TCCTGACCGGCATCATCAGCTGGGGCGAGGAGTGCGCCATGAAGGGCAAGTACGGCATCTACACCAAGGTG
AGCCGCTACGTGAACTGGATCAAGGAGAAGACCAAGCTGACCTAATGAAAGATGGATTTCCAAGGTTAATT
CATTGGAATTGAAAATTAACAGCCCCCCCCCCCCCCCCCTGCAAATAAAGATCTTTATTTTCATTAGAT
CTGTGTGTTGGTTTTTTGTGTGCCGGTGGATCTCGATAGCAGGCATGCTGGGGAGAGATCG

Figure 14

SEQ ID NO.14: pAAVss-TTRm-MVM-coFVIIIdeltaB-Sv40pA

CCTGCAGGCAGCTGCGCGCTCGCTCGCTCACTGAGGCCGCCCGGGCAAAGCCCGGGCGTCGGGCGACCTTT
GGTCGCCCGGCCTCAGTGAGCGAGCGAGCGCGCAGAGAGGGAGTGGCCAACTCCATCACTAGGGGTTCCTG
CGGCCGCGGTACCGTCTGTCTGCACATTTCGTAGAGCGAGTGTTCCGATACTCTAATCTCCCTAGGCAAGG
TTCATATTTGTGTAGGTTACTTATTCTCCTTTTGTTGACTAAGTCAATAATCAGAATCAGCAGGTTTGGAG
TCAGCTTGGCAGGGATCAGCAGCCTGGGTTGGAAGGAGGGGGTATAAAAGCCCCTTCACCAGGAGAAGCCG
TCACACAGATCCACAAGCTCCTGAAGAGGTAAGGGTTTAAGGGATGGTTGGTTGGTGGGGTATTAATGTTT
AATTACCTGGAGCACCTGCCTGAAATCACTTTTTTTCAGGTTGGCTAGTATGCAGATCGAGCTGTCCACCT
GCTTTTTTCTGTGCCTGCTGCGGTTCTGCTTCAGCGCCACCCGGCGGTACTACCTGGGCGCCGTGGAGCTG
TCCTGGGACTACATGCAGAGCGACCTGGGCGAGCTGCCCGTGGACGCCCGGTTCCCCCCAGAGTGCCCAA
GAGCTTCCCCTTCAACACCAGCGTGGTGTACAAGAAAACCCTGTTCGTGGAGTTCACCGACCACCTGTTCA
ATATCGCCAAGCCCAGGCCCCCCTGGATGGGCCTGCTGGGCCCCACCATCCAGGCCGAGGTGTACGACACC
GTGGTGATCACCCTGAAGAACATGGCCAGCCACCCCGTGAGCCTGCACGCCGTGGGCGTGAGCTACTGGAA
GGCCAGCGAGGGCGCCGAGTACGACGACCAGACCAGCCAGCGGGAGAAAGAAGATGACAAGGTGTTCCCTG
GCGGCAGCCACACCTACGTGTGGCAGGTGCTGAAAGAAAACGGCCCCATGGCCTCCGACCCCCTGTGCCTG
ACCTACAGCTACCTGAGCCACGTGGACCTGGTGAAGGACCTGAACAGCGGCCTGATCGGCGCTCTGCTCGT
CTGCCGGGAGGGCAGCCTGGCCAAAGAGAAAACCCAGACCCTGCACAAGTTCATCCTGCTGTTCGCCGTGT
TCGACGAGGGCAAGAGCTGGCACAGCGAGACAAAGAACAGCCTGATGCAGGACCGGGACGCCGCCTCTGCC
AGAGCCTGGCCCAAGATGCACACCGTGAACGGCTACGTGAACAGAAGCCTGCCCGGCCTGATTGGCTGCCA
CCGGAAGAGCGTGTACTGGCACGTGATCGGCATGGGCACCACACCCGAGGTGCACAGCATCTTTCTGGAAG
GGCACACCTTTCTGGTCCGGAACCACCGGCAGGCCAGCCTGGAAATCAGCCCTATCACCTTCCTGACCGCC
CAGACACTGCTGATGGACCTGGGCCAGTTCCTGCTGTTTTGCCACATCAGCTCTCACCAGCACGACGGCAT
GGAAGCCTACGTGAAGGTGGACTCTTGCCCCGAGGAACCCCAGCTGCGGATGAAGAACAACGAGGAAGCCG
AGGACTACGACGACGACCTGACCGACAGCGAGATGGACGTGGTGCGGTTCGACGACGACAACAGCCCCAGC
TTCATCCAGATCAGAAGCGTGGCCAAGAAGCACCCCAAGACCTGGGTGCACTATATCGCCGCCGAGGAAGA
GGACTGGGACTACGCCCCCCTGGTGCTGGCCCCGACGACAGAAGCTACAAGAGCCAGTACCTGAACAATG
GCCCCCAGCGGATCGGCCGGAAGTACAAGAAAGTGCGGTTCATGGCCTACACCGACGAGACATTCAAGACC
CGGGAGGCCATCCAGCACGAGAGCGGCATCCTGGGCCCCCTGCTGTACGGCGAAGTGGGCGACACACTGCT
GATCATCTTCAAGAACCAGGCTAGCCGGCCCTACAACATCTACCCCACGGCATCACCGACGTGCGGCCCC
TGTACAGCAGGCGGCTGCCCAAGGGCGTGAAGCACCTGAAGGACTTCCCCATCCTGCCCGGCGAGATCTTC
AAGTACAAGTGGACCGTGACCGTGGAGGACGGCCCCACCAAGAGCGACCCCAGATGCCTGACCCGGTACTA
CAGCAGCTTCGTGAACATGGAACGGGACCTGGCCTCCGGGCTGATCGGACCTCTGCTGATCTGCTACAAAG
AAAGCGTGGACCAGCGGGGCAACCAGATCATGAGCGACAAGCGGAACGTGATCCTGTTCAGCGTGTTCGAT
GAGAACCGGTCCTGGTATCTGACCGAGAACATCCAGCGGTTTCTGCCCAACCCTGCCGGCGTGCAGCTGGA
AGATCCCGAGTTCCAGGCCAGCAACATCATGCACTCCATCAATGGCTACGTGTTCGACTCTCTGCAGCTCT
CCGTGTGTCTGCACGAGGTGGCCTACTGGTACATCCTGAGCATCGGCGCCCAGACCGACTTCCTGAGCGTG
TTCTTCAGCGGCTACACCTTCAAGCACAAGATGGTGTACGAGGACACCCTGACCCTGTTCCCTTTCAGCGG
CGAGACAGTGTTCATGAGCATGGAAAACCCCGGCCTGTGGATTCTGGGCTGCCACAACAGCGACTTCCGGA
ACCGGGGCATGACCGCCCTGCTGAAGGTGTCCAGCTGCGACAAGAACACCGGCGACTACTACGAGGACAGC
TACGAGGATATCAGCGCCTACCTGCTGTCCAAGAACAACGCCATCGAACCCCGGAGCTTCAGCCAGAACCC
CCCCGTGCTGACGCGTCACCAGCGGGAGATCACCCGGACAACCCTGCAGTCCGACCAGGAAGAGATCGATT
ACGACGACACCATCAGCGTGGAGATGAAGAAGAGGATTTCGATATCTACGACGAGGACGAGAACCAGAGC
CCCAGAAGCTTCCAGAAGAAAACCCGGCACTACTTCATTGCCGCCGTGGAGAGGCTGTGGGACTACGGCAT
GAGTTCTAGCCCCCACGTGCTGCGGAACCGGGCCCAGAGCGGCAGCGTGCCCCAGTTCAAGAAAGTGGTGT
TCCAGGAATTCACAGACGGCAGCTTCACCCAGCCTCTGTATAGAGGCGAGCTGAACGAGCACCTGGGGCTG
CTGGGGCCCTACATCAGGGCCGAAGTGGAGGACAACATCATGGTGACCTTCCGGAATCAGGCCAGCAGACC
CTACTCCTTCTACAGCAGCCTGATCAGCTACGAAGAGGACCAGCGGCAGGGCGCCGAACCCCGGAAGAACT
TCGTGAAGCCCAACGAAACCAAGACCTACTTCTGGAAAGTGCAGCACCACATGGCCCCCACCAAGGACGAG
TTCGACTGCAAGGCCTGGGCCTACTTCAGCGACGTGGATCTGGAAAAGGACGTGCACTCTGGACTGATTGG
CCCACTCCTGGTCTGCCACACTAACACCCTCAACCCCGCCCACGGCCGCCAGGTGACCGTGCAGGAATTCG
CCCTGTTCTTCACCATCTTCGACGAGACAAAGTCCTGGTACTTCACCGAGAATATGGAACGGAACTGCAGA
GCCCCCTGCAACATCCAGATGGAAGATCCTACCTTCAAAGAGAACTACCGGTTCCACGCCATCAACGGCTA

Figure 14 (continued)

```
CATCATGGACACCCTGCCTGGCCTGGTGATGGCCCAGGACCAGAGAATCCGGTGGTATCTGCTGTCCATGG
GCAGCAACGAGAATATCCACAGCATCCACTTCAGCGGCCACGTGTTCACCGTGCGGAAGAAAGAAGAGTAC
AAGATGGCCCTGTACAACCTGTACCCCGGCGTGTTCGAGACAGTGGAGATGCTGCCCAGCAAGGCCGGCAT
CTGGCGGGTGGAGTGTCTGATCGGCGAGCACCTGCACGCTGGCATGAGCACCCTGTTTCTGGTGTACAGCA
ACAAGTGCCAGACCCCACTGGGCATGGCCTCTGGCCACATCCGGGACTTCCAGATCACCGCCTCCGGCCAG
TACGGCCAGTGGGCCCCCAAGCTGGCCAGACTGCACTACAGCGGCAGCATCAACGCCTGGTCCACCAAAGA
GCCCTTCAGCTGGATCAAGGTGGACCTGCTGGCCCCTATGATCATCCACGGCATTAAGACCCAGGGCGCCA
GGCAGAAGTTCAGCAGCCTGTACATCAGCCAGTTCATCATCATGTACAGCCTGGACGGCAAGAAGTGGCAG
ACCTACCGGGGCAACAGCACCGGCACCCTGATGGTGTTCTTCGGCAATGTGGACAGCAGCGGCATCAAGCA
CAACATCTTCAACCCCCCCATCATTGCCCGGTACATCCGGCTGCACCCCACCCACTACAGCATTAGATCCA
CACTGAGAATGGAACTGATGGGCTGCGACCTGAACTCCTGCAGCATGCCTCTGGGCATGGAAAGCAAGGCC
ATCAGCGACGCCCAGATCACAGCCAGCAGCTACTTCACCAACATGTTCGCCACCTGGTCCCCCTCCAAGGC
CAGGCTGCACCTGCAGGGCCGGTCCAACGCCTGGCGGCCTCAGGTCAACAACCCCAAAGAATGGCTGCAGG
TGGACTTTCAGAAAACCATGAAGGTGACCGGCGTGACCACCCAGGGCGTGAAAAGCCTGCTGACCAGCATG
TACGTGAAAGAGTTTCTGATCAGCAGCTCTCAGGATGGCCACCAGTGGACCCTGTTCTTTCAGAACGGCAA
GGTGAAAGTGTTCCAGGGCAACCAGGACTCCTTCACCCCCGTGGTGAACTCCCTGGACCCCCCCCTGCTGA
CCCGCTACCTGAGAATCCACCCCCAGTCTTGGGTGCACCAGATCGCCCTCAGGATGGAAGTCCTGGGATGT
GAGGCCCAGGATCTGTACTGATGAGGATCTAGGCTCGACATGCTTTATTTGTGAAATTTGTGATGCTATTG
CTTTATTTGTAACCATTATAAGCTGCAATAAACAAGTTAACAACAACAATTGCATTCATTTTATGTTTCAG
GTTCAGGGGGAGGTGTGGGAGGTTTTTTAAACTCGAGATCCACGGCCGCAGGAACCCCTAGTGATGGAGTT
GGCCACTCCCTCTCTGCGCGCTCGCTCGCTCACTGAGGCCGGGCGACCAAAGGTCGCCCGACGCCCGGGCT
TTGCCCGGGCGGCCTCAGTGAGCGAGCGAGCGCGCAGCTGCCTGCAGGGGCGCCTGATGCGGTATTTTCTC
CTTACGCATCTGTGCGGTATTTCACACCGCATACGTCAAAGCAACCATAGTACGCGCCCTGTAGCGGCGCA
TTAAGCGCGGCGGGTGTGGTGGTTACGCGCAGCGTGACCGCTACACTTGCCAGCGCCCTAGCGCCCGCTCC
TTTCGCTTTCTTCCCTTCCTTTCTCGCCACGTTCGCCGGCTTTCCCCGTCAAGCTCTAAATCGGGGCTCC
CTTTAGGGTTCCGATTTAGTGCTTTACGGCACCTCGACCCCAAAAAACTTGATTTGGGTGATGGTTCACGT
AGTGGGCCATCGCCCTGATAGACGGTTTTTCGCCCTTTGACGTTGGAGTCCACGTTCTTTAATAGTGGACT
CTTGTTCCAAACTGGAACAACACTCAACCCTATCTCGGGCTATTCTTTTGATTTATAAGGGATTTTGCCGA
TTTCGGCCTATTGGTTAAAAAATGAGCTGATTTAACAAAAATTTAACGCGAATTTTAACAAAATATTAACG
TTTACAATTTTATGGTGCACTCTCAGTACAATCTGCTCTGATGCCGCATAGTTAAGCCAGCCCCGACACCC
GCCAACACCCGCTGACGCGCCCTGACGGGCTTGTCTGCTCCCGGCATCCGCTTACAGACAAGCTGTGACCG
TCTCCGGGAGCTGCATGTGTCAGAGGTTTTCACCGTCATCACCGAAACGCGCGAGACGAAAGGGCCTCGTG
ATACGCCTATTTTTATAGGTTAATGTCATGATAATAATGGTTTCTTAGACGTCAGGTGGCACTTTTCGGGG
AAATGTGCGCGGAACCCCTATTTGTTTATTTTTCTAAATACATTCAAATATGTATCCGCTCATGAGACAAT
AACCCTGATAAATGCTTCAATAATATTGAAAAAGGAAGAGTATGAGTATTCAACATTTCCGTGTCGCCCTT
ATTCCCTTTTTTGCGGCATTTTGCCTTCCTGTTTTTGCTCACCCAGAAACGCTGGTGAAAGTAAAAGATGC
TGAAGATCAGTTGGGTGCACGAGTGGGTTACATCGAACTGGATCTCAACAGCGGTAAGATCCTTGAGAGTT
TTCGCCCCGAAGAACGTTTTCCAATGATGAGCACTTTTAAAGTTCTGCTATGTGGCGCGGTATTATCCCGT
ATTGACGCCGGGCAAGAGCAACTCGGTCGCCGCATACACTATTCTCAGAATGACTTGGTTGAGTACTCACC
AGTCACAGAAAAGCATCTTACGGATGGCATGACAGTAAGAGAATTATGCAGTGCTGCCATAACCATGAGTG
ATAACACTGCGGCCAACTTACTTCTGACAACGATCGGAGGACCGAAGGAGCTAACCGCTTTTTGCACAAC
ATGGGGGATCATGTAACTCGCCTTGATCGTTGGGAACCGGAGCTGAATGAAGCCATACCAAACGACGAGCG
TGACACCACGATGCCTGTAGCAATGGCAACAACGTTGCGCAAACTATTAACTGGCGAACTACTTACTCTAG
CTTCCCGGCAACAATTAATAGACTGGATGGAGGCGGATAAAGTTGCAGGACCACTTCTGCGCTCGGCCCTT
CCGGCTGGCTGGTTTATTGCTGATAAATCTGGAGCCGGTGAGCGTGGGTCTCGCGGTATCATTGCAGCACT
GGGGCCAGATGGTAAGCCCTCCCGTATCGTAGTTATCTACACGACGGGGAGTCAGGCAACTATGGATGAAC
GAAATAGACAGATCGCTGAGATAGGTGCCTCACTGATTAAGCATTGGTAACTGTCAGACCAAGTTTACTCA
TATATACTTTAGATTGATTTAAAACTTCATTTTTAATTTAAAAGGATCTAGGTGAAGATCCTTTTTGATAA
TCTCATGACCAAAATCCCTTAACGTGAGTTTTCGTTCCACTGAGCGTCAGACCCCGTAGAAAGATCAAAG
GATCTTCTTGAGATCCTTTTTTTCTGCGCGTAATCTGCTGCTTGCAAACAAAAAAACCACCGCTACCAGCG
GTGGTTTGTTTGCCGGATCAAGAGCTACCAACTCTTTTTCCGAAGGTAACTGGCTTCAGCAGAGCGCAGAT
ACCAAATACTGTCCTTCTAGTGTAGCCGTAGTTAGGCCACCACTTCAAGAACTCTGTAGCACCGCCTACAT
ACCTCGCTCTGCTAATCCTGTTACCAGTGGCTGCTGCCAGTGGCGATAAGTCGTGTCTTACCGGGTTGGAC
TCAAGACGATAGTTACCGGATAAGGCGCAGCGGTCGGGCTGAACGGGGGGTTCGTGCACACAGCCCAGCTT
GGAGCGAACGACCTACACCGAACTGAGATACCTACAGCGTGAGCTATGAGAAAGCGCCACGCTTCCCGAAG
```

Figure 14 (continued)

```
GGAGAAAGGCGGACAGGTATCCGGTAAGCGGCAGGGTCGGAACAGGAGAGCGCACGAGGGAGCTTCCAGGG
GGAAACGCCTGGTATCTTTATAGTCCTGTCGGGTTTCGCCACCTCTGACTTGAGCGTCGATTTTTGTGATG
CTCGTCAGGGGGGCGGAGCCTATGGAAAAACGCCAGCAACGCGGCCTTTTTACGGTTCCTGGCCTTTTGCT
GGCCTTTTGCTCACATGT

SEQ ID NO.15: pAAVss-SerpEnh-TTRm-MVM-coFVIIIdeltaB-Sv40pA

CCTGCAGGCAGCTGCGCGCTCGCTCGCTCACTGAGGCCGCCCGGGCAAAGCCCGGGCGTCGGGCGACCTTT
GGTCGCCCGGCCTCAGTGAGCGAGCGAGCGCGCAGAGAGGGAGTGGCCAACTCCATCACTAGGGGTTCCTG
CGGCCGCGGTACCGGCGCGCCGGGGGAGGCTGCTGGTGAATATTAACCAAGGTCACCCCAGTTATCGGAGG
AGCAAACAGGGGCTAAGTCCACACGCGTGGTACCGTCTGTCTGCACATTTCGTAGAGCGAGTGTTCCGATA
CTCTAATCTCCCTAGGCAAGGTTCATATTTGTGTAGGTTACTTATTCTCCTTTTGTTGACTAAGTCAATAA
TCAGAATCAGCAGGTTTGGAGTCAGCTTGGCAGGGATCAGCAGCCTGGGTTGGAAGGAGGGGGTATAAAAG
CCCCTTCACCAGGAGAAGCCGTCACACAGATCCACAAGCTCCTGAAGAGGTAAGGGTTTAAGGGATGGTTG
GTTGGTGGGGTATTAATGTTTAATTACCTGGAGCACCTGCCTGAAATCACTTTTTTTCAGGTTGGCTAGTA
TGCAGATCGAGCTGTCCACCTGCTTTTTTCTGTGCCTGCTGCGGTTCTGCTTCAGCGCCACCGGCGGTAC
TACCTGGGCGCCGTGGAGCTGTCCTGGGACTACATGCAGAGCGACCTGGGCGAGCTGCCCGTGGACGCCCG
GTTCCCCCCCAGAGTGCCCAAGAGCTTCCCCTTCAACACCAGCGTGGTGTACAAGAAAACCCTGTTCGTGG
AGTTCACCGACCACCTGTTCAATATCGCCAAGCCCAGGCCCCCCTGGATGGGCCTGCTGGGCCCCACCATC
CAGGCCGAGGTGTACGACACCGTGGTGATCACCCTGAAGAACATGGCCAGCCACCCCGTGAGCCTGCACGC
CGTGGGCGTGAGCTACTGGAAGGCCAGCGAGGGCGCCGAGTACGACGACCAGACCAGCCAGCGGGAGAAAG
AAGATGACAAGGTGTTCCCTGGCGGCAGCCACACCTACGTGTGGCAGGTGCTGAAAGAAAACGGCCCCATG
GCCTCCGACCCCCTGTGCCTGACCTACAGCTACCTGAGCCACGTGGACCTGGTGAAGGACCTGAACAGCGG
CCTGATCGGCGCTCTGCTCGTCTGCCGGGAGGGCAGCCTGGCCAAAGAGAAAACCCAGACCCTGCACAAGT
TCATCCTGCTGTTCGCCGTGTTCGACGAGGGCAAGAGCTGGCACAGCGAGACAAAGAACAGCCTGATGCAG
GACCGGGACGCCGCCTCTGCCAGAGCCTGGCCCAAGATGCACACCGTGAACGGCTACGTGAACAGAAGCCT
GCCCGGCCTGATTGGCTGCCACCGGAAGAGCGTGTACTGGCACGTGATCGGCATGGGCACCACACCCGAGG
TGCACAGCATCTTTCTGGAAGGGCACACCTTTCTGGTCCGGAACCACCGGCAGGCCAGCCTGGAAATCAGC
CCTATCACCTTCCTGACCGCCCAGACACTGCTGATGGACCTGGGCCAGTTCCTGCTGTTTTGCCACATCAG
CTCTCACCAGCACGACGGCATGGAAGCCTACGTGAAGGTGGACTCTTGCCCCGAGGAACCCCAGCTGCGGA
TGAAGAACAACGAGGAAGCCGAGGACTACGACGACGACCTGACCGACAGCGAGATGGACGTGGTGCGGTTC
GACGACGACAACAGCCCCAGCTTCATCCAGATCAGAAGCGTGGCCAAGAAGCACCCCAAGACCTGGGTGCA
CTATATCGCCGCCGAGGAAGAGGACTGGGACTACGCCCCCCTGGTGCTGGCCCCGACGACAGAAGCTACA
AGAGCCAGTACCTGAACAATGGCCCCCAGCGGATCGGCCGGAAGTACAAGAAAGTGCGGTTCATGGCCTAC
ACCGACGAGACATTCAAGACCCGGGAGGCCATCCAGCACGAGAGCGGCATCCTGGGCCCCCTGCTGTACGG
CGAAGTGGGCGACACACTGCTGATCATCTTCAAGAACCAGGCTAGCCGGCCCTACAACATCTACCCCCACG
GCATCACCGACGTGCGGCCCCTGTACAGCAGGCGGCTGCCCAAGGGCGTGAAGCACCTGAAGGACTTCCCC
ATCCTGCCCGGCGAGATCTTCAAGTACAAGTGGACCGTGACCGTGGAGGACGGCCCCACCAAGAGCGACCC
CAGATGCCTGACCCGGTACTACAGCAGCTTCGTGAACATGGAACGGGACCTGGCCTCCGGGCTGATCGGAC
CTCTGCTGATCTGCTACAAAGAAAGCGTGGACCAGCGGGGCAACCAGATCATGAGCGACAAGCGGAACGTG
ATCCTGTTCAGCGTGTTCGATGAGAACCGGTCCTGGTATCTGACCGAGAACATCCAGCGGTTTCTGCCCAA
CCCTGCCGGCGTGCAGCTGGAAGATCCCGAGTTCCAGGCCAGCAACATCATGCACTCCATCAATGGCTACG
TGTTCGACTCTCTGCAGCTCTCCGTGTGTCTGCACGAGGTGGCCTACTGGTACATCCTGAGCATCGGCGCC
CAGACCGACTTCCTGAGCGTGTTCTTCAGCGGCTACACCTTCAAGCACAAGATGGTGTACGAGGACACCCT
GACCCTGTTCCCTTTCAGCGGCGAGACAGTGTTCATGAGCATGGAAAACCCCGGCCTGTGGATTCTGGGCT
GCCACAACAGCGACTTCCGGAACCGGGGCATGACCGCCCTGCTGAAGGTGTCCAGCTGCGACAAGAACACC
GGCGACTACTACGAGGACAGCTACGAGGATATCAGCGCCTACCTGCTGTCCAAGAACAACGCCATCGAACC
CCGGAGCTTCAGCCAGAACCCCCCGTGCTGACGCGTCACCAGCGGGAGATCACCCGGACAACCCTGCAGT
CCGACCAGGAAGAGATCGATTACGACGACACCATCAGCGTGGAGATGAAGAAAGAGGATTTCGATATCTAC
GACGAGGACGAGAACCAGAGCCCCAGAAGCTTCCAGAAGAAAACCCGGCACTACTTCATTGCCGCCGTGGA
GAGGCTGTGGGACTACGGCATGAGTTCTAGCCCCCACGTGCTGCGGAACCGGGCCCAGAGCGGCAGCGTGC
CCCAGTTCAAGAAAGTGGTGTTCCAGGAATTCACAGACGGCAGCTTCACCCAGCCTCTGTATAGAGGCGAG
CTGAACGAGCACCTGGGGCTGCTGGGGCCCTACATCAGGGCCGAAGTGGAGGACAACATCATGGTGACCTT
CCGGAATCAGGCCAGCAGACCCTACTCCTTCTACAGCAGCCTGATCAGCTACGAAGAGGACCAGCGGCAGG
GCGCCGAACCCCGGAAGAACTTCGTGAAGCCCAACGAAACCAAGACCTACTTCTGGAAAGTGCAGCACCAC
```

Figure 14 (continued)

```
ATGGCCCCCACCAAGGACGAGTTCGACTGCAAGGCCTGGGCCTACTTCAGCGACGTGGATCTGGAAAAGGA
CGTGCACTCTGGACTGATTGGCCCACTCCTGGTCTGCCACACTAACACCCTCAACCCCGCCCACGGCCGCC
AGGTGACCGTGCAGGAATTCGCCCTGTTCTTCACCATCTTCGACGAGACAAAGTCCTGGTACTTCACCGAG
AATATGGAACGGAACTGCAGAGCCCCTGCAACATCCAGATGGAAGATCCTACCTTCAAAGAGAACTACCG
GTTCCACGCCATCAACGGCTACATCATGGACACCCTGCCTGGCCTGGTGATGGCCCAGGACCAGAGAATCC
GGTGGTATCTGCTGTCCATGGGCAGCAACGAGAATATCCACAGCATCCACTTCAGCGGCCACGTGTTCACC
GTGCGGAAGAAAGAAGAGTACAAGATGGCCCTGTACAACCTGTACCCCGGCGTGTTCGAGACAGTGGAGAT
GCTGCCCAGCAAGGCCGGCATCTGGCGGGTGGAGTGTCTGATCGGCGAGCACCTGCACGCTGGCATGAGCA
CCCTGTTTCTGGTGTACAGCAACAAGTGCCAGACCCCACTGGGCATGGCCTCTGGCCACATCCGGGACTTC
CAGATCACCGCCTCCGGCCAGTACGGCCAGTGGGCCCCCAAGCTGGCCAGACTGCACTACAGCGGCAGCAT
CAACGCCTGGTCCACCAAAGAGCCCTTCAGCTGGATCAAGGTGGACCTGCTGGCCCCTATGATCATCCACG
GCATTAAGACCCAGGGCGCCAGGCAGAAGTTCAGCAGCCTGTACATCAGCCAGTTCATCATCATGTACAGC
CTGGACGGCAAGAAGTGGCAGACCTACCGGGGCAACAGCACCGGCACCCTGATGGTGTTCTTCGGCAATGT
GGACAGCAGCGGCATCAAGCACAACATCTTCAACCCCCCCATCATTGCCCGGTACATCCGGCTGCACCCCA
CCCACTACAGCATTAGATCCACACTGAGAATGGAACTGATGGGCTGCGACCTGAACTCCTGCAGCATGCCT
CTGGGCATGGAAAGCAAGGCCATCAGCGACGCCCAGATCACAGCCAGCAGCTACTTCACCAACATGTTCGC
CACCTGGTCCCCCTCCAAGGCCAGGCTGCACCTGCAGGGCCGGTCCAACGCCTGGCGGCCTCAGGTCAACA
ACCCCAAAGAATGGCTGCAGGTGGACTTTCAGAAAACCATGAAGGTGACCGGCGTGACCACCCAGGGCGTG
AAAAGCCTGCTGACCAGCATGTACGTGAAAGAGTTTCTGATCAGCAGCTCTCAGGATGGCCACCAGTGGAC
CCTGTTCTTTCAGAACGGCAAGGTGAAAGTGTTCCAGGGCAACCAGGACTCCTTCACCCCCGTGGTGAACT
CCCTGGACCCCCCCCTGCTGACCCGCTACCTGAGAATCCACCCCCAGTCTTGGGTGCACCAGATCGCCCTC
AGGATGGAAGTCCTGGGATGTGAGGCCCAGGATCTGTACTGATGAGGATCTAGGCTCGACATGCTTTATTT
GTGAAATTTGTGATGCTATTGCTTTATTTGTAACCATTATAAGCTGCAATAAACAAGTTAACAACAACAAT
TGCATTCATTTTATGTTTCAGGTTCAGGGGGAGGTGTGGGAGGTTTTTTAAACTCGAGATCCACGGCCGCA
GGAACCCCTAGTGATGGAGTTGGCCACTCCCTCTCTGCGCGCTCGCTCGCTCACTGAGGCCGGGCGACCAA
AGGTCGCCCGACGCCCGGGCTTTGCCCGGGCGGCCTCAGTGAGCGAGCGAGCGCGCAGCTGCCTGCAGGGG
CGCCTGATGCGGTATTTTCTCCTTACGCATCTGTGCGGTATTTCACACCGCATACGTCAAAGCAACCATAG
TACGCGCCCTGTAGCGGCGCATTAAGCGCGGCGGGTGTGGTGGTTACGCGCAGCGTGACCGCTACACTTGC
CAGCGCCCTAGCGCCCGCTCCTTTCGCTTTCTTCCCTTCCTTTCTCGCCACGTTCGCCGGCTTTCCCCGTC
AAGCTCTAAATCGGGGGCTCCCTTTAGGGTTCCGATTTAGTGCTTTACGGCACCTCGACCCCAAAAAACTT
GATTTGGGTGATGGTTCACGTAGTGGGCCATCGCCCTGATAGACGGTTTTTCGCCCTTTGACGTTGGAGTC
CACGTTCTTTAATAGTGGACTCTTGTTCCAAACTGGAACAACACTCAACCCTATCTCGGGCTATTCTTTTG
ATTTATAAGGGATTTTGCCGATTTCGGCCTATTGGTTAAAAAATGAGCTGATTTAACAAAAATTTAACGCG
AATTTTAACAAAATATTAACGTTTACAATTTTATGGTGCACTCTCAGTACAATCTGCTCTGATGCCGCATA
GTTAAGCCAGCCCCGACACCCGCCAACACCCGCTGACGCGCCCTGACGGGCTTGTCTGCTCCCGGCATCCG
CTTACAGACAAGCTGTGACCGTCTCCGGGAGCTGCATGTGTCAGAGGTTTTCACCGTCATCACCGAAACGC
GCGAGACGAAAGGGCCTCGTGATACGCCTATTTTTATAGGTTAATGTCATGATAATAATGGTTTCTTAGAC
GTCAGGTGGCACTTTTCGGGGAAATGTGCGCGGAACCCCTATTTGTTTATTTTTCTAAATACATTCAAATA
TGTATCCGCTCATGAGACAATAACCCTGATAAATGCTTCAATAATATTGAAAAGGAAGAGTATGAGTATT
CAACATTTCCGTGTCGCCCTTATTCCCTTTTTTGCGGCATTTTGCCTTCCTGTTTTTGCTCACCCAGAAAC
GCTGGTGAAAGTAAAAGATGCTGAAGATCAGTTGGGTGCACGAGTGGGTTACATCGAACTGGATCTCAACA
GCGGTAAGATCCTTGAGAGTTTTCGCCCCGAAGAACGTTTTCCAATGATGAGCACTTTTAAAGTTCTGCTA
TGTGGCGCGGTATTATCCCGTATTGACGCCGGGCAAGAGCAACTCGGTCGCCGCATACACTATTCTCAGAA
TGACTTGGTTGAGTACTCACCAGTCACAGAAAAGCATCTTACGGATGGCATGACAGTAAGAGAATTATGCA
GTGCTGCCATAACCATGAGTGATAACACTGCGGCCAACTTACTTCTGACAACGATCGGAGGACCGAAGGAG
CTAACCGCTTTTTTGCACAACATGGGGGATCATGTAACTCGCCTTGATCGTTGGGAACCGGAGCTGAATGA
AGCCATACCAAACGACGAGCGTGACACCACGATGCCTGTAGCAATGGCAACAACGTTGCGCAAACTATTAA
CTGGCGAACTACTTACTCTAGCTTCCCGGCAACAATTAATAGACTGGATGGAGGCGGATAAAGTTGCAGGA
CCACTTCTGCGCTCGGCCCTTCCGGCTGGCTGGTTTATTGCTGATAAATCTGGAGCCGGTGAGCGTGGGTC
TCGCGGTATCATTGCAGCACTGGGGCCAGATGGTAAGCCCTCCCGTATCGTAGTTATCTACACGACGGGGA
GTCAGGCAACTATGGATGAACGAAATAGACAGATCGCTGAGATAGGTGCCTCACTGATTAAGCATTGGTAA
CTGTCAGACCAAGTTTACTCATATATACTTTAGATTGATTTAAAACTTCATTTTTAATTTAAAAGGATCTA
GGTGAAGATCCTTTTTGATAATCTCATGACCAAAATCCCTTAACGTGAGTTTTCGTTCCACTGAGCGTCAG
ACCCCGTAGAAAAGATCAAAGGATCTTCTTGAGATCCTTTTTTTCTGCGCGTAATCTGCTGCTTGCAAACA
AAAAAACCACCGCTACCAGCGGTGGTTTGTTTGCCGGATCAAGAGCTACCAACTCTTTTTCCGAAGGTAAC
```

Figure 14 (continued)

```
TGGCTTCAGCAGAGCGCAGATACCAAATACTGTCCTTCTAGTGTAGCCGTAGTTAGGCCACCACTTCAAGA
ACTCTGTAGCACCGCCTACATACCTCGCTCTGCTAATCCTGTTACCAGTGGCTGCTGCCAGTGGCGATAAG
TCGTGTCTTACCGGGTTGGACTCAAGACGATAGTTACCGGATAAGGCGCAGCGGTCGGGCTGAACGGGGGG
TTCGTGCACACAGCCCAGCTTGGAGCGAACGACCTACACCGAACTGAGATACCTACAGCGTGAGCTATGAG
AAAGCGCCACGCTTCCCGAAGGGAGAAAGGCGGACAGGTATCCGGTAAGCGGCAGGGTCGGAACAGGAGAG
CGCACGAGGGAGCTTCCAGGGGGAAACGCCTGGTATCTTTATAGTCCTGTCGGGTTTCGCCACCTCTGACT
TGAGCGTCGATTTTTGTGATGCTCGTCAGGGGGGCGGAGCCTATGGAAAAACGCCAGCAACGCGGCCTTTT
TACGGTTCCTGGCCTTTTGCTGGCCTTTTGCTCACATGT

SEQ ID NO.16: pAAVss-3xSerpEnh-TTRm-MVM-coFVIIIdeltaB-Sv40pA

CCTGCAGGCAGCTGCGCGCTCGCTCGCTCACTGAGGCCGCCCGGGCAAAGCCCGGGCGTCGGGCGACCTTT
GGTCGCCCGGCCTCAGTGAGCGAGCGAGCGCGCAGAGAGGGAGTGGCCAACTCCATCACTAGGGGTTCCTG
CGGCCGCGGTACGCGGGGGAGGCTGCTGGTGAATATTAACCAAGGTCACCCCAGTTATCGGAGGAGCAAAC
AGGGGCTAAGTCCACCGGGGGAGGCTGCTGGTGAATATTAACCAAGGTCACCCCAGTTATCGGAGGAGCAA
ACAGGGGCTAAGTCCACCGGGGGAGGCTGCTGGTGAATATTAACCAAGGTCACCCCAGTTATCGGAGGAGC
AAACAGGGGCTAAGTCCACTGTACAACGCGTGAATTCGCTAGCGTCTGTCTGCACATTTCGTAGAGCGAGT
GTTCCGATACTCTAATCTCCCTAGGCAAGGTTCATATTTGTGTAGGTTACTTATTCTCCTTTTGTTGACTA
AGTCAATAATCAGAATCAGCAGGTTTGGAGTCAGCTTGGCAGGGATCAGCAGCCTGGGTTGGAAGGAGGGG
GTATAAAAGCCCCTTCACCAGGAGAAGCCGTCACACAGATCCACAAGCTCCTGTCTAGAAAGAGGTAAGGG
TTTAAGGGATGGTTGGTTGGTGGGGTATTAATGTTTAATTACCTGGAGCACCTGCCTGAAATCACTTTTTT
TCAGGTTGGGCTAGCATGCAGATCGAGCTGTCCACCTGCTTTTTTCTGTGCCTGCTGCGGTTCTGCTTCAG
CGCCACCCGGCGGTACTACCTGGGCGCCGTGGAGCTGTCCTGGGACTACATGCAGAGCGACCTGGGCGAGC
TGCCCGTGGACGCCCGGTTCCCCCCCAGAGTGCCCAAGAGCTTCCCCTTCAACACCAGCGTGGTGTACAAG
AAAACCCTGTTCGTGGAGTTCACCGACCACCTGTTCAATATCGCCAAGCCCAGGCCCCCTGGATGGGCCT
GCTGGGCCCCACCATCCAGGCCGAGGTGTACGACACCGTGGTGATCACCCTGAAGAACATGGCCAGCCACC
CCGTGAGCCTGCACGCCGTGGGCGTGAGCTACTGGAAGGCCAGCGAGGGCGCCGAGTACGACGACCAGACC
AGCCAGCGGGAGAAAGAAGATGACAAGGTGTTCCCTGGCGGCAGCCACACCTACGTGTGGCAGGTGCTGAA
AGAAAACGGCCCCATGGCCTCCGACCCCCTGTGCCTGACCTACAGCTACCTGAGCCACGTGGACCTGGTGA
AGGACCTGAACAGCGGCCTGATCGGCGCTCTGCTCGTCTGCCGGGAGGGCAGCCTGGCCAAAGAGAAAACC
CAGACCCTGCACAAGTTCATCCTGCTGTTCGCCGTGTTCGACGAGGGCAAGAGCTGGCACAGCGAGACAAA
GAACAGCCTGATGCAGGACCGGGACGCCGCCTCTGCCAGAGCCTGGCCCAAGATGCACACCGTGAACGGCT
ACGTGAACAGAAGCCTGCCCGGCCTGATTGGCTGCCACCGGAAGAGCGTGTACTGGCACGTGATCGGCATG
GGCACCACACCCGAGGTGCACAGCATCTTTCTGGAAGGGCACACCTTTCTGGTCCGGAACCACCGGCAGGC
CAGCCTGGAAATCAGCCCTATCACCTTCCTGACCGCCCAGACACTGCTGATGGACCTGGGCCAGTTCCTGC
TGTTTTGCCACATCAGCTCTCACCAGCACGACGGCATGGAAGCCTACGTGAAGGTGGACTCTTGCCCCGAG
GAACCCCAGCTGCGGATGAAGAACAACGAGGAAGCCGAGGACTACGACGACGACCTGACCGACAGCGAGAT
GGACGTGGTGCGGTTCGACGACGACAACAGCCCCAGCTTCATCCAGATCAGAAGCGTGGCCAAGAAGCACC
CCAAGACCTGGGTGCACTATATCGCCGCCGAGGAAGAGGACTGGGACTACGCCCCCCTGGTGCTGGCCCCC
GACGACAGAAGCTACAAGAGCCAGTACCTGAACAATGGCCCCCAGCGGATCGGCCGGAAGTACAAGAAAGT
GCGGTTCATGGCCTACACCGACGAGACATTCAAGACCCGGGAGGCCATCCAGCACGAGAGCGGCATCCTGG
GCCCCCTGCTGTACGGCGAAGTGGGCGACACACTGCTGATCATCTTCAAGAACCAGGCTAGCCGGCCCTAC
AACATCTACCCCCACGGCATCACCGACGTGCGGCCCCTGTACAGCAGGCGGCTGCCCAAGGGCGTGAAGCA
CCTGAAGGACTTCCCCATCCTGCCCGGCGAGATCTTCAAGTACAAGTGGACCGTGACCGTGGAGGACGGCC
CCACCAAGAGCGACCCCAGATGCCTGACCCGGTACTACAGCAGCTTCGTGAACATGGAACGGGACCTGGCC
TCCGGGCTGATCGGACCTCTGCTGATCTGCTACAAAGAAAGCGTGGACCAGCGGGGCAACCAGATCATGAG
CGACAAGCGGAACGTGATCCTGTTCAGCGTGTTCGATGAGAACCGGTCCTGGTATCTGACCGAGAACATCC
AGCGGTTTCTGCCCAACCCTGCCGGCGTGCAGCTGGAAGATCCCGAGTTCCAGGCCAGCAACATCATGCAC
TCCATCAATGGCTACGTGTTCGACTCTCTGCAGCTCTCCGTGTGTCTGCACGAGGTGGCCTACTGGTACAT
CCTGAGCATCGGCGCCCAGACCGACTTCCTGAGCGTGTTCTTCAGCGGCTACACCTTCAAGCACAAGATGG
TGTACGAGGACACCCTGACCCTGTTCCCTTTCAGCGGCGAGACAGTGTTCATGAGCATGGAAAACCCCGGC
CTGTGGATTCTGGGCTGCCACAACAGCGACTTCCGGAACCGGGGCATGACCGCCCTGCTGAAGGTGTCCAG
CTGCGACAAGAACACCGGCGACTACTACGAGGACAGCTACGAGGATATCAGCGCCTACCTGCTGTCCAAGA
ACAACGCCATCGAACCCCGGAGCTTCAGCCAGAACCCCCCGTGCTGACGCGTCACCAGCGGGAGATCACC
CGGACAACCCTGCAGTCCGACCAGGAAGAGATCGATTACGACGACACCATCAGCGTGGAGATGAAGAAAGA
```

Figure 14 (continued)

```
GGATTTCGATATCTACGACGAGGACGAGAACCAGAGCCCCAGAAGCTTCCAGAAGAAAACCCGGCACTACT
TCATTGCCGCCGTGGAGAGGCTGTGGGACTACGGCATGAGTTCTAGCCCCCACGTGCTGCGGAACCGGGCC
CAGAGCGGCAGCGTGCCCCAGTTCAAGAAAGTGGTGTTCCAGGAATTCACAGACGGCAGCTTCACCCAGCC
TCTGTATAGAGGCGAGCTGAACGAGCACCTGGGGCTGCTGGGGCCCTACATCAGGGCCGAAGTGGAGGACA
ACATCATGGTGACCTTCCGGAATCAGGCCAGCAGACCCTACTCCTTCTACAGCAGCCTGATCAGCTACGAA
GAGGACCAGCGGCAGGGCGCCGAACCCCGGAAGAACTTCGTGAAGCCCAACGAAACCAAGACCTACTTCTG
GAAAGTGCAGCACCACATGGCCCCCACCAAGGACGAGTTCGACTGCAAGGCCTGGGCCTACTTCAGCGACG
TGGATCTGGAAAAGGACGTGCACTCTGGACTGATTGGCCCACTCCTGGTCTGCCACACTAACACCCTCAAC
CCCGCCCACGGCCGCCAGGTGACCGTGCAGGAATTCGCCCTGTTCTTCACCATCTTCGACGAGACAAAGTC
CTGGTACTTCACCGAGAATATGGAACGGAACTGCAGAGCCCCCTGCAACATCCAGATGGAAGATCCTACCT
TCAAAGAGAACTACCGGTTCCACGCCATCAACGGCTACATCATGGACACCCTGCCTGGCCTGGTGATGGCC
CAGGACCAGAGAATCCGGTGGTATCTGCTGTCCATGGGCAGCAACGAGAATATCCACAGCATCCACTTCAG
CGGCCACGTGTTCACCGTGCGGAAGAAAGAAGAGTACAAGATGGCCCTGTACAACCTGTACCCCGGCGTGT
TCGAGACAGTGGAGATGCTGCCCAGCAAGGCCGGCATCTGGCGGGTGGAGTGTCTGATCGGCGAGCACCTG
CACGCTGGCATGAGCACCCTGTTTCTGGTGTACAGCAACAAGTGCCAGACCCCACTGGGCATGGCCTCTGG
CCACATCCGGGACTTCCAGATCACCGCCTCCGGCCAGTACGGCCAGTGGGCCCCCAAGCTGGCCAGACTGC
ACTACAGCGGCAGCATCAACGCCTGGTCCACCAAAGAGCCCTTCAGCTGGATCAAGGTGGACCTGCTGGCC
CCTATGATCATCCACGGCATTAAGACCCAGGGCGCCAGGCAGAAGTTCAGCAGCCTGTACATCAGCCAGTT
CATCATCATGTACAGCCTGGACGGCAAGAAGTGGCAGACCTACCGGGGCAACAGCACCGGCACCCTGATGG
TGTTCTTCGGCAATGTGGACAGCAGCGGCATCAAGCACAACATCTTCAACCCCCCCATCATTGCCCGGTAC
ATCCGGCTGCACCCCACCCACTACAGCATTAGATCCACACTGAGAATGGAACTGATGGGCTGCGACCTGAA
CTCCTGCAGCATGCCTCTGGGCATGGAAAGCAAGGCCATCAGCGACGCCCAGATCACAGCCAGCAGCTACT
TCACCAACATGTTCGCCACCTGGTCCCCCTCCAAGGCCAGGCTGCACCTGCAGGGCCGGTCCAACGCCTGG
CGGCCTCAGGTCAACAACCCCAAAGAATGGCTGCAGGTGGACTTTCAGAAAACCATGAAGGTGACCGGCGT
GACCACCCAGGGCGTGAAAAGCCTGCTGACCAGCATGTACGTGAAAGAGTTTCTGATCAGCAGCTCTCAGG
ATGGCCACCAGTGGACCCTGTTCTTTCAGAACGGCAAGGTGAAAGTGTTCCAGGGCAACAGGACTCCTTC
ACCCCGTGGTGAACTCCCTGGACCCCCCCCTGCTGACCCGCTACCTGAGAATCCACCCCCAGTCTTGGGT
GCACCAGATCGCCCTCAGGATGGAAGTCCTGGGATGTGAGGCCCAGGATCTGTACTGATGAGGATCTAGGC
TCGACATGCTTTATTTGTGAAATTTGTGATGCTATTGCTTTATTTGTAACCATTATAAGCTGCAATAAACA
AGTTAACAACAACAATTGCATTCATTTTATGTTTCAGGTTCAGGGGGAGGTGTGGGAGGTTTTTTAAACTC
GAGATCCACGGCCGCAGGAACCCCTAGTGATGGAGTTGGCCACTCCCTCTCTGCGCGCTCGCTCGCTCACT
GAGGCCGGGCGACCAAAGGTCGCCCGACGCCCGGGCTTTGCCCGGGCGGCCTCAGTGAGCGAGCGAGCGCG
CAGCTGCCTGCAGGGGCGCCTGATGCGGTATTTTCTCCTTACGCATCTGTGCGGTATTTCACACCGCATAC
GTCAAAGCAACCATAGTACGCGCCCTGTAGCGGCGCATTAAGCGCGGCGGGTGTGGTGGTTACGCGCAGCG
TGACCGCTACACTTGCCAGCGCCCTAGCGCCCGCTCCTTTCGCTTTCTTCCCTTCCTTTCTCGCCACGTTC
GCCGGCTTTCCCCGTCAAGCTCTAAATCGGGGGCTCCCTTTAGGGTTCCGATTTAGTGCTTTACGGCACCT
CGACCCCAAAAAACTTGATTTGGGTGATGGTTCACGTAGTGGGCCATCGCCCTGATAGACGGTTTTTCGCC
CTTTGACGTTGGAGTCCACGTTCTTTAATAGTGGACTCTTGTTCCAAACTGGAACAACACTCAACCCTATC
TCGGGCTATTCTTTTGATTTATAAGGGATTTTGCCGATTTCGGCCTATTGGTTAAAAAATGAGCTGATTTA
ACAAAAATTTAACGCGAATTTTAACAAAATATTAACGTTTACAATTTTATGGTGCACTCTCAGTACAATCT
GCTCTGATGCCGCATAGTTAAGCCAGCCCCGACACCCGCCAACACCCGCTGACGCGCCCTGACGGGCTTGT
CTGCTCCCGGCATCCGCTTACAGACAAGCTGTGACCGTCTCCGGGAGCTGCATGTGTCAGAGGTTTTCACC
GTCATCACCGAAACGCGCGAGACGAAAGGGCCTCGTGATACGCCTATTTTTATAGGTTAATGTCATGATAA
TAATGGTTTCTTAGACGTCAGGTGGCACTTTTCGGGGAAATGTGCGCGGAACCCCTATTTGTTTATTTTTC
TAAATACATTCAAATATGTATCCGCTCATGAGACAATAACCCTGATAAATGCTTCAATAATATTGAAAAG
GAAGAGTATGAGTATTCAACATTTCCGTGTCGCCCTTATTCCCTTTTTTGCGGCATTTTGCCTTCCTGTTT
TTGCTCACCCAGAAACGCTGGTGAAAGTAAAAGATGCTGAAGATCAGTTGGGTGCACGAGTGGGTTACATC
GAACTGGATCTCAACAGCGGTAAGATCCTTGAGAGTTTTCGCCCCGAAGAACGTTTTCCAATGATGAGCAC
TTTTAAAGTTCTGCTATGTGGCGCGGTATTATCCCGTATTGACGCCGGGCAAGAGCAACTCGGTCGCCGCA
TACACTATTCTCAGAATGACTTGGTTGAGTACTCACCAGTCACAGAAAAGCATCTTACGGATGGCATGACA
GTAAGAGAATTATGCAGTGCTGCCATAACCATGAGTGATAACACTGCGGCCAACTTACTTCTGACAACGAT
CGGAGGACCGAAGGAGCTAACCGCTTTTTTGCACAACATGGGGGATCATGTAACTCGCCTTGATCGTTGGG
AACCGGAGCTGAATGAAGCCATACCAAACGACGAGCGTGACACCACGATGCCTGTAGCAATGGCAACAACG
TTGCGCAAACTATTAACTGGCGAACTACTTACTCTAGCTTCCCGGCAACAATTAATAGACTGGATGGAGGC
GGATAAAGTTGCAGGACCACTTCTGCGCTCGGCCCTTCCGGCTGGCTGGTTTATTGCTGATAAATCTGGAG
```

Figure 14 (continued)

CCGGTGAGCGTGGGTCTCGCGGTATCATTGCAGCACTGGGGCCAGATGGTAAGCCCTCCCGTATCGTAGTT
ATCTACACGACGGGGAGTCAGGCAACTATGGATGAACGAAATAGACAGATCGCTGAGATAGGTGCCTCACT
GATTAAGCATTGGTAACTGTCAGACCAAGTTTACTCATATATACTTTAGATTGATTTAAAACTTCATTTTT
AATTTAAAAGGATCTAGGTGAAGATCCTTTTTGATAATCTCATGACCAAAATCCCTTAACGTGAGTTTTCG
TTCCACTGAGCGTCAGACCCCGTAGAAAAGATCAAAGGATCTTCTTGAGATCCTTTTTTTCTGCGCGTAAT
CTGCTGCTTGCAAACAAAAAAACCACCGCTACCAGCGGTGGTTTGTTTGCCGGATCAAGAGCTACCAACTC
TTTTTCCGAAGGTAACTGGCTTCAGCAGAGCGCAGATACCAAATACTGTCCTTCTAGTGTAGCCGTAGTTA
GGCCACCACTTCAAGAACTCTGTAGCACCGCCTACATACCTCGCTCTGCTAATCCTGTTACCAGTGGCTGC
TGCCAGTGGCGATAAGTCGTGTCTTACCGGGTTGGACTCAAGACGATAGTTACCGGATAAGGCGCAGCGGT
CGGGCTGAACGGGGGGTTCGTGCACACAGCCCAGCTTGGAGCGAACGACCTACACCGAACTGAGATACCTA
CAGCGTGAGCTATGAGAAAGCGCCACGCTTCCCGAAGGGAGAAAGGCGGACAGGTATCCGGTAAGCGGCAG
GGTCGGAACAGGAGAGCGCACGAGGGAGCTTCCAGGGGGAAACGCCTGGTATCTTTATAGTCCTGTCGGGT
TTCGCCACCTCTGACTTGAGCGTCGATTTTTGTGATGCTCGTCAGGGGGCGGAGCCTATGGAAAAACGCC
AGCAACGCGGCCTTTTTACGGTTCCTGGCCTTTTGCTGGCCTTTTGCTCACATGT

SEQ ID NO.17: pAAVss-TTRe-TTRm-MVM-coFVIIIdeltaB-Sv40pA

CCTGCAGGCAGCTGCGCGCTCGCTCGCTCACTGAGGCCGCCCGGGCAAAGCCCGGGCGTCGGGCGACCTTT
GGTCGCCCGGCCTCAGTGAGCGAGCGAGCGCGCAGAGAGGGAGTGGCCAACTCCATCACTAGGGGTTCCTG
CGGCCGCGGTACCCACTGGGAGGATGTTGAGTAAGATGGAAAACTACTGATGACCCTTGCAGAGACAGAGT
ATTAGGACATGTTTGAACAGGGGCCGGGCGATCAGCAGGTAGCTCTAGAGGATCCCCGTCTGTCTGCACAT
TTCGTAGAGCGAGTGTTCCGATACTCTAATCTCCCTAGGCAAGGTTCATATTTGTGTAGGTTACTTATTCT
CCTTTTGTTGACTAAGTCAATAATCAGAATCAGCAGGTTTGGAGTCAGCTTGGCAGGGATCAGCAGCCTGG
GTTGGAAGGAGGGGGTATAAAAGCCCCTTCACCAGGAGAAGCCGTCACACAGATCCACAAGCTCCTGAAGA
GGTAAGGGTTTAAGGGATGGTTGGTTGGTGGGGTATTAATGTTTAATTACCTGGAGCACCTGCCTGAAATC
ACTTTTTTTCAGGTTGGCTAGTATGCAGATCGAGCTGTCCACCTGCTTTTTTCTGTGCCTGCTGCGGTTCT
GCTTCAGCGCCACCCGGCGGTACTACCTGGGCGCCGTGGAGCTGTCCTGGGACTACATGCAGAGCGACCTG
GGCGAGCTGCCCGTGGACGCCCGGTTCCCCCCAGAGTGCCCAAGAGCTTCCCCTTCAACACCAGCGTGGT
GTACAAGAAAACCCTGTTCGTGGAGTTCACCGACCACCTGTTCAATATCGCCAAGCCCAGGCCCCCTGGA
TGGGCCTGCTGGGCCCCACCATCCAGGCCGAGGTGTACGACACCGTGGTGATCACCCTGAAGAACATGGCC
AGCCACCCCGTGAGCCTGCACGCCGTGGGCGTGAGCTACTGGAAGGCCAGCGAGGGCGCCGAGTACGACGA
CCAGACCAGCCAGCGGGAGAAAGAAGATGACAAGGTGTTCCCTGGCGGCAGCCACACCTACGTGTGGCAGG
TGCTGAAAGAAAACGGCCCCATGGCCTCCGACCCCCTGTGCCTGACCTACAGCTACCTGAGCCACGTGGAC
CTGGTGAAGGACCTGAACAGCGGCCTGATCGGCGCTCTGCTCGTCTGCCGGGAGGGCAGCCTGGCCAAAGA
GAAACCCAGACCCTGCACAAGTTCATCCTGCTGTTCGCCGTGTTCGACGAGGGCAAGAGCTGGCACAGCG
AGACAAAGAACAGCCTGATGCAGGACCGGGACGCCGCCTCTGCCAGAGCCTGGCCCAAGATGCACACCGTG
AACGGCTACGTGAACAGAAGCCTGCCCGGCCTGATTGGCTGCCACCGGAAGAGCGTGTACTGGCACGTGAT
CGGCATGGGCACCACACCCGAGGTGCACAGCATCTTTCTGGAAGGGCACACCTTTCTGGTCCGGAACCACC
GGCAGGCCAGCCTGGAAATCAGCCCTATCACCTTCCTGACCGCCCAGACACTGCTGATGGACCTGGGCCAG
TTCCTGCTGTTTTGCCACATCAGCTCTCACCAGCACGACGGCATGGAAGCCTACGTGAAGGTGGACTCTTG
CCCCGAGGAACCCCAGCTGCGGATGAAGAACAACGAGGAAGCCGAGGACTACGACGACGACCTGACCGACA
GCGAGATGGACGTGGTGCGGTTCGACGACGACAACAGCCCCAGCTTCATCCAGATCAGAAGCGTGGCCAAG
AAGCACCCCAAGACCTGGGTGCACTATATCGCCGCCGAGGAAGAGGACTGGGACTACGCCCCCCTGGTGCT
GGCCCCCGACGACAGAAGCTACAAGAGCCAGTACCTGAACAATGGCCCCCAGCGGATCGGCCGGAAGTACA
AGAAAGTGCGGTTCATGGCCTACACCGACGAGACATTCAAGACCCGGGAGGCCATCCAGCACGAGAGCGGC
ATCCTGGGCCCCCTGCTGTACGGCGAAGTGGGCGACACACTGCTGATCATCTTCAAGAACCAGGCTAGCCG
GCCCTACAACATCTACCCCCACGGCATCACCGACGTGCGGCCCCTGTACAGCAGGCGGCTGCCCAAGGGCG
TGAAGCACCTGAAGGACTTCCCCATCCTGCCCGGCGAGATCTTCAAGTACAAGTGGACCGTGACCGTGGAG
GACGGCCCCACCAAGAGCGACCCCAGATGCCTGACCCGGTACTACAGCAGCTTCGTGAACATGGAACGGGA
CCTGGCCTCCGGGCTGATCGGACCTCTGCTGATCTGCTACAAAGAAAGCGTGGACCAGCGGGGCAACCAGA
TCATGAGCGACAAGCGGAACGTGATCCTGTTCAGCGTGTTCGATGAGAACCGGTCCTGGTATCTGACCGAG
AACATCCAGCGGTTTCTGCCCAACCCTGCCGGCGTGCAGCTGGAAGATCCCGAGTTCCAGGCCAGCAACAT
CATGCACTCCATCAATGGCTACGTGTTCGACTCTCTGCAGCTCTCCGTGTGTCTGCACGAGGTGGCCTACT
GGTACATCCTGAGCATCGGCGCCCAGACCGACTTCCTGAGCGTGTTCTTCAGCGGCTACACCTTCAAGCAC
AAGATGGTGTACGAGGACACCCTGACCCTGTTCCCTTTCAGCGGCGAGACAGTGTTCATGAGCATGGAAAA

Figure 14 (continued)

```
CCCCGGCCTGTGGATTCTGGGCTGCCACAACAGCGACTTCCGGAACCGGGGCATGACCGCCCTGCTGAAGG
TGTCCAGCTGCGACAAGAACACCGGCGACTACTACGAGGACAGCTACGAGGATATCAGCGCCTACCTGCTG
TCCAAGAACAACGCCATCGAACCCCGGAGCTTCAGCCAGAACCCCCCGTGCTGACGCGTCACCAGCGGGA
GATCACCCGGACAACCCTGCAGTCCGACCAGGAAGAGATCGATTACGACGACACCATCAGCGTGGAGATGA
AGAAAGAGGATTTCGATATCTACGACGAGGACGAGAACCAGAGCCCCAGAAGCTTCCAGAAGAAAACCCGG
CACTACTTCATTGCCGCCGTGGAGAGGCTGTGGGACTACGGCATGAGTTCTAGCCCCCACGTGCTGCGGAA
CCGGGCCCAGAGCGGCAGCGTGCCCCAGTTCAAGAAAGTGGTGTTCCAGGAATTCACAGACGGCAGCTTCA
CCCAGCCTCTGTATAGAGGCGAGCTGAACGAGCACCTGGGGCTGCTGGGGCCCTACATCAGGGCCGAAGTG
GAGGACAACATCATGGTGACCTTCCGGAATCAGGCCAGCAGACCCTACTCCTTCTACAGCAGCCTGATCAG
CTACGAAGAGGACCAGCGGCAGGGCGCCGAACCCCGGAAGAACTTCGTGAAGCCCAACGAAACCAAGACCT
ACTTCTGGAAAGTGCAGCACCACATGGCCCCCACCAAGGACGAGTTCGACTGCAAGGCCTGGGCCTACTTC
AGCGACGTGGATCTGGAAAAGGACGTGCACTCTGGACTGATTGGCCCACTCCTGGTCTGCCACACTAACAC
CCTCAACCCCGCCCACGGCCGCCAGGTGACCGTGCAGGAATTCGCCCTGTTCTTCACCATCTTCGACGAGA
CAAAGTCCTGGTACTTCACCGAGAATATGGAACGGAACTGCAGAGCCCCTGCAACATCCAGATGGAAGAT
CCTACCTTCAAAGAGAACTACCGGTTCCACGCCATCAACGGCTACATCATGGACACCCTGCCTGGCCTGGT
GATGGCCCAGGACCAGAGAATCCGGTGGTATCTGCTGTCCATGGGCAGCAACGAGAATATCCACAGCATCC
ACTTCAGCGGCCACGTGTTCACCGTGCGGAAGAAAGAAGAGTACAAGATGGCCCTGTACAACCTGTACCCC
GGCGTGTTCGAGACAGTGGAGATGCTGCCCAGCAAGGCCGGCATCTGGCGGGTGGAGTGTCTGATCGGCGA
GCACCTGCACGCTGGCATGAGCACCCTGTTTCTGGTGTACAGCAACAAGTGCCAGACCCCACTGGGCATGG
CCTCTGGCCACATCCGGGACTTCCAGATCACCGCCTCCGGCCAGTACGGCCAGTGGGCCCCCAAGCTGGCC
AGACTGCACTACAGCGGCAGCATCAACGCCTGGTCCACCAAAGAGCCCTTCAGCTGGATCAAGGTGGACCT
GCTGGCCCCTATGATCATCCACGGCATTAAGACCCAGGGCGCCAGGCAGAAGTTCAGCAGCCTGTACATCA
GCCAGTTCATCATCATGTACAGCCTGGACGGCAAGAAGTGGCAGACCTACCGGGGCAACAGCACCGGCACC
CTGATGGTGTTCTTCGGCAATGTGGACAGCAGCGGCATCAAGCACAACATCTTCAACCCCCCCATCATTGC
CCGGTACATCCGGCTGCACCCCACCCACTACAGCATTAGATCCACACTGAGAATGGAACTGATGGGCTGCG
ACCTGAACTCCTGCAGCATGCCTCTGGGCATGGAAAGCAAGGCCATCAGCGACGCCCAGATCACAGCCAGC
AGCTACTTCACCAACATGTTCGCCACCTGGTCCCCTCCAAGGCCAGGCTGCACCTGCAGGGCCGGTCCAA
CGCCTGGCGGCCTCAGGTCAACAACCCCAAAGAATGGCTGCAGGTGGACTTTCAGAAAACCATGAAGGTGA
CCGGCGTGACCACCCAGGGCGTGAAAAGCCTGCTGACCAGCATGTACGTGAAAGAGTTTCTGATCAGCAGC
TCTCAGGATGGCCACCAGTGGACCCTGTTCTTTCAGAACGGCAAGGTGAAAGTGTTCCAGGGCAACCAGGA
CTCCTTCACCCCCGTGGTGAACTCCCTGGACCCCCCCCTGCTGACCCGCTACCTGAGAATCCACCCCCAGT
CTTGGGTGCACCAGATCGCCCTCAGGATGGAAGTCCTGGGATGTGAGGCCCAGGATCTGTACTGATGAGGA
TCTAGGCTCGACATGCTTTATTTGTGAAATTTGTGATGCTATTGCTTTATTTGTAACCATTATAAGCTGCA
ATAAACAAGTTAACAACAACAATTGCATTCATTTTATGTTTCAGGTTCAGGGGGAGGTGTGGGAGGTTTTT
TAAACTCGAGATCCACGGCCGCAGGAACCCCTAGTGATGGAGTTGGCCACTCCCTCTCTGCGCGCTCGCTC
GCTCACTGAGGCCGGGCGACCAAAGGTCGCCCGACGCCCGGGCTTTGCCCGGGCGGCCTCAGTGAGCGAGC
GAGCGCGCAGCTGCCTGCAGGGGCGCCTGATGCGGTATTTTCTCCTTACGCATCTGTGCGGTATTTCACAC
CGCATACGTCAAAGCAACCATAGTACGCGCCCTGTAGCGGCGCATTAAGCGCGGCGGGTGTGGTGGTTACG
CGCAGCGTGACCGCTACACTTGCCAGCGCCCTAGCGCCCGCTCCTTTCGCTTTCTTCCCTTCCTTTCTCGC
CACGTTCGCCGGCTTTCCCCGTCAAGCTCTAAATCGGGGGCTCCCTTTAGGGTTCCGATTTAGTGCTTTAC
GGCACCTCGACCCCAAAAAACTTGATTTGGGTGATGGTTCACGTAGTGGGCCATCGCCCTGATAGACGGTT
TTTCGCCCTTTGACGTTGGAGTCCACGTTCTTTAATAGTGGACTCTTGTTCCAAACTGGAACAACACTCAA
CCCTATCTCGGGCTATTCTTTTGATTTATAAGGGATTTTGCCGATTTCGGCCTATTGGTTAAAAAATGAGC
TGATTTAACAAAAATTTAACGCGAATTTTAACAAAATATTAACGTTTACAATTTTATGGTGCACTCTCAGT
ACAATCTGCTCTGATGCCGCATAGTTAAGCCAGCCCCGACACCCGCCAACACCCGCTGACGCGCCCTGACG
GGCTTGTCTGCTCCCGGCATCCGCTTACAGACAAGCTGTGACCGTCTCCGGGAGCTGCATGTGTCAGAGGT
TTTCACCGTCATCACCGAAACGCGCGAGACGAAAGGGCCTCGTGATACGCCTATTTTTATAGGTTAATGTC
ATGATAATAATGGTTTCTTAGACGTCAGGTGGCACTTTTCGGGGAAATGTGCGCGGAACCCCTATTTGTTT
ATTTTTCTAAATACATTCAAATATGTATCCGCTCATGAGACAATAACCCTGATAAATGCTTCAATAATATT
GAAAAAGGAAGAGTATGAGTATTCAACATTTCCGTGTCGCCCTTATTCCCTTTTTTGCGGCATTTTGCCTT
CCTGTTTTTGCTCACCCAGAAACGCTGGTGAAAGTAAAAGATGCTGAAGATCAGTTGGGTGCACGAGTGGG
TTACATCGAACTGGATCTCAACAGCGGTAAGATCCTTGAGAGTTTTCGCCCCGAAGAACGTTTTCCAATGA
TGAGCACTTTTAAAGTTCTGCTATGTGGCGCGGTATTATCCCGTATTGACGCCGGGCAAGAGCAACTCGGT
CGCCGCATACACTATTCTCAGAATGACTTGGTTGAGTACTCACCAGTCACAGAAAAGCATCTTACGGATGG
CATGACAGTAAGAGAATTATGCAGTGCTGCCATAACCATGAGTGATAACACTGCGGCCAACTTACTTCTGA
```

Figure 14 (continued)

```
CAACGATCGGAGGACCGAAGGAGCTAACCGCTTTTTTGCACAACATGGGGGATCATGTAACTCGCCTTGAT
CGTTGGGAACCGGAGCTGAATGAAGCCATACCAAACGACGAGCGTGACACCACGATGCCTGTAGCAATGGC
AACAACGTTGCGCAAACTATTAACTGGCGAACTACTTACTCTAGCTTCCCGGCAACAATTAATAGACTGGA
TGGAGGCGGATAAAGTTGCAGGACCACTTCTGCGCTCGGCCCTTCCGGCTGGCTGGTTTATTGCTGATAAA
TCTGGAGCCGGTGAGCGTGGGTCTCGCGGTATCATTGCAGCACTGGGGCCAGATGGTAAGCCCTCCCGTAT
CGTAGTTATCTACACGACGGGGAGTCAGGCAACTATGGATGAACGAAATAGACAGATCGCTGAGATAGGTG
CCTCACTGATTAAGCATTGGTAACTGTCAGACCAAGTTTACTCATATATACTTTAGATTGATTTAAAACTT
CATTTTTAATTTAAAAGGATCTAGGTGAAGATCCTTTTTGATAATCTCATGACCAAAATCCCTTAACGTGA
GTTTTCGTTCCACTGAGCGTCAGACCCCGTAGAAAAGATCAAAGGATCTTCTTGAGATCCTTTTTTTCTGC
GCGTAATCTGCTGCTTGCAAACAAAAAAACCACCGCTACCAGCGGTGGTTTGTTTGCCGGATCAAGAGCTA
CCAACTCTTTTTCCGAAGGTAACTGGCTTCAGCAGAGCGCAGATACCAAATACTGTCCTTCTAGTGTAGCC
GTAGTTAGGCCACCACTTCAAGAACTCTGTAGCACCGCCTACATACCTCGCTCTGCTAATCCTGTTACCAG
TGGCTGCTGCCAGTGGCGATAAGTCGTGTCTTACCGGGTTGGACTCAAGACGATAGTTACCGGATAAGGCG
CAGCGGTCGGGCTGAACGGGGGGTTCGTGCACACAGCCCAGCTTGGAGCGAACGACCTACACCGAACTGAG
ATACCTACAGCGTGAGCTATGAGAAAGCGCCACGCTTCCCGAAGGGAGAAAGCGGACAGGTATCCGGTAA
GCGGCAGGGTCGGAACAGGAGAGCGCACGAGGGAGCTTCCAGGGGAAACGCCTGGTATCTTTATAGTCCT
GTCGGGTTTCGCCACCTCTGACTTGAGCGTCGATTTTTGTGATGCTCGTCAGGGGGCGGAGCCTATGGAA
AAACGCCAGCAACGCGGCCTTTTTACGGTTCCTGGCCTTTTGCTGGCCTTTTGCTCACATGT

SEQ ID NO.18: coFVIIIdeltaB

ATGCAGATCGAGCTGTCCACCTGCTTTTTTCTGTGCCTGCTGCGGTTCTGCTTCAGCGCCACCCGGCGGTA
CTACCTGGGCGCCGTGGAGCTGTCCTGGGACTACATGCAGAGCGACCTGGGCGAGCTGCCCGTGGACGCCC
GGTTCCCCCCCAGAGTGCCCAAGAGCTTCCCCTTCAACACCAGCGTGGTGTACAAGAAACCCTGTTCGTG
GAGTTCACCGACCACCTGTTCAATATCGCCAAGCCCAGGCCCCCTGGATGGGCCTGCTGGGCCCCACCAT
CCAGGCCGAGGTGTACGACACCGTGGTGATCACCCTGAAGAACATGGCCAGCCACCCCGTGAGCCTGCACG
CCGTGGGCGTGAGCTACTGGAAGGCCAGCGAGGGCGCCGAGTACGACGACCAGACCAGCCAGCGGGAGAAA
GAAGATGACAAGGTGTTCCCTGGCGGCAGCCACACCTACGTGTGGCAGGTGCTGAAAGAAAACGGCCCCAT
GGCCTCCGACCCCCTGTGCCTGACCTACAGCTACCTGAGCCACGTGGACCTGGTGAAGGACCTGAACAGCG
GCCTGATCGGCGCTCTGCTCGTCTGCCGGGAGGGCAGCCTGGCCAAAGAGAAAACCCAGACCCTGCACAAG
TTCATCCTGCTGTTCGCCGTGTTCGACGAGGGCAAGAGCTGGCACAGCGAGACAAAGAACAGCCTGATGCA
GGACCGGGACGCCGCCTCTGCCAGAGCCTGGCCCAAGATGCACACCGTGAACGGCTACGTGAACAGAAGCC
TGCCCGGCCTGATTGGCTGCCACCGGAAGAGCGTGTACTGGCACGTGATCGGCATGGGCACCACACCCGAG
GTGCACAGCATCTTTCTGGAAGGGCACACCTTTCTGGTCCGGAACCACCGGCAGGCCAGCCTGGAAATCAG
CCCTATCACCTTCCTGACCGCCCAGACACTGCTGATGGACCTGGGCCAGTTCCTGCTGTTTTGCCACATCA
GCTCTCACCAGCACGACGGCATGGAAGCCTACGTGAAGGTGGACTCTTGCCCCGAGGAACCCCAGCTGCGG
ATGAAGAACAACGAGGAAGCCGAGGACTACGACGACGACCTGACCGACAGCGAGATGGACGTGGTGCGGTT
CGACGACGACAACAGCCCCAGCTTCATCCAGATCAGAAGCGTGGCCAAGAAGCACCCCAAGACCTGGGTGC
ACTATATCGCCGCCGAGGAAGAGGACTGGGACTACGCCCCCTGGTGCTGGCCCCGACGACAGAAGCTAC
AAGAGCCAGTACCTGAACAATGGCCCCCAGCGGATCGGCCGGAAGTACAAGAAAGTGCGGTTCATGGCCTA
CACCGACGAGACATTCAAGACCCGGGAGGCCATCCAGCACGAGAGCGGCATCCTGGGCCCCCTGCTGTACG
GCGAAGTGGGCGACACACTGCTGATCATCTTCAAGAACCAGGCTAGCCGGCCCTACAACATCTACCCCCAC
GGCATCACCGACGTGCGGCCCCTGTACAGCAGGCGGCTGCCCAAGGGCGTGAAGCACCTGAAGGACTTCCC
CATCCTGCCCGGCGAGATCTTCAAGTACAAGTGGACCGTGACCGTGGAGGACGGCCCCACCAAGAGCGACC
CCAGATGCCTGACCCGGTACTACAGCAGCTTCGTGAACATGGAACGGGACCTGGCCTCCGGGCTGATCGGA
CCTCTGCTGATCTGCTACAAAGAAAGCGTGGACCAGCGGGGCAACCAGATCATGAGCGACAAGCGGAACGT
GATCCTGTTCAGCGTGTTCGATGAGAACCGGTCCTGGTATCTGACCGAGAACATCCAGCGGTTTCTGCCCA
ACCCTGCCGGCGTGCAGCTGGAAGATCCCGAGTTCCAGGCCAGCAACATCATGCACTCCATCAATGGCTAC
GTGTTCGACTCTCTGCAGCTCTCCGTGTGTCTGCACGAGGTGGCCTACTGGTACATCCTGAGCATCGGCGC
CCAGACCGACTTCCTGAGCGTGTTCTTCAGCGGCTACACCTTCAAGCACAAGATGGTGTACGAGGACACCC
TGACCCTGTTCCCTTTCAGCGGCGAGACAGTGTTCATGAGCATGGAAAACCCCGGCCTGTGGATTCTGGGC
TGCCACAACAGCGACTTCCGGAACCGGGGCATGACCGCCCTGCTGAAGGTGTCCAGCTGCGACAAGAACAC
CGGCGACTACTACGAGGACAGCTACGAGGATATCAGCGCCTACCTGCTGTCCAAGAACAACGCCATCGAAC
CCCGGAGCTTCAGCCAGAACCCCCCGTGCTGACGCGTCACCAGCGGGAGATCACCCGGACAACCCTGCAG
TCCGACCAGGAAGAGATCGATTACGACGACACCATCAGCGTGGAGATGAAGAAAGAGGATTTCGATATCTA
```

Figure 14 (continued)

CGACGAGGACGAGAACCAGAGCCCCAGAAGCTTCCAGAAGAAAACCCGGCACTACTTCATTGCCGCCGTGG
AGAGGCTGTGGGACTACGGCATGAGTTCTAGCCCCCACGTGCTGCGGAACCGGGCCCAGAGCGGCAGCGTG
CCCCAGTTCAAGAAAGTGGTGTTCCAGGAATTCACAGACGGCAGCTTCACCCAGCCTCTGTATAGAGGCGA
GCTGAACGAGCACCTGGGGCTGCTGGGGCCCTACATCAGGGCCGAAGTGGAGGACAACATCATGGTGACCT
TCCGGAATCAGGCCAGCAGACCCTACTCCTTCTACAGCAGCCTGATCAGCTACGAAGAGGACCAGCGGCAG
GGCGCCGAACCCCGGAAGAACTTCGTGAAGCCCAACGAAACCAAGACCTACTTCTGGAAAGTGCAGCACCA
CATGGCCCCCACCAAGGACGAGTTCGACTGCAAGGCCTGGGCCTACTTCAGCGACGTGGATCTGGAAAAGG
ACGTGCACTCTGGACTGATTGGCCCACTCCTGGTCTGCCACACTAACACCCTCAACCCCGCCCACGGCCGC
CAGGTGACCGTGCAGGAATTCGCCCTGTTCTTCACCATCTTCGACGAGACAAAGTCCTGGTACTTCACCGA
GAATATGGAACGGAACTGCAGAGCCCCCTGCAACATCCAGATGGAAGATCCTACCTTCAAAGAGAACTACC
GGTTCCACGCCATCAACGGCTACATCATGGACACCCTGCCTGGCCTGGTGATGGCCCAGGACCAGAGAATC
CGGTGGTATCTGCTGTCCATGGGCAGCAACGAGAATATCCACAGCATCCACTTCAGCGGCCACGTGTTCAC
CGTGCGGAAGAAAGAAGAGTACAAGATGGCCCTGTACAACCTGTACCCCGGCGTGTTCGAGACAGTGGAGA
TGCTGCCCAGCAAGGCCGGCATCTGGCGGGTGGAGTGTCTGATCGGCGAGCACCTGCACGCTGGCATGAGC
ACCCTGTTTCTGGTGTACAGCAACAAGTGCCAGACCCCACTGGGCATGGCCTCTGGCCACATCCGGGACTT
CCAGATCACCGCCTCCGGCCAGTACGGCCAGTGGGCCCCCAAGCTGGCCAGACTGCACTACAGCGGCAGCA
TCAACGCCTGGTCCACCAAAGAGCCCTTCAGCTGGATCAAGGTGGACCTGCTGGCCCCTATGATCATCCAC
GGCATTAAGACCCAGGGCGCCAGGCAGAAGTTCAGCAGCCTGTACATCAGCCAGTTCATCATCATGTACAG
CCTGGACGGCAAGAAGTGGCAGACCTACCGGGGCAACAGCACCGGCACCCTGATGGTGTTCTTCGGCAATG
TGGACAGCAGCGGCATCAAGCACAACATCTTCAACCCCCCCATCATTGCCCGGTACATCCGGCTGCACCCC
ACCCACTACAGCATTAGATCCACACTGAGAATGGAACTGATGGGCTGCGACCTGAACTCCTGCAGCATGCC
TCTGGGCATGGAAAGCAAGGCCATCAGCGACGCCCAGATCACAGCCAGCAGCTACTTCACCAACATGTTCG
CCACCTGGTCCCCCTCCAAGGCCAGGCTGCACCTGCAGGGCCGGTCCAACGCCTGGCGGCCTCAGGTCAAC
AACCCCAAAGAATGGCTGCAGGTGGACTTTCAGAAAACCATGAAGGTGACCGGCGTGACCACCCAGGGCGT
GAAAGCCTGCTGACCAGCATGTACGTGAAAGAGTTTCTGATCAGCAGCTCTCAGGATGGCCACCAGTGGA
CCCTGTTCTTTCAGAACGGCAAGGTGAAAGTGTTCCAGGGCAACCAGGACTCCTTCACCCCCGTGGTGAAC
TCCCTGGACCCCCCCTGCTGACCCGCTACCTGAGAATCCACCCCAGTCTTGGGTGCACCAGATCGCCCT
CAGGATGGAAGTCCTGGGATGTGAGGCCCAGGATCTGTACTGATGA

SEQ ID NO.19: SV40polyA

ATGCTTTATTTGTGAAATTTGTGATGCTATTGCTTTATTTGTAACCATTATAAGCTGCAATAAACAAGTTA
ACAACAACAATTGCATTCATTTTATGTTTCAGGTTCAGGGGGAGGTGTGGGAGGTTTTTTAAA

SEQ ID NO.20: pAAVss-3xSerpEnh-TTRm-MVM-coFVIIIdeltaB-Synt.pA

CCTGCAGGCAGCTGCGCGCTCGCTCGCTCACTGAGGCCGCCCGGGCAAAGCCCGGGCGTCGGGCGACCTTT
GGTCGCCCGGCCTCAGTGAGCGAGCGAGCGCGCAGAGAGGGAGTGGCCAACTCCATCACTAGGGGTTCCTG
CGGCCGCGGTACGCGGGGGAGGCTGCTGGTGAATATTAACCAAGGTCACCCCAGTTATCGGAGGAGCAAAC
AGGGGCTAAGTCCACCGGGGGAGGCTGCTGGTGAATATTAACCAAGGTCACCCCAGTTATCGGAGGAGCAA
ACAGGGGCTAAGTCCACCGGGGGAGGCTGCTGGTGAATATTAACCAAGGTCACCCCAGTTATCGGAGGAGC
AAACAGGGGCTAAGTCCACTGTACAACGCGTGAATTCGCTAGCGTCTGTCTGCACATTTCGTAGAGCGAGT
GTTCCGATACTCTAATCTCCCTAGGCAAGGTTCATATTTGTGTAGGTTACTTATTCTCCTTTTGTTGACTA
AGTCAATAATCAGAATCAGCAGGTTTGGAGTCAGCTTGGCAGGGATCAGCAGCCTGGGTTGGAAGGAGGGG
GTATAAAAGCCCCTTCACCAGGAGAAGCCGTCACACAGATCCACAAGCTCCTGTCTAGAAAGAGGTAAGGG
TTTAAGGGATGGTTGGTTGGTGGGGTATTAATGTTTAATTACCTGGAGCACCTGCCTGAAATCACTTTTTT
TCAGGTTGGGCTAGCATGCAGATCGAGCTGTCCACCTGCTTTTTTCTGTGCCTGCTGCGGTTCTGCTTCAG
CGCCACCCGGCGGTACTACCTGGGCGCCGTGGAGCTGTCCTGGGACTACATGCAGAGCGACCTGGGCGAGC
TGCCCGTGGACGCCCGGTTCCCCCCAGAGTGCCCAAGAGCTTCCCCTTCAACACCAGCGTGGTGTACAAG
AAAACCCTGTTCGTGGAGTTCACCGACCACCTGTTCAATATCGCCAAGCCCAGGCCCCCTGGATGGGCCT
GCTGGGCCCCACCATCCAGGCCGAGGTGTACGACACCGTGGTGATCACCCTGAAGAACATGGCCAGCCACC
CCGTGAGCCTGCACGCCGTGGGCGTGAGCTACTGGAAGGCCAGCGAGGGCGCCGAGTACGACGACCAGACC
AGCCAGCGGGAGAAGAAGATGACAAGGTGTTCCCTGGCGGCAGCCACACCTACGTGTGGCAGGTGCTGAA
AGAAAACGGCCCCATGGCCTCCGACCCCCTGTGCCTGACCTACAGCTACCTGAGCCACGTGGACCTGGTGA
AGGACCTGAACAGCGGCCTGATCGGCGCTCTGCTCGTCTGCCGGGAGGGCAGCCTGGCCAAAGAGAAACC

Figure 14 (continued)

```
CAGACCCTGCACAAGTTCATCCTGCTGTTCGCCGTGTTCGACGAGGGCAAGAGCTGGCACAGCGAGACAAA
GAACAGCCTGATGCAGGACCGGGACGCCGCCTCTGCCAGAGCCTGGCCCAAGATGCACACCGTGAACGGCT
ACGTGAACAGAAGCCTGCCCGGCCTGATTGGCTGCCACCGGAAGAGCGTGTACTGGCACGTGATCGGCATG
GGCACCACACCCGAGGTGCACAGCATCTTTCTGGAAGGGCACACCTTTCTGGTCCGGAACCACCGGCAGGC
CAGCCTGGAAATCAGCCCTATCACCTTCCTGACCGCCCAGACACTGCTGATGGACCTGGGCCAGTTCCTGC
TGTTTTGCCACATCAGCTCTCACCAGCACGACGGCATGGAAGCCTACGTGAAGGTGGACTCTTGCCCCGAG
GAACCCCAGCTGCGGATGAAGAACAACGAGGAAGCCGAGGACTACGACGACGACCTGACCGACAGCGAGAT
GGACGTGGTGCGGTTCGACGACGACAACAGCCCCAGCTTCATCCAGATCAGAAGCGTGGCCAAGAAGCACC
CCAAGACCTGGGTGCACTATATCGCCGCCGAGGAAGAGGACTGGGACTACGCCCCCCTGGTGCTGGCCCCC
GACGACAGAAGCTACAAGAGCCAGTACCTGAACAATGGCCCCCAGCGGATCGGCCGGAAGTACAAGAAAGT
GCGGTTCATGGCCTACACCGACGAGACATTCAAGACCCGGGAGGCCATCCAGCACGAGAGCGGCATCCTGG
GCCCCCTGCTGTACGGCGAAGTGGGCGACACACTGCTGATCATCTTCAAGAACCAGGCTAGCCGGCCCTAC
AACATCTACCCCCACGGCATCACCGACGTGCGGCCCCTGTACAGCAGGCGGCTGCCCAAGGGCGTGAAGCA
CCTGAAGGACTTCCCCATCCTGCCCGGCGAGATCTTCAAGTACAAGTGGACCGTGACCGTGGAGGACGGCC
CCACCAAGAGCGACCCCAGATGCCTGACCCGGTACTACAGCAGCTTCGTGAACATGGAACGGGACCTGGCC
TCCGGGCTGATCGGACCTCTGCTGATCTGCTACAAAGAAAGCGTGGACCAGCGGGGCAACCAGATCATGAG
CGACAAGCGGAACGTGATCCTGTTCAGCGTGTTCGATGAGAACCGGTCCTGGTATCTGACCGAGAACATCC
AGCGGTTTCTGCCCAACCCTGCCGGCGTGCAGCTGGAAGATCCCGAGTTCCAGGCCAGCAACATCATGCAC
TCCATCAATGGCTACGTGTTCGACTCTCTGCAGCTCTCCGTGTGTCTGCACGAGGTGGCCTACTGGTACAT
CCTGAGCATCGGCGCCCAGACCGACTTCCTGAGCGTGTTCTTCAGCGGCTACACCTTCAAGCACAAGATGG
TGTACGAGGACACCCTGACCCTGTTCCCTTTCAGCGGCGAGACAGTGTTCATGAGCATGGAAAACCCCGGC
CTGTGGATTCTGGGCTGCCACAACAGCGACTTCCGGAACCGGGGCATGACCGCCCTGCTGAAGGTGTCCAG
CTGCGACAAGAACACCGGCGACTACTACGAGGACAGCTACGAGGATATCAGCGCCTACCTGCTGTCCAAGA
ACAACGCCATCGAACCCCGGAGCTTCAGCCAGAACCCCCCGTGCTGACGCGTCACCAGCGGGAGATCACC
CGGACAACCCTGCAGTCCGACCAGGAAGAGATCGATTACGACGACACCATCAGCGTGGAGATGAAGAAAGA
GGATTTCGATATCTACGACGAGGACGAGAACCAGAGCCCCAGAAGCTTCCAGAAGAAAACCCGGCACTACT
TCATTGCCGCCGTGGAGAGGCTGTGGGACTACGGCATGAGTTCTAGCCCCCACGTGCTGCGGAACCGGGCC
CAGAGCGGCAGCGTGCCCCAGTTCAAGAAAGTGGTGTTCCAGGAATTCACAGACGGCAGCTTCACCCAGCC
TCTGTATAGAGGCGAGCTGAACGAGCACCTGGGGCTGCTGGGGCCCTACATCAGGGCCGAAGTGGAGGACA
ACATCATGGTGACCTTCCGGAATCAGGCCAGCAGACCCTACTCCTTCTACAGCAGCCTGATCAGCTACGAA
GAGGACCAGCGGCAGGGCGCCGAACCCCGGAAGAACTTCGTGAAGCCCAACGAAACCAAGACCTACTTCTG
GAAAGTGCAGCACCACATGGCCCCCACCAAGGACGAGTTCGACTGCAAGGCCTGGGCCTACTTCAGCGACG
TGGATCTGGAAAAGGACGTGCACTCTGGACTGATTGGCCCACTCCTGGTCTGCCACACTAACACCCTCAAC
CCCGCCCACGGCCGCCAGGTGACCGTGCAGGAATTCGCCCTGTTCTTCACCATCTTCGACGAGACAAAGTC
CTGGTACTTCACCGAGAATATGGAACGGAACTGCAGAGCCCCCTGCAACATCCAGATGGAAGATCCTACCT
TCAAAGAGAACTACCGGTTCCACGCCATCAACGGCTACATCATGGACACCCTGCCTGGCCTGGTGATGGCC
CAGGACCAGAGAATCCGGTGGTATCTGCTGTCCATGGGCAGCAACGAGAATATCCACAGCATCCACTTCAG
CGGCCACGTGTTCACCGTGCGGAAGAAAGAAGAGTACAAGATGGCCCTGTACAACCTGTACCCCGGCGTGT
TCGAGACAGTGGAGATGCTGCCCAGCAAGGCCGGCATCTGGCGGGTGGAGTGTCTGATCGGCGAGCACCTG
CACGCTGGCATGAGCACCCTGTTTCTGGTGTACAGCAACAAGTGCCAGACCCCACTGGGCATGGCCTCTGG
CCACATCCGGGACTTCCAGATCACCGCCTCCGGCCAGTACGGCCAGTGGGCCCCCAAGCTGGCCAGACTGC
ACTACAGCGGCAGCATCAACGCCTGGTCCACCAAAGAGCCCTTCAGCTGGATCAAGGTGGACCTGCTGGCC
CCTATGATCATCCACGGCATTAAGACCCAGGGCGCCAGGCAGAAGTTCAGCAGCCTGTACATCAGCCAGTT
CATCATCATGTACAGCCTGGACGGCAAGAAGTGGCAGACCTACCGGGGCAACAGCACCGGCACCCTGATGG
TGTTCTTCGGCAATGTGGACAGCAGCGGCATCAAGCACAACATCTTCAACCCCCCCATCATTGCCCGGTAC
ATCCGGCTGCACCCCACCCACTACAGCATTAGATCCACACTGAGAATGGAACTGATGGGCTGCGACCTGAA
CTCCTGCAGCATGCCTCTGGGCATGGAAAGCAAGGCCATCAGCGACGCCCAGATCACAGCCAGCAGCTACT
TCACCAACATGTTCGCCACCTGGTCCCCCTCCAAGGCCAGGCTGCACCTGCAGGGCCGGTCCAACGCCTGG
CGGCCTCAGGTCAACAACCCCAAAGAATGGCTGCAGGTGGACTTTCAGAAAACCATGAAGGTGACCGGCGT
GACCACCCAGGGCGTGAAAAGCCTGCTGACCAGCATGTACGTGAAAGAGTTTCTGATCAGCAGCTCTCAGG
ATGGCCACCAGTGGACCCTGTTCTTTCAGAACGGCAAGGTGAAAGTGTTCCAGGGCAACCAGGACTCCTTC
ACCCCCGTGGTGAACTCCCTGGACCCCCCCCTGCTGACCCGCTACCTGAGAATCCACCCCCAGTCTTGGGT
GCACCAGATCGCCCTCAGGATGGAAGTCCTGGGATGTGAGGCCCAGGATCTGTACTGATGAGGATCTAGGC
TCGACAATAAAAGATCTTTATTTTCATTAGATCTGTGTGTTGGTTTTTTGTGTGCTCAGATCCACGGCCG
CAGGAACCCCTAGTGATGGAGTTGGCCACTCCCTCTCTGCGCGCTCGCTCGCTCACTGAGGCCGGGCGACC
```

Figure 14 (continued)

```
AAAGGTCGCCCGACGCCCGGGCTTTGCCCGGGCGGCCTCAGTGAGCGAGCGAGCGCGCAGCTGCCTGCAGG
GGCGCCTGATGCGGTATTTTCTCCTTACGCATCTGTGCGGTATTTCACACCGCATACGTCAAAGCAACCAT
AGTACGCGCCCTGTAGCGGCGCATTAAGCGCGGCGGGTGTGGTGGTTACGCGCAGCGTGACCGCTACACTT
GCCAGCGCCCTAGCGCCCGCTCCTTTCGCTTTCTTCCCTTCCTTTCTCGCCACGTTCGCCGGCTTTCCCCG
TCAAGCTCTAAATCGGGGGCTCCCTTTAGGGTTCCGATTTAGTGCTTTACGGCACCTCGACCCCAAAAAAC
TTGATTTGGGTGATGGTTCACGTAGTGGGCCATCGCCCTGATAGACGGTTTTTCGCCCTTTGACGTTGGAG
TCCACGTTCTTTAATAGTGGACTCTTGTTCCAAACTGGAACAACACTCAACCCTATCTCGGGCTATTCTTT
TGATTTATAAGGGATTTTGCCGATTTCGGCCTATTGGTTAAAAAATGAGCTGATTTAACAAAAATTTAACG
CGAATTTTAACAAAATATTAACGTTTACAATTTTATGGTGCACTCTCAGTACAATCTGCTCTGATGCCGCA
TAGTTAAGCCAGCCCCGACACCCGCCAACACCCGCTGACGCGCCCTGACGGGCTTGTCTGCTCCCGGCATC
CGCTTACAGACAAGCTGTGACCGTCTCCGGGAGCTGCATGTGTCAGAGGTTTTCACCGTCATCACCGAAAC
GCGCGAGACGAAAGGGCCTCGTGATACGCCTATTTTTATAGGTTAATGTCATGATAATAATGGTTTCTTAG
ACGTCAGGTGGCACTTTTCGGGGAAATGTGCGCGGAACCCCTATTTGTTTATTTTTCTAAATACATTCAAA
TATGTATCCGCTCATGAGACAATAACCCTGATAAATGCTTCAATAATATTGAAAAAGGAAGAGTATGAGTA
TTCAACATTTCCGTGTCGCCCTTATTCCCTTTTTTGCGGCATTTTGCCTTCCTGTTTTTGCTCACCCAGAA
ACGCTGGTGAAAGTAAAAGATGCTGAAGATCAGTTGGGTGCACGAGTGGGTTACATCGAACTGGATCTCAA
CAGCGGTAAGATCCTTGAGAGTTTTCGCCCCGAAGAACGTTTTCCAATGATGAGCACTTTTAAAGTTCTGC
TATGTGGCGCGGTATTATCCCGTATTGACGCCGGGCAAGAGCAACTCGGTCGCCGCATACACTATTCTCAG
AATGACTTGGTTGAGTACTCACCAGTCACAGAAAAGCATCTTACGGATGGCATGACAGTAAGAGAATTATG
CAGTGCTGCCATAACCATGAGTGATAACACTGCGGCCAACTTACTTCTGACAACGATCGGAGGACCGAAGG
AGCTAACCGCTTTTTTGCACAACATGGGGGATCATGTAACTCGCCTTGATCGTTGGGAACCGGAGCTGAAT
GAAGCCATACCAAACGACGAGCGTGACACCACGATGCCTGTAGCAATGGCAACAACGTTGCGCAAACTATT
AACTGGCGAACTACTTACTCTAGCTTCCCGGCAACAATTAATAGACTGGATGGAGGCGGATAAAGTTGCAG
GACCACTTCTGCGCTCGGCCCTTCCGGCTGGCTGGTTTATTGCTGATAAATCTGGAGCCGGTGAGCGTGGG
TCTCGCGGTATCATTGCAGCACTGGGGCCAGATGGTAAGCCCTCCCGTATCGTAGTTATCTACACGACGGG
GAGTCAGGCAACTATGGATGAACGAAATAGACAGATCGCTGAGATAGGTGCCTCACTGATTAAGCATTGGT
AACTGTCAGACCAAGTTTACTCATATATACTTTAGATTGATTTAAAACTTCATTTTTAATTTAAAAGGATC
TAGGTGAAGATCCTTTTTGATAATCTCATGACCAAAATCCCTTAACGTGAGTTTTCGTTCCACTGAGCGTC
AGACCCCGTAGAAAAGATCAAAGGATCTTCTTGAGATCCTTTTTTTCTGCGCGTAATCTGCTGCTTGCAAA
CAAAAAAACCACCGCTACCAGCGGTGGTTTGTTTGCCGGATCAAGAGCTACCAACTCTTTTTCCGAAGGTA
ACTGGCTTCAGCAGAGCGCAGATACCAAATACTGTCCTTCTAGTGTAGCCGTAGTTAGGCCACCACTTCAA
GAACTCTGTAGCACCGCCTACATACCTCGCTCTGCTAATCCTGTTACCAGTGGCTGCTGCCAGTGGCGATA
AGTCGTGTCTTACCGGGTTGGACTCAAGACGATAGTTACCGGATAAGGCGCAGCGGTCGGGCTGAACGGGG
GGTTCGTGCACACAGCCCAGCTTGGAGCGAACGACCTACACCGAACTGAGATACCTACAGCGTGAGCTATG
AGAAAGCGCCACGCTTCCCGAAGGGAGAAAGGCGGACAGGTATCCGGTAAGCGGCAGGGTCGGAACAGGAG
AGCGCACGAGGGAGCTTCCAGGGGGAAACGCCTGGTATCTTTATAGTCCTGTCGGGTTTCGCCACCTCTGA
CTTGAGCGTCGATTTTTGTGATGCTCGTCAGGGGGGCGGAGCCTATGGAAAAACGCCAGCAACGCGGCCTT
TTTACGGTTCCTGGCCTTTTGCTGGCCTTTTGCTCACATGT

SEQ ID NO.21: pAAVss-3xSerpEnh-TTRm-coFVIIIdeltaB-Synt.pA

CCTGCAGGCAGCTGCGCGCTCGCTCGCTCACTGAGGCCGCCCGGGCAAAGCCCGGGCGTCGGGCGACCTTT
GGTCGCCCGGCCTCAGTGAGCGAGCGAGCGCGCAGAGAGGGAGTGGCCAACTCCATCACTAGGGGTTCCTG
CGGCCGCGGTACGCGGGGAGGCTGCTGGTGAATATTAACCAAGGTCACCCCAGTTATCGGAGGAGCAAAC
AGGGGCTAAGTCCACCGGGGGAGGCTGCTGGTGAATATTAACCAAGGTCACCCCAGTTATCGGAGGAGCAA
ACAGGGGCTAAGTCCACCGGGGGAGGCTGCTGGTGAATATTAACCAAGGTCACCCCAGTTATCGGAGGAGC
AAACAGGGGCTAAGTCCACTGTACAACGCGTGAATTCGCTAGCGTCTGTCTGCACATTTCGTAGAGCGAGT
GTTCCGATACTCTAATCTCCCTAGGCAAGGTTCATATTTGTGTAGGTTACTTATTCTCCTTTTGTTGACTA
AGTCAATAATCAGAATCAGCAGGTTTGGAGTCAGCTTGGCAGGGATCAGCAGCCTGGGTTGGAAGGAGGGG
GTATAAAAGCCCCTTCACCAGGAGAAGCCGTCACACAGATCCACAAGCTCCTGCTAGTATGCAGATCGAGC
TGTCCACCTGCTTTTTTCTGTGCCTGCTGCGGTTCTGCTTCAGCGCCACCGGCGGTACTACCTGGGCGCC
GTGGAGCTGTCCTGGGACTACATGCAGAGCGACCTGGGCGAGCTGCCCGTGGACGCCCGGTTCCCCCCAG
AGTGCCCAAGAGCTTCCCCTTCAACACCAGCGTGGTGTACAAGAAAACCCTGTTCGTGGAGTTCACCGACC
ACCTGTTCAATATCGCCAAGCCCAGGCCCCCCTGGATGGGCCTGCTGGGCCCCACCATCCAGGCCGAGGTG
TACGACACCGTGGTGATCACCCTGAAGAACATGGCCAGCCACCCCGTGAGCCTGCACGCCGTGGGCGTGAG
```

Figure 14 (continued)

```
CTACTGGAAGGCCAGCGAGGGCGCCGAGTACGACGACCAGACCAGCCAGCGGGAGAAAGAAGATGACAAGG
TGTTCCCTGGCGGCAGCCACACCTACGTGTGGCAGGTGCTGAAAGAAAACGGCCCCATGGCCTCCGACCCC
CTGTGCCTGACCTACAGCTACCTGAGCCACGTGGACCTGGTGAAGGACCTGAACAGCGGCCTGATCGGCGC
TCTGCTCGTCTGCCGGGAGGGCAGCCTGGCCAAAGAGAAAACCCAGACCCTGCACAAGTTCATCCTGCTGT
TCGCCGTGTTCGACGAGGGCAAGAGCTGGCACAGCGAGACAAAGAACAGCCTGATGCAGGACCGGGACGCC
GCCTCTGCCAGAGCCTGGCCCAAGATGCACACCGTGAACGGCTACGTGAACAGAAGCCTGCCCGGCCTGAT
TGGCTGCCACCGGAAGAGCGTGTACTGGCACGTGATCGGCATGGGCACCACACCCGAGGTGCACAGCATCT
TTCTGGAAGGGCACACCTTTCTGGTCCGGAACCACCGGCAGGCCAGCCTGGAAATCAGCCCTATCACCTTC
CTGACCGCCCAGACACTGCTGATGGACCTGGGCCAGTTCCTGCTGTTTTGCCACATCAGCTCTCACCAGCA
CGACGGCATGGAAGCCTACGTGAAGGTGGACTCTTGCCCCGAGGAACCCCAGCTGCGGATGAAGAACAACG
AGGAAGCCGAGGACTACGACGACGACCTGACCGACAGCGAGATGGACGTGGTGCGGTTCGACGACGACAAC
AGCCCCAGCTTCATCCAGATCAGAAGCGTGGCCAAGAAGCACCCCAAGACCTGGGTGCACTATATCGCCGC
CGAGGAAGAGGACTGGGACTACGCCCCCCTGGTGCTGGCCCCCGACGACAGAAGCTACAAGAGCCAGTACC
TGAACAATGGCCCCCAGCGGATCGGCCGGAAGTACAAGAAAGTGCGGTTCATGGCCTACACCGACGAGACA
TTCAAGACCCGGGAGGCCATCCAGCACGAGAGCGGCATCCTGGGCCCCCTGCTGTACGGCGAAGTGGGCGA
CACACTGCTGATCATCTTCAAGAACCAGGCTAGCCGGCCCTACAACATCTACCCCCACGGCATCACCGACG
TGCGGCCCCTGTACAGCAGGCGGCTGCCCAAGGGCGTGAAGCACCTGAAGGACTTCCCCATCCTGCCCGGC
GAGATCTTCAAGTACAAGTGGACCGTGACCGTGGAGGACGGCCCCACCAAGAGCGACCCCAGATGCCTGAC
CCGGTACTACAGCAGCTTCGTGAACATGGAACGGGACCTGGCCTCCGGGCTGATCGGACCTCTGCTGATCT
GCTACAAAGAAAGCGTGGACCAGCGGGGCAACCAGATCATGAGCGACAAGCGGAACGTGATCCTGTTCAGC
GTGTTCGATGAGAACCGGTCCTGGTATCTGACCGAGAACATCCAGCGGTTTCTGCCCAACCCTGCCGGCGT
GCAGCTGGAAGATCCCGAGTTCCAGGCCAGCAACATCATGCACTCCATCAATGGCTACGTGTTCGACTCTC
TGCAGCTCTCCGTGTGTCTGCACGAGGTGGCCTACTGGTACATCCTGAGCATCGGCGCCCAGACCGACTTC
CTGAGCGTGTTCTTCAGCGGCTACACCTTCAAGCACAAGATGGTGTACGAGGACACCCTGACCCTGTTCCC
TTTCAGCGGCGAGACAGTGTTCATGAGCATGGAAAACCCCGGCCTGTGGATTCTGGGCTGCCACAACAGCG
ACTTCCGGAACCGGGGCATGACCGCCCTGCTGAAGGTGTCCAGCTGCGACAAGAACACCGGCGACTACTAC
GAGGACAGCTACGAGGATATCAGCGCCTACCTGCTGTCCAAGAACAACGCCATCGAACCCCGGAGCTTCAG
CCAGAACCCCCCGTGCTGACGCGTCACCAGCGGGAGATCACCCGGACAACCCTGCAGTCCGACCAGGAAG
AGATCGATTACGACGACACCATCAGCGTGGAGATGAAGAAAGAGGATTTCGATATCTACGACGAGGACGAG
AACCAGAGCCCCAGAAGCTTCCAGAAGAAAACCCGGCACTACTTCATTGCCGCCGTGGAGAGGCTGTGGGA
CTACGGCATGAGTTCTAGCCCCCACGTGCTGCGGAACCGGGCCCAGAGCGGCAGCGTGCCCCAGTTCAAGA
AAGTGGTGTTCCAGGAATTCACAGACGGCAGCTTCACCCAGCCTCTGTATAGAGGCGAGCTGAACGAGCAC
CTGGGGCTGCTGGGGCCCTACATCAGGGCCGAAGTGGAGGACAACATCATGGTGACCTTCCGGAATCAGGC
CAGCAGACCCTACTCCTTCTACAGCAGCCTGATCAGCTACGAAGAGGACCAGCGGCAGGGCGCCGAACCCC
GGAAGAACTTCGTGAAGCCCAACGAAACCAAGACCTACTTCTGGAAAGTGCAGCACCACATGGCCCCCACC
AAGGACGAGTTCGACTGCAAGGCCTGGGCCTACTTCAGCGACGTGGATCTGGAAAAGGACGTGCACTCTGG
ACTGATTGGCCCACTCCTGGTCTGCCACACTAACACCCTCAACCCCGCCCACGGCCGCCAGGTGACCGTGC
AGGAATTCGCCCTGTTCTTCACCATCTTCGACGAGACAAAGTCCTGGTACTTCACCGAGAATATGGAACGG
AACTGCAGAGCCCCCTGCAACATCCAGATGGAAGATCCTACCTTCAAAGAGAACTACCGGTTCCACGCCAT
CAACGGCTACATCATGGACACCCTGCCTGGCCTGGTGATGGCCCAGGACCAGAGAATCCGGTGGTATCTGC
TGTCCATGGGCAGCAACGAGAATATCCACAGCATCCACTTCAGCGGCCACGTGTTCACCGTGCGGAAGAAA
GAAGAGTACAAGATGGCCCTGTACAACCTGTACCCCGGCGTGTTCGAGACAGTGGAGATGCTGCCCAGCAA
GGCCGGCATCTGGCGGGTGGAGTGTCTGATCGGCGAGCACCTGCACGCTGGCATGAGCACCCTGTTTCTGG
TGTACAGCAACAAGTGCCAGACCCCACTGGGCATGGCCTCTGGCCACATCCGGGACTTCCAGATCACCGCC
TCCGGCCAGTACGGCCAGTGGGCCCCCAAGCTGGCCAGACTGCACTACAGCGGCAGCATCAACGCCTGGTC
CACCAAAGAGCCCTTCAGCTGGATCAAGGTGGACCTGCTGGCCCCTATGATCATCCACGGCATTAAGACCC
AGGGCGCCAGGCAGAAGTTCAGCAGCCTGTACATCAGCCAGTTCATCATCATGTACAGCCTGGACGGCAAG
AAGTGGCAGACCTACCGGGGCAACAGCACCGGCACCCTGATGGTGTTCTTCGGCAATGTGGACAGCAGCGG
CATCAAGCACAACATCTTCAACCCCCCCATCATTGCCCGGTACATCCGGCTGCACCCCACCCACTACAGCA
TTAGATCCACACTGAGAATGGAACTGATGGGCTGCGACCTGAACTCCTGCAGCATGCCTCTGGGCATGGAA
AGCAAGGCCATCAGCGACGCCCAGATCACAGCCAGCAGCTACTTCACCAACATGTTCGCCACCTGGTCCCC
CTCCAAGGCCAGGCTGCACCTGCAGGGCCGGTCCAACGCCTGGCGGCCTCAGGTCAACAACCCCAAAGAAT
GGCTGCAGGTGGACTTTCAGAAAACCATGAAGGTGACCGGCGTGACCACCCAGGGCGTGAAAAGCCTGCTG
ACCAGCATGTACGTGAAAGAGTTTCTGATCAGCAGCTCTCAGGATGGCCACCAGTGGACCCTGTTCTTTCA
GAACGGCAAGGTGAAAGTGTTCCAGGGCAACCAGGACTCCTTCACCCCCGTGGTGAACTCCCTGGACCCCC
```

Figure 14 (continued)

```
CCCTGCTGACCCGCTACCTGAGAATCCACCCCCAGTCTTGGGTGCACCAGATCGCCCTCAGGATGGAAGTC
CTGGGATGTGAGGCCCAGGATCTGTACTGATGAGGATCCAATAAAAGATCTTTATTTTCATTAGATCTGTG
TGTTGGTTTTTTGTGTGCTCGAGATCCACGGCCGCAGGAACCCCTAGTGATGGAGTTGGCCACTCCCTCTC
TGCGCGCTCGCTCGCTCACTGAGGCCGGGCGACCAAAGGTCGCCCGACGCCCGGGCTTTGCCCGGGCGGCC
TCAGTGAGCGAGCGAGCGCGCAGCTGCCTGCAGGGGCGCCTGATGCGGTATTTTCTCCTTACGCATCTGTG
CGGTATTTCACACCGCATACGTCAAAGCAACCATAGTACGCGCCCTGTAGCGGCGCATTAAGCGCGGCGGG
TGTGGTGGTTACGCGCAGCGTGACCGCTACACTTGCCAGCGCCCTAGCGCCCGCTCCTTTCGCTTTCTTCC
CTTCCTTTCTCGCCACGTTCGCCGGCTTTCCCCGTCAAGCTCTAAATCGGGGGCTCCCTTTAGGGTTCCGA
TTTAGTGCTTTACGGCACCTCGACCCCAAAAAACTTGATTTGGGTGATGGTTCACGTAGTGGGCCATCGCC
CTGATAGACGGTTTTTCGCCCTTTGACGTTGGAGTCCACGTTCTTTAATAGTGGACTCTTGTTCCAAACTG
GAACAACACTCAACCCTATCTCGGGCTATTCTTTTGATTTATAAGGGATTTTGCCGATTTCGGCCTATTGG
TTAAAAAATGAGCTGATTTAACAAAAATTTAACGCGAATTTTAACAAAATATTAACGTTTACAATTTTATG
GTGCACTCTCAGTACAATCTGCTCTGATGCCGCATAGTTAAGCCAGCCCCGACACCCGCCAACACCCGCTG
ACGCGCCCTGACGGGCTTGTCTGCTCCCGGCATCCGCTTACAGACAAGCTGTGACCGTCTCCGGGAGCTGC
ATGTGTCAGAGGTTTTCACCGTCATCACCGAAACGCGCGAGACGAAAGGGCCTCGTGATACGCCTATTTTT
ATAGGTTAATGTCATGATAATAATGGTTTCTTAGACGTCAGGTGGCACTTTTCGGGGAAATGTGCGCGGAA
CCCCTATTTGTTTATTTTTCTAAATACATTCAAATATGTATCCGCTCATGAGACAATAACCCTGATAAATG
CTTCAATAATATTGAAAAAGGAAGAGTATGAGTATTCAACATTTCCGTGTCGCCCTTATTCCCTTTTTTGC
GGCATTTTGCCTTCCTGTTTTTGCTCACCCAGAAACGCTGGTGAAAGTAAAAGATGCTGAAGATCAGTTGG
GTGCACGAGTGGGTTACATCGAACTGGATCTCAACAGCGGTAAGATCCTTGAGAGTTTTCGCCCCGAAGAA
CGTTTTCCAATGATGAGCACTTTTAAAGTTCTGCTATGTGGCGCGGTATTATCCCGTATTGACGCCGGGCA
AGAGCAACTCGGTCGCCGCATACACTATTCTCAGAATGACTTGGTTGAGTACTCACCAGTCACAGAAAAGC
ATCTTACGGATGGCATGACAGTAAGAGAATTATGCAGTGCTGCCATAACCATGAGTGATAACACTGCGGCC
AACTTACTTCTGACAACGATCGGAGGACCGAAGGAGCTAACCGCTTTTTTGCACAACATGGGGGATCATGT
AACTCGCCTTGATCGTTGGGAACCGGAGCTGAATGAAGCCATACCAAACGACGAGCGTGACACCACGATGC
CTGTAGCAATGGCAACAACGTTGCGCAAACTATTAACTGGCGAACTACTTACTCTAGCTTCCCGGCAACAA
TTAATAGACTGGATGGAGGCGGATAAAGTTGCAGGACCACTTCTGCGCTCGGCCCTTCCGGCTGGCTGGTT
TATTGCTGATAAATCTGGAGCCGGTGAGCGTGGGTCTCGCGGTATCATTGCAGCACTGGGGCCAGATGGTA
AGCCCTCCCGTATCGTAGTTATCTACACGACGGGGAGTCAGGCAACTATGGATGAACGAAATAGACAGATC
GCTGAGATAGGTGCCTCACTGATTAAGCATTGGTAACTGTCAGACCAAGTTTACTCATATATACTTTAGAT
TGATTTAAAACTTCATTTTTAATTTAAAAGGATCTAGGTGAAGATCCTTTTTGATAATCTCATGACCAAAA
TCCCTTAACGTGAGTTTTCGTTCCACTGAGCGTCAGACCCCGTAGAAAAGATCAAAGGATCTTCTTGAGAT
CCTTTTTTTCTGCGCGTAATCTGCTGCTTGCAAACAAAAAAACCACCGCTACCAGCGGTGGTTTGTTTGCC
GGATCAAGAGCTACCAACTCTTTTTCCGAAGGTAACTGGCTTCAGCAGAGCGCAGATACCAAATACTGTCC
TTCTAGTGTAGCCGTAGTTAGGCCACCACTTCAAGAACTCTGTAGCACCGCCTACATACCTCGCTCTGCTA
ATCCTGTTACCAGTGGCTGCTGCCAGTGGCGATAAGTCGTGTCTTACCGGGTTGGACTCAAGACGATAGTT
ACCGGATAAGGCGCAGCGGTCGGGCTGAACGGGGGGTTCGTGCACACAGCCCAGCTTGGAGCGAACGACCT
ACACCGAACTGAGATACCTACAGCGTGAGCTATGAGAAAGCGCCACGCTTCCCGAAGGGAGAAAGGCGGAC
AGGTATCCGGTAAGCGGCAGGGTCGGAACAGGAGAGCGCACGAGGGAGCTTCCAGGGGGAAACGCCTGGTA
TCTTTATAGTCCTGTCGGGTTTCGCCACCTCTGACTTGAGCGTCGATTTTTGTGATGCTCGTCAGGGGGC
GGAGCCTATGGAAAAACGCCAGCAACGCGGCCTTTTTACGGTTCCTGGCCTTTTGCTGGCCTTTTGCTCAC
ATGT

SEQ ID NO.22: pAAVss-3xSerpEnh-TTRe-TTRm-MVM-coFVIIIdeltaB-Sv40pA

CCTGCAGGCAGCTGCGCGCTCGCTCGCTCACTGAGGCCGCCCGGGCAAAGCCCGGGCGTCGGGCGACCTTT
GGTCGCCCGGCCTCAGTGAGCGAGCGAGCGCGCAGAGAGGGAGTGGCCAACTCCATCACTAGGGGTTCCTG
CGGCCGCGGGGGAGGCTGCTGGTGAATATTAACCAAGGTCACCCCAGTTATCGGAGGAGCAAACAGGGGCT
AAGTCCACCGGGGGAGGCTGCTGGTGAATATTAACCAAGGTCACCCCAGTTATCGGAGGAGCAAACAGGGG
CTAAGTCCACCGGGGGAGGCTGCTGGTGAATATTAACCAAGGTCACCCCAGTTATCGGAGGAGCAAACAGG
GGCTAAGTCCACGGTACCCACTGGGAGGATGTTGAGTAAGATGGAAAACTACTGATGACCCTTGCAGAGAC
AGAGTATTAGGACATGTTTGAACAGGGGCCGGGCGATCAGCAGGTAGCTCTAGAGGATCCCGTCTGTCTG
CACATTTCGTAGAGCGAGTGTTCCGATACTCTAATCTCCCTAGGCAAGGTTCATATTTGTGTAGGTTACTT
ATTCTCCTTTTGTTGACTAAGTCAATAATCAGAATCAGCAGGTTTGGAGTCAGCTTGGCAGGGATCAGCAG
CCTGGGTTGGAAGGAGGGGGTATAAAAGCCCCTTCACCAGGAGAAGCCGTCACACAGATCCACAAGCTCCT
```

Figure 14 (continued)

```
GAAGAGGTAAGGGTTTAAGGGATGGTTGGTTGGTGGGGTATTAATGTTTAATTACCTGGAGCACCTGCCTG
AAATCACTTTTTTTCAGGTTGGCTAGTATGCAGATCGAGCTGTCCACCTGCTTTTTTCTGTGCCTGCTGCG
GTTCTGCTTCAGCGCCACCCGGCGGTACTACCTGGGCGCCGTGGAGCTGTCCTGGGACTACATGCAGAGCG
ACCTGGGCGAGCTGCCCGTGGACGCCCGGTTCCCCCCCAGAGTGCCCAAGAGCTTCCCCTTCAACACCAGC
GTGGTGTACAAGAAAACCCTGTTCGTGGAGTTCACCGACCACCTGTTCAATATCGCCAAGCCCAGGCCCCC
CTGGATGGGCCTGCTGGGCCCCACCATCCAGGCCGAGGTGTACGACACCGTGGTGATCACCCTGAAGAACA
TGGCCAGCCACCCCGTGAGCCTGCACGCCGTGGGCGTGAGCTACTGGAAGGCCAGCGAGGGCGCCGAGTAC
GACGACCAGACCAGCCAGCGGGAGAAAGAAGATGACAAGGTGTTCCCTGGCGGCAGCCACACCTACGTGTG
GCAGGTGCTGAAAGAAAACGGCCCCATGGCCTCCGACCCCTGTGCCTGACCTACAGCTACCTGAGCCACG
TGGACCTGGTGAAGGACCTGAACAGCGGCCTGATCGGCGCTCTGCTCGTCTGCCGGGAGGGCAGCCTGGCC
AAAGAGAAAACCCAGACCCTGCACAAGTTCATCCTGCTGTTCGCCGTGTTCGACGAGGGCAAGAGCTGGCA
CAGCGAGACAAAGAACAGCCTGATGCAGGACGGGACGCCGCCTCTGCCAGAGCCTGGCCCAAGATGCACA
CCGTGAACGGCTACGTGAACAGAAGCCTGCCCGGCCTGATTGGCTGCCACCGGAAGAGCGTGTACTGGCAC
GTGATCGGCATGGGCACCACACCCGAGGTGCACAGCATCTTTCTGGAAGGGCACACCTTTCTGGTCCGGAA
CCACCGGCAGGCCAGCCTGGAAATCAGCCCTATCACCTTCCTGACCGCCCAGACACTGCTGATGGACCTGG
GCCAGTTCCTGCTGTTTTGCCACATCAGCTCTCACCAGCACGACGGCATGGAAGCCTACGTGAAGGTGGAC
TCTTGCCCCGAGGAACCCCAGCTGCGGATGAAGAACAACGAGGAAGCCGAGGACTACGACGACGACCTGAC
CGACAGCGAGATGGACGTGGTGCGGTTCGACGACGACAACAGCCCCAGCTTCATCCAGATCAGAAGCGTGG
CCAAGAAGCACCCCAAGACCTGGGTGCACTATATCGCCGCCGAGGAAGAGGACTGGGACTACGCCCCCCTG
GTGCTGGCCCCCGACGACAGAAGCTACAAGAGCCAGTACCTGAACAATGGCCCCCAGCGGATCGGCCGGAA
GTACAAGAAAGTGCGGTTCATGGCCTACACCGACGAGACATTCAAGACCCGGGAGGCCATCCAGCACGAGA
GCGGCATCCTGGGCCCCCTGCTGTACGGCGAAGTGGGCGACACACTGCTGATCATCTTCAAGAACCAGGCT
AGCCGGCCCTACAACATCTACCCCCACGGCATCACCGACGTGCGGCCCCTGTACAGCAGGCGGCTGCCCAA
GGGCGTGAAGCACCTGAAGGACTTCCCCATCCTGCCCGGCGAGATCTTCAAGTACAAGTGGACCGTGACCG
TGGAGGACGGCCCCACCAAGAGCGACCCCAGATGCCTGACCCGGTACTACAGCAGCTTCGTGAACATGGAA
CGGGACCTGGCCTCCGGGCTGATCGGACCTCTGCTGATCTGCTACAAAGAAAGCGTGGACCAGCGGGGCAA
CCAGATCATGAGCGACAAGCGGAACGTGATCCTGTTCAGCGTGTTCGATGAGAACCGGTCCTGGTATCTGA
CCGAGAACATCCAGCGGTTTCTGCCCAACCCTGCCGGCGTGCAGCTGGAAGATCCCGAGTTCCAGGCCAGC
AACATCATGCACTCCATCAATGGCTACGTGTTCGACTCTCTGCAGCTCTCCGTGTGTCTGCACGAGGTGGC
CTACTGGTACATCCTGAGCATCGGCGCCCAGACCGACTTCCTGAGCGTGTTCTTCAGCGGCTACACCTTCA
AGCACAAGATGGTGTACGAGGACACCCTGACCCTGTTCCCTTTCAGCGGCGAGACAGTGTTCATGAGCATG
GAAAACCCCGGCCTGTGGATTCTGGGCTGCCACAACAGCGACTTCCGGAACCGGGGCATGACCGCCCTGCT
GAAGGTGTCCAGCTGCGACAAGAACACCGGCGACTACTACGAGGACAGCTACGAGGATATCAGCGCCTACC
TGCTGTCCAAGAACAACGCCATCGAACCCCGGAGCTTCAGCCAGAACCCCCCGTGCTGACGCGTCACCAG
CGGGAGATCACCCGGACAACCCTGCAGTCCGACCAGGAAGAGATCGATTACGACGACACCATCAGCGTGGA
GATGAAGAAGAGGATTTCGATATCTACGACGAGGACGAGAACCAGAGCCCCAGAAGCTTCCAGAAGAAAA
CCCGGCACTACTTCATTGCCGCCGTGGAGAGGCTGTGGGACTACGGCATGAGTTCTAGCCCCCACGTGCTG
CGGAACCGGGCCCAGAGCGGCAGCGTGCCCCAGTTCAAGAAAGTGGTGTTCCAGGAATTCACAGACGGCAG
CTTCACCCAGCCTCTGTATAGAGGCGAGCTGAACGAGCACCTGGGGCTGCTGGGGCCCTACATCAGGGCCG
AAGTGGAGGACAACATCATGGTGACCTTCCGGAATCAGGCCAGCAGACCCTACTCCTTCTACAGCAGCCTG
ATCAGCTACGAAGAGGACCAGCGGCAGGGCGCCGAACCCCGGAAGAACTTCGTGAAGCCCAACGAAACCAA
GACCTACTTCTGGAAAGTGCAGCACCACATGGCCCCCACCAAGGACGAGTTCGACTGCAAGGCCTGGGCCT
ACTTCAGCGACGTGGATCTGGAAAAGGACGTGCACTCTGGACTGATTGGCCCACTCCTGGTCTGCCACACT
AACACCCTCAACCCCGCCCACGGCCGCCAGGTGACCGTGCAGGAATTCGCCCTGTTCTTCACCATCTTCGA
CGAGACAAAGTCCTGGTACTTCACCGAGAATATGGAACGGAACTGCAGAGCCCCTGCAACATCCAGATGG
AAGATCCTACCTTCAAAGAGAACTACCGGTTCCACGCCATCAACGGCTACATCATGGACACCCTGCCTGGC
CTGGTGATGGCCCAGGACCAGAGAATCCGGTGGTATCTGCTGTCCATGGGCAGCAACGAGAATATCCACAG
CATCCACTTCAGCGGCCACGTGTTCACCGTGCGGAAGAAAGAAGAGTACAAGATGGCCCTGTACAACCTGT
ACCCCGGCGTGTTCGAGACAGTGGAGATGCTGCCCAGCAAGGCCGGCATCTGGCGGGTGGAGTGTCTGATC
GGCGAGCACCTGCACGCTGGCATGAGCACCCTGTTTCTGGTGTACAGCAACAAGTGCCAGACCCCACTGGG
CATGGCCTCTGGCCACATCCGGGACTTCCAGATCACCGCCTCCGGCCAGTACGGCCAGTGGGCCCCCAAGC
TGGCCAGACTGCACTACAGCGGCAGCATCAACGCCTGGTCCACCAAAGAGCCCTTCAGCTGGATCAAGGTG
GACCTGCTGGCCCCTATGATCATCCACGGCATTAAGACCCAGGGCGCCAGGCAGAAGTTCAGCAGCCTGTA
CATCAGCCAGTTCATCATCATGTACAGCCTGGACGGCAAGAAGTGGCAGACCTACCGGGGCAACAGCACCG
GCACCCTGATGGTGTTCTTCGGCAATGTGGACAGCAGCGGCATCAAGCACAACATCTTCAACCCCCCCATC
```

Figure 14 (continued)

```
ATTGCCCGGTACATCCGGCTGCACCCCACCCACTACAGCATTAGATCCACACTGAGAATGGAACTGATGGG
CTGCGACCTGAACTCCTGCAGCATGCCTCTGGGCATGGAAAGCAAGGCCATCAGCGACGCCCAGATCACAG
CCAGCAGCTACTTCACCAACATGTTCGCCACCTGGTCCCCCTCCAAGGCCAGGCTGCACCTGCAGGGCCGG
TCCAACGCCTGGCGGCCTCAGGTCAACAACCCCAAAGAATGGCTGCAGGTGGACTTTCAGAAAACCATGAA
GGTGACCGGCGTGACCACCCAGGGCGTGAAAAGCCTGCTGACCAGCATGTACGTGAAAGAGTTTCTGATCA
GCAGCTCTCAGGATGGCCACCAGTGGACCCTGTTCTTTCAGAACGGCAAGGTGAAAGTGTTCCAGGGCAAC
CAGGACTCCTTCACCCCCGTGGTGAACTCCCTGGACCCCCCCTGCTGACCCGCTACCTGAGAATCCACCC
CCAGTCTTGGGTGCACCAGATCGCCCTCAGGATGGAAGTCCTGGGATGTGAGGCCCAGGATCTGTACTGAT
GAGGATCTAGGCTCGACATGCTTTATTTGTGAAATTTGTGATGCTATTGCTTTATTTGTAACCATTATAAG
CTGCAATAAACAAGTTAACAACAACAATTGCATTCATTTTATGTTTCAGGTTCAGGGGGAGGTGTGGGAGG
TTTTTTAAACTCGAGATCCACGGCCGCAGGAACCCCTAGTGATGGAGTTGGCCACTCCCTCTCTGCGCGCT
CGCTCGCTCACTGAGGCCGGGCGACCAAAGGTCGCCCGACGCCCGGGCTTTGCCCGGGCGGCCTCAGTGAG
CGAGCGAGCGCGCAGCTGCCTGCAGGGGCGCCTGATGCGGTATTTCTCCTTACGCATCTGTGCGGTATTT
CACACCGCATACGTCAAAGCAACCATAGTACGCGCCCTGTAGCGGCGCATTAAGCGCGGCGGGTGTGGTGG
TTACGCGCAGCGTGACCGCTACACTTGCCAGCGCCCTAGCGCCCGCTCCTTTCGCTTTCTTCCCTTCCTTT
CTCGCCACGTTCGCCGGCTTTCCCCGTCAAGCTCTAAATCGGGGGCTCCCTTTAGGGTTCCGATTTAGTGC
TTTACGGCACCTCGACCCCAAAAAACTTGATTTGGGTGATGGTTCACGTAGTGGGCCATCGCCCTGATAGA
CGGTTTTTCGCCCTTTGACGTTGGAGTCCACGTTCTTTAATAGTGGACTCTTGTTCCAAACTGGAACAACA
CTCAACCCTATCTCGGGCTATTCTTTTGATTTATAAGGGATTTTGCCGATTTCGGCCTATTGGTTAAAAAA
TGAGCTGATTTAACAAAAATTTAACGCGAATTTTAACAAAATATTAACGTTTACAATTTTATGGTGCACTC
TCAGTACAATCTGCTCTGATGCCGCATAGTTAAGCCAGCCCCGACACCCGCCAACACCCGCTGACGCGCCC
TGACGGGCTTGTCTGCTCCCGGCATCCGCTTACAGACAAGCTGTGACCGTCTCCGGGAGCTGCATGTGTCA
GAGGTTTTCACCGTCATCACCGAAACGCGCGAGACGAAAGGGCCTCGTGATACGCCTATTTTTATAGGTTA
ATGTCATGATAATAATGGTTTCTTAGACGTCAGGTGGCACTTTTCGGGGAAATGTGCGCGGAACCCCTATT
TGTTTATTTTTCTAAATACATTCAAATATGTATCCGCTCATGAGACAATAACCCTGATAAATGCTTCAATA
ATATTGAAAAAGGAAGAGTATGAGTATTCAACATTTCCGTGTCGCCCTTATTCCCTTTTTTGCGGCATTTT
GCCTTCCTGTTTTTGCTCACCCAGAAACGCTGGTGAAAGTAAAAGATGCTGAAGATCAGTTGGGTGCACGA
GTGGGTTACATCGAACTGGATCTCAACAGCGGTAAGATCCTTGAGAGTTTTCGCCCCGAAGAACGTTTTCC
AATGATGAGCACTTTTAAAGTTCTGCTATGTGGCGCGGTATTATCCCGTATTGACGCCGGGCAAGAGCAAC
TCGGTCGCCGCATACACTATTCTCAGAATGACTTGGTTGAGTACTCACCAGTCACAGAAAAGCATCTTACG
GATGGCATGACAGTAAGAGAATTATGCAGTGCTGCCATAACCATGAGTGATAACACTGCGGCCAACTTACT
TCTGACAACGATCGGAGGACCGAAGGAGCTAACCGCTTTTTTGCACAACATGGGGGATCATGTAACTCGCC
TTGATCGTTGGGAACCGGAGCTGAATGAAGCCATACCAAACGACGAGCGTGACACCACGATGCCTGTAGCA
ATGGCAACAACGTTGCGCAAACTATTAACTGGCGAACTACTTACTCTAGCTTCCCGGCAACAATTAATAGA
CTGGATGGAGGCGGATAAAGTTGCAGGACCACTTCTGCGCTCGGCCCTTCCGGCTGGCTGGTTTATTGCTG
ATAAATCTGGAGCCGGTGAGCGTGGGTCTCGCGGTATCATTGCAGCACTGGGGCCAGATGGTAAGCCCTCC
CGTATCGTAGTTATCTACACGACGGGGAGTCAGGCAACTATGGATGAACGAAATAGACAGATCGCTGAGAT
AGGTGCCTCACTGATTAAGCATTGGTAACTGTCAGACCAAGTTTACTCATATATACTTTAGATTGATTTAA
AACTTCATTTTTAATTTAAAAGGATCTAGGTGAAGATCCTTTTTGATAATCTCATGACCAAAATCCCTTAA
CGTGAGTTTTCGTTCCACTGAGCGTCAGACCCCGTAGAAAAGATCAAAGGATCTTCTTGAGATCCTTTTTT
TCTGCGCGTAATCTGCTGCTTGCAAACAAAAAAACCACCGCTACCAGCGGTGGTTTGTTTGCCGGATCAAG
AGCTACCAACTCTTTTTCCGAAGGTAACTGGCTTCAGCAGAGCGCAGATACCAAATACTGTCCTTCTAGTG
TAGCCGTAGTTAGGCCACCACTTCAAGAACTCTGTAGCACCGCCTACATACCTCGCTCTGCTAATCCTGTT
ACCAGTGGCTGCTGCCAGTGGCGATAAGTCGTGTCTTACCGGGTTGGACTCAAGACGATAGTTACCGGATA
AGGCGCAGCGGTCGGGCTGAACGGGGGGTTCGTGCACACAGCCCAGCTTGGAGCGAACGACCTACACCGAA
CTGAGATACCTACAGCGTGAGCTATGAGAAAGCGCCACGCTTCCCGAAGGGAGAAAGGCGGACAGGTATCC
GGTAAGCGGCAGGGTCGGAACAGGAGAGCGCACGAGGGAGCTTCCAGGGGGAAACGCCTGGTATCTTTATA
GTCCTGTCGGGTTTCGCCACCTCTGACTTGAGCGTCGATTTTTGTGATGCTCGTCAGGGGGCGGAGCCTA
TGGAAAAACGCCAGCAACGCGGCCTTTTTACGGTTCCTGGCCTTTTGCTGGCCTTTTGCTCACATGT
```

SEQ ID NO.23: pAAVss-3xSerpEnh-TTRe-TTRm-coFVIIIdeltaB-Synt.pA

```
CCTGCAGGCAGCTGCGCGCTCGCTCGCTCACTGAGGCCGCCCGGGCAAAGCCCGGGCGTCGGGCGACCTTT
GGTCGCCCGGCCTCAGTGAGCGAGCGAGCGCGCAGAGAGGGAGTGGCCAACTCCATCACTAGGGGTTCCTG
CGGCCGCGGGGGAGGCTGCTGGTGAATATTAACCAAGGTCACCCCAGTTATCGGAGGAGCAAACAGGGGCT
```

Figure 14 (continued)

```
AAGTCCACCGGGGGAGGCTGCTGGTGAATATTAACCAAGGTCACCCCAGTTATCGGAGGAGCAAACAGGGG
CTAAGTCCACCGGGGGAGGCTGCTGGTGAATATTAACCAAGGTCACCCCAGTTATCGGAGGAGCAAACAGG
GGCTAAGTCCACGGTACCCACTGGGAGGATGTTGAGTAAGATGGAAAACTACTGATGACCCTTGCAGAGAC
AGAGTATTAGGACATGTTTGAACAGGGGCCGGGCGATCAGCAGGTAGCTCTAGAGGATCCCCGTCTGTCTG
CACATTTCGTAGAGCGAGTGTTCCGATACTCTAATCTCCCTAGGCAAGGTTCATATTTGTGTAGGTTACTT
ATTCTCCTTTTGTTGACTAAGTCAATAATCAGAATCAGCAGGTTTGGAGTCAGCTTGGCAGGGATCAGCAG
CCTGGGTTGGAAGGAGGGGTATAAAAGCCCCTTCACCAGGAGAAGCCGTCACACAGATCCACAAGCTCCT
GCTAGTATGCAGATCGAGCTGTCCACCTGCTTTTTTCTGTGCCTGCTGCGGTTCTGCTTCAGCGCCACCCG
GCGGTACTACCTGGGCGCCGTGGAGCTGTCCTGGGACTACATGCAGAGCGACCTGGGCGAGCTGCCCGTGG
ACGCCCGGTTCCCCCCAGAGTGCCCAAGAGCTTCCCCTTCAACACCAGCGTGGTGTACAAGAAAACCCTG
TTCGTGGAGTTCACCGACCACCTGTTCAATATCGCCAAGCCCAGGCCCCCTGGATGGGCCTGCTGGGCCC
CACCATCCAGGCCGAGGTGTACGACACCGTGGTGATCACCCTGAAGAACATGGCCAGCCACCCCGTGAGCC
TGCACGCCGTGGGCGTGAGCTACTGGAAGGCCAGCGAGGGCGCCGAGTACGACGACCAGACCAGCCAGCGG
GAGAAGAAGATGACAAGGTGTTCCCTGGCGGCAGCCACACCTACGTGTGGCAGGTGCTGAAAGAAAACGG
CCCCATGGCCTCCGACCCCCTGTGCCTGACCTACAGCTACCTGAGCCACGTGGACCTGGTGAAGGACCTGA
ACAGCGGCCTGATCGGCGCTCTGCTCGTCTGCCGGGAGGGCAGCCTGGCCAAAGAGAAACCCAGACCCTG
CACAAGTTCATCCTGCTGTTCGCCGTGTTCGACGAGGGCAAGAGCTGGCACAGCGAGACAAAGAACAGCCT
GATGCAGGACCGGGACGCCGCCTCTGCCAGAGCCTGGCCCAAGATGCACACCGTGAACGGCTACGTGAACA
GAAGCCTGCCCGGCCTGATTGGCTGCCACCGGAAGAGCGTGTACTGGCACGTGATCGGCATGGGCACCACA
CCCGAGGTGCACAGCATCTTTCTGGAAGGGCACACCTTTCTGGTCCGGAACCACCGGCAGGCCAGCCTGGA
AATCAGCCCTATCACCTTCCTGACCGCCCAGACACTGCTGATGGACCTGGGCCAGTTCCTGCTGTTTTGCC
ACATCAGCTCTCACCAGCACGACGGCATGGAAGCCTACGTGAAGGTGGACTCTTGCCCCGAGGAACCCCAG
CTGCGGATGAAGAACAACGAGGAAGCCGAGGACTACGACGACGACCTGACCGACAGCGAGATGGACGTGGT
GCGGTTCGACGACGACAACAGCCCCAGCTTCATCCAGATCAGAAGCGTGGCCAAGAAGCACCCCAAGACCT
GGGTGCACTATATCGCCGCCGAGGAAGAGGACTGGGACTACGCCCCCTGGTGCTGGCCCCGACGACAGA
AGCTACAAGAGCCAGTACCTGAACAATGGCCCCAGCGGATCGGCCGGAAGTACAAGAAAGTGCGGTTCAT
GGCCTACACCGACGAGACATTCAAGACCCGGGAGGCCATCCAGCACGAGAGCGGCATCCTGGGCCCCCTGC
TGTACGGCGAAGTGGGCGACACACTGCTGATCATCTTCAAGAACCAGGCTAGCCGGCCCTACAACATCTAC
CCCCACGGCATCACCGACGTGCGGCCCCTGTACAGCAGGCGGCTGCCCAAGGGCGTGAAGCACCTGAAGGA
CTTCCCCATCCTGCCCGGCGAGATCTTCAAGTACAAGTGGACCGTGACCGTGGAGGACGGCCCCACCAAGA
GCGACCCCAGATGCCTGACCCGGTACTACAGCAGCTTCGTGAACATGGAACGGGACCTGGCCTCCGGGCTG
ATCGGACCTCTGCTGATCTGCTACAAAGAAAGCGTGGACCAGCGGGGCAACCAGATCATGAGCGACAAGCG
GAACGTGATCCTGTTCAGCGTGTTCGATGAGAACCGGTCCTGGTATCTGACCGAGAACATCCAGCGGTTTC
TGCCCAACCCTGCCGGCGTGCAGCTGGAAGATCCCGAGTTCCAGGCCAGCAACATCATGCACTCCATCAAT
GGCTACGTGTTCGACTCTCTGCAGCTCTCCGTGTGTCTGCACGAGGTGGCCTACTGGTACATCCTGAGCAT
CGGCGCCCAGACCGACTTCCTGAGCGTGTTCTTCAGCGGCTACACCTTCAAGCACAAGATGGTGTACGAGG
ACACCCTGACCCTGTTCCCTTTCAGCGGCGAGACAGTGTTCATGAGCATGGAAAACCCCGGCCTGTGGATT
CTGGGCTGCCACAACAGCGACTTCCGGAACCGGGGCATGACCGCCCTGCTGAAGGTGTCCAGCTGCGACAA
GAACACCGGCGACTACTACGAGGACAGCTACGAGGATATCAGCGCCTACCTGCTGTCCAAGAACAACGCCA
TCGAACCCCGGAGCTTCAGCCAGAACCCCCCGTGCTGACGCGTCACCAGCGGGAGATCACCCGGACAACC
CTGCAGTCCGACCAGGAAGAGATCGATTACGACGACACCATCAGCGTGGAGATGAAGAAGAGGATTTCGA
TATCTACGACGAGGACGAGAACCAGAGCCCCAGAAGCTTCCAGAAGAAACCCGGCACTACTTCATTGCCG
CCGTGGAGAGGCTGTGGGACTACGGCATGAGTTCTAGCCCCCACGTGCTGCGGAACCGGGCCCAGAGCGGC
AGCGTGCCCCAGTTCAAGAAAGTGGTGTTCCAGGAATTCACAGACGGCAGCTTCACCCAGCCTCTGTATAG
AGGCGAGCTGAACGAGCACCTGGGCTGCTGGGCCCTACATCAGGGCCGAAGTGGAGGACAACATCATGG
TGACCTTCCGGAATCAGGCCAGCAGACCCTACTCCTTCTACAGCAGCCTGATCAGCTACGAAGAGGACCAG
CGGCAGGGCGCCGAACCCCGGAAGAACTTCGTGAAGCCCAACGAAACCAAGACCTACTTCTGGAAAGTGCA
GCACCACATGGCCCCCACCAAGGACGAGTTCGACTGCAAGGCCTGGGCCTACTTCAGCGACGTGGATCTGG
AAAAGGACGTGCACTCTGGACTGATTGGCCCACTCCTGGTCTGCCACACTAACACCCTCAACCCCGCCCAC
GGCCGCCAGGTGACCGTGCAGGAATTCGCCCTGTTCTTCACCATCTTCGACGAGACAAAGTCCTGGTACTT
CACCGAGAATATGGAACGGAACTGCAGAGCCCCTGCAACATCCAGATGGAAGATCCTACCTTCAAAGAGA
ACTACCGGTTCCACGCCATCAACGGCTACATCATGGACACCCTGCCTGGCCTGGTGATGGCCCAGGACCAG
AGAATCCGGTGGTATCTGCTGTCCATGGGCAGCAACGAGAATATCCACAGCATCCACTTCAGCGGCCACGT
GTTCACCGTGCGGAAGAAAGAAGAGTACAAGATGGCCCTGTACAACCTGTACCCCGGCGTGTTCGAGACAG
TGGAGATGCTGCCCAGCAAGGCCGGCATCTGGCGGGTGGAGTGTCTGATCGGCGAGCACCTGCACGCTGGC
```

Figure 14 (continued)

```
ATGAGCACCCTGTTTCTGGTGTACAGCAACAAGTGCCAGACCCCACTGGGCATGGCCTCTGGCCACATCCG
GGACTTCCAGATCACCGCCTCCGGCCAGTACGGCCAGTGGGCCCCCAAGCTGGCCAGACTGCACTACAGCG
GCAGCATCAACGCCTGGTCCACCAAAGAGCCCTTCAGCTGGATCAAGGTGGACCTGCTGGCCCCTATGATC
ATCCACGGCATTAAGACCCAGGGCGCCAGGCAGAAGTTCAGCAGCCTGTACATCAGCCAGTTCATCATCAT
GTACAGCCTGGACGGCAAGAAGTGGCAGACCTACCGGGGCAACAGCACCGGCACCCTGATGGTGTTCTTCG
GCAATGTGGACAGCAGCGGCATCAAGCACAACATCTTCAACCCCCCCATCATTGCCCGGTACATCCGGCTG
CACCCCACCCACTACAGCATTAGATCCACACTGAGAATGGAACTGATGGGCTGCGACCTGAACTCCTGCAG
CATGCCTCTGGGCATGGAAAGCAAGGCCATCAGCGACGCCCAGATCACAGCCAGCAGCTACTTCACCAACA
TGTTCGCCACCTGGTCCCCCTCCAAGGCCAGGCTGCACCTGCAGGGCCGGTCCAACGCCTGGCGGCCTCAG
GTCAACAACCCCAAAGAATGGCTGCAGGTGGACTTTCAGAAAACCATGAAGGTGACCGGCGTGACCACCCA
GGGCGTGAAAAGCCTGCTGACCAGCATGTACGTGAAAGAGTTTCTGATCAGCAGCTCTCAGGATGGCCACC
AGTGGACCCTGTTCTTTCAGAACGGCAAGGTGAAAGTGTTCCAGGGCAACCAGGACTCCTTCACCCCCGTG
GTGAACTCCCTGGACCCCCCCCTGCTGACCCGCTACCTGAGAATCCACCCCCAGTCTTGGGTGCACCAGAT
CGCCCTCAGGATGGAAGTCCTGGGATGTGAGGCCCAGGATCTGTACTGATGAGGATCCAATAAAAGATCTT
TATTTTCATTAGATCTGTGTGTTGGTTTTTTGTGTGCTCGAGATCCACGGCCGCAGGAACCCCTAGTGATG
GAGTTGGCCACTCCCTCTCTGCGCGCTCGCTCGCTCACTGAGGCCGGGCGACCAAAGGTCGCCCGACGCCC
GGGCTTTGCCCGGGCGGCCTCAGTGAGCGAGCGAGCGCGCAGCTGCCTGCAGGGGCGCCTGATGCGGTATT
TTCTCCTTACGCATCTGTGCGGTATTTCACACCGCATACGTCAAAGCAACCATAGTACGCGCCCTGTAGCG
GCGCATTAAGCGCGGCGGGTGTGGTGGTTACGCGCAGCGTGACCGCTACACTTGCCAGCGCCCTAGCGCCC
GCTCCTTTCGCTTTCTTCCCTTCCTTTCTCGCCACGTTCGCCGGCTTTCCCCGTCAAGCTCTAAATCGGGG
GCTCCCTTTAGGGTTCCGATTTAGTGCTTTACGGCACCTCGACCCCAAAAAACTTGATTTGGGTGATGGTT
CACGTAGTGGGCCATCGCCCTGATAGACGGTTTTCGCCCTTTGACGTTGGAGTCCACGTTCTTTAATAGT
GGACTCTTGTTCCAAACTGGAACAACACTCAACCCTATCTCGGGCTATTCTTTTGATTTATAAGGGATTTT
GCCGATTTCGGCCTATTGGTTAAAAAATGAGCTGATTTAACAAAAATTTAACGCGAATTTTAACAAAATAT
TAACGTTTACAATTTTATGGTGCACTCTCAGTACAATCTGCTCTGATGCCGCATAGTTAAGCCAGCCCCGA
CACCCGCCAACACCCGCTGACGCGCCCTGACGGGCTTGTCTGCTCCCGGCATCCGCTTACAGACAAGCTGT
GACCGTCTCCGGGAGCTGCATGTGTCAGAGGTTTTCACCGTCATCACCGAAACGCGCGAGACGAAAGGGCC
TCGTGATACGCCTATTTTTATAGGTTAATGTCATGATAATAATGGTTTCTTAGACGTCAGGTGGCACTTTT
CGGGGAAATGTGCGCGGAACCCCTATTTGTTTATTTTTCTAAATACATTCAAATATGTATCCGCTCATGAG
ACAATAACCCTGATAAATGCTTCAATAATATTGAAAAAGGAAGAGTATGAGTATTCAACATTTCCGTGTCG
CCCTTATTCCCTTTTTTGCGGCATTTTGCCTTCCTGTTTTTGCTCACCCAGAAACGCTGGTGAAAGTAAAA
GATGCTGAAGATCAGTTGGGTGCACGAGTGGGTTACATCGAACTGGATCTCAACAGCGGTAAGATCCTTGA
GAGTTTTCGCCCCGAAGAACGTTTTCCAATGATGAGCACTTTTAAAGTTCTGCTATGTGGCGCGGTATTAT
CCCGTATTGACGCCGGGCAAGAGCAACTCGGTCGCCGCATACACTATTCTCAGAATGACTTGGTTGAGTAC
TCACCAGTCACAGAAAAGCATCTTACGGATGGCATGACAGTAAGAGAATTATGCAGTGCTGCCATAACCAT
GAGTGATAACACTGCGGCCAACTTACTTCTGACAACGATCGGAGGACCGAAGGAGCTAACCGCTTTTTTGC
ACAACATGGGGGATCATGTAACTCGCCTTGATCGTTGGGAACCGGAGCTGAATGAAGCCATACCAAACGAC
GAGCGTGACACCACGATGCCTGTAGCAATGGCAACAACGTTGCGCAAACTATTAACTGGCGAACTACTTAC
TCTAGCTTCCCGGCAACAATTAATAGACTGGATGGAGGCGGATAAAGTTGCAGGACCACTTCTGCGCTCGG
CCCTTCCGGCTGGCTGGTTTATTGCTGATAAATCTGGAGCCGGTGAGCGTGGGTCTCGCGGTATCATTGCA
GCACTGGGGCCAGATGGTAAGCCCTCCCGTATCGTAGTTATCTACACGACGGGGAGTCAGGCAACTATGGA
TGAACGAAATAGACAGATCGCTGAGATAGGTGCCTCACTGATTAAGCATTGGTAACTGTCAGACCAAGTTT
ACTCATATATACTTTAGATTGATTTAAAACTTCATTTTTAATTTAAAAGGATCTAGGTGAAGATCCTTTTT
GATAATCTCATGACCAAAATCCCTTAACGTGAGTTTTCGTTCCACTGAGCGTCAGACCCCGTAGAAAAGAT
CAAAGGATCTTCTTGAGATCCTTTTTTTCTGCGCGTAATCTGCTGCTTGCAAACAAAAAAACCACCGCTAC
CAGCGGTGGTTTGTTTGCCGGATCAAGAGCTACCAACTCTTTTTCCGAAGGTAACTGGCTTCAGCAGAGCG
CAGATACCAAATACTGTCCTTCTAGTGTAGCCGTAGTTAGGCCACCACTTCAAGAACTCTGTAGCACCGCC
TACATACCTCGCTCTGCTAATCCTGTTACCAGTGGCTGCTGCCAGTGGCGATAAGTCGTGTCTTACCGGGT
TGGACTCAAGACGATAGTTACCGGATAAGGCGCAGCGGTCGGGCTGAACGGGGGGTTCGTGCACACAGCCC
AGCTTGGAGCGAACGACCTACACCGAACTGAGATACCTACAGCGTGAGCTATGAGAAAGCGCCACGCTTCC
CGAAGGGAGAAAGGCGGACAGGTATCCGGTAAGCGGCAGGGTCGGAACAGGAGAGCGCACGAGGGAGCTTC
CAGGGGGAAACGCCTGGTATCTTTATAGTCCTGTCGGGTTTCGCCACCTCTGACTTGAGCGTCGATTTTTG
TGATGCTCGTCAGGGGGCGGAGCCTATGGAAAAACGCCAGCAACGCGGCCTTTTTACGGTTCCTGGCCTT
TTGCTGGCCTTTTGCTCACATGT
```

Figure 14 (continued)

SEQ ID NO.24: pAAVss-TTRe-TTRm-coFVIIIdeltaB-Synt.pA

CCTGCAGGCAGCTGCGCGCTCGCTCGCTCACTGAGGCCGCCCGGGCAAAGCCCGGGCGTCGGGCGACCTTT
GGTCGCCCGGCCTCAGTGAGCGAGCGAGCGCGCAGAGAGGGAGTGGCCAACTCCATCACTAGGGGTTCCTG
CGGCCGTACCCACTGGGAGGATGTTGAGTAAGATGGAAAACTACTGATGACCCTTGCAGAGACAGAGTATT
AGGACATGTTTGAACAGGGGCCGGGCGATCAGCAGGTAGCTCTAGAGGATCCCCGTCTGTCTGCACATTTC
GTAGAGCGAGTGTTCCGATACTCTAATCTCCCTAGGCAAGGTTCATATTTGTGTAGGTTACTTATTCTCCT
TTTGTTGACTAAGTCAATAATCAGAATCAGCAGGTTTGGAGTCAGCTTGGCAGGGATCAGCAGCCTGGGTT
GGAAGGAGGGGGTATAAAAGCCCCTTCACCAGGAGAAGCCGTCACACAGATCCACAAGCTCCTGCTAGTAT
GCAGATCGAGCTGTCCACCTGCTTTTTTCTGTGCCTGCTGCGGTTCTGCTTCAGCGCCACCCGGCGGTACT
ACCTGGGCGCCGTGGAGCTGTCCTGGGACTACATGCAGAGCGACCTGGGCGAGCTGCCCGTGGACGCCCGG
TTCCCCCCCAGAGTGCCCAAGAGCTTCCCCTTCAACACCAGCGTGGTGTACAAGAAAACCCTGTTCGTGGA
GTTCACCGACCACCTGTTCAATATCGCCAAGCCCAGGCCCCCTGGATGGGCCTGCTGGGCCCCACCATCC
AGGCCGAGGTGTACGACACCGTGGTGATCACCCTGAAGAACATGGCCAGCCACCCCGTGAGCCTGCACGCC
GTGGGCGTGAGCTACTGGAAGGCCAGCGAGGGCGCCGAGTACGACGACCAGACCAGCCAGCGGGAGAAAGA
AGATGACAAGGTGTTCCCTGGCGGCAGCCACACCTACGTGTGGCAGGTGCTGAAAGAAAACGGCCCCATGG
CCTCCGACCCCCTGTGCCTGACCTACAGCTACCTGAGCCACGTGGACCTGGTGAAGGACCTGAACAGCGGC
CTGATCGGCGCTCTGCTCGTCTGCCGGGAGGGCAGCCTGGCCAAAGAGAAAACCCAGACCCTGCACAAGTT
CATCCTGCTGTTCGCCGTGTTCGACGAGGGCAAGAGCTGGCACAGCGAGACAAAGAACAGCCTGATGCAGG
ACCGGGACGCCGCCTCTGCCAGAGCCTGGCCCAAGATGCACACCGTGAACGGCTACGTGAACAGAAGCCTG
CCCGGCCTGATTGGCTGCCACCGGAAGAGCGTGTACTGGCACGTGATCGGCATGGGCACCACACCCGAGGT
GCACAGCATCTTTCTGGAAGGGCACACCTTTCTGGTCCGGAACCACCGGCAGGCCAGCCTGGAAATCAGCC
CTATCACCTTCCTGACCGCCCAGACACTGCTGATGGACCTGGGCCAGTTCCTGCTGTTTTGCCACATCAGC
TCTCACCAGCACGACGGCATGGAAGCCTACGTGAAGGTGGACTCTTGCCCCGAGGAACCCCAGCTGCGGAT
GAAGAACAACGAGGAAGCCGAGGACTACGACGACGACCTGACCGACAGCGAGATGGACGTGGTGCGGTTCG
ACGACGACAACAGCCCCAGCTTCATCCAGATCAGAAGCGTGGCCAAGAAGCACCCCAAGACCTGGGTGCAC
TATATCGCCGCCGAGGAAGAGGACTGGGACTACGCCCCCCTGGTGCTGGCCCCCGACGACAGAAGCTACAA
GAGCCAGTACCTGAACAATGGCCCCCAGCGGATCGGCCGGAAGTACAAGAAAGTGCGGTTCATGGCCTACA
CCGACGAGACATTCAAGACCCGGGAGGCCATCCAGCACGAGAGCGGCATCCTGGGCCCCCTGCTGTACGGC
GAAGTGGGCGACACACTGCTGATCATCTTCAAGAACCAGGCTAGCCGGCCCTACAACATCTACCCCCACGG
CATCACCGACGTGCGGCCCCTGTACAGCAGGCGGCTGCCCAAGGGCGTGAAGCACCTGAAGGACTTCCCCA
TCCTGCCCGGCGAGATCTTCAAGTACAAGTGGACCGTGACCGTGGAGGACGGCCCCACCAAGAGCGACCCC
AGATGCCTGACCCGGTACTACAGCAGCTTCGTGAACATGGAACGGGACCTGGCCTCCGGGCTGATCGGACC
TCTGCTGATCTGCTACAAAGAAAGCGTGGACCAGCGGGGCAACCAGATCATGAGCGACAAGCGGAACGTGA
TCCTGTTCAGCGTGTTCGATGAGAACCGGTCCTGGTATCTGACCGAGAACATCCAGCGGTTTCTGCCCAAC
CCTGCCGGCGTGCAGCTGGAAGATCCCGAGTTCCAGGCCAGCAACATCATGCACTCCATCAATGGCTACGT
GTTCGACTCTCTGCAGCTCTCCGTGTGTCTGCACGAGGTGGCCTACTGGTACATCCTGAGCATCGGCGCCC
AGACCGACTTCCTGAGCGTGTTCTTCAGCGGCTACACCTTCAAGCACAAGATGGTGTACGAGGACACCCTG
ACCCTGTTCCCTTTCAGCGGCGAGACAGTGTTCATGAGCATGGAAAACCCCGGCCTGTGGATTCTGGGCTG
CCACAACAGCGACTTCCGGAACCGGGGCATGACCGCCCTGCTGAAGGTGTCCAGCTGCGACAAGAACACCG
GCGACTACTACGAGGACAGCTACGAGGATATCAGCGCCTACCTGCTGTCCAAGAACAACGCCATCGAACCC
CGGAGCTTCAGCCAGAACCCCCCCGTGCTGACGCGTCACCAGCGGGAGATCACCCGGACAACCCTGCAGTC
CGACCAGGAAGAGATCGATTACGACGACACCATCAGCGTGGAGATGAAGAAAGAGGATTTCGATATCTACG
ACGAGGACGAGAACCAGAGCCCCAGAAGCTTCCAGAAGAAAACCCGGCACTACTTCATTGCCGCCGTGGAG
AGGCTGTGGGACTACGGCATGAGTTCTAGCCCCCACGTGCTGCGGAACCGGGCCCAGAGCGGCAGCGTGCC
CCAGTTCAAGAAAGTGGTGTTCCAGGAATTCACAGACGGCAGCTTCACCCAGCCTCTGTATAGAGGCGAGC
TGAACGAGCACCTGGGGCTGCTGGGCCCTACATCAGGGCCGAAGTGGAGGACAACATCATGGTGACCTTC
CGGAATCAGGCCAGCAGACCCTACTCCTTCTACAGCAGCCTGATCAGCTACGAAGAGGACCAGCGGCAGGG
CGCCGAACCCCGGAAGAACTTCGTGAAGCCCAACGAAACCAAGACCTACTTCTGGAAAGTGCAGCACCACA
TGGCCCCCACCAAGGACGAGTTCGACTGCAAGGCCTGGCCTACTTCAGCGACGTGGATCTGGAAAAGGAC
GTGCACTCTGGACTGATTGCCCACTCCTGGTCTGCCACACTAACACCCTCAACCCCGCCCACGGCCGCCA
GGTGACCGTGCAGGAATTCGCCCTGTTCTTCACCATCTTCGACGAGACAAAGTCCTGGTACTTCACCGAGA
ATATGGAACGGAACTGCAGAGCCCCCTGCAACATCCAGATGGAAGATCCTACCTTCAAAGAGAACTACCGG
TTCCACGCCATCAACGGCTACATCATGGACACCCTGCCTGGCCTGGTGATGGCCCAGGACCAGAGAATCCG
GTGGTATCTGCTGTCCATGGGCAGCAACGAGAATATCCACAGCATCCACTTCAGCGGCCACGTGTTCACCG

Figure 14 (continued)

```
TGCGGAAGAAAGAAGAGTACAAGATGGCCCTGTACAACCTGTACCCCGGCGTGTTCGAGACAGTGGAGATG
CTGCCCAGCAAGGCCGGCATCTGGCGGGTGGAGTGTCTGATCGGCGAGCACCTGCACGCTGGCATGAGCAC
CCTGTTTCTGGTGTACAGCAACAAGTGCCAGACCCCACTGGGCATGGCCTCTGGCCACATCCGGGACTTCC
AGATCACCGCCTCCGGCCAGTACGGCCAGTGGGCCCCCAAGCTGGCCAGACTGCACTACAGCGGCAGCATC
AACGCCTGGTCCACCAAAGAGCCCTTCAGCTGGATCAAGGTGGACCTGCTGGCCCCTATGATCATCCACGG
CATTAAGACCCAGGGCGCCAGGCAGAAGTTCAGCAGCCTGTACATCAGCCAGTTCATCATCATGTACAGCC
TGGACGGCAAGAAGTGGCAGACCTACCGGGGCAACAGCACCGGCACCCTGATGGTGTTCTTCGGCAATGTG
GACAGCAGCGGCATCAAGCACAACATCTTCAACCCCCCATCATTGCCCGGTACATCCGGCTGCACCCCAC
CCACTACAGCATTAGATCCACACTGAGAATGGAACTGATGGGCTGCGACCTGAACTCCTGCAGCATGCCTC
TGGGCATGGAAAGCAAGGCCATCAGCGACGCCCAGATCACAGCCAGCAGCTACTTCACCAACATGTTCGCC
ACCTGGTCCCCCTCCAAGGCCAGGCTGCACCTGCAGGGCCGGTCCAACGCCTGGCGGCCTCAGGTCAACAA
CCCCAAAGAATGGCTGCAGGTGGACTTTCAGAAAACCATGAAGGTGACCGGCGTGACCACCCAGGGCGTGA
AAAGCCTGCTGACCAGCATGTACGTGAAAGAGTTTCTGATCAGCAGCTCTCAGGATGGCCACCAGTGGACC
CTGTTCTTTCAGAACGGCAAGGTGAAAGTGTTCCAGGGCAACCAGGACTCCTTCACCCCCGTGGTGAACTC
CCTGGACCCCCCCCTGCTGACCCGCTACCTGAGAATCCACCCCCAGTCTTGGGTGCACCAGATCGCCCTCA
GGATGGAAGTCCTGGGATGTGAGGCCCAGGATCTGTACTGATGAGGATCCAATAAAAGATCTTTATTTTCA
TTAGATCTGTGTGTTGGTTTTTTGTGTGCTCGAGATCCACGGCCGCAGGAACCCCTAGTGATGGAGTTGGC
CACTCCCTCTCTGCGCGCTCGCTCGCTCACTGAGGCCGGGCGACCAAAGGTCGCCCGACGCCCGGGCTTTG
CCCGGGCGGCCTCAGTGAGCGAGCGAGCGCGCAGCTGCCTGCAGGGGCGCCTGATGCGGTATTTTCTCCTT
ACGCATCTGTGCGGTATTTCACACCGCATACGTCAAAGCAACCATAGTACGCGCCCTGTAGCGGCGCATTA
AGCGCGGCGGGTGTGGTGGTTACGCGCAGCGTGACCGCTACACTTGCCAGCGCCCTAGCGCCCGCTCCTTT
CGCTTTCTTCCCTTCCTTTCTCGCCACGTTCGCCGGCTTTCCCCGTCAAGCTCTAAATCGGGGGCTCCCTT
TAGGGTTCCGATTTAGTGCTTTACGGCACCTCGACCCCAAAAAACTTGATTTGGGTGATGGTTCACGTAGT
GGGCCATCGCCCTGATAGACGGTTTTTCGCCCTTTGACGTTGGAGTCCACGTTCTTTAATAGTGGACTCTT
GTTCCAAACTGGAACAACACTCAACCCTATCTCGGGCTATTCTTTTGATTTATAAGGGATTTTGCCGATTT
CGGCCTATTGGTTAAAAAATGAGCTGATTTAACAAAAATTTAACGCGAATTTTAACAAAATATTAACGTTT
ACAATTTTATGGTGCACTCTCAGTACAATCTGCTCTGATGCCGCATAGTTAAGCCAGCCCCGACACCCGCC
AACACCCGCTGACGCGCCCTGACGGGCTTGTCTGCTCCCGGCATCCGCTTACAGACAAGCTGTGACCGTCT
CCGGGAGCTGCATGTGTCAGAGGTTTTCACCGTCATCACCGAAACGCGCGAGACGAAAGGGCCTCGTGATA
CGCCTATTTTTATAGGTTAATGTCATGATAATAATGGTTTCTTAGACGTCAGGTGGCACTTTTCGGGGAAA
TGTGCGCGGAACCCCTATTTGTTTATTTTTCTAAATACATTCAAATATGTATCCGCTCATGAGACAATAAC
CCTGATAAATGCTTCAATAATATTGAAAAAGGAAGAGTATGAGTATTCAACATTTCCGTGTCGCCCTTATT
CCCTTTTTTGCGGCATTTTGCCTTCCTGTTTTTGCTCACCCAGAAACGCTGGTGAAAGTAAAAGATGCTGA
AGATCAGTTGGGTGCACGAGTGGGTTACATCGAACTGGATCTCAACAGCGGTAAGATCCTTGAGAGTTTTC
GCCCCGAAGAACGTTTTCCAATGATGAGCACTTTTAAAGTTCTGCTATGTGGCGCGGTATTATCCCGTATT
GACGCCGGGCAAGAGCAACTCGGTCGCCGCATACACTATTCTCAGAATGACTTGGTTGAGTACTCACCAGT
CACAGAAAAGCATCTTACGGATGGCATGACAGTAAGAGAATTATGCAGTGCTGCCATAACCATGAGTGATA
ACACTGCGGCCAACTTACTTCTGACAACGATCGGAGGACCGAAGGAGCTAACCGCTTTTTTGCACAACATG
GGGGATCATGTAACTCGCCTTGATCGTTGGGAACCGGAGCTGAATGAAGCCATACCAAACGACGAGCGTGA
CACCACGATGCCTGTAGCAATGGCAACAACGTTGCGCAAACTATTAACTGGCGAACTACTTACTCTAGCTT
CCCGGCAACAATTAATAGACTGGATGGAGGCGGATAAAGTTGCAGGACCACTTCTGCGCTCGGCCCTTCCG
GCTGGCTGGTTTATTGCTGATAAATCTGGAGCCGGTGAGCGTGGGTCTCGCGGTATCATTGCAGCACTGGG
GCCAGATGGTAAGCCCTCCCGTATCGTAGTTATCTACACGACGGGGAGTCAGGCAACTATGGATGAACGAA
ATAGACAGATCGCTGAGATAGGTGCCTCACTGATTAAGCATTGGTAACTGTCAGACCAAGTTTACTCATAT
ATACTTTAGATTGATTTAAAACTTCATTTTTAATTTAAAAGGATCTAGGTGAAGATCCTTTTTGATAATCT
CATGACCAAAATCCCTTAACGTGAGTTTTCGTTCCACTGAGCGTCAGACCCCGTAGAAAGATCAAAGGAT
CTTCTTGAGATCCTTTTTTTCTGCGCGTAATCTGCTGCTTGCAAACAAAAAAACCACCGCTACCAGCGGTG
GTTTGTTTGCCGGATCAAGAGCTACCAACTCTTTTTCCGAAGGTAACTGGCTTCAGCAGAGCGCAGATACC
AAATACTGTCCTTCTAGTGTAGCCGTAGTTAGGCCACCACTTCAAGAACTCTGTAGCACCGCCTACATACC
TCGCTCTGCTAATCCTGTTACCAGTGGCTGCTGCCAGTGGCGATAAGTCGTGTCTTACCGGGTTGGACTCA
AGACGATAGTTACCGGATAAGGCGCAGCGGTCGGGCTGAACGGGGGGTTCGTGCACACAGCCCAGCTTGGA
GCGAACGACCTACACCGAACTGAGATACCTACAGCGTGAGCTATGAGAAAGCGCCACGCTTCCCGAAGGGA
GAAAGGCGGACAGGTATCCGGTAAGCGGCAGGGTCGGAACAGGAGAGCGCACGAGGGAGCTTCCAGGGGGA
AACGCCTGGTATCTTTATAGTCCTGTCGGGTTTCGCCACCTCTGACTTGAGCGTCGATTTTTGTGATGCTC
```

Figure 14 (continued)

GTCAGGGGGCGGAGCCTATGGAAAAACGCCAGCAACGCGGCCTTTTTACGGTTCCTGGCCTTTTGCTGGC
CTTTTGCTCACATGT

SEQ ID NO.38: Flank-3xSERP-*Flank*

GCGGCCGCGGTACGCGGGGGAGGCTGCTGGTGAATATTAACCAAGGTCACCCCAGTTATCGGAGGAGCAAA
CAGGGGCTAAGTCCACCGGGGGAGGCTGCTGGTGAATATTAACCAAGGTCACCCCAGTTATCGGAGGAGCA
AACAGGGGCTAAGTCCACCGGGGGAGGCTGCTGGTGAATATTAACCAAGGTCACCCCAGTTATCGGAGGAG
CAAACAGGGGCTAAGTCCACGGTACC

SEQ ID NO.39: Flank-3xSERP-Flank-*TTRe*
GCGGCCGCGGTACGCGGGGGAGGCTGCTGGTGAATATTAACCAAGGTCACCCCAGTTATCGGAGGAGCAAA
CAGGGGCTAAGTCCACCGGGGGAGGCTGCTGGTGAATATTAACCAAGGTCACCCCAGTTATCGGAGGAGCA
AACAGGGGCTAAGTCCACCGGGGGAGGCTGCTGGTGAATATTAACCAAGGTCACCCCAGTTATCGGAGGAG
CAAACAGGGGCTAAGTCCACGGTACC*CACTGGGAGGATGTTGAGTAAGATGGAAAACTACTGATGACCCTT
GCAGAGACAGAGTATTAGGACATGTTTGAACAGGGGCCGGGCGATCAGCAGGTAG*

SEQ ID NO.40: Flank-3xSERP-Flank-*TTRe*-Flank

GCGGCCGCGGTACGCGGGGGAGGCTGCTGGTGAATATTAACCAAGGTCACCCCAGTTATCGGAGGAGCAAA
CAGGGGCTAAGTCCACCGGGGGAGGCTGCTGGTGAATATTAACCAAGGTCACCCCAGTTATCGGAGGAGCA
AACAGGGGCTAAGTCCACCGGGGGAGGCTGCTGGTGAATATTAACCAAGGTCACCCCAGTTATCGGAGGAG
CAAACAGGGGCTAAGTCCACGGTACC*CACTGGGAGGATGTTGAGTAAGATGGAAAACTACTGATGACCCTT
GCAGAGACAGAGTATTAGGACATGTTTGAACAGGGGCCGGGCGATCAGCAGGTAG*CTCTAGAGGATCCCC

SEQ ID NO.41: Flank-3xSERP-Flank-*TTRe*-Flank-TTRm

GCGGCCGCGGTACGCGGGGGAGGCTGCTGGTGAATATTAACCAAGGTCACCCCAGTTATCGGAGGAGCAAA
CAGGGGCTAAGTCCACCGGGGGAGGCTGCTGGTGAATATTAACCAAGGTCACCCCAGTTATCGGAGGAGCA
AACAGGGGCTAAGTCCACCGGGGGAGGCTGCTGGTGAATATTAACCAAGGTCACCCCAGTTATCGGAGGAG
CAAACAGGGGCTAAGTCCACGGTACC*CACTGGGAGGATGTTGAGTAAGATGGAAAACTACTGATGACCCTT
GCAGAGACAGAGTATTAGGACATGTTTGAACAGGGGCCGGGCGATCAGCAGGTAG*CTCTAGAGGATCCCCG
TCTGTCTGCACATTTCGTAGAGCGAGTGTTCCGATACTCTAATCTCCCTAGGCAAGGTTCATATTTGTGTA
GGTTACTTATTCTCCTTTTGTTGACTAAGTCAATAATCAGAATCAGCAGGTTTGGAGTCAGCTTGGCAGGG
ATCAGCAGCCTGGGTTGGAAGGAGGGGGTATAAAAGCCCCTTCACCAGGAGAAGCCGTC

SEQ ID NO.42: Flank-3xSERP-Flank-*TTRe*-Flank-TTRm-Flank

GCGGCCGCGGTACGCGGGGGAGGCTGCTGGTGAATATTAACCAAGGTCACCCCAGTTATCGGAGGAGCAAA
CAGGGGCTAAGTCCACCGGGGGAGGCTGCTGGTGAATATTAACCAAGGTCACCCCAGTTATCGGAGGAGCA
AACAGGGGCTAAGTCCACCGGGGGAGGCTGCTGGTGAATATTAACCAAGGTCACCCCAGTTATCGGAGGAG
CAAACAGGGGCTAAGTCCACGGTACC*CACTGGGAGGATGTTGAGTAAGATGGAAAACTACTGATGACCCTT
GCAGAGACAGAGTATTAGGACATGTTTGAACAGGGGCCGGGCGATCAGCAGGTAG*CTCTAGAGGATCCCCG
TCTGTCTGCACATTTCGTAGAGCGAGTGTTCCGATACTCTAATCTCCCTAGGCAAGGTTCATATTTGTGTA
GGTTACTTATTCTCCTTTTGTTGACTAAGTCAATAATCAGAATCAGCAGGTTTGGAGTCAGCTTGGCAGGG
ATCAGCAGCCTGGGTTGGAAGGAGGGGGTATAAAAGCCCCTTCACCAGGAGAAGCCGTCCTAGT

SEQ ID NO.43: Flank-3xSERP-Flank-*TTRe*-Flank-TTRm-Flank-coFVIIIdeltaB

GCGGCCGCGGTACGCGGGGGAGGCTGCTGGTGAATATTAACCAAGGTCACCCCAGTTATCGGAGGAGCAAA
CAGGGGCTAAGTCCACCGGGGGAGGCTGCTGGTGAATATTAACCAAGGTCACCCCAGTTATCGGAGGAGCA
AACAGGGGCTAAGTCCACCGGGGGAGGCTGCTGGTGAATATTAACCAAGGTCACCCCAGTTATCGGAGGAG
CAAACAGGGGCTAAGTCCACGGTACC*CACTGGGAGGATGTTGAGTAAGATGGAAAACTACTGATGACCCTT
GCAGAGACAGAGTATTAGGACATGTTTGAACAGGGGCCGGGCGATCAGCAGGTAG*CTCTAGAGGATCCCCG
TCTGTCTGCACATTTCGTAGAGCGAGTGTTCCGATACTCTAATCTCCCTAGGCAAGGTTCATATTTGTGTA

Figure 14 (continued)

```
GGTTACTTATTCTCCTTTTGTTGACTAAGTCAATAATCAGAATCAGCAGGTTTGGAGTCAGCTTGGCAGGG
ATCAGCAGCCTGGGTTGGAAGGAGGGGGTATAAAAGCCCCTTCACCAGGAGAAGCCGTCCTAGTATGCAGA
TCGAGCTGTCCACCTGCTTTTTTCTGTGCCTGCTGCGGTTCTGCTTCAGCGCCACCCGGCGGTACTACCTG
GGCGCCGTGGAGCTGTCCTGGGACTACATGCAGAGCGACCTGGGCGAGCTGCCCGTGGACGCCCGGTTCCC
CCCCAGAGTGCCCAAGAGCTTCCCCTTCAACACCAGCGTGGTGTACAAGAAAACCCTGTTCGTGGAGTTCA
CCGACCACCTGTTCAATATCGCCAAGCCCAGGCCCCCTGGATGGGCCTGCTGGGCCCCACCATCCAGGCC
GAGGTGTACGACACCGTGGTGATCACCCTGAAGAACATGGCCAGCCACCCCGTGAGCCTGCACGCCGTGGG
CGTGAGCTACTGGAAGGCCAGCGAGGGCGCCGAGTACGACGACCAGACCAGCCAGCGGGAGAAAGAAGATG
ACAAGGTGTTCCCTGGCGGCAGCCACACCTACGTGTGGCAGGTGCTGAAAGAAAACGGCCCCATGGCCTCC
GACCCCCTGTGCCTGACCTACAGCTACCTGAGCCACGTGGACCTGGTGAAGGACCTGAACAGCGGCCTGAT
CGGCGCTCTGCTCGTCTGCCGGGAGGGCAGCCTGGCCAAAGAGAAAACCCAGACCCTGCACAAGTTCATCC
TGCTGTTCGCCGTGTTCGACGAGGGCAAGAGCTGGCACAGCGAGACAAAGAACAGCCTGATGCAGGACCGG
GACGCCGCCTCTGCCAGAGCCTGGCCCAAGATGCACACCGTGAACGGCTACGTGAACAGAAGCCTGCCCGG
CCTGATTGGCTGCCACCGGAAGAGCGTGTACTGGCACGTGATCGGCATGGGCACCACACCCGAGGTGCACA
GCATCTTTCTGGAAGGGCACACCTTTCTGGTCCGGAACCACCGGCAGGCCAGCCTGGAAATCAGCCCTATC
ACCTTCCTGACCGCCCAGACACTGCTGATGGACCTGGGCCAGTTCCTGCTGTTTTGCCACATCAGCTCTCA
CCAGCACGACGGCATGGAAGCCTACGTGAAGGTGGACTCTTGCCCCGAGGAACCCCAGCTGCGGATGAAGA
ACAACGAGGAAGCCGAGGACTACGACGACGACCTGACCGACAGCGAGATGGACGTGGTGCGGTTCGACGAC
GACAACAGCCCCAGCTTCATCCAGATCAGAAGCGTGGCCAAGAAGCACCCCAAGACCTGGGTGCACTATAT
CGCCGCCGAGGAAGAGGACTGGGACTACGCCCCCCTGGTGCTGGCCCCGACGACAGAAGCTACAAGAGCC
AGTACCTGAACAATGGCCCCCAGCGGATCGGCCGGAAGTACAAGAAAGTGCGGTTCATGGCCTACACCGAC
GAGACATTCAAGACCCGGGAGGCCATCCAGCACGAGAGCGGCATCCTGGGCCCCCTGCTGTACGGCGAAGT
GGGCGACACACTGCTGATCATCTTCAAGAACCAGGCTAGCCGGCCCTACAACATCTACCCCCACGGCATCA
CCGACGTGCGGCCCCTGTACAGCAGGCGGCTGCCCAAGGGCGTGAAGCACCTGAAGGACTTCCCCATCCTG
CCCGGCGAGATCTTCAAGTACAAGTGGACCGTGACCGTGGAGGACGGCCCCACCAAGAGCGACCCCAGATG
CCTGACCCGGTACTACAGCAGCTTCGTGAACATGGAACGGGACCTGGCCTCCGGGCTGATCGGACCTCTGC
TGATCTGCTACAAAGAAAGCGTGGACCAGCGGGGCAACCAGATCATGAGCGACAAGCGGAACGTGATCCTG
TTCAGCGTGTTCGATGAGAACCGGTCCTGGTATCTGACCGAGAACATCCAGCGGTTTCTGCCCAACCCTGC
CGGCGTGCAGCTGGAAGATCCCGAGTTCCAGGCCAGCAACATCATGCACTCCATCAATGGCTACGTGTTCG
ACTCTCTGCAGCTCTCCGTGTGTCTGCACGAGGTGGCCTACTGGTACATCCTGAGCATCGGCGCCCAGACC
GACTTCCTGAGCGTGTTCTTCAGCGGCTACACCTTCAAGCACAAGATGGTGTACGAGGACACCCTGACCCT
GTTCCCTTTTCAGCGGCGAGACAGTGTTCATGAGCATGGAAAACCCCGGCCTGTGGATTCTGGGCTGCCACA
ACAGCGACTTCCGGAACCGGGGCATGACCGCCCTGCTGAAGGTGTCCAGCTGCGACAAGAACACCGGCGAC
TACTACGAGGACAGCTACGAGGATATCAGCGCCTACCTGCTGTCCAAGAACAACGCCATCGAACCCCGGAG
CTTCAGCCAGAACCCCCCCGTGCTGACGCGTCACCAGCGGGAGATCACCCGGACAACCCTGCAGTCCGACC
AGGAAGAGATCGATTACGACGACACCATCAGCGTGGAGATGAAGAAAGAGGATTTCGATATCTACGACGAG
GACGAGAACCAGAGCCCCAGAAGCTTCCAGAAGAAAACCCGGCACTACTTCATTGCCGCCGTGGAGAGGCT
GTGGGACTACGGCATGAGTTCTAGCCCCCACGTGCTGCGGAACCGGGCCCAGAGCGGCAGCGTGCCCCAGT
TCAAGAAAGTGGTGTTCCAGGAATTCACAGACGGCAGCTTCACCCAGCCTCTGTATAGAGGCGAGCTGAAC
GAGCACCTGGGGCTGCTGGGGCCCTACATCAGGGCCGAAGTGGAGGACAACATCATGGTGACCTTCCGGAA
TCAGGCCAGCAGACCCTACTCCTTCTACAGCAGCCTGATCAGCTACGAAGAGGACCAGCGGCAGGGCGCCG
AACCCCGGAAGAACTTCGTGAAGCCCAACGAAACCAAGACCTACTTCTGGAAAGTGCAGCACCACATGGCC
CCCACCAAGGACGAGTTCGACTGCAAGGCCTGGGCCTACTTCAGCGACGTGGATCTGGAAAAGGACGTGCA
CTCTGGACTGATTGGCCCACTCCTGGTCTGCCACACTAACACCCTCAACCCCGCCCACGGCCGCCAGGTGA
CCGTGCAGGAATTCGCCCTGTTCTTCACCATCTTCGACGAGACAAAGTCCTGGTACTTCACCGAGAATATG
GAACGGAACTGCAGAGCCCCCTGCAACATCCAGATGGAAGATCCTACCTTCAAAGAGAACTACCGGTTCCA
CGCCATCAACGGCTACATCATGGACACCCTGCCTGGCCTGGTGATGGCCCAGGACCAGAGAATCCGGTGGT
ATCTGCTGTCCATGGGCAGCAACGAGAATATCCACAGCATCCACTTCAGCGGCCACGTGTTCACCGTGCGG
AAGAAAGAAGAGTACAAGATGGCCCTGTACAACCTGTACCCCGGCGTGTTCGAGACAGTGGAGATGCTGCC
CAGCAAGGCCGGCATCTGGCGGGTGGAGTGTCTGATCGGCGAGCACCTGCACGCTGGCATGAGCACCCTGT
TTCTGGTGTACAGCAACAAGTGCCAGACCCCACTGGGCATGGCCTCTGGCCACATCCGGGACTTCCAGATC
ACCGCCTCCGGCCAGTACGGCCAGTGGGCCCCCAAGCTGGCCAGACTGCACTACAGCGGCAGCATCAACGC
CTGGTCCACCAAAGAGCCCTTCAGCTGGATCAAGGTGGACCTGCTGGCCCCTATGATCATCCACGGCATTA
AGACCCAGGGCGCCAGGCAGAAGTTCAGCAGCCTGTACATCAGCCAGTTCATCATCATGTACAGCCTGGAC
GGCAAGAAGTGGCAGACCTACCGGGGCAACAGCACCGGCACCCTGATGGTGTTCTTCGGCAATGTGGACAG
```

Figure 14 (continued)

CAGCGGCATCAAGCACAACATCTTCAACCCCCCCATCATTGCCCGGTACATCCGGCTGCACCCCACCCACT
ACAGCATTAGATCCACACTGAGAATGGAACTGATGGGCTGCGACCTGAACTCCTGCAGCATGCCTCTGGGC
ATGGAAAGCAAGGCCATCAGCGACGCCCAGATCACAGCCAGCAGCTACTTCACCAACATGTTCGCCACCTG
GTCCCCCTCCAAGGCCAGGCTGCACCTGCAGGGCCGGTCCAACGCCTGGCGGCCTCAGGTCAACAACCCCA
AAGAATGGCTGCAGGTGGACTTTCAGAAAACCATGAAGGTGACCGGCGTGACCACCCAGGGCGTGAAAAGC
CTGCTGACCAGCATGTACGTGAAAGAGTTTCTGATCAGCAGCTCTCAGGATGGCCACCAGTGGACCCTGTT
CTTTCAGAACGGCAAGGTGAAAGTGTTCCAGGGCAACCAGGACTCCTTCACCCCCGTGGTGAACTCCCTGG
ACCCCCCCCTGCTGACCCGCTACCTGAGAATCCACCCCCAGTCTTGGGTGCACCAGATCGCCCTCAGGATG
GAAGTCCTGGGATGTGAGGCCCAGGATCTGTACTGATGA

SEQ ID NO.44: Flank-3xSERP-Flank-*TTRe*-Flank-TTRm-Flank-coFVIIIdeltaB-Flank

GCGGCCGCGGTACGCGGGGGAGGCTGCTGGTGAATATTAACCAAGGTCACCCCAGTTATCGGAGGAGCAAA
CAGGGGCTAAGTCCACCGGGGGAGGCTGCTGGTGAATATTAACCAAGGTCACCCCAGTTATCGGAGGAGCA
AACAGGGGCTAAGTCCACCGGGGGAGGCTGCTGGTGAATATTAACCAAGGTCACCCCAGTTATCGGAGGAG
CAAACAGGGGCTAAGTCCACGGTACC*CACTGGGAGGATGTTGAGTAAGATGGAAAACTACTGATGACCCTT*
*GCAGAGACAGAGTATTAGGACATGTTTGAACAGGGGCCGGGCGATCAGCAGGTAG*CTCTAGAGGATCCCCG
TCTGTCTGCACATTTCGTAGAGCGAGTGTTCCGATACTCTAATCTCCCTAGGCAAGGTTCATATTTGTGTA
GGTTACTTATTCTCCTTTTGTTGACTAAGTCAATAATCAGAATCAGCAGGTTTGGAGTCAGCTTGGCAGGG
ATCAGCAGCCTGGGTTGGAAGGAGGGGGTATAAAAGCCCCTTCACCAGGAGAAGCCGTC**CTAGTATGCAGA
TCGAGCTGTCCACCTGCTTTTTTCTGTGCCTGCTGCGGTTCTGCTTCAGCGCCACCCGGCGGTACTACCTG
GGCGCCGTGGAGCTGTCCTGGGACTACATGCAGAGCGACCTGGGCGAGCTGCCCGTGGACGCCCGGTTCCC
CCCCAGAGTGCCCAAGAGCTTCCCCTTCAACACCAGCGTGGTGTACAAGAAAACCCTGTTCGTGGAGTTCA
CCGACCACCTGTTCAATATCGCCAAGCCCAGGCCCCCTGGATGGGCCTGCTGGGCCCCACCATCCAGGCC
GAGGTGTACGACACCGTGGTGATCACCCTGAAGAACATGGCCAGCCACCCCGTGAGCCTGCACGCCGTGGG
CGTGAGCTACTGGAAGGCCAGCGAGGGCGCCGAGTACGACGACCAGACCAGCCAGCGGGAGAAAGAAGATG
ACAAGGTGTTCCCTGGCGGCAGCCACACCTACGTGTGGCAGGTGCTGAAAGAAAACGGCCCCATGGCCTCC
GACCCCCTGTGCCTGACCTACAGCTACCTGAGCCACGTGGACCTGGTGAAGGACCTGAACAGCGGCCTGAT
CGGCGCTCTGCTCGTCTGCCGGGAGGGCAGCCTGGCCAAAGAGAAAACCCAGACCCTGCACAAGTTCATCC
TGCTGTTCGCCGTGTTCGACGAGGGCAAGAGCTGGCACAGCGAGACAAAGAACAGCCTGATGCAGGACCGG
GACGCCGCCTCTGCCAGAGCCTGGCCCAAGATGCACACCGTGAACGGCTACGTGAACAGAAGCCTGCCCGG
CCTGATTGGCTGCCACCGGAAGAGCGTGTACTGGCACGTGATCGGCATGGGCACCACACCCGAGGTGCACA
GCATCTTTCTGGAAGGGCACACCTTTCTGGTCCGGAACCACCGGCAGGCCAGCCTGGAAATCAGCCCTATC
ACCTTCCTGACCGCCCAGACACTGCTGATGGACCTGGGCCAGTTCCTGCTGTTTTGCCACATCAGCTCTCA
CCAGCACGACGGCATGGAAGCCTACGTGAAGGTGGACTCTTGCCCCGAGGAACCCCAGCTGCGGATGAAGA
ACAACGAGGAAGCCGAGGACTACGACGACGACCTGACCGACAGCGAGATGGACGTGGTGCGGTTCGACGAC
GACAACAGCCCCAGCTTCATCCAGATCAGAAGCGTGGCCAAGAAGCACCCCAAGACCTGGGTGCACTATAT
CGCCGCCGAGGAAGAGGACTGGGACTACGCCCCCCTGGTGCTGGCCCCCGACGACAGAAGCTACAAGAGCC
AGTACCTGAACAATGGCCCCCAGCGGATCGGCCGGAAGTACAAGAAAGTGCGGTTCATGGCCTACACCGAC
GAGACATTCAAGACCCGGGAGGCCATCCAGCACGAGAGCGGCATCCTGGGCCCCCTGCTGTACGGCGAAGT
GGGCGACACACTGCTGATCATCTTCAAGAACCAGGCTAGCCGGCCCTACAACATCTACCCCCACGGCATCA
CCGACGTGCGGCCCCTGTACAGCAGGCGGCTGCCCAAGGGCGTGAAGCACCTGAAGGACTTCCCCATCCTG
CCCGGCGAGATCTTCAAGTACAAGTGGACCGTGACCGTGGAGGACGGCCCCACCAAGAGCGACCCCAGATG
CCTGACCCGGTACTACAGCAGCTTCGTGAACATGGAACGGGACCTGGCCTCCGGGCTGATCGGACCTCTGC
TGATCTGCTACAAAGAAAGCGTGGACCAGCGGGGCAACCAGATCATGAGCGACAAGCGGAACGTGATCCTG
TTCAGCGTGTTCGATGAGAACCGGTCCTGGTATCTGACCGAGAACATCCAGCGGTTTCTGCCCAACCCTGC
CGGCGTGCAGCTGGAAGATCCCGAGTTCCAGGCCAGCAACATCATGCACTCCATCAATGGCTACGTGTTCG
ACTCTCTGCAGCTCTCCGTGTGTCTGCACGAGGTGGCCTACTGGTACATCCTGAGCATCGGCGCCCAGACC
GACTTCCTGAGCGTGTTCTTCAGCGGCTACACCTTCAAGCACAAGATGGTGTACGAGGACACCCTGACCCT
GTTCCCTTTCAGCGGCGAGACAGTGTTCATGAGCATGGAAAACCCCGGCCTGTGGATTCTGGGCTGCCACA
ACAGCGACTTCCGGAACCGGGGCATGACCGCCCTGCTGAAGGTGTCCAGCTGCGACAAGAACACCGGCGAC
TACTACGAGGACAGCTACGAGGATATCAGCGCCTACCTGCTGTCCAAGAACAACGCCATCGAACCCCGGAG
CTTCAGCCAGAACCCCCCCGTGCTGACGCGTCACCAGCGGGAGATCACCCGGACAACCCTGCAGTCCGACC
AGGAAGAGATCGATTACGACGACACCATCAGCGTGGAGATGAAGAAAGAGGATTTCGATATCTACGACGAG

Figure 14 (continued)

```
GACGAGAACCAGAGCCCCAGAAGCTTCCAGAAGAAAACCCGGCACTACTTCATTGCCGCCGTGGAGAGGCT
GTGGGACTACGGCATGAGTTCTAGCCCCCACGTGCTGCGGAACCGGGCCCAGAGCGGCAGCGTGCCCCAGT
TCAAGAAAGTGGTGTTCCAGGAATTCACAGACGGCAGCTTCACCCAGCCTCTGTATAGAGGCGAGCTGAAC
GAGCACCTGGGGCTGCTGGGGCCCTACATCAGGGCCGAAGTGGAGGACAACATCATGGTGACCTTCCGGAA
TCAGGCCAGCAGACCCTACTCCTTCTACAGCAGCCTGATCAGCTACGAAGAGGACCAGCGGCAGGGCGCCG
AACCCCGGAAGAACTTCGTGAAGCCCAACGAAACCAAGACCTACTTCTGGAAAGTGCAGCACCACATGGCC
CCCACCAAGGACGAGTTCGACTGCAAGGCCTGGGCCTACTTCAGCGACGTGGATCTGGAAAAGGACGTGCA
CTCTGGACTGATTGGCCCACTCCTGGTCTGCCACACTAACACCCTCAACCCCGCCCACGGCCGCCAGGTGA
CCGTGCAGGAATTCGCCCTGTTCTTCACCATCTTCGACGAGACAAAGTCCTGGTACTTCACCGAGAATATG
GAACGGAACTGCAGAGCCCCCTGCAACATCCAGATGGAAGATCCTACCTTCAAAGAGAACTACCGGTTCCA
CGCCATCAACGGCTACATCATGGACACCCTGCCTGGCCTGGTGATGGCCCAGGACCAGAGAATCCGGTGGT
ATCTGCTGTCCATGGGCAGCAACGAGAATATCCACAGCATCCACTTCAGCGGCCACGTGTTCACCGTGCGG
AAGAAAGAAGAGTACAAGATGGCCCTGTACAACCTGTACCCCGGCGTGTTCGAGACAGTGGAGATGCTGCC
CAGCAAGGCCGGCATCTGGCGGGTGGAGTGTCTGATCGGCGAGCACCTGCACGCTGGCATGAGCACCCTGT
TTCTGGTGTACAGCAACAAGTGCCAGACCCCACTGGGCATGGCCTCTGGCCACATCCGGGACTTCCAGATC
ACCGCCTCCGGCCAGTACGGCCAGTGGGCCCCCAAGCTGGCCAGACTGCACTACAGCGGCAGCATCAACGC
CTGGTCCACCAAAGAGCCCTTCAGCTGGATCAAGGTGGACCTGCTGGCCCCTATGATCATCCACGGCATTA
AGACCCAGGGCGCCAGGCAGAAGTTCAGCAGCCTGTACATCAGCCAGTTCATCATCATGTACAGCCTGGAC
GGCAAGAAGTGGCAGACCTACCGGGGCAACAGCACCGGCACCCTGATGGTGTTCTTCGGCAATGTGGACAG
CAGCGGCATCAAGCACAACATCTTCAACCCCCCCATCATTGCCCGGTACATCCGGCTGCACCCCACCCACT
ACAGCATTAGATCCACACTGAGAATGGAACTGATGGGCTGCGACCTGAACTCCTGCAGCATGCCTCTGGGC
ATGGAAAGCAAGGCCATCAGCGACGCCCAGATCACAGCCAGCAGCTACTTCACCAACATGTTCGCCACCTG
GTCCCCCTCCAAGGCCAGGCTGCACCTGCAGGGCCGGTCCAACGCCTGGCGGCCTCAGGTCAACAACCCCA
AAGAATGGCTGCAGGTGGACTTTCAGAAAACCATGAAGGTGACCGGCGTGACCACCCAGGGCGTGAAAAGC
CTGCTGACCAGCATGTACGTGAAAGAGTTTCTGATCAGCAGCTCTCAGGATGGCCACCAGTGGACCCTGTT
CTTTCAGAACGGCAAGGTGAAAGTGTTCCAGGGCAACCAGGACTCCTTCACCCCCGTGGTGAACTCCCTGG
ACCCCCCCCTGCTGACCCGCTACCTGAGAATCCACCCCCAGTCTTGGGTGCACCAGATCGCCCTCAGGATG
GAAGTCCTGGGATGTGAGGCCCAGGATCTGTACTGATGAGGATCC
```

SEQ ID NO.45: Flank-3xSERP-Flank-TTRe-Flank-TTRm-Flank-coFVIIIdeltaB-Flank-SV40pA

GCGGCCGCGGTACGCGGGGGAGGCTGCTGGTGAATATTAACCAAGGTCACCCCAGTTATCGGAGGAGCAAA
CAGGGGCTAAGTCCACCGGGGGAGGCTGCTGGTGAATATTAACCAAGGTCACCCCAGTTATCGGAGGAGCA
AACAGGGGCTAAGTCCACCGGGGGAGGCTGCTGGTGAATATTAACCAAGGTCACCCCAGTTATCGGAGGAG
CAAACAGGGGCTAAGTCCACGGTACCCACTGGGAGGATGTTGAGTAAGATGGAAAACTACTGATGACCCTT
GCAGAGACAGAGTATTAGGACATGTTTGAACAGGGGCCGGGCGATCAGCAGGTAGCTCTAGAGGATCCCCG
TCTGTCTGCACATTTCGTAGAGCGAGTGTTCCGATACTCTAATCTCCCTAGGCAAGGTTCATATTTGTGTA
GGTTACTTATTCTCCTTTTGTTGACTAAGTCAATAATCAGAATCAGCAGGTTTGGAGTCAGCTTGGCAGGG
ATCAGCAGCCTGGGTTGGAAGGAGGGGGTATAAAAGCCCCTTCACCAGGAGAAGCCGTCCTAGTATGCAGA
TCGAGCTGTCCACCTGCTTTTTTCTGTGCCTGCTGCGGTTCTGCTTCAGCGCCACCCGGCGGTACTACCTG
GGCGCCGTGGAGCTGTCCTGGGACTACATGCAGAGCGACCTGGGCGAGCTGCCCGTGGACGCCCGGTTCCC
CCCCAGAGTGCCCAAGAGCTTCCCCTTCAACACCAGCGTGGTGTACAAGAAAACCCTGTTCGTGGAGTTCA
CCGACCACCTGTTCAATATCGCCAAGCCCAGGCCCCCCTGGATGGGCCTGCTGGGCCCCACCATCCAGGCC
GAGGTGTACGACACCGTGGTGATCACCCTGAAGAACATGGCCAGCCACCCCGTGAGCCTGCACGCCGTGGG
CGTGAGCTACTGGAAGGCCAGCGAGGGCGCCGAGTACGACGACCAGACCAGCCAGCGGGAGAAGAAGATG
ACAAGGTGTTCCCTGGCGGCAGCCACACCTACGTGTGGCAGGTGCTGAAAGAAAACGGCCCCATGGCCTCC
GACCCCCTGTGCCTGACCTACAGCTACCTGAGCCACGTGGACCTGGTGAAGGACCTGAACAGCGGCCTGAT
CGGCGCTCTGCTCGTCTGCCGGGAGGGCAGCCTGGCCAAAGAGAAAACCCAGACCCTGCACAAGTTCATCC
TGCTGTTCGCCGTGTTCGACGAGGGCAAGAGCTGGCACAGCGAGACAAAGAACAGCCTGATGCAGGACCGG
GACGCCGCCTCTGCCAGAGCCTGGCCCAAGATGCACACCGTGAACGGCTACGTGAACAGAAGCCTGCCCGG
CCTGATTGGCTGCCACCGGAAGAGCGTGTACTGGCACGTGATCGGCATGGGCACCACACCCGAGGTGCACA
GCATCTTTCTGGAAGGGCACACCTTTCTGGTCCGGAACCACCGGCAGGCCAGCCTGGAAATCAGCCCTATC
ACCTTCCTGACCGCCCAGACACTGCTGATGGACCTGGGCCAGTTCCTGCTGTTTTGCCACATCAGCTCTCA
CCAGCACGACGGCATGGAAGCCTACGTGAAGGTGGACTCTTGCCCCGAGGAACCCCAGCTGCGGATGAAGA

Figure 14 (continued)

ACAACGAGGAAGCCGAGGACTACGACGACGACCTGACCGACAGCGAGATGGACGTGGTGCGGTTCGACGAC
GACAACAGCCCCAGCTTCATCCAGATCAGAAGCGTGGCCAAGAAGCACCCCAAGACCTGGGTGCACTATAT
CGCCGCCGAGGAAGAGGACTGGGACTACGCCCCCTGGTGCTGGCCCCGACGACAGAAGCTACAAGAGCC
AGTACCTGAACAATGGCCCCCAGCGGATCGGCCGGAAGTACAAGAAAGTGCGGTTCATGGCCTACACCGAC
GAGACATTCAAGACCCGGGAGGCCATCCAGCACGAGAGCGGCATCCTGGGCCCCTGCTGTACGGCGAAGT
GGGCGACACACTGCTGATCATCTTCAAGAACCAGGCTAGCCGGCCCTACAACATCTACCCCACGGCATCA
CCGACGTGCGGCCCCTGTACAGCAGGCGGCTGCCCAAGGGCGTGAAGCACCTGAAGGACTTCCCCATCCTG
CCCGGCGAGATCTTCAAGTACAAGTGGACCGTGACCGTGGAGGACGGCCCCACCAAGAGCGACCCCAGATG
CCTGACCCGGTACTACAGCAGCTTCGTGAACATGGAACGGGACCTGGCCTCCGGGCTGATCGGACCTCTGC
TGATCTGCTACAAAGAAAGCGTGGACCAGCGGGGCAACCAGATCATGAGCGACAAGCGGAACGTGATCCTG
TTCAGCGTGTTCGATGAGAACCGGTCCTGGTATCTGACCGAGAACATCCAGCGGTTTCTGCCCAACCCTGC
CGGCGTGCAGCTGGAAGATCCCGAGTTCCAGGCCAGCAACATCATGCACTCCATCAATGGCTACGTGTTCG
ACTCTCTGCAGCTCTCCGTGTGTCTGCACGAGGTGGCCTACTGGTACATCCTGAGCATCGGCGCCCAGACC
GACTTCCTGAGCGTGTTCTTCAGCGGCTACACCTTCAAGCACAAGATGGTGTACGAGGACACCCTGACCCT
GTTCCCTTTCAGCGGCGAGACAGTGTTCATGAGCATGGAAAACCCCGGCCTGTGGATTCTGGGCTGCCACA
ACAGCGACTTCCGGAACCGGGGCATGACCGCCCTGCTGAAGGTGTCCAGCTGCGACAAGAACACCGGCGAC
TACTACGAGGACAGCTACGAGGATATCAGCGCCTACCTGCTGTCCAAGAACAACGCCATCGAACCCCGGAG
CTTCAGCCAGAACCCCCCCGTGCTGACGCGTCACCAGCGGGAGATCACCCGGACAACCCTGCAGTCCGACC
AGGAAGAGATCGATTACGACGACACCATCAGCGTGGAGATGAAGAAAGAGGATTTCGATATCTACGACGAG
GACGAGAACCAGAGCCCCAGAAGCTTCCAGAAGAAAACCCGGCACTACTTCATTGCCGCCGTGGAGAGGCT
GTGGGACTACGGCATGAGTTCTAGCCCCCACGTGCTGCGGAACCGGGCCCAGAGCGGCAGCGTGCCCCAGT
TCAAGAAAGTGGTGTTCCAGGAATTCACAGACGGCAGCTTCACCCAGCCTCTGTATAGAGGCGAGCTGAAC
GAGCACCTGGGGCTGCTGGGCCCTACATCAGGGCCGAAGTGGAGGACAACATCATGGTGACCTTCCGGAA
TCAGGCCAGCAGACCCTACTCCTTCTACAGCAGCCTGATCAGCTACGAAGAGGACCAGCGGCAGGGCGCCG
AACCCCGGAAGAACTTCGTGAAGCCCAACGAAACCAAGACCTACTTCTGGAAAGTGCAGCACCACATGGCC
CCCACCAAGGACGAGTTCGACTGCAAGGCCTGGGCCTACTTCAGCGACGTGGATCTGGAAAAGGACGTGCA
CTCTGGACTGATTGGCCCACTCCTGGTCTGCCACACTAACACCCTCAACCCCGCCCACGGCCGCCAGGTGA
CCGTGCAGGAATTCGCCCTGTTCTTCACCATCTTCGACGAGACAAAGTCCTGGTACTTCACCGAGAATATG
GAACGGAACTGCAGAGCCCCCTGCAACATCCAGATGGAAGATCCTACCTTCAAAGAGAACTACCGGTTCCA
CGCCATCAACGGCTACATCATGGACACCCTGCCTGGCCTGGTGATGGCCCAGGACCAGAGAATCCGGTGGT
ATCTGCTGTCCATGGGCAGCAACGAGAATATCCACAGCATCCACTTCAGCGGCCACGTGTTCACCGTGCGG
AAGAAAGAAGAGTACAAGATGGCCCTGTACAACCTGTACCCCGGCGTGTTCGAGACAGTGGAGATGCTGCC
CAGCAAGGCCGGCATCTGGCGGGTGGAGTGTCTGATCGGCGAGCACCTGCACGCTGGCATGAGCACCCTGT
TTCTGGTGTACAGCAACAAGTGCCAGACCCCACTGGGCATGGCCTCTGGCCACATCCGGGACTTCCAGATC
ACCGCCTCCGGCCAGTACGGCCAGTGGGCCCCCAAGCTGGCCAGACTGCACTACAGCGGCAGCATCAACGC
CTGGTCCACCAAAGAGCCCTTCAGCTGGATCAAGGTGGACCTGCTGGCCCCTATGATCATCCACGGCATTA
AGACCCAGGGCGCCAGGCAGAAGTTCAGCAGCCTGTACATCAGCCAGTTCATCATCATGTACAGCCTGGAC
GGCAAGAAGTGGCAGACCTACCGGGGCAACAGCACCGGCACCCTGATGGTGTTCTTCGGCAATGTGGACAG
CAGCGGCATCAAGCACAACATCTTCAACCCCCCATCATTGCCCGGTACATCCGGCTGCACCCCACCCACT
ACAGCATTAGATCCACACTGAGAATGGAACTGATGGGCTGCGACCTGAACTCCTGCAGCATGCCTCTGGGC
ATGGAAAGCAAGGCCATCAGCGACGCCCAGATCACAGCCAGCAGCTACTTCACCAACATGTTCGCCACCTG
GTCCCCCTCCAAGGCCAGGCTGCACCTGCAGGGCCGGTCCAACGCCTGGCGGCCTCAGGTCAACAACCCCA
AAGAATGGCTGCAGGTGGACTTTCAGAAAACCATGAAGGTGACCGGCGTGACCACCCAGGGCGTGAAAAGC
CTGCTGACCAGCATGTACGTGAAAGAGTTTCTGATCAGCAGCTCTCAGGATGGCCACCAGTGGACCCTGTT
CTTTCAGAACGGCAAGGTGAAAGTGTTCCAGGGCAACCAGGACTCCTTCACCCCCGTGGTGAACTCCCTGG
ACCCCCCCCTGCTGACCCGCTACCTGAGAATCCACCCCCAGTCTTGGGTGCACCAGATCGCCCTCAGGATG
GAAGTCCTGGGATGTGAGGCCCAGGATCTGTACTGATGAGGATCCATGCTTTATTTGTGAAATTTGTGATG
CTATTGCTTTATTTGTAACCATTATAAGCTGCAATAAACAAGTTAACAACAACAATTGCATTCATTTTATG
TTTCAGGTTCAGGGGGAGGTGTGGGAGGTTTTTTAAA

SEQ ID NO.46: Flank-3xSERP-Flank-*TTRe*-Flank-TTRm-Flank-coFVIIIdeltaB-Flank-SV40pA-Flank

GCGGCCGCGGTACGCGGGGGAGGCTGCTGGTGAATATTAACCAAGGTCACCCCAGTTATCGGAGGAGCAAA
CAGGGGCTAAGTCCACCGGGGGAGGCTGCTGGTGAATATTAACCAAGGTCACCCCAGTTATCGGAGGAGCA

Figure 14 (continued)

```
AACAGGGGCTAAGTCCACCGGGGGAGGCTGCTGGTGAATATTAACCAAGGTCACCCCAGTTATCGGAGGAG
CAAACAGGGGCTAAGTCCACGGTACCCACTGGGAGGATGTTGAGTAAGATGGAAAACTACTGATGACCCTT
GCAGAGACAGAGTATTAGGACATGTTTGAACAGGGGCCGGGCGATCAGCAGGTAGCTCTAGAGGATCCCCG
TCTGTCTGCACATTTCGTAGAGCGAGTGTTCCGATACTCTAATCTCCCTAGGCAAGGTTCATATTTGTGTA
GGTTACTTATTCTCCTTTTGTTGACTAAGTCAATAATCAGAATCAGCAGGTTTGGAGTCAGCTTGGCAGGG
ATCAGCAGCCTGGGTTGGAAGGAGGGGGTATAAAAGCCCCTTCACCAGGAGAAGCCGTCCTAGTATGCAGA
TCGAGCTGTCCACCTGCTTTTTTCTGTGCCTGCTGCGGTTCTGCTTCAGCGCCACCCGGCGGTACTACCTG
GGCGCCGTGGAGCTGTCCTGGGACTACATGCAGAGCGACCTGGGCGAGCTGCCCGTGGACGCCCGGTTCCC
CCCCAGAGTGCCCAAGAGCTTCCCCTTCAACACCAGCGTGGTGTACAAGAAAACCCTGTTCGTGGAGTTCA
CCGACCACCTGTTCAATATCGCCAAGCCCAGGCCCCCCTGGATGGGCCTGCTGGGCCCCACCATCCAGGCC
GAGGTGTACGACACCGTGGTGATCACCCTGAAGAACATGGCCAGCCACCCCGTGAGCCTGCACGCCGTGGG
CGTGAGCTACTGGAAGGCCAGCGAGGGCGCCGAGTACGACGACCAGACCAGCCAGCGGGAGAAAGAAGATG
ACAAGGTGTTCCCTGGCGGCAGCCACACCTACGTGTGGCAGGTGCTGAAAGAAAACGGCCCCATGGCCTCC
GACCCCCTGTGCCTGACCTACAGCTACCTGAGCCACGTGGACCTGGTGAAGGACCTGAACAGCGGCCTGAT
CGGCGCTCTGCTCGTCTGCCGGGAGGGCAGCCTGGCCAAAGAGAAAACCCAGACCCTGCACAAGTTCATCC
TGCTGTTCGCCGTGTTCGACGAGGGCAAGAGCTGGCACAGCGAGACAAAGAACAGCCTGATGCAGGACCGG
GACGCCGCCTCTGCCAGAGCCTGGCCCAAGATGCACACCGTGAACGGCTACGTGAACAGAAGCCTGCCCGG
CCTGATTGGCTGCCACCGGAAGAGCGTGTACTGGCACGTGATCGGCATGGGCACCACACCCGAGGTGCACA
GCATCTTTCTGGAAGGGCACACCTTTCTGGTCCGGAACCACCGGCAGGCCAGCCTGGAAATCAGCCCTATC
ACCTTCCTGACCGCCCAGACACTGCTGATGGACCTGGGCCAGTTCCTGCTGTTTTGCCACATCAGCTCTCA
CCAGCACGACGGCATGGAAGCCTACGTGAAGGTGGACTCTTGCCCCGAGGAACCCCAGCTGCGGATGAAGA
ACAACGAGGAAGCCGAGGACTACGACGACGACCTGACCGACAGCGAGATGGACGTGGTGCGGTTCGACGAC
GACAACAGCCCCAGCTTCATCCAGATCAGAAGCGTGGCCAAGAAGCACCCCAAGACCTGGGTGCACTATAT
CGCCGCCGAGGAAGAGGACTGGGACTACGCCCCCCTGGTGCTGGCCCCGACGACAGAAGCTACAAGAGCC
AGTACCTGAACAATGGCCCCCAGCGGATCGGCCGGAAGTACAAGAAAGTGCGGTTCATGGCCTACACCGAC
GAGACATTCAAGACCCGGGAGGCCATCCAGCACGAGAGCGGCATCCTGGGCCCCCTGCTGTACGGCGAAGT
GGGCGACACACTGCTGATCATCTTCAAGAACCAGGCTAGCCGGCCCTACAACATCTACCCCCACGGCATCA
CCGACGTGCGGCCCCTGTACAGCAGGCGGCTGCCCAAGGGCGTGAAGCACCTGAAGGACTTCCCCATCCTG
CCCGGCGAGATCTTCAAGTACAAGTGGACCGTGACCGTGGAGGACGGCCCCACCAAGAGCGACCCCAGATG
CCTGACCCGGTACTACAGCAGCTTCGTGAACATGGAACGGGACCTGGCCTCCGGGCTGATCGGACCTCTGC
TGATCTGCTACAAAGAAAGCGTGGACCAGCGGGGCAACCAGATCATGAGCGACAAGCGGAACGTGATCCTG
TTCAGCGTGTTCGATGAGAACCGGTCCTGGTATCTGACCGAGAACATCCAGCGGTTTCTGCCCAACCCTGC
CGGCGTGCAGCTGGAAGATCCCGAGTTCCAGGCCAGCAACATCATGCACTCCATCAATGGCTACGTGTTCG
ACTCTCTGCAGCTCTCCGTGTGTCTGCACGAGGTGGCCTACTGGTACATCCTGAGCATCGGCGCCCAGACC
GACTTCCTGAGCGTGTTCTTCAGCGGCTACACCTTCAAGCACAAGATGGTGTACGAGGACACCCTGACCCT
GTTCCCTTTTCAGCGGCGAGACAGTGTTCATGAGCATGGAAAACCCCGGCCTGTGGATTCTGGGCTGCCACA
ACAGCGACTTCCGGAACCGGGGCATGACCGCCCTGCTGAAGGTGTCCAGCTGCGACAAGAACACCGGCGAC
TACTACGAGGACAGCTACGAGGATATCAGCGCCTACCTGCTGTCCAAGAACAACGCCATCGAACCCCGGAG
CTTCAGCCAGAACCCCCCCGTGCTGACGCGTCACCAGCGGGAGATCACCCGGACAACCCTGCAGTCCGACC
AGGAAGAGATCGATTACGACGACACCATCAGCGTGGAGATGAAGAAAGAGGATTTCGATATCTACGACGAG
GACGAGAACCAGAGCCCCAGAAGCTTCCAGAAGAAAACCCGGCACTACTTCATTGCCGCCGTGGAGAGGCT
GTGGGACTACGGCATGAGTTCTAGCCCCCACGTGCTGCGGAACCGGGCCCAGAGCGGCAGCGTGCCCCAGT
TCAAGAAAGTGGTGTTCCAGGAATTCACAGACGGCAGCTTCACCCAGCCTCTGTATAGAGGCGAGCTGAAC
GAGCACCTGGGGCTGCTGGGGCCCTACATCAGGGCCGAAGTGGAGGACAACATCATGGTGACCTTCCGGAA
TCAGGCCAGCAGACCCTACTCCTTCTACAGCAGCCTGATCAGCTACGAAGAGGACCAGCGGCAGGGCGCCG
AACCCCGGAAGAACTTCGTGAAGCCCAACGAAACCAAGACCTACTTCTGGAAAGTGCAGCACCACATGGCC
CCCACCAAGGACGAGTTCGACTGCAAGGCCTGGGCCTACTTCAGCGACGTGGATCTGGAAAAGGACGTGCA
CTCTGGACTGATTGGCCCACTCCTGGTCTGCCACACTAACACCCTCAACCCCGCCCACGGCCGCCAGGTGA
CCGTGCAGGAATTCGCCCTGTTCTTCACCATCTTCGACGAGACAAAGTCCTGGTACTTCACCGAGAATATG
GAACGGAACTGCAGAGCCCCCTGCAACATCCAGATGGAAGATCCTACCTTCAAAGAGAACTACCGGTTCCA
CGCCATCAACGGCTACATCATGGACACCCTGCCTGGCCTGGTGATGGCCCAGGACCAGAGAATCCGGTGGT
ATCTGCTGTCCATGGGCAGCAACGAGAATATCCACAGCATCCACTTCAGCGGCCACGTGTTCACCGTGCGG
AAGAAAGAAGAGTACAAGATGGCCCTGTACAACCTGTACCCCGGCGTGTTCGAGACAGTGGAGATGCTGCC
CAGCAAGGCCGGCATCTGGCGGGTGGAGTGTCTGATCGGCGAGCACCTGCACGCTGGCATGAGCACCCTGT
TTCTGGTGTACAGCAACAAGTGCCAGACCCCACTGGGCATGGCCTCTGGCCACATCCGGGACTTCCAGATC
```

Figure 14 (continued)

ACCGCCTCCGGCCAGTACGGCCAGTGGGCCCCCAAGCTGGCCAGACTGCACTACAGCGGCAGCATCAACGC
CTGGTCCACCAAAGAGCCCTTCAGCTGGATCAAGGTGGACCTGCTGGCCCCTATGATCATCCACGGCATTA
AGACCCAGGGCGCCAGGCAGAAGTTCAGCAGCCTGTACATCAGCCAGTTCATCATCATGTACAGCCTGGAC
GGCAAGAAGTGGCAGACCTACCGGGGCAACAGCACCGGCACCCTGATGGTGTTCTTCGGCAATGTGGACAG
CAGCGGCATCAAGCACAACATCTTCAACCCCCCCATCATTGCCCGGTACATCCGGCTGCACCCCACCCACT
ACAGCATTAGATCCACACTGAGAATGGAACTGATGGGCTGCGACCTGAACTCCTGCAGCATGCCTCTGGGC
ATGGAAAGCAAGGCCATCAGCGACGCCCAGATCACAGCCAGCAGCTACTTCACCAACATGTTCGCCACCTG
GTCCCCCTCCAAGGCCAGGCTGCACCTGCAGGGCCGGTCCAACGCCTGGCGGCCTCAGGTCAACAACCCCA
AAGAATGGCTGCAGGTGGACTTTCAGAAAACCATGAAGGTGACCGGCGTGACCACCCAGGGCGTGAAAAGC
CTGCTGACCAGCATGTACGTGAAAGAGTTTCTGATCAGCAGCTCTCAGGATGGCCACCAGTGGACCCTGTT
CTTTCAGAACGGCAAGGTGAAAGTGTTCCAGGGCAACCAGGACTCCTTCACCCCCGTGGTGAACTCCCTGG
ACCCCCCCCTGCTGACCCGCTACCTGAGAATCCACCCCAGTCTTGGGTGCACCAGATCGCCCTCAGGATG
GAAGTCCTGGGATGTGAGGCCCAGGATCTGTACTGATGAGGATCC**ATGCTTTATTTGTGAAATTTGTGATG
CTATTGCTTTATTTGTAACCATTATAAGCTGCAATAAACAAGTTAACAACAACAATTGCATTCATTTTATG
TTTCAGGTTCAGGGGGAGGTGTGGGAGGTTTTTTAAACTCGAGATCCACGGCCGC**

SEQ ID NO.47: Flank-<u>3xSERP</u>-Flank-*TTRe*-Flank-TTRm-Flank-<u>coFVIIIdeltaB</u>-
Flank-Synt.pA

GCGGCCGCGGTACGCGGGGGAGGCTGCTGGTGAATATTAACCAAGGTCACCCCAGTTATCGGAGGAGCAAA
CAGGGGCTAAGTCCACCGGGGGAGGCTGCTGGTGAATATTAACCAAGGTCACCCCAGTTATCGGAGGAGCA
AACAGGGGCTAAGTCCACCGGGGGAGGCTGCTGGTGAATATTAACCAAGGTCACCCCAGTTATCGGAGGAG
CAAACAGGGGCTAAGTCCACGGTACC*CACTGGGAGGATGTTGAGTAAGATGGAAAACTACTGATGACCCTT
GCAGAGACAGAGTATTAGGACATGTTTGAACAGGGGCCGGGCGATCAGCAGGTAG*CTCTAGAGGATCCCCG
TCTGTCTGCACATTTCGTAGAGCGAGTGTTCCGATACTCTAATCTCCCTAGGCAAGGTTCATATTTGTGTA
GGTTACTTATTCTCCTTTTGTTGACTAAGTCAATAATCAGAATCAGCAGGTTTGGAGTCAGCTTGGCAGGG
ATCAGCAGCCTGGGTTGGAAGGAGGGGGTATAAAAGCCCCTTCACCAGGAGAAGCCGTCCTAGTATGCAGA
TCGAGCTGTCCACCTGCTTTTTTCTGTGCCTGCTGCGGTTCTGCTTCAGCGCCACCCGGCGGTACTACCTG
GGCGCCGTGGAGCTGTCCTGGGACTACATGCAGAGCGACCTGGGCGAGCTGCCCGTGGACGCCCGGTTCCC
CCCCAGAGTGCCCAAGAGCTTCCCCTTCAACACCAGCGTGGTGTACAAGAAAACCCTGTTCGTGGAGTTCA
CCGACCACCTGTTCAATATCGCCAAGCCCAGGCCCCCCTGGATGGGCCTGCTGGGCCCCACCATCCAGGCC
GAGGTGTACGACACCGTGGTGATCACCCTGAAGAACATGGCCAGCCACCCCGTGAGCCTGCACGCCGTGGG
CGTGAGCTACTGGAAGGCCAGCGAGGGCGCCGAGTACGACGACCAGACCAGCCAGCGGGAGAAAGAAGATG
ACAAGGTGTTCCCTGGCGGCAGCCACACCTACGTGTGGCAGGTGCTGAAAGAAAACGGCCCCATGGCCTCC
GACCCCCTGTGCCTGACCTACAGCTACCTGAGCCACGTGGACCTGGTGAAGGACCTGAACAGCGGCCTGAT
CGGCGCTCTGCTCGTCTGCCGGGAGGGCAGCCTGGCCAAAGAGAAAACCCAGACCCTGCACAAGTTCATCC
TGCTGTTCGCCGTGTTCGACGAGGGCAAGAGCTGGCACAGCGAGACAAAGAACAGCCTGATGCAGGACCGG
GACGCCGCCTCTGCCAGAGCCTGGCCCAAGATGCACACCGTGAACGGCTACGTGAACAGAAGCCTGCCCGG
CCTGATTGGCTGCCACCGGAAGAGCGTGTACTGGCACGTGATCGGCATGGGCACCACACCCGAGGTGCACA
GCATCTTTCTGGAAGGGCACACCTTTCTGGTCCGGAACCACCGGCAGGCCAGCCTGGAAATCAGCCCTATC
ACCTTCCTGACCGCCCAGACACTGCTGATGGACCTGGGCCAGTTCCTGCTGTTTTGCCACATCAGCTCTCA
CCAGCACGACGGCATGGAAGCCTACGTGAAGGTGGACTCTTGCCCCGAGGAACCCCAGCTGCGGATGAAGA
ACAACGAGGAAGCCGAGGACTACGACGACGACCTGACCGACAGCGAGATGGACGTGGTGCGGTTCGACGAC
GACAACAGCCCCAGCTTCATCCAGATCAGAAGCGTGGCCAAGAAGCACCCCAAGACCTGGGTGCACTATAT
CGCCGCCGAGGAAGAGGACTGGGACTACGCCCCCCTGGTGCTGGCCCCGACGACAGAAGCTACAAGAGCC
AGTACCTGAACAATGGCCCCCAGCGGATCGGCCGGAAGTACAAGAAAGTGCGGTTCATGGCCTACACCGAC
GAGACATTCAAGACCCGGGAGGCCATCCAGCACGAGAGCGGCATCCTGGGCCCCCTGCTGTACGGCGAAGT
GGGCGACACACTGCTGATCATCTTCAAGAACCAGGCTAGCCGGCCCTACAACATCTACCCCCACGGCATCA
CCGACGTGCGGCCCCTGTACAGCAGGCGGCTGCCCAAGGGCGTGAAGCACCTGAAGGACTTCCCCATCCTG
CCCGGCGAGATCTTCAAGTACAAGTGGACCGTGACCGTGGAGGACGGCCCCACCAAGAGCGACCCCAGATG
CCTGACCCGGTACTACAGCAGCTTCGTGAACATGGAACGGGACCTGGCCTCCGGGCTGATCGGACCTCTGC
TGATCTGCTACAAAGAAAGCGTGGACCAGCGGGGCAACCAGATCATGAGCGACAAGCGGAACGTGATCCTG
TTCAGCGTGTTCGATGAGAACCGGTCCTGGTATCTGACCGAGAACATCCAGCGGTTTCTGCCCAACCCTGC
CGGCGTGCAGCTGGAAGATCCCGAGTTCCAGGCCAGCAACATCATGCACTCCATCAATGGCTACGTGTTCG
ACTCTCTGCAGCTCTCCGTGTGTCTGCACGAGGTGGCCTACTGGTACATCCTGAGCATCGGCGCCCAGACC

Figure 14 (continued)

```
GACTTCCTGAGCGTGTTCTTCAGCGGCTACACCTTCAAGCACAAGATGGTGTACGAGGACACCCTGACCCT
GTTCCCTTTCAGCGGCGAGACAGTGTTCATGAGCATGGAAAACCCCGGCCTGTGGATTCTGGGCTGCCACA
ACAGCGACTTCCGGAACCGGGGCATGACCGCCCTGCTGAAGGTGTCCAGCTGCGACAAGAACACCGGCGAC
TACTACGAGGACAGCTACGAGGATATCAGCGCCTACCTGCTGTCCAAGAACAACGCCATCGAACCCCGGAG
CTTCAGCCAGAACCCCCCGTGCTGACGCGTCACCAGCGGGAGATCACCCGGACAACCCTGCAGTCCGACC
AGGAAGAGATCGATTACGACGACACCATCAGCGTGGAGATGAAGAAAGAGGATTTCGATATCTACGACGAG
GACGAGAACCAGAGCCCCAGAAGCTTCCAGAAGAAAACCCGGCACTACTTCATTGCCGCCGTGGAGAGGCT
GTGGGACTACGGCATGAGTTCTAGCCCCCACGTGCTGCGGAACCGGGCCCAGAGCGGCAGCGTGCCCCAGT
TCAAGAAAGTGGTGTTCCAGGAATTCACAGACGGCAGCTTCACCCAGCCTCTGTATAGAGGCGAGCTGAAC
GAGCACCTGGGGCTGCTGGGGCCCTACATCAGGGCCGAAGTGGAGGACAACATCATGGTGACCTTCCGGAA
TCAGGCCAGCAGACCCTACTCCTTCTACAGCAGCCTGATCAGCTACGAAGAGGACCAGCGGCAGGGCGCCG
AACCCCGGAAGAACTTCGTGAAGCCCAACGAAACCAAGACCTACTTCTGGAAAGTGCAGCACCACATGGCC
CCCACCAAGGACGAGTTCGACTGCAAGGCCTGGGCCTACTTCAGCGACGTGGATCTGGAAAAGGACGTGCA
CTCTGGACTGATTGGCCCACTCCTGGTCTGCCACACTAACACCCTCAACCCCGCCCACGGCCGCCAGGTGA
CCGTGCAGGAATTCGCCCTGTTCTTCACCATCTTCGACGAGACAAAGTCCTGGTACTTCACCGAGAATATG
GAACGGAACTGCAGAGCCCCCTGCAACATCCAGATGGAAGATCCTACCTTCAAAGAGAACTACCGGTTCCA
CGCCATCAACGGCTACATCATGGACACCCTGCCTGGCCTGGTGATGGCCCAGGACCAGAGAATCCGGTGGT
ATCTGCTGTCCATGGGCAGCAACGAGAATATCCACAGCATCCACTTCAGCGGCCACGTGTTCACCGTGCGG
AAGAAAGAAGAGTACAAGATGGCCCTGTACAACCTGTACCCCGGCGTGTTCGAGACAGTGGAGATGCTGCC
CAGCAAGGCCGGCATCTGGCGGGTGGAGTGTCTGATCGGCGAGCACCTGCACGCTGGCATGAGCACCCTGT
TTCTGGTGTACAGCAACAAGTGCCAGACCCCACTGGGCATGGCCTCTGGCCACATCCGGGACTTCCAGATC
ACCGCCTCCGGCCAGTACGGCCAGTGGGCCCCCAAGCTGGCCAGACTGCACTACAGCGGCAGCATCAACGC
CTGGTCCACCAAAGAGCCCTTCAGCTGGATCAAGGTGGACCTGCTGGCCCCTATGATCATCCACGGCATTA
AGACCCAGGGCGCCAGGCAGAAGTTCAGCAGCCTGTACATCAGCCAGTTCATCATCATGTACAGCCTGGAC
GGCAAGAAGTGGCAGACCTACCGGGGCAACAGCACCGGCACCCTGATGGTGTTCTTCGGCAATGTGGACAG
CAGCGGCATCAAGCACAACATCTTCAACCCCCCCATCATTGCCCGGTACATCCGGCTGCACCCCACCCACT
ACAGCATTAGATCCACACTGAGAATGGAACTGATGGGCTGCGACCTGAACTCCTGCAGCATGCCTCTGGGC
ATGGAAAGCAAGGCCATCAGCGACGCCCAGATCACAGCCAGCAGCTACTTCACCAACATGTTCGCCACCTG
GTCCCCCTCCAAGGCCAGGCTGCACCTGCAGGGCCGGTCCAACGCCTGGCGGCCTCAGGTCAACAACCCCA
AAGAATGGCTGCAGGTGGACTTTCAGAAAACCATGAAGGTGACCGGCGTGACCACCCAGGGCGTGAAAAGC
CTGCTGACCAGCATGTACGTGAAAGAGTTTCTGATCAGCAGCTCTCAGGATGGCCACCAGTGGACCCTGTT
CTTTCAGAACGGCAAGGTGAAAGTGTTCCAGGGCAACCAGGACTCCTTCACCCCCGTGGTGAACTCCCTGG
ACCCCCCCCTGCTGACCCGCTACCTGAGAATCCACCCCCAGTCTTGGGTGCACCAGATCGCCCTCAGGATG
GAAGTCCTGGGATGTGAGGCCCAGGATCTGTATACTGATGAGGATCCAATAAAAGATCTTTATTTTCATTAGA
TCTGTGTGTTGGTTTTTTGTGTG
```

SEQ ID NO.48: Flank-3xSERP-Flank-*TTRe*-Flank-TTRm-Flank-coFVIIIdeltaB-Flank- SyntpA-Flank

```
GCGGCCGCGGTACGCGGGGGAGGCTGCTGGTGAATATTAACCAAGGTCACCCCAGTTATCGGAGGAGCAAA
CAGGGGCTAAGTCCACCGGGGGAGGCTGCTGGTGAATATTAACCAAGGTCACCCCAGTTATCGGAGGAGCA
AACAGGGGCTAAGTCCACCGGGGGAGGCTGCTGGTGAATATTAACCAAGGTCACCCCAGTTATCGGAGGAG
CAAACAGGGGCTAAGTCCACGGTACCCACTGGGAGGATGTTGAGTAAGATGGAAAACTACTGATGACCCTT
GCAGAGACAGAGTATTAGGACATGTTTGAACAGGGGCCGGGCGATCAGCAGGTAGCTCTAGAGGATCCCCG
TCTGTCTGCACATTTCGTAGAGCGAGTGTTCCGATACTCTAATCTCCCTAGGCAAGGTTCATATTTGTGTA
GGTTACTTATTCTCCTTTTGTTGACTAAGTCAATAATCAGAATCAGCAGGTTTGGAGTCAGCTTGGCAGGG
ATCAGCAGCCTGGGTTGGAAGGAGGGGGTATAAAAGCCCCTTCACCAGGAGAAGCCGTCCTAGTATGCAGA
TCGAGCTGTCCACCTGCTTTTTTCTGTGCCTGCTGCGGTTCTGCTTCAGCGCCACCCGGCGGTACTACCTG
GGCGCCGTGGAGCTGTCCTGGGACTACATGCAGAGCGACCTGGGCGAGCTGCCCGTGGACGCCCGGTTCCC
CCCCAGAGTGCCCAAGAGCTTCCCCTTCAACACCAGCGTGGTGTACAAGAAAACCCTGTTCGTGGAGTTCA
CCGACCACCTGTTCAATATCGCCAAGCCCAGGCCCCCCTGGATGGGCCTGCTGGGCCCCACCATCCAGGCC
GAGGTGTACGACACCGTGGTGATCACCCTGAAGAACATGGCCAGCCACCCCGTGAGCCTGCACGCCGTGGG
CGTGAGCTACTGGAAGGCCAGCGAGGGCGCCGAGTACGACGACCAGACCAGCCAGCGGGAGAAGAAGATG
ACAAGGTGTTCCCTGGCGGCAGCCACACCTACGTGTGGCAGGTGCTGAAAGAAAACGGCCCCATGGCCTCC
GACCCCCTGTGCCTGACCTACAGCTACCTGAGCCACGTGGACCTGGTGAAGGACCTGAACAGCGGCCTGAT
```

Figure 14 (continued)

```
CGGCGCTCTGCTCGTCTGCCGGGAGGGCAGCCTGGCCAAAGAGAAAACCCAGACCCTGCACAAGTTCATCC
TGCTGTTCGCCGTGTTCGACGAGGGCAAGAGCTGGCACAGCGAGACAAAGAACAGCCTGATGCAGGACCGG
GACGCCGCCTCTGCCAGAGCCTGGCCCAAGATGCACACCGTGAACGGCTACGTGAACAGAAGCCTGCCCGG
CCTGATTGGCTGCCACCGGAAGAGCGTGTACTGGCACGTGATCGGCATGGGCACCACACCCGAGGTGCACA
GCATCTTTCTGGAAGGGCACACCTTTCTGGTCCGGAACCACCGGCAGGCCAGCCTGGAAATCAGCCCTATC
ACCTTCCTGACCGCCCAGACACTGCTGATGGACCTGGGCCAGTTCCTGCTGTTTTGCCACATCAGCTCTCA
CCAGCACGACGGCATGGAAGCCTACGTGAAGGTGGACTCTTGCCCCGAGGAACCCCAGCTGCGGATGAAGA
ACAACGAGGAAGCCGAGGACTACGACGACGACCTGACCGACAGCGAGATGGACGTGGTGCGGTTCGACGAC
GACAACAGCCCCAGCTTCATCCAGATCAGAAGCGTGGCCAAGAAGCACCCCAAGACCTGGGTGCACTATAT
CGCCGCCGAGGAAGAGGACTGGGACTACGCCCCCCTGGTGCTGGCCCCCGACGACAGAAGCTACAAGAGCC
AGTACCTGAACAATGGCCCCCAGCGGATCGGCCGGAAGTACAAGAAAGTGCGGTTCATGGCCTACACCGAC
GAGACATTCAAGACCCGGGAGGCCATCCAGCACGAGAGCGGCATCCTGGGCCCCCTGCTGTACGGCGAAGT
GGGCGACACACTGCTGATCATCTTCAAGAACCAGGCTAGCCGGCCCTACAACATCTACCCCCACGGCATCA
CCGACGTGCGGCCCCTGTACAGCAGGCGGCTGCCCAAGGGCGTGAAGCACCTGAAGGACTTCCCCATCCTG
CCCGGCGAGATCTTCAAGTACAAGTGGACCGTGACCGTGGAGGACGGCCCCACCAAGAGCGACCCCAGATG
CCTGACCCGGTACTACAGCAGCTTCGTGAACATGGAACGGGACCTGGCCTCCGGGCTGATCGGACCTCTGC
TGATCTGCTACAAAGAAAGCGTGGACCAGCGGGGCAACCAGATCATGAGCGACAAGCGGAACGTGATCCTG
TTCAGCGTGTTCGATGAGAACCGGTCCTGGTATCTGACCGAGAACATCCAGCGGTTTCTGCCCAACCCTGC
CGGCGTGCAGCTGGAAGATCCCGAGTTCCAGGCCAGCAACATCATGCACTCCATCAATGGCTACGTGTTCG
ACTCTCTGCAGCTCTCCGTGTGTCTGCACGAGGTGGCCTACTGGTACATCCTGAGCATCGGCGCCCAGACC
GACTTCCTGAGCGTGTTCTTCAGCGGCTACACCTTCAAGCACAAGATGGTGTACGAGGACACCCTGACCCT
GTTCCCTTTTCAGCGGCGAGACAGTGTTCATGAGCATGGAAAACCCCGGCCTGTGGATTCTGGGCTGCCACA
ACAGCGACTTCCGGAACCGGGGCATGACCGCCCTGCTGAAGGTGTCCAGCTGCGACAAGAACACCGGCGAC
TACTACGAGGACAGCTACGAGGATATCAGCGCCTACCTGCTGTCCAAGAACAACGCCATCGAACCCCGGAG
CTTCAGCCAGAACCCCCCGTGCTGACGCGTCACCAGCGGGAGATCACCCGGACAACCCTGCAGTCCGACC
AGGAAGAGATCGATTACGACGACACCATCAGCGTGGAGATGAAGAAAGAGGATTTCGATATCTACGACGAG
GACGAGAACCAGAGCCCCAGAAGCTTCCAGAAGAAAACCCGGCACTACTTCATTGCCGCCGTGGAGAGGCT
GTGGGACTACGGCATGAGTTCTAGCCCCCACGTGCTGCGGAACCGGGCCCAGAGCGGCAGCGTGCCCCAGT
TCAAGAAAGTGGTGTTCCAGGAATTCACAGACGGCAGCTTCACCCAGCCTCTGTATAGAGGCGAGCTGAAC
GAGCACCTGGGGCTGCTGGGGCCCTACATCAGGGCCGAAGTGGAGGACAACATCATGGTGACCTTCCGGAA
TCAGGCCAGCAGACCCTACTCCTTCTACAGCAGCCTGATCAGCTACGAAGAGGACCAGCGGCAGGGCGCCG
AACCCCGGAAGAACTTCGTGAAGCCCAACGAAACCAAGACCTACTTCTGGAAAGTGCAGCACCACATGGCC
CCCACCAAGGACGAGTTCGACTGCAAGGCCTGGGCCTACTTCAGCGACGTGGATCTGGAAAAGGACGTGCA
CTCTGGACTGATTGGCCCACTCCTGGTCTGCCACACTAACACCCTCAACCCCGCCCACGGCCGCCAGGTGA
CCGTGCAGGAATTCGCCCTGTTCTTCACCATCTTCGACGAGACAAAGTCCTGGTACTTCACCGAGAATATG
GAACGGAACTGCAGAGCCCCCTGCAACATCCAGATGGAAGATCCTACCTTCAAAGAGAACTACCGGTTCCA
CGCCATCAACGGCTACATCATGGACACCCTGCCTGGCCTGGTGATGGCCCAGGACCAGAGAATCCGGTGGT
ATCTGCTGTCCATGGGCAGCAACGAGAATATCCACAGCATCCACTTCAGCGGCCACGTGTTCACCGTGCGG
AAGAAGAAGAGTACAAGATGGCCCTGTACAACCTGTACCCCGGCGTGTTCGAGACAGTGGAGATGCTGCC
CAGCAAGGCCGGCATCTGGCGGGTGGAGTGTCTGATCGGCGAGCACCTGCACGCTGGCATGAGCACCCTGT
TTCTGGTGTACAGCAACAAGTGCCAGACCCCACTGGGCATGGCCTCTGGCCACATCCGGGACTTCCAGATC
ACCGCCTCCGGCCAGTACGGCCAGTGGGCCCCCAAGCTGGCCAGACTGCACTACAGCGGCAGCATCAACGC
CTGGTCCACCAAAGAGCCCTTCAGCTGGATCAAGGTGGACCTGCTGGCCCCTATGATCATCCACGGCATTA
AGACCCAGGGCGCCAGGCAGAAGTTCAGCAGCCTGTACATCAGCCAGTTCATCATCATGTACAGCCTGGAC
GGCAAGAAGTGGCAGACCTACCGGGGCAACAGCACCGGCACCCTGATGGTGTTCTTCGGCAATGTGGACAG
CAGCGGCATCAAGCACAACATCTTCAACCCCCCCATCATTGCCCGGTACATCCGGCTGCACCCCACCCACT
ACAGCATTAGATCCACACTGAGAATGGAACTGATGGGCTGCGACCTGAACTCCTGCAGCATGCCTCTGGGC
ATGGAAAGCAAGGCCATCAGCGACGCCCAGATCACAGCCAGCAGCTACTTCACCAACATGTTCGCCACCTG
GTCCCCCTCCAAGGCCAGGCTGCACCTGCAGGGCCGGTCCAACGCCTGGCGGCCTCAGGTCAACAACCCCA
AAGAATGGCTGCAGGTGGACTTTCAGAAAACCATGAAGGTGACCGGCGTGACCACCCAGGGCGTGAAAAGC
CTGCTGACCAGCATGTACGTGAAAGAGTTTCTGATCAGCAGCTCTCAGGATGGCCACCAGTGGACCCTGTT
CTTTCAGAACGGCAAGGTGAAAGTGTTCCAGGGCAACCAGGACTCCTTCACCCCCGTGGTGAACTCCCTGG
ACCCCCCCCTGCTGACCCGCTACCTGAGAATCCACCCCCAGTCTTGGGTGCACCAGATCGCCCTCAGGATG
GAAGTCCTGGGATGTGAGGCCCAGGATCTGTACTGATGAGGATCCAATAAAGATCTTTATTTTCATTAGA
TCTGTGTGTTGGTTTTTTGTGTGCTCGAGATCCACGGCCGC
```

Figure 14 (continued)

SEQ ID NO.49: Flank-<u>3xSERP</u>-Flank-*TTRe*-Flank-TTRm-*MVM*-Flank

GCGGCCGCGGTACGCGGGGGAGGCTGCTGGTGAATATTAACCAAGGTCACCCCAGTTATCGGAGGAGCAAA
<u>CAGGGGCTAAGTCCAC</u>CGGGGGAGGCTGCTGGTGAATATTAACCAAGGTCACCCCAGTTATCGGAGGAGCA
<u>AACAGGGGCTAAGTCCAC</u>CGGGGGAGGCTGCTGGTGAATATTAACCAAGGTCACCCCAGTTATCGGAGGAG
<u>CAAACAGGGGCTAAGTCCAC</u>GGTACC*CACTGGGAGGATGTTGAGTAAGATGGAAAACTACTGATGACCCTT*
*GCAGAGACAGAGTATTAGGACATGTTTGAACAGGGGCCGGGCGATCAGCAGGTAG*CTCTAGAGGATCCCCG
TCTGTCTGCACATTTCGTAGAGCGAGTGTTCCGATACTCTAATCTCCCTAGGCAAGGTTCATATTTGTGTA
GGTTACTTATTCTCCTTTTGTTGACTAAGTCAATAATCAGAATCAGCAGGTTTGGAGTCAGCTTGGCAGGG
ATCAGCAGCCTGGGTTGGAAGGAGGGGGTATAAAAGCCCCTTCACCAGGAGAAGCCGTC*AAGAGGTAAGGG*
*TTTAAGGGATGGTTGGTTGGTGGGGTATTAATGTTTAATTACCTGGAGCACCTGCCTGAAATCACTTTTTT*
*TCAGGTTGG*CTAGT

SEQ ID NO.50: Flank-<u>3xSERP</u>-Flank-*TTRe*-Flank-TTRm-*MVM*-Flank-coFVIIIdeltaB

GCGGCCGCGGTACGCGGGGGAGGCTGCTGGTGAATATTAACCAAGGTCACCCCAGTTATCGGAGGAGCAAA
<u>CAGGGGCTAAGTCCAC</u>CGGGGGAGGCTGCTGGTGAATATTAACCAAGGTCACCCCAGTTATCGGAGGAGCA
<u>AACAGGGGCTAAGTCCAC</u>CGGGGGAGGCTGCTGGTGAATATTAACCAAGGTCACCCCAGTTATCGGAGGAG
<u>CAAACAGGGGCTAAGTCCAC</u>GGTACC*CACTGGGAGGATGTTGAGTAAGATGGAAAACTACTGATGACCCTT*
*GCAGAGACAGAGTATTAGGACATGTTTGAACAGGGGCCGGGCGATCAGCAGGTAG*CTCTAGAGGATCCCCG
TCTGTCTGCACATTTCGTAGAGCGAGTGTTCCGATACTCTAATCTCCCTAGGCAAGGTTCATATTTGTGTA
GGTTACTTATTCTCCTTTTGTTGACTAAGTCAATAATCAGAATCAGCAGGTTTGGAGTCAGCTTGGCAGGG
ATCAGCAGCCTGGGTTGGAAGGAGGGGGTATAAAAGCCCCTTCACCAGGAGAAGCCGTC*AAGAGGTAAGGG*
*TTTAAGGGATGGTTGGTTGGTGGGGTATTAATGTTTAATTACCTGGAGCACCTGCCTGAAATCACTTTTTT*
*TCAGGTTGG*CTAGT<u>ATGCAGATCGAGCTGTCCACCTGCTTTTTTCTGTGCCTGCTGCGGTTCTGCTTCAGC
GCCACCCGGCGGTACTACCTGGGCGCCGTGGAGCTGTCCTGGGACTACATGCAGAGCGACCTGGGCGAGCT
GCCCGTGGACGCCCGGTTCCCCCCCAGAGTGCCCAAGAGCTTCCCCTTCAACACCAGCGTGGTGTACAAGA
AAACCCTGTTCGTGGAGTTCACCGACCACCTGTTCAATATCGCCAAGCCCAGGCCCCCTGGATGGGCCTG
CTGGGCCCCACCATCCAGGCCGAGGTGTACGACACCGTGGTGATCACCCTGAAGAACATGGCCAGCCACCC
CGTGAGCCTGCACGCCGTGGGCGTGAGCTACTGGAAGGCCAGCGAGGGCGCCGAGTACGACGACCAGACCA
GCCAGCGGGAGAAAGAAGATGACAAGGTGTTCCCTGGCGGCAGCCACACCTACGTGTGGCAGGTGCTGAAA
GAAAACGGCCCCATGGCCTCCGACCCCCTGTGCCTGACCTACAGCTACCTGAGCCACGTGGACCTGGTGAA
GGACCTGAACAGCGGCCTGATCGGCGCTCTGCTCGTCTGCCGGGAGGGCAGCCTGGCCAAAGAGAAAACCC
AGACCCTGCACAAGTTCATCCTGCTGTTCGCCGTGTTCGACGAGGGCAAGAGCTGGCACAGCGAGACAAAG
AACAGCCTGATGCAGGACCGGGACGCCGCCTCTGCCAGAGCCTGGCCCAAGATGCACACCGTGAACGGCTA
CGTGAACAGAAGCCTGCCCGGCCTGATTGGCTGCCACCGGAAGAGCGTGTACTGGCACGTGATCGGCATGG
GCACCACACCCGAGGTGCACAGCATCTTTCTGGAAGGGCACACCTTTCTGGTCCGGAACCACCGGCAGGCC
AGCCTGGAAATCAGCCCTATCACCTTCCTGACCGCCCAGACACTGCTGATGGACCTGGGCCAGTTCCTGCT
GTTTTGCCACATCAGCTCTCACCAGCACGACGGCATGGAAGCCTACGTGAAGGTGGACTCTTGCCCCGAGG
AACCCCAGCTGCGGATGAAGAACAACGAGGAAGCCGAGGACTACGACGACGACCTGACCGACAGCGAGATG
GACGTGGTGCGGTTCGACGACGACAACAGCCCCAGCTTCATCCAGATCAGAAGCGTGGCCAAGAAGCACCC
CAAGACCTGGGTGCACTATATCGCCGCCGAGGAAGAGGACTGGGACTACGCCCCCTGGTGCTGGCCCCCG
ACGACAGAAGCTACAAGAGCCAGTACCTGAACAATGGCCCCCAGCGGATCGGCCGGAAGTACAAGAAAGTG
CGGTTCATGGCCTACACCGACGAGACATTCAAGACCCGGGAGGCCATCCAGCACGAGAGCGGCATCCTGGG
CCCCCTGCTGTACGGCGAAGTGGGCGACACACTGCTGATCATCTTCAAGAACCAGGCTAGCCGGCCCTACA
ACATCTACCCCCACGGCATCACCGACGTGCGGCCCCTGTACAGCAGGCGGCTGCCCAAGGGCGTGAAGCAC
CTGAAGGACTTCCCCATCCTGCCCGGCGAGATCTTCAAGTACAAGTGGACCGTGACCGTGGAGGACGGCCC
CACCAAGAGCGACCCCAGATGCCTGACCCGGTACTACAGCAGCTTCGTGAACATGGAACGGGACCTGGCCT
CCGGGCTGATCGGACCTCTGCTGATCTGCTACAAAGAAAGCGTGGACCAGCGGGGCAACCAGATCATGAGC
GACAAGCGGAACGTGATCCTGTTCAGCGTGTTCGATGAGAACCGGTCCTGGTATCTGACCGAGAACATCCA
GCGGTTTCTGCCCAACCCTGCCGGCGTGCAGCTGGAAGATCCCGAGTTCCAGGCCAGCAACATCATGCACT
CCATCAATGGCTACGTGTTCGACTCTCTGCAGCTCTCCGTGTGTCTGCACGAGGTGGCCTACTGGTACATC
CTGAGCATCGGCGCCCAGACCGACTTCCTGAGCGTGTTCTTCAGCGGCTACACCTTCAAGCACAAGATGGT</u>

Figure 14 (continued)

GTACGAGGACACCCTGACCCTGTTCCCTTTCAGCGGCGAGACAGTGTTCATGAGCATGGAAAACCCCGGCC
TGTGGATTCTGGGCTGCCACAACAGCGACTTCCGGAACCGGGGCATGACCGCCCTGCTGAAGGTGTCCAGC
TGCGACAAGAACACCGGCGACTACTACGAGGACAGCTACGAGGATATCAGCGCCTACCTGCTGTCCAAGAA
CAACGCCATCGAACCCCGGAGCTTCAGCCAGAACCCCCCGTGCTGACGCGTCACCAGCGGGAGATCACCC
GGACAACCCTGCAGTCCGACCAGGAAGAGATCGATTACGACGACACCATCAGCGTGGAGATGAAGAAAGAG
GATTTCGATATCTACGACGAGGACGAGAACCAGAGCCCCAGAAGCTTCCAGAAGAAAACCCGGCACTACTT
CATTGCCGCCGTGGGAGAGGCTGTGGGACTACGGCATGAGTTCTAGCCCCCACGTGCTGCGGAACCGGGCCC
AGAGCGGCAGCGTGCCCCAGTTCAAGAAAGTGGTGTTCCAGGAATTCACAGACGGCAGCTTCACCCAGCCT
CTGTATAGAGGCGAGCTGAACGAGCACCTGGGGCTGCTGGGGCCCTACATCAGGGCCGAAGTGGAGGACAA
CATCATGGTGACCTTCCGGAATCAGGCCAGCAGACCCTACTCCTTCTACAGCAGCCTGATCAGCTACGAAG
AGGACCAGCGGCAGGGCGCCGAACCCCGGAAGAACTTCGTGAAGCCCAACGAAACCAAGACCTACTTCTGG
AAAGTGCAGCACCACATGGCCCCCACCAAGGACGAGTTCGACTGCAAGGCCTGGGCCTACTTCAGCGACGT
GGATCTGGAAAAGGACGTGCACTCTGGACTGATTGGCCCACTCCTGGTCTGCCACACTAACACCCTCAACC
CCGCCCACGGCCGCCAGGTGACCGTGCAGGAATTCGCCCTGTTCTTCACCATCTTCGACGAGACAAAGTCC
TGGTACTTCACCGAGAATATGGAACGGAACTGCAGAGCCCCCTGCAACATCCAGATGGAAGATCCTACCTT
CAAAGAGAACTACCGGTTCCACGCCATCAACGGCTACATCATGGACACCCTGCCTGGCCTGGTGATGGCCC
AGGACCAGAGAATCCGGTGGTATCTGCTGTCCATGGGCAGCAACGAGAATATCCACAGCATCCACTTCAGC
GGCCACGTGTTCACCGTGCGGAAGAAAGAAGAGTACAAGATGGCCCTGTACAACCTGTACCCCGGCGTGTT
CGAGACAGTGGAGATGCTGCCCAGCAAGGCCGGCATCTGGCGGGTGGAGTGTCTGATCGGCGAGCACCTGC
ACGCTGGCATGAGCACCCTGTTTCTGGTGTACAGCAACAAGTGCCAGACCCCACTGGGCATGGCCTCTGGC
CACATCCGGGACTTCCAGATCACCGCCTCCGGCCAGTACGGCCAGTGGGCCCCCAAGCTGGCCAGACTGCA
CTACAGCGGCAGCATCAACGCCTGGTCCACCAAAGAGCCCTTCAGCTGGATCAAGGTGGACCTGCTGGCCC
CTATGATCATCCACGGCATTAAGACCCAGGGCGCCAGGCAGAAGTTCAGCAGCCTGTACATCAGCCAGTTC
ATCATCATGTACAGCCTGGACGGCAAGAAGTGGCAGACCTACCGGGGCAACAGCACCGGCACCCTGATGGT
GTTCTTCGGCAATGTGGACAGCAGCGGCATCAAGCACAACATCTTCAACCCCCCCATCATTGCCCGGTACA
TCCGGCTGCACCCCACCCACTACAGCATTAGATCCACACTGAGAATGGAACTGATGGGCTGCGACCTGAAC
TCCTGCAGCATGCCTCTGGGCATGGAAAGCAAGGCCATCAGCGACGCCCAGATCACAGCCAGCAGCTACTT
CACCAACATGTTCGCCACCTGGTCCCCCTCCAAGGCCAGGCTGCACCTGCAGGGCCGGTCCAACGCCTGGC
GGCCTCAGGTCAACAACCCCAAAGAATGGCTGCAGGTGGACTTTCAGAAAACCATGAAGGTGACCGGCGTG
ACCACCCAGGGCGTGAAAAGCCTGCTGACCAGCATGTACGTGAAAGAGTTTCTGATCAGCAGCTCTCAGGA
TGGCCACCAGTGGACCCTGTTCTTTCAGAACGGCAAGGTGAAAGTGTTCCAGGGCAACCAGGACTCCTTCA
CCCCCGTGGTGAACTCCCTGGACCCCCCCCTGCTGACCCGCTACCTGAGAATCCACCCCCAGTCTTGGGTG
CACCAGATCGCCCTCAGGATGGAAGTCCTGGGATGTGAGGCCCAGGATCTGTACTGATGA

SEQ ID NO.51: Flank-3xSERP-Flank-*TTRe*-Flank-TTRm-*MVM*-Flank-
coFVIIIdeltaB-Flank

GCGGCCGCGGTACGCGGGGGAGGCTGCTGGTGAATATTAACCAAGGTCACCCCAGTTATCGGAGGAGCAAA
CAGGGGCTAAGTCCACCGGGGGAGGCTGCTGGTGAATATTAACCAAGGTCACCCCAGTTATCGGAGGAGCA
AACAGGGGCTAAGTCCACCGGGGGAGGCTGCTGGTGAATATTAACCAAGGTCACCCCAGTTATCGGAGGAG
CAAACAGGGGCTAAGTCCACGGTACC*CACTGGGAGGATGTTGAGTAAGATGGAAAACTACTGATGACCCTT*
*GCAGAGACAGAGTATTAGGACATGTTTGAACAGGGGCCGGGCGATCAGCAGGTAG*CTCTAGAGGATCCCCG
TCTGTCTGCACATTTCGTAGAGCGAGTGTTCCGATACTCTAATCTCCCTAGGCAAGGTTCATATTTGTGTA
GGTTACTTATTCTCCTTTTGTTGACTAAGTCAATAATCAGAATCAGCAGGTTTGGAGTCAGCTTGGCAGGG
ATCAGCAGCCTGGGTTGGAAGGAGGGGGTATAAAAGCCCCTTCACCAGGAGAAGCCGTC*AAGAGGTAAGGG*
*TTTAAGGGATGGTTGGTTGGTGGGGTATTAATGTTTAATTACCTGGAGCACCTGCCTGAAATCACTTTTTT*
*TCAGGTTGG***CTAGTATGCAGATCGAGCTGTCCACCTGCTTTTTTCTGTGCCTGCTGCGGTTCTGCTTCAGC
GCCACCCGGCGGTACTACCTGGGCGCCGTGGAGCTGTCCTGGGACTACATGCAGAGCGACCTGGGCGAGCT
GCCCGTGGACGCCCGGTTCCCCCCCAGAGTGCCCAAGAGCTTCCCCTTCAACACCAGCGTGGTGTACAAGA
AAACCCTGTTCGTGGAGTTCACCGACCACCTGTTCAATATCGCCAAGCCCAGGCCCCCTGGATGGGCCTG
CTGGGCCCCACCATCCAGGCCGAGGTGTACGACACCGTGGTGATCACCCTGAAGAACATGGCCAGCCACCC
CGTGAGCCTGCACGCCGTGGGCGTGAGCTACTGGAAGGCCAGCGAGGGCGCCGAGTACGACGACCAGACCA
GCCAGCGGGAGAAGAAGATGACAAGGTGTTCCCTGGCGGCAGCCACACCTACGTGTGGCAGGTGCTGAAA
GAAAACGGCCCCATGGCCTCCGACCCCCTGTGCCTGACCTACAGCTACCTGAGCCACGTGGACCTGGTGAA
GGACCTGAACAGCGGCCTGATCGGCGCTCTGCTCGTCTGCCGGGAGGGCAGCCTGGCCAAAGAGAAACCC

Figure 14 (continued)

```
AGACCCTGCACAAGTTCATCCTGCTGTTCGCCGTGTTCGACGAGGGCAAGAGCTGGCACAGCGAGACAAAG
AACAGCCTGATGCAGGACCGGGACGCCGCCTCTGCCAGAGCCTGGCCCAAGATGCACACCGTGAACGGCTA
CGTGAACAGAAGCCTGCCCGGCCTGATTGGCTGCCACCGGAAGAGCGTGTACTGGCACGTGATCGGCATGG
GCACCACACCCGAGGTGCACAGCATCTTTCTGGAAGGGCACACCTTTCTGGTCCGGAACCACCGGCAGGCC
AGCCTGGAAATCAGCCCTATCACCTTCCTGACCGCCCAGACACTGCTGATGGACCTGGGCCAGTTCCTGCT
GTTTTGCCACATCAGCTCTCACCAGCACGACGGCATGGAAGCCTACGTGAAGGTGGACTCTTGCCCCGAGG
AACCCCAGCTGCGGATGAAGAACAACGAGGAAGCCGAGGACTACGACGACGACCTGACCGACAGCGAGATG
GACGTGGTGCGGTTCGACGACGACAACAGCCCCAGCTTCATCCAGATCAGAAGCGTGGCCAAGAAGCACCC
CAAGACCTGGGTGCACTATATCGCCGCCGAGGAAGAGGACTGGGACTACGCCCCCCTGGTGCTGGCCCCCG
ACGACAGAAGCTACAAGAGCCAGTACCTGAACAATGGCCCCCAGCGGATCGGCCGGAAGTACAAGAAAGTG
CGGTTCATGGCCTACACCGACGAGACATTCAAGACCCGGGAGGCCATCCAGCACGAGAGCGGCATCCTGGG
CCCCCTGCTGTACGGCGAAGTGGGCGACACACTGCTGATCATCTTCAAGAACCAGGCTAGCCGGCCCTACA
ACATCTACCCCACGGCATCACCGACGTGCGGCCCTGTACAGCAGGCGGCTGCCCAAGGGCGTGAAGCAC
CTGAAGGACTTCCCCATCCTGCCCGGCGAGATCTTCAAGTACAAGTGGACCGTGACCGTGGAGGACGGCCC
CACCAAGAGCGACCCCAGATGCCTGACCCGGTACTACAGCAGCTTCGTGAACATGGAACGGGACCTGGCCT
CCGGGCTGATCGGACCTCTGCTGATCTGCTACAAAGAAAGCGTGGACCAGCGGGGCAACCAGATCATGAGC
GACAAGCGGAACGTGATCCTGTTCAGCGTGTTCGATGAGAACCGGTCCTGGTATCTGACCGAGAACATCCA
GCGGTTTCTGCCCAACCCTGCCGGCGTGCAGCTGGAAGATCCCGAGTTCCAGGCCAGCAACATCATGCACT
CCATCAATGGCTACGTGTTCGACTCTCTGCAGCTCTCCGTGTGTCTGCACGAGGTGGCCTACTGGTACATC
CTGAGCATCGGCGCCCAGACCGACTTCCTGAGCGTGTTCTTCAGCGGCTACACCTTCAAGCACAAGATGGT
GTACGAGGACACCCTGACCCTGTTCCCTTTCAGCGGCGAGACAGTGTTCATGAGCATGGAAAACCCCGGCC
TGTGGATTCTGGGCTGCCACAACAGCGACTTCCGGAACCGGGGCATGACCGCCCTGCTGAAGGTGTCCAGC
TGCGACAAGAACACCGGCGACTACTACGAGGACAGCTACGAGGATATCAGCGCCTACCTGCTGTCCAAGAA
CAACGCCATCGAACCCCGGAGCTTCAGCCAGAACCCCCCGTGCTGACGCGTCACCAGCGGGAGATCACCC
GGACAACCCTGCAGTCCGACCAGGAAGAGATCGATTACGACGACACCATCAGCGTGGAGATGAAGAAAGAG
GATTTCGATATCTACGACGAGGACGAGAACCAGAGCCCCAGAAGCTTCCAGAAGAAAACCCGGCACTACTT
CATTGCCGCCGTGGAGAGGCTGTGGGACTACGGCATGAGTTCTAGCCCCCACGTGCTGCGGAACCGGGCCC
AGAGCGGCAGCGTGCCCCAGTTCAAGAAAGTGGTGTTCCAGGAATTCACAGACGGCAGCTTCACCCAGCCT
CTGTATAGAGGCGAGCTGAACGAGCACCTGGGGCTGCTGGGGCCCTACATCAGGGCCGAAGTGGAGGACAA
CATCATGGTGACCTTCCGGAATCAGGCCAGCAGACCCTACTCCTTCTACAGCAGCCTGATCAGCTACGAAG
AGGACCAGCGGCAGGGCGCCGAACCCCGGAAGAACTTCGTGAAGCCCAACGAAACCAAGACCTACTTCTGG
AAAGTGCAGCACCACATGGCCCCCACCAAGGACGAGTTCGACTGCAAGGCCTGGGCCTACTTCAGCGACGT
GGATCTGGAAAAGGACGTGCACTCTGGACTGATTGGCCCACTCCTGGTCTGCCACACTAACACCCTCAACC
CCGCCCACGGCCGCCAGGTGACCGTGCAGGAATTCGCCCTGTTCTTCACCATCTTCGACGAGACAAAGTCC
TGGTACTTCACCGAGAATATGGAACGGAACTGCAGAGCCCCCTGCAACATCCAGATGGAAGATCCTACCTT
CAAAGAGAACTACCGGTTCCACGCCATCAACGGCTACATCATGGACACCCTGCCTGGCCTGGTGATGGCCC
AGGACCAGAGAATCCGGTGGTATCTGCTGTCCATGGGCAGCAACGAGAATATCCACAGCATCCACTTCAGC
GGCCACGTGTTCACCGTGCGGAAGAAAGAAGAGTACAAGATGGCCCTGTACAACCTGTACCCCGGCGTGTT
CGAGACAGTGGAGATGCTGCCCAGCAAGGCCGGCATCTGGCGGGTGGAGTGTCTGATCGGCGAGCACCTGC
ACGCTGGCATGAGCACCCTGTTTCTGGTGTACAGCAACAAGTGCCAGACCCCACTGGGCATGGCCTCTGGC
CACATCCGGGACTTCCAGATCACCGCCTCCGGCCAGTACGGCCAGTGGGCCCCCAAGCTGGCCAGACTGCA
CTACAGCGGCAGCATCAACGCCTGGTCCACCAAAGAGCCCTTCAGCTGGATCAAGGTGGACCTGCTGGCCC
CTATGATCATCCACGGCATTAAGACCCAGGGCGCCAGGCAGAAGTTCAGCAGCCTGTACATCAGCCAGTTC
ATCATCATGTACAGCCTGGACGGCAAGAAGTGGCAGACCTACCGGGGCAACAGCACCGGCACCCTGATGGT
GTTCTTCGGCAATGTGGACAGCAGCGGCATCAAGCACAACATCTTCAACCCCCCCATCATTGCCCGGTACA
TCCGGCTGCACCCCACCCACTACAGCATTAGATCCACACTGAGAATGGAACTGATGGGCTGCGACCTGAAC
TCCTGCAGCATGCCTCTGGGCATGGAAAGCAAGGCCATCAGCGACGCCCAGATCACAGCCAGCAGCTACTT
CACCAACATGTTCGCCACCTGGTCCCCCTCCAAGGCCAGGCTGCACCTGCAGGGCCGGTCCAACGCCTGGC
GGCCTCAGGTCAACAACCCCAAAGAATGGCTGCAGGTGGACTTTCAGAAAACCATGAAGGTGACCGGCGTG
ACCACCCAGGGCGTGAAAAGCCTGCTGACCAGCATGTACGTGAAAGAGTTTCTGATCAGCAGCTCTCAGGA
TGGCCACCAGTGGACCCTGTTCTTTCAGAACGGCAAGGTGAAAGTGTTCCAGGGCAACCAGGACTCCTTCA
CCCCCGTGGTGAACTCCCTGGACCCCCCCCTGCTGACCCGCTACCTGAGAATCCACCCCCAGTCTTGGGTG
CACCAGATCGCCCTCAGGATGGAAGTCCTGGGATGTGAGGCCCAGGATCTGTACTGATGAGGATCC
```

Figure 14 (continued)

SEQ ID NO.52: Flank-3xSERP-Flank-*TTRe*-Flank-TTRm-*MVM*-Flank-
<ins>coFVIIIdeltaB</ins>-Flank-SV40pA

GCGGCCGCGGTACGCGGGGGAGGCTGCTGGTGAATATTAACCAAGGTCACCCCAGTTATCGGAGGAGCAAA
CAGGGGCTAAGTCCACCGGGGGAGGCTGCTGGTGAATATTAACCAAGGTCACCCCAGTTATCGGAGGAGCA
AACAGGGGCTAAGTCCACCGGGGGAGGCTGCTGGTGAATATTAACCAAGGTCACCCCAGTTATCGGAGGAG
CAAACAGGGGCTAAGTCCACGGTACC*CACTGGGAGGATGTTGAGTAAGATGGAAAACTACTGATGACCCTT*
*GCAGAGACAGAGTATTAGGACATGTTTGAACAGGGGCCGGGCGATCAGCAGGTAG*CTCTAGAGGATCCCCG
TCTGTCTGCACATTTCGTAGAGCGAGTGTTCCGATACTCTAATCTCCCTAGGCAAGGTTCATATTTGTGTA
GGTTACTTATTCTCCTTTTGTTGACTAAGTCAATAATCAGAATCAGCAGGTTTGGAGTCAGCTTGGCAGGG
ATCAGCAGCCTGGGTTGGAAGGAGGGGGTATAAAAGCCCCTTCACCAGGAGAAGCCGTC*AAGAGGTAAGGG*
*TTTAAGGGATGGTTGGTTGGTGGGGTATTAATGTTTAATTACCTGGAGCACCTGCCTGAAATCACTTTTTT*
*TCAGGTTGG***CTAGTATGCAGATCGAGCTGTCCACCTGCTTTTTTCTGTGCCTGCTGCGGTTCTGCTTCAGC
GCCACCCGGCGGTACTACCTGGGCGCCGTGGAGCTGTCCTGGGACTACATGCAGAGCGACCTGGGCGAGCT
GCCCGTGGACGCCCGGTTCCCCCCCAGAGTGCCCAAGAGCTTCCCCTTCAACACCAGCGTGGTGTACAAGA
AAACCCTGTTCGTGGAGTTCACCGACCACCTGTTCAATATCGCCAAGCCCAGGCCCCCTGGATGGGCCTG
CTGGGCCCCACCATCCAGGCCGAGGTGTACGACACCGTGGTGATCACCCTGAAGAACATGGCCAGCCACCC
CGTGAGCCTGCACGCCGTGGGCGTGAGCTACTGGAAGGCCAGCGAGGGCGCCGAGTACGACGACCAGACCA
GCCAGCGGGAGAAAGAAGATGACAAGGTGTTCCCTGGCGGCAGCCACACCTACGTGTGGCAGGTGCTGAAA
GAAAACGGCCCCATGGCCTCCGACCCCCTGTGCCTGACCTACAGCTACCTGAGCCACGTGGACCTGGTGAA
GGACCTGAACAGCGGCCTGATCGGCGCTCTGCTCGTCTGCCGGGAGGGCAGCCTGGCCAAAGAGAAAACCC
AGACCCTGCACAAGTTCATCCTGCTGTTCGCCGTGTTCGACGAGGGCAAGAGCTGGCACAGCGAGACAAAG
AACAGCCTGATGCAGGACCGGGACGCCGCCTCTGCCAGAGCCTGGCCCAAGATGCACACCGTGAACGGCTA
CGTGAACAGAAGCCTGCCCGGCCTGATTGGCTGCCACCGGAAGAGCGTGTACTGGCACGTGATCGGCATGG
GCACCACACCCGAGGTGCACAGCATCTTTCTGGAAGGGCACACCTTTCTGGTCCGGAACCACCGGCAGGCC
AGCCTGGAAATCAGCCCTATCACCTTCCTGACCGCCCAGACACTGCTGATGGACCTGGGCCAGTTCCTGCT
GTTTTGCCACATCAGCTCTCACCAGCACGACGGCATGGAAGCCTACGTGAAGGTGGACTCTTGCCCCGAGG
AACCCCAGCTGCGGATGAAGAACAACGAGGAAGCCGAGGACTACGACGACGACCTGACCGACAGCGAGATG
GACGTGGTGCGGTTCGACGACGACAACAGCCCCAGCTTCATCCAGATCAGAAGCGTGGCCAAGAAGCACCC
CAAGACCTGGGTGCACTATATCGCCGCCGAGGAAGAGGACTGGGACTACGCCCCCCTGGTGCTGGCCCCCG
ACGACAGAAGCTACAAGAGCCAGTACCTGAACAATGGCCCCCAGCGGATCGGCCGGAAGTACAAGAAAGTG
CGGTTCATGGCCTACACCGACGAGACATTCAAGACCCGGGAGGCCATCCAGCACGAGAGCGGCATCCTGGG
CCCCCTGCTGTACGGCGAAGTGGGCGACACACTGCTGATCATCTTCAAGAACCAGGCTAGCCGGCCCTACA
ACATCTACCCCCACGGCATCACCGACGTGCGGCCCCTGTACAGCAGGCGGCTGCCCAAGGGCGTGAAGCAC
CTGAAGGACTTCCCCATCCTGCCCGGCGAGATCTTCAAGTACAAGTGGACCGTGACCGTGGAGGACGGCCC
CACCAAGAGCGACCCCAGATGCCTGACCCGGTACTACAGCAGCTTCGTGAACATGGAACGGGACCTGGCCT
CCGGGCTGATCGGACCTCTGCTGATCTGCTACAAAGAAAGCGTGGACCAGCGGGGCAACCAGATCATGAGC
GACAAGCGGAACGTGATCCTGTTCAGCGTGTTCGATGAGAACCGGTCCTGGTATCTGACCGAGAACATCCA
GCGGTTTCTGCCCAACCCTGCCGGCGTGCAGCTGGAAGATCCCGAGTTCCAGGCCAGCAACATCATGCACT
CCATCAATGGCTACGTGTTCGACTCTCTGCAGCTCTCCGTGTGTCTGCACGAGGTGGCCTACTGGTACATC
CTGAGCATCGGCGCCCAGACCGACTTCCTGAGCGTGTTCTTCAGCGGCTACACCTTCAAGCACAAGATGGT
GTACGAGGACACCCTGACCCTGTTCCCTTTCAGCGGCGAGACAGTGTTCATGAGCATGGAAAACCCCGGCC
TGTGGATTCTGGGCTGCCACAACAGCGACTTCCGGAACCGGGGCATGACCGCCCTGCTGAAGGTGTCCAGC
TGCGACAAGAACACCGGCGACTACTACGAGGACAGCTACGAGGATATCAGCGCCTACCTGCTGTCCAAGAA
CAACGCCATCGAACCCCGGAGCTTCAGCCAGAACCCCCCGTGCTGACGCGTCACCAGCGGGAGATCACCC
GGACAACCCTGCAGTCCGACCAGGAAGAGATCGATTACGACGACACCATCAGCGTGGAGATGAAGAAAGAG
GATTTCGATATCTACGACGAGGACGAGAACCAGAGCCCCAGAAGCTTCCAGAAGAAAACCCGGCACTACTT
CATTGCCGCCGTGGAGAGGCTGTGGGACTACGGCATGAGTTCTAGCCCCCACGTGCTGCGGAACCGGGCCC
AGAGCGGCAGCGTGCCCCAGTTCAAGAAAGTGGTGTTCCAGGAATTCACAGACGGCAGCTTCACCCAGCCT
CTGTATAGAGGCGAGCTGAACGAGCACCTGGGGCTGCTGGGCCCTACATCAGGGCCGAAGTGGAGGACAA
CATCATGGTGACCTTCCGGAATCAGGCCAGCAGACCCTACTCCTTCTACAGCAGCCTGATCAGCTACGAAG
AGGACCAGCGGCAGGGCGCCGAACCCCGGAAGAACTTCGTGAAGCCCAACGAAACCAAGACCTACTTCTGG
AAAGTGCAGCACCACATGGCCCCCACCAAGGACGAGTTCGACTGCAAGGCCTGGGCCTACTTCAGCGACGT
GGATCTGGAAAAGGACGTGCACTCTGGACTGATTGGCCCACTCCTGGTCTGCCACACTAACACCCTCAACC
CCGCCCACGGCCGCCAGGTGACCGTGCAGGAATTCGCCCTGTTCTTCACCATCTTCGACGAGACAAAGTCC

Figure 14 (continued)

TGGTACTTCACCGAGAATATGGAACGGAACTGCAGAGCCCCTGCAACATCCAGATGGAAGATCCTACCTT
CAAAGAGAACTACCGGTTCCACGCCATCAACGGCTACATCATGGACACCCTGCCTGGCCTGGTGATGGCCC
AGGACCAGAGAATCCGGTGGTATCTGCTGTCCATGGGCAGCAACGAGAATATCCACAGCATCCACTTCAGC
GGCCACGTGTTCACCGTGCGGAAGAAAGAAGAGTACAAGATGGCCCTGTACAACCTGTACCCCGGCGTGTT
CGAGACAGTGGAGATGCTGCCCAGCAAGGCCGGCATCTGGCGGGTGGAGTGTCTGATCGGCGAGCACCTGC
ACGCTGGCATGAGCACCCTGTTTCTGGTGTACAGCAACAAGTGCCAGACCCCACTGGGCATGGCCTCTGGC
CACATCCGGGACTTCCAGATCACCGCCTCCGGCCAGTACGGCCAGTGGGCCCCCAAGCTGGCCAGACTGCA
CTACAGCGGCAGCATCAACGCCTGGTCCACCAAAGAGCCCTTCAGCTGGATCAAGGTGGACCTGCTGGCCC
CTATGATCATCCACGGCATTAAGACCCAGGGCGCCAGGCAGAAGTTCAGCAGCCTGTACATCAGCCAGTTC
ATCATCATGTACAGCCTGGACGGCAAGAAGTGGCAGACCTACCGGGGCAACAGCACCGGCACCCTGATGGT
GTTCTTCGGCAATGTGGACAGCAGCGGCATCAAGCACAACATCTTCAACCCCCCCATCATTGCCCGGTACA
TCCGGCTGCACCCCACCCACTACAGCATTAGATCCACACTGAGAATGGAACTGATGGGCTGCGACCTGAAC
TCCTGCAGCATGCCTCTGGGCATGGAAAGCAAGGCCATCAGCGACGCCCAGATCACAGCCAGCAGCTACTT
CACCAACATGTTCGCCACCTGGTCCCCCTCCAAGGCCAGGCTGCACCTGCAGGGCCGGTCCAACGCCTGGC
GGCCTCAGGTCAACAACCCCAAAGAATGGCTGCAGGTGGACTTTCAGAAAACCATGAAGGTGACCGGCGTG
ACCACCCAGGGCGTGAAAAGCCTGCTGACCAGCATGTACGTGAAAGAGTTTCTGATCAGCAGCTCTCAGGA
TGGCCACCAGTGGACCCTGTTCTTTCAGAACGGCAAGGTGAAAGTGTTCCAGGGCAACCAGGACTCCTTCA
CCCCCGTGGTGAACTCCCTGGACCCCCCCCTGCTGACCCGCTACCTGAGAATCCACCCCCAGTCTTGGGTG
CACCAGATCGCCCTCAGGATGGAAGTCCTGGGATGTGAGGCCCAGGATCTGTACTGATGAGGATCCATGCT
TTATTTGTGAAATTTGTGATGCTATTGCTTTATTTGTAACCATTATAAGCTGCAATAAACAAGTTAACAAC
AACAATTGCATTCATTTTATGTTTCAGGTTCAGGGGGAGGTGTGGGAGGTTTTTTAAA

SEQ ID NO.53: Flank-3xSERP-Flank-*TTRe*-Flank-TTRm-*MVM*-Flank-
coFVIIIdeltaB-Flank-SV40pA-Flank

GCGGCCGCGGTACGCGGGGGAGGCTGCTGGTGAATATTAACCAAGGTCACCCCAGTTATCGGAGGAGCAAA
CAGGGGCTAAGTCCACCGGGGGAGGCTGCTGGTGAATATTAACCAAGGTCACCCCAGTTATCGGAGGAGCA
AACAGGGGCTAAGTCCACCGGGGGAGGCTGCTGGTGAATATTAACCAAGGTCACCCCAGTTATCGGAGGAG
CAAACAGGGGCTAAGTCCACGGTACC*CACTGGGAGGATGTTGAGTAAGATGGAAAACTACTGATGACCCTT*
*GCAGAGACAGAGTATTAGGACATGTTTGAACAGGGGCCGGGCGATCAGCAGGTAG*CTCTAGAGGATCCCCG
TCTGTCTGCACATTTCGTAGAGCGAGTGTTCCGATACTCTAATCTCCCTAGGCAAGGTTCATATTTGTGTA
GGTTACTTATTCTCCTTTTGTTGACTAAGTCAATAATCAGAATCAGCAGGTTTGGAGTCAGCTTGGCAGGG
ATCAGCAGCCTGGGTTGGAAGGAGGGGGTATAAAAGCCCCTTCACCAGGAGAAGCCGTC*AAGAGGTAAGGG*
*TTTAAGGGATGGTTGGTTGGTGGGGTATTAATGTTTAATTACCTGGAGCACCTGCCTGAAATCACTTTTTT*
*TCAGGTTGG***CTAGTATGCAGATCGAGCTGTCCACCTGCTTTTTTCTGTGCCTGCTGCGGTTCTGCTTCAGC
GCCACCCGGCGGTACTACCTGGGCGCCGTGGAGCTGTCCTGGGACTACATGCAGAGCGACCTGGGCGAGCT
GCCCGTGGACGCCCGGTTCCCCCCCAGAGTGCCCAAGAGCTTCCCCTTCAACACCAGCGTGGTGTACAAGA
AAACCCTGTTCGTGGAGTTCACCGACCACCTGTTCAATATCGCCAAGCCCAGGCCCCCCTGGATGGGCCTG
CTGGGCCCCACCATCCAGGCCGAGGTGTACGACACCGTGGTGATCACCCTGAAGAACATGGCCAGCCACCC
CGTGAGCCTGCACGCCGTGGGCGTGAGCTACTGGAAGGCCAGCGAGGGCGCCGAGTACGACGACCAGACCA
GCCAGCGGGAGAAAGAAGATGACAAGGTGTTCCCTGGCGGCAGCCACACCTACGTGTGGCAGGTGCTGAAA
GAAAACGGCCCCATGGCCTCCGACCCCCTGTGCCTGACCTACAGCTACCTGAGCCACGTGGACCTGGTGAA
GGACCTGAACAGCGGCCTGATCGGCGCTCTGCTCGTCTGCCGGGAGGGCAGCCTGGCCAAAGAGAAAACCC
AGACCCTGCACAAGTTCATCCTGCTGTTCGCCGTGTTCGACGAGGGCAAGAGCTGGCACAGCGAGACAAAG
AACAGCCTGATGCAGGACCGGGACGCCGCCTCTGCCAGAGCCTGGCCCAAGATGCACACCGTGAACGGCTA
CGTGAACAGAAGCCTGCCCGGCCTGATTGGCTGCCACCGGAAGAGCGTGTACTGGCACGTGATCGGCATGG
GCACCACACCCGAGGTGCACAGCATCTTTCTGGAAGGGCACACCTTTCTGGTCCGGAACCACCGGCAGGCC
AGCCTGGAAATCAGCCCTATCACCTTCCTGACCGCCCAGACACTGCTGATGGACCTGGGCCAGTTCCTGCT
GTTTTGCCACATCAGCTCTCACCAGCACGACGGCATGGAAGCCTACGTGAAGGTGGACTCTTGCCCCGAGG
AACCCCAGCTGCGGATGAAGAACAACGAGGAAGCCGAGGACTACGACGACGACCTGACCGACAGCGAGATG
GACGTGGTGCGGTTCGACGACGACAACAGCCCCAGCTTCATCCAGATCAGAAGCGTGGCCAAGAAGCACCC
CAAGACCTGGGTGCACTATATCGCCGCCGAGGAAGAGGACTGGGACTACGCCCCCTGGTGCTGGCCCCCG
ACGACAGAAGCTACAAGAGCCAGTACCTGAACAATGGCCCCCAGCGGATCGGCCGGAAGTACAAGAAAGTG
CGGTTCATGGCCTACACCGACGAGACATTCAAGACCCGGGAGGCCATCCAGCACGAGAGCGGCATCCTGGG
CCCCCTGCTGTACGGCGAAGTGGGCGACACACTGCTGATCATCTTCAAGAACCAGGCTAGCCGGCCCTACA

Figure 14 (continued)

ACATCTACCCCCACGGCATCACCGACGTGCGGCCCCTGTACAGCAGGCGGCTGCCCAAGGGCGTGAAGCAC
CTGAAGGACTTCCCCATCCTGCCCGGCGAGATCTTCAAGTACAAGTGGACCGTGACCGTGGAGGACGGCCC
CACCAAGAGCGACCCCAGATGCCTGACCCGGTACTACAGCAGCTTCGTGAACATGGAACGGGACCTGGCCT
CCGGGCTGATCGGACCTCTGCTGATCTGCTACAAAGAAAGCGTGGACCAGCGGGGCAACCAGATCATGAGC
GACAAGCGGAACGTGATCCTGTTCAGCGTGTTCGATGAGAACCGGTCCTGGTATCTGACCGAGAACATCCA
GCGGTTTCTGCCCAACCCTGCCGGCGTGCAGCTGGAAGATCCCGAGTTCCAGGCCAGCAACATCATGCACT
CCATCAATGGCTACGTGTTCGACTCTCTGCAGCTCTCCGTGTGTCTGCACGAGGTGGCCTACTGGTACATC
CTGAGCATCGGCGCCCAGACCGACTTCCTGAGCGTGTTCTTCAGCGGCTACACCTTCAAGCACAAGATGGT
GTACGAGGACACCCTGACCCTGTTCCCTTTCAGCGGCGAGACAGTGTTCATGAGCATGGAAAACCCCGGCC
TGTGGATTCTGGGCTGCCACAACAGCGACTTCCGGAACCGGGGCATGACCGCCCTGCTGAAGGTGTCCAGC
TGCGACAAGAACACCGGCGACTACTACGAGGACAGCTACGAGGATATCAGCGCCTACCTGCTGTCCAAGAA
CAACGCCATCGAACCCCGGAGCTTCAGCCAGAACCCCCCGTGCTGACGCGTCACCAGCGGGAGATCACCC
GGACAACCCTGCAGTCCGACCAGGAAGAGATCGATTACGACGACACCATCAGCGTGGAGATGAAGAAAGAG
GATTTCGATATCTACGACGAGGACGAGAACCAGAGCCCCAGAAGCTTCCAGAAGAAAACCCGGCACTACTT
CATTGCCGCCGTGGAGAGGCTGTGGGACTACGGCATGAGTTCTAGCCCCCACGTGCTGCGGAACCGGGCCC
AGAGCGGCAGCGTGCCCCAGTTCAAGAAAGTGGTGTTCCAGGAATTCACAGACGGCAGCTTCACCCAGCCT
CTGTATAGAGGCGAGCTGAACGAGCACCTGGGGCTGCTGGGGCCCTACATCAGGGCCGAAGTGGAGGACAA
CATCATGGTGACCTTCCGGAATCAGGCCAGCAGACCCTACTCCTTCTACAGCAGCCTGATCAGCTACGAAG
AGGACCAGCGGCAGGGCGCCGAACCCCGGAAGAACTTCGTGAAGCCCAACGAAACCAAGACCTACTTCTGG
AAAGTGCAGCACCACATGGCCCCCACCAAGGACGAGTTCGACTGCAAGGCCTGGGCCTACTTCAGCGACGT
GGATCTGGAAAAGGACGTGCACTCTGGACTGATTGGCCCACTCCTGGTCTGCCACACTAACACCCTCAACC
CCGCCCACGGCCGCCAGGTGACCGTGCAGGAATTCGCCCTGTTCTTCACCATCTTCGACGAGACAAAGTCC
TGGTACTTCACCGAGAATATGGAACGGAACTGCAGAGCCCCCTGCAACATCCAGATGGAAGATCCTACCTT
CAAAGAGAACTACCGGTTCCACGCCATCAACGGCTACATCATGGACACCCTGCCTGGCCTGGTGATGGCCC
AGGACCAGAGAATCCGGTGGTATCTGCTGTCCATGGGCAGCAACGAGAATATCCACAGCATCCACTTCAGC
GGCCACGTGTTCACCGTGCGGAAGAAAGAAGAGTACAAGATGGCCCTGTACAACCTGTACCCCGGCGTGTT
CGAGACAGTGGAGATGCTGCCCAGCAAGGCCGGCATCTGGCGGGTGGAGTGTCTGATCGGCGAGCACCTGC
ACGCTGGCATGAGCACCCTGTTTCTGGTGTACAGCAACAAGTGCCAGACCCCACTGGGCATGGCCTCTGGC
CACATCCGGGACTTCCAGATCACCGCCTCCGGCCAGTACGGCCAGTGGGCCCCCAAGCTGGCCAGACTGCA
CTACAGCGGCAGCATCAACGCCTGGTCCACCAAAGAGCCCTTCAGCTGGATCAAGGTGGACCTGCTGGCCC
CTATGATCATCCACGGCATTAAGACCCAGGGCGCCAGGCAGAAGTTCAGCAGCCTGTACATCAGCCAGTTC
ATCATCATGTACAGCCTGGACGGCAAGAAGTGGCAGACCTACCGGGGCAACAGCACCGGCACCCTGATGGT
GTTCTTCGGCAATGTGGACAGCAGCGGCATCAAGCACAACATCTTCAACCCCCCCATCATTGCCCGGTACA
TCCGGCTGCACCCCACCCACTACAGCATTAGATCCACACTGAGAATGGAACTGATGGGCTGCGACCTGAAC
TCCTGCAGCATGCCTCTGGGCATGGAAAGCAAGGCCATCAGCGACGCCCAGATCACAGCCAGCAGCTACTT
CACCAACATGTTCGCCACCTGGTCCCCCTCCAAGGCCAGGCTGCACCTGCAGGGCCGGTCCAACGCCTGGC
GGCCTCAGGTCAACAACCCCAAAGAATGGCTGCAGGTGGACTTTCAGAAAACCATGAAGGTGACCGGCGTG
ACCACCCAGGGCGTGAAAAGCCTGCTGACCAGCATGTACGTGAAAGAGTTTCTGATCAGCAGCTCTCAGGA
TGGCCACCAGTGGACCCTGTTCTTTCAGAACGGCAAGGTGAAAGTGTTCCAGGGCAACCAGGACTCCTTCA
CCCCCGTGGTGAACTCCCTGGACCCCCCCCTGCTGACCCGCTACCTGAGAATCCACCCCCAGTCTTGGGTG
CACCAGATCGCCCTCAGGATGGAAGTCCTGGGATGTGAGGCCCAGGATCTGTACTGATGAGGATCCATGCT
TTATTTGTGAAATTTGTGATGCTATTGCTTTATTTGTAACCATTATAAGCTGCAATAAACAAGTTAACAAC
AACAATTGCATTCATTTTATGTTTCAGGTTCAGGGGGAGGTGTGGGAGGTTTTTTAAA**CTCGAGATCCACG
GCCGC**

SEQ ID NO.54: Flank-<u>3xSERP</u>-Flank-*TTRe*-Flank-TTRm-*MVM*-Flank-
coFVIIIdeltaB-Flank-Synt.pA

GCGGCCGCGGTACGCGGGGGAGGCTGCTGGTGAATATTAACCAAGGTCACCCCAGTTATCGGAGGAGCAAA
CAGGGGCTAAGTCCACCGGGGGAGGCTGCTGGTGAATATTAACCAAGGTCACCCCAGTTATCGGAGGAGCA
AACAGGGGCTAAGTCCACCGGGGGAGGCTGCTGGTGAATATTAACCAAGGTCACCCCAGTTATCGGAGGAG
<u>CAAACAGGGGCTAAGTCCAC</u>GGTACC*CACTGGGAGGATGTTGAGTAAGATGGAAAACTACTGATGACCCTT*
*GCAGAGACAGAGTATTAGGACATGTTTGAACAGGGGCCGGGCGATCAGCAGGTAG*CTCTAGAGGATCCCCG
TCTGTCTGCACATTTCGTAGAGCGAGTGTTCCGATACTCTAATCTCCCTAGGCAAGGTTCATATTTGTGTA
GGTTACTTATTCTCCTTTTGTTGACTAAGTCAATAATCAGAATCAGCAGGTTTGGAGTCAGCTTGGCAGGG

Figure 14 (continued)

```
ATCAGCAGCCTGGGTTGGAAGGAGGGGGTATAAAAGCCCCTTCACCAGGAGAAGCCGTCAAGAGGTAAGGG
TTTAAGGGATGGTTGGTTGGTGGGGTATTAATGTTTAATTACCTGGAGCACCTGCCTGAAATCACTTTTTT
TCAGGTTGGCTAGTATGCAGATCGAGCTGTCCACCTGCTTTTTTCTGTGCCTGCTGCGGTTCTGCTTCAGC
GCCACCCGGCGGTACTACCTGGGCGCCGTGGAGCTGTCCTGGGACTACATGCAGAGCGACCTGGGCGAGCT
GCCCGTGGACGCCCGGTTCCCCCCCAGAGTGCCCAAGAGCTTCCCCTTCAACACCAGCGTGGTGTACAAGA
AAACCCTGTTCGTGGAGTTCACCGACCACCTGTTCAATATCGCCAAGCCCAGGCCCCCCTGGATGGGCCTG
CTGGGCCCCACCATCCAGGCCGAGGTGTACGACACCGTGGTGATCACCCTGAAGAACATGGCCAGCCACCC
CGTGAGCCTGCACGCCGTGGGCGTGAGCTACTGGAAGGCCAGCGAGGGCGCCGAGTACGACGACCAGACCA
GCCAGCGGGAGAAAGAAGATGACAAGGTGTTCCCTGGCGGCAGCCACACCTACGTGTGGCAGGTGCTGAAA
GAAAACGGCCCCATGGCCTCCGACCCCCTGTGCCTGACCTACAGCTACCTGAGCCACGTGGACCTGGTGAA
GGACCTGAACAGCGGCCTGATCGGCGCTCTGCTCGTCTGCCGGGAGGGCAGCCTGGCCAAAGAGAAAACCC
AGACCCTGCACAAGTTCATCCTGCTGTTCGCCGTGTTCGACGAGGGCAAGAGCTGGCACAGCGAGACAAAG
AACAGCCTGATGCAGGACCGGGACGCCGCCTCTGCCAGAGCCTGGCCCAAGATGCACACCGTGAACGGCTA
CGTGAACAGAAGCCTGCCCGGCCTGATTGGCTGCCACCGGAAGAGCGTGTACTGGCACGTGATCGGCATGG
GCACCACACCCGAGGTGCACAGCATCTTTCTGGAAGGGCACACCTTTCTGGTCCGGAACCACCGGCAGGCC
AGCCTGGAAATCAGCCCTATCACCTTCCTGACCGCCCAGACACTGCTGATGGACCTGGGCCAGTTCCTGCT
GTTTTGCCACATCAGCTCTCACCAGCACGACGGCATGGAAGCCTACGTGAAGGTGGACTCTTGCCCCGAGG
AACCCCAGCTGCGGATGAAGAACAACGAGGAAGCCGAGGACTACGACGACGACCTGACCGACAGCGAGATG
GACGTGGTGCGGTTCGACGACGACAACAGCCCCAGCTTCATCCAGATCAGAAGCGTGGCCAAGAAGCACCC
CAAGACCTGGGTGCACTATATCGCCGCCGAGGAAGAGGACTGGGACTACGCCCCCCTGGTGCTGGCCCCCG
ACGACAGAAGCTACAAGAGCCAGTACCTGAACAATGGCCCCCAGCGGATCGGCCGGAAGTACAAGAAAGTG
CGGTTCATGGCCTACACCGACGAGACATTCAAGACCCGGGAGGCCATCCAGCACGAGAGCGGCATCCTGGG
CCCCCTGCTGTACGGCGAAGTGGGCGACACACTGCTGATCATCTTCAAGAACCAGGCTAGCCGGCCCTACA
ACATCTACCCCCACGGCATCACCGACGTGCGGCCCCTGTACAGCAGGCGGCTGCCCAAGGGCGTGAAGCAC
CTGAAGGACTTCCCCATCCTGCCCGGCGAGATCTTCAAGTACAAGTGGACCGTGACCGTGGAGGACGGCCC
CACCAAGAGCGACCCCAGATGCCTGACCCGGTACTACAGCAGCTTCGTGAACATGGAACGGGACCTGGCCT
CCGGGCTGATCGGACCTCTGCTGATCTGCTACAAAGAAAGCGTGGACCAGCGGGGCAACCAGATCATGAGC
GACAAGCGGAACGTGATCCTGTTCAGCGTGTTCGATGAGAACCGGTCCTGGTATCTGACCGAGAACATCCA
GCGGTTTCTGCCCAACCCTGCCGGCGTGCAGCTGGAAGATCCCGAGTTCCAGGCCAGCAACATCATGCACT
CCATCAATGGCTACGTGTTCGACTCTCTGCAGCTCTCCGTGTGTCTGCACGAGGTGGCCTACTGGTACATC
CTGAGCATCGGCGCCCAGACCGACTTCCTGAGCGTGTTCTTCAGCGGCTACACCTTCAAGCACAAGATGGT
GTACGAGGACACCCTGACCCTGTTCCCTTTCAGCGGCGAGACAGTGTTCATGAGCATGGAAAACCCCGGCC
TGTGGATTCTGGGCTGCCACAACAGCGACTTCCGGAACCGGGGCATGACCGCCCTGCTGAAGGTGTCCAGC
TGCGACAAGAACACCGGCGACTACTACGAGGACAGCTACGAGGATATCAGCGCCTACCTGCTGTCCAAGAA
CAACGCCATCGAACCCCGGAGCTTCAGCCAGAACCCCCCGTGCTGACGCGTCACCAGCGGGAGATCACCC
GGACAACCCTGCAGTCCGACCAGGAAGAGATCGATTACGACGACACCATCAGCGTGGAGATGAAGAAAGAG
GATTTCGATATCTACGACGAGGACGAGAACCAGAGCCCCAGAAGCTTCCAGAAGAAAACCCGGCACTACTT
CATTGCCGCCGTGGAGAGGCTGTGGGACTACGGCATGAGTTCTAGCCCCCACGTGCTGCGGAACCGGGCCC
AGAGCGGCAGCGTGCCCCAGTTCAAGAAAGTGGTGTTCCAGGAATTCACAGACGGCAGCTTCACCCAGCCT
CTGTATAGAGGCGAGCTGAACGAGCACCTGGGGCTGCTGGGCCCTACATCAGGGCCGAAGTGGAGGACAA
CATCATGGTGACCTTCCGGAATCAGGCCAGCAGACCCTACTCCTTCTACAGCAGCCTGATCAGCTACGAAG
AGGACCAGCGGCAGGGCGCCGAACCCCGGAAGAACTTCGTGAAGCCCAACGAAACCAAGACCTACTTCTGG
AAAGTGCAGCACCACATGGCCCCCACCAAGGACGAGTTCGACTGCAAGGCCTGGGCCTACTTCAGCGACGT
GGATCTGGAAAAGGACGTGCACTCTGGACTGATTGGCCCACTCCTGGTCTGCCACACTAACACCCTCAACC
CCGCCCACGGCCGCCAGGTGACCGTGCAGGAATTCGCCCTGTTCTTCACCATCTTCGACGAGACAAAGTCC
TGGTACTTCACCGAGAATATGGAACGGAACTGCAGAGCCCCCTGCAACATCCAGATGGAAGATCCTACCTT
CAAAGAGAACTACCGGTTCCACGCCATCAACGGCTACATCATGGACACCCTGCCTGGCCTGGTGATGGCCC
AGGACCAGAGAATCCGGTGGTATCTGCTGTCCATGGGCAGCAACGAGAATATCCACAGCATCCACTTCAGC
GGCCACGTGTTCACCGTGCGGAAGAAAGAAGAGTACAAGATGGCCCTGTACAACCTGTACCCCGGCGTGTT
CGAGACAGTGGAGATGCTGCCCAGCAAGGCCGGCATCTGGCGGGTGGAGTGTCTGATCGGCGAGCACCTGC
ACGCTGGCATGAGCACCCTGTTTCTGGTGTACAGCAACAAGTGCCAGACCCCACTGGGCATGGCCTCTGGC
CACATCCGGGACTTCCAGATCACCGCCTCCGGCCAGTACGGCCAGTGGGCCCCAAGCTGGCCAGACTGCA
CTACAGCGGCAGCATCAACGCCTGGTCCACCAAAGAGCCCTTCAGCTGGATCAAGGTGGACCTGCTGGCCC
CTATGATCATCCACGGCATTAAGACCCAGGGCGCCAGGCAGAAGTTCAGCAGCCTGTACATCAGCCAGTTC
ATCATCATGTACAGCCTGGACGGCAAGAAGTGGCAGACCTACCGGGGCAACAGCACCGGCACCCTGATGGT
```

Figure 14 (continued)

GTTCTTCGGCAATGTGGACAGCAGCGGCATCAAGCACAACATCTTCAACCCCCCCATCATTGCCCGGTACA
TCCGGCTGCACCCCACCCACTACAGCATTAGATCCACACTGAGAATGGAACTGATGGGCTGCGACCTGAAC
TCCTGCAGCATGCCTCTGGGCATGGAAAGCAAGGCCATCAGCGACGCCCAGATCACAGCCAGCAGCTACTT
CACCAACATGTTCGCCACCTGGTCCCCCTCCAAGGCCAGGCTGCACCTGCAGGGCCGGTCCAACGCCTGGC
GGCCTCAGGTCAACAACCCCAAAGAATGGCTGCAGGTGGACTTTCAGAAAACCATGAAGGTGACCGGCGTG
ACCACCCAGGGCGTGAAAAGCCTGCTGACCAGCATGTACGTGAAAGAGTTTCTGATCAGCAGCTCTCAGGA
TGGCCACCAGTGGACCCTGTTCTTTCAGAACGGCAAGGTGAAAGTGTTCCAGGGCAACCAGGACTCCTTCA
CCCCCGTGGTGAACTCCCTGGACCCCCCCCTGCTGACCCGCTACCTGAGAATCCACCCCCAGTCTTGGGTG
CACCAGATCGCCCTCAGGATGGAAGTCCTGGGATGTGAGGCCCAGGATCTGTACTGATGAGGATCCAATAA
AAGATCTTTATTTTCATTAGATCTGTGTGTTGGTTTTTTGTGTG

SEQ ID NO.55: Flank-<u>3xSERP</u>-Flank-*TTRe*-Flank-TTRm-*MVM*-Flank-
coFVIIIdeltaB-Flank-Synt.pA-Flank

GCGGCCGCGGTACGCGGGGGAGGCTGCTGGTGAATATTAACCAAGGTCACCCCAGTTATCGGAGGAGCAAA
CAGGGGCTAAGTCCACCGGGGGAGGCTGCTGGTGAATATTAACCAAGGTCACCCCAGTTATCGGAGGAGCA
AACAGGGGCTAAGTCCACCGGGGGAGGCTGCTGGTGAATATTAACCAAGGTCACCCCAGTTATCGGAGGAG
CAAACAGGGGCTAAGTCCACGGTACC<i>CACTGGGAGGATGTTGAGTAAGATGGAAAACTACTGATGACCCTT
GCAGAGACAGAGTATTAGGACATGTTTGAACAGGGGCCGGGCGATCAGCAGGTAG</i>CTCTAGAGGATCCCCG
TCTGTCTGCACATTTCGTAGAGCGAGTGTTCCGATACTCTAATCTCCCTAGGCAAGGTTCATATTTGTGTA
GGTTACTTATTCTCCTTTTGTTGACTAAGTCAATAATCAGAATCAGCAGGTTTGGAGTCAGCTTGGCAGGG
ATCAGCAGCCTGGGTTGGAAGGAGGGGGTATAAAAGCCCCTTCACCAGGAGAAGCCGTC<i>AAGAGGTAAGGG
TTTAAGGGATGGTTGGTTGGTGGGGTATTAATGTTTAATTACCTGGAGCACCTGCCTGAAATCACTTTTTT
TCAGGTTGG</i>**CTAGTATGCAGATCGAGCTGTCCACCTGCTTTTTTCTGTGCCTGCTGCGGTTCTGCTTCAGC
GCCACCCGGCGGTACTACCTGGGCGCCGTGGAGCTGTCCTGGGACTACATGCAGAGCGACCTGGGCGAGCT
GCCCGTGGACGCCCGGTTCCCCCCCAGAGTGCCCAAGAGCTTCCCCTTCAACACCAGCGTGGTGTACAAGA
AAACCCTGTTCGTGGAGTTCACCGACCACCTGTTCAATATCGCCAAGCCCAGGCCCCCTGGATGGGCCTG
CTGGGCCCCACCATCCAGGCCGAGGTGTACGACACCGTGGTGATCACCCTGAAGAACATGGCCAGCCACCC
CGTGAGCCTGCACGCCGTGGGCGTGAGCTACTGGAAGGCCAGCGAGGGCGCCGAGTACGACGACCAGACCA
GCCAGCGGGAGAAAGAAGATGACAAGGTGTTCCCTGGCGGCAGCCACACCTACGTGTGGCAGGTGCTGAAA
GAAAACGGCCCCATGGCCTCCGACCCCCTGTGCCTGACCTACAGCTACCTGAGCCACGTGGACCTGGTGAA
GGACCTGAACAGCGGCCTGATCGGCGCTCTGCTCGTCTGCCGGGAGGGCAGCCTGGCCAAAGAGAAACCC
AGACCCTGCACAAGTTCATCCTGCTGTTCGCCGTGTTCGACGAGGGCAAGAGCTGGCACAGCGAGACAAAG
AACAGCCTGATGCAGGACCGGGACGCCGCCTCTGCCAGAGCCTGGCCCAAGATGCACACCGTGAACGGCTA
CGTGAACAGAAGCCTGCCCGGCCTGATTGGCTGCCACCGGAAGAGCGTGTACTGGCACGTGATCGGCATGG
GCACCACACCCGAGGTGCACAGCATCTTTCTGGAAGGGCACACCTTTCTGGTCCGGAACCACCGGCAGGCC
AGCCTGGAAATCAGCCCTATCACCTTCCTGACCGCCCAGACACTGCTGATGGACCTGGGCCAGTTCCTGCT
GTTTTGCCACATCAGCTCTCACCAGCACGACGGCATGGAAGCCTACGTGAAGGTGGACTCTTGCCCCGAGG
AACCCCAGCTGCGGATGAAGAACAACGAGGAAGCCGAGGACTACGACGACGACCTGACCGACAGCGAGATG
GACGTGGTGCGGTTCGACGACGACAACAGCCCCAGCTTCATCCAGATCAGAAGCGTGGCCAAGAAGCACCC
CAAGACCTGGGTGCACTATATCGCCGCCGAGGAAGAGGACTGGGACTACGCCCCCTGGTGCTGGCCCCCG
ACGACAGAAGCTACAAGAGCCAGTACCTGAACAATGGCCCCCAGCGGATCGGCCGGAAGTACAAGAAAGTG
CGGTTCATGGCCTACACCGACGAGACATTCAAGACCCGGGAGGCCATCCAGCACGAGAGCGGCATCCTGGG
CCCCCTGCTGTACGGCGAAGTGGGCGACACACTGCTGATCATCTTCAAGAACCAGGCTAGCCGGCCCTACA
ACATCTACCCCACGGCATCACCGACGTGCGGCCCCTGTACAGCAGGCGGCTGCCCAAGGGCGTGAAGCAC
CTGAAGGACTTCCCCATCCTGCCCGGCGAGATCTTCAAGTACAAGTGGACCGTGACCGTGGAGGACGGCCC
CACCAAGAGCGACCCCAGATGCCTGACCCGGTACTACAGCAGCTTCGTGAACATGGAACGGGACCTGGCCT
CCGGGCTGATCGGACCTCTGCTGATCTGCTACAAAGAAAGCGTGGACCAGCGGGGCAACCAGATCATGAGC
GACAAGCGGAACGTGATCCTGTTCAGCGTGTTCGATGAGAACCGGTCCTGGTATCTGACCGAGAACATCCA
GCGGTTTCTGCCCAACCCTGCCGGCGTGCAGCTGGAAGATCCCGAGTTCCAGGCCAGCAACATCATGCACT
CCATCAATGGCTACGTGTTCGACTCTCTGCAGCTCTCCGTGTGTCTGCACGAGGTGGCCTACTGGTACATC
CTGAGCATCGGCGCCCAGACCGACTTCCTGAGCGTGTTCTTCAGCGGCTACACCTTCAAGCACAAGATGGT
GTACGAGGACACCCTGACCCTGTTCCCTTTCAGCGGCGAGACAGTGTTCATGAGCATGGAAAACCCCGGCC
TGTGGATTCTGGGCTGCCACAACAGCGACTTCCGGAACCGGGGCATGACCGCCCTGCTGAAGGTGTCCAGC
TGCGACAAGAACACCGGCGACTACTACGAGGACAGCTACGAGGATATCAGCGCCTACCTGCTGTCCAAGAA

Figure 14 (continued)

CAACGCCATCGAACCCCGGAGCTTCAGCCAGAACCCCCCGTGCTGACGCGTCACCAGCGGGAGATCACCC
GGACAACCCTGCAGTCCGACCAGGAAGAGATCGATTACGACGACACCATCAGCGTGGAGATGAAGAAAGAG
GATTTCGATATCTACGACGAGGACGAGAACCAGAGCCCCAGAAGCTTCCAGAAGAAAACCCGGCACTACTT
CATTGCCGCCGTGGAGAGGCTGTGGGACTACGGCATGAGTTCTAGCCCCCACGTGCTGCGGAACCGGGCCC
AGAGCGGCAGCGTGCCCCAGTTCAAGAAAGTGGTGTTCCAGGAATTCACAGACGGCAGCTTCACCCAGCCT
CTGTATAGAGGCGAGCTGAACGAGCACCTGGGGCTGCTGGGGCCCTACATCAGGGCCGAAGTGGAGGACAA
CATCATGGTGACCTTCCGGAATCAGGCCAGCAGACCCTACTCCTTCTACAGCAGCCTGATCAGCTACGAAG
AGGACCAGCGGCAGGGCGCCGAACCCCGGAAGAACTTCGTGAAGCCCAACGAAACCAAGACCTACTTCTGG
AAAGTGCAGCACCACATGGCCCCCACCAAGGACGAGTTCGACTGCAAGGCCTGGGCCTACTTCAGCGACGT
GGATCTGGAAAAGGACGTGCACTCTGGACTGATTGGCCCACTCCTGGTCTGCCACACTAACACCCTCAACC
CCGCCCACGGCCGCCAGGTGACCGTGCAGGAATTCGCCCTGTTCTTCACCATCTTCGACGAGACAAAGTCC
TGGTACTTCACCGAGAATATGGAACGGAACTGCAGAGCCCCCTGCAACATCCAGATGGAAGATCCTACCTT
CAAAGAGAACTACCGGTTCCACGCCATCAACGGCTACATCATGGACACCCTGCCTGGCCTGGTGATGGCCC
AGGACCAGAGAATCCGGTGGTATCTGCTGTCCATGGGCAGCAACGAGAATATCCACAGCATCCACTTCAGC
GGCCACGTGTTCACCGTGCGGAAGAAAGAAGAGTACAAGATGGCCCTGTACAACCTGTACCCCGGCGTGTT
CGAGACAGTGGAGATGCTGCCCAGCAAGGCCGGCATCTGGCGGGTGGAGTGTCTGATCGGCGAGCACCTGC
ACGCTGGCATGAGCACCCTGTTTCTGGTGTACAGCAACAAGTGCCAGACCCCACTGGGCATGGCCTCTGGC
CACATCCGGGACTTCCAGATCACCGCCTCCGGCCAGTACGGCCAGTGGGCCCCCAAGCTGGCCAGACTGCA
CTACAGCGGCAGCATCAACGCCTGGTCCACCAAAGAGCCCTTCAGCTGGATCAAGGTGGACCTGCTGGCCC
CTATGATCATCCACGGCATTAAGACCCAGGGCGCCAGGCAGAAGTTCAGCAGCCTGTACATCAGCCAGTTC
ATCATCATGTACAGCCTGGACGGCAAGAAGTGGCAGACCTACCGGGGCAACAGCACCGGCACCCTGATGGT
GTTCTTCGGCAATGTGGACAGCAGCGGCATCAAGCACAACATCTTCAACCCCCCCATCATTGCCCGGTACA
TCCGGCTGCACCCCACCCACTACAGCATTAGATCCACACTGAGAATGGAACTGATGGGCTGCGACCTGAAC
TCCTGCAGCATGCCTCTGGGCATGGAAAGCAAGGCCATCAGCGACGCCCAGATCACAGCCAGCAGCTACTT
CACCAACATGTTCGCCACCTGGTCCCCCTCCAAGGCCAGGCTGCACCTGCAGGGCCGGTCCAACGCCTGGC
GGCCTCAGGTCAACAACCCCAAAGAATGGCTGCAGGTGGACTTTCAGAAAACCATGAAGGTGACCGGCGTG
ACCACCCAGGGCGTGAAAAGCCTGCTGACCAGCATGTACGTGAAAGAGTTTCTGATCAGCAGCTCTCAGGA
TGGCCACCAGTGGACCCTGTTCTTTCAGAACGGCAAGGTGAAAGTGTTCCAGGGCAACCAGGACTCCTTCA
CCCCCGTGGTGAACTCCCTGGACCCCCCCCTGCTGACCCGCTACCTGAGAATCCACCCCCAGTCTTGGGTG
CACCAGATCGCCCTCAGGATGGAAGTCCTGGGATGTGAGGCCCAGGATCTGTACTGATGAGGATCCAATAA
AAGATCTTTATTTTCATTAGATCTGTGTGTTGGTTTTTTGTGTGCTCGAGATCCACGGCCGC

SEQ ID NO.56: Synt.pA

AATAAAGATCTTTATTTTCATTAGATCTGTGTGTTGGTTTTTTGTGTG

SEQ ID NO.57: 3xSERP-Flank-*TTRe*-Flank

GGGGGAGGCTGCTGGTGAATATTAACCAAGGTCACCCCAGTTATCGGAGGAGCAAACAGGGGCTAAGTCCA
CC**GGGGGAGGCTGCTGGTGAATATTAACCAAGGTCACCCCAGTTATCGGAGGAGCAAACAGGGGCTAAGTC
CAC**C*GGGGGAGGCTGCTGGTGAATATTAACCAAGGTCACCCCAGTTATCGGAGGAGCAAACAGGGGCTAAG
TCCAC*GGTACC*CACTGGGAGGATGTTGAGTAAGATGGAAAACTACTGATGACCCTTGCAGAGACAGAGTAT
TAGGACATGTTTGAACAGGGGCCGGGCGATCAGCAGGTAG*CTCTAGAGGATCCCC*

SEQ ID NO.58: 3xSERP-Flank-*TTRe*-Flank-TTRm

GGGGGAGGCTGCTGGTGAATATTAACCAAGGTCACCCCAGTTATCGGAGGAGCAAACAGGGGCTAAGTCCA
CC**GGGGGAGGCTGCTGGTGAATATTAACCAAGGTCACCCCAGTTATCGGAGGAGCAAACAGGGGCTAAGTC
CAC**C*GGGGGAGGCTGCTGGTGAATATTAACCAAGGTCACCCCAGTTATCGGAGGAGCAAACAGGGGCTAAG
TCCAC*GGTACC*CACTGGGAGGATGTTGAGTAAGATGGAAAACTACTGATGACCCTTGCAGAGACAGAGTAT
TAGGACATGTTTGAACAGGGGCCGGGCGATCAGCAGGTAG*CTCTAGAGGATCCCC*GTCTGTCTGCACATTT
CGTAGAGCGAGTGTTCCGATACTCTAATCTCCCTAGGCAAGGTTCATATTTGTGTAGGTTACTTATTCTCC
TTTTGTTGACTAAGTCAATAATCAGAATCAGCAGGTTTGGAGTCAGCTTGGCAGGGATCAGCAGCCTGGGT
TGGAAGGAGGGGGTATAAAAGCCCCTTCACCAGGAGAAGCCGTC

Figure 24

SEQ ID NO:64: AAT promoter

GGATCTTGCTACCAGTGGAACAGCCACTAAGGATTCTGCAGTGAGAGCAGAGGGCCAGC
TAAGTGGTACTCTCCCAGAGACTGTCTGACTCACGCCACCCCCTCCACCTTGGACACAG
GACGCTGTGGTTTCTGAGCCAGGTACAATGACTCCTTTCGGTAAGTGCAGTGGAAGCTG
TACACTGCCCAGGCAAAGCGTCCGGGCAGCGTAGGCGGGCGACTCAGATCCCAGCCAGT
GGACTTAGCCCCTGTTTGCTCCTCCGATAACTGGGGTGACCTTGGTTAATATTCACCAG
CAGCCTCCCCGTTGCCCCTCTGGATCCACTGCTTAAATACGGACGAGGACAGGGCCCT
GTCTCCTCAGCTTCAGGCACCACCACTGACCTGGGACAGTGAATGATCCCCCTGATCTG
CGGCC

SEQ ID NO:65: pAAVsc-3xSerpEnh-TTRe-AAT-FIX-co-R338L-BGHpA

AGCTGGCGTAATAGCGAAGAGGCCCGCACCGATCGCCCTTCCCAACAGTTGCGCAGCCT
GAATGGCGAATGGCGATTCCGTTGCAATGGCTGGCGGTAATATTGTTCTGGATATTACC
AGCAAGGCCGATAGTTTGAGTTCTTCTACTCAGGCAAGTGATGTTATTACTAATCAAAG
AAGTATTGCGACAACGGTTAATTTGCGTGATGGACAGACTCTTTTACTCGGTGGCCTCA
CTGATTATAAAAACACTTCTCAGGATTCTGGCGTACCGTTCCTGTCTAAAATCCCTTTA
ATCGGCCTCCTGTTTAGCTCCCGCTCTGATTCTAACGAGGAAAGCACGTTATACGTGCT
CGTCAAAGCAACCATAGTACGCGCCCTGTAGCGGCGCATTAAGCGCGGCGGGTGTGGTG
GTTACGCGCAGCGTGACCGCTACACTTGCCAGCGCCCTAGCGCCCGCTCCTTTCGCTTT
CTTCCCTTCCTTTCTCGCCACGTTCGCCGGCTTTCCCCGTCAAGCTCTAAATCGGGGGC
TCCCTTTAGGGTTCCGATTTAGTGCTTTACGGCACCTCGACCCCAAAAAACTTGATTAG
GGTGATGGTTCACGTAGTGGGCCATCGCCCTGATAGACGGTTTTTCGCCCTTTGACGTT
GGAGTCCACGTTCTTTAATAGTGGACTCTTGTTCCAAACTGGAACAACACTCAACCCTA
TCTCGGTCTATTCTTTTGATTTATAAGGGATTTTGCCGATTTCGGCCTATTGGTTAAAA
AATGAGCTGATTTAACAAAAATTTAACGCGAACTTTAACAAAATATTAACGTTTACAAT
TTAAATATTTGCTTATACAATCTTCCTGTTTTTGGGGCTTTTCTGATTATCAACCGGGG
TACATATGATTGACATGCTAGTTTTACGATTACCGTTCATCGCCCTGCGCGCTCGCTCG
CTCACTGAGGCCGCCCGGGCAAAGCCCGGGCGTCGGGCGACCTTTGGTCGCCCGGCCTC
AGTGAGCGAGCGAGCGCGCAGAGAGGGAGTGGAATTCACGCGTCGGGGGAGGCTGCTGG
TGAATATTAACCAAGGTCACCCCAGTTATCGGAGGAGCAAACAGGGGCTAAGTCCACCG
GGGGAGGCTGCTGGTGAATATTAACCAAGGTCACCCCAGTTATCGGAGGAGCAAACAGG
GGCTAAGTCCACCGGGGGAGGCTGCTGGTGAATATTAACCAAGGTCACCCCAGTTATCG
GAGGAGCAAACAGGGGCTAAGTCCACGGCGCGCCCACTGGGAGGATGTTGAGTAAGATG
GAAAACTACTGATGACCCTTGCAGAGACAGAGTATTAGGACATGTTTGAACAGGGGCCG
GGCGATCAGCAGGTAGGGTACCGGATCTTGCTACCAGTGGAACAGCCACTAAGGATTCT
GCAGTGAGAGCAGAGGGCCAGCTAAGTGGTACTCTCCCAGAGACTGTCTGACTCACGCC
ACCCCCTCCACCTTGGACACAGGACGCTGTGGTTTCTGAGCCAGGTACAATGACTCCTT
TCGGTAAGTGCAGTGGAAGCTGTACACTGCCCAGGCAAAGCGTCCGGGCAGCGTAGGCG
GGCGACTCAGATCCCAGCCAGTGGACTTAGCCCCTGTTTGCTCCTCCGATAACTGGGGT
GACCTTGGTTAATATTCACCAGCAGCCTCCCCGTTGCCCCTCTGGATCCACTGCTTAA
ATACGGACGAGGACAGGGCCCTGTCTCCTCAGCTTCAGGCACCACCACTGACCTGGGAC
AGTGAATGATCCCCCTGATCTGCGGCCTCTAGAAAGAGGTAAGGGTTTAAGGGATGGTT

Figure 24 (continued)

```
GGTTGGTGGGGTATTAATGTTTAATTACCTGGAGCACCTGCCTGAAATCACTTTTTTTC
AGGTTGGGCTAGCCCACCATGCAGCGCGTGAACATGATCATGGCCGAGAGCCCCGGCCT
GATCACCATCTGCCTGCTGGGCTACCTGCTGAGCGCCGAGTGCACCGTGTTCCTGGACC
ACGAGAACGCCAACAAGATCCTGAACCGCCCCAAGCGCTACAACAGCGGCAAGCTGGAG
GAGTTCGTGCAGGGCAACCTGGAGCGCGAGTGCATGGAGGAGAAGTGCAGCTTCGAGGA
GGCCCGCGAGGTGTTCGAGAACACCGAGCGCACCACCGAGTTCTGGAAGCAGTACGTGG
ACGGCGACCAGTGCGAGAGCAACCCCTGCCTGAACGGCGGCAGCTGCAAGGACGACATC
AACAGCTACGAGTGCTGGTGCCCCTTCGGCTTCGAGGGCAAGAACTGCGAGCTGGACGT
GACCTGCAACATCAAGAACGGCCGCTGCGAGCAGTTCTGCAAGAACAGCGCCGACAACA
AGGTGGTGTGCAGCTGCACCGAGGGCTACCGCCTGGCCGAGAACCAGAAGAGCTGCGAG
CCCGCCGTGCCCTTCCCCTGCGGCCGCGTGAGCGTGAGCCAGACCAGCAAGCTGACCCG
CGCCGAGGCCGTGTTCCCCGACGTGGACTACGTGAACAGCACCGAGGCCGAGACCATCC
TGGACAACATCACCCAGAGCACCCAGAGCTTCAACGACTTCACCCGCGTGGTGGGCGGC
GAGGACGCCAAGCCCGGCCAGTTCCCCTGGCAGGTGGTGCTGAACGGCAAGGTGGACGC
CTTCTGCGGCGGCAGCATCGTGAACGAGAAGTGGATCGTGACCGCCGCCCACTGCGTGG
AGACCGGCGTGAAGATCACCGTGGTGGCCGGCGAGCACAACATCGAGGAGACCGAGCAC
ACCGAGCAGAAGCGCAACGTGATCCGCATCATCCCCCACCACAACTACAACGCCGCCAT
CAACAAGTACAACCACGACATCGCCCTGCTGGAGCTGGACGAGCCCCTGGTGCTGAACA
GCTACGTGACCCCCATCTGCATCGCCGACAAGGAGTACACCAACATCTTCCTGAAGTTC
GGCAGCGGCTACGTGAGCGGCTGGGGCCGCGTGTTCCACAAGGGCCGCAGCGCCCTGGT
GCTGCAGTACCTGCGCGTGCCCCTGGTGGACCGCGCCACCTGCCTGCTGAGCACCAAGT
TCACCATCTACAACAACATGTTCTGCGCCGGCTTCCACGAGGGCGGCCGCGACAGCTGC
CAGGGCGACAGCGGCGGCCCCCACGTGACCGAGGTGGAGGGCACCAGCTTCCTGACCGG
CATCATCAGCTGGGGCGAGGAGTGCGCCATGAAGGGCAAGTACGGCATCTACACCAAGG
TGAGCCGCTACGTGAACTGGATCAAGGAGAAGACCAAGCTGACCTAATGAAAGATGGAT
TTCCAAGGTTAATTCATTGGAATTGAAAATTAACAGCCCCCCCCCCCCCCCCTGCAG
ATCTGAGCCGAATTCCTGCAGCCCGGGGGATCAGCCTCGACTGTGCCTTCTAGTTGCCA
GCCATCTGTTGTTTGCCCCTCCCCGTGCCTTCCTTGACCCTGGAAGGTGCCACTCCCA
CTGTCCTTTCCTAATAAAATGAGGAAATTGCATCGCATTGTCTGAGTAGGTGTCATTCT
ATTCTGGGGGGTGGGGTGGGCAGGACAGCAAGGGGGAGGATTGGGAAGACAATAGCAG
GCATGCTGGGGATGCGGTGGGCTCTATGGCTTCTGAGGCGGAAAGAACCAGCTGGGGAC
CGGTGGATCTCGATAGCAGGCATGCTGGGGAGAGATCGATCTGAGGAACCCCTAGTGAT
GGAGTTGGCCACTCCCTCTCTGCGCGCTCGCTCGCTCACTGAGGCCGCCCGGGCAAAGC
CCGGGCGTCGGGCGACCTTTGGTCGCCCGGCCTCAGTGAGCGAGCGAGCGCGCAGAGAG
GGAGTGGCCAACCCCCCCCCCCCCCCCGGCGATTCTCTTGTTTGCTCCAGACTCT
CAGGCAATGACCTGATAGCCTTTGTAGAGACCTCTCAAAAATAGCTACCCTCTCCGGCA
TGAATTTATCAGCTAGAACGGTTGAATATCATATTGATGGTGATTTGACTGTCTCCGGC
CTTTCTCACCCGTTTGAATCTTTACCTACACATTACTCAGGCATTGCATTTAAAATATA
TGAGGGTTCTAAAAATTTTTATCCTTGCGTTGAAATAAAGGCTTCTCCCGCAAAAGTAT
TACAGGGTCATAATGTTTTTGGTACAACCGATTTAGCTTTATGCTCTGAGGCTTTATTG
CTTAATTTTGCTAATTCTTTGCCTTGCCTGTATGATTTATTGGATGTTGGAATCGCCTG
ATGCGGTATTTTCTCCTTACGCATCTGTGCGGTATTTCACACCGCATATGGTGCACTCT
CAGTACAATCTGCTCTGATGCCGCATAGTTATATGGTGCACTCTCAGTACAATCTGCTC
TGATGCCGCATAGTTAAGCCAGCCCCGACACCCGCCAACACAGCCAGCCCCGACACCCG
CCAACACCCGCTGACGCGCCCTGACGGGCTTGTCTGCTCCCGGCATCCGCTTACAGACA
AGCTGTGACCGTCTCCGGGAGCTGCATGTGTCAGAGGTTTTCACCGTCATCACCGAAAC
```

Figure 24 (continued)

```
GCGCGAGACGAAAGGGCCTCGTGATACGCCTATTTTTATAGGTTAATGTCATGATAATA
ATGGTTTCTTAGACGTCAGGTGGCACTTTTCGGGGAAATGTGCGCGGAACCCCTATTTG
TTTATTTTTCTAAATACATTCAAATATGTATCCGCTCATGAGACAATAACCCTGATAAA
TGCTCAATAATATTGAAAAAGGAAGAGTATGAGTATTCAACATTTCCGTGTCGCCCTTA
TTCCCTTTTTTGCGGCATTTTGCCTTCCTGTTTTTGCTCACCCAGAAACGCTGGTGAAA
GTAAAAGATGCTGAAGATCAGTTGGGTGCACGAGTGGGTTACATCGAACTGGATCTCAA
CAGCGGTAAGATCCTTGAGAGTTTTCGCCCCGAAGAACGTTTTCCAATGATGAGCACTT
TTAAAGTTCTGCTATGTGGCGCGGTATTATCCCGTATTGACGCCGGGCAAGAGCAACTC
GGTCGCCGCATACACTATTCTCAGAATGACTTGGTTGAGTACTCACCAGTCACAGAAAA
GCATCTTACGGATGGCATGACAGTAAGAGAATTATGCAGTGCTGCCATAACCATGAGTG
ATAACACTGCGGCCAACTTACTTCTGACAACGATCGGAGGACCGAAGGAGCTAACCGCT
TTTTTGCACAACATGGGGGATCATGTAACTCGCCTTGATCGTTGGGAACCGGAGCTGAA
TGAAGCCATACCAAACGACGAGCGTGACACCACGATGCCTGTAGCAATGGCAACAACGT
TGCGCAAACTATTAACTGGCGAACTACTTACTCTAGCTTCCCGGCAACAATTAATAGAC
TGGATGGAGGCGGATAAAGTTGCAGGACCACTTCTGCGCTCGGCCCTTCCGGCTGGCTG
GTTTATTGCTGATAAATCTGGAGCCGGTGAGCGTGGGTCTCGCGGTATCATTGCAGCAC
TGGGGCCAGATGGTAAGCCCTCCCGTATCGTAGTTATCTACACGACGGGGAGTCAGGCA
ACTATGGATGAACGAAATAGACAGATCGCTGAGATAGGTGCCTCACTGATTAAGCATTG
GTAACTGTCAGACCAAGTTTACTCATATATACTTTAGATTGATTTAAAACTTCATTTTT
AATTTAAAAGGATCTAGGTGAAGATCCTTTTTGATAATCTCATGACCAAAATCCCTTAA
CGTGAGTTTTCGTTCCACTGAGCGTCAGACCCCGTAGAAAAGATCAAAGGATCTTCTTG
AGATCCTTTTTTTCTGCGCGTAATCTGCTGCTTGCAAACAAAAAAACCACCGCTACCAG
CGGTGGTTTGTTTGCCGGATCAAGAGCTACCAACTCTTTTTCCGAAGGTAACTGGCTTC
AGCAGAGCGCAGATACCAAATACTGTCCTTCTAGTGTAGCCGTAGTTAGGCCACCACTT
CAAGAACTCTGTAGCACCGCCTACATACCTCGCTCTGCTAATCCTGTTACCAGTGGCTG
CTGCCAGTGGCGATAAGTCGTGTCTTACCGGGTTGGACTCAAGACGATAGTTACCGGAT
AAGGCGCAGCGGTCGGGCTGAACGGGGGGTTCGTGCACACAGCCCAGCTTGGAGCGAAC
GACCTACACCGAACTGAGATACCTACAGCGTGAGCTATGAGAAAGCGCCACGCTTCCCG
AAGGGAGAAAGGCGGACAGGTATCCGGTAAGCGGCAGGGTCGGAACAGGAGAGCGCACG
AGGGAGCTTCCAGGGGGAAACGCCTGGTATCTTTATAGTCCTGTCGGGTTTCGCCACCT
CTGACTTGAGCGTCGATTTTTGTGATGCTCGTCAGGGGGCGGAGCCTATGGAAAAACG
CCAGCAACGCGGCCTTTTTACGGTTCCTGGCCTTTTGCTGGCCTTTTGCTCACATGTTC
TTTCCTGCGTTATCCCCTGATTCTGTGGATAACCGTATTACCGCCTTTGAGTGAGCTGA
TACCGCTCGCCGCAGCCGAACGACCGAGCGCAGCGAGTCAGTGAGCGAGGAAGCGGAAG
AGCGCCCAATACGCAAACCGCCTCTCCCCGCGCGTTGGCCGATTCATTAATG
```

SEQ ID NO:66: pAAVsc-3xSerpEnh-AAT-FIX-co-R338L-BGHpA

```
AGCTGGCGTAATAGCGAAGAGGCCCGCACCGATCGCCCTTCCCAACAGTTGCGCAGCCT
GAATGGCGAATGGCGATTCCGTTGCAATGGCTGGCGGTAATATTGTTCTGGATATTACC
AGCAAGGCCGATAGTTTGAGTTCTTCTACTCAGGCAAGTGATGTTATTACTAATCAAAG
AAGTATTGCGACAACGGTTAATTTGCGTGATGGACAGACTCTTTTACTCGGTGGCCTCA
CTGATTATAAAAACACTTCTCAGGATTCTGGCGTACCGTTCCTGTCTAAAATCCCTTTA
ATCGGCCTCCTGTTTAGCTCCCGCTCTGATTCTAACGAGGAAAGCACGTTATACGTGCT
CGTCAAAGCAACCATAGTACGCGCCCTGTAGCGGCGCATTAAGCGCGGCGGGTGTGGTG
GTTACGCGCAGCGTGACCGCTACACTTGCCAGCGCCCTAGCGCCCGCTCCTTTCGCTTT
```

Figure 24 (continued)

```
CTTCCCTTCCTTTCTCGCCACGTTCGCCGGCTTTCCCCGTCAAGCTCTAAATCGGGGGC
TCCCTTTAGGGTTCCGATTTAGTGCTTTACGGCACCTCGACCCCAAAAAACTTGATTAG
GGTGATGGTTCACGTAGTGGGCCATCGCCCTGATAGACGGTTTTTCGCCCTTTGACGTT
GGAGTCCACGTTCTTTAATAGTGGACTCTTGTTCCAAACTGGAACAACACTCAACCCTA
TCTCGGTCTATTCTTTTGATTTATAAGGGATTTTGCCGATTTCGGCCTATTGGTTAAAA
AATGAGCTGATTTAACAAAATTTAACGCGAACTTTAACAAAATATTAACGTTTACAAT
TTAAATATTTGCTTATACAATCTTCCTGTTTTTGGGGCTTTTCTGATTATCAACCGGGG
TACATATGATTGACATGCTAGTTTTACGATTACCGTTCATCGCCCTGCGCGCTCGCTCG
CTCACTGAGGCCGCCCGGGCAAAGCCCGGGCGTCGGGCGACCTTTGGTCGCCCGGCCTC
AGTGAGCGAGCGAGCGCGCAGAGAGGGAGTGGAATTCACGCGCCCGGGGGAGGCTGCTG
GTGAATATTAACCAAGGTCACCCCAGTTATCGGAGGAGCAAACAGGGGCTAAGTCCACC
GGGGGAGGCTGCTGGTGAATATTAACCAAGGTCACCCCAGTTATCGGAGGAGCAAACAG
GGGCTAAGTCCACCGGGGGAGGCTGCTGGTGAATATTAACCAAGGTCACCCCAGTTATC
GGAGGAGCAAACAGGGGCTAAGTCCACGGTACCGGATCTTGCTACCAGTGGAACAGCCA
CTAAGGATTCTGCAGTGAGAGCAGAGGGCCAGCTAAGTGGTACTCTCCCAGAGACTGTC
TGACTCACGCCACCCCTCCACCTTGGACACAGGACGCTGTGGTTTCTGAGCCAGGTAC
AATGACTCCTTTCGGTAAGTGCAGTGGAAGCTGTACACTGCCCAGGCAAAGCGTCCGGG
CAGCGTAGGCGGGCGACTCAGATCCCAGCCAGTGGACTTAGCCCCTGTTTGCTCCTCCG
ATAACTGGGGTGACCTTGGTTAATATTCACCAGCAGCCTCCCCGTTGCCCCTCTGGAT
CCACTGCTTAAATACGGACGAGGACAGGGCCCTGTCTCCTCAGCTTCAGGCACCACCAC
TGACCTGGGACAGTGAATGATCCCCCTGATCTGCGGCCTCTAGAAAGAGGTAAGGGTTT
AAGGGATGGTTGGTTGGTGGGTATTAATGTTTAATTACCTGGAGCACCTGCCTGAAAT
CACTTTTTTTCAGGTTGGGCTAGCCCACCATGCAGCGCGTGAACATGATCATGGCCGAG
AGCCCCGGCCTGATCACCATCTGCCTGCTGGGCTACCTGCTGAGCGCCGAGTGCACCGT
GTTCCTGGACCACGAGAACGCCAACAAGATCCTGAACCGCCCCAAGCGCTACAACAGCG
GCAAGCTGGAGGAGTTCGTGCAGGGCAACCTGGAGCGCGAGTGCATGGAGGAGAAGTGC
AGCTTCGAGGAGGCCCGCGAGGTGTTCGAGAACACCGAGCGCACCACCGAGTTCTGGAA
GCAGTACGTGGACGGCGACCAGTGCGAGAGCAACCCCTGCCTGAACGGCGGCAGCTGCA
AGGACGACATCAACAGCTACGAGTGCTGGTGCCCCTTCGGCTTCGAGGGCAAGAACTGC
GAGCTGGACGTGACCTGCAACATCAAGAACGGCCGCTGCGAGCAGTTCTGCAAGAACAG
CGCCGACAACAAGGTGGTGTGCAGCTGCACCGAGGGCTACCGCCTGGCCGAGAACCAGA
AGAGCTGCGAGCCCGCCGTGCCCTTCCCCTGCGGCCGCGTGAGCGTGAGCCAGACCAGC
AAGCTGACCCGCGCCGAGGCCGTGTTCCCCGACGTGGACTACGTGAACAGCACCGAGGC
CGAGACCATCCTGGACAACATCACCCAGAGCACCCAGAGCTTCAACGACTTCACCCGCG
TGGTGGGCGGCGAGGACGCCAAGCCCGGCCAGTTCCCCTGGCAGGTGGTGCTGAACGGC
AAGGTGGACGCCTTCTGCGGCGGCAGCATCGTGAACGAGAAGTGGATCGTGACCGCCGC
CCACTGCGTGGAGACCGGCGTGAAGATCACCGTGGTGGCCGGCGAGCACAACATCGAGG
AGACCGAGCACACCGAGCAGAAGCGCAACGTGATCCGCATCATCCCCCACCACAACTAC
AACGCCGCCATCAACAAGTACAACCACGACATCGCCCTGCTGGAGCTGGACGAGCCCCT
GGTGCTGAACAGCTACGTGACCCCCATCTGCATCGCCGACAAGGAGTACACCAACATCT
TCCTGAAGTTCGGCAGCGGCTACGTGAGCGGCTGGGGCCGCGTGTTCCACAAGGGCCGC
AGCGCCCTGGTGCTGCAGTACCTGCGCGTGCCCCTGGTGGACCGCGCCACCTGCCTGCT
GAGCACCAAGTTCACCATCTACAACAACATGTTCTGCGCCGGCTTCCACGAGGGCGGCC
GCGACAGCTGCCAGGGCGACAGCGGCGGCCCCCACGTGACCGAGGTGGAGGGCACCAGC
TTCCTGACCGGCATCATCAGCTGGGGCGAGGAGTGCGCCATGAAGGGCAAGTACGGCAT
CTACACCAAGGTGAGCCGCTACGTGAACTGGATCAAGGAGAAGACCAAGCTGACCTAAT
```

Figure 24 (continued)

```
GAAAGATGGATTTCCAAGGTTAATTCATTGGAATTGAAAATTAACAGCCCCCCCCCCC
CCCCCCTGCAGATCTGAGCCGAATTCCTGCAGCCCGGGGGATCAGCCTCGACTGTGCCT
TCTAGTTGCCAGCCATCTGTTGTTTGCCCCTCCCCCGTGCCTTCCTTGACCCTGGAAGG
TGCCACTCCCACTGTCCTTTCCTAATAAAATGAGGAAATTGCATCGCATTGTCTGAGTA
GGTGTCATTCTATTCTGGGGGGTGGGGTGGGGCAGGACAGCAAGGGGGAGGATTGGGAA
GACAATAGCAGGCATGCTGGGGATGCGGTGGGCTCTATGGCTTCTGAGGCGGAAAGAAC
CAGCTGGGGACCGGTGGATCTCGATAGCAGGCATGCTGGGGAGAGATCGATCTGAGGAA
CCCCTAGTGATGGAGTTGGCCACTCCCTCTCTGCGCGCTCGCTCGCTCACTGAGGCCGC
CCGGGCAAAGCCCGGGCGTCGGGCGACCTTTGGTCGCCCGGCCTCAGTGAGCGAGCGAG
CGCGCAGAGAGGGAGTGGCCAACCCCCCCCCCCCCCCCCCCGGCGATTCTCTTGTTTG
CTCCAGACTCTCAGGCAATGACCTGATAGCCTTTGTAGAGACCTCTCAAAAATAGCTAC
CCTCTCCGGCATGAATTTATCAGCTAGAACGGTTGAATATCATATTGATGGTGATTTGA
CTGTCTCCGGCCTTTCTCACCCGTTTGAATCTTTACCTACACATTACTCAGGCATTGCA
TTTAAAATATATGAGGGTTCTAAAAATTTTTATCCTTGCGTTGAAATAAAGGCTTCTCC
CGCAAAAGTATTACAGGGTCATAATGTTTTTGGTACAACCGATTTAGCTTTATGCTCTG
AGGCTTTATTGCTTAATTTTGCTAATTCTTTGCCTTGCCTGTATGATTTATTGGATGTT
GGAATCGCCTGATGCGGTATTTTCTCCTTACGCATCTGTGCGGTATTTCACACCGCATA
TGGTGCACTCTCAGTACAATCTGCTCTGATGCCGCATAGTTATATGGTGCACTCTCAGT
ACAATCTGCTCTGATGCCGCATAGTTAAGCCAGCCCCGACACCCGCCAACACAGCCAGC
CCCGACACCCGCCAACACCCGCTGACGCGCCCTGACGGGCTTGTCTGCTCCCGGCATCC
GCTTACAGACAAGCTGTGACCGTCTCCGGGAGCTGCATGTGTCAGAGGTTTTCACCGTC
ATCACCGAAACGCGCGAGACGAAAGGGCCTCGTGATACGCCTATTTTATAGGTTAATG
TCATGATAATAATGGTTTCTTAGACGTCAGGTGGCACTTTTCGGGGAAATGTGCGCGGA
ACCCCTATTTGTTTATTTTTCTAAATACATTCAAATATGTATCCGCTCATGAGACAATA
ACCCTGATAAATGCTCAATAATATTGAAAAAGGAAGAGTATGAGTATTCAACATTTCCG
TGTCGCCCTTATTCCCTTTTTTGCGGCATTTTGCCTTCCTGTTTTTGCTCACCCAGAAA
CGCTGGTGAAAGTAAAAGATGCTGAAGATCAGTTGGGTGCACGAGTGGGTTACATCGAA
CTGGATCTCAACAGCGGTAAGATCCTTGAGAGTTTTCGCCCCGAAGAACGTTTTCCAAT
GATGAGCACTTTTAAAGTTCTGCTATGTGGCGCGGTATTATCCCGTATTGACGCCGGGC
AAGAGCAACTCGGTCGCCGCATACACTATTCTCAGAATGACTTGGTTGAGTACTCACCA
GTCACAGAAAAGCATCTTACGGATGGCATGACAGTAAGAGAATTATGCAGTGCTGCCAT
AACCATGAGTGATAACACTGCGGCCAACTTACTTCTGACAACGATCGGAGGACCGAAGG
AGCTAACCGCTTTTTTGCACAACATGGGGGATCATGTAACTCGCCTTGATCGTTGGGAA
CCGGAGCTGAATGAAGCCATACCAAACGACGAGCGTGACACCACGATGCCTGTAGCAAT
GGCAACAACGTTGCGCAAACTATTAACTGGCGAACTACTTACTCTAGCTTCCCGGCAAC
AATTAATAGACTGGATGGAGGCGGATAAAGTTGCAGGACCACTTCTGCGCTCGGCCCTT
CCGGCTGGCTGGTTTATTGCTGATAAATCTGGAGCCGGTGAGCGTGGGTCTCGCGGTAT
CATTGCAGCACTGGGGCCAGATGGTAAGCCCTCCCGTATCGTAGTTATCTACACGACGG
GGAGTCAGGCAACTATGGATGAACGAAATAGACAGATCGCTGAGATAGGTGCCTCACTG
ATTAAGCATTGGTAACTGTCAGACCAAGTTTACTCATATATACTTTAGATTGATTTAAA
ACTTCATTTTTAATTTAAAAGGATCTAGGTGAAGATCCTTTTTGATAATCTCATGACCA
AAATCCCTTAACGTGAGTTTTCGTTCCACTGAGCGTCAGACCCCGTAGAAAGATCAAA
GGATCTTCTTGAGATCCTTTTTTTCTGCGCGTAATCTGCTGCTTGCAAACAAAAAAACC
ACCGCTACCAGCGGTGGTTTGTTTGCCGGATCAAGAGCTACCAACTCTTTTTCCGAAGG
TAACTGGCTTCAGCAGAGCGCAGATACCAAATACTGTCCTTCTAGTGTAGCCGTAGTTA
GGCCACCACTTCAAGAACTCTGTAGCACCGCCTACATACCTCGCTCTGCTAATCCTGTT
```

Figure 24 (continued)

ACCAGTGGCTGCTGCCAGTGGCGATAAGTCGTGTCTTACCGGGTTGGACTCAAGACGAT
AGTTACCGGATAAGGCGCAGCGGTCGGGCTGAACGGGGGGTTCGTGCACACAGCCCAGC
TTGGAGCGAACGACCTACACCGAACTGAGATACCTACAGCGTGAGCTATGAGAAAGCGC
CACGCTTCCCGAAGGGAGAAAGGCGGACAGGTATCCGGTAAGCGGCAGGGTCGGAACAG
GAGAGCGCACGAGGGAGCTTCCAGGGGGAAACGCCTGGTATCTTTATAGTCCTGTCGGG
TTTCGCCACCTCTGACTTGAGCGTCGATTTTTGTGATGCTCGTCAGGGGGGCGGAGCCT
ATGGAAAAACGCCAGCAACGCGGCCTTTTTACGGTTCCTGGCCTTTTGCTGGCCTTTTG
CTCACATGTTCTTTCCTGCGTTATCCCTGATTCTGTGGATAACCGTATTACCGCCTTT
GAGTGAGCTGATACCGCTCGCCGCAGCCGAACGACCGAGCGCAGCGAGTCAGTGAGCGA
GGAAGCGGAAGAGCGCCCAATACGCAAACCGCCTCTCCCCGCGCGTTGGCCGATTCATT
AATG

SEQ ID NO:67: pAAVsc-TTRe-AAT-FIX-co-R338L-BGHpA

AGCTGGCGTAATAGCGAAGAGGCCCGCACCGATCGCCCTTCCCAACAGTTGCGCAGCCT
GAATGGCGAATGGCGATTCCGTTGCAATGGCTGGCGGTAATATTGTTCTGGATATTACC
AGCAAGGCCGATAGTTTGAGTTCTTCTACTCAGGCAAGTGATGTTATTACTAATCAAAG
AAGTATTGCGACAACGGTTAATTTGCGTGATGGACAGACTCTTTTACTCGGTGGCCTCA
CTGATTATAAAAACACTTCTCAGGATTCTGGCGTACCGTTCCTGTCTAAAATCCCTTTA
ATCGGCCTCCTGTTTAGCTCCCGCTCTGATTCTAACGAGGAAAGCACGTTATACGTGCT
CGTCAAAGCAACCATAGTACGCGCCCTGTAGCGGCGCATTAAGCGCGGCGGGTGTGGTG
GTTACGCGCAGCGTGACCGCTACACTTGCCAGCGCCCTAGCGCCCGCTCCTTTCGCTTT
CTTCCCTTCCTTTCTCGCCACGTTCGCCGGCTTTCCCCGTCAAGCTCTAAATCGGGGGC
TCCCTTTAGGGTTCCGATTTAGTGCTTTACGGCACCTCGACCCCAAAAAACTTGATTAG
GGTGATGGTTCACGTAGTGGGCCATCGCCCTGATAGACGGTTTTTCGCCCTTTGACGTT
GGAGTCCACGTTCTTTAATAGTGGACTCTTGTTCCAAACTGGAACAACACTCAACCCTA
TCTCGGTCTATTCTTTTGATTTATAAGGGATTTTGCCGATTTCGGCCTATTGGTTAAAA
AATGAGCTGATTTAACAAAAATTTAACGCGAACTTTAACAAAATATTAACGTTTACAAT
TTAAATATTTGCTTATACAATCTTCCTGTTTTTGGGGCTTTTCTGATTATCAACCGGGG
TACATATGATTGACATGCTAGTTTTACGATTACCGTTCATCGCCCTGCGCGCTCGCTCG
CTCACTGAGGCCGCCCGGGCAAAGCCCGGGCGTCGGGCGACCTTTGGTCGCCCGGCCTC
AGTGAGCGAGCGAGCGCGCAGAGAGGGAGTGGAATTCACGCGCCCACTGGGAGGATGTT
GAGTAAGATGGAAAACTACTGATGACCCTTGCAGAGACAGAGTATTAGGACATGTTTGA
ACAGGGGCCGGGCGATCAGCAGGTAGGGTACCGGATCTTGCTACCAGTGGAACAGCCAC
TAAGGATTCTGCAGTGAGAGCAGAGGGCCAGCTAAGTGGTACTCTCCCAGAGACTGTCT
GACTCACGCCACCCCTCCACCTTGGACACAGGACGCTGTGGTTTCTGAGCCAGGTACA
ATGACTCCTTTCGGTAAGTGCAGTGGAAGCTGTACACTGCCCAGGCAAAGCGTCCGGGC
AGCGTAGGCGGGCGACTCAGATCCCAGCCAGTGGACTTAGCCCCTGTTTGCTCCTCCGA
TAACTGGGGTGACCTTGGTTAATATTCACCAGCAGCCTCCCCGTTGCCCCTCTGGATC
CACTGCTTAAATACGGACGAGGACAGGGCCCTGTCTCCTCAGCTTCAGGCACCACCACT
GACCTGGGACAGTGAATGATCCCCCTGATCTGCGGCCTCTAGAAAGAGGTAAGGGTTTA
AGGGATGGTTGGTTGGTGGGTATTAATGTTTAATTACCTGGAGCACCTGCCTGAAATC
ACTTTTTTTCAGGTTGGGCTAGCCCACCATGCAGCGCGTGAACATGATCATGGCCGAGA
GCCCCGGCCTGATCACCATCTGCCTGCTGGGCTACCTGCTGAGCGCCGAGTGCACCGTG
TTCCTGGACCACGAGAACGCCAACAAGATCCTGAACCGCCCCAAGCGCTACAACAGCGG
CAAGCTGGAGGAGTTCGTGCAGGGCAACCTGGAGCGCGAGTGCATGGAGGAGAAGTGCA

Figure 24 (continued)

```
GCTTCGAGGAGGCCCGCGAGGTGTTCGAGAACACCGAGCGCACCACCGAGTTCTGGAAG
CAGTACGTGGACGGCGACCAGTGCGAGAGCAACCCCTGCCTGAACGGCGGCAGCTGCAA
GGACGACATCAACAGCTACGAGTGCTGGTGCCCCTTCGGCTTCGAGGGCAAGAACTGCG
AGCTGGACGTGACCTGCAACATCAAGAACGGCCGCTGCGAGCAGTTCTGCAAGAACAGC
GCCGACAACAAGGTGGTGTGCAGCTGCACCGAGGGCTACCGCCTGGCCGAGAACCAGAA
GAGCTGCGAGCCCGCCGTGCCCTTCCCCTGCGGCCGCGTGAGCGTGAGCCAGACCAGCA
AGCTGACCCGCGCCGAGGCCGTGTTCCCCGACGTGGACTACGTGAACAGCACCGAGGCC
GAGACCATCCTGGACAACATCACCCAGAGCACCCAGAGCTTCAACGACTTCACCCGCGT
GGTGGGCGGCGAGGACGCCAAGCCCGGCCAGTTCCCCTGGCAGGTGGTGCTGAACGGCA
AGGTGGACGCCTTCTGCGGCGGCAGCATCGTGAACGAGAAGTGGATCGTGACCGCCGCC
CACTGCGTGGAGACCGGCGTGAAGATCACCGTGGTGGCCGGCGAGCACAACATCGAGGA
GACCGAGCACACCGAGCAGAAGCGCAACGTGATCCGCATCATCCCCCACCACAACTACA
ACGCCGCCATCAACAAGTACAACCACGACATCGCCCTGCTGGAGCTGGACGAGCCCCTG
GTGCTGAACAGCTACGTGACCCCCATCTGCATCGCCGACAAGGAGTACACCAACATCTT
CCTGAAGTTCGGCAGCGGCTACGTGAGCGGCTGGGGCCGCGTGTTCCACAAGGGCCGCA
GCGCCCTGGTGCTGCAGTACCTGCGCGTGCCCCTGGTGGACCGCGCCACCTGCCTGCTG
AGCACCAAGTTCACCATCTACAACAACATGTTCTGCGCCGGCTTCCACGAGGGCGGCCG
CGACAGCTGCCAGGGCGACAGCGGCGGCCCCACGTGACCGAGGTGGAGGGCACCAGCT
TCCTGACCGGCATCATCAGCTGGGGCGAGGAGTGCGCCATGAAGGGCAAGTACGGCATC
TACACCAAGGTGAGCCGCTACGTGAACTGGATCAAGGAGAAGACCAAGCTGACCTAATG
AAAGATGGATTTCCAAGGTTAATTCATTGGAATTGAAAATTAACAGCCCCCCCCCCCCC
CCCCCTGCAGATCTGAGCCGAATTCCTGCAGCCCGGGGGATCAGCCTCGACTGTGCCTT
CTAGTTGCCAGCCATCTGTTGTTTGCCCCTCCCCGTGCCTTCCTTGACCCTGGAAGGT
GCCACTCCCACTGTCCTTTCCTAATAAAATGAGGAAATTGCATCGCATTGTCTGAGTAG
GTGTCATTCTATTCTGGGGGGTGGGGTGGGGCAGGACAGCAAGGGGGAGGATTGGGAAG
ACAATAGCAGGCATGCTGGGGATGCGGTGGCTCTATGGCTTCTGAGGCGGAAAGAACC
AGCTGGGGACCGGTGGATCTCGATAGCAGGCATGCTGGGGAGAGATCGATCTGAGGAAC
CCCTAGTGATGGAGTTGGCCACTCCCTCTCTGCGCGCTCGCTCGCTCACTGAGGCCGCC
CGGGCAAAGCCCGGGCGTCGGGCGACCTTTGGTCGCCCGGCCTCAGTGAGCGAGCGAGC
GCGCAGAGAGGGAGTGGCCAACCCCCCCCCCCCCCCCCCGGCGATTCTCTTGTTTGC
TCCAGACTCTCAGGCAATGACCTGATAGCCTTTGTAGAGACCTCTCAAAAATAGCTACC
CTCTCCGGCATGAATTTATCAGCTAGAACGGTTGAATATCATATTGATGGTGATTTGAC
TGTCTCCGGCCTTTCTCACCCGTTTGAATCTTTACCTACACATTACTCAGGCATTGCAT
TTAAAATATATGAGGGTTCTAAAAATTTTTATCCTTGCGTTGAAATAAAGGCTTCTCCC
GCAAAAGTATTACAGGGTCATAATGTTTTGGTACAACCGATTTAGCTTTATGCTCTGA
GGCTTTATTGCTTAATTTTGCTAATTCTTTGCCTTGCCTGTATGATTTATTGGATGTTG
GAATCGCCTGATGCGGTATTTTCTCCTTACGCATCTGTGCGGTATTTCACACCGCATAT
GGTGCACTCTCAGTACAATCTGCTCTGATGCCGCATAGTTATATGGTGCACTCTCAGTA
CAATCTGCTCTGATGCCGCATAGTTAAGCCAGCCCCGACACCCGCCAACACAGCCAGCC
CCGACACCCGCCAACACCCGCTGACGCGCCCTGACGGGCTTGTCTGCTCCCGGCATCCG
CTTACAGACAAGCTGTGACCGTCTCCGGGAGCTGCATGTGTCAGAGGTTTTCACCGTCA
TCACCGAAACGCGCGAGACGAAAGGGCCTCGTGATACGCCTATTTTTATAGGTTAATGT
CATGATAATAATGGTTTCTTAGACGTCAGGTGGCACTTTTCGGGGAAATGTGCGCGGAA
CCCCTATTTGTTTATTTTTCTAAATACATTCAAATATGTATCCGCTCATGAGACAATAA
CCCTGATAAATGCTCAATAATATTGAAAAGGAAGAGTATGAGTATTCAACATTTCCGT
GTCGCCCTTATTCCCTTTTTTGCGGCATTTTGCCTTCCTGTTTTTGCTCACCCAGAAAC
```

Figure 24 (continued)

```
GCTGGTGAAAGTAAAAGATGCTGAAGATCAGTTGGGTGCACGAGTGGGTTACATCGAAC
TGGATCTCAACAGCGGTAAGATCCTTGAGAGTTTTCGCCCCGAAGAACGTTTTCCAATG
ATGAGCACTTTTAAAGTTCTGCTATGTGGCGCGGTATTATCCCGTATTGACGCCGGGCA
AGAGCAACTCGGTCGCCGCATACACTATTCTCAGAATGACTTGGTTGAGTACTCACCAG
TCACAGAAAAGCATCTTACGGATGGCATGACAGTAAGAGAATTATGCAGTGCTGCCATA
ACCATGAGTGATAACACTGCGGCCAACTTACTTCTGACAACGATCGGAGGACCGAAGGA
GCTAACCGCTTTTTGCACAACATGGGGGATCATGTAACTCGCCTTGATCGTTGGGAAC
CGGAGCTGAATGAAGCCATACCAAACGACGAGCGTGACACCACGATGCCTGTAGCAATG
GCAACAACGTTGCGCAAACTATTAACTGGCGAACTACTTACTCTAGCTTCCCGGCAACA
ATTAATAGACTGGATGGAGGCGGATAAAGTTGCAGGACCACTTCTGCGCTCGGCCCTTC
CGGCTGGCTGGTTTATTGCTGATAAATCTGGAGCCGGTGAGCGTGGGTCTCGCGGTATC
ATTGCAGCACTGGGGCCAGATGGTAAGCCCTCCCGTATCGTAGTTATCTACACGACGGG
GAGTCAGGCAACTATGGATGAACGAAATAGACAGATCGCTGAGATAGGTGCCTCACTGA
TTAAGCATTGGTAACTGTCAGACCAAGTTTACTCATATATACTTTAGATTGATTTAAAA
CTTCATTTTTAATTTAAAAGGATCTAGGTGAAGATCCTTTTTGATAATCTCATGACCAA
AATCCCTTAACGTGAGTTTTCGTTCCACTGAGCGTCAGACCCCGTAGAAAAGATCAAAG
GATCTTCTTGAGATCCTTTTTTTCTGCGCGTAATCTGCTGCTTGCAAACAAAAAAACCA
CCGCTACCAGCGGTGGTTTGTTTGCCGGATCAAGAGCTACCAACTCTTTTTCCGAAGGT
AACTGGCTTCAGCAGAGCGCAGATACCAAATACTGTCCTTCTAGTGTAGCCGTAGTTAG
GCCACCACTTCAAGAACTCTGTAGCACCGCCTACATACCTCGCTCTGCTAATCCTGTTA
CCAGTGGCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAGCCCAGCT
TGGAGCGAACGACCTACACCGAACTGAGATACCTACAGCGTGAGCTATGAGAAAGCGCC
ACGCTTCCCGAAGGGAGAAAGGCGGACAGGTATCCGGTAAGCGGCAGGGTCGGAACAGG
AGAGCGCACGAGGGAGCTTCCAGGGGGAAACGCCTGGTATCTTTATAGTCCTGTCGGGT
TTCGCCACCTCTGACTTGAGCGTCGATTTTTGTGATGCTCGTCAGGGGGGCGGAGCCTA
TGGAAAAACGCCAGCAACGCGGCCTTTTTACGGTTCCTGGCCTTTTGCTGGCCTTTTGC
TCACATGTTCTTTCCTGCGTTATCCCCTGATTCTGTGGATAACCGTATTACCGCCTTTG
AGTGAGCTGATACCGCTCGCCGCAGCCGAACGACCGAGCGCAGCGAGTCAGTGAGCGAG
GAAGCGGAAGAGCGCCCAATACGCAAACCGCCTCTCCCCGCGCGTTGGCCGATTCATTA
ATG
```

SEQ ID NO:68: pAAVsc-TTRe-3xSerpEnh-AAT-FIX-co-R338L-BGHpA

```
AGCTGGCGTAATAGCGAAGAGGCCCGCACCGATCGCCCTTCCCAACAGTTGCGCAGCCT
GAATGGCGAATGGCGATTCCGTTGCAATGGCTGGCGGTAATATTGTTCTGGATATTACC
AGCAAGGCCGATAGTTTGAGTTCTTCTACTCAGGCAAGTGATGTTATTACTAATCAAAG
AAGTATTGCGACAACGGTTAATTTGCGTGATGGACAGACTCTTTTACTCGGTGGCCTCA
CTGATTATAAAACACTTCTCAGGATTCTGGCGTACCGTTCCTGTCTAAAATCCCTTTA
ATCGGCCTCCTGTTTAGCTCCCGCTCTGATTCTAACGAGGAAAGCACGTTATACGTGCT
CGTCAAAGCAACCATAGTACGCGCCCTGTAGCGGCGCATTAAGCGCGGCGGGTGTGGTG
GTTACGCGCAGCGTGACCGCTACACTTGCCAGCGCCCTAGCGCCCGCTCCTTTCGCTTT
CTTCCCTTCCTTTCTCGCCACGTTCGCCGGCTTTCCCCGTCAAGCTCTAAATCGGGGGC
TCCCTTTAGGGTTCCGATTTAGTGCTTTACGGCACCTCGACCCCAAAAAACTTGATTAG
GGTGATGGTTCACGTAGTGGGCCATCGCCCTGATAGACGGTTTTTCGCCCTTTGACGTT
GGAGTCCACGTTCTTTAATAGTGGACTCTTGTTCCAAACTGGAACAACACTCAACCCTA
```

Figure 24 (continued)

```
TCTCGGTCTATTCTTTTGATTTATAAGGGATTTTGCCGATTTCGGCCTATTGGTTAAAA
AATGAGCTGATTTAACAAAAATTTAACGCGAACTTTAACAAAATATTAACGTTTACAAT
TTAAATATTTGCTTATACAATCTTCCTGTTTTTGGGGCTTTTCTGATTATCAACCGGGG
TACATATGATTGACATGCTAGTTTTACGATTACCGTTCATCGCCCTGCGCGCTCGCTCG
CTCACTGAGGCCGCCCGGGCAAAGCCCGGGCGTCGGGCGACCTTTGGTCGCCCGGCCTC
AGTGAGCGAGCGAGCGCGCAGAGAGGGAGTGGAATTCACGCGTCACTGGGAGGATGTTG
AGTAAGATGGAAAACTACTGATGACCCTTGCAGAGACAGAGTATTAGGACATGTTTGAA
CAGGGGCCGGGCGATCAGCAGGTAGGGCGCGCCCGGGGGAGGCTGCTGGTGAATATTAA
CCAAGGTCACCCCAGTTATCGGAGGAGCAAACAGGGGCTAAGTCCACCGGGGGAGGCTG
CTGGTGAATATTAACCAAGGTCACCCCAGTTATCGGAGGAGCAAACAGGGGCTAAGTCC
ACCGGGGGAGGCTGCTGGTGAATATTAACCAAGGTCACCCCAGTTATCGGAGGAGCAAA
CAGGGGCTAAGTCCACGGTACCGGATCTTGCTACCAGTGGAACAGCCACTAAGGATTCT
GCAGTGAGAGCAGAGGGCCAGCTAAGTGGTACTCTCCCAGAGACTGTCTGACTCACGCC
ACCCCCTCCACCTTGGACACAGGACGCTGTGGTTTCTGAGCCAGGTACAATGACTCCTT
TCGGTAAGTGCAGTGGAAGCTGTACACTGCCCAGGCAAAGCGTCCGGGCAGCGTAGGCG
GGCGACTCAGATCCCAGCCAGTGGACTTAGCCCCTGTTTGCTCCTCCGATAACTGGGGT
GACCTTGGTTAATATTCACCAGCAGCCTCCCCGTTGCCCCTCTGGATCCACTGCTTAA
ATACGGACGAGGACAGGGCCCTGTCTCCTCAGCTTCAGGCACCACCACTGACCTGGGAC
AGTGAATGATCCCCCTGATCTGCGGCCTCTAGAAAGAGGTAAGGGTTTAAGGGATGGTT
GGTTGGTGGGGTATTAATGTTTAATTACCTGGAGCACCTGCCTGAAATCACTTTTTTTC
AGGTTGGGCTAGCCCACCATGCAGCGCGTGAACATGATCATGGCCGAGAGCCCCGGCCT
GATCACCATCTGCCTGCTGGGCTACCTGCTGAGCGCCGAGTGCACCGTGTTCCTGGACC
ACGAGAACGCCAACAAGATCCTGAACCGCCCCAAGCGCTACAACAGCGGCAAGCTGGAG
GAGTTCGTGCAGGGCAACCTGGAGCGCGAGTGCATGGAGGAGAAGTGCAGCTTCGAGGA
GGCCCGCGAGGTGTTCGAGAACACCGAGCGCACCACCGAGTTCTGGAAGCAGTACGTGG
ACGGCGACCAGTGCGAGAGCAACCCCTGCCTGAACGGCGGCAGCTGCAAGGACGACATC
AACAGCTACGAGTGCTGGTGCCCCTTCGGCTTCGAGGGCAAGAACTGCGAGCTGGACGT
GACCTGCAACATCAAGAACGGCCGCTGCGAGCAGTTCTGCAAGAACAGCGCCGACAACA
AGGTGGTGTGCAGCTGCACCGAGGGCTACCGCCTGGCCGAGAACCAGAAGAGCTGCGAG
CCCGCCGTGCCCTTCCCCTGCGGCCGCGTGAGCGTGAGCCAGACCAGCAAGCTGACCCG
CGCCGAGGCCGTGTTCCCCGACGTGGACTACGTGAACAGCACCGAGGCCGAGACCATCC
TGGACAACATCACCCAGAGCACCCAGAGCTTCAACGACTTCACCCGCGTGGTGGGCGGC
GAGGACGCCAAGCCCGGCCAGTTCCCCTGGCAGGTGGTGCTGAACGGCAAGGTGGACGC
CTTCTGCGGCGGCAGCATCGTGAACGAGAAGTGGATCGTGACCGCCGCCCACTGCGTGG
AGACCGGCGTGAAGATCACCGTGGTGGCCGGCGAGCACAACATCGAGGAGACCGAGCAC
ACCGAGCAGAAGCGCAACGTGATCCGCATCATCCCCCACCACAACTACAACGCCGCCAT
CAACAAGTACAACCACGACATCGCCCTGCTGGAGCTGGACGAGCCCCTGGTGCTGAACA
GCTACGTGACCCCCATCTGCATCGCCGACAAGGAGTACACCAACATCTTCCTGAAGTTC
GGCAGCGGCTACGTGAGCGGCTGGGGCCGCGTGTTCCACAAGGGCCGCAGCGCCCTGGT
GCTGCAGTACCTGCGCGTGCCCCTGGTGGACCGCGCCACCTGCCTGCTGAGCACCAAGT
TCACCATCTACAACAACATGTTCTGCGCCGGCTTCCACGAGGGCGGCCGCGACAGCTGC
CAGGGCGACAGCGGCGGCCCCACGTGACCGAGGTGGAGGGCACCAGCTTCCTGACCGG
CATCATCAGCTGGGGCGAGGAGTGCGCCATGAAGGGCAAGTACGGCATCTACACCAAGG
TGAGCCGCTACGTGAACTGGATCAAGGAGAAGACCAAGCTGACCTAATGAAAGATGGAT
TTCCAAGGTTAATTCATTGGAATTGAAAATTAACAGCCCCCCCCCCCCCCCCTGCAG
ATCTGAGCCGAATTCCTGCAGCCCGGGGGATCAGCCTCGACTGTGCCTTCTAGTTGCCA
```

Figure 24 (continued)

```
GCCATCTGTTGTTTGCCCCTCCCCCGTGCCTTCCTTGACCCTGGAAGGTGCCACTCCCA
CTGTCCTTTCCTAATAAAATGAGGAAATTGCATCGCATTGTCTGAGTAGGTGTCATTCT
ATTCTGGGGGGTGGGGTGGGGCAGGACAGCAAGGGGGAGGATTGGGAAGACAATAGCAG
GCATGCTGGGGATGCGGTGGGCTCTATGGCTTCTGAGGCGGAAAGAACCAGCTGGGGAC
CGGTGGATCTCGATAGCAGGCATGCTGGGGAGAGATCGATCTGAGGAACCCCTAGTGAT
GGAGTTGGCCACTCCCTCTCTGCGCGCTCGCTCGCTCACTGAGGCCGCCCGGGCAAAGC
CCGGGCGTCGGGCGACCTTTGGTCGCCCGGCCTCAGTGAGCGAGCGAGCGCGCAGAGAG
GGAGTGGCCAACCCCCCCCCCCCCCCCCGGCGATTCTCTTGTTTGCTCCAGACTCT
CAGGCAATGACCTGATAGCCTTTGTAGAGACCTCTCAAAAATAGCTACCCTCTCCGGCA
TGAATTTATCAGCTAGAACGGTTGAATATCATATTGATGGTGATTTGACTGTCTCCGGC
CTTTCTCACCCGTTTGAATCTTTACCTACACATTACTCAGGCATTGCATTTAAAATATA
TGAGGGTTCTAAAAATTTTTATCCTTGCGTTGAAATAAAGGCTTCTCCCGCAAAAGTAT
TACAGGGTCATAATGTTTTTGGTACAACCGATTTAGCTTTATGCTCTGAGGCTTTATTG
CTTAATTTTGCTAATTCTTTGCCTTGCCTGTATGATTTATTGGATGTTGGAATCGCCTG
ATGCGGTATTTTCTCCTTACGCATCTGTGCGGTATTTCACACCGCATATGGTGCACTCT
CAGTACAATCTGCTCTGATGCCGCATAGTTATATGGTGCACTCTCAGTACAATCTGCTC
TGATGCCGCATAGTTAAGCCAGCCCCGACACCCGCCAACACAGCCAGCCCCGACACCCG
CCAACACCCGCTGACGCGCCCTGACGGGCTTGTCTGCTCCCGGCATCCGCTTACAGACA
AGCTGTGACCGTCTCCGGGAGCTGCATGTGTCAGAGGTTTTCACCGTCATCACCGAAAC
GCGCGAGACGAAAGGGCCTCGTGATACGCCTATTTTTATAGGTTAATGTCATGATAATA
ATGGTTTCTTAGACGTCAGGTGGCACTTTTCGGGGAAATGTGCGCGGAACCCCTATTTG
TTTATTTTTCTAAATACATTCAAATATGTATCCGCTCATGAGACAATAACCCTGATAAA
TGCTCAATAATATTGAAAAAGGAAGAGTATGAGTATTCAACATTTCCGTGTCGCCCTTA
TTCCCTTTTTTGCGGCATTTTGCCTTCCTGTTTTTGCTCACCCAGAAACGCTGGTGAAA
GTAAAAGATGCTGAAGATCAGTTGGGTGCACGAGTGGGTTACATCGAACTGGATCTCAA
CAGCGGTAAGATCCTTGAGAGTTTTCGCCCCGAAGAACGTTTTCCAATGATGAGCACTT
TTAAAGTTCTGCTATGTGGCGCGGTATTATCCCGTATTGACGCCGGGCAAGAGCAACTC
GGTCGCCGCATACACTATTCTCAGAATGACTTGGTTGAGTACTCACCAGTCACAGAAAA
GCATCTTACGGATGGCATGACAGTAAGAGAATTATGCAGTGCTGCCATAACCATGAGTG
ATAACACTGCGGCCAACTTACTTCTGACAACGATCGGAGGACCGAAGGAGCTAACCGCT
TTTTTGCACAACATGGGGGATCATGTAACTCGCCTTGATCGTTGGGAACCGGAGCTGAA
TGAAGCCATACCAAACGACGAGCGTGACACCACGATGCCTGTAGCAATGGCAACAACGT
TGCGCAAACTATTAACTGGCGAACTACTTACTCTAGCTTCCCGGCAACAATTAATAGAC
TGGATGGAGGCGGATAAAGTTGCAGGACCACTTCTGCGCTCGGCCCTTCCGGCTGGCTG
GTTTATTGCTGATAAATCTGGAGCCGGTGAGCGTGGGTCTCGCGGTATCATTGCAGCAC
TGGGGCCAGATGGTAAGCCCTCCCGTATCGTAGTTATCTACACGACGGGGAGTCAGGCA
ACTATGGATGAACGAAATAGACAGATCGCTGAGATAGGTGCCTCACTGATTAAGCATTG
GTAACTGTCAGACCAAGTTTACTCATATATACTTTAGATTGATTTAAAACTTCATTTTT
AATTTAAAAGGATCTAGGTGAAGATCCTTTTTGATAATCTCATGACCAAAATCCCTTAA
CGTGAGTTTTCGTTCCACTGAGCGTCAGACCCCGTAGAAAGATCAAAGGATCTTCTTG
AGATCCTTTTTTTCTGCGCGTAATCTGCTGCTTGCAAACAAAAAAACCACCGCTACCAG
CGGTGGTTTGTTTGCCGGATCAAGAGCTACCAACTCTTTTTCCGAAGGTAACTGGCTTC
AGCAGAGCGCAGATACCAAATACTGTCCTTCTAGTGTAGCCGTAGTTAGGCCACCACTT
CAAGAACTCTGTAGCACCGCCTACATACCTCGCTCTGCTAATCCTGTTACCAGTGGCTG
CTGCCAGTGGCGATAAGTCGTGTCTTACCGGGTTGGACTCAAGACGATAGTTACCGGAT
AAGGCGCAGCGGTCGGGCTGAACGGGGGGTTCGTGCACACAGCCCAGCTTGGAGCGAAC
```

Figure 24 (continued)

```
GACCTACACCGAACTGAGATACCTACAGCGTGAGCTATGAGAAAGCGCCACGCTTCCCG
AAGGGAGAAAGGCGGACAGGTATCCGGTAAGCGGCAGGGTCGGAACAGGAGAGCGCACG
AGGGAGCTTCCAGGGGGAAACGCCTGGTATCTTTATAGTCCTGTCGGGTTTCGCCACCT
CTGACTTGAGCGTCGATTTTTGTGATGCTCGTCAGGGGGGCGGAGCCTATGGAAAAACG
CCAGCAACGCGGCCTTTTTACGGTTCCTGGCCTTTTGCTGGCCTTTTGCTCACATGTTC
TTTCCTGCGTTATCCCCTGATTCTGTGGATAACCGTATTACCGCCTTTGAGTGAGCTGA
TACCGCTCGCCGCAGCCGAACGACCGAGCGCAGCGAGTCAGTGAGCGAGGAAGCGGAAG
AGCGCCCAATACGCAAACCGCCTCTCCCCGCGCGTTGGCCGATTCATTAATG
```

SEQ ID NO:69: TTRe-TTRm

```
CACTGGGAGGATGTTGAGTAAGATGGAAAACTACTGATGACCCTTGCAGAGACAGAGTA
TTAGGACATGTTTGAACAGGGGCCGGGCGATCAGCAGGTAGCTCTAGAGGATCCCCGTC
TGTCTGCACATTTCGTAGAGCGAGTGTTCCGATACTCTAATCTCCCTAGGCAAGGTTCA
TATTTGTGTAGGTTACTTATTCTCCTTTTGTTGACTAAGTCAATAATCAGAATCAGCAG
GTTTGGAGTCAGCTTGGCAGGGATCAGCAGCCTGGGTTGGAAGGAGGGGGTATAAAAGC
CCCTTCACCAGGAGAAGCCGTC
```

OPTIMIZED LIVER-SPECIFIC EXPRESSION SYSTEMS FOR FVIII AND FIX

INCORPORATION BY CROSS-REFERENCE

This application is a U.S. National Phase of International Application No. PCT/EP2016/055825, filed Mar. 17, 2016, which claims priority to European Patent Application No. 15159395.1, filed Mar. 17, 2015, the disclosure of each of which is hereby incorporated by cross-reference in its entirety.

FIELD OF THE INVENTION

The invention relates to nucleic acid expression cassettes and expression vectors for gene therapy with improved liver-specific expression capabilities, particularly for use as a gene therapy means for the treatment of hemophilia, more particularly for restoring coagulation factor IX (FIX) and/or coagulation factor VIII (FVIII) deficiency in liver-directed gene therapy of respectively, hemophilia B and hemophilia A.

BACKGROUND OF THE INVENTION

Hemophilia B is an X-linked, recessive bleeding disorder caused by deficiency of clotting factor IX (FIX). Hemophilia A is a serious bleeding disorder caused by a deficiency in, or complete absence of, the blood coagulation factor VIII (FVIII). The clinical presentation for hemophilia A and B is characterized by episodes of spontaneous and prolonged bleeding. There are an estimated 1 in 5,000 and 1 in 20,000 individuals suffer from hemophilia A and B, respectively. Currently, hemophilia A and B is treated with protein replacement therapy using either plasma-derived or recombinant FVIII or FIX. Although protein replacement markedly improved the life expectancy of patients suffering from hemophilia, they are still at risk for severe bleeding episodes and chronic joint damage, since prophylactic treatment is restricted by the short half-life, the limited availability and the high cost of purified clotting factors, which can approach 100.000$/patient/year. In addition, the use of plasma-derived factors obtained from contaminated blood sources increases the risk of viral transmission. Gene therapy offers the promise of a new method of treating hemophilia B, since the therapeutic window is relatively broad and levels slightly above 1% of normal physiologic levels are therapeutic. If successful, gene therapy could provide constant FVIII or FIX synthesis which may lead to a cure for this disease. The different modalities for gene therapy of hemophilia have been extensively reviewed (Chuah et al., 2012a, 2012b, 2012c; VandenDriessche et al., 2012; High 2001, 2011; Matrai et al., 2010a, 2010b).

The severity of hemophilia A and hemophilia B has been classified by the subcommittee on Factor VIII and Factor IX of the Scientific and Standardization Committee of the International Society on Thrombosis and Haemostasis into three forms, depending on respectively, the FVIII level and the FIX level: 1) severe form (FVIII or FIX level less than 0.01 international units (IU)/ml, i.e. less than 1% of normal FVIII or FIX level), 2) moderate form (FVIII or FIX level from 0.01 to 0.05 IU/ml, i.e. from 1 to 5% of normal FVIII or FIX level), and 3) mild from (FVIII or FIX level higher than 0.05 to 0.4 IU/ml, i.e. higher than 5 to 40% of normal FVIII or FIX level). Hemophilia A is the most common hereditary coagulation disorder with an incidence approaching approximately 1 in 5000 males.

Protein substitution therapy (PST) with purified or recombinant FVIII and FIX has significantly improved the patients' quality of life. However, PST is not curative and patients are still at risk of developing potentially life-threatening hemorrhages and crippling joint inflammation. Unfortunately, many patients suffering from hemophilia A (up to 40%) develop neutralizing antibodies to FVIII (i.e. "inhibitors") following PST. Similarly, an estimated 10% of patients suffering from hemophilia B develop "inhibitors" to FIX. These inhibitors complicate the management of bleeding episodes and can render further PST ineffective. These limitations of PST, justify the development of gene therapy as a potential alternative for hemophilia treatment. Furthermore, only a modest increase in FIX or FVIII plasma concentration is needed for therapeutic benefit, with levels of more than 1% of normal levels able to achieve markedly reduced rates of spontaneous bleeding and long-term arthropathy.

The liver is the main physiological site of FIX and FVIII synthesis and hence, hepatocytes are well suited target cells for hemophilia gene therapy. From this location, FIX or FVIII protein can easily enter into the circulation. Moreover, the hepatic niche may favor the induction of immune tolerance towards the transgene product (Annoni et al., 2007; Follenzi et al., 2004; Brown et al., 2007; Herzog et al., 1999; Matrai et al., 2011; Matsui et al., 2009). Liver-directed gene therapy for hemophilia can be accomplished with different viral vectors including retroviral (Axelrod et al., 1990; Kay et al., 1992; VandenDriessche et al., 1999, Xu et al., 2003, 2005), lentiviral (Ward et al., 2011, Brown et al., 2007, Matrai et al., 2011), adeno-associated viral (AAV) (Herzog et al., 1999) and adenoviral vectors (Brown et al., 2004; Ehrhardt & Kay, 2002). In particular, AAV is a naturally occurring replication defective non-pathogenic virus with a single stranded DNA genome. AAV vectors have a favorable safety profile and are capable of achieving persistent transgene expression. Long-term expression is predominantly mediated by episomally retained AAV genomes. More than 90% of the stably transduced vector genomes are extra-chromosomal, mostly organized as high-molecular-weight concatamers. Therefore, the risk of insertional oncogenesis is minimal, especially in the context of hemophilia gene therapy where no selective expansion of transduced cells is expected to occur. Nevertheless, oncogenic events have been reported following AAV-based gene transfer (Donsante et al., 2007) but it has been difficult to reproduce these findings in other model systems (Li et al., 2011). The major limitation of AAV vectors is the limited packaging capacity of the vector particles (i.e. approximately 5.0 kb, including the AAV inverted terminal repeats), constraining the size of the transgene expression cassette to obtain functional vectors (Jiang et al., 2006). Several immunologically distinct AAV serotypes have been isolated from human and non-human primates (Gao et al., 2002, Gao et al. 2004), although most vectors for hemophilia gene therapy were initially derived from the most prevalent AAV serotype 2. The first clinical success of AAV-based gene therapy for congenital blindness underscores the potential of this gene transfer technology (Bainbridge et al., 2008).

AAV-mediated hepatic gene transfer is an attractive alternative for gene therapy of hemophilia for both liver and muscle-directed gene therapy (Herzog et al., 1997, 1999, 2002; Arruda et al., 2010; Fields et al., 2001; Buchlis et al., 2012; Jiang et al., 2006; Kay et al., 2000). Preclinical studies with the AAV vectors in murine and canine models of hemophilia or non-human primates have demonstrated persistent therapeutic expression, leading to partial or complete correction of the bleeding phenotype in the hemophilic models (Snyder et al., 1997, 1999; Wang et al., 1999, 2000; Mount et al., 2002; Nathwani et al., 2002). Particularly, hepatic transduction conveniently induces immune tolerance to FIX that required induction of regulatory T cells (Tregs) (Mingozzi et al., 2003; Dobrzynski et al., 2006). Long-term correction of the hemophilia phenotype without inhibitor development was achieved in inhibitor-prone null mutation hemophilia B dogs treated with liver-directed AAV2-FIX gene therapy (Mount et al, 2002). In order to further reduce the vector dose, more potent FIX expression cassettes have been developed. This could be accomplished by using stronger promoter/enhancer elements, codon-optimized FIX or self-complementary, double-stranded AAV vectors (scAAV) that overcome one of the limiting steps in AAV transduction (i.e. single-stranded to double-stranded AAV conversion) (McCarty, 2001, 2003; Nathwani et al, 2002, 2006, 2011; Wu et al., 2008). Alternative AAV serotypes could be used (e.g. AAV8 or AAV5) that result in increased transduction into hepatocytes, improve intra-nuclear vector import and may reduce the risk of T cell activation (Gao et al., 2002; Vandenberghe et al., 2006) though it is not certain that this would necessarily also translate to human subjects since the epitopes are conserved between distinct AAV serotypes (Mingozzi et al., 2007). Liver-directed gene therapy for hemophilia B with AAV8 or AAV9 is more efficient than when lentiviral vectors are used, at least in mice, and resulted in less inflammation (VandenDriessche et al., 2007, 2002). Furthermore, recent studies indicate that mutations of the surface-exposed tyrosine residues allow the vector particles to evade phosphorylation and subsequent ubiquitination and, thus, prevent proteasome-mediated degradation, which resulted in a 10-fold increase in hepatic expression of FIX in mice (Zhong et al., 2008).

These liver-directed preclinical studies paved the way toward the use of AAV vectors for clinical gene therapy in patients suffering from severe hemophilia B. Hepatic delivery of AAV-FIX vectors resulted in transient therapeutic FIX levels (maximum 12% of normal levels) in subjects receiving AAV-FIX by hepatic artery catheterization (Kay et al., 2000). However, the transduced hepatocytes were able to present AAV capsid-derived antigens in association with MHC class I to T cells (Manno et al., 2006, Mingozzi et al., 2007). Although antigen presentation was modest, it was sufficient to flag the transduced hepatocytes for T cell-mediated destruction. Recently, gene therapy for hemophilia made an important step forward (Nathwani et al., 2011; Commentary by VandenDriessche & Chuah, 2012). Subjects suffering from severe hemophilia B (<1% FIX) were injected intravenously with self-complementary (sc) AAV8 vectors expressing codon-optimized FIX from a liver-specific promoter. This AAV8 serotype exhibits reduced cross-reactivity with pre-existing anti-AAV2 antibodies. Interestingly, its uptake by dendritic cells may be reduced compared to conventional AAV2 vectors, resulting in reduced T cell activation (Vandenberghe et al., 2006). In mice, AAV8 allows for a substantial increase in hepatic transduction compared to AAV2, though this advantage may be lost in higher species, like dog, rhesus monkeys and man. Subjects received escalating doses of the scAAV8-FIX vector, with two participants per dose. All of the treated subjects expressed FIX above the therapeutic 1% threshold for several months after vector administration, yielding sustained variable expression levels (i.e. 2 to 11% of normal levels). The main difference with the previous liver-directed AAV trial is that for the first time sustained therapeutic FIX levels could be achieved after gene therapy. Despite this progress, T-cell mediated clearance of AAV-transduced hepatocytes remains a concern consistent with elevated liver enzyme levels in some of the patients. Transient immune suppression using a short course of glucocorticoids was used in an attempt to limit this vector-specific immune response.

One of the significant limitations in the generation of efficient viral gene delivery systems for the treatment of hemophilia A by gene therapy is the large size of the FVIII cDNA. Previous viral vector-based gene therapy studies for hemophilia A typically relied on the use of small but weak promoters, required excessively high vector doses that were not clinically relevant or resulted in severely compromised vector titers. Several other ad hoc strategies were explored, such as the use of split or dual vector design to overcome the packaging constraints of AAV, but these approaches were overall relatively inefficient and raised additional immunogenicity concerns (reviewed in Petrus et al., 2010). It has been found that the FVIII B domain is dispensable for procoagulant activity. Consequently, FVIII constructs in which the B domain is deleted are used for gene transfer purposes since their smaller size is more easily incorporated into vectors. Furthermore, it has been shown that deletion of the B domain leads to a 17-fold increase in mRNA and primary translation product. FVIII wherein the B domain is deleted and replaced by a short 14-amino acid linker is currently produced as a recombinant product and marketed as Refacto® for clinical use (Wyeth Pharma) (Sandberg et al., 2001). Miao et al. (2004) added back a short B domain sequence to a B domain deleted FVIII, optimally 226 amino acids and retaining 6 sites for N-linked glycosylation, to improve secretion. McIntosh et al. (2013) replaced the 226 amino-acid spacer of Miao et al. with a 17 amino-acid peptide in which six glycosylation triplets from the B-domain were juxtaposed. Yet, production was still not sufficient for therapeutic purposes.

Non-viral vectors typically rely on a plasmid-based gene delivery system, where only the naked DNA is delivered, potentially in conjunction with physicochemical methods that facilitate transfection. Consequently, the non-viral approach may be less immunogenic and potentially safer than viral vectors, though innate immune response may still occur. The non-viral gene transfer method is simple, but the efficiency is generally low compared to most viral vector-mediated gene transfer approaches. Efficient in vivo gene delivery of non-viral vectors remains a bottleneck. Typically, for hepatic gene delivery, plasmids are administered by hydrodynamic injection. In this case, a hydrodynamic pressure is generated by rapid injection of a large volume of DNA solution into the circulation, in order to deliver the gene of interest in the liver (Miao et al., 2000). Efforts are being made to adapt hydrodynamic injection towards a clinically relevant modality by reducing the volume of injection along with maintaining localized hydrodynamic pressure for gene transfer. Alternative approaches based on targetable nanoparticles are being explored to achieve target specific delivery of FIX into hepatocytes. Expression could be prolonged by removing bacterial backbone sequences which interfere with long term expression (i.e. mini-circle DNA). Finally, to increase the stability of FIX expression after non-viral transfection, transposons could be used that result in stable genomic transgene integration. We and others have shown that transposons could be used to obtain stable clotting factor expression following in vivo gene therapy (Yant et al., 2000; Mates, Chuah et al., 2009, VandenDriessche et al., 2009; Kren et al., 2009; Ohlfest et al., 2004).

An exemplary state of the art vector for liver-specific expression of FIX is described in WO 2009/130208 and is composed of a single-stranded AAV vector that contains the TTR/Serp regulatory sequences driving a factor cDNA. A FIX first intron was included in the vector, together with a poly-adenylation signal. Using said improved vector yielded about 25-30% stable circulating factor IX.

In order to translate viral-vector based gene therapy for hemophilia to the clinic, the safety concerns associated with administering large vector doses to the liver and the need for manufacturing large amounts of clinical-grade vector must be addressed. Increasing the potency (efficacy per dose) of gene transfer vectors is crucial towards achieving these goals. It would allow using lower doses to obtain therapeutic benefit, thus reducing potential toxicities and immune activation associated with in vivo administration, and easing manufacturing needs.

One way to increase potency is to engineer the transgene sequence itself to maximize expression and biological activity per vector copy. We have shown that FIX transgenes optimized for codon usage and carrying an R338L amino acid substitution associated with clotting hyperactivity and thrombophilia (Simioni et al., 2009), increase the efficacy of gene therapy using lentiviral vector up to 15-fold in hemophilia B mice, without detectable adverse effects, substantially reducing the dose requirement for reaching therapeutic efficacy and thus facilitating future scale up and its clinical translation (Cantore et al., 2012, Nair et al., 2014).

Also codon optimization of human factor VIII cDNAs leads to high-level expression. Significantly greater levels (up to a 44-fold increase and in excess of 200% normal human levels) of active FVIII protein were detected in the plasma of neonatal hemophilia A mice transduced with lentiviral vector expressing FVIII from a codon-optimized cDNA sequence, thereby successfully correcting the disease model (Ward et al., 2011).

In WO 2014/064277 expression vectors are described which combine the robust Serpin enhancer with codon-optimized transgenes encoding FIX or FVIII, resulting in increased liver-specific expression of FIX and FVIII, respectively.

It is an object of the present invention to further increase the efficiency and safety of liver-directed gene therapy for hemophilia A and B.

SUMMARY OF THE INVENTION

It is an object of the present invention to increase the efficiency and safety of liver-directed gene therapy for hemophilia B. The above objective is accomplished by providing a nucleic acid expression cassette and a vector, either a viral vector, in particular an AAV-based vector, or a non-viral vector, comprising specific regulatory elements that enhance liver-directed gene expression, while retaining tissue specificity, in conjunction with the use of a transgene, preferably a codon-optimized transgene, encoding human FIX, preferably human FIX containing a hyper-activating mutation.

The resulting vector and nucleic acid expression cassette result in unexpectedly high expression levels of FIX in the liver, due to its unique combination of regulatory elements. The combined effect of these elements could not have been predicted. Previously, we reported on a new regulatory element that in combination with other vector elements represented a more than 20-fold increase in FIX levels (cf. WO2014/064277). In the present invention, it is shown that combining 3 copies of the serpin enhancer with the known natural TTR enhancer further increases FIX expression by 6 to 10 fold. This increase in hFIX activity was shown to be synergistic. It is another object of the present invention to increase the efficiency and safety of liver-directed gene therapy for hemophilia A. As shown in the experimental section, this objective is accomplished by providing a vector, either a viral vector, in particular an AAV-based vector, or a non-viral vector, comprising a nucleic acid expression cassette with specific regulatory elements that enhance liver-directed gene expression, while retaining tissue specificity, in conjunction with the use of a codon-optimized human FVIII construct, in particular a codon-optimized B domain deleted FVIII construct driven from a minimal transthyretin promoter. The resulting AAV-based vector and nucleic acid expression cassette resulted in unprecedented, supra-physiologic FVIII expression levels (cf. WO2014/064277). The inventors now demonstrated that the specific combination of three copies of the Serpin enhancer with the natural TTR enhancer, and the codon-optimized B domain deleted FVIII transgene or the codon optimized padua mutant FIX transgene driven from a minimal transthyretin promoter provides for a synergistic effect on FVIII or FIX expression levels compared to expression cassettes containing the natural TTR enhancer and the codon-optimized B domain deleted FVIII transgene or the codon optimized padua mutant FIX transgene driven from a minimal transthyretin promoter.

The combination of the triple repeat of the Serpin enhancer defined by SEQ ID NO:5 and the transthyretin enhancer defined by SEQ ID NO:12 has been shown to be unexpectedly potent in increasing expression of a transgene operably linked to it. Said regulatory element is defined by SEQ ID NO:13. Said regulatory element can further be combined with the transthyretin minimal promotor as defined by SEQ ID NO.6. This creates a combination of 3× the SerpEnh (3× SEQ ID NO.5, e.g. such as in SEQ ID NO.11) with the TTRe and TTRm nucleic acid sequence e.g. as defined by SEQ ID NO.69. For example, such a construct results in a regulatory element as defined by SEQ ID NO:58, which has been tested to increase the expression of both FVIII and FIX transgenes as shown herein.

The invention therefore provides the following aspects:

Aspect 1. A nucleic acid expression cassette comprising a triple repeat, preferably a tandem repeat, of a liver-specific nucleic acid regulatory element comprising or consisting of the nucleic acid fragment defined by SEQ ID NO:5 or a sequence having at least 95% identity to said sequence, preferably a liver-specific nucleic acid regulatory element of 150 nucleotides or less, comprising or consisting of the nucleic acid fragment defined by SEQ ID NO:5 or a sequence having at least 95% identity to said sequence, more preferably the regulatory element (3×SERP) as defined by SEQ ID NO:11, operably linked to a promoter and a transgene, preferably a codon-optimized transgene, wherein the promoter is a liver-specific promoter.

Preferably said promoter is derived from the transthyretin (TTR) promoter, more preferably said promoter is the minimal TTR promotor (TTRm) as defined by SEQ ID NO:6.

In another preferred embodiment, said liver-specific promoter is derived from the AAT promoter, e.g. as defined by SEQ ID NO.64.

In further embodiments, the liver-specific promotor is selected from the group comprising: the transthyretin (TTR) promoter or TTR-minimal promoter (TTRm), the alpha 1-antitrypsin (AAT) promoter, the albumin promotor (ALB) or minimal albumin promoter (ALBm), the apolipoprotein A1 (APOA1) promoter, the complement factor B (CFB) promoter, the ketohexokinase (KHK) promoter, the hemopexin (HPX) promoter, the nicotinamide N-methyltransferase (NNMT) promoter, the (liver) carboxylesterase 1

(CES1) promoter, the protein C (PROC) promoter, the apolipoprotein C3 (APOC3) promoter, the mannan-binding lectin serine protease 2 (MASP2) promoter, the hepcidin antimicrobial peptide (HAMP) promoter, or the serpin peptidase inhibitor, clade C (antithrombin), member 1 (SERPINC1) promoter.

Aspect 2. The nucleic acid expression cassette according to aspect 1, further comprising a nucleic acid regulatory element comprising or consisting of the nucleic acid fragment defined by SEQ ID NO:12 (TTRe), or a sequence having at least 95% identity to said sequence, preferably a nucleic acid regulatory element of 150 nucleotides or less comprising or consisting of the nucleic acid fragment defined by SEQ ID NO:12, or a sequence having at least 95% identity to said sequence. In a preferred embodiment, the combination of the TTRe and TTRm nucleic acid modules is defined by SEQ ID NO.69.

Aspect 3, The nucleic acid expression cassette according to aspect 2, comprising the nucleic acid regulatory element as defined by SEQ ID NO:13, preferably the nucleic acid regulatory element as defined by SEQ ID NO:57, operably linked to a promotor and a transgene, or the nucleic acid regulatory element as defined by SEQ ID NO:58, operably linked to a transgene.

Aspect 4. The nucleic acid expression cassette according to any one of aspects 1 to 3, wherein said transgene encodes for coagulation factor VIII or coagulation factor IX.

Aspect 5. The nucleic acid expression cassette according to aspect 4, wherein said coagulation factor VIII has a deletion of the B domain.

Aspect 6. The nucleic acid expression cassette according to aspect 5, wherein said B domain of said FVIII is replaced by a linker defined by SEQ ID NO:59.

Aspect 7. The nucleic acid expression cassette according to any one of aspects 4 to 6, wherein said transgene encoding for coagulation factor VIII is defined by SEQ ID NO: 18.

Aspect 8. The nucleic acid expression cassette according to aspect 4, wherein said coagulation factor IX contains a hyper-activating mutation.

Aspect 9. The nucleic acid expression cassette according to aspect 8, wherein said hyper-activating mutation in coagulation factor IX corresponds to an R338L amino acid substitution.

Aspect 10. The nucleic acid expression cassette according to any one of aspects 4, 8 or 9, wherein said transgene encoding for coagulation factor IX is defined by SEQ ID NO:9.

Aspect 11. The nucleic acid expression cassette according to any one of aspects 1 to 10, wherein said promoter is a liver-specific promoter, preferably a promoter derived from the transthyretin (TTR) promoter, preferably the minimal TTR promotor as defined by SEQ ID NO:6.

Aspect 12. The nucleic acid expression cassette according to any one of aspects 1 to 11, further comprising a minute virus of mouse (MVM) intron, preferably the MVM intron as defined by SEQ ID NO:8.

Aspect 13. The nucleic acid expression cassette according to any one of aspects 1 to 12, further comprising a transcriptional termination signal derived from the bovine growth hormone polyadenylation signal (BGHpA), preferably the BGHpA as defined by SEQ ID NO:10, or derived from the Simian virus 40 polyadenylation signal (SV40 pA), preferably the SV40pA as defined by SEQ ID NO:19, or a synthetic polyadenylation signal, preferably the synthetic polyadenylation signal as defined by SEQ ID NO: 56.

Aspect 14. A vector comprising the nucleic acid expression cassette according to any one of aspects 1 to 13.

Aspect 15. The vector according to aspect 14, wherein said vector is a viral vector.

Aspect 16. The vector according to aspect 15, wherein said vector is derived from an adeno-associated virus (AAV).

Aspect 17. The vector according to aspect 16, wherein said vector is a single-stranded AAV vector, preferably a single-stranded AAV serotype 8 vector.

Aspect 18. The vector according to any one of aspects 14 to 17, defined by SEQ ID NO: 16, SEQ ID NO:20, SEQ ID NO:21, SEQ ID NO:22 or SEQ ID NO:23, preferably SEQ ID NO:22 or SEQ ID NO:23, more preferably SEQ ID NO:22.

Aspect 19. The vector according to aspect 16, wherein said vector is a self-complementary AAV vector, preferably a self-complementary AAV serotype 9 vector.

Aspect 20. The vector according to any one of aspects 14 to 16, or 19, defined by SEQ ID NO: 2, SEQ ID NO:4, or SEQ ID NO:25, preferably SEQ ID NO:4 or SEQ ID NO:25, more preferably SEQ ID NO:4, or the vector according to any one of aspects 14 to 16, or 19, defined by SEQ ID NO: 65, SEQ ID NO:66, or SEQ ID NO:68, preferably SEQ ID NO:65 or 68, more preferably SEQ ID NO:65. Aspect 21. The vector according to aspect 14, wherein said vector is a non-viral vector, such as a transposon-based vector (e.g. a PiggyBac (PB)-based vector or a Sleeping Beauty (SB)-based vector).

Aspect 22. A method to obtain levels of factor VIII in plasma equal to or higher than the therapeutic threshold concentration of 10 mU/ml plasma in a subject, comprising the transduction or transfection of the vector according to any one of aspects 14 to 18, or 21 into a subject.

Aspect 23. The method according to aspect 22, wherein the transduction of the vector according to any one of aspects 14 to 18, or 21 into the subject is done at a dose lower than $2.5 \times 10^{11}$ vg/kg.

Aspect 24. A method to obtain levels of factor IX in plasma equal to or higher than the therapeutic threshold concentration of 10 mU/ml plasma in a subject, comprising the transduction or transfection of the vector according to any one of aspects 14 to 16, or 19 to 21 into a subject.

Aspect 25. The method according to aspect 24, wherein the transduction of the vector according to any one of aspects 14 to 16, or 19 to 21 into the subject is done at a dose lower than $2 \times 10^{11}$ vg/kg.

Aspect 26. The method according to any one of aspects 22 to 25, wherein said transduction or transfection is by intravenous administration.

Aspect 27. The method according to any one of aspects 22 to 26, wherein said subject is a mammalian subject, preferably a human subject.

Aspect 28. A method for treating hemophilia A in a mammalian subject, comprising performing the method according to any one of aspects 22, 23, 26 or 27.

Aspect 29. The use of the vector according to any one of aspects 14 to 18, or 21 for the manufacture of a medicament to treat hemophilia A.

Aspect 30. The vector according to any one of aspects 14 to 18, or 21 for use in the treatment of hemophilia A.

Aspect 31. A method for treating hemophilia B in a mammalian subject, comprising performing the method according to any one of aspects 24 to 27.

Aspect 32. The use of the vector according to any one of aspects 14 to 16, or 19 to 21 for the manufacture of a medicament to treat hemophilia B.

Aspect 33. The vector according to any one of aspects 14 to 16, 19 to 21 for use in the treatment of hemophilia B.

Aspect 34. A pharmaceutical composition comprising a vector according to any one of aspects 14 to 18, or 21 and a pharmaceutically acceptable carrier, optionally further comprising an active ingredient for treating hemophilia A.

Aspect 35. The pharmaceutical composition according to aspect 34 for use in treating hemophilia A.

Aspect 36. The pharmaceutical composition for use according to aspect 35, or the vector for use according to aspect 30, wherein said treatment results in levels of factor VIII in plasma of the treated subject that are equal to or higher than the therapeutic threshold concentration of 10 mU/ml plasma in a subject.

Aspect 37. The pharmaceutical composition for use according to any one of aspects 35 or 35, or the vector for use according to any one of aspects 30 or 36, wherein said treatment comprises the transduction of the vector according to any one of aspects 14 to 18 into the subject at a dose lower than or equal than $2.5 \times 10^{11}$ vg/kg.

Aspect 38. A pharmaceutical composition comprising a vector according to any one of aspects 14 to 16, 19 to 21 and a pharmaceutically acceptable carrier, optionally further comprising an active ingredient for treating hemophilia B.

Aspect 39. The pharmaceutical composition according to aspect 38, for use in treating hemophilia B.

Aspect 40. The pharmaceutical composition for use according to aspect 39, or the vector for use according to aspect 33, wherein said treatment results in levels of factor IX in plasma of the treated subject that are equal to or higher than the therapeutic threshold concentration of 10 mU/ml plasma in a subject, preferably equal to or higher than the therapeutic concentration of 50 mU/ml plasma in a subject, more preferably equal to or higher than the therapeutic concentration of 100 mU/ml plasma in a subject, even more preferably equal to or higher than the therapeutic concentration of 150 mU/ml plasma in a subject and even more preferably equal to or higher than the therapeutic concentration of 200 mU/ml plasma in a subject.

Aspect 41. The pharmaceutical composition for use according to aspect 39 or 40, or the vector for use according to aspect 33 or 40, wherein said treatment comprises the transduction of the vector according to any one of aspects 14 to 16, 19 or 20 into the subject at a dose lower than or equal than $2 \times 10^{12}$ vg/kg, preferably at a dose lower than or equal than $6 \times 10^{11}$ vg/kg, more preferably at a dose lower than or equal than $2 \times 10^{11}$ vg/kg.

BRIEF DESCRIPTION OF THE FIGURES

The present invention is illustrated by the following figures which are to be considered for illustrative purposes only and in no way limit the invention to the embodiments disclosed therein:

FIG. 13: Nucleotide sequence of pAAVsc-SerpEnh-TTRm-MVM-co-FIX-R338L-BGHpA (SEQ ID NO:1); pAAVsc-3×SerpEnh-TTRm-MVM-co-FIX-R338L-BGHpA (SEQ ID NO:2); pAAVsc-TTRe-TTRm-MVM-co-FIX-R338L-BGHpA (SEQ ID NO:3); pAAVsc-3×SerpEnh- TTRe-TTRm-MVM-co-FIX-R338L-BGHpA (SEQ ID NO:4); the Serpin enhancer (SerpEnh) (SEQ ID NO:5); the minimal transthyretin (TTRm) promoter (SEQ ID NO:6); the 5' untranslated region (UTR) of TTRm (TTRm5'UTR) (SEQ ID NO:7); the Minute Virus of Mouse (MVM) intron (SEQ ID NO:8); the codon-optimized transgene encoding human FIX Padua mutant (Co-FIX-R338L) (SEQ ID NO:9); the Bovine Growth Hormone polyadenylation signal (BGHpA) (SEQ ID NO: 10); triple tandem repeat of the Serpin enhancer (3×SERP) (SEQ ID NO: 11, the nucleotide linking the repeats is indicated in bold); the transthyretin enhancer (TTRe) (SEQ ID NO:12); a triple tandem repeat of the Serpin enhancer (underlined) linked to the transthyretin enhancer (italics) (3×SERP-Flank-TTRe) (SEQ ID NO:13); pAAVsc-3×SerpEnh-TTREnh-TTRm-MVM-co-FIX-R338L-Synt.pA (SEQ ID NO:25); Flank-3×SERP-Flank-TTRe (SEQ ID NO:26); Flank-3×SERP-Flank-TTRe-Flank (SEQ ID NO:27); Flank-3×SERP-Flank-TTRe-Flank-TTRm (SEQ ID NO:28); Flank-3×SERP-Flank-TTRe-Flank-TTRm-Flank (SEQ ID NO:29); Flank-3×SERP-Flank-TTRe-Flank-TTRm-Flank-MVM (SEQ ID NO:30); Flank-3×SERP-Flank-TTRe-Flank-TTRm-Flank-MVM-Flank (SEQ ID NO:31); Flank-3×SERP-Flank-TTRe-Flank-TTRm-Flank-MVM-Flank-co-FIX-R338L (SEQ ID NO:32), Flank-3×SERP-Flank-TTRe-Flank-TTRm-Flank-MVM-Flank-co-FIX-R338L-Flank (SEQ ID NO:33); Flank-3×SERP-Flank-TTRe-Flank-TTRm-Flank-MVM-Flank-co-FIX-R338L-Flank-BGHpA (SEQ ID NO:34); Flank-3×SERP-Flank-TTRe-Flank-TTRm-Flank-MVM-Flank-co-FIX-R338L-Flank-BGHpA-Flank (SEQ ID NO:35); Flank-3×SERP-Flank-TTRe-Flank-TTRm-Flank-MVM-Flank-co-FIX-R338L-Flank-Synt.pA (SEQ ID NO:36); Flank-3×SERP-Flank-TTRe-Flank-TTRm-Flank-MVM-Flank-co-FIX-R338L-Flank-Synt.pA-Flank (SEQ ID NO:37).

FIG. 14: Nucleotide sequence of pAAVss-TTRm-MVM-coFVIIIdeltaB-Sv40pA (SEQ ID NO:14); pAAVss-SerpEnh-TTRm-MVM-coFVIIIdeltaB-Sv40pA (SEQ ID NO:15); pAAVss-3×SerpEnh-TTRm-MVM-coFVIIIdeltaB-Sv40pA (SEQ ID NO:16); pAAVss-TTRe-TTRm-MVM-coFVIIIdeltaB-Sv40pA (SEQ ID NO:17); codon-optimized transgene encoding B domain deleted human factor VIII (coFVIIIdeltaB) (SEQ ID NO:18); Simian virus 40 polyadenylation signal (SV40polyA) (SEQ ID NO:19); pAAVss-3×SerpEnh-TTRm-MVM-coFVIIIdeltaB-Synt.pA (SEQ ID NO:20); pAAVss-3×SerpEnh-TTRm-coFVIIIdeltaB-Synt.pA (SEQ ID NO:21); pAAVss-3×SerpEnh-TTRe-TTRm-MVM-coFVIIIdeltaB-Sv40pA (SEQ ID NO:22); pAAVss-3×SerpEnh-TTRe-TTRm-coFVIIIdeltaB-Synt.pA (SEQ ID NO:23); pAAVss-TTRe-TTRm-coFVIIIdeltaB-Synt.pA (SEQ ID NO:24); Flank-3×SERP-Flank (SEQ ID NO:38); Flank-3×SERP-Flank-TTRe (SEQ ID NO:39); Flank-3×SERP-Flank-TTRe-Flank (SEQ ID NO:40); Flank-3×SERP-Flank-TTRe-Flank-TTRm (SEQ ID NO:41); Flank-3×SERP-Flank-TTRe-Flank-TTRm-Flank (SEQ ID NO:42); Flank-3×SERP-Flank-TTRe-Flank-TTRm-Flank-coFVIIIdeltaB (SEQ ID NO:43); Flank-3×SERP-Flank-TTRe-Flank-TTRm-Flank-coFVIIIdeltaB-Flank (SEQ ID NO:44); Flank-3×SERP-Flank-TTRe-Flank-TTRm-Flank-coFVIIIdeltaB-Flank-SV40pA (SEQ ID NO:45); Flank-3×SERP-Flank-TTRe-Flank-TTRm-Flank-coFVIIIdeltaB-Flank-SV40pA-Flank (SEQ ID NO:46); Flank-3×SERP-Flank-TTRe-Flank-TTRm-Flank-coFVIIIdeltaB-Flank-Synt.pA (SEQ ID NO:47); Flank-3×SERP-Flank-TTRe-Flank-TTRm-Flank-coFVIIIdeltaB-Flank-SyntpA-Flank (SEQ ID NO:48); Flank-3×SERP-Flank-TTRe-Flank-TTRm-MVM-Flank (SEQ ID NO:49); Flank-3×SERP-Flank-TTRe-Flank-TTRm-MVM-Flank-coFVIIIdeltaB (SEQ ID NO:50); Flank-3×SERP-Flank-TTRe-Flank-TTRm-MVM-Flank-coFVIIIdeltaB-Flank (SEQ ID NO:51); Flank-3×SERP-Flank-TTRe-Flank-TTRm-MVM-Flank-coFVIIIdeltaB-Flank-SV40pA (SEQ ID NO:52); Flank-3×SERP-Flank-TTRe-Flank-TTRm-MVM-Flank-coFVIIIdeltaB-Flank-SV40pA-Flank (SEQ ID NO:53); Flank-3×SERP-Flank-TTRe-Flank-TTRm-MVM-Flank-coFVIIIdeltaB-Flank-Synt.pA (SEQ ID NO:54); Flank-3×SERP-Flank-TTRe-Flank-TTRm-MVM-Flank-coFVIIIdeltaB-Flank-Synt.pA-Flank (SEQ ID NO:55); synthetic polyadenylation signal (Synt.pA) (SEQ ID NO:56); 3×SERP-Flank-TTRe-Flank (SEQ ID NO:57); 3×SERP-Flank-TTRe-Flank-TTRm (SEQ ID NO:58).

FIG. 24: Nucleotide sequence of AAT promotor (SEQ ID 64); pAAVss-3×SerpEnh-TTRe-AAT-MVM-co-FIX-R338L-BGHpA (SEQ ID NO:65); pAAVss-3×SerpEnh-TTRe-AAT-MVM-co-FIX-R338L-BGHpA (SEQ ID NO:66); pAAVss-3×SerpEnh-TTRe-AAT-MVM-co-FIX- R338L-BGHpA (SEQ ID NO:67); and pAAVss-3×SerpEnh-TTRe-AAT-MVM-co-FIX-R338L-BGHpA (SEQ ID NO:68).

DETAILED DESCRIPTION OF THE INVENTION

Figure 1:
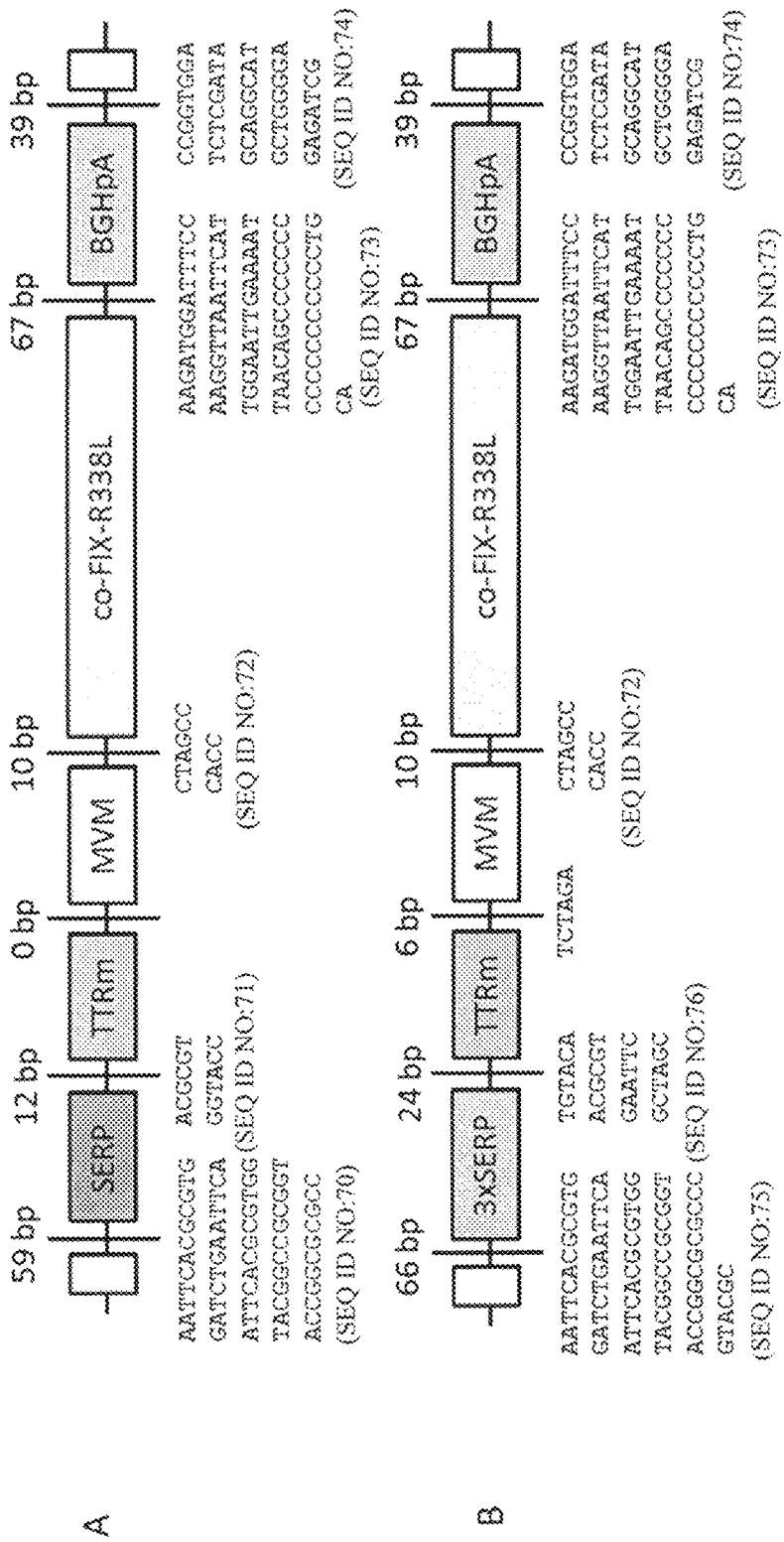
FIG. 1: Design of the self-complementary (sc), double-stranded adeno-associated viral (AAV) vectors AAVsc-SerpEnh-TTRm-MVM-co-FIX-R338L-BGHpA (2510 bp) (A), AAVsc-3×SerpEnh-TTRm-MVM-co-FIX-R338L-BGHpA (2683 bp) (B), AAVsc-TTREnh-TTRm-MVM-co-FIX-R338L-BGHpA (2540 bp) (C), AAVsc-3×SerpEnh-TTREnh-TTRm-MVM-co-FIX-R338L-BGHpA (2760 bp) (D), and AAVsc-3×SerpEnh-TTREnh-TTRm-MVM-co-FIX-R338L-Synt.pA (2519 bp) (E). The minimal transthyretin promoter (TTRm) is driving the expression of the codon-optimized human factor IX (co-FIX-R338L) containing the hyper-activating, thrombophilic FIX mutation (R338L). Either the native TTR enhancer (TTRe), the Serpin enhancer (SERP), a triplet of the Serpin enhancer (3×SERP), or a combination of a triplet of the Serpin enhancer (3×SERP) and the native TTR enhancer (TTRe) is cloned upstream of TTRm. The minute virus of mouse intron (MVM), the bovine growth hormone polyadenylation site (BGHpA) or a synthetic polyadenylation site (Synt.pA), and the inverted terminal repeats (ITR) are indicated. The sequences flanking/linking the different elements are indicated. The indicated vector sizes includes both ITR's.
Figure 1:
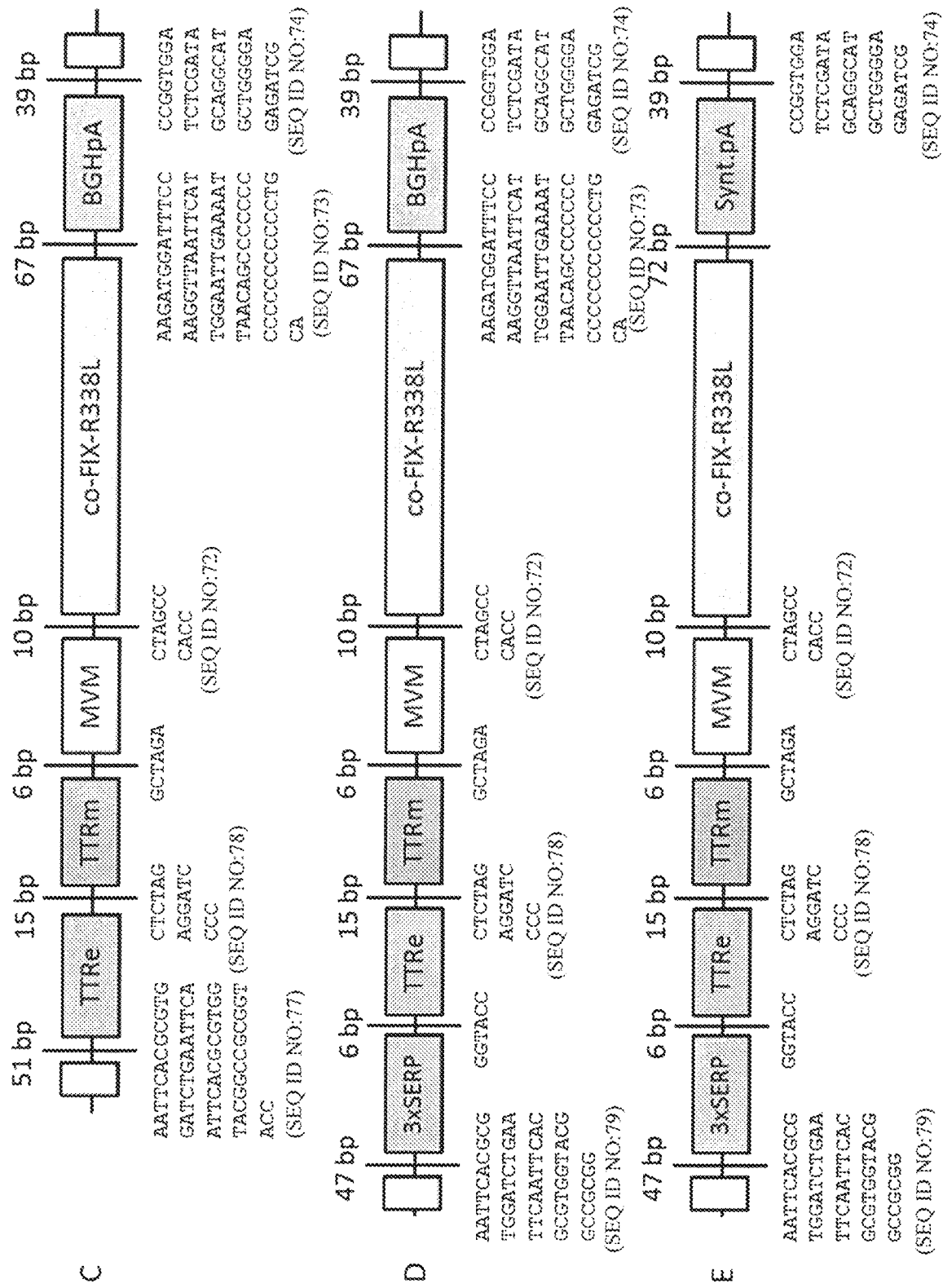

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes.

Where the term "comprising" is used in the present description and claims, it does not exclude other elements or steps. The term "comprising" also encompasses the more specific embodiments defined as "consisting of" and "consisting essentially of".

Where an indefinite or definite article is used when referring to a singular noun e.g. "a" or "an", "the", this includes a plural of that noun unless something else is specifically stated. Furthermore, the terms first, second, third and the like in the description and in the claims, are used for distinguishing between similar elements and not necessarily for describing a sequential or chronological order.

It is to be understood that the terms so used are interchangeable under appropriate circumstances and that the embodiments of the invention described herein are capable of operation in other sequences than described or illustrated herein.

The following terms or definitions are provided to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 2nd ed., Cold Spring Harbor Press, Plainsview, N.Y. (1989); and Ausubel et al., Current Protocols in Molecular Biology (Supplement 47), John Wiley & Sons, New York (1999), for definitions and terms of the art.

The definitions provided herein should not be construed to have a scope less than understood by a person of ordinary skill in the art.

The invention relates to nucleic acid expression cassettes and expression vectors comprising said nucleic acid expression cassettes for enhancing liver-specific expression of a (trans)gene.

As used herein, the term "nucleic acid expression cassette" refers to nucleic acid molecules that include one or more transcriptional control elements (such as, but not limited to promoters, enhancers and/or regulatory elements, polyadenylation sequences, and introns) that direct (trans) gene expression in one or more desired cell types, tissues or organs. Typically, the nucleic acid expression cassettes described herein will contain the FIX transgene or the FVIII transgene as defined herein.

The invention provides nucleic acid expression cassettes comprising one or more liver-specific nucleic acid regulatory elements, operably linked to a promoter and a transgene.

The term "operably linked" as used herein refers to the arrangement of various nucleic acid molecule elements relative to each such that the elements are functionally connected and are able to interact with each other. Such elements may include, without limitation, a promoter, an enhancer and/or a regulatory element, a polyadenylation sequence, one or more introns and/or exons, and a coding sequence of a gene of interest to be expressed (i.e., the transgene). The nucleic acid sequence elements, when properly oriented or operably linked, act together to modulate the activity of one another, and ultimately may affect the level of expression of the transgene. By modulate is meant increasing, decreasing, or maintaining the level of activity of a particular element. The position of each element relative to other elements may be expressed in terms of the 5' terminus and the 3' terminus of each element, and the distance between any particular elements may be referenced by the number of intervening nucleotides, or base pairs, between the elements.

A "regulatory element" as used herein refers to transcriptional control elements, in particular non-coding cis-acting transcriptional control elements, capable of regulating and/or controlling transcription of a gene, in particular tissue-specific transcription of a gene. Regulatory elements comprise at least one transcription factor binding site (TFBS), more in particular at least one binding site for a tissue-specific transcription factor, most particularly at least one binding site for a liver-specific transcription factor. Typically, regulatory elements as used herein increase or enhance promoter-driven gene expression when compared to the transcription of the gene from the promoter alone, without the regulatory elements. Thus, regulatory elements particularly comprise enhancer sequences, although it is to be understood that the regulatory elements enhancing transcription are not limited to typical far upstream enhancer sequences, but may occur at any distance of the gene they regulate. Indeed, it is known in the art that sequences regulating transcription may be situated either upstream (e.g. in the promoter region) or downstream (e.g. in the 3'UTR) of the gene they regulate in vivo, and may be located in the immediate vicinity of the gene or further away. Of note, although regulatory elements as disclosed herein typically are naturally occurring sequences, combinations of (parts of) such regulatory elements or several copies of a regulatory element, i.e. non-naturally occurring sequences, are themselves also envisaged as regulatory element. Regulatory elements as used herein may be part of a larger sequence involved in transcriptional control, e.g. part of a promoter sequence. However, regulatory elements alone are typically not sufficient to initiate transcription, but require a promoter to this end.

The one or more regulatory elements contained in the nucleic acid expression cassettes and vectors disclosed herein are preferably liver-specific. Non-limiting examples of liver-specific regulatory elements are disclosed in WO 2009/130208, which is specifically incorporated by reference herein. Another example of a liver-specific regulatory element is a regulatory element derived from the transthyretin (TTR) gene, such as the regulatory element defined by SEQ ID NO:12, also referred to herein as "TTRe" or "TTREnh" (Wu et al., 2008). 'Liver-specific expression', as used in the application, refers to the preferential or predominant expression of a (trans)gene (as RNA and/or polypeptide) in the liver as compared to other tissues. According to particular embodiments, at least 50% of the (trans)gene expression occurs within the liver. According to more particular embodiments, at least 60%, at least 70%, at least 75%, at least 80%, at least 85%, at least 90%, at least 95%, at least 97%, at least 99% or 100% of the (trans)gene expression occurs within the liver. According to a particular embodiment, liver-specific expression entails that there is no 'leakage' of expressed gene product to other organs, such as spleen, muscle, heart and/or lung. The same applies mutatis mutandis for hepatocyte-specific expression, which may be considered as a particular form of liver-specific expression. Throughout the application, where liver-specific is mentioned in the context of expression, hepatocyte-specific expression is also explicitly envisaged. Similarly, where tissue-specific expression is used in the application, cell-type specific expression of the cell type(s) predominantly making up the tissue is also envisaged.

Preferably, the one or more regulatory element in the nucleic acid expression cassettes and vectors disclosed herein is fully functional while being only of limited length. This allows its use in vectors or nucleic acid expression cassettes without unduly restricting their payload capacity. Accordingly, in embodiments, the one or more regulatory element in the expression cassettes and vectors disclosed herein is a nucleic acid of 1000 nucleotides or less, 800 nucleotides or less, or 600 nucleotides or less, preferably 400 nucleotides or less, such as 300 nucleotides or less, 200 nucleotides or less, 150 nucleotides or less, or 100 nucleotides or less (i.e. the nucleic acid regulatory element has a maximal length of 1000 nucleotides, 800 nucleotides, 600 nucleotides, 400 nucleotides, 300 nucleotides, 200 nucleotides, 150 nucleotides, or 100 nucleotides).

However, it is to be understood that the disclosed nucleic acid regulatory elements retain regulatory activity (i.e. with regard to specificity and/or activity of transcription) and thus they particularly have a minimum length of 20 nucleotides, 25 nucleotides, 30 nucleotides, 35 nucleotides, 40 nucleotides, 45 nucleotides, 50 nucleotides, 55 nucleotides, 60 nucleotides, 65 nucleotides, or 70 nucleotides. In preferred embodiments, the one or more regulatory element in the nucleic acid expression cassettes and vectors disclosed herein comprises a sequence from SERPINA1 regulatory elements, i.e. regulatory elements that control expression of the SERPINA1 gene in vivo. Said regulatory element preferably comprises, consists essentially of or consists of the sequence as defined in SEQ ID NO:5, a sequence having at least 85%, preferably at least 90%, more preferably at least 95%, such as 96%, 97%, 98% or 99%, identity to said sequence, or a functional fragment thereof. Also preferably, said regulatory element has a maximal length of 150 nucleotides or less, preferably 100 nucleotides or less, and comprises, consists essentially of or consists of the sequence as defined in SEQ ID NO:5, a sequence having at least 85%, preferably at least 90%, more preferably at least 95%, such as 96%, 97%, 98% or 99%, identity to said sequence, or a functional fragment thereof. The liver-specific nucleic acid regulatory element consisting of SEQ ID NO:5 is herein referred to as "the Serpin enhancer", "SerpEnh", or "Serp".

In particularly preferred embodiments, the nucleic acid expression cassettes and vectors disclosed herein comprise two or more, such as two, three, four, five or six, preferably three, (tandem) repeats of a liver-specific regulatory element comprising, consisting essentially of or consisting of SEQ ID NO:5, or a sequence having at least 85%, preferably at least 90%, more preferably at least 95%, such as 96%, 97%, 98% or 99%, identity to said sequence, more preferably a liver-specific regulatory element of 150 nucleotides or less, preferably 100 nucleotides or less, more preferably 80 nucleotides or less, comprising, consisting essentially of or consisting of SEQ ID NO:5, or a sequence having at least 85%, preferably at least 90%, more preferably at least 95%, such as 96%, 97%, 98% or 99%, identity to said sequence. A preferred nucleic acid regulatory element comprising three tandem repeats of SEQ ID NO:5 is herein referred to as "3×Serp" and is defined by SEQ ID NO:11.

In further embodiments, the nucleic acid expression cassettes and vectors disclosed herein comprise two or more, such as two, three, four, five or six, more preferably three, (tandem) repeats of a liver-specific regulatory element comprising, consisting essentially of or consisting of SEQ ID NO:5, or a sequence having at least 85%, preferably at least 90%, more preferably at least 95%, such as 96%, 97%, 98% or 99%, identity to said sequence, preferably a liver-specific regulatory element of 150 nucleotides or less, preferably 100 nucleotides or less, more preferably 80 nucleotides or less, comprising, consisting essentially of or consisting of SEQ ID NO:5, or a sequence having at least 85%, preferably at least 90%, more preferably at least 95%, such as 96%, 97%, 98% or 99%, identity to said sequence; and a regulatory element comprising, consisting essentially of or consisting of SEQ ID NO:12, preferably a regulatory element of 150 nucleotides or less, preferably 120 nucleotides or less, comprising, consisting essentially of or consisting of SEQ ID NO:12. A preferred liver-specific nucleic acid regulatory element comprising three tandem repeats of SEQ ID NO:5, and SEQ ID NO:12, is herein referred to as "3×Serp-flank-TTRe" and is defined by SEQ ID NO:13 A further preferred liver-specific nucleic acid regulatory element comprising three tandem repeats of SEQ ID NO:5, and SEQ ID NO:12, is herein referred to as "3×Serp-flank-TTRe-flank" and is defined by SEQ ID NO:57. Preferably, the liver-specific nucleic acid regulatory element in the nucleic acid expression cassettes and vectors disclosed herein comprises three tandem repeats of SEQ ID NO:5, and SEQ ID NO:12; more preferably SEQ ID NO:13; even more preferably SEQ ID NO:57, such as SEQ ID NO:27 or SEQ ID NO:39. It has been shown herein that said specific combinations of liver-specific regulatory elements resulted in unexpectedly enhanced liver-specific expression of the transgene, in particular the FIX transgene or FVIII transgene described herein, operably linked thereto.

In further embodiments, said nucleic acid expression cassettes and vectors disclosed herein comprise three tandem repeats of SEQ ID NO:5 (such as SEQ ID NO.13), and a further enhancer element TTRe defined by SEQ ID NO:12, for example as defined by SEQ ID NO:13, in combination with a liver-specific promotor. In one particular example, said promotor is the TTRm minimal promoter as defined by SEQ ID NO.6. In an alternative embodiment, said liver-specific promoter is the AAT promoter, such as the promoter defined by SEQ ID NO.64. It has been shown herein that said specific combinations of liver-specific regulatory elements resulted in unexpectedly enhanced liver-specific expression of the transgene, in particular the FIX transgene or FVIII transgene described herein, operably linked thereto As used herein, the terms "identity" and "identical" and the like refer to the sequence similarity between two polymeric molecules, e.g., between two nucleic acid molecules, e.g., two DNA molecules. Sequence alignments and determination of sequence identity can be done, e.g., using the Basic Local Alignment Search Tool (BLAST) originally described by Altschul et al. 1990 (J Mol Biol 215: 403-10), such as the "Blast 2 sequences" algorithm described by Tatusova and Madden 1999 (FEMS Microbiol Lett 174: 247-250). Typically, the percentage sequence identity is calculated over the entire length of the sequence. As used herein, the term "substantially identical" denotes at least 90%, preferably at least 95%, such as 95%, 96%, 97%, 98% or 99%, sequence identity.

The term "functional fragment" as used in the application refers to fragments of the sequences disclosed herein that retain the capability of regulating liver-specific expression, i.e. they still confer tissue specificity and they are capable of regulating expression of a (trans)gene in the same way (although possibly not to the same extent) as the sequence from which they are derived. Fragments comprise at least 10 contiguous nucleotides from the sequence from which they are derived. In further particular embodiments, fragments comprise at least 15, at least 20, at least 25, at least 30, at least 35 or at least 40 contiguous nucleotides from the sequence from which they are derived. Also preferably, functional fragments may comprise at least 1, more preferably at least 2, at least 3, or at least 4, even more preferably at least 5, at least 10, or at least 15, of the transcription factor binding sites (TFBS) that are present in the sequence from which they are derived.

As used in the application, the term "promoter" refers to nucleic acid sequences that regulate, either directly or indirectly, the transcription of corresponding nucleic acid coding sequences to which they are operably linked (e.g. a transgene or endogenous gene). A promoter may function alone to regulate transcription or may act in concert with one or more other regulatory sequences (e.g. enhancers or silencers). In the context of the present application, a promoter is typically operably linked to regulatory elements to regulate transcription of a transgene.

When a regulatory element as described herein is operably linked to both a promoter and a transgene, the regulatory element can (1) confer a significant degree of liver specific expression in vivo (and/or in hepatocytes/hepatic cell lines in vitro) of the transgene, and/or (2) can increase the level of expression of the transgene in the liver (and/or in hepatocytes/hepatocyte cell lines in vitro).

According to a particular embodiment, the promoter contained in the nucleic acid expression cassettes and vectors disclosed herein is a liver-specific promoter. This is to increase liver specificity and/or avoid leakage of expression in other tissues. According to a further particular embodiment, the liver-specific promoter is from the transthyretin (TTR) gene or from the Alpha-1-antitrypsin (AAT) gene. According to yet a further particular embodiment, the TTR promoter is a minimal promoter (also referred to as TTRm or TRRmin herein), most particularly the minimal TTR promoter as defined in SEQ ID NO: 6. According to yet a further particular embodiment, the AAT promoter is as defined in SEQ ID NO: 64.

According to particular embodiments, the promoter in the nucleic acid expression cassettes and vectors disclosed herein is a minimal promoter.

A 'minimal promoter' as used herein is part of a full-size promoter still capable of driving expression, but lacking at least part of the sequence that contributes to regulating (e.g. tissue-specific) expression. This definition covers both promoters from which (tissue-specific) regulatory elements have been deleted—that are capable of driving expression of a gene but have lost their ability to express that gene in a tissue-specific fashion and promoters from which (tissue-specific) regulatory elements have been deleted that are capable of driving (possibly decreased) expression of a gene but have not necessarily lost their ability to express that gene in a tissue-specific fashion. Minimal promoters have been extensively documented in the art, a non-limiting list of minimal promoters is provided in the specification.

The term "liver-specific promoter" encompasses any promoter that confers liver-specific expression to a (trans)gene. Non-limiting examples of liver-specific promoters are provided on the Liver Specific Gene Promoter Database (LSPD, rulai.cshl.edu/LSPD/), and include, for example, the transthyretin (TTR) promoter or TTR-minimal promoter (TTRm), the alpha 1-antitrypsin (AAT) promoter, the albumin (ALB) promotor or minimal promoter, the apolipoprotein A1 (APOA1) promoter or minimal promoter, the complement factor B (CFB) promoter, the ketohexokinase (KHK) promoter, the hemopexin (HPX) promoter or minimal promoter, the nicotinamide N-methyltransferase (NNMT) promoter or minimal promoter, the (liver) carboxylesterase 1 (CES1) promoter or minimal promoter, the protein C (PROC) promoter or minimal promoter, the apolipoprotein C3 (APOC3) promoter or minimal promoter, the mannan-binding lectin serine protease 2 (MASP2) promoter or minimal promoter, the hepcidin antimicrobial peptide (HAMP) promoter or minimal promoter, and the serpin peptidase inhibitor, clade C (antithrombin), member 1 (SERPINC1) promoter or minimal promoter.

In particularly preferred embodiments, the promoter is a mammalian liver-specific promoter, in particular a murine or human liver-specific promoter. More preferably, said promoters are the respective minimal promoters The term "liver-specific expression" as used in the application, refers to the preferential or predominant expression of a (trans)gene (as RNA and/or polypeptide) in the liver, in liver tissue or in liver cells, as compared to other (i.e. non-liver) tissues or cells. According to particular embodiments, at least 50%, more particularly at least 60%, at least 70%, at least 75%, at least 80%, at least 85%, at least 90%, at least 95%, at least 98%, at least 99% or 100% of the (trans)gene expression occurs within liver tissue or liver cells. According to a particular embodiment, liver-specific expression entails that there is no 'leakage' of expressed gene product to other organs or tissue than liver, such as lung, muscle, brain, kidney and/or spleen. The same applies mutatis mutandis for hepatocyte-specific expression and hepatoblast-specific expression, which may be considered as particular forms of liver-specific expression. Throughout the application, where liver-specific is mentioned in the context of expression, hepatocyte-specific expression and hepatoblast-specific expression are also explicitly envisaged.

As used herein, the term "liver cells" encompasses the cells predominantly populating the liver and encompasses mainly hepatocytes, oval cells, liver sinusoidal endothelial cells (LSEC) and cholangiocytes (epithelial cells forming the bile ducts).

The term "hepatocyte," as used herein, refers to a cell that has been differentiated from a progenitor hepatoblast such that it is capable of expressing liver-specific phenotype under appropriate conditions. The term "hepatocyte" also refers to hepatocytes that are de-differentiated. The term includes cells in vivo and cells cultured ex vivo regardless of whether such cells are primary or passaged.

The term "hepatoblast" as used herein, refers to an embryonic cell in the mesoderm that differentiates to give rise to a hepatocyte, an oval cell, or a cholangiocyte. The term includes cells in vivo and cells cultured ex vivo regardless of whether such cells are primary or passaged.

The term "transgene" or "(trans)gene" as used herein refers to particular nucleic acid sequences encoding a polypeptide or a portion of a polypeptide to be expressed in a cell into which the nucleic acid sequence is inserted. However, it is also possible that transgenes are expressed as RNA, typically to lower the amount of a particular polypeptide in a cell into which the nucleic acid sequence is inserted. These RNA molecules include but are not limited to molecules that exert their function through RNA interference (shRNA, RNAi), micro-RNA regulation (miRNA), catalytic RNA, antisense RNA, RNA aptamers, etc. How the nucleic acid sequence is introduced into a cell is not essential to the invention, it may for instance be through integration in the genome or as an episomal plasmid. Of note, expression of the transgene may be restricted to a subset of the cells into which the nucleic acid sequence is inserted. The term 'transgene' is meant to include (1) a nucleic acid sequence that is not naturally found in the cell (i.e., a heterologous nucleic acid sequence); (2) a nucleic acid sequence that is a mutant form of a nucleic acid sequence naturally found in the cell into which it has been introduced; (3) a nucleic acid sequence that serves to add additional copies of the same (i.e., homologous) or a similar nucleic acid sequence naturally occurring in the cell into which it has been introduced; or (4) a silent naturally occurring or homologous nucleic acid sequence whose expression is induced in the cell into which it has been introduced. By 'mutant form' is meant a nucleic acid sequence that contains one or more nucleotides that are different from the wild-type or naturally occurring sequence, i.e., the mutant nucleic acid sequence contains one or more nucleotide substitutions, deletions, and/or insertions. In some cases, the transgene may also include a sequence encoding a leader peptide or signal sequence such that the transgene product will be secreted from the cell.

Typically, the transgenes in the expression cassettes and vectors described herein encode coagulation factor IX or coagulation factor VIII.

The term "coagulation factor IX" has the meaning as known in the art. Synonyms of coagulation factor IX are "FIX" or "Christmas factor" or "F9" and can be used interchangeably. In particular, the term "coagulation factor IX" encompasses the human protein encoded by the mRNA sequence as defined in Genbank accession number NM_000133.

Preferably, said FIX is a mutated FIX, which is hyperactive or hyper-functional as compared to the wild type FIX. Modifying functional activity of human coagulation factor can be done by bioengineering e.g. by introduction of point mutations. By this approach a hyperactive R338A variant was reported, which showed a 3 fold increased clotting activity compared to the wild type human FIX in an in vitro activated partial thromboplastin time assay (APPT) (Chang et al., 1998) and a 2 to 6-fold higher specific activity in hemophilia B mice transduced with the mutant FIX gene (Schuettrumpf et al., 2005). Further exemplary FIX point-mutants or domain exchange mutants with even higher clotting activities have been described: FIX, with the EGF-1 domain replaced with the EGF-1 domain from FVII, alone or in combination with a R338A point mutation (Brunetti-Pierri et al., 2009), the V86A/E277A/R338A triple mutant (Lin et al., 2010), the Y259F, K265T, and/or Y345T single, double or triple mutants (Milanov, et al., 2012), and the G190V point mutant (Kao et al., 2010), all incorporated herein by reference. In a particularly preferred embodiment, the FIX mutant is the one described by Simioni et al., in 2009 and denominated as the "factor IX Padua" mutant, causing X-linked thrombophilia. Said mutant factor IX is hyperactive and carries an R338L amino acid substitution. In a preferred embodiment of the present invention, the FIX transgene used in nucleic acid expression cassettes and expression vectors described herein encodes the human FIX protein, most preferably the FIX transgene encodes for the Padua mutant of the human FIX protein. Accordingly, in a particularly preferred embodiment of the present invention, the transgene has SEQ ID NO:9 (i.e. codon-optimized transgene encoding for the Padua mutant of the human FIX protein).

The term "coagulation factor VIII" has the meaning as known in the art. Synonyms of coagulation factor VIII are "FVIII" or "anti-hemophilic factor" or "AHF" and can be used interchangeably herein. The term "coagulation factor VIII" encompasses, for example, the human protein having the amino acid sequence as defined in Uniprot accession number P00451.

In embodiments, said FVIII is a FVIII wherein the B domain is deleted (i.e. B domain deleted FVIII, also referred to as BDD FVIII or FVIIIΔB or FVIIIdeltaB herein). The term "B domain deleted FVIII" encompasses for example, but without limitation, FVIII mutants wherein whole or a part of the B domain is deleted and FVIII mutants wherein the B domain is replaced by a linker. Non-limiting examples of B domain deleted FVIII are described in Ward et al. (2011) and WO 2011/005968, which are specifically incorporated by reference herein.

In preferred embodiments, said FVIII is B domain deleted FVIII wherein the B domain is replaced by a linker having the following sequence: SFSQNPPVLTRHQR (SEQ ID NO: 59) (i.e. SQ FVIII as defined in Ward et al. (2011)). In particularly preferred embodiments, said transgene encoding FVIII has SEQ ID NO:18 (i.e. codon-optimized transgene encoding B domain deleted human FVIII, also referred to herein as (h)FVIIIcopt or co(h)FVIIIdeltaB or co(h)FVIIIdeltaB transgene), as disclosed also in WO 2011/005968.

Other sequences may be incorporated in the nucleic acid expression cassette disclosed herein as well, typically to further increase or stabilize the expression of the transgene product (e.g. introns and/or polyadenylation sequences).

Any intron can be utilized in the expression cassettes described herein. The term "intron" encompasses any portion of a whole intron that is large enough to be recognized and spliced by the nuclear splicing apparatus. Typically, short, functional, intron sequences are preferred in order to keep the size of the expression cassette as small as possible which facilitates the construction and manipulation of the expression cassette. In some embodiments, the intron is obtained from a gene that encodes the protein that is encoded by the coding sequence within the expression cassette. The intron can be located 5' to the coding sequence, 3' to the coding sequence, or within the coding sequence. An advantage of locating the intron 5' to the coding sequence is to minimize the chance of the intron interfering with the function of the polyadenylation signal. In embodiments, the nucleic acid expression cassette disclosed herein further comprises an intron. Non-limiting examples of suitable introns are Minute Virus of Mice (MVM) intron, beta-globin intron (betaIVS-II), factor IX (FIX) intron A, Simian virus 40 (SV40) small-t intron, and beta-actin intron. Preferably, the intron is an MVM intron, more preferably the MVM mini-intron as defined by SEQ ID NO: 8. The cloning of the MVM intron into a nucleic acid expression cassette described herein was shown to result in unexpectedly high expression levels of the transgene operably linked thereto.

Any polyadenylation signal that directs the synthesis of a polyA tail is useful in the expression cassettes described herein, examples of those are well known to one of skill in the art. Exemplary polyadenylation signals include, but are not limited to, polyA sequences derived from the Simian virus 40 (SV40) late gene, the bovine growth hormone (BGH) polyadenylation signal, the minimal rabbit β-globin (mRBG) gene, and the synthetic polyA (SPA) site as described in Levitt et al. (1989, Genes Dev 3:1019-1025) (SEQ ID NO:56). Preferably, the polyadenylation signal is the bovine growth hormone (BGH) polyadenylation signal (SEQ ID NO:10) or the Simian virus 40 (SV40) polyadenylation signal (SEQ ID NO:19).

Typically, the nucleic acid expression cassette according to the invention comprises a promotor, an enhancer, a (trans)gene, and a transcription terminator.

In a typical embodiment of the present invention, a nucleic acid expression cassette is disclosed and comprises:
- a liver-specific nucleic acid regulatory element, preferably a regulatory element comprising three tandem repeats of the Serpin enhancer (e.g. SEQ ID NO.5), such as a regulatory element comprising SEQ ID NO:11 and the transthyretin enhancer (TTRe) as defined by SEQ ID NO.12,
- a liver-specific promoter, and
- a transgene.

In a typical embodiment of the present invention, a nucleic acid expression cassette is disclosed and comprises:
- a liver-specific nucleic acid regulatory element, preferably a regulatory element comprising three tandem repeats of the Serpin enhancer (e.g. SEQ ID NO.5), such as a regulatory element comprising SEQ ID NO:11 and the transthyretin enhancer (TTRe) as defined by SEQ ID NO.12,
- the liver-specific TTRm promoter (e.g. defined by SEQ ID NO.6, and
- a transgene, preferably wherein the combination of the TTRe and TTRm nucleic acids is defined by SEQ ID NO.69.

In a typical embodiment of the present invention, a nucleic acid expression cassette is disclosed and comprises:
- a liver-specific nucleic acid regulatory element, preferably a regulatory element comprising three tandem repeats of the Serpin enhancer (e.g. SEQ ID NO.5), such as a regulatory element comprising SEQ ID NO:11 and the transthyretin enhancer (TTRe) as defined by SEQ ID NO.12,
- the liver-specific TTRm promoter, e.g. as defined by SEQ ID NO.6,
- an intron, preferably the MVM intron, e.g. as defined by SEQ ID NO.8, and
- a transgene preferably wherein the combination of the TTRe and TTRm nucleic acids is defined by SEQ ID NO.69.

In a typical embodiment of the present invention, a nucleic acid expression cassette is disclosed and comprises:
- a liver-specific nucleic acid regulatory element, preferably a regulatory element comprising three tandem repeats of the Serpin enhancer (e.g. SEQ ID NO.5), such as a regulatory element comprising SEQ ID NO:11 and the transthyretin enhancer (TTRe) as defined by SEQ ID NO.12,
- the liver-specific TTRm promoter, e.g. as defined by SEQ ID NO.6,
- an intron, preferably the MVM intron, e.g. as defined by SEQ ID NO.8, and
- a transgene, preferably the FIX or FVIII transgene as defined herein elsewhere and optionally a transcription terminator as defined herein elsewhere, preferably wherein the combination of the TTRe and TTRm nucleic acids is defined by SEQ ID NO.69.

In another preferred embodiment of the present invention, a nucleic acid expression cassette is disclosed and comprises:
- a liver-specific nucleic acid regulatory element, preferably a regulatory element comprising three tandem repeats of the Serpin enhancer (e.g. SEQ ID NO.5), such as a regulatory element comprising SEQ ID NO:11 and the transthyretin enhancer (TTRe) as defined by SEQ ID NO.12,
- the liver-specific AAT promoter, e.g. as defined by SEQ ID NO.64, and
- a transgene.

In another preferred embodiment of the present invention, a nucleic acid expression cassette is disclosed and comprises:
- a liver-specific nucleic acid regulatory element, preferably a regulatory element comprising three tandem repeats of the Serpin enhancer (e.g. SEQ ID NO.5), such as a regulatory element comprising SEQ ID NO:11 and the transthyretin enhancer (TTRe) as defined by SEQ ID NO.12,
- the liver-specific AAT promoter, e.g. as defined by SEQ ID NO.64, and
- an intron, preferably the MVM intron, e.g. as defined by SEQ ID NO.8, and
- a transgene.

In another preferred embodiment of the present invention, a nucleic acid expression cassette is disclosed and comprises:
- a liver-specific nucleic acid regulatory element, preferably a regulatory element comprising three tandem repeats of the Serpin enhancer (e.g. SEQ ID NO.5), such as a regulatory element comprising SEQ ID NO:11 and the transthyretin enhancer (TTRe) as defined by SEQ ID NO.12,
- the liver-specific AAT promoter, e.g. as defined by SEQ ID NO.64, and
- an intron, preferably the MVM intron, e.g. as defined by SEQ ID NO.8, and
- a transgene, preferably the FIX or FVIII transgene as defined herein elsewhere and optionally a transcription terminator as defined herein elsewhere.

In a typical embodiment of the invention, said nucleic acid expression cassette disclosed herein comprises:
- a liver-specific regulatory element, preferably three tandem repeats of the Serpin enhancer (SEQ ID NO.5), e.g. a regulatory element as defined by SEQ ID NO:11,
- a promoter, preferably the minimal TTR promoter,
- an intron, preferably the MVM intron
- a transgene, preferably codon-optimized factor IX cDNA, even more preferably codon-optimized factor IX Padua cDNA
- a transcription terminator, preferably a polyadenylation signal such as the bovine growth hormone polyadenylation signal (BGHpA) e.g. as defined by SEQ ID NO.10, or the synthetic polyA site as defined by SEQ ID NO:56.

In a further typical embodiment of the present invention, said nucleic acid expression cassette disclosed herein comprises:
- a liver-specific regulatory element, preferably three tandem repeats of the Serpin enhancer and the transthyretin enhancer (TTRe) (e.g. a regulatory element comprising SEQ ID NO:13, preferably comprising SEQ ID NO:57),
- a promoter, preferably the minimal TTR promoter,
- an intron, preferably the MVM intron, a (trans)gene, preferably codon-optimized factor IX cDNA, even more preferably codon-optimized factor IX Padua cDNA, a transcription terminator, preferably a polyadenylation signal such as the bovine growth hormone polyadenylation signal (BGHpA) or the synthetic polyA site as defined by SEQ ID NO:56.

In another typical embodiment of the present invention, said nucleic acid expression cassette disclosed herein comprises:

a liver-specific regulatory element, preferably a regulatory element comprising three tandem repeats of the Serpin enhancer (e.g. a regulatory element comprising SEQ ID NO:11), more preferably three tandem repeats of the Serpin enhancer and the transthyretin enhancer (TTRe) (e.g. a regulatory element comprising SEQ ID NO:13, preferably comprising SEQ ID NO:57), a promoter, preferably the minimal TTR promoter, an intron, preferably the MVM intron, a (trans)gene, preferably codon-optimized factor VIII cDNA, even more preferably codon-optimized B domain deleted factor VIII cDNA, a transcription terminator, preferably a polyadenylation signal such as the Simian vacuolating virus 40 or Simian virus 40 (SV40) polyadenylation signal or the synthetic polyA site as defined by SEQ ID NO:56.

In another typical embodiment of the present invention, said nucleic acid expression cassette disclosed herein comprises:

a liver-specific regulatory element, preferably a regulatory element comprising three tandem repeats of the Serpin enhancer (e.g. SEQ ID NO.5), such as a regulatory element comprising SEQ ID NO:11 and the transthyretin enhancer (TTRe) as defined by SEQ ID NO.12, such as the regulatory element comprising SEQ ID NO:13, preferably comprising SEQ ID NO:57, a promoter, preferably the AAT promoter such as the promoter as defined by SEQ ID NO. 64, an intron, preferably the MVM intron such as the MVM intron as defined by SEQ ID NO.8, a (trans)gene, preferably codon-optimized factor IX cDNA, even more preferably codon-optimized factor IX Padua cDNA, a transcription terminator, preferably a polyadenylation signal such as the bovine growth hormone polyadenylation signal (BGHpA) as defined by SEQ ID NO.10, or the synthetic polyA site as defined by SEQ ID NO:56. As a non-limiting example, such a vector is defined by SEQ ID NO. 65 (cf. FIG. 25).

In another typical embodiment of the present invention, said nucleic acid expression cassette disclosed herein comprises:

a liver-specific regulatory element, preferably a regulatory element comprising three tandem repeats of the Serpin enhancer (e.g. SEQ ID NO.5), such as a regulatory element comprising SEQ ID NO:11, a promoter, preferably the AAT promoter such as the promoter as defined by SEQ ID NO. 64, an intron, preferably the MVM intron such as the MVM intron as defined by SEQ ID NO.8, a (trans)gene, preferably codon-optimized factor IX cDNA, even more preferably codon-optimized factor IX Padua cDNA, a transcription terminator, preferably a polyadenylation signal such as the bovine growth hormone polyadenylation signal (BGHpA) as defined by SEQ ID NO.10, or the synthetic polyA site as defined by SEQ ID NO:56. As a non-limiting example, such a vector is defined by SEQ ID NO. 66 (cf. FIG. 25).

In another typical embodiment of the present invention, said nucleic acid expression cassette disclosed herein comprises:

a liver-specific regulatory element, preferably a regulatory element comprising the transthyretin enhancer (TTRe) as defined by SEQ ID NO.12, operably linked to three tandem repeats of the Serpin enhancer (e.g. SEQ ID NO.5), more preferably as defined by SEQ ID NO:11, a promoter, preferably the AAT promoter such as the promoter as defined by SEQ ID NO. 64, an intron, preferably the MVM intron such as the MVM intron as defined by SEQ ID NO.8, a (trans)gene, preferably codon-optimized factor IX cDNA, even more preferably codon-optimized factor IX Padua cDNA, a transcription terminator, preferably a polyadenylation signal such as the bovine growth hormone polyadenylation signal (BGHpA) as defined by SEQ ID NO.10, or the synthetic polyA site as defined by SEQ ID NO:56. As a non-limiting example, such a vector is defined by SEQ ID NO.68 (cf. FIG. 25).

The expression cassettes disclosed herein may be used as such, or typically, they may be part of a nucleic acid vector. Accordingly, a further aspect relates to the use of a nucleic acid expression cassette as described herein in a vector, in particular a nucleic acid vector.

In an aspect, the invention also provides a vector comprising a nucleic acid expression cassette as disclosed herein.

The term 'vector' as used in the application refers to nucleic acid molecules, usually double-stranded DNA, which may have inserted into it another nucleic acid molecule (the insert nucleic acid molecule) such as, but not limited to, a cDNA molecule. The vector is used to transport the insert nucleic acid molecule into a suitable host cell. A vector may contain the necessary elements that permit transcribing the insert nucleic acid molecule, and, optionally, translating the transcript into a polypeptide. The insert nucleic acid molecule may be derived from the host cell, or may be derived from a different cell or organism. Once in the host cell, the vector can replicate independently of, or coincidental with, the host chromosomal DNA, and several copies of the vector and its inserted nucleic acid molecule may be generated.

The term "vector" may thus also be defined as a gene delivery vehicle that facilitates gene transfer into a target cell. This definition includes both non-viral and viral vectors. Non-viral vectors include but are not limited to cationic lipids, liposomes, nanoparticles, PEG, PEI, etc. Viral vectors are derived from viruses including but not limited to: retrovirus, lentivirus, adeno-associated virus, adenovirus, herpesvirus, hepatitis virus or the like. Alternatively, gene delivery systems can be used to combine viral and non-viral components, such as nanoparticles or virosomes (Yamada et al., 2003).

Typically, but not necessarily, viral vectors are replication-deficient as they have lost the ability to propagate in a given cell since viral genes essential for replication have been eliminated from the viral vector. However, some viral vectors can also be adapted to replicate specifically in a given cell, such as e.g. a cancer cell, and are typically used to trigger the (cancer) cell-specific (onco)lysis. Preferred vectors are derived from adeno-associated virus, adenovirus, retroviruses and Antiviruses.

Retroviruses and Antiviruses are RNA viruses that have the ability to insert their genes into host cell chromosomes after infection. Retroviral and lentiviral vectors have been developed that lack the genes encoding viral proteins, but retain the ability to infect cells and insert their genes into the chromosomes of the target cell (Miller, 1990; Naldini et al., 1996, VandenDriessche et al., 1999). The difference between a lentiviral and a classical Moloney-murine leukemia-virus (MLV) based retroviral vector is that lentiviral vectors can transduce both dividing and non-dividing cells whereas MLV-based retroviral vectors can only transduce dividing cells.

Adenoviral vectors are designed to be administered directly to a living subject. Unlike retroviral vectors, most of the adenoviral vector genomes do not integrate into the chromosome of the host cell. Instead, genes introduced into cells using adenoviral vectors are maintained in the nucleus as an extrachromosomal element (episome) that persists for an extended period of time. Adenoviral vectors will transduce dividing and nondividing cells in many different tissues in vivo including airway epithelial cells, endothelial cells, hepatocytes and various tumors (Trapnell, 1993; Chuah et al., 2003). Another viral vector is derived from the herpes simplex virus, a large, double-stranded DNA virus. Recombinant forms of the vaccinia virus, another dsDNA virus, can accommodate large inserts and are generated by homologous recombination.

Adeno-associated virus (AAV) is a small ssDNA virus which infects humans and some other primate species, not known to cause disease and consequently causing only a very mild immune response. AAV can infect both dividing and non-dividing cells and may incorporate its genome into that of the host cell. These features make AAV a very attractive candidate for creating viral vectors for gene therapy, although the cloning capacity of the vector is relatively limited. Accordingly, in preferred embodiments of the invention, the vector used is derived from adeno-associated virus (i.e. AAV vector).

Different serotypes of AAVs have been isolated and characterized, such as, for example AAV serotype 2, AAV serotype 5, AAV serotype 8, and AAV serotype 9, and all AAV serotypes are contemplated herein. In particular, AAV vectors that comprise a FIX transgene as disclosed herein are preferably AAV serotype 9 vectors, and AAV vectors that comprise a FVIII transgene as disclosed herein are preferably AAV serotype 8 vectors.

The AAV vectors disclosed herein may be single-stranded (i.e. ssAAV vectors) or self-complementary (i.e. scAAV vectors). In particular, AAV vectors that comprise a FIX transgene as disclosed herein are preferably self-complementary, and AAV vectors that comprise a FVIII transgene as disclosed herein are preferably single-stranded. With the term "self-complementary AAV" is meant herein a recombinant AAV-derived vector wherein the coding region has been designed to form an intra-molecular double-stranded DNA template.

Gene therapy with adeno-associated viral vectors disclosed herein was shown to induce immune tolerance towards the transgene comprised in the vector.

Figure 6:
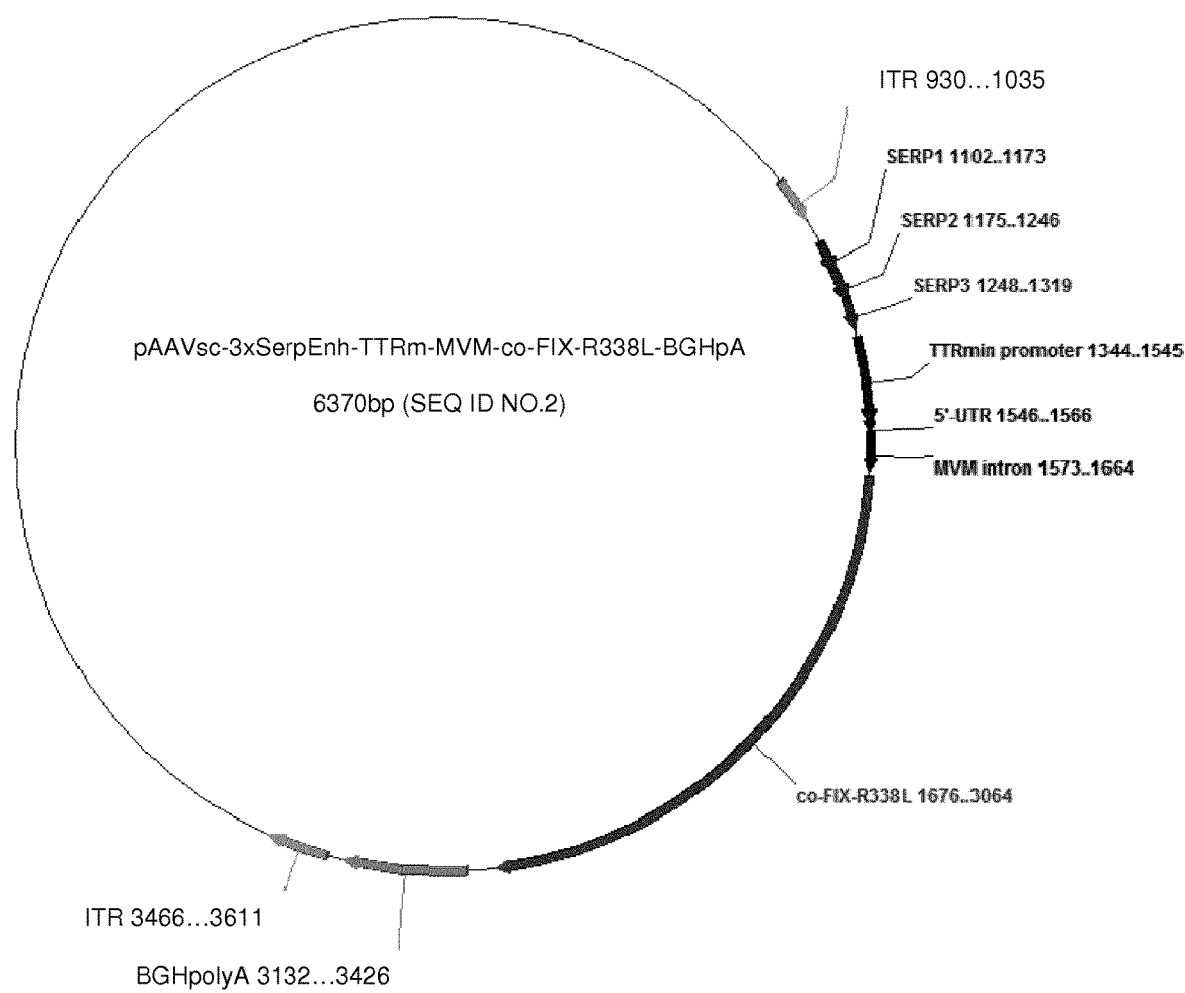
FIG. 6: Plasmid map of the pAAVsc-3×SerpEnh-TTRm-MVM-co-FIX-R338L-BGHpA vector
Figure 7:
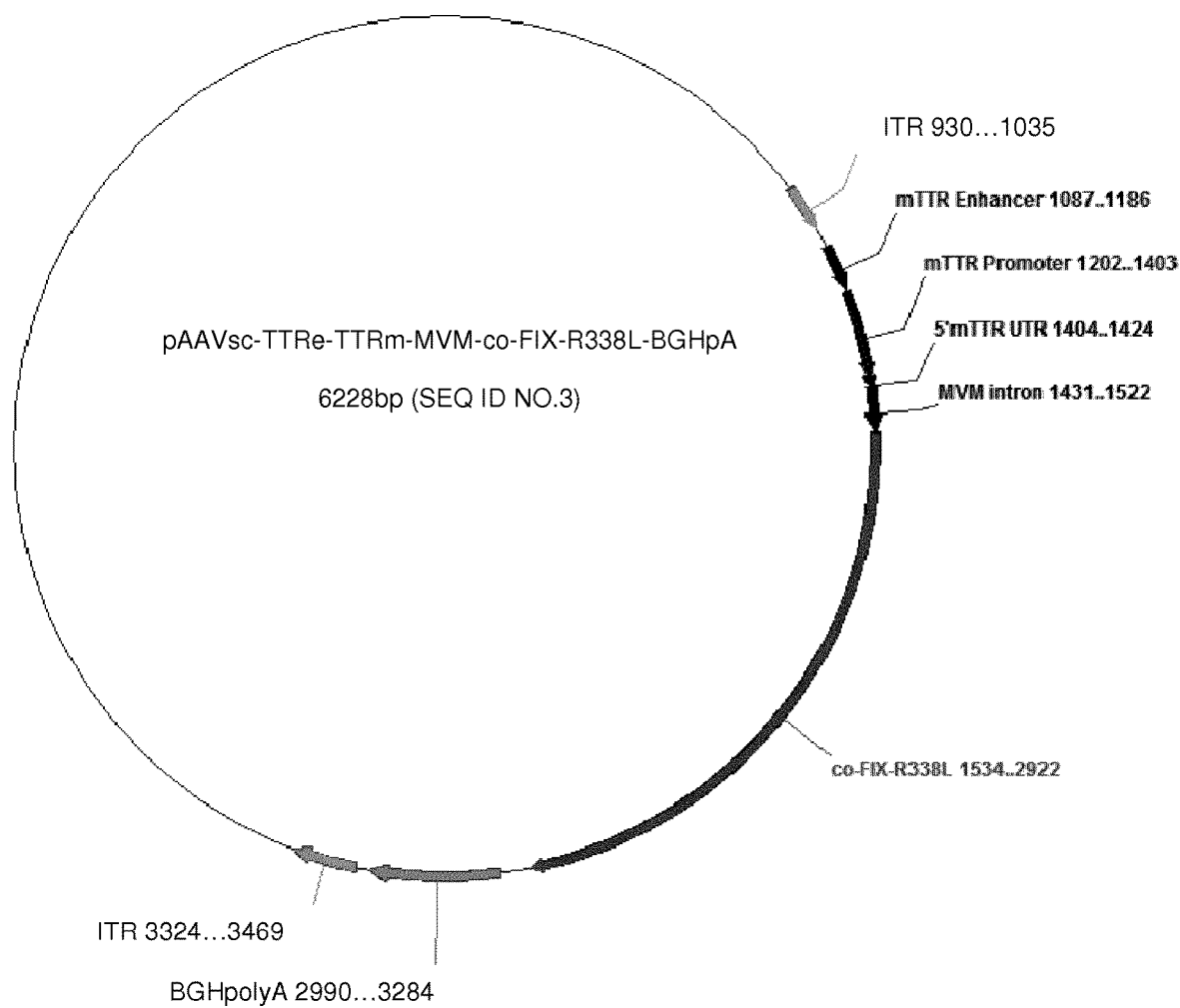
FIG. 7: Plasmid map of the pAAVsc-TTRe-TTRm-MVM-co-FIX-R338L-BGHpA vector

In embodiments, the vector according to the invention comprises the following elements (cfr. FIG. 6):
an Inverted Terminal Repeat sequence (ITR), optionally mutated,
a liver-specific regulatory element, preferably a regulatory element comprising three tandem repeats of the Serpin enhancer ("Serp" or "SerpEnh") (e.g. a regulatory element comprising the nucleic acid fragment defined by SEQ ID NO:11),
a promoter, preferably the minimal TTR promoter (TTRm),
an intron, preferably the MVM intron,
a (trans)gene, preferably codon-optimized factor IX cDNA, even more preferably codon-optimized factor IX Padua cDNA,
a transcription terminator, preferably a polyadenylation signal such as the BGHpA or the synthetic polyA site as defined by SEQ ID NO:56,
an Inverted Terminal Repeat sequence (ITR).

Preferably, the vector is an adeno-associated virus-derived vector, more preferably a self-complementary AAV vector, even more preferably a self-complementary AAV serotype 9 vector, such as the vector as defined by SEQ ID NO:2.

Figure 8:
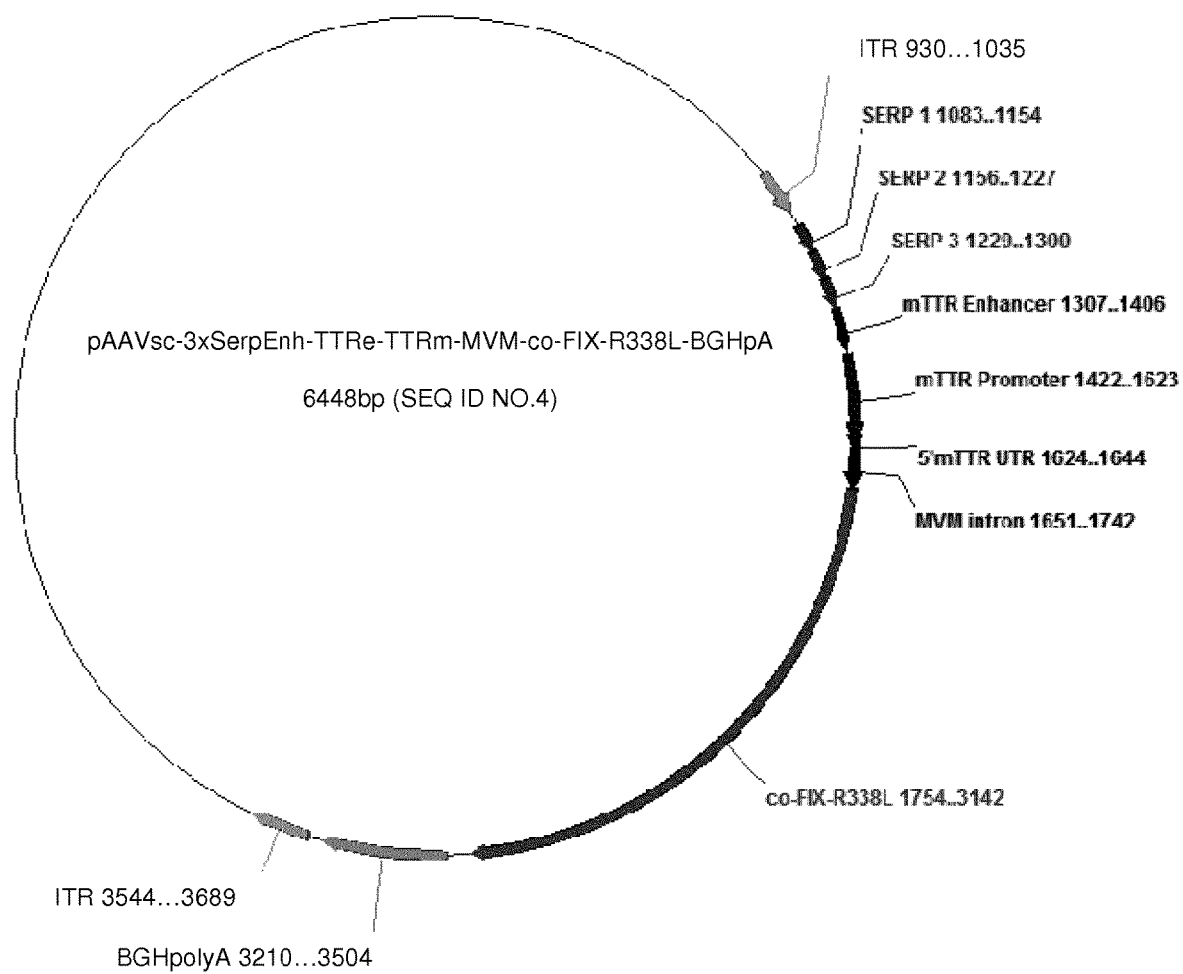
FIG. 8: Plasmid map of the pAAVsc-3×SerpEnh-TTRe-TTRm-MVM-co-FIX-R338L-BGHpA vector
Figure 9:
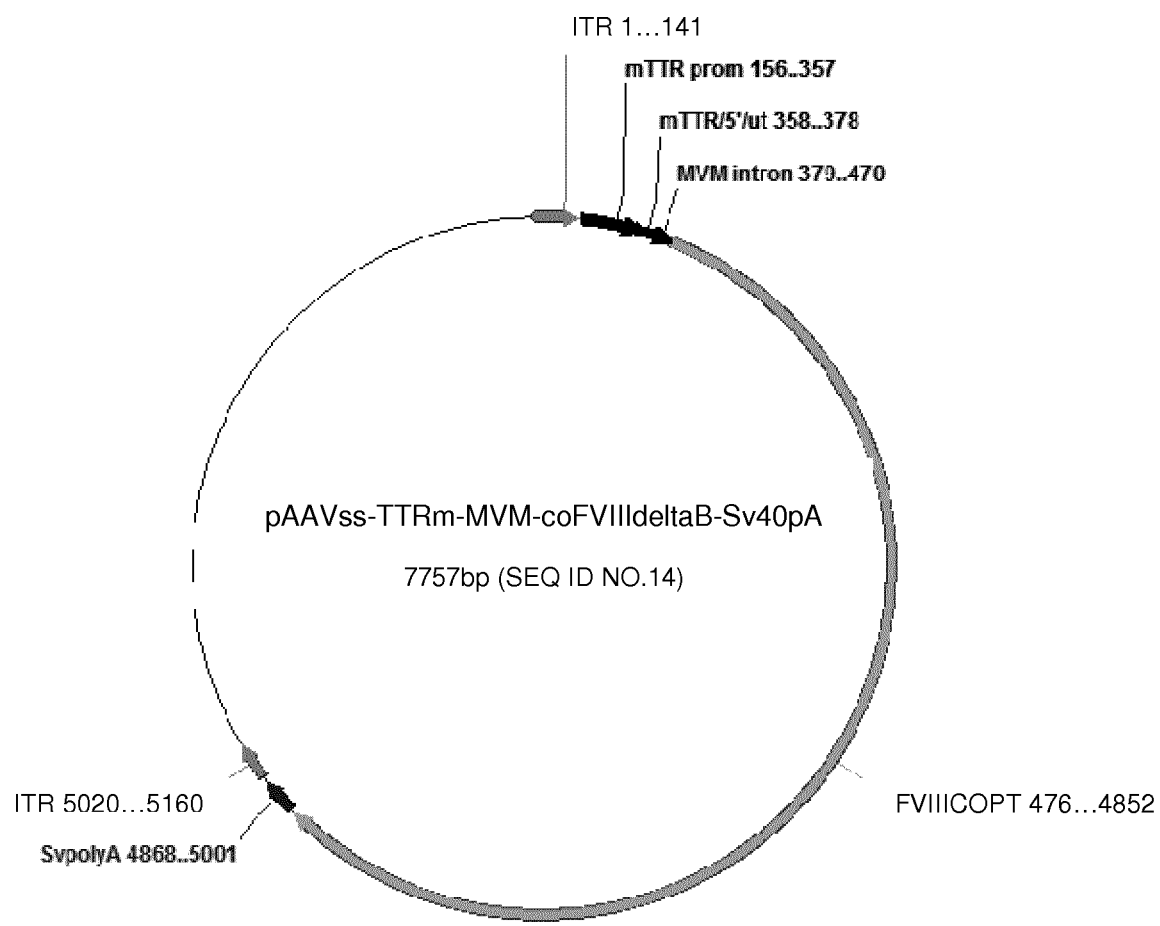
FIG. 9: Plasmid map of the pAAVss-TTRm-MVM-coFVIIIdeltaB-Sv40pA vector
Figure 10:
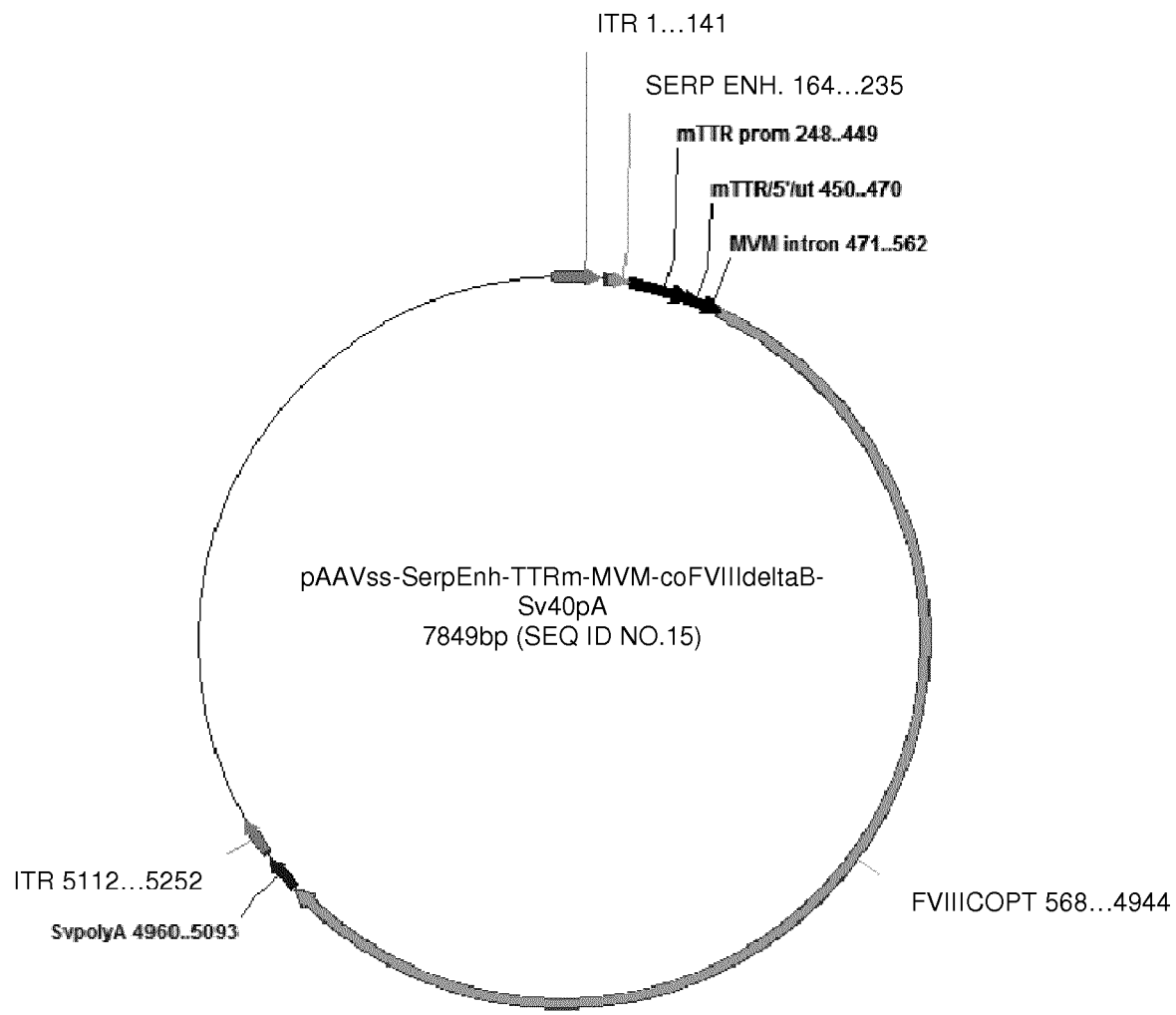
FIG. 10: Plasmid map of the pAAVss-SerpEnh-TTRm-MVM-coFVIIIdeltaB-Sv40pA vector
Figure 16:
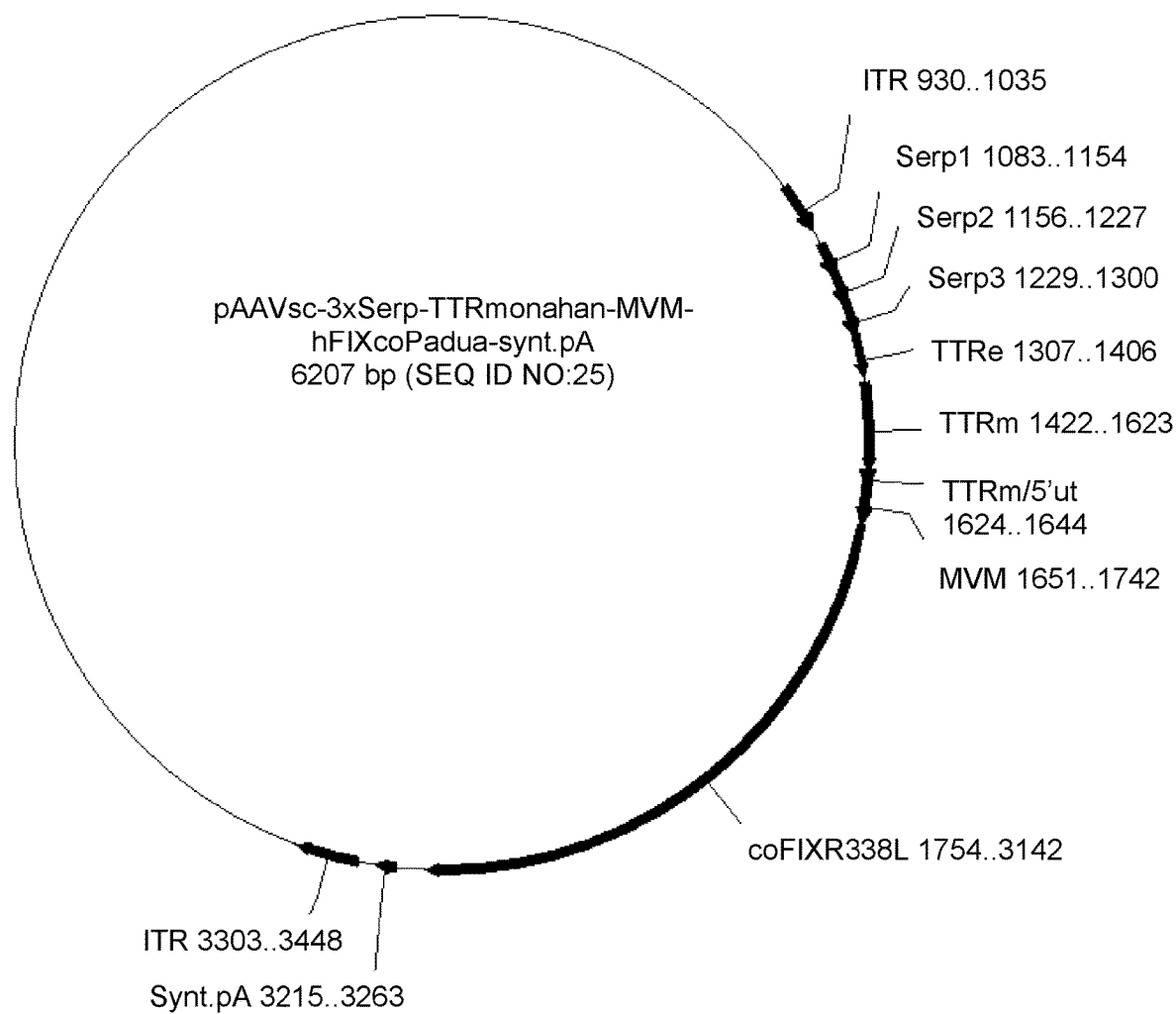
FIG. 16: Plasmid map of the pAAVsc-3×SerpEnh-TTRe-TTRm-MVM-co-FIX-R338L-Synt.pA vector

In a further typical embodiment of the present invention, said vector comprises the following elements (cf. FIG. 8 and FIG. 16):
an Inverted Terminal Repeat sequence (ITR), optionally mutated,
a liver-specific regulatory element, preferably a regulatory element comprising three tandem repeats of the Serpin enhancer ("Serp" or "SerpEnh") and the transthyretin enhancer (TTRe) (e.g. a regulatory element comprising SEQ ID NO:13, preferably comprising SEQ ID NO:57),
a promoter, preferably the minimal TTR promoter (TTRm),
an intron, preferably the MVM intron,
a (trans)gene, preferably codon-optimized factor IX cDNA, even more preferably codon-optimized factor IX Padua cDNA,
a transcription terminator, preferably a polyadenylation signal such as the BGHpA or the synthetic polyA site as defined by SEQ ID NO:56, and
an Inverted Terminal Repeat sequence (ITR).

The combination of said elements resulted in an unexpectedly high expression level of FIX, and in particular of the Padua mutant thereof, in the liver of subjects. Preferably, the vector is an adeno-associated virus-derived vector, more preferably a self-complementary AAV vector, even more preferably a self-complementary AAV serotype 9 vector, such as the vector as defined by SEQ ID NO:4 or SEQ ID NO:25.

Figure 11:
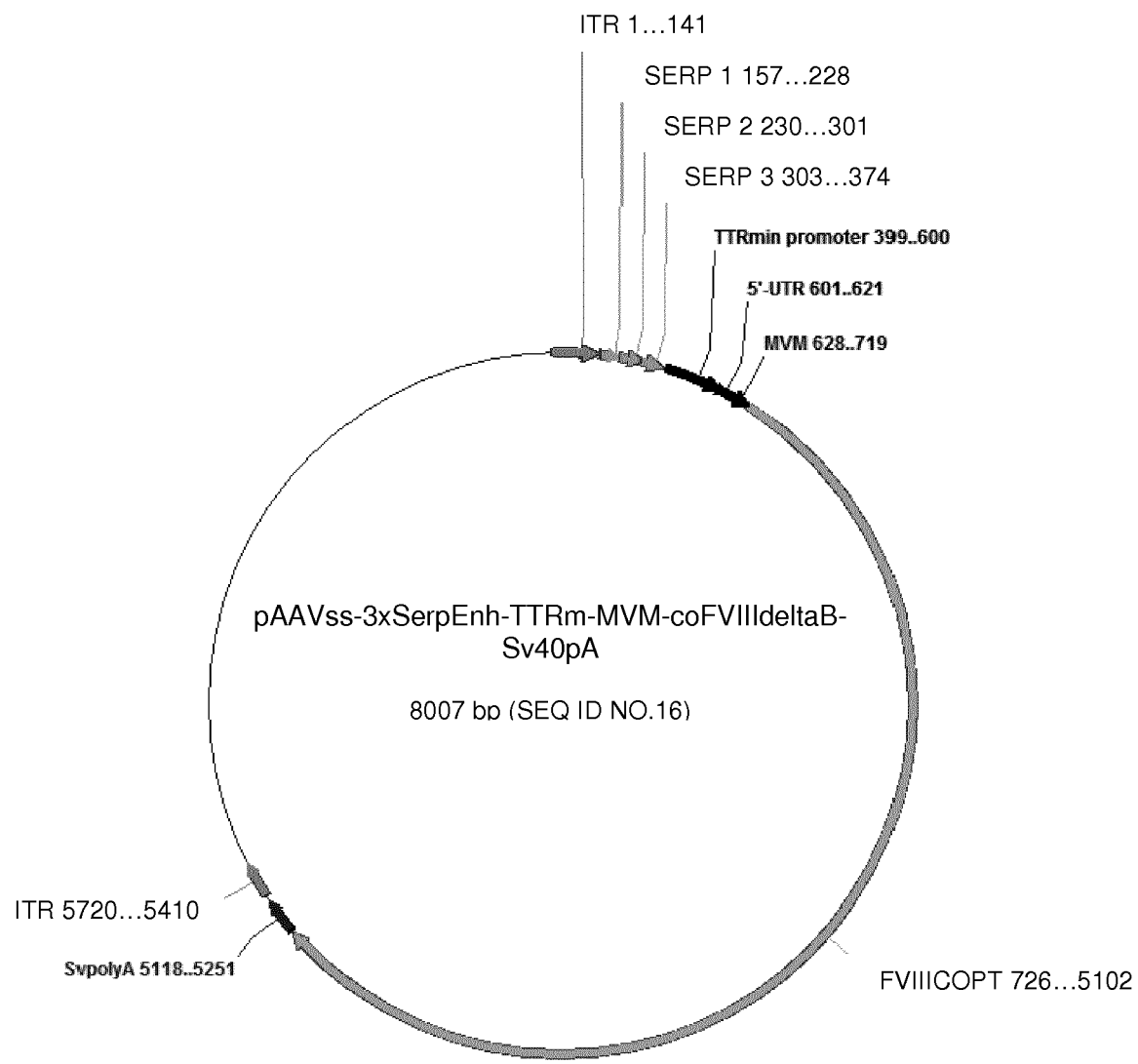
FIG. 11: Plasmid map of the pAAVss-3×SerpEnh-TTRm-MVM-coFVIIIdeltaB-Sv40pA vector
Figure 12:
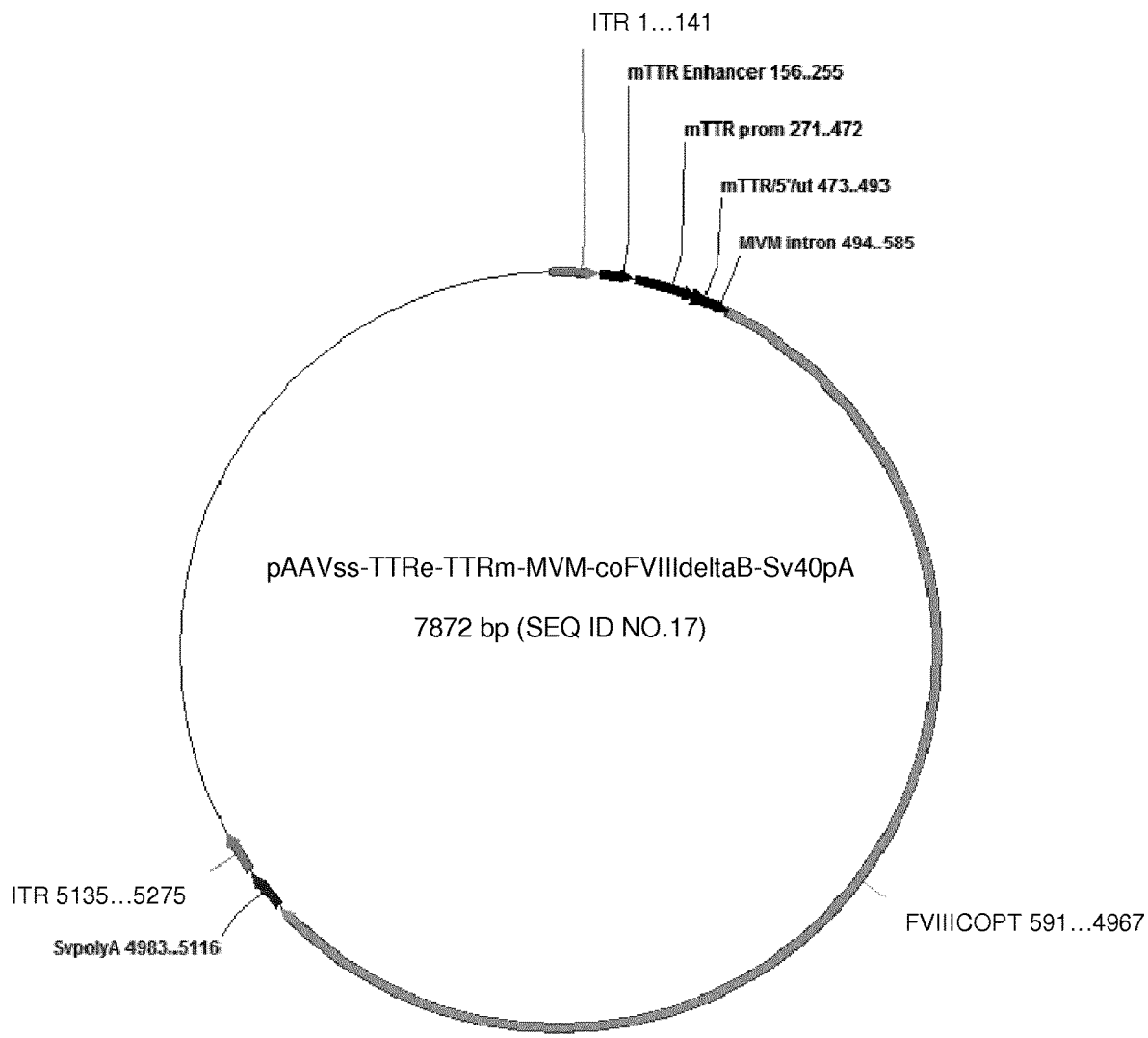
FIG. 12: Plasmid map of the pAAVss-TTRe-TTRm-MVM-coFVIIIdeltaB-Sv40pA vector
Figure 17:
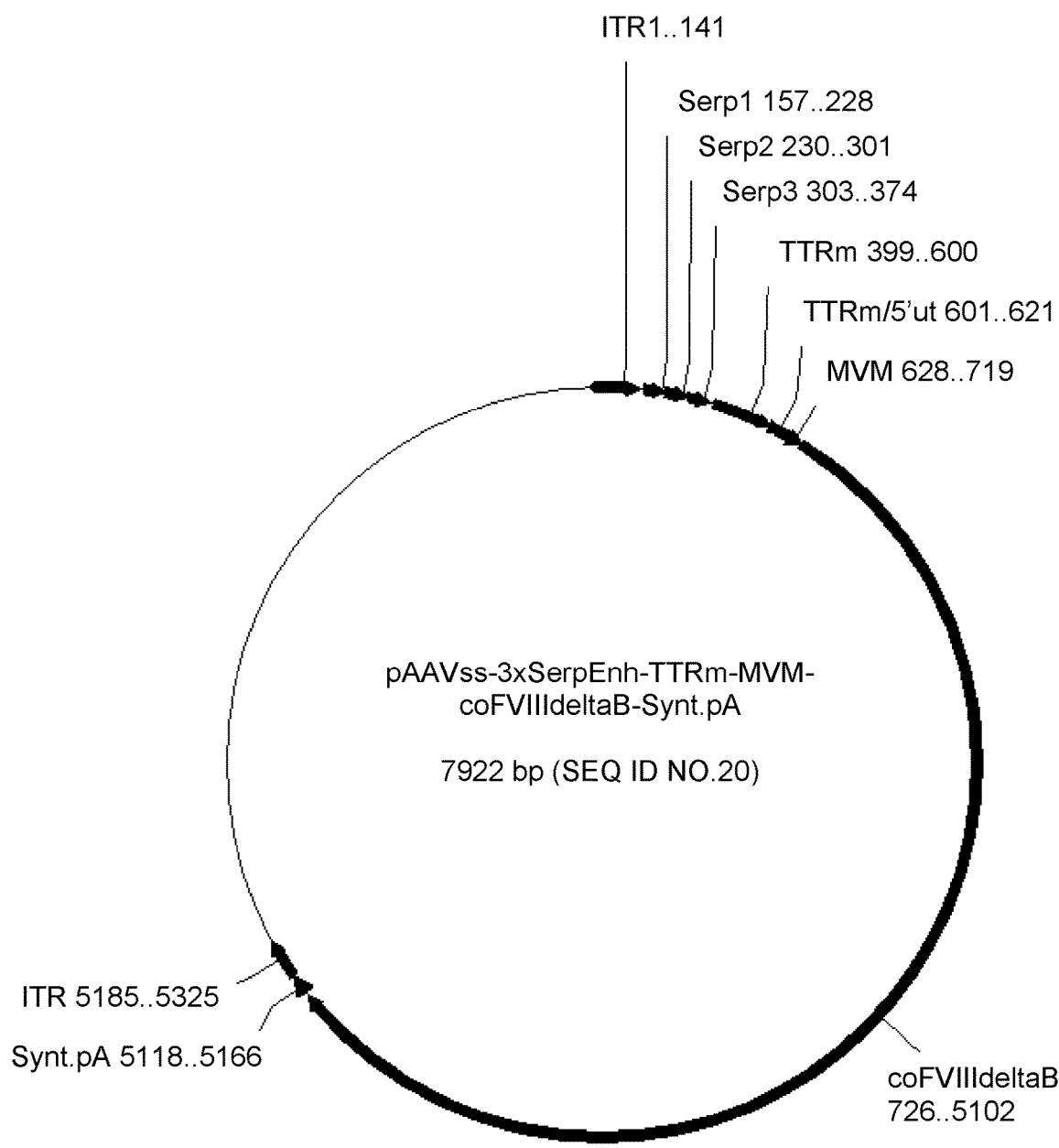
FIG. 17: Plasmid map of the pAAVss-3×SerpEnh-TTRm-MVM-coFVIIIdeltaB-Synt.pA vector
Figure 18:
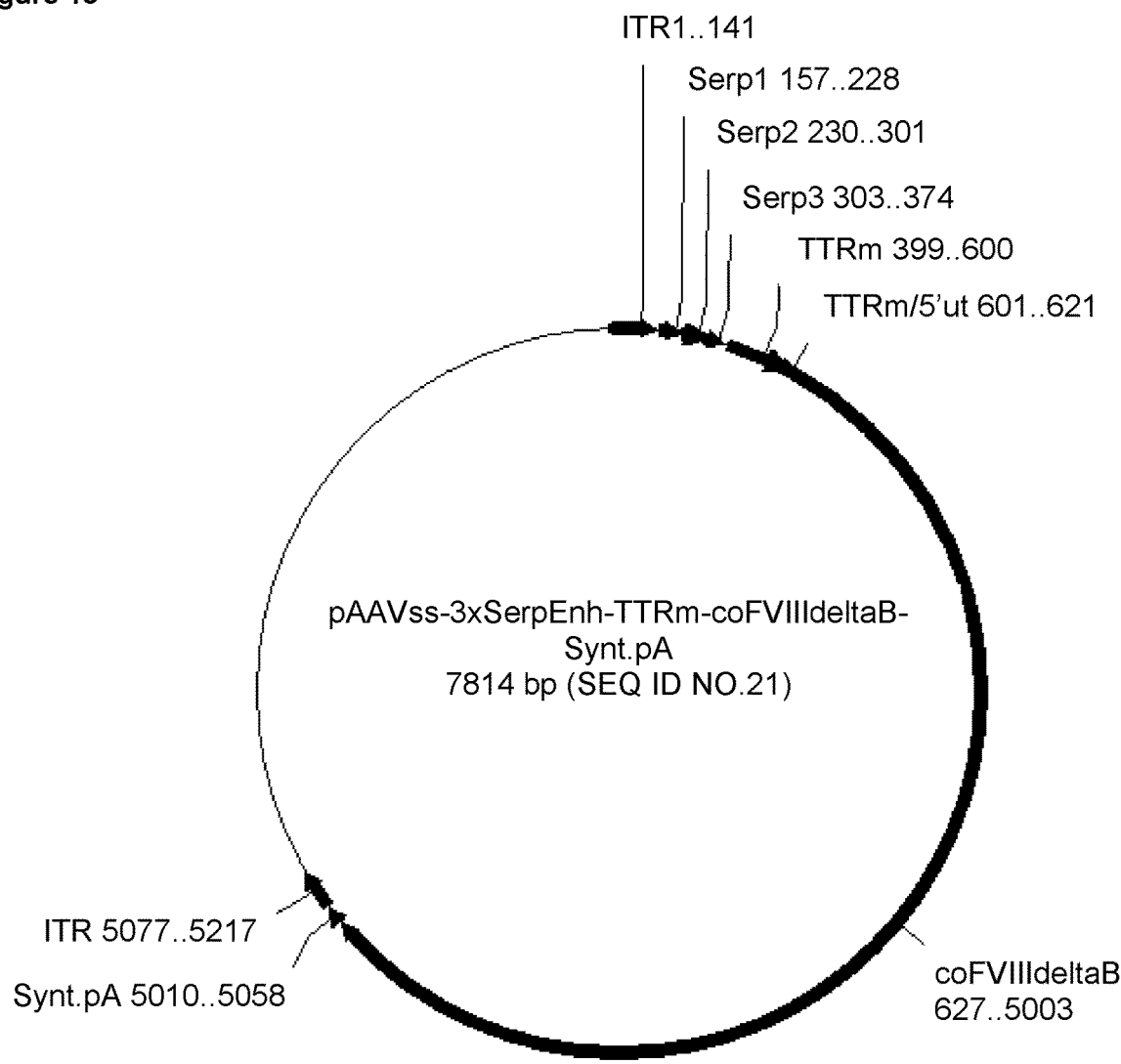
FIG. 18: Plasmid map of the pAAVss-3×SerpEnh-TTRm-coFVIIIdeltaB-Synt.pA vector

In another typical embodiment of the present invention, said vector comprises the following elements (cfr. FIG. 11, 17 or 18):
an Inverted Terminal Repeat sequence (ITR), optionally mutated,
a liver-specific regulatory element, preferably a regulatory element comprising three tandem repeats of the Serpin enhancer (e.g. a regulatory element comprising SEQ ID NO: 1),
a promoter, preferably the minimal TTR promoter,
an intron, preferably the MVM intron,
a (trans)gene, preferably codon-optimized factor VIII cDNA, even more preferably codon-optimized B domain deleted factor VIII cDNA,
a transcription terminator, preferably a polyadenylation signal such as the Simian vacuolating virus 40 or Simian virus 40 (SV40) polyadenylation signal or the synthetic polyA site as defined by SEQ ID NO:56, and
an Inverted Terminal Repeat sequence (ITR).

The combination of said elements resulted in an unexpectedly high expression level of FVIII specifically in the liver of subjects. Preferably, the vector is an adeno-associated virus (AAV)-derived vector, more preferably a single-stranded AAV vector, even more preferably a single-stranded AAV serotype 8 vector, such as the vector as defined by SEQ ID NO:16, SEQ ID NO:20 or SEQ ID NO:21.

Figure 19:
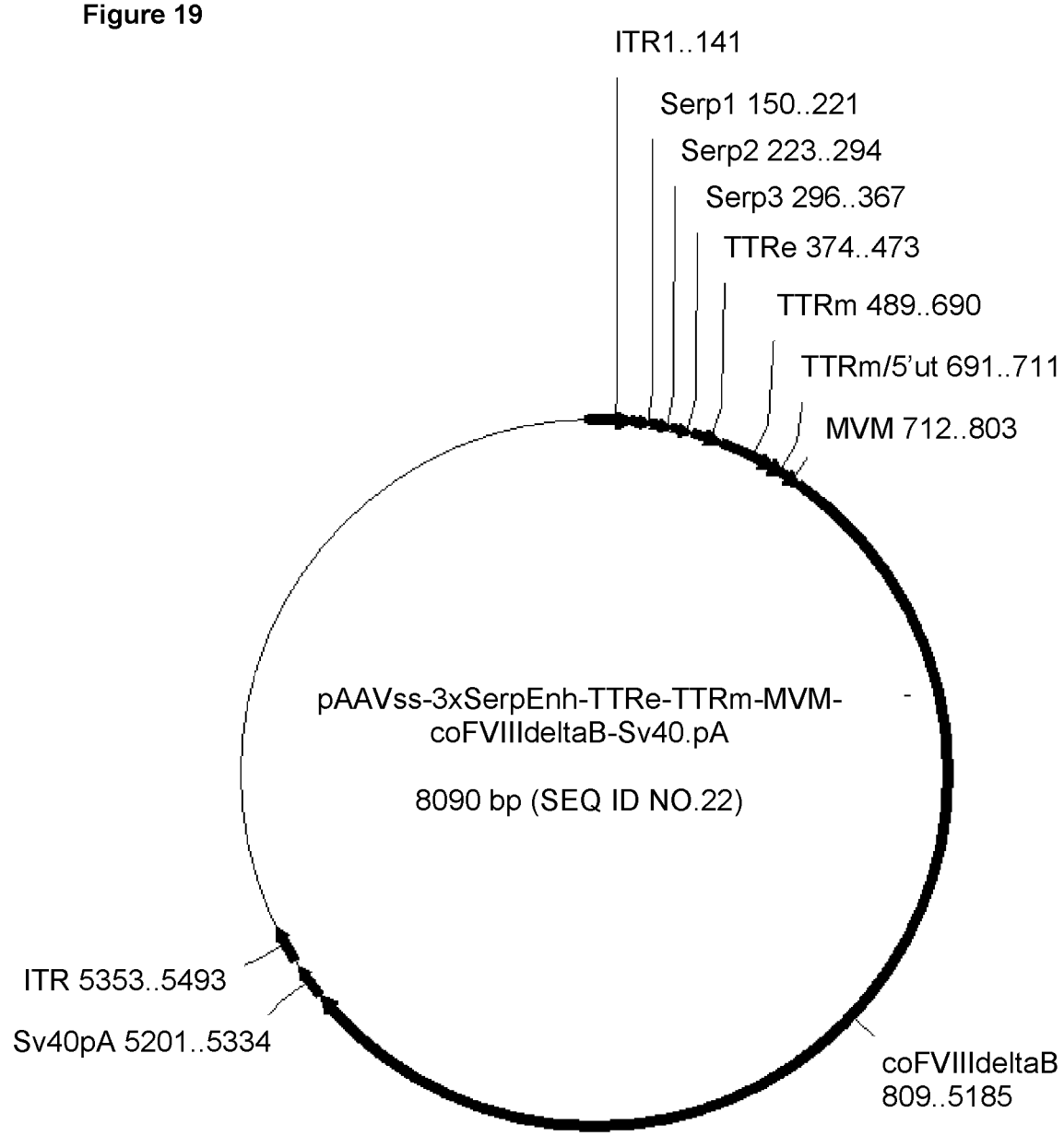
FIG. 19: Plasmid map of the pAAVss-3×SerpEnh-TTRe-TTRm-MVM-coFVIIIdeltaB-Sv40pA vector
Figure 20:
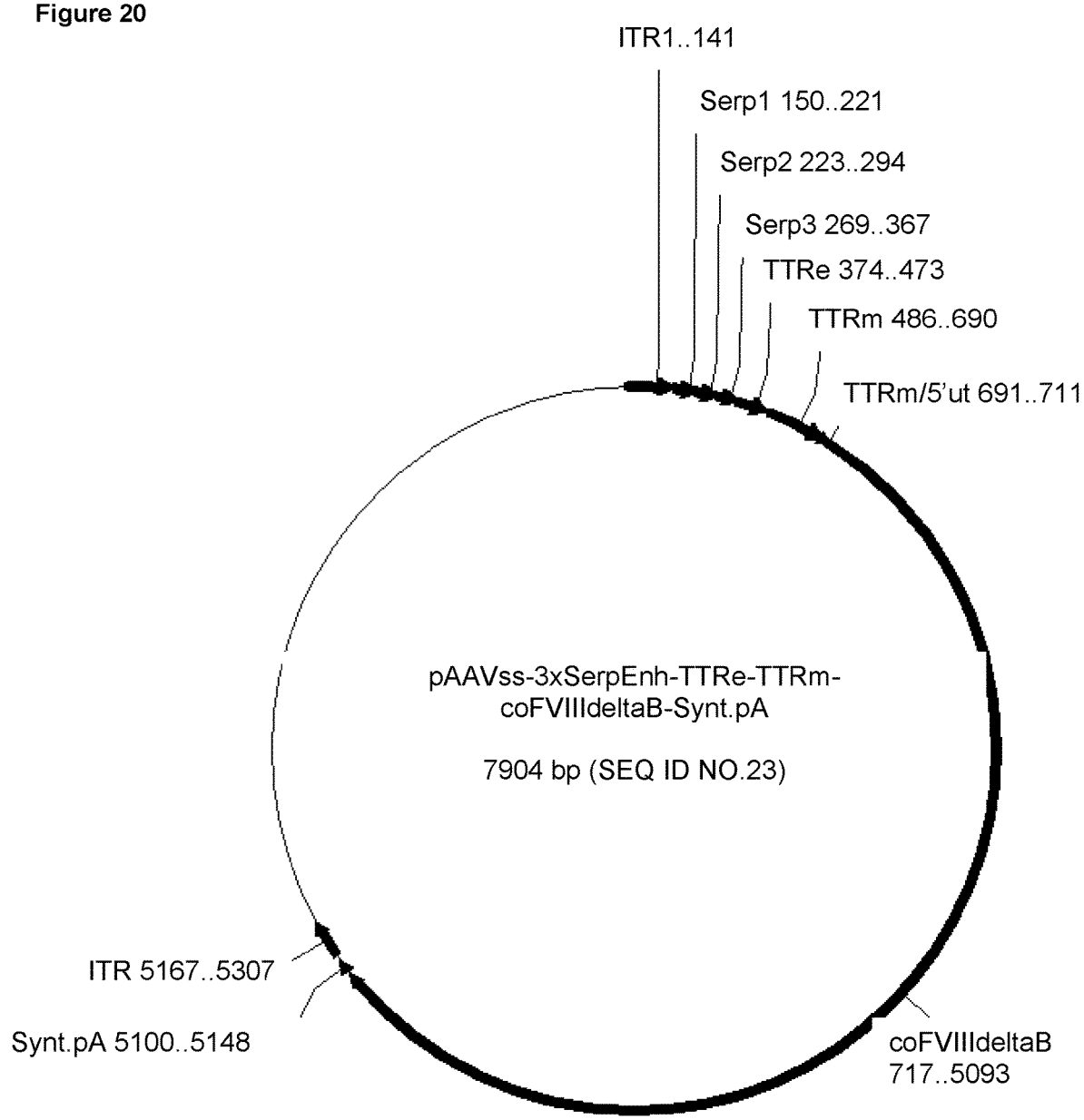
FIG. 20: Plasmid map of the pAAVss-3×SerpEnh-TTRe-TTRm-coFVIIIdeltaB-Synt.pA vector
Figure 21:
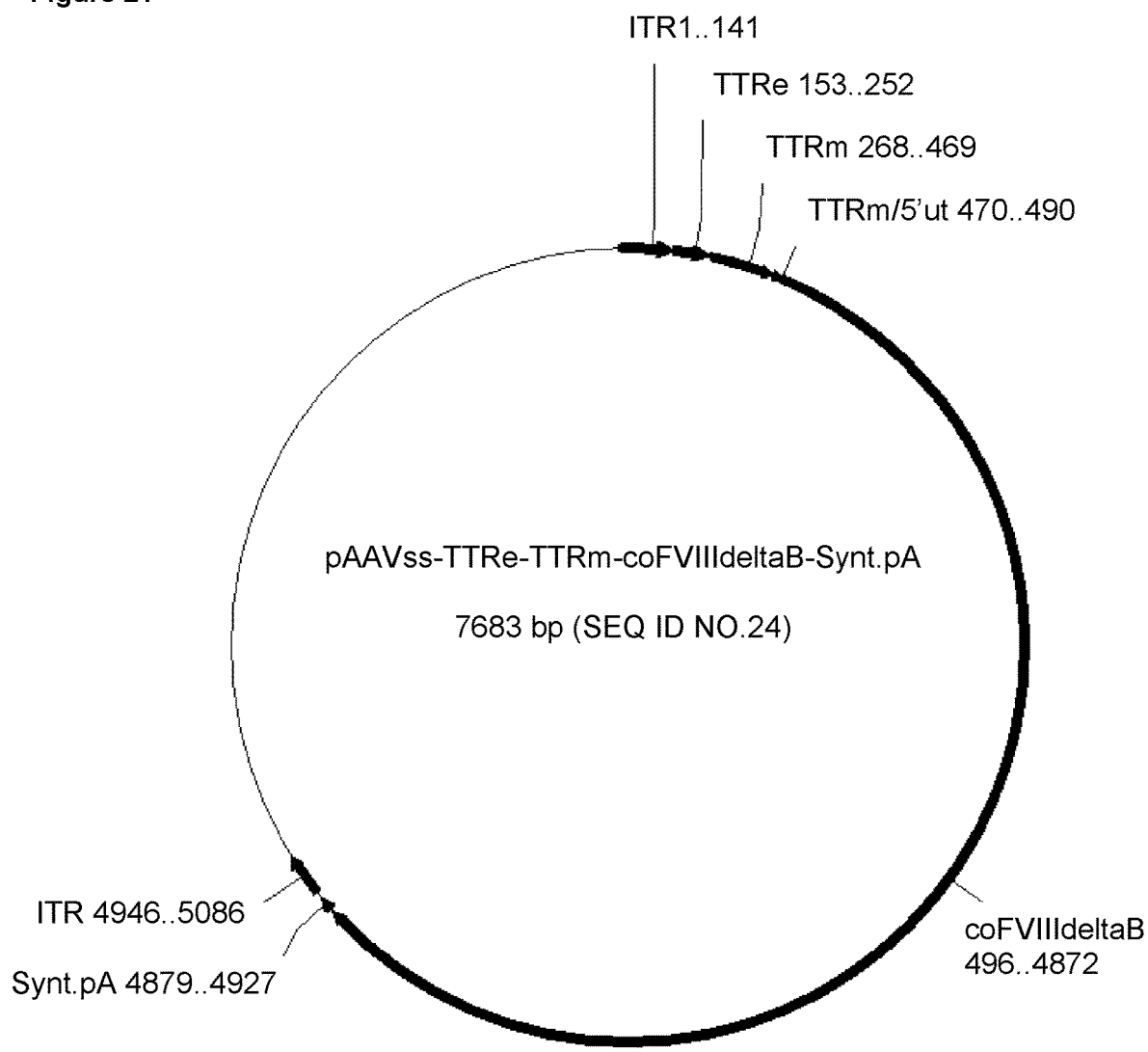
FIG. 21: Plasmid map of the pAAVss-TTRe-TTRm-coFVIIIdeltaB-Synt.pA vector.

In a further embodiment, said vector comprises the following elements (cfr. FIG. 19 or 20):
- an Inverted Terminal Repeat sequence (ITR), optionally mutated,
- a liver-specific regulatory element, preferably a regulatory element comprising three tandem repeats of the Serpin enhancer ("Serp" or "SerpEnh") and the transthyretin enhancer (TTRe) (e.g. a regulatory element comprising SEQ ID NO:13, preferably comprising SEQ ID NO:57),
- a promoter, preferably the minimal TTR promoter,
- an intron, preferably the MVM intron,
- a (trans)gene, preferably codon-optimized factor VIII cDNA, even more preferably codon-optimized B domain deleted factor VIII cDNA,
- a transcription terminator, preferably a polyadenylation signal such as the Simian vacuolating virus 40 or Simian virus 40 (SV40) polyadenylation signal or the synthetic polyA site as defined by SEQ ID NO:56, and
- an Inverted Terminal Repeat sequence (ITR).

The combination of said elements resulted in an unexpectedly high expression level of FVIII specifically in the liver of subjects. Preferably, the vector is an adeno-associated virus (AAV)-derived vector, more preferably a single-stranded AAV vector, even more preferably a single-stranded AAV serotype 8 vector, such as the vector as defined by SEQ ID NO:22 or SEQ ID NO:23.

The combination of the triple repeat of the Serpin enhancer defined by SEQ ID NO. 5 and the transthyretin enhancer defined by SEQ ID NO:12 including a specific spacer fragment has been shown to be unexpectedly potent in increasing expression of a transgene operably linked to it. Said regulatory element is defined by SEQ ID NO:13. Said regulatory element can further be combined with the transthyretin minimal promotor as defined by SEQ ID NO.6. This creates a combination of 3× the SerpEnh (3×SEQ ID NO.5, e.g. such as in SEQ ID NO.11) with the TTRe and TTRm nucleic acid sequence e.g. as defined by SEQ ID NO.69. For example, such a construct results in a regulatory element as defined by SEQ ID NO:58, which has been tested to increase the expression of both FVIII and FIX transgenes as shown herein.

In specific embodiments the following plasmids/vectors are provided:
pAAVsc-3×CRM8-TTRe-TTRm-MVM-FIXcoR338L-BGHpA,
pAAVss-3×CRM8-TTRe-TTRm-MVM-FVIIIcodeltaB-sv40pA,
pAAVsc-TTRe-3×CRM8-TTRm-MVM-FIXcoR338L-BGHpA,
pAAVss-TTRe-3×CRM8-TTRm-MVM-FVIIIcodeltaB-sv40pA,
pAAVsc-CRM8-TTRe-TTRm-MVM-FIXcoR338L-BGHpA,
pAAVss-CRM8-TTRe-TTRm-MVM-FVIIIcodeltaB-sv40pA,
pAAVsc-3×CRM8-TTRe-AAT-MVM-FIXcoR338L-BGHpA,
pAAVss-3×CRM8-TTRe-AAT-MVM-FVIIIcodeltaB-sv40pA,
pAAVsc-TTRe-3×CRM8-AAT-MVM-FIXcoR338L-BGHpA,
pAAVss-TTRe-3×CRM8-AAT-MVM-FVIIIcodeltaB-sv40pA,
pAAVsc-CRM8-TTRe-AAT-MVM-FIXcoR338L-BGHpA,
pAAVss-CRM8-TTRe-AAT-MVM-FVIIIcodeltaB-sv40pA,
pAAVsc-3×CRM8-TTRe-ALBp-MVM-FIXcoR338L-BGHpA,
pAAVss-3×CRM8-TTRe-ALBp-MVM-FVIIIcodeltaB-sv40pA,
pAAVsc-TTRe-3×CRM8-ALBp-MVM-FIXcoR338L-BGHpA,
pAAVss-TTRe-3×CRM8-ALBp-MVM-FVIIIcodeltaB-sv40pA,
pAAVsc-CRM8-TTRe-ALBp-MVM-FIXcoR338L-BGHpA,
pAAVss-CRM8-TTRe-ALBp-MVM-FVIIIcodeltaB-sv40pA,
pAAVsc-3×CRM8-TTRe-APOA1p-MVM-FIXcoR338L-BGHpA,
pAAVss-3×CRM8-TTRe-APOA1p-MVM-FVIIIcodeltaB-sv40pA
pAAVsc-TTRe-3×CRM8-APOA1p-MVM-FIXcoR338L-BGHpA,
pAAVss-TTRe-3×CRM8-APOA1p-MVM-FVIIIcodeltaB-sv40pA
pAAVsc-CRM8-TTRe-APOA1p-MVM-FIXcoR338L-BGHpA,
pAAVss-CRM8-TTRe-APOA1p-MVM-FVIIIcodeltaB-sv40pA,
pAAVsc-3×CRM8-TTRe-CFBp-MVM-FIXcoR338L-BGHpA,
pAAVss-3×CRM8-TTRe-CFBp-MVM-FVIIIcodeltaB-sv40pA,
pAAVsc-TTRe-3×CRM8-CFBp-MVM-FIXcoR338L-BGHpA,
pAAVss-TTRe-3×CRM8-CFBp-MVM-FVIIIcodeltaB-sv40pA,
pAAVsc-CRM8-TTRe-CFBp-MVM-FIXcoR338L-BGHpA,
pAAVss-CRM8-TTRe-CFBp-MVM-FVIIIcodeltaB-sv40pA,
pAAVsc-3×CRM8-TTRe-KHKp-MVM-FIXcoR338L-BGHpA,
pAAVss-3×CRM8-TTRe-KHKp-MVM-FVIIIcodeltaB-sv40pA,
pAAVsc-TTRe-3×CRM8-KHKp-MVM-FIXcoR338L-BGHpA,
pAAVss-TTRe-3×CRM8-KHKp-MVM-FVIIIcodeltaB-sv40pA,
pAAVsc-CRM8-TTRe-KHKp-MVM-FIXcoR338L-BGHpA,
pAAVss-CRM8-TTRe-KHKp-MVM-FVIIIcodeltaB-sv40pA,
pAAVsc-3×CRM8-TTRe-HPXp-MVM-FIXcoR338L-BGHpA,
pAAVss-3×CRM8-TTRe-HPXp-MVM-FVIIIcodeltaB-sv40pA,
pAAVsc-TTRe-3×CRM8-HPXp-MVM-FIXcoR338L-BGHpA,
pAAVss-TTRe-3×CRM8-HPXp-MVM-FVIIIcodeltaB-sv40pA,
pAAVsc-CRM8-TTRe-HPXp-MVM-FIXcoR338L-BGHpA, pAAVss-CRM8-TTRe-HPXp-MVM-FVIIIcodeltaB-sv40pA,
pAAVsc-3×CRM8-TTRe-NNMTp-MVM-FIXcoR338L-BGHpA,
pAAVss-3×CRM8-TTRe-NNMTp-MVM-FVIII-codeltaB-sv40pA,
pAAVsc-TTRe-3×CRM8-NNMTp-MVM-FIXcoR338L-BGHpA,
pAAVss-TTRe-3×CRM8-NNMTp-MVM-FVIII-codeltaB-sv40pA,
pAAVsc-CRM8-TTRe-NNMTp-MVM-FIXcoR338L-BGHpA,
pAAVss-CRM8-TTRe-NNMTp-MVM-FVIIIcodeltaB-sv40pA,
pAAVsc-3×CRM8-TTRe-CES1p-MVM-FIXcoR338L-BGHpA,
pAAVss-3×CRM8-TTRe-CES1p-MVM-FVIIIcodeltaB-sv40pA,
pAAVsc-TTRe-3×CRM8-CES1p-MVM-FIXcoR338L-BGHpA,
pAAVss-TTRe-3×CRM8-CES1p-MVM-FVIIIcodeltaB-sv40pA,
pAAVsc-CRM8-TTRe-CES1p-MVM-FIXcoR338L-BGHpA,
pAAVss-CRM8-TTRe-CES1p-MVM-FVIIIcodeltaB-sv40pA,
pAAVsc-3×CRM8-TTRe-PROCp-MVM-FIXcoR338L-BGHpA,
pAAVss-3×CRM8-TTRe-PROCp-MVM-FVIIIcodeltaB-sv40pA,
pAAVsc-TTRe-3×CRM8-PROCp-MVM-FIXcoR338L-BGHpA,
pAAVss-TTRe-3×CRM8-PROCp-MVM-FVIIIcodeltaB-sv40pA,
pAAVsc-CRM8-TTRe-PROCp-MVM-FIXcoR338L-BGHpA,
pAAVss-CRM8-TTRe-PROCp-MVM-FVIIIcodeltaB-sv40pA,
pAAVsc-3×CRM8-TTRe-APOC3p-MVM-FIXcoR338L-BGHpA,
pAAVss-3×CRM8-TTRe-APOC3p-MVM-FVIII-codeltaB-sv40pA,
pAAVsc-TTRe-3×CRM8-APOC3p-MVM-FIXcoR338L-BGHpA,
pAAVss-TTRe-3×CRM8-APOC3p-MVM-FVIII-codeltaB-sv40pA,
pAAVsc-CRM8-TTRe-APOC3p-MVM-FIXcoR338L-BGHpA,
pAAVss-CRM8-TTRe-APOC3p-MVM-FVIIIcodeltaB-sv40pA,
pAAVsc-3×CRM8-TTRe-MASP2p-MVM-FIXcoR338L-BGHpA,
pAAVss-3×CRM8-TTRe-MASP2p-MVM-FVIII-codeltaB-sv40pA,
pAAVsc-TTRe-3×CRM8-MASP2p-MVM-FIXcoR338L-BGHpA,
pAAVss-TTRe-3×CRM8-MASP2p-MVM-FVIII-codeltaB-sv40pA,
pAAVsc-CRM8-TTRe-MASP2p-MVM-FIXcoR338L-BGHpA,
pAAVss-CRM8-TTRe-MASP2p-MVM-FVIIIcodeltaB-sv40pA,
pAAVsc-3×CRM8-TTRe-SERPINC1p-MVM-FIXcoR338L-BGHpA,
pAAVss-3×CRM8-TTRe-SERPINC1p-MVM-FVIII-codeltaB-sv40pA,
pAAVsc-TTRe-3×CRM8-SERPINC1p-MVM-FIXcoR338L-BGHpA,
pAAVss-TTRe-3×CRM8-SERPINC1p-MVM-FVIII-codeltaB-sv40pA,
pAAVsc-CRM8-TTRe-SERPINC1p-MVM-FIXcoR338L-BGHpA, pAAVss-CRM8-TTRe-SERPINC1p-MVM-FVIII-codeltaB-sv40pA, pAAVsc-3×CRM8-TTRe-HAMPp-MVM-FIXcoR338L-BGHpA, pAAVss-3×CRM8-TTRe-HAMPp-MVM-FVIII-codeltaB-sv40pA pAAVsc-TTRe-3×CRM8-HAMPp-MVM-FIXcoR338L-BGHpA, pAAVss-TTRe-3×CRM8-HAMPp-MVM-FVIII-codeltaB-sv40pA pAAVsc-CRM8-TTRe-HAMPp-MVM-FIXcoR338L-BGHpA, or pAAVss-CRM8-TTRe-HAMPp-MVM-FVIIIcodeltaB-sv40pA.

In any one of said plasmids the poly adenylation signal can be replaced by any other poly adenylation signal such as e.g. the synthetic polyA site as defined by SEQ ID NO:56 (Synth.pA).

In other embodiments, the vector is a non-viral vector, such as a transposon-based vector.

Preferably, said transposon-based vectors are derived from Sleeping Beauty (SB) or PiggyBac (PB). A preferred SB transposon has been described in Ivics et al. (1997) and its hyperactive versions, including SB100X, as described in Mates et al. (2009). PiggyBac-based transposons are safe vectors in that they do no enhance the tumorigenic risk. Furthermore, liver-directed gene therapy with these vectors was shown to induce immune tolerance towards the transgene, in particular the hFIX or hFVIII transgene, comprised in the vector.

The transposon-based vectors are preferably administered in combination with a vector encoding a transposase for gene therapy. For example, the PiggyBac-derived transposon-based vector can be administered with wild-type PiggyBac transposase (Pbase) or mouse codon-optimized PiggyBac transposase (mPBase) Preferably, said transposases are hyperactive transposases, such as, for example, hyperactive PB (hyPB) transposase containing seven amino acid substitutions (130V, S103P, G165S, M282V, S509G, N538K, N570S) as described in Yusa et al. (2011), which is specifically incorporated by reference herein.

Transposon/transposase constructs can be delivered by hydrodynamic injection or using non-viral nanoparticles to transfect hepatocytes.

In a further aspect, the nucleic acid regulatory elements, the nucleic acid expression cassettes and the vectors described herein can be used in gene therapy. Gene therapy protocols, intended to achieve therapeutic gene product expression in target cells, in vitro, but also particularly in vivo, have been extensively described in the art. These include, but are not limited to, intramuscular injection of plasmid DNA (naked or in liposomes), interstitial injection, instillation in airways, application to endothelium, intra-hepatic parenchyme, and intravenous or intra-arterial administration (e.g. intra-hepatic artery, intra-hepatic vein). Various devices have been developed for enhancing the availability of DNA to the target cell. A simple approach is to contact the target cell physically with catheters or implantable materials containing DNA. Another approach is to utilize needle-free, jet injection devices which project a column of liquid directly into the target tissue under high pressure. These delivery paradigms can also be used to deliver viral vectors. Another approach to targeted gene delivery is the use of molecular conjugates, which consist of protein or synthetic ligands to which a nucleic acid- or DNA-binding agent has been attached for the specific targeting of nucleic acids to cells (Cristiano et al., 1993).

According to particular embodiments, the use of the nucleic acid expression cassettes and vectors as described herein is envisaged for gene therapy of liver cells (i.e. liver-directed gene therapy). According to a further particular embodiment, the use of the regulatory elements, expression cassettes or vectors is for gene therapy, in particular liver-directed gene therapy, in vivo. According to yet a further particular embodiment, the use is for a method of gene therapy, in particular liver-directed gene therapy, to treat hemophilia, in particular to treat hemophilia B or hemophilia A.

Gene transfer into mammalian hepatocytes has been performed using both ex vivo and in vivo procedures. The ex vivo approach requires harvesting of the liver cells, in vitro transduction with long-term expression vectors, and reintroduction of the transduced hepatocytes into the portal circulation (Kay et al., 1992; Chowdhury et al., 1991). In vivo targeting has been done by injecting DNA or viral vectors into the liver parenchyma, hepatic artery, or portal vein, as well as via transcriptional targeting (Kuriyama et al., 1991; Kistner et al., 1996). Recent methods also include intraportal delivery of naked DNA (Budker et al., 1996) and hydrodynamic tail vein transfection (Liu et al., 1999; Zhang et al., 1999). According to a further aspect, methods for expressing a protein in liver cells are provided, comprising the steps of introducing in liver cells the nucleic acid expression cassette or a vector as described herein and expressing the transgene protein product in the liver cells. These methods may be performed both in vitro and in vivo.

Methods of gene therapy for a subject in need thereof are also provided, comprising the steps of introducing in the liver of the subject a nucleic acid expression cassette containing a transgene encoding a therapeutic protein, and expressing a therapeutic amount of the therapeutic protein in the liver. According to a further embodiment, the method comprises the steps of introducing in the liver of the subject a vector comprising the nucleic acid expression cassette containing a transgene encoding a therapeutic protein, and expressing a therapeutic amount of the therapeutic protein in the liver.

According to a very specific embodiment, the therapeutic protein encoded by the transgene in the nucleic acid expression cassette or the vector is factor IX, and the method is a method for treating hemophilia B. By expressing factor IX in the liver via gene therapy, hemophilia B can be treated (Snyder et al., 1999). According to another very specific embodiment, the therapeutic protein encoded by the transgene in the nucleic acid expression cassette or the vector is factor VIII, and the method is a method for treating hemophilia A.

Except when noted differently, the terms "subject" or "patient" are used interchangeably and refer to animals, preferably vertebrates, more preferably mammals, and specifically includes human patients and non-human mammals, such as e.g. mice. Preferred patients or subjects are human subjects.

As used herein, the terms "treat" or "treatment" refer to both therapeutic treatment and prophylactic or preventative measures, wherein the object is to prevent or slow down (lessen) an undesired physiological change or disorder, such as the development or spread of proliferative disease, e.g., cancer. Beneficial or desired clinical results include, but are not limited to, alleviation of symptoms, diminishment of extent of disease, stabilised (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

As used herein, a phrase such as "a subject in need of treatment" includes subjects, such as mammalian subjects, that would benefit from treatment of a given condition, such as, hemophilia B or hemophilia A. Such subjects will typically include, without limitation, those that have been diagnosed with the condition, those prone to have or develop the said condition and/or those in whom the condition is to be prevented.

The term "therapeutically effective amount" refers to an amount of a compound or pharmaceutical composition effective to treat a disease or disorder in a subject, i.e., to obtain a desired local or systemic effect and performance. In a particular embodiment, the term implies that levels of factor IX in plasma equal to or higher than the therapeutic threshold concentration of 10 mU/ml (milli-units per milliliter) plasma, 50 mU/ml plasma, 100 mU/ml plasma, 150 mU/ml or 200 mU/ml plasma in a subject can be obtained by transduction or transfection of the vector according to any one the embodiments described herein into a subject. Due to the very high efficiency of the vectors and nucleic acid expression cassettes of the present invention, this high physiological level of factor IX in the subject can be obtained even by administering relatively low doses of vector. In another particular embodiment, the term implies that levels of factor VIII in plasma equal to or higher than the therapeutic threshold concentration of 10 mU/ml (milli-units per milliliter) plasma, 50 mU/ml plasma, 100 mU/ml plasma, 150 mU/ml plasma, 200 mU/ml plasma or higher can be obtained by transduction or transfection of any of the vectors disclosed herein into a subject. Due to the very high efficiency of the vectors and nucleic acid expression cassettes disclosed herein, these high physiological levels of factor VIII in the subject can be obtained even by administering relatively low doses of vector. The term thus refers to the quantity of compound or pharmaceutical composition that elicits the biological or medicinal response in a tissue, system, animal, or human that is being sought by a researcher, veterinarian, medical doctor or other clinician, which includes alleviation of the symptoms of the hemophilia being treated. In particular, these terms refer to the quantity of compound or pharmaceutical composition according to the invention which is necessary to prevent, cure, ameliorate, or at least minimize the clinical impairment, symptoms, or complications associated with hemophilia, in particular hemophilia B or hemophilia A, in either a single or multiple dose.

In particular, the transduction of the vector according to any one of the embodiments defined herein into the subject can be done at a dose lower than $2 \times 10^{11}$ vg/kg (viral genomes per kilogram) to obtain a therapeutic factor IX level of 10 mU/ml plasma or of 50 mU/ml plasma in a subject.

Alternatively, if a level of factor IX of 100 mU/ml plasma needs to be reached in a subject, the transduction of the vector according to any one of the embodiments defined herein into the subject can be done at a dose lower than or equal to $6 \times 10^{11}$ vg/kg.

Further, if a level of factor IX equal to 150 mU/ml plasma or higher needs to be reached, the transduction of the vector according to any one of the embodiments defined herein into the subject can be done at a dose lower than or equal than $2 \times 10^{12}$ vg/kg.

In a preferred embodiment, a level of factor IX of 200 mU/ml plasma or higher can be reached in a subject, when the transduction of the vector according to any one of the embodiments defined herein into the subject is done at a dose lower than or equal to $2 \times 10^{12}$ vg/kg.

In particular, the transduction of the vector according to any one of the embodiments defined herein into the subject can be done at a dose lower than or equal to $2 \times 10^{12}$ vg/kg (viral genomes per kilogram), such as lower than or equal to $1 \times 10^{12}$ vg/kg, $5 \times 10^{11}$ vg/kg, $2.5 \times 10^{11}$ vg/kg, $1 \times 10^{11}$ vg/kg, $5 \times 10^{10}$ vg/kg, $1 \times 10^{10}$ vg/kg, $5 \times 10^{9}$ vg/kg, or $1 \times 10^{9}$ vg/kg preferably at a dose lower than or equal to $2.5 \times 10^{11}$ vg/kg, to obtain a therapeutic factor VIII level of 10 mU/ml plasma, 50 mU/ml plasma, 100 mU/ml plasma, 150 mU/ml plasma, 200 mU/ml plasma, or higher in a subject.

For hemophilia therapy, efficacy of the treatment can, for example, be measured by assessing the hemophilia-caused bleeding in the subject. In vitro tests such as, but not limited to the in vitro activated partial thromboplastin time assay (APPT), test factor IX chromogenic activity assays, blood clotting times, factor IX or human factor VIII-specific ELISAs are also available. Any other tests for assessing the efficacy of the treatment known in the art can of course be used.

The nucleic acid expression cassette, the vector or the pharmaceutical composition of the invention may be used alone or in combination with any of the know hemophilia therapies, such as the administration of recombinant or purified clotting factors. The nucleic acid expression cassette, the vector or the pharmaceutical composition of the invention can thus be administered alone or in combination with one or more active compounds. The latter can be administered before, after or simultaneously with the administration of the said agent(s).

A further object of the invention are pharmaceutical preparations which comprise a therapeutically effective amount of the nucleic acid expression cassette or the expression vector as defined herein, and a pharmaceutically acceptable carrier, i.e., one or more pharmaceutically acceptable carrier substances and/or additives, e.g., buffers, carriers, excipients, stabilisers, etc. The term "pharmaceutically acceptable" as used herein is consistent with the art and means compatible with the other ingredients of a pharmaceutical composition and not deleterious to the recipient thereof. The term "pharmaceutically acceptable salts" as used herein means an inorganic acid addition salt such as hydrochloride, sulfate, and phosphate, or an organic acid addition salt such as acetate, maleate, fumarate, tartrate, and citrate. Examples of pharmaceutically acceptable metal salts are alkali metal salts such as sodium salt and potassium salt, alkaline earth metal salts such as magnesium salt and calcium salt, aluminum salt, and zinc salt. Examples of pharmaceutically acceptable ammonium salts are ammonium salt and tetramethylammonium salt. Examples of pharmaceutically acceptable organic amine addition salts are salts with morpholine and piperidine. Examples of pharmaceutically acceptable amino acid addition salts are salts with lysine, glycine, and phenylalanine. The pharmaceutical composition according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The pharmaceutical composition can be prepared in a manner known per se to one of skill in the art. For this purpose, the nucleic acid expression cassette or the expression vector as defined herein, one or more solid or liquid pharmaceutically acceptable excipients and, if desired, in combination with other pharmaceutical active compounds, are brought into a suitable administration form or dosage form which can then be used as a pharmaceutical in human medicine or veterinary medicine.

According to another aspect, a pharmaceutical composition is provided comprising a nucleic acid expression cassette containing a transgene encoding a therapeutic protein, and a pharmaceutically acceptable carrier. According to another embodiment, the pharmaceutical composition comprises a vector containing the nucleic acid expression cassette containing a transgene encoding a therapeutic protein, and a pharmaceutically acceptable carrier. According to further particular embodiments, the transgene encodes factor IX and the pharmaceutical composition is for treating hemophilia B or the transgene encodes factor VIII and the pharmaceutical composition is for treating hemophilia A.

The use of the nucleic acid expression cassette, its regulatory elements and the vector components as disclosed herein for the manufacture of these pharmaceutical compositions for use in treating hemophilia, preferably hemophilia B or hemophilia A, is also envisaged.

It is to be understood that although particular embodiments, specific constructions and configurations, as well as materials, have been discussed herein for methods and applications according to the present invention, various changes or modifications in form and detail may be made without departing from the scope and spirit of this invention.

The following examples are provided to better illustrate particular embodiments, and they should not be considered limiting the application. The application is limited only by the claims.

EXAMPLES

Example 1: Design of the AAV Vectors Used

The design of the self-complementary (sc), double-stranded adeno-associated viral (AAV) vectors is depicted in FIG. 1. The minimal transthyretin promoter (TTRm) is driving the expression of the human codon-optimized factor IX (co-FIX-R338L) containing the hyper-activating, thrombophilic FIX mutation (R338L). The minimal TTR promoter (TTRm) is used in conjunction with either the Serpin enhancer (SERP), a triple repeat of the Serpin enhancer (3×SERP), the native TTR enhancer (TTRe), or a combination of a triple repeat of the Serpin enhancer and the native TTR enhancer (3×SERP-TTRe). The minute virus of mouse intron (MVM), the bovine growth hormone polyadenylation site (BGHpA) or a synthetic polyadenylation site (Synt.pA), and the inverted terminal repeats (ITR) are indicated; 3×SerpEnh means that this element was cloned as a triplet repeat upstream of the TTRm. The vector size (including both ITR's) is indicated.

Figure 2:
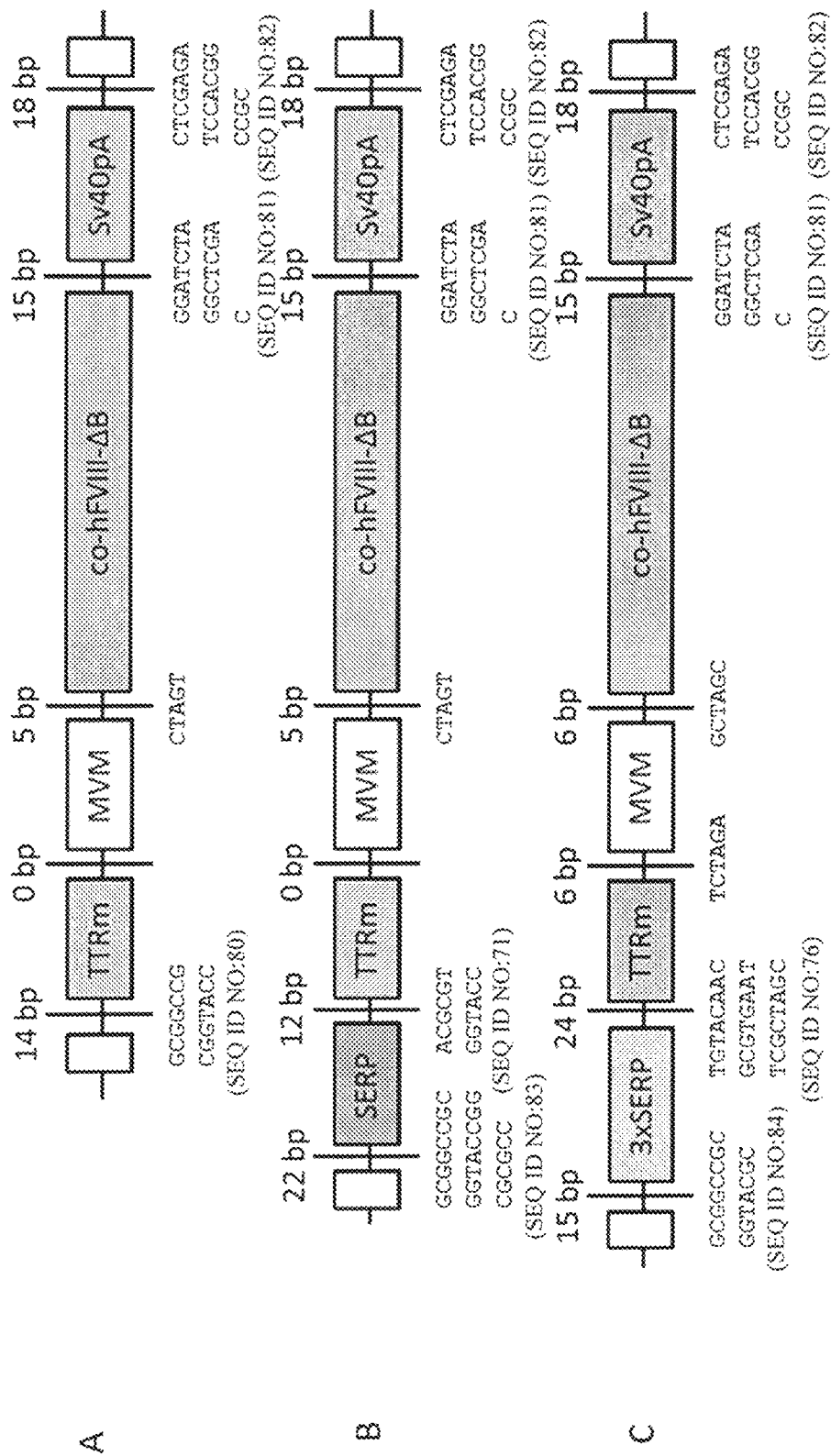
FIG. 2: Design of the single-stranded (ss) adeno-associated viral (AAV) vectors AAVss-TTRm-MVM-co-hFVIII-ΔB-Sv40pA (5160 bp) (A), AAVss-SerpEnh-TTRm-MVM-co-hFVIII-ΔB-Sv40pA (5252 bp) (B), AAVss-3×SerpEnh-TTRm-MVM-co-hFVIII-ΔB-Sv40pA (5410 bp) (C), AAVss-TTREnh-TTRm-MVM-co-hFVIII-ΔB-Sv40pA (5272 bp) (D), AAVss-3×SerpEnh-TTRm-MVM-co-hFVIII-ΔB-Synt.pA (5325 bp) (E), AAVss-3×SerpEnh-TTRm-co-hFVIII-ΔB-Synt.pA (5217 bp) (F), AAVss-3×SerpEnh-TTREnh-TTRm-MVM-co-hFVIII-ΔB-Sv40pA (5493 bp) (G), AAVss-3×SerpEnh-TTREnh-TTRm-co-hFVIII-ΔB-Synt.pA (5307 bp) (H), and AAVss-TTREnh-TTRm-co-hFVIII-ΔB-Synt.pA (5083 bp) (I). The minimal transthyretin promoter (TTRm) is driving the expression of the human codon-optimized B-domain deleted factor VIII (cohFVII-IdeltaB). The native TTR enhancer (TTRe), the Serpin enhancer (SERP), a triplet of the Serpin enhancer (3×SERP), or a combination of a triplet of the Serpin enhancer (3×SERP) and the native TTR enhancer (TTRe) may be cloned upstream of TTRm. The minute virus of mouse intron (MVM), the Simian Virus 40 (SV40) polyadenylation site (SV40pA) or a synthetic polyadenylation site (Synt.pA), and the inverted terminal repeats (ITR) are indicated. The sequences flanking/linking the different elements are indicated. The indicated vector sizes include both ITR's.
Figure 2:
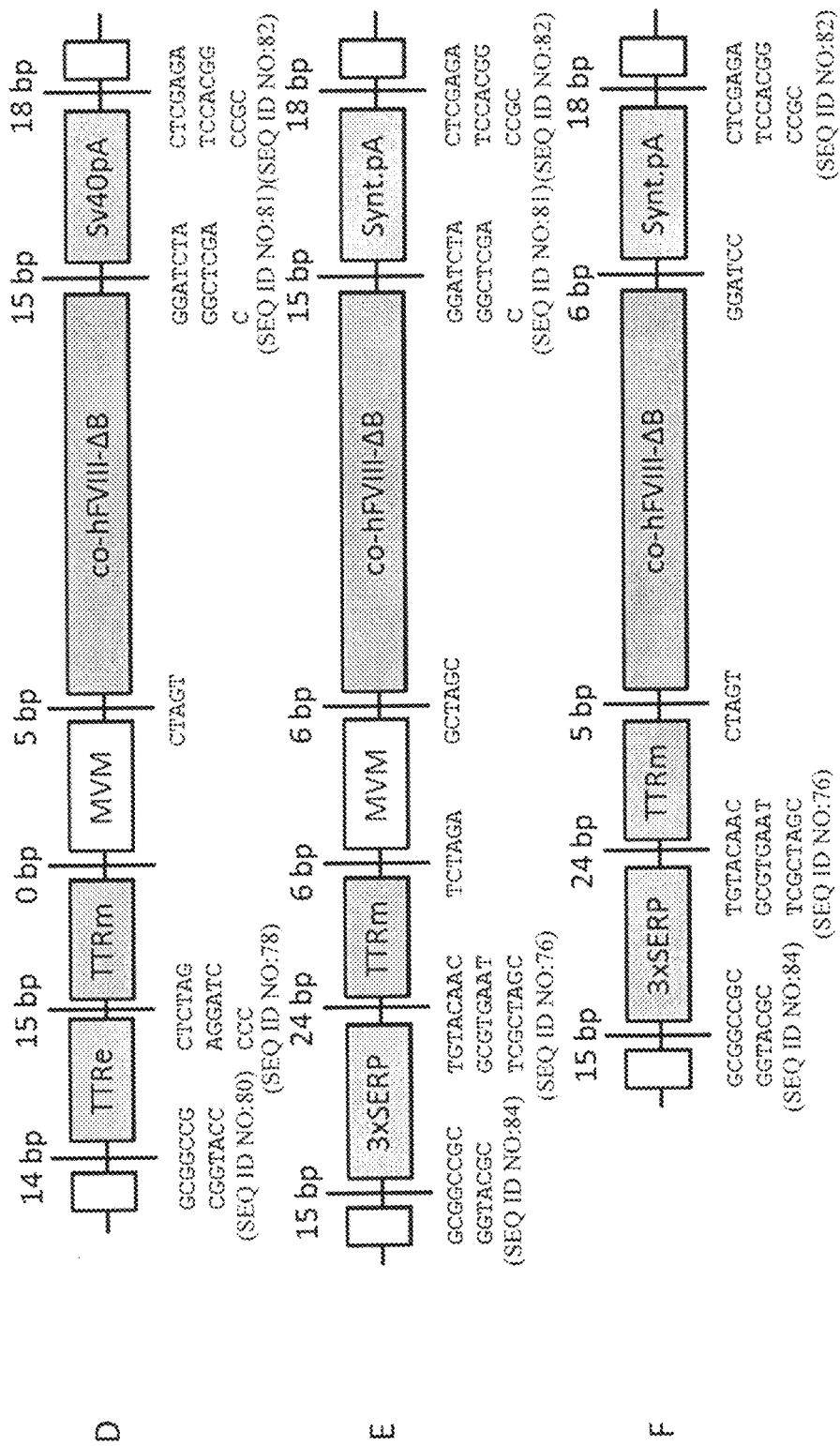
Figure 2:
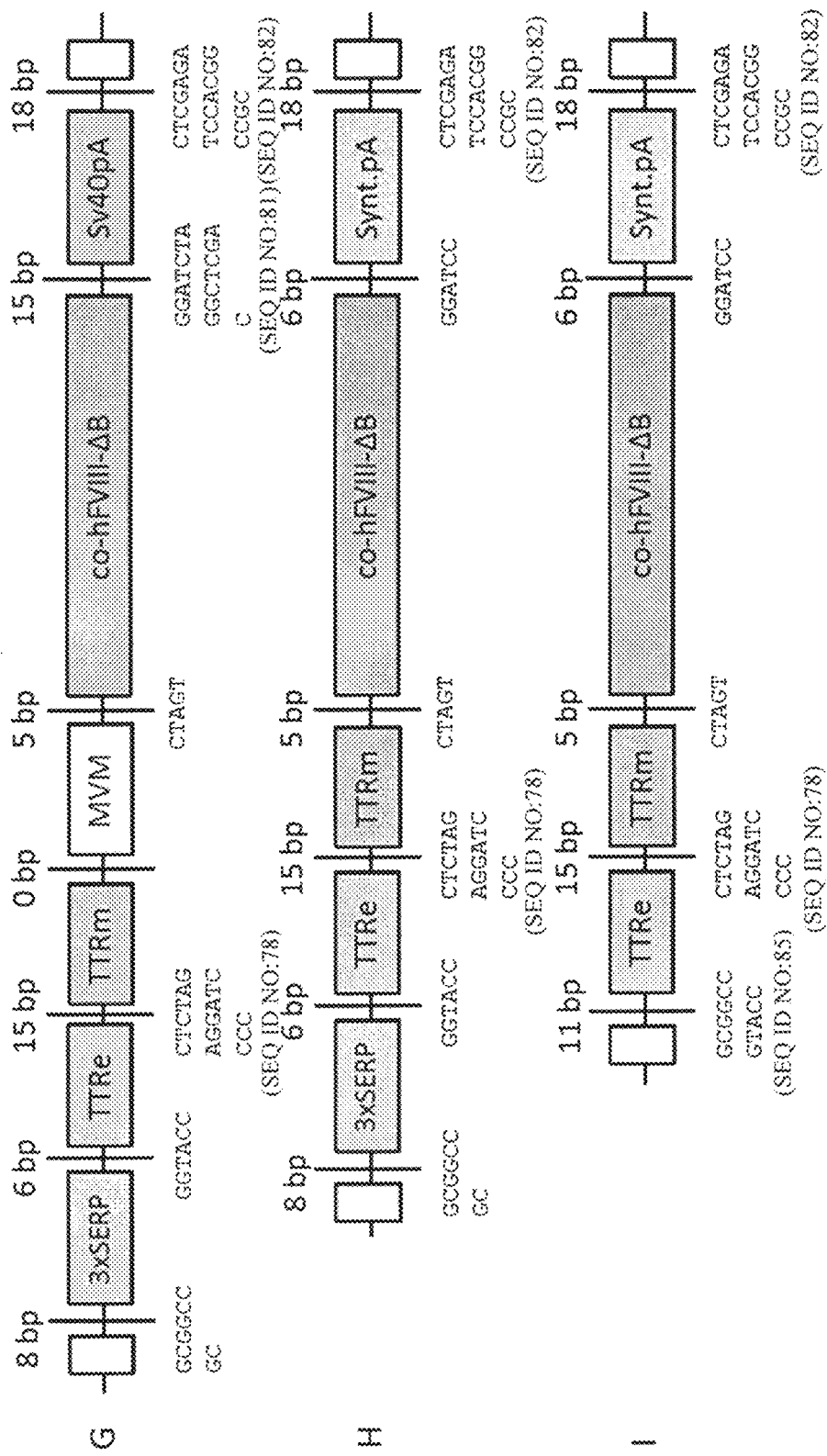

FIG. 2 shows the design of the single-stranded (ss) adeno-associated viral (AAV) vectors. The minimal transthyretin promoter (TTRm) is driving the expression of the human codon-optimized B-domain deleted factor VIII (cohFVIIIdeltaB). Optionally, the Serpin enhancer (SERP), a triple repeat of the Serpin enhancer (3×SERP), the native TTR enhancer (TTRe), or a combination of a triple repeat of the Serpin enhancer and the native TTR enhancer (3×SERP-TTRe) are cloned upstream of the TTRm. The minute virus of mouse intron (MVM), the Simian Virus 40 (SV40) polyadenylation site (Sv40pA) or a synthetic polyadenylation site (Synt.pA), and the inverted terminal repeats (ITR) are indicated. The vector size (including both ITR's) is indicated.

Materials and Methods:
Cloning Strategy

FIX constructs: The basic AAVsc-SerpEnh-TTRm-MVM-co-FIX-R338L-BGHpA plasmid (Nair et al. Blood, 2014) was used to create the other AAV-FIX constructs. This plasmid contains the Serp enhancer (SerpEnh), a liver-specific transthyretin (TTRm) promoter, a minute virus of mouse (MVM) small intron, a codon optimized human FIX transgene containing a R338L mutation, and a bovine growth hormone poly A (BGHpA). The 3×SerpEnh-TTRm-MVM sequence was synthesized by GeneArt (Life Technologies, Regensburg, Germany) and cloned into the basic construct using AscI and NheI, thereby replacing SerpEnh-TTRm-MVM, creating pAAVsc-3×SerpEnh-TTRm-MVM-co-FIX-R338L-BGHpA. Into this plasmid, the 3×SerpEnh sequence was replaced by the TTR enhancer (TTREnh) or 3×SerpEnh-TTREnh (constructed by GeneArt), thereby respectively creating pAAVsc-TTREnh-TTRm-MVM-co-FIX-R338L-BGHpA and pAAVsc-3×SerpEnh-TTREnh-TTRm-MVM-co-FIX-R338L-BGHpA respectively.

FVIII constructs: The basic AAVss-SerpEnh-TTRm-MVM-FVIIIcopt-Sv40pA plasmid was used to create the other AAV-FVIII constructs. This plasmid contains the Serp enhancer (SerpEnh), a liver-specific transthyretin (TTRm) promoter, an MVM intron, a codon optimized human FVIII transgene (Di Matteo et al., 2014), and an SV40 poly A. The SerpEnh was removed using KpnI, followed by re-ligation of the backbone, thereby creating pAAVss-TTRm-MVM-FVIIIcopt-Sv40pA. To create pAAVsc-3×SerpEnh-TTRm-MVM-FVIIIcopt-Sv40pA, the 3×SerpEnh was first cloned into a FVIIIcopt plasmid with a different backbone, after which the entire expression cassette (3×SerpEnh-TTRm-MVM-FVIIIcopt-Sv40pA) was cloned into the AAVss backbone using NotI and XhoI. From this final plasmid, 3×SerpEnh was removed and replaced with the TTREnh (constructed by GeneArt), thereby creating pAAVss-TTREnh-TTRm-MVM-FVIIIcopt-Sv40pA. In order to generate pAAVss-3×SerpEnh-TTREnh-TTRm-MVM-cohFVIIIdeltaB-SV40pA (5493 bp), pAAVss-TTREnh-TTRm-MVM-cohFVIIIdeltaB-SV40pA (the vector) was restricted with NotI-Acc651. A fragment with 3×Serp flanked by NotI/Acc651 was synthesized by GenArt and ligated into the restricted vector.

AAV Vector Production, Purification and Titration

AAV vectors were produced by calcium phosphate (Invitrogen Corp, Carlsbad, Calif.) co-transfection of AAV-293 human embryonic kidney carcinoma cells (Stratagene, Carlsbad, Calif., catalog No 240073; with the pAAV plasmid of interest, an adenoviral helper plasmid and a chimeric packaging constructs that delivers the AAV2 Rep gene together with the AAV8 or AAV9 Cap gene, as described previously (VandenDriessche et al, 2007, VandenDriessche et al; 2007, J. Thromb. Haemost. JTH 5:16-24). For the AAV-FIX vectors, the AAV9 serotype was used and for the AAV-FVIII vectors the AAV8 serotype. The AAV-293 cells are free of microbial contamination as determined by PCR for detection of mycoplasma. Briefly, two days post transfection, cells were harvested and vector particles were purified using isopycnic centrifugation methods. Harvested cells were lysed by successive freeze/thaw cycles and sonication, treated with benzonase (Novagen, Madison, Wis.) and deoxycholic acid (Sigma-Aldrich, St. Louis, Mo.) and subsequently subjected to 2 successive rounds of cesium chloride (Invitrogen Corp, Carlsbad, Calif.) density gradient ultracentrifugation. Fractions containing the AAV vector were collected, concentrated in 1 mM $MgCl_2$ in Dulbecco's phosphate buffered saline (PBS) (Gibco, BRL) and stored at −80° C. The vector titers (in viral genomes (vg)/ml) were determined by quantitative real-time PCR using specific primers. For the FIX vectors, primers specific for the bovine growth hormone poly A sequence were used. The forward and reverse primers used were 5'-GCCTTCTAGTTGCCAGCCAT-3' (SEQ ID NO:60) and 5'-GGCACCTTCCAGGGTCAAG-3' (SEQ ID NO:61), respectively. For the FVIII vectors, primers specific for the FVIII gene sequence were used. The forward and reverse primers used were 5'-AACGGCTACGTGAACAGAAG-3' (SEQ ID NO:62) and 5'-GATAGGGCTGATTTCCAGGC-3' (SEQ ID NO:63), respectively. Reactions were performed in SybrGreen PCR Master Mix (Applied Biosystems, Foster City, Calif., USA), on an ABI 7500 Real-Time PCR System (Applied Biosystems, Foster City, Calif., USA). Known copy numbers (102-107) of the respective vector plasmids used to generate the corresponding AAV vectors, carrying the appropriate cDNAs were used to generate the standard curves.

Animal Study and Blood Collection

AAV vector administration is carried out by tail vein injection on adult C57B6 mice at two different doses: $1 \times 10^9$ (low dose) and $5 \times 10^9$ (high dose) vector genomes (vg) per mouse as detailed below. Mice were bled at different time points after gene transfer in order to evaluate the FIX/FVIII gene expression. The pAAVss-TTREnh-TTRm-MVM-co-hFVIII-deltaB-SV40pA and pAAVss-3×SerpEnh-TTREnh-TTRm-MVM-co-hFVIII-deltaB-SV40pA plasmid constructs were administered by hydrodynamic delivery into C57BL/6 mice at a dose of 300 ng per mouse. Animals were anesthetized using isoflurane and blood samples were taken by retro-orbital bleeding on trisodium citrate. Plasma was prepared immediately after blood collection by centrifugation at 14000 rpm for 3 minutes at 4° C. Plasma was immediately stored at −80° C. for further analysis.

FIX ELISA

The concentration of hFIX antigens in citrated plasma was measured by enzyme-linked immunosorbent assay (ELISA) using manufacturer's protocol (Diagnostica Stago, France). The hFIX standards (available in the kit) were serially diluted using the dilution buffer and used for calibration. Here the 100% of the standard corresponds to 5000 ng of FIX protein. The aliquots of the plasma samples were thawed and diluted in order to make their reading fall in the linear range of standards. Standards and samples were then added to a 96 well plate pre-coated with primary anti-human FIX antibodies. After an incubation of 1 hour at room temperature, the plate was washed and a solution containing secondary antibodies coupled to peroxidase were added followed by another incubation of 1 hour at room temperature. After incubation, the peroxidase substrate TMB (chromogenic solution) was added which resulted in color development. After exact 5 minutes of incubation 1M H2SO4 was added to all wells to stop the reaction. After an incubation of 15 minutes the absorbance was measured at 450 nm using the microplate reader. Using the obtained standard curve, FIX levels were determined.

FVIII ELISA

The concentration of hFVIII antigens in citrated plasma was measured by enzyme-linked immunosorbent assay (ELISA) using manufacturer's protocol (Diagnostica Stago, France). The hFVIII standards (available in the kit) were serially diluted using the dilution buffer and used for calibration. Here the 100% of the standard corresponds to 200 ng of FVIII protein. The aliquots of the plasma samples were thawed and diluted in order to make their reading fall in the linear range of standards. Standards and samples were then added to a 96 well plate pre-coated with primary anti-human FVIII antibodies. After an incubation of 2 hour at room temperature, the plate was washed and a solution containing secondary antibodies coupled to peroxidase was added followed by another incubation of 2 hour at room temperature. After incubation, the peroxidase substrate TMB (chromogenic solution) was added which resulted in color development. After exact 5 minutes of incubation 1M H2SO4 was added to all wells to stop the reaction. After an incubation of 15 minutes the absorbance was measured at 450 nm using the microplate reader. Using the obtained standard curve, FIX levels were determined.

Statistics

Figure 3A:
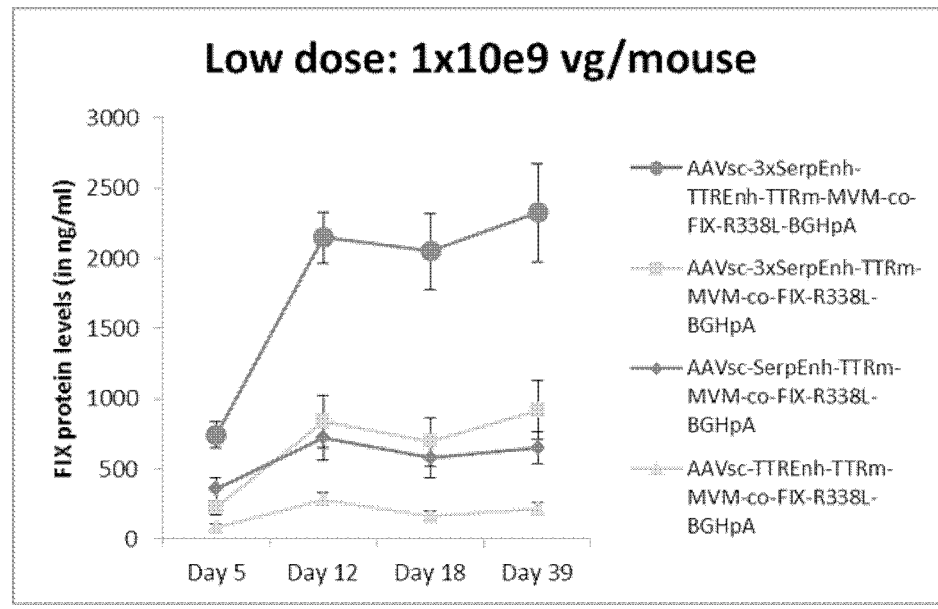
FIG. 3: FIX protein levels upon transduction of the described SC-vectors. 3a): the protein expression levels achieved upon transduction with 1×10e9 vg/mouse (Low Dose) for the different vector systems described in FIG. 1; 3b): the protein expression levels achieved upon transduction with 5×10e9 vg/mouse (High Dose) for the different vector systems described in FIG. 1.
Figure 3B:
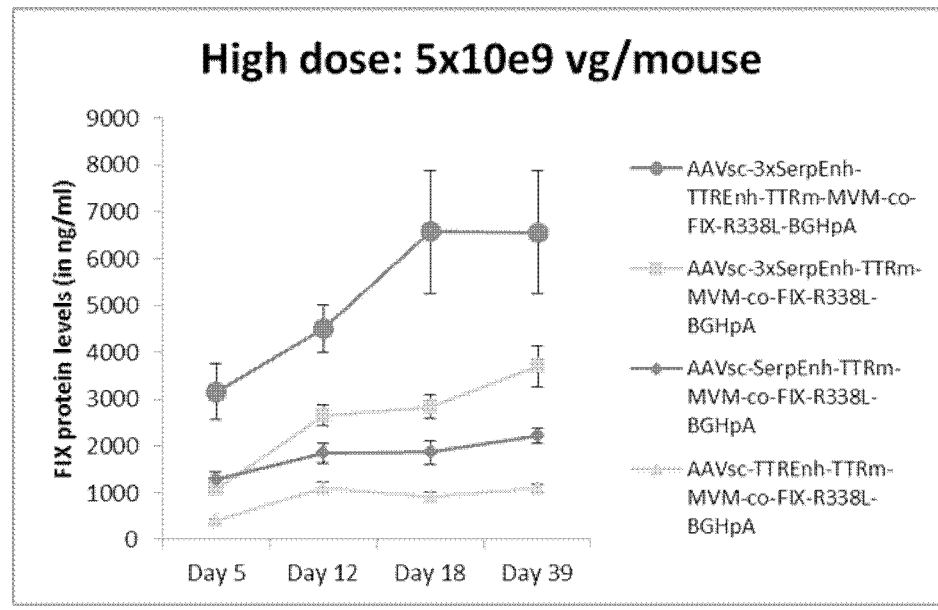
Figure 4A:
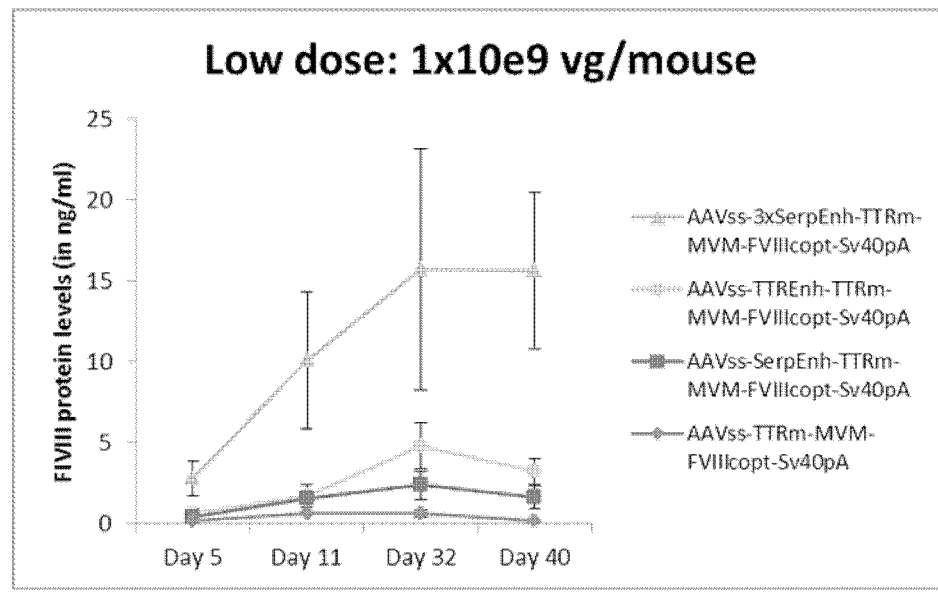
FIG. 4: FVIII protein levels upon transduction of the described SS-vectors. 4a): the protein expression levels achieved upon transduction with 1×10e9 vg/mouse (Low Dose) for the different vector systems described in FIG. 2; 4b): the protein expression levels achieved upon transduction with 5×10e9 vg/mouse (High Dose) for the different vector systems described in FIG. 2.
Figure 4B:
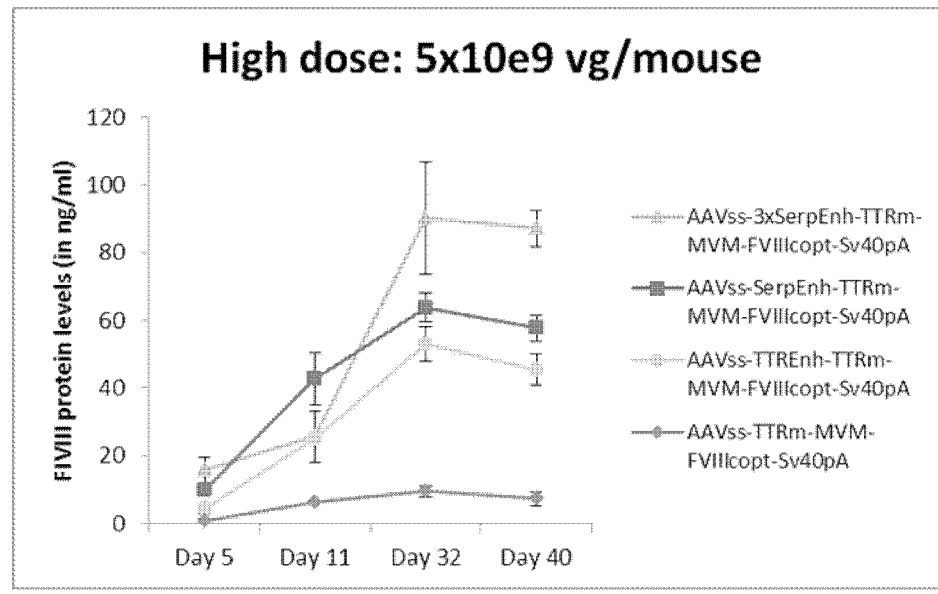
Figure 5:
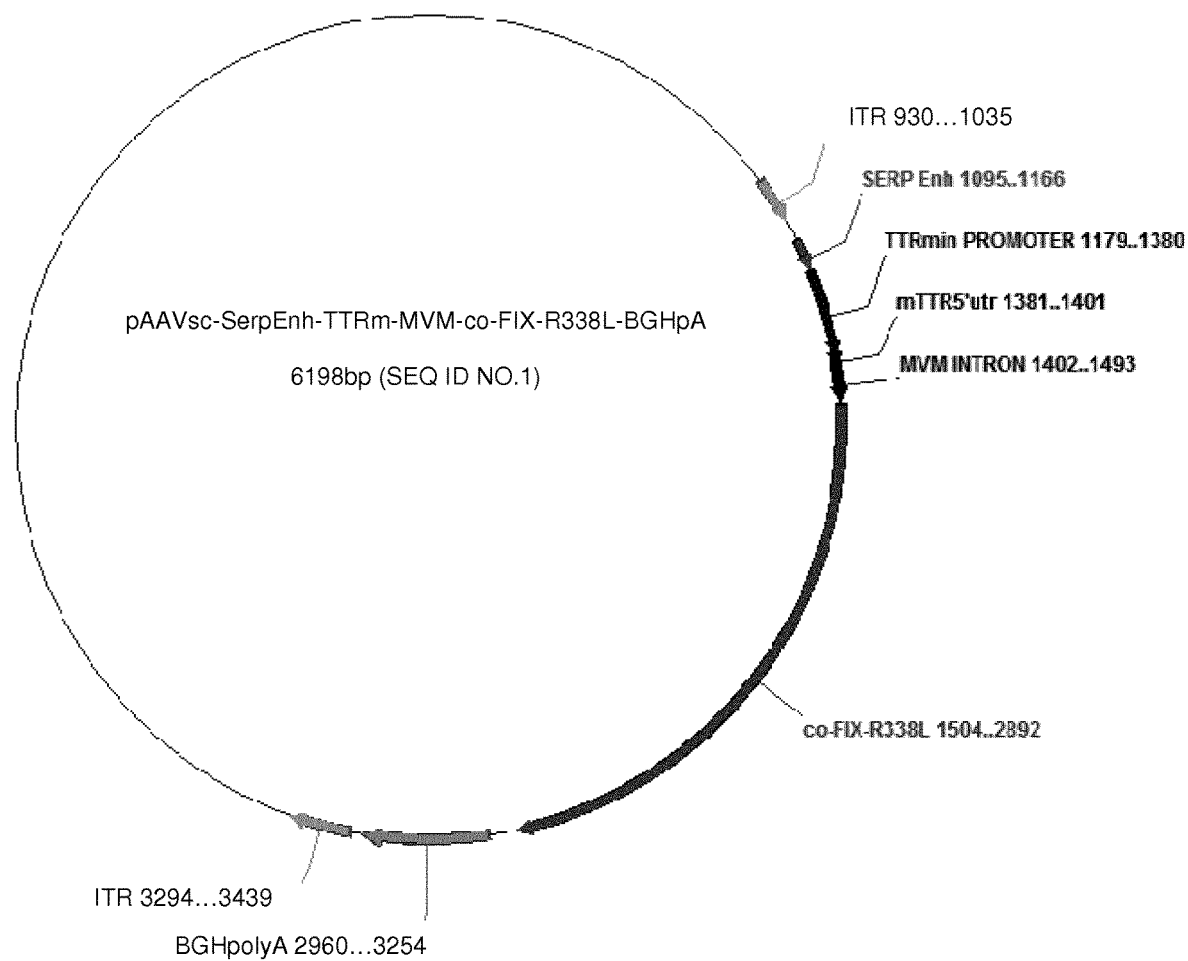
FIG. 5: Plasmid map of the pAAVsc-SerpEnh-TTRm-MVM-co-FIX-R338L-BGHpA vector

Data were analyzed using Microsoft Excel Statistics package. Values shown in FIGS. 3 and 4 are the mean+SEM. Significance values were obtained by comparison using t-test.

Viral Administration

Male adult C57BL/6 mice (18-20 grams) were administrated with AAV9 FIX vectors (see the table below) by tail vain injection at doses of $1 \times 10^9$ vg/mouse and $5 \times 10^9$ vg/mouse.

| Construct | Size | Dose | Mice |
|---|---|---|---|
| AAV9sc-SerpEnh-TTRm-MVM-co-FIX-R338L-BGHpolyA | 2510 bp | $1 \times 10^9$ | 4 |
| | | $5 \times 10^9$ | 4 |
| AAV9sc-3xSerpEnh-TTRm-MVM-co-FIX-R338L-BGHpolyA | 2682 bp | $1 \times 10^9$ | 4 |
| | | $5 \times 10^9$ | 4 |
| AAV9sc-TTREnh-TTRm-MVM-co-FIX-R338L-BGHpolyA | 2540 bp | $1 \times 10^9$ | 4 |
| | | $5 \times 10^9$ | 4 |
| AAV9sc-3xSerpEnh-TTREnh-TTRm-MVM-co-FIX-R338L-BGHpolyA | 2760 bp | $1 \times 10^9$ | 4 |
| | | $5 \times 10^9$ | 4 |

Male adult CB17SCID mice (18-20 grams) were administrated with AAV8 XVIII vectors (see the table below) by tail vain injection at doses of $1 \times 10^9$ vg/mouse and $5 \times 10^9$ vg/mouse.

| Construct | Size | Dose | Mice |
|---|---|---|---|
| AAV8ss-TTRm-MVM-FVIIIcopt-sv40pA | 5160 bp | $1 \times 10^9$ | 4 |
| | | $5 \times 10^9$ | 4 |
| AAV8ss-SerpEnh-TTRm-MVM-FVIIIcopt-sv40pA | 5252 bp | $1 \times 10^9$ | 4 |
| | | $5 \times 10^9$ | 4 |
| AAV8ss-3xSerpEnh-TTRm-MVM-FVIIIcopt-sv40pA | 5410 bp | $1 \times 10^9$ | 4 |
| | | $5 \times 10^9$ | 4 |
| AAV8ss-TTREnh-TTRm-MVM-FVIIIcopt-sv40pA | 5272 bp | $1 \times 10^9$ | 4 |
| | | $5 \times 10^9$ | 4 |

Plasmid Administration

Male adult C57BL/6 mice (22-24 grams) were administrated with respective plasmids (see the table below) by hydrodynamic tail vein injection at doses of 300 ng.

| Construct | Size | Dose | Mice |
|---|---|---|---|
| pAAVss-TTREnh-TTRm-MVM-co-hFVIII-deltaB-SV40pA | 5272 p | 300 ng | 2 |
| pAAVss-3XSerpEnh-TTREnh-TTRm-MVM-co-hFVIII-deltaB-SV40pA | 5493 bp | 300 ng | 2 |

Results

Factor IX:

The AAV vector containing 3xSerpEnh-TTREnh-TTRm, with 3 copies of the Serp enhancer combined with the natural TTRe enhancer, and in combination with the TTRm promoter, led to the highest FIX levels compared to any of the other expression cassettes, over 4 time points until at least day 39 after AAV vector injection. The FIX expression showed a continuous increase over time.

The AAV vector containing the most robust 3xSerpEnh-TTREnh-TTRm regulatory elements showed about 11 to 6 fold (at low and high vector dose, respectively) higher FIX expression when compared to a control AAV vector that expressed FIX from the TTREnh-TTRm enhancer/promoter (i.e. lacking the SerpEnh enhancer).

The AAV vector containing the most robust 3xSerpEnh-TTREnh-TTRm regulatory elements showed about 4 to 3 fold (low and high vector dose, respectively) higher FIX expression when compared to a vector that expressed FIX from the SerpEnh-TTRm enhancer/promoter, which contains only one instead of 3 copies of the Serp enhancer, and no TTRe enhancer.

The AAV vector containing the most robust 3xSerpEnh-TTREnh-TTRm showed about 3 to 2 fold (low and high vector dose, respectively) higher expression when compared to a vector that expressed FIX from the 3xSerpEnh-TTRm enhancer/promoter which also 3 copies of the Serp enhancer, but is devoid of the TTR enhancer.

Factor VIII

The AAV vector containing 3xSerpEnh-TTRm, with 3 copies of the Serp enhancer, led to the highest FVIII levels compared to any of the other expression cassettes, until at least day 40 after AAV vector injection. The FVIII expression showed a continuous increase over time.

The AAV vector containing the 3xSerpEnh-TTRm regulatory elements showed about 30 to 12 fold (low and high vector dose, respectively) higher FVIII expression when compared to a reference control cassette (TTRm) which consist of only the TTR minimal promoter and that do not contain any enhancer.

The AAV vector containing the 3xSerpEnh-TTRm regulatory elements showed about 10 to 1.5-fold (low and high vector dose, respectively) higher FVIII expression when compared to an AAV vector containing SerpEnh-TTRm with only one copy of the Serp enhancer.

Figure 15:
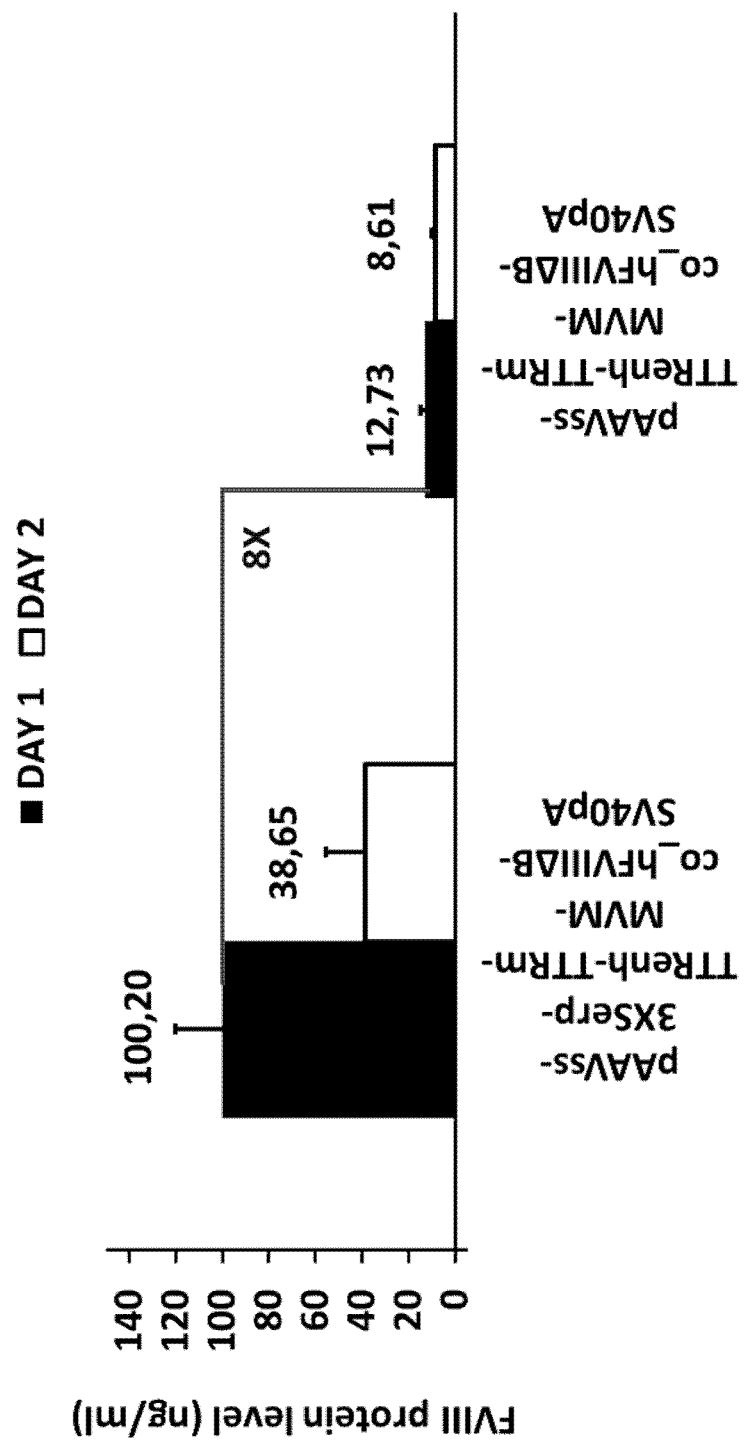
FIG. 15: FVIII protein levels in C57BL6 mice injected with the pAAVss-3×SerpEnh-TTREnh-TTRm-MVM-co-hFVIII-deltaB-SV40pA and pAAVss-TTREnh-TTRm-MVM-co-hFVIII-deltaB-SV40pA plasmids as described in FIG. 2. C57BL6 mice were injected with 300 ng of the respective plasmids. FVIII protein levels were measured by ELISA in plasma samples collected on day 1 (black bar) and day 2 (white bar) post injection.

The AAV vector containing the 3xSerpEnh-TTRm regulatory elements showed about 5 to 2 fold (low and high vector dose, respectively) higher expression when compared to an AAV vector containing the TTREnh-TTRm enhancer/promoter. The 3x SerpEnh regulatory element could further increase FVIII expression from the TTRenh-TTRm enhancer/promoter (FIG. 15). FVIII protein levels were about 8 to 5 fold higher in mice injected with the pAAVss-3xSerpEnh-TTREnh-TTRm-MVM-co-hFVIII-deltaB- SV40pA plasmid as compared to the pAAVss-TTREnh-TTRm-MVM-co-hFVIII-deltaB-SV40pA plasmid.

Example 2 Studying the In Vivo Effect of 3×CRM8 and TTRenhancer on FVIII Expression in Various Constructs by Hydrodynamic Injection (2 ml) into CB17-SCID Mice The aim of this example was to study the in vivo effect of 3×CRM8 and TTRenhancer on FVIII expression in various constructs by hydrodynamic injection (2 ml) into CB17-SCID mice.

Figure 22:
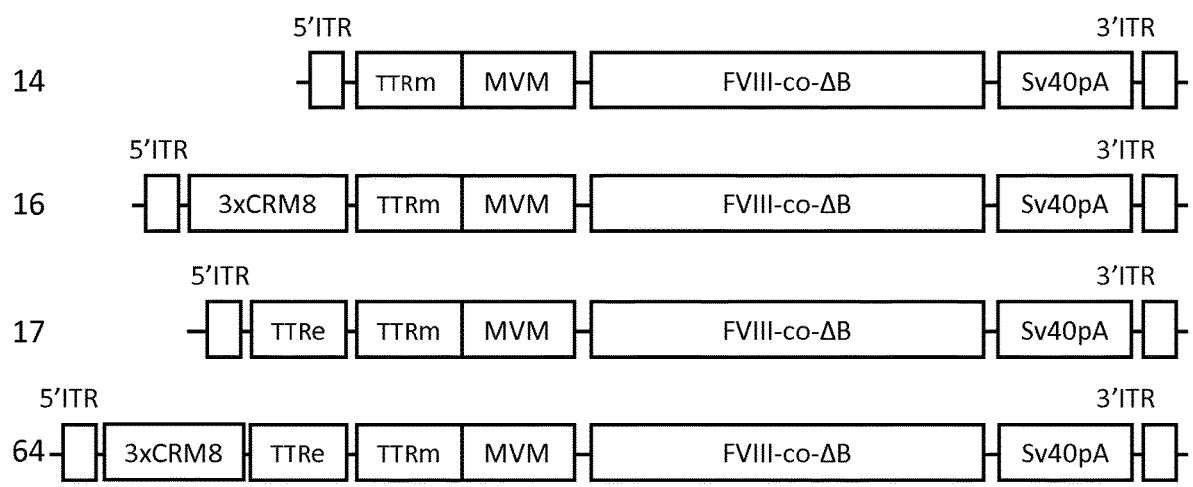
FIG. 22: Design of comparative example of self-complementary (sc), double-stranded adeno-associated viral (AAV) vectors expressing co-FVIII delta-B. The following vectors were compared for FVIII expression levels: pAAVss-TTRm-MVM-coFVIIIdeltaB-Sv40pA (SEQ ID NO. 14); pAAVss-3×SerpEnh-TTRm-MVM-coFVIIIdeltaB-Sv40pA (SEQ ID NO:16); pAAVss-TTRe-TTRm-MVM-coFVIIIdeltaB-Sv40pA (SEQ ID NO:17) and pAAVss-3×SerpEnh-TTRe-TTRm-MVM-coFVIIIdeltaB-Sv40pA (SEQ ID NO:22).

Constructs:

The following vectors were compared for FVIII expression levels (cf. FIG. 22):

pAAVss-TTRm-MVM-coFVIIIdeltaB-Sv40pA (SEQ ID NO. 14);

pAAVss-3×SerpEnh-TTRm-MVM-coFVIIIdeltaB-Sv40pA (SEQ ID NO:16);

pAAVss-TTRe-TTRm-MVM-coFVIIIdeltaB-Sv40pA (SEQ ID NO:17); and pAAVss-3×SerpEnh-TTRe-TTRm-MVM-coFVIIIdeltaB-Sv40pA (SEQ ID NO:22).

In a first experiment, the following conditions were used:

Mouse Model:
CB17-SCID, male, adult mice of 18-20 grams
Doses:
150 ng plasmid/mouse
Analysis Points:
Blood collection at Day1
No of Mice:
3 per condition
Design:
See the table below

| Construct | condition | |
|---|---|---|
| | Dose | Mice |
| PBS control | — | 3 |
| 1. pAAVss-TTRe-TTRm-MVM-FVIIIcoΔB-sv40pA | 300 ng | 3 |
| 2. pAAVss-3xCRM8-TTRe-TTRm-MVM-FVIIIcoΔB-sv40pA | 300 ng | 3 |

Figure 25A:
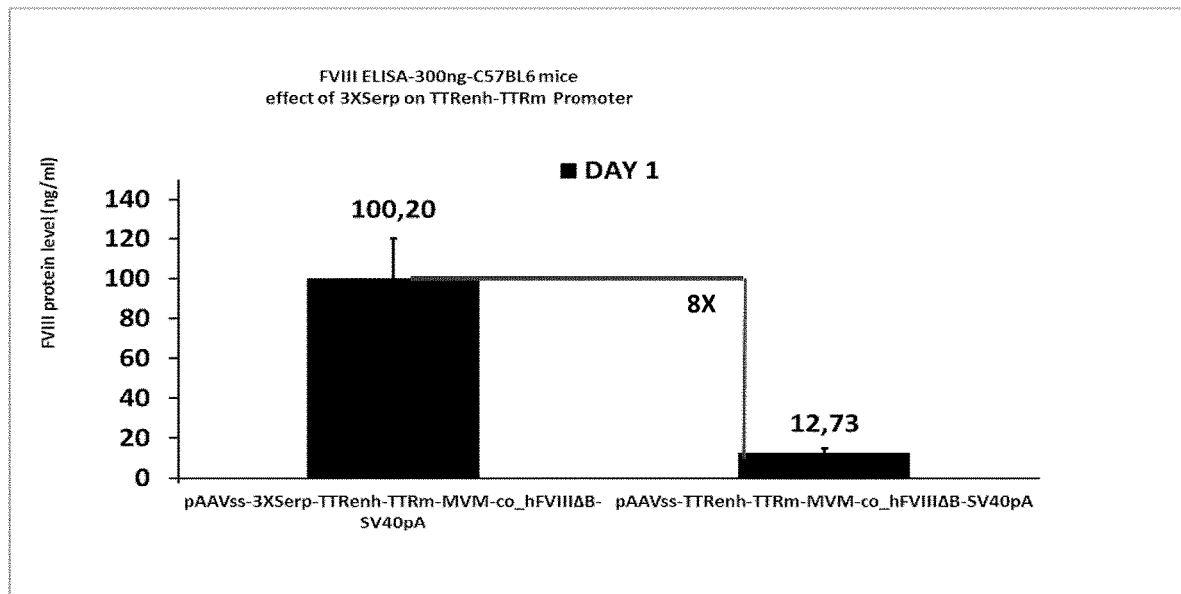
FIG. 25: a) Graph depicting the effect of the 3×Serp enhancer on the TTRenh-TTRm promoter in regulating the FVIII expression in C57BL6 mice injected with 300 ng of respective plasmids. The FVIII expression profile was tested using the ELISA, in the plasma samples collected Day 1. The presence of 3×Serp enhancer seems to elevate the FVIII expression by 8 fold. b) Graph comparing different constructs tested on FVIII expression as outlined in example 2.

Results:

The expression level of FVIII was analysed and compared. FIG. 25a example shows a graph depicting the effect of the 3×Serp enhancer on the TTRenh-TTRm promoter in regulating the FVIII expression in C57BL6 mice injected with 300 ng of respective plasmids. The FVIII expression profile was tested using the ELISA, in the plasma samples collected Day 1. The presence of 3×Serp enhancer seems to elevate the FVIII expression by 8 fold.

In a second experiment the following conditions were used:

Mouse Model:
CB17-SCID, male, adult mice of 18-20 grams
Doses:
150 ng plasmid/mouse
Analysis Points:
Blood collection at Day1
No of Mice:
3 per condition
Design:
See the table below

| Construct | condition | |
|---|---|---|
| | Dose | Mice |
| PBS control | — | 3 |
| 1. pAAVss-TTRm-MVM-FVIIIcoΔB-sv40pA | 150 ng | 3 |
| 2. pAAVss-3xCRM8-TTRm-MVM-FVIIIcoΔB-sv40pA | 150 ng | 3 |
| 3. pAAVss-TTRe-TTRm-MVM-FVIIIcoΔB-sv40pA | 150 ng | 3 |
| 4. pAAVss-3xCRM8-TTRe-TTRm-MVM-FVIIIcoΔB-sv40pA | 150 ng | 3 |

Figure 25B:
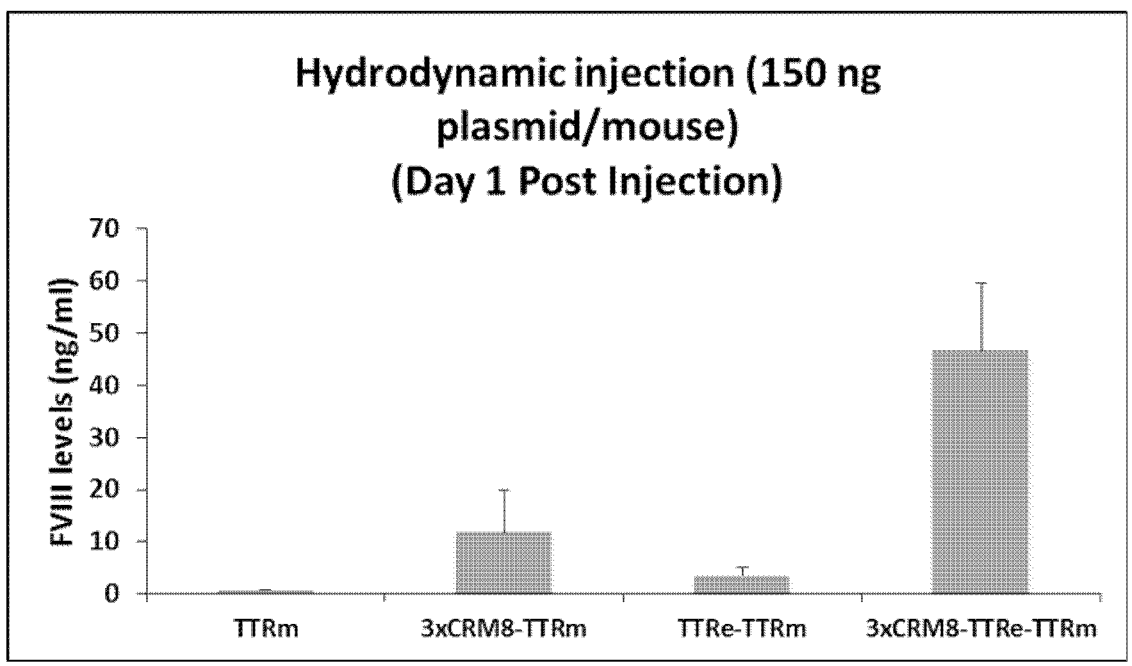

Results:

FIG. 25b shows the compiled data from comparing the 4 constructs (see table below for actual FVIII expression values). Addition of 3×SERP to the TTRm construct enhances FVIII expression 17 fold. Addition of 3×SERP to the TTRe-TTRm construct enhances FVIII expression 13 fold. Addition of TTRe to the 3×SERP-TTRm construct still enhances FVIII expression 4 fold.

| Vectors | FVIII level (ng/ml) |
|---|---|
| TTRm | 0.68 |
| 3xCRM8-TTRm | 11.74 |
| TTRe-TTRm | 3.52 |
| 3xCRM8-TTRe-TTRm | 46.67 |

Example 3: Studying the In Vivo Effect of 3×CRM8 and TTRenhancer in Combination with an AAT Promoter on FIX Expression in Various Constructs by Hydrodynamic Injection (2 ml) into C57BL/6 Mice In this experiment, the TTRm minimal promotor is replaced by another liver-specific promotor to show the versatility of the regulator element.

As a first example, the AAT liver-specific promoter (AAT) is tested.

Figure 23:
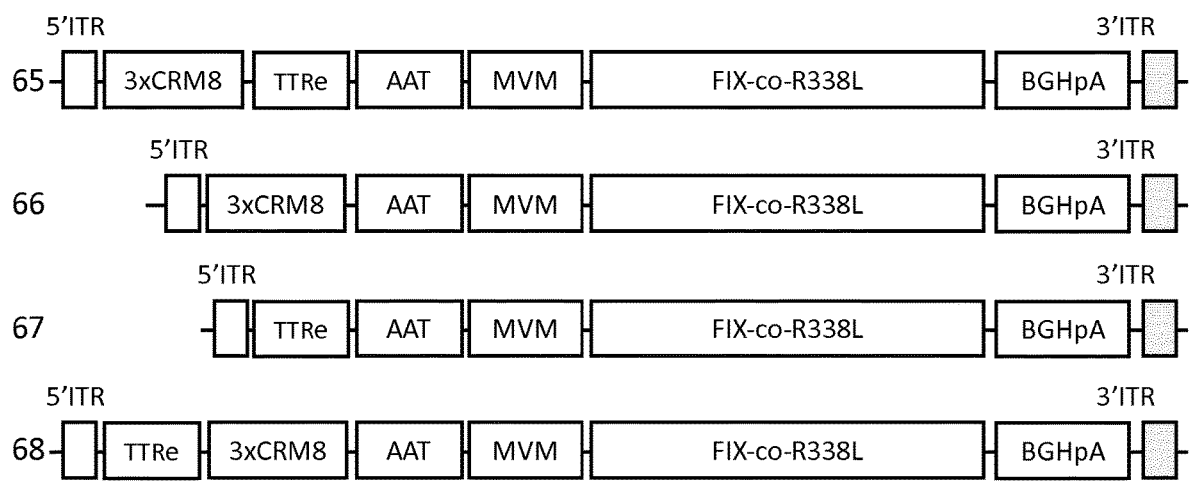
FIG. 23: Design of comparative example of self-complementary (sc), double-stranded adeno-associated viral (AAV) vectors expressing co-FIX. The following vectors were compared for FIX expression: pAAVss-3×SerpEnh-TTRe-AAT-MVM-co-FIX-R338L-BGHpA (SEQ ID NO:65); pAAVss-3×SerpEnh-TTRe-AAT-MVM-co-FIX-R338L-BGHpA (SEQ ID NO:66); pAAVss-3×SerpEnh-TTRe-AAT-MVM-co-FIX-R338L-BGHpA (SEQ ID NO:67); and pAAVss-3×SerpEnh-TTRe-AAT-MVM-co-FIX-R338L-BGHpA (SEQ ID NO:68).

Constructs:

Four different constructs were prepared as depicted in FIG. 23 (the sequences are depicted in FIG. 24):

pAAVss-3×SerpEnh-TTRe-AAT-MVM-co-FIX-R338L-BGHpA (SEQ ID NO:65);

pAAVss-3×SerpEnh-AAT-MVM-co-FIX-R338L-BGHpA (SEQ ID NO:66);

pAAVss-TTRe-AAT-MVM-co-FIX-R338L-BGHpA (SEQ ID NO:67); and pAAVss-TTRe-3×SerpEnh-AAT-MVM-co-FIX-R338L-BGHpA (SEQ ID NO:68);

All constructs tested make use of the AAT promoter (SEQ ID NO.64).

Mouse Model:
C57BL/6, male, adult mice of 18-20 grams
Doses:
1 µg and 2 µg plasmid/mouse
Analysis Points:
Blood collection at D1, D2
No of Mice:
3 per condition
Design:
See the table below

| Construct | condition | |
|---|---|---|
| | Dose | Mice |
| PBS control | — | 3 |
| 1. pAAVsc-3xCRM8-TTRe-AAT-MVM-FIXcoR338L-BGHpA | 1 µg | 3 |
| | 2 µg | 3 |
| 2. pAAVsc-3xCRM8-AAT-MVM-FIXcoR338L-BGHpA | 1 µg | 3 |
| | 2 µg | 3 |
| 3. pAAVsc-TTRe-AAT-MVM-FIXcoR338L-BGHpA | 1 µg | 3 |
| | 2 µg | 3 |
| 4. pAAVsc-TTRe-3xCRM8-AAT-MVM-FIXcoR338L-BGHpA | 1 µg | 3 |
| | 2 µg | 3 |

Also the corresponding FVIII constructs will be tested for FVIII expression with the AAT promotor, hence encompassing the following constructs:
pAAVss-CRM8-TTRe-AAT-MVM-FVIIIcodeltaB-sv40pA.
pAAVss-3×CRM8-AAT-MVM-FVIIIcodeltaB-sv40pA.
pAAVss-3×CRM8-TTRe-AAT-MVM-FVIIIcodeltaB-sv40pA and
pAAVss-TTRe-3×CRM8-AAT-MVM-FVIIIcodeltaB-sv40pA.

In analogy, the following examples follow the outline of the example with the AAT promoter above, but each time with a different liver-specific promoter or minimal promoter.

In further examples, the albumin promotor (ALBp) is used to replace the TTRm promotor in said constructs, hence encompassing the following constructs:
pAAVsc-3×CRM8-TTRe-ALBp-MVM-FIXcoR338L-BGHpA,
pAAVss-3×CRM8-TTRe-ALBp-MVM-FVIIIcodeltaB-sv40pA,
pAAVsc-TTRe-3×CRM8-ALBp-MVM-FIXcoR338L-BGHpA,
pAAVss-TTRe-3×CRM8-ALBp-MVM-FVIIIcodeltaB-sv40pA,
pAAVsc-CRM8-TTRe-ALBp-MVM-FIXcoR338L-BGHpA, or
pAAVss-CRM8-TTRe-ALBp-MVM-FVIIIcodeltaB-sv40pA.

In further examples, the apolipoprotein A1 promotor (APOA1p) is used to replace the TTRm promotor in said constructs, hence encompassing the following constructs:
pAAVsc-3×CRM8-TTRe-APOA1p-MVM-FIXcoR338L-BGHpA,
pAAVss-3×CRM8-TTRe-APOA1p-MVM-FVIIIcodeltaB-sv40pA
pAAVsc-TTRe-3×CRM8-APOA1p-MVM-FIXcoR338L-BGHpA,
pAAVss-TTRe-3×CRM8-APOA1p-MVM-FVIIIcodeltaB-sv40pA
pAAVsc-CRM8-TTRe-APOA1p-MVM-FIXcoR338L-BGHpA, or
pAAVss-CRM8-TTRe-APOA1p-MVM-FVIIIcodeltaB-sv40pA.

In further examples, the complement factor B promoter (CFBp) is used to replace the TTRm promotor in said constructs, hence encompassing the following construct:
pAAVsc-3×CRM8-TTRe-CFBp-MVM-FIXcoR338L-BGHpA,
pAAVss-3×CRM8-TTRe-CFBp-MVM-FVIIIcodeltaB-sv40pA,
pAAVsc-TTRe-3×CRM8-CFBp-MVM-FIXcoR338L-BGHpA,
pAAVss-TTRe-3×CRM8-CFBp-MVM-FVIIIcodeltaB-sv40pA,
pAAVsc-CRM8-TTRe-CFBp-MVM-FIXcoR338L-BGHpA, or
pAAVss-CRM8-TTRe-CFBp-MVM-FVIIIcodeltaB-sv40pA.

In further examples, the ketohexokinase promoter (KHKp) is used to replace the TTRm promotor in said constructs, hence encompassing the following construct:
pAAVsc-3×CRM8-TTRe-KHKp-MVM-FIXcoR338L-BGHpA,
pAAVss-3×CRM8-TTRe-KHKp-MVM-FVIIIcodeltaB-sv40pA,
pAAVsc-TTRe-3×CRM8-KHKp-MVM-FIXcoR338L-BGHpA,
pAAVss-TTRe-3×CRM8-KHKp-MVM-FVIIIcodeltaB-sv40pA,
pAAVsc-CRM8-TTRe-KHKp-MVM-FIXcoR338L-BGHpA, or
pAAVss-CRM8-TTRe-KHKp-MVM-FVIIIcodeltaB-sv40pA.

In further examples, the hemopexin promoter (HPXp) is used to replace the TTRm promotor in said constructs, hence encompassing the following construct:
pAAVsc-3×CRM8-TTRe-HPXp-MVM-FIXcoR338L-BGHpA,
pAAVss-3×CRM8-TTRe-HPXp-MVM-FVIIIcodeltaB-sv40pA,
pAAVsc-TTRe-3×CRM8-HPXp-MVM-FIXcoR338L-BGHpA,
pAAVss-TTRe-3×CRM8-HPXp-MVM-FVIIIcodeltaB-sv40pA,
pAAVsc-CRM8-TTRe-HPXp-MVM-FIXcoR338L-BGHpA, or
pAAVss-CRM8-TTRe-HPXp-MVM-FVIIIcodeltaB-sv40pA.

In further examples, the nicotinamide N-methyltransferase promoter (NNMTp) is used to replace the TTRm promotor in said constructs, hence encompassing the following construct:
pAAVsc-3×CRM8-TTRe-NNMTp-MVM-FIXcoR338L-BGHpA,
pAAVss-3×CRM8-TTRe-NNMTp-MVM-FVIII-codeltaB-sv40pA,
pAAVsc-TTRe-3×CRM8-NNMTp-MVM-FIXcoR338L-BGHpA,
pAAVss-TTRe-3×CRM8-NNMTp-MVM-FVIII-codeltaB-sv40pA,
pAAVsc-CRM8-TTRe-NNMTp-MVM-FIXcoR338L-BGHpA, or
pAAVss-CRM8-TTRe-NNMTp-MVM-FVIIIcodeltaB-sv40pA.

In further examples, the (liver) carboxylesterase 1 promoter (CES1p) is used to replace the TTRm promotor in said constructs, hence encompassing the following construct:
pAAVsc-3×CRM8-TTRe-CES1p-MVM-FIXcoR338L-BGHpA,
pAAVss-3×CRM8-TTRe-CES1p-MVM-FVIIIcodeltaB-sv40pA,
pAAVsc-TTRe-3×CRM8-CES1p-MVM-FIXcoR338L-BGHpA,
pAAVss-TTRe-3×CRM8-CES1p-MVM-FVIIIcodeltaB-sv40pA,
pAAVsc-CRM8-TTRe-CES1p-MVM-FIXcoR338L-BGHpA, or
pAAVss-CRM8-TTRe-CES1p-MVM-FVIIIcodeltaB-sv40pA.

In further examples, the protein C promoter (PROCp) is used to replace the TTRm promotor in said constructs, hence encompassing the following construct:

pAAVsc-3×CRM8-TTRe-PROCp-MVM-FIXcoR338L-BGHpA,
pAAVss-3×CRM8-TTRe-PROCp-MVM-FVIIIcodeltaB-sv40pA,
pAAVsc-TTRe-3×CRM8-PROCp-MVM-FIXcoR338L-BGHpA,
pAAVss-TTRe-3×CRM8-PROCp-MVM-FVIIIcodeltaB-sv40pA,
pAAVsc-CRM8-TTRe-PROCp-MVM-FIXcoR338L-BGHpA, or
pAAVss-CRM8-TTRe-PROCp-MVM-FVIIIcodeltaB-sv40pA.

In further examples, the apolipoprotein C3 promoter (APOC3p) is used to replace the TTRm promotor in said constructs, hence encompassing the following construct:

pAAVsc-3×CRM8-TTRe-APOC3p-MVM-FIXcoR338L-BGHpA,
pAAVss-3×CRM8-TTRe-APOC3p-MVM-FVIII-codeltaB-sv40pA,
pAAVsc-TTRe-3×CRM8-APOC3p-MVM-FIXcoR338L-BGHpA,
pAAVss-TTRe-3×CRM8-APOC3p-MVM-FVIII-codeltaB-sv40pA,
pAAVsc-CRM8-TTRe-APOC3p-MVM-FIXcoR338L-BGHpA, or
pAAVss-CRM8-TTRe-APOC3p-MVM-FVIIIcodeltaB-sv40pA.

In further examples, the mannan-binding lectin serine protease 2 (MASP2p) is used to replace the TTRm promotor in said constructs, hence encompassing the following construct:

pAAVsc-3×CRM8-TTRe-MASP2p-MVM-FIXcoR338L-BGHpA,
pAAVss-3×CRM8-TTRe-MASP2p-MVM-FVIII-codeltaB-sv40pA,
pAAVsc-TTRe-3×CRM8-MASP2p-MVM-FIXcoR338L-BGHpA,
pAAVss-TTRe-3×CRM8-MASP2p-MVM-FVIII-codeltaB-sv40pA,
pAAVsc-CRM8-TTRe-MASP2p-MVM-FIXcoR338L-BGHpA, or
pAAVss-CRM8-TTRe-MASP2p-MVM-FVIIIcodeltaB-sv40pA.

In further examples, the serpin peptidase inhibitor, clade C (antithrombin) promoter (SERPINC1p) is used to replace the TTRm promotor in said constructs, hence encompassing the following construct:

pAAVsc-3×CRM8-TTRe-SERPINC1p-MVM-FIXcoR338L-BGHpA,
pAAVss-3×CRM8-TTRe-SERPINC1p-MVM-FVIII-codeltaB-sv40pA,
pAAVsc-TTRe-3×CRM8-SERPINC1p-MVM-FIXcoR338L-BGHpA,
pAAVss-TTRe-3×CRM8-SERPINC1p-MVM-FVIII-codeltaB-sv40pA,
pAAVsc-CRM8-TTRe-SERPINC1p-MVM-FIXcoR338L-BGHpA, or
pAAVss-CRM8-TTRe-SERPINC1p-MVM-FVIII-codeltaB-sv40pA.

In further examples, the serpin peptidase inhibitor promoter (HAMPp) is used to replace the TTRm promotor in said constructs, hence encompassing the following construct:

pAAVsc-3×CRM8-TTRe-HAMPp-MVM-FIXcoR338L-BGHpA,
pAAVss-3×CRM8-TTRe-HAMPp-MVM-FVIII-codeltaB-sv40pA
pAAVsc-TTRe-3×CRM8-HAMPp-MVM-FIXcoR338L-BGHpA,
pAAVss-TTRe-3×CRM8-HAMPp-MVM-FVIII-codeltaB-sv40pA,
pAAVsc-CRM8-TTRe-HAMPp-MVM-FIXcoR338L-BGHpA, or
pAAVss-CRM8-TTRe-HAMPp-MVM-FVIIIcodeltaB-sv40pA.

Results:
The expression level of FIX or FVIII will be analysed and compared as explained in Example 2.

REFERENCES

ANNONI A, BROWN B D, CANTORE A, SERGI L S, NALDINI L, and RONCAROLO M G. (2009). In vivo delivery of a microRNA-regulated transgene induces antigen-specific regulatory T cells and promotes immunologic tolerance. Blood 114, 5152-5161

ARRUDA V R, STEDMAN H H, HAURIGOT V, and BUCHLIS G. (2010). Peripheral transvenular delivery of adeno-associated viral vectors to skeletal muscle as a novel therapy for hemophilia B. Blood 115, 4678-88.

AXELROD J H, READ M S, BRINKHOUS K M, and VERMA I M. (1990). Phenotypic correction of factor IX deficiency in skin fibroblasts of hemophilic dogs. Proc Natl Acad Sci USA; 87, 5173-7.

BROWN B D, SHI C X, POWELL S HURLBUT D, GRAHAM F L, and LILLICRAP D. (2004). Helper-dependent adenoviral vectors mediate therapeutic factor VIII expression for several months with minimal accompanying toxicity in a canine model of severe hemophilia A. Blood 103, 804-10.

BROWN B D, CANTORE A, ANNONI A, SERGI L S, LOMBARDO A, DELLA VALLE P, D'ANGELO A, and NALDINI L. (2007). A microRNA-regulated lentiviral vector mediates stable correction of hemophilia B mice. Blood 110, 4144-52.

Brunetti-Pierri N, Grove N C, Zuo Y, Edwards R, Palmer D, Cerullo V, Teruya J, Ng P. Bioengineered factor IX molecules with increased catalytic activity improve the therapeutic index of gene therapy vectors for hemophilia B. Hum Gene Ther. 2009 May; 20(5):479-85.

BUCHLIS G, PODSAKOFF G M, RADU A, HAWK S M, FLAKE A W, MINGOZZI F, and HIGH K A. (2012). Factor IX expression in skeletal muscle of a severe hemophilia B patient 10 years after AAV-mediated gene transfer. Blood 119, 3038-41.

BUDKER V, ZHANG G, KNECHTLE S, WOLFF J A. Naked DNA delivered intraportally expresses efficiently in hepatocytes. (1996) Gene Ther. July; 3(7):593-8.

CANTORE A, NAIR N, DELLA VALLE P, DI MATTEO M, MÁTRAI J, SANVITO F, BROMBIN C, DI SERIO C, D'ANGELO A, CHUAH M, NALDINI L, VANDENDRIESSCHE T. Hyper-functional coagulation factor IX improves the efficacy of gene therapy in hemophilic mice. Blood. 2012. Oct. 4.

CHANG, J., JIN, J., LOLLAR, P., BODE, W., BRANDSTETTER, H., HAMAGUCHI, N., STRAIGHT, D. L. & STAFFORD, D. W. (1998). Changing residue 338 in human factor IX from arginine to alanine causes an increase in catalytic activity. J Biol Chem 273(20): 12089-12094.

CHOWDHURY J R, GROSSMAN M, GUPTA S, CHOWDHURY N R, BAKER J R JR, WILSON J M. (1991) Long-term improvement of hypercholesterolemia after ex vivo gene therapy in LDLR-deficient rabbits. Science. December 20; 254(5039): 1802-5.

CHUAH M K, SCHIEDNER G, THORREZ L, BROWN B, JOHNSTON M, GILLIJNS V, HERTEL S, VAN ROOIJEN N, LILLICRAP D, COLLEN D, VANDENDRIESSCHE T, and KOCHANEK S. (2003). Therapeutic factor VIII levels and negligible toxicity in mouse and dog models of hemophilia A following gene therapy with high-capacity adenoviral vectors. Blood 101, 1734-43.

Chuah M K, Nair N, VandenDriessche T. Recent progress in gene therapy for hemophilia. Hum Gene Ther. 2012a June; 23(6):557-65.

Chuah M K, Nair N, VandenDriessche T. Recent progress in gene therapy for hemophilia. Hum Gene Ther. 2012b June; 23(6):557-65.

Chuah M K, VandenDriessche T. Platelet-directed gene therapy overcomes inhibitory antibodies to factor VIII. J Thromb Haemost. 2012c August; 10(8):1566-9

DONSANTE A, MILLER D G, LI Y, VOGLER C, BRUNT E M, RUSSELL D W, and SANDS M S. (2007). AAV vector integration sites in mouse hepatocellular carcinoma. Science 317, 477.

DOBRZYNSKI E, FITZGERALD J C, CAO O, MINGOZZI F, WANG L, and HERZOG R W (2006) Prevention of cytotoxic T lymphocyte responses to factor IX-expressing hepatocytes by gene transfer-induced regulatory T cells. Proc Natl Acad Sci USA 103, 4592-4597.

EHRHARDT A, and KAY M A. (2002). A new adenoviral helper-dependent vector results in long-term therapeutic levels of human coagulation factor IX at low doses in vivo. Blood 99, 3923-30.

FIELDS P A, ARRUDA V R, ARMSTRONG E, KIRK CHU, MINGOZZI, F. HAGSTROM, J., HERZOG R, HIGH K A. (2001). Risk and prevention of anti-factor IX formation in AAV-mediated gene transfer in the context of a large deletion of F9. Mol. Ther. 4, 201-210.

FOLLENZI A, BATTAGLIA M, LOMBARDO A, ANNONI A, RONCAROLO M G, and NALDINI L. (2004). Targeting lentiviral vector expression to hepatocytes limits transgene-specific immune response and establishes long-term expression of human antihemophilic factor IX in mice. Blood 103, 3700-9.

GAO G P, ALVIRA M R, WANG L, JOHNSTON J, WILSON J M. (2002). Novel adeno-associated viruses from rhesus monkeys as vectors for human gene therapy. Proc Natl Acad Sci USA 99, 11854-9.

GAO G, VANDENBERGH L H, ALVIRA M R LU Y, CALCEDO R, ZHOU X, and WILSON J M. (2004). Clades of Adeno-associated viruses are widely disseminated in human tissues. J. Viro I178, 6381-6388.

HERZOG R W, YANG E Y, COUTO L B, HAGSTROM J N, ELWELL D, FIELDS P A, BURTON M, BELLINGER D A, READ M S, BRINKHOUS K M, PODSAKOFF G M, NICHOLS T C, KURTZMAN G J, and HIGH K A. (1999). Long-term correction of canine hemophilia B by gene transfer of blood coagulation factor IX mediated by adeno-associated viral vector. Nat Med. 5, 56-63.

HERZOG R W, MOUNT J D, ARRUDA V R, HIGH K A, and LOTHROP C D Jr. (2001). Muscle-directed gene transfer and transient immune suppression result in sustained partial correction of canine hemophilia B caused by a null mutation. Mol Ther. 4, 192-200.

HERZOG R W, HAGSTROM J N, KUNG S H, TAI S J, WILSON J M, FISHER K J, and HIGH K A. (1997) Stable gene transfer and expression of human blood coagulation factor IX after intramuscular injection of recombinant adeno-associated virus. Proc Natl Acad Sci USA. 94, 5804-5809.

HERZOG R W, FIELDS P A, ARRUDA V R, BRUBAKER J O, ARMSTRONG E, MCCLINTOCK D, BELLINGER D A, COUTO L B, NICHOLS T C, HIGH K A (2002) Influence of vector dose on factor IX-specific T and B cell responses in muscle-directed gene therapy. Hum Gene Ther 13, 1281-1291.

HIGH K A. (2001). Gene Transfer as an approach to treating Hemophilia. Circ Res. 88, 137-144.

HIGH K A. (2011) Gene therapy for hemophilia: a long and winding road. J Thromb Haemost. 9 Suppl. 1: 2-11.

BAINBRIDGE J, SMITH A J, BARKER S, et al. (2008) Effect of Gene Therapy on Visual Function in Leber's Congenital Amaurosis. N Engl J Med. 358, 2231-2239.

JIANG H, LILLICRAP D, and PATARROYO-WHITE S. (2006). Multiyear therapeutic benefit of AAV serotypes 2, 6, and 8 delivering factor VIII to hemophilia A mice and dogs. Blood. 108, 107-15.

KAO, C. Y., LIN, C. N., YU, I. S., TAO, M. H., WU, H. L., SHI, G. Y., YANG, Y. L., KAO, J. T. & LIN, S. W. (2010). FIX-Triple, a gain-of-function factor IX variant, improves haemostasis in mouse models without increased risk of thrombosis. Thromb Haemost 104(2): 355-365.

KAY M A, BALEY P, ROTHENBERG S, LELAND F, FLEMING L, PONDER K P, LIU T, FINEGOLD M, DARLINGTON G, POKORNY W, WOO SLC. (1992) Expression of human alpha 1-antitrypsin in dogs after autologous transplantation of retroviral transduced hepatocytes. Proc Natl Acad Sci USA. January 1; 89(1):89-93.

KAY M A, MANNO C S, RAGNI M V, COUTO L B, MCCLELLAND A, GLADER B, CHEW A J, TAI S J, HERZOG R W, ARRUDA V, JOHNSON F, SCALLAN C, SKARSGARD E, FLAKE A W, and HIGH K A. (2000). Evidence for gene transfer and expression of factor IX in hemophilia B patients treated with an AAV vector. Nat Genet. 24, 257-61.

KISTNER A, GOSSEN M, ZIMMERMANN F, JERECIC J, ULLMER C, LYBBERT H, BUJARD H. (1996) Doxycycline-mediated quantitative and tissue-specific control of gene expression in transgenic mice. Proc Natl Acad Sci USA. October 1; 93(20): 10933-8.

KREN B T, UNGER G M, SJEKLOCHA L, TROSSEN A A, KORMAN V, DIETHELEM-OKITA B M, REDING M T, and STEER C J. (2009). Nanocapsule-delivered Sleeping Beauty mediates therapeutic Factor VIII expression in liver sinusoidal endothelial cells of hemophilia A mice. J Clin Invest. 19, 2086-99.

KURIYAMA S, YOSHIKAWA M, ISHIZAKA S, TSUJII T, LKENAKA K, KAGAWA T, MORITA N, MIKOSHIBA K. (1991) A potential approach for gene therapy targeting hepatoma using a liver-specific promoter on a retroviral vector. Cell Struct Funct. December; 16(6):503-10.

LI H, MALANI N, HAMILTON S R, SCHLACHTERMAN A, BUSSADORI G, EDMONSON S E, SHAH R, ARRUDA V R, MINGOZZI F, WRIGHT J F, BUSHMAN F D, and HIGH K A. (2011). Assessing the potential for AAV vector genotoxicity in a murine model. Blood. 117, 3311-9.

LIN, C. N., KAO, C. Y., MIAO, C. H., HAMAGUCHI, N., WU, H. L., SHI, G. Y., LIU, Y. L., HIGH, K. A. & LIN, S. W. (2010). Generation of a novel factor IX with augmented clotting activities in vitro and in vivo. J Thromb Haemost 8(8): 1773-1783.

LIU F, SONG Y, LIU D. (1999) Hydrodynamics-based transfection in animals by systemic administration of plasmid DNA. Gene Ther. July; 6(7):1258-66.

MANNO C S, PIERCE G F, and ARRUDA V R. (2006). Successful transduction of liver in hemophilia by AAV-Factor IX and limitations imposed by the host immune response. Nat Med. 12, 342-7.

MÁTÉS L, CHUAH M K, BELAY E, JERCHOW B, MANOJ N, ACOSTA-SANCHEZ A, GRZELA D P, SCHMITT A, BECKER K, MATRAI J, M A L, SAMARA-KUKO E, GYSEMANS C, PRYPUTNIEWICZ D, MISKEY C, FLETCHER B, VANDENDRIESSCHE T, IVICS Z, and IZSVAK Z. (2009). Molecular evolution of a novel hyperactive Sleeping Beauty transposase enables robust stable gene transfer in vertebrates. Nat Genet. 41, 753-61.

MÁTRAI J, CHUAH M K, and VANDENDRIESSCHE T. (2010a). Pre clinical and clinical progress in hemophilia gene therapy. Curr Opin Hematol. 17, 387-92.

MÁTRAI J, CHUAH M K, and VANDENDRIESSCHE T. (2010b). Recent advances in lentiviral vector development and applications. Mol Ther. 18, 477-90.

MÁTRAI J, CANTORE A, BARTHOLOMAE C C, ANNONI A, WANG W, ACOSTA-SANCHEZ A, SAMARA-KUKO E, DE WAELE L, MA L, GENOVESE P, DAMO M, ARENS A, GOUDY K, NICHOLS T C, VON KALLE C, L CHUAH M K, RONCAROLO M G, SCHMIDT M, VANDENDRIESSCHE T, and NALDINI L. (2011). Hepatocyte-targeted expression by integrase-defective lentiviral vectors induces antigen-specific tolerance in mice with low genotoxic risk. Hepatology 53, 1696-707.

MATSUI H, SHIBATA M, BROWN B, LABELLE A, HEGADRON C, ANDREWS C, CHUAH M, VANDENDRIESSCHE T, MIAO C H, HOUGH C, and LILLICRAP D. (2009). A murine model for induction of long-term immunologic tolerance to factor VIII does not require persistent detectable levels of plasma factor VIII and involves contributions from Foxp3+ T regulatory cells. Blood. 114, 677-85.

MATSUI H, HEGADORN C, OZELO M, BURNETT E, TUTTLE A, LABELLE A, McCARY P B Jr., NALDINI L, BROWN B, HOUGH C, and LILLICRAP D. (2011). A microRNA-regulated and GP64-pseudotyped lentiviral vector mediates stable expression of FVIII in a murine model of Hemophilia A. Mol Ther. 19, 723-30.

McCARTY D M, MONAHAN P E, and SAMULSKI R J. (2001). Self-complementary recombinant adeno-associated virus (scAAV) vectors promote efficient transduction independently of DNA synthesis. Gene Ther. 8, 1248-54.

McCARTY D M, FU H, MONAHAN P E, TOULSON C E, NAIK P, and SAMULSKI R J. (2003). Adeno-associated virus terminal repeat (TR) mutant generates self-complementary vectors to overcome the rate-limiting step to transduction in vivo. Gene Ther. 10, 2112-8.

McIntosh, J. et al. Therapeutic levels of FVIII following a single peripheral vein administration of rAAV vector encoding a novel human factor VIII variant. Blood (2013).

MIAO C H, OHASHI K, PATIJN G A, MEUSE L, YE X, THOMPSON A R, and KAY M A. (2000). Inclusion of the hepatic locus control region, an intron, and untranslated region increases and stabilizes hepatic factor IX gene expression in vivo but not in vitro. Mol Ther. 1, 522-32.

MIAO H. Z., SIRACHAINAN N., PALMER L., et al. (2004). Bioengineering of coagulation factor VIII for improved secretion. Blood 103(9):3412-3419.

MILANOV, ET AL., 2012 Engineered factor IX variants bypass FVIII and correct hemophilia A phenotype in mice Blood 119:602-611.

MILLER A D. (1990) Retrovirus packaging cells. Hum Gene Ther. Spring; 1 (1):5-14.

MINGOZZI F, LIU Y L, DOBRZYNSKI E, KAUFHOLD A, LIU J H, WANG Y, ARRUDA V R, HIGH K A, and HERZOG R W. (2003). Induction of immune tolerance to coagulation factor IX antigen by in vivo hepatic gene transfer. J Clin Invest. 111, 1347-56.

MINGOZZI F, MAUS M V, HUI D J, SABATINO D E, MURPHY S L, RASKO J E, RAGINI M V, MANNO C S, SOMMER J, JIANG H, PIERCE G F, ERTL H C, and HIGH K A. (2007). CD8(+) T-cell responses to adeno-associated virus capsid in humans. Nat Med. 13, 419-22.

MOUNT J D, HERZOG R W, TILLSON D M, GOODMAN S A, ROBINSON N, MCCLELAND M L, BELLINGER D, NICHOLS T C, ARRUDA V R, LOTHROP C D JR, and HIGH K A. (2002). Sustained phenotypic correction of hemophilia B dogs with a factor IX null mutation by liver-directed gene therapy. Blood 99, 2670-6.

NAIR N, RINCON M Y, EVENS H, SARCAR S, DASTIDAR S, SAMARA-KUKO E, GHANDEHARIAN O, MAN VIECELLI H, THONY B, DE BLESER P, VANDENDRIESSCHE T, CHUAH M K. (2014). Computationally designed liver-specific transcriptional modules and hyperactive factor IX improve hepatic gene therapy. Blood 123, 3195-9.

NALDINI L, BLOMER U, GALLAY P, ORY D, MULLIGAN R, GAGE F H, VERMA I M, TRONO D. (1996) In vivo gene delivery and stable transduction of nondividing cells by a lentiviral vector. Science. April 12; 272(5259): 263-7.

NATHWANI A C, DAVIDOFF A M, HANAWA H, YUNYU H U, HOFFER F A, NIKANOROV A, SLAUGHTER C, N G CYC, ZHOU J, LOZIER J, MANDRELL T D, VANIN E F, and NIENHUIS A W. (2002). Sustained high-level expression of human factor IX (hFIX) after liver-targeted delivery of recombinant adeno-associated virus encoding the hFIX gene in rhesus macaques. Blood 100, 1662-1669.

NATHWANI A C, GRAY J T, NG C Y, ZHOU J, SPENCE Y, WADDINGTON S N, TUDDENHAM E G, KEMBALL COOK G, McINTOSH J, BOON-SPIJKER M, MERTENS K, DAVIDOFF A M. (2006). Self-complementary adeno-associated virus vectors containing a novel liver-specific human factor IX expression cassette enable highly efficient transduction of murine and non-human primate liver. Blood 107, 2653-61.

NATHWANI A C, TUDDENHAM E G, RANGARAJAN S, ROSALES C, MCINTOSH J, LINCH D C, CHOWDARY P, RIDDELL A, PIE A J, HARRINGTON C, O'BEIRNE J, SMITH K, PASI J, GLADER B, RUSTAGI P, NG C Y, KAY M A, ZHOU J, SPENCE Y, MORTON C L, ALLAY J, COLEMAN J, SLEEP S, CUNNINGHAM J M, SRIVASTAVA D, BASNER-TSCHAKARJAN E, MINGOZZI F, HIGH K A, GRAY J T, REISS U M, NIENHUIS A W, and DAVIDOFF A M. (2011). Adenovirus-associated virus vector-mediated gene transfer in hemophilia B. N Engl J Med. 365, 2357-2365.

OHLFEST J R, FRANDSEN J L, FRITZ S, LOBITZ P D, PERKINSON S G, CLARK K J, NELSESTUEN G, KEY N S, MCLVOR R S, HACKETT P B, and LARGAES- PADA D A. (2004). Phenotypic correction and long-term expression of factor VIII in hemophilic mice by immunotolerization and nonviral gene transfer using the Sleeping Beauty transposon system. Blood 105, 2691-8.

Petrus, I., Chuah, M. & VandenDriessche, T. Gene therapy strategies for hemophilia: benefits versus risks. J Gene Med 12, 797-809 (2010). SANDBERG H, ALMSTEDT A, BRANDT J, et al. (2001). Structural and functional characteristics of the B domain-deleted recombinant factor VIII proteint, r-VIII SQ. Thromb Haemost. 85(1): 93-100.

SCHUETTRUMPF, J., HERZOG, R. W., SCHLACHTERMAN, A., KAUFHOLD, A., STAFFORD, D. W. & ARRUDA, V. R. (2005). Factor IX variants improve gene therapy efficacy for hemophilia B. Blood 105(6): 2316-2323.

SIMIONI, P., TORMENE, D., TOGNIN, G., GAVASSO, S., BULATO, C., IACOBELLI, N. P., FINN, J. D., SPIEZIA, L., RADU, C. & ARRUDA, V. R. (2009). X-linked thrombophilia with a mutant factor IX (factor IX Padua). N Engl J Med 361(17): 1671-1675.

SNYDER R O, MIAO C H, PATIJN G A, SPRATT S K, DANOS O, NAGY D, GOWN A M, WINTHER B, MEUSE L, COHEN L K, THOMPSON A R, and KAY M A. (1997). Persistent and therapeutic concentrations of human factor IX in mice after hepatic gene transfer of recombinant AAV vectors. Nat Genet. 16, 270-276.

SNYDER R O, MIAO C, MEUSE L, TUBB J, DONAHUE B A, HUI-FENG LIN, STAFFORD D W, PATEL S, THOMPSON A R, NICHOLS T, READ M S, BELLINGER D A, BRINKHOUS K M, and KAY M A. (1999). Correction of hemophilia B in canine and murine models using recombinant adeno-associated viral vectors. Nat Med. 5, 64-70.

TRAPNELL B C. (1993) Adenoviral vectors for gene transfer. Adv. Drug Del. Rev. 12: 185-199.

VANDENBERGHE L H, WANG L, SOMANATHAN S, ZHI Y, FIGUEREDO J, CALCEDO R, SANMIGUEL J, DESAI R A, CHEN C S, JOHNSTON J, GRANT R L, GAO G, and WILSON J M. (2006). Heparin binding directs activation of T cells against adeno-associated virus serotype 2 capsid. Nat Med. 12, 967-71.

VANDRIESSCHE T, VANSLEMBROUCK V, GOOVAERTS I, ZWINNEN H, VANDERHAEGHEN M L, COLLEN D, and CHUAH M K. (1999). Long-term expression of human coagulation factor VIII and correction of hemophilia A after in vivo retroviral gene transfer in factor VIII-deficient mice. Proc Natl Acad Sci USA. 96, 10379-84.

VANDENDRIESSCHE T, THORREZ L, NALDINI L, FOLLENZI A, MOONS L, ZWI BERNEMAN, COLLEN D, and CHUAH M K. (2002). Lentiviral vectors containing the human immunodeficiency virus type-1 central polypurine tract can efficiently transduce nondividing hepatocytes and antigen-presenting cells in vivo. Blood 100, 813-22.

VANDENDRIESSCHE T, THORREZ L, ACOSTA-SANCHEZ A, PETRUS I, WANG L, MA L, DE WAELE L, IWASAKI Y, GILLIJNS V, WILSON J M, COLLEN D, and CHUAH M K. (2007). Efficacy and safety of adeno-associated viral vectors based on serotype 8 and 9 vs. lentiviral vectors for hemophilia B gene therapy. J Thromb Haemost. 5, 16-24.

VANDENDRIESSCHE T, IVICS Z, IZSVAK Z, and CHUAH M K. (2009). Emerging potential of transposons for gene therapy and generation of induced pluripotent stem cells. Blood 114, 1461-8.

VANDENDRIESSCHE T, and CHUAH M K. (2012). Clinical progress in gene therapy: sustained partial correction of the bleeding disorder in patients suffering from severe hemophilia B. Hum Gene Ther. 23, 4-6.

WANG L, TAKABE K, BIDLINGMAIER S M, ILL C R, and VERMA I M. (1999). Sustained correction of bleeding disorder in hemophilia B mice by gene therapy. Proc Natl Acad Sci USA 96, 3906-3910.

WANG L, NICHOLS T C, READ M S, BELLINGER D A, and VERMA I M. (2000). Sustained expression of therapeutic level of factor IX in hemophilia B dogs by AAV-mediated gene therapy in liver. Mol Ther. 1, 154-158.

WANG L, CAO O, SWALM B, DOBRZYNSKI E, MINGOZZI F, and HERZOG R W (2005) Major role of local immune responses in antibody formation to factor IX in AAV gene transfer. Gene Ther 12, 1453-464.

WARD N J, BUCKLEY S M, WADDINGTON S N, VANDENDRIESSCHE T, CHUAH M K, NATHWANI A C, McINTOSH J, TUDDENHAM E G, KINNON C, THRASHER A J, and McVEY J H (2010) Codon optimization of human factor VIII cDNAs leads to high-level expression. Blood 117, 798-807.

Ward, N. J. et al. Codon optimization of human factor VIII cDNAs leads to high-level expression. *Blood* 117, 798-807 (2011).

WU Z, SUN J, ZHANG T, YIN C, YIN F, VAN DYKE T, SAMULSKI R J, and MONAHAN P E. (2008). Optimization of self-complementary AAV vectors for liver-directed expression results in sustained correction of hemophilia B at low vector dose. Mol Ther. 16, 280-9.

XU L, GAO C, and SANDS M S. (2003). Neonatal or hepatocyte growth factor-potentiated adult gene therapy with a retroviral vector results in therapeutic levels of canine factor IX for hemophilia B. Blood 101, 3924-3932.

XU L, NICHOLS T C, SARKAR R, Mc CORQUODALE S, BELLINGER D A, PONDER K P. (2005). Absence of a desmopressin response after therapeutic expression of factor VIII in hemophilia A dogs with liver-directed neonatal gene therapy. Proc Natl Acad Sci USA 102, 6080-6085.

YAMADA T, IWASAKI Y, TADA H, IWABUKI H, CHUAH M K, VANDENDRIESSCHE T, FUKUDA H, KONDO A, UEDA M, SENO M, TANIZAWA K, KURODA S. (2003) Nanoparticles for the delivery of genes and drugs to human hepatocytes. Nat Biotechnol. August; 21 (8):885-90.

YANT S R, MEUSE L, CHIU W, IVICS Z, IZSVAK Z, and KAY M A. (2000). Somatic integration and long-term transgene expression in normal and haemophilic mice using a DNA transposon system. Nat Genet. 25, 35-41.

Yusa et al. A hyperactive piggyBac transposase for mammalian applications. Proc Natl Acad Sci USA. 2011; 108(4):1531-6.

ZHANG G, BUDKER V, WOLFF J A. (1999) High levels of foreign gene expression in hepatocytes after tail vein injections of naked plasmid DNA. Hum Gene Ther. July 1; 10(10):1735-7.

ZHONG L, LI B, MAH C S, GOVINDASAMY L, AGBANDJE-MCKENNA, COOPER M, HERZOG R W, ZOLOTUKHIN I, WARRINGTON JR. K H, WEIGEL-VAN AKEN K, HOBBS J A, ZOLOTUKHIN S, MUZYCZKA N, and SRIVASTAVA A (2008). Next generation of adeno-associated virus 2 vectors: point mutations in tyrosines lead to high-efficiency transduction at lower doses. Proc Natl Acad Sci USA 105, 7827-32.

The invention claimed is:

1. A nucleic acid expression cassette comprising a triple repeat of a liver-specific nucleic acid regulatory element, said triple repeat consisting of the nucleic acid fragment defined by SEQ ID NO:11 or a triple repeat of the nucleic acid fragment defined by SEQ ID NO:5, wherein a single nucleotide separates each nucleic acid fragment defined by SEQ ID NO:5; and a nucleic acid regulatory element comprising the nucleic acid fragment defined by SEQ ID NO:12; wherein said triple repeat and said regulatory element are operably linked to a liver-specific promoter and a transgene.

2. The nucleic acid expression cassette according to claim 1, wherein the liver-specific promoter is selected from the group consisting of: a minimal TTR promotor (TTRm), an AAT promoter, an albumin (ALB) promotor or minimal promoter, an apolipoprotein A1 (APOA1) promoter or minimal promoter, a complement factor B (CFB) promoter, a ketohexokinase (KHK) promoter, a hemopexin (HPX) promoter or minimal promoter, a nicotinamide N-methyltransferase (NNMT) promoter or minimal promoter, a carboxylesterase 1 (CES1) promoter or minimal promoter, a protein C (PROC) promoter or minimal promoter, an apolipoprotein C3 (APOC3) promoter or minimal promoter, a mannan-binding lectin serine protease 2 (MASP2) promoter or minimal promoter, a hepcidin antimicrobial peptide (HAMP) promoter or minimal promoter, or a serpin peptidase inhibitor, clade C (antithrombin), member 1 (SERPINC1) promoter or minimal promoter.

3. The nucleic acid expression cassette according to claim 1, wherein said liver-specific promoter is the minimal TTR promotor (TTRm) as defined by SEQ ID NO:6.

4. The nucleic acid expression cassette according to claim 1, wherein said liver-specific promoter is the AAT promoter as defined by SEQ ID NO:64.

5. The nucleic acid expression cassette according to claim 1, comprising a regulatory element as defined by SEQ ID NO: 13 or SEQ ID NO:57, operably linked to the liver-specific promoter and the transgene.

6. The nucleic acid expression cassette according to claim 1, wherein said transgene encodes for coagulation factor IX (FIX) or a coagulation factor FIX containing a hyper-activating mutation.

7. The nucleic acid expression cassette according to claim 1, wherein said transgene encodes for coagulation factor VIII (FVIII) or a coagulation factor VIII having a deletion of the B domain.

8. The nucleic acid expression cassette according to claim 1, comprising the combination of the nucleic acid regulatory element transthyretin enhancer (TTRe) defined by SEQ ID NO:12, and the liver-specific promoter TTRm, wherein said combination is encoded by SEQ ID NO:69.

9. The nucleic acid expression cassette according to claim 1, further comprising a minute virus of mouse (MVM) intron.

10. The nucleic acid expression cassette according to claim 1, further comprising a transcriptional termination signal derived from the bovine growth hormone polyadenylation signal (BGHpA), or derived from the Simian virus 40 polyadenylation signal (SV40 pA), or the synthetic polyadenylation signal as defined by SEQ ID NO:56.

11. A vector comprising the nucleic acid expression cassette according to claim 1.

12. A method of treating hemophilia A or hemophilia B comprising transduction or transfection of the vector according to claim 11 into a subject, wherein the vector comprises a FVIII transgene for use in treating hemophilia A or the vector comprises a FIX transgene for use in treating hemophilia B.

13. The method according to claim 12, wherein after transduction or transfection of the vector into a subject, levels of factor IX or FVIII in plasma are equal to or higher than the therapeutic threshold concentration of 10 mU/ml plasma in the subject are obtained.

14. The method according to claim 13, wherein the transduction of a viral vector into the subject is done at a dose lower than $2\times10^{11}$ vg/kg.

15. The method according to claim 14, wherein the transduction of the viral vector into the subject is done at a dose lower than or equal to $6\times10^{11}$ vg/kg, and wherein levels of factor IX or FVIII in plasma equal to or higher than the therapeutic concentration of 100 mU/ml are obtained in said subject; or wherein the transduction of the viral vector into the subject is done at a dose lower than or equal to $6\times10^{11}$ vg/kg, and wherein levels of factor IX or FVIII in plasma equal to or higher than the therapeutic concentration of 50 mU/ml are obtained in said subject; or wherein the transduction of the viral vector into the subject is done at a dose lower than or equal to $2\times10^{12}$ vg/kg, and wherein levels of factor IX or FVIII in plasma equal to or higher than the therapeutic concentration of 200 mU/ml are obtained in said subject; or wherein the transduction of the viral vector into the subject is done at a dose lower than or equal to $2\times10^{12}$ vg/kg, and wherein levels of factor IX or FVIII in plasma equal to or higher than the therapeutic concentration of 150 mU/ml are obtained in said subject.

16. A pharmaceutical composition comprising a vector according to claim 11 and a pharmaceutically acceptable carrier, optionally further comprising an active ingredient for treating hemophilia A when the transgene in said vector is FVIII; or an active ingredient for treating hemophilia B when the transgene in said vector is FIX.

17. The nucleic acid expression cassette according to claim 6, wherein the coagulation factor FIX containing a hyper-activating mutation is encoded by SEQ ID NO:9.

18. The nucleic acid expression cassette according to claim 7, wherein the B domain of the FVIII is replaced by a linker defined by SEQ ID NO:59.

19. The vector of claim 11, wherein the vector is a viral vector.

* * * * *

UNITED STATES PATENT AND TRADEMARK OFFICE
CERTIFICATE OF CORRECTION

PATENT NO. : 11,007,280 B2
APPLICATION NO. : 15/558725
DATED : May 18, 2021
INVENTOR(S) : Chuah et al.

Page 1 of 1

It is certified that error appears in the above-identified patent and that said Letters Patent is hereby corrected as shown below:

Claim 2, at Column 259 Line 57:
"(HAMP) promoter or minimal promoter, or a serpin pepti-"

Should be:
"(HAMP) promoter or minimal promoter, and a serpin pepti-"

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 85

<210> SEQ ID NO 1
<211> LENGTH: 6198
<212> TYPE: DNA
<213> ORGANISM: Artificial Sequence
<220> FEATURE:
<223> OTHER INFORMATION: pAAVsc-SerpEnh-TTRm-MVM-co-FIX-R338L-BGHpA

<400> SEQUENCE: 1

| | | | | | |
|---|---|---|---|---|---|
| agctggcgta | atagcgaaga | ggcccgcacc | gatcgcccct | cccaacagtt | gcgcagcctg | 60 |
| aatggcgaat | ggcgattccg | ttgcaatggc | tggcggtaat | attgttctgg | atattaccag | 120 |
| caaggccgat | agtttgagtt | cttctactca | ggcaagtgat | gttattacta | atcaaagaag | 180 |
| tattgcgaca | acggttaatt | tgcgtgatgg | acagactctt | ttactcggtg | gcctcactga | 240 |
| ttataaaaac | acttctcagg | attctggcgt | accgttcctg | tctaaaatcc | ctttaatcgg | 300 |
| cctcctgttt | agctcccgct | ctgattctaa | cgaggaaagc | acgttatacg | tgctcgtcaa | 360 |
| agcaaccata | gtacgcgccc | tgtagcggcg | cattaagcgc | ggcgggtgtg | gtggttacgc | 420 |
| gcagcgtgac | cgctacactt | gccagcgccc | tagcgcccgc | tcctttcgct | ttcttccctt | 480 |
| cctttctcgc | cacgttcgcc | ggctttcccc | gtcaagctct | aaatcggggg | ctccctttag | 540 |
| ggttccgatt | tagtgcttta | cggcacctcg | accccaaaaa | acttgattag | ggtgatggtt | 600 |
| cacgtagtgg | gccatcgccc | tgatagacgg | tttttcgccc | tttgacgttg | gagtccacgt | 660 |
| tctttaatag | tggactcttg | ttccaaactg | gaacaacact | caaccctatc | tcggtctatt | 720 |
| cttttgattt | ataagggatt | ttgccgattt | cggcctattg | gttaaaaaat | gagctgattt | 780 |
| aacaaaaatt | taacgcgaac | tttaacaaaa | tattaacgtt | tacaatttaa | atatttgctt | 840 |
| atacaatctt | cctgtttttg | gggcttttct | gattatcaac | cggggtacat | atgattgaca | 900 |
| tgctagtttt | acgattaccg | ttcatcgccc | tgcgcgctcg | ctcgctcact | gaggccgccc | 960 |
| gggcaaagcc | cgggcgtcgg | gcgacctttg | gtcgcccggc | ctcagtgagc | gagcgagcgc | 1020 |
| gcagagaggg | agtggaattc | acgcgtggat | ctgaattcaa | ttcacgcgtg | gtacggccgc | 1080 |
| ggtaccggcg | cgccggggga | ggctgctggt | gaatattaac | caaggtcacc | ccagttatcg | 1140 |
| gaggagcaaa | caggggctaa | gtccacacgc | gtggtaccgt | ctgtctgcac | atttcgtaga | 1200 |
| gcgagtgttc | cgatactcta | atctccctag | gcaaggttca | tatttgtgta | ggttacttat | 1260 |
| tctccttttg | ttgactaagt | caataatcag | aatcagcagg | tttggagtca | gcttggcagg | 1320 |
| gatcagcagc | ctgggttgga | aggaggggt | ataaaagccc | cttcaccagg | agaagccgtc | 1380 |
| acacagatcc | acaagctcct | gaagaggtaa | gggtttaagg | gatggttggt | tggtggggta | 1440 |
| ttaatgttta | attacctgga | gcacctgcct | gaaatcactt | ttttcaggt | tggctagccc | 1500 |
| accatgcagc | gcgtgaacat | gatcatggcc | gagagccccg | gcctgatcac | catctgcctg | 1560 |
| ctgggctacc | tgctgagcgc | cgagtgcacc | gtgttcctgg | accacgagaa | cgccaacaag | 1620 |
| atcctgaacc | gccccaagcg | ctacaacagc | ggcaagctgg | aggagttcgt | gcagggcaac | 1680 |
| ctggagcgcg | agtgcatgga | ggagaagtgc | agcttcgagg | aggcccgcga | ggtgttcgag | 1740 |
| aacaccgagc | gcaccaccga | gttctggaag | cagtacgtgg | acggcgacca | gtgcgagagc | 1800 |
| aaccccctgcc | tgaacggcgg | cagctgcaag | gacgacatca | cagctacga | gtgctggtgc | 1860 |
| cccttcggct | tcgagggcaa | gaactgcgag | ctggacgtga | cctgcaacat | caagaacggc | 1920 |
| cgctgcgagc | agttctgcaa | gaacagcgcc | gacaacaagg | tggtgtgcag | ctgcaccgag | 1980 |
| ggctaccgcc | tggccgagaa | ccagaagagc | tgcgagcccg | ccgtgccctt | ccctgcggc | 2040 |

```
cgcgtgagcg tgagccagac cagcaagctg acccgcgccg aggccgtgtt ccccgacgtg    2100
gactacgtga acagcaccga ggccgagacc atcctggaca acatcaccca gagcacccag    2160
agcttcaacg acttcacccg cgtggtgggc ggcgaggacg ccaagcccgg ccagttcccc    2220
tggcaggtgg tgctgaacgg caaggtggac gccttctgcg gcggcagcat cgtgaacgag    2280
aagtggatcg tgaccgccgc ccactgcgtg gagaccggcg tgaagatcac cgtggtggcc    2340
ggcgagcaca catcgagga gaccgagcac accgagcaga gcgcaacgt gatccgcatc    2400 atcccccacc acaactacaa cgccgccatc aacaagtaca ccacgacat cgccctgctg    2460 gagctggacg agcccctggt gctgaacagc tacgtgaccc ccatctgcat cgccgacaag    2520
gagtacacca catcttcct gaagttcggc agcggctacg tgagcggctg ggccgcgtg    2580 ttccacaagg gccgcagcgc cctggtgctg cagtacctgc gcgtgcccct ggtggaccgc    2640
gccacctgcc tgctgagcac caagttcacc atctacaaca acatgttctg cgccggcttc    2700
cacgagggcg gccgcgacag ctgccagggc gacagcggcg gccccacgt gaccgaggtg    2760 gagggcacca gcttcctgac cggcatcatc agctggggcg aggagtgcgc catgaagggc    2820
aagtacggca tctacaccaa ggtgagccgc tacgtgaact ggatcaagga agaccaag    2880 ctgacctaat gaaagatgga tttccaaggt taattcattg gaattgaaaa ttaacagccc    2940 ccccccccc cccctgcag atctgagccg aattcctgca gcccggggga tcagcctcga    3000
ctgtgccttc tagttgccag ccatctgttg tttgcccctc cccgtgcct tccttgaccc    3060 tggaaggtgc cactcccact gtcctttcct aataaaatga ggaaattgca tcgcattgtc    3120
tgagtaggtg tcattctatt ctggggggtg ggtggggca ggacagcaag ggggaggatt    3180
gggaagacaa tagcaggcat gctggggatg cggtgggctc tatggcttct gaggcggaaa    3240
gaaccagctg gggaccggtg gatctcgata gcaggcatgc tggggagaga tcgatctgag    3300 gaaccctag tgatggagtt ggccactccc tctctgcgcg ctcgctcgct cactgaggcc    3360
gcccgggcaa agcccggcg tcgggcgacc tttggtcgcc cggcctcagt gagcgagcga    3420
gcgcgcagag agggagtggc caacccccc cccccccc ccggcgatt ctcttgtttg    3480 ctccagactc tcaggcaatg acctgatagc ctttgtagag acctctcaaa atagctacc    3540 ctctccggca tgaatttatc agctagaacg gttgaatatc atattgatgg tgatttgact    3600
gtctccggcc tttctcaccc gtttgaatct ttacctacac attactcagg cattgcattt    3660
aaaatatatg agggttctaa aaattttat ccttgcgttg aaataaaggc ttctcccgca    3720
aaagtattac agggtcataa tgtttttggt acaaccgatt tagctttatg ctctgaggct    3780
ttattgctta attttgctaa ttctttgcct tgcctgtatg atttattgga tgttggaatc    3840
gcctgatgcg gtattttctc cttacgcatc tgtgcggtat ttcacaccgc atatggtgca    3900
ctctcagtac aatctgctct gatgccgcat agttatatgg tgcactctca gtacaatctg    3960
ctctgatgcc gcatagttaa gccagccccg acacccgcca acacagccag ccccgacacc    4020
cgccaacacc cgctgacgcg ccctgacggg cttgtctgct cccggcatcc gcttacagac    4080
aagctgtgac cgtctccggg agctgcatgt gtcagaggtt ttcaccgtca tcaccgaaac    4140
gcgcgagacg aaagggcctc gtgatacgcc tatttttata ggttaatgtc atgataataa    4200
tggtttctta gacgtcaggt ggcactttc ggggaaatgt gcgcggaacc cctatttgtt    4260
tatttttcta aatacattca aatatgtatc cgctcatgag acaataaccc tgataaatgc    4320
tcaataatat tgaaaaagga agagtatgag tattcaacat ttccgtgtcg cccttattcc    4380
```

| | |
|---|---|
| cttttttgcg gcattttgcc ttcctgtttt tgctcaccca gaaacgctgg tgaaagtaaa | 4440 |
| agatgctgaa gatcagttgg gtgcacgagt gggttacatc gaactggatc tcaacagcgg | 4500 |
| taagatcctt gagagttttc gccccgaaga cgttttcca atgatgagca cttttaaagt | 4560 |
| tctgctatgt ggcgcggtat tatcccgtat tgacgccggg caagagcaac tcggtcgccg | 4620 |
| catacactat tctcagaatg acttggttga gtactcacca gtcacagaaa agcatcttac | 4680 |
| ggatggcatg acagtaagag aattatgcag tgctgccata accatgagtg ataacactgc | 4740 |
| ggccaactta cttctgacaa cgatcggagg accgaaggag ctaaccgctt ttttgcacaa | 4800 |
| catgggggat catgtaactc gccttgatcg ttgggaaccg gagctgaatg aagccatacc | 4860 |
| aaacgacgag cgtgacacca cgatgcctgt agcaatggca acaacgttgc gcaaactatt | 4920 |
| aactggcgaa ctacttactc tagcttcccg gcaacaatta atagactgga tggaggcgga | 4980 |
| taaagttgca ggaccacttc tgcgctcggc ccttccggct ggctggttta ttgctgataa | 5040 |
| atctggagcc ggtgagcgtg ggtctcgcgg tatcattgca gcactggggc cagatggtaa | 5100 |
| gccctcccgt atcgtagtta tctacacgac ggggagtcag gcaactatgg atgaacgaaa | 5160 |
| tagacagatc gctgagatag gtgcctcact gattaagcat tggtaactgt cagaccaagt | 5220 |
| ttactcatat atactttaga ttgatttaaa acttcatttt taatttaaaa ggatctaggt | 5280 |
| gaagatcctt tttgataatc tcatgaccaa aatcccttaa cgtgagtttt cgttccactg | 5340 |
| agcgtcagac cccgtagaaa agatcaaagg atcttcttga gatcctttt ttctgcgcgt | 5400 |
| aatctgctgc ttgcaaacaa aaaaaccacc gctaccagcg gtggtttgtt tgccggatca | 5460 |
| agagctacca actctttttc cgaaggtaac tggcttcagc agagcgcaga taccaaatac | 5520 |
| tgtccttcta gtgtagccgt agttaggcca ccacttcaag aactctgtag caccgcctac | 5580 |
| atacctcgct ctgctaatcc tgttaccagt ggctgctgcc agtggcgata agtcgtgtct | 5640 |
| taccgggttg gactcaagac gatagttacc ggataaggcg cagcggtcgg gctgaacggg | 5700 |
| gggttcgtgc acacagccca gcttggagcg aacgacctac accgaactga gatacctaca | 5760 |
| gcgtgagcta tgagaaagcg ccacgcttcc cgaagggaga aaggcggaca ggtatccggt | 5820 |
| aagcggcagg gtcggaacag gagagcgcac gagggagctt ccagggggaa acgcctggta | 5880 |
| tctttatagt cctgtcgggt ttcgccacct ctgacttgag cgtcgatttt tgtgatgctc | 5940 |
| gtcaggggg cggagcctat ggaaaaacgc cagcaacgcg gccttttac ggttcctggc | 6000 |
| cttttgctgg ccttttgctc acatgttctt tcctgcgtta tccctgatt ctgtggataa | 6060 |
| ccgtattacc gcctttgagt gagctgatac cgctcgccgc agccgaacga ccagcgcag | 6120 |
| cgagtcagtg agcgaggaag cggaagagcg cccaatacgc aaaccgcctc tccccgcgcg | 6180 |
| ttggccgatt cattaatg | 6198 |

<210> SEQ ID NO 2
<211> LENGTH: 6370
<212> TYPE: DNA
<213> ORGANISM: Artificial Sequence
<220> FEATURE:
<223> OTHER INFORMATION: pAAVsc-3xSerpEnh-TTRm-MVM-co-FIX-R338L-BGHpA

<400> SEQUENCE: 2

| | |
|---|---|
| agctggcgta atagcgaaga ggcccgcacc gatcgccctt cccaacagtt gcgcagcctg | 60 |
| aatggcgaat ggcgattccg ttgcaatggc tggcggtaat attgttctgg atattaccag | 120 |
| caaggccgat agtttgagtt cttctactca ggcaagtgat gttattacta atcaaagaag | 180 |
| tattgcgaca acggttaatt tgcgtgatgg acagactctt ttactcggtg gcctcactga | 240 |

```
ttataaaaac acttctcagg attctggcgt accgttcctg tctaaaatcc ctttaatcgg      300
cctcctgttt agctcccgct ctgattctaa cgaggaaagc acgttatacg tgctcgtcaa      360
agcaaccata gtacgcgccc tgtagcggcg cattaagcgc ggcgggtgtg gtggttacgc      420
gcagcgtgac cgctacactt gccagcgccc tagcgcccgc tcctttcgct ttcttccctt      480
cctttctcgc cacgttcgcc ggctttcccc gtcaagctct aaatcggggg ctccctttag      540
ggttccgatt tagtgcttta cggcacctcg accccaaaaa acttgattag ggtgatggtt      600
cacgtagtgg gccatcgccc tgatagacgg ttttcgccc tttgacgttg gagtccacgt      660
tctttaatag tggactcttg ttccaaactg gaacaacact caaccctatc tcggtctatt      720
cttttgattt ataagggatt ttgccgattt cggcctattg gttaaaaaat gagctgattt      780
aacaaaaatt taacgcgaac tttaacaaaa tattaacgtt tacaatttaa atatttgctt      840
atacaatctt cctgtttttg gggcttttct gattatcaac cggggtacat atgattgaca      900
tgctagtttt acgattaccg ttcatcgccc tgcgcgctcg ctcgctcact gaggccgccc      960
gggcaaagcc cggcgtcgg gcgacctttg gtcgcccggc ctcagtgagc gagcgagcgc     1020
gcagagaggg agtggaattc acgcgtggat ctgaattcaa ttcacgcgtg gtacggccgc     1080
ggtaccggcg cgcccgtacg cggggaggc tgctggtgaa tattaaccaa ggtcacccca     1140
gttatcggag gagcaaacag gggctaagtc caccggggga ggctgctggt gaatattaac     1200
caaggtcacc ccagttatcg gaggagcaaa caggggctaa gtccaccggg ggaggctgct     1260
ggtgaatatt aaccaaggtc accccagtta tcggaggagc aaacaggggc taagtccact     1320
gtacaacgcg tgaattcgct agcgtctgtc tgcacatttc gtagagcgag tgttccgata     1380
ctctaatctc cctaggcaag gttcatattt gtgtaggtta cttattctcc ttttgttgac     1440
taagtcaata atcagaatca gcaggtttgg agtcagcttg cagggatca gcagcctggg     1500 ttggaaggag ggggtataaa agccccttca ccaggagaag ccgtcacaca gatccacaag     1560
ctcctgtcta gaaagaggta agggtttaag ggatggttgg ttggtggggt attaatgttt     1620
aattacctgg agcacctgcc tgaaatcact ttttttcagg ttgggctagc ccaccatgca     1680
gcgcgtgaac atgatcatgg ccgagagccc cggcctgatc accatctgcc tgctgggcta     1740
cctgctgagc gccgagtgca ccgtgttcct ggaccacgag aacgccaaca agatcctgaa     1800
ccgccccaag cgctacaaca gcggcaagct ggaggagttc gtgcagggca acctggagcg     1860
cgagtgcatg gaggagaagt gcagcttcga ggaggcccgc gaggtgttcg agaacaccga     1920
gcgcaccacc gagttctgga agcagtacgt ggacggcgac cagtgcgaga gcaaccctg     1980 cctgaacggc ggcagctgca aggacgacat caacagctac gagtgctggt gccccttcgg     2040
cttcgagggc aagaactgcg agctggacgt gacctgcaac atcaagaacg gccgctgcga     2100
gcagttctgc aagaacagcg ccgacaacaa ggtggtgtgc agctgcaccg agggctaccg     2160
cctggccgag aaccagaaga gctgcgagcc cgccgtgccc ttcccctgcg gccgcgtgag     2220
cgtgagccag accagcaagc tgacccgcgc cgaggccgtg ttccccgacg tggactacgt     2280
gaacagcacc gaggccgaga ccatcctgga caacatcacc cagagcaccc agagcttcaa     2340
cgacttcacc cgcgtggtgg gcggcgagga cgccaagccc ggccagttcc cctgcaggt     2400 ggtgctgaac ggcaaggtgg acgccttctg cggcggcagc atcgtgaacg agaagtggat     2460
cgtgaccgcc gcccactgcg tggagaccgg cgtgaagatc accgtggtgg ccggcgagca     2520
caacatcgag gagaccgagc acaccgagca gaagcgcaac gtgatccgca tcatccccca     2580
```

```
ccacaactac aacgccgcca tcaacaagta caaccacgac atcgccctgc tggagctgga    2640
cgagcccctg gtgctgaaca gctacgtgac ccccatctgc atcgccgaca aggagtacac    2700
caacatcttc ctgaagttcg gcagcggcta cgtgagcggc tggggccgcg tgttccacaa    2760
gggccgcagc gccctggtgc tgcagtacct cgcgtgccc ctggtggacc cgccacctg     2820 cctgctgagc accaagttca ccatctacaa caacatgttc tgcgccggct ccacgaggg    2880 cggccgcgac agctgccagg cgacagcgg cggccccac gtgaccgagg tggagggcac     2940
cagcttcctg accggcatca tcagctgggg cgaggagtgc gccatgaagg gcaagtacgg    3000
catctacacc aaggtgagcc gctacgtgaa ctggatcaag gagaagacca agctgaccta    3060
atgaaagatg gatttccaag gttaattcat tggaattgaa aattaacagc ccccccccc    3120 ccccccctgc agatctgagc cgaattcctg cagcccgggg gatcagcctc gactgtgcct    3180
tctagttgcc agccatctgt tgtttgcccc tccccgtgc cttccttgac cctggaaggt    3240
gccactccca ctgtcctttc ctaataaaat gaggaaattg catcgcattg tctgagtagg    3300
tgtcattcta ttctgggggg tggggtgggg caggacagca aggggagga ttgggaagac    3360 aatagcaggc atgctgggga tgcggtgggc tctatggctt ctgaggcgga agaaccagc    3420 tggggaccgg tggatctcga tagcaggcat gctggggaga gatcgatctg aggaacccct    3480
agtgatggag ttggccactc cctctctgcg cgctcgctcg ctcactgagg ccgcccgggc    3540
aaagcccggg cgtcgggcga cctttggtcg cccggcctca gtgagcgagc gagcgcgcag    3600
agagggagtg gccaacccc cccccccccc ccccggcga ttctcttgtt tgctccagac      3660
tctcaggcaa tgacctgata gcctttgtag agacctctca aaatagcta ccctctccgg     3720 catgaattta tcagctagaa cggttgaata tcatattgat ggtgatttga ctgtctccgg    3780
cctttctcac ccgtttgaat ctttacctac acattactca ggcattgcat ttaaaatata    3840
tgagggttct aaaaattttt atccttgcgt tgaaataaag gcttctcccg caaaagtatt    3900
acagggtcat aatgtttttg gtacaaccga tttagcttta tgctctgagg ctttattgct    3960
taattttgct aattctttgc cttgcctgta tgatttattg gatgttggaa tcgcctgatg    4020 cggtatttc tccttacgca tctgtgcggt atttcacacc gcatatggtg cactctcagt    4080
acaatctgct ctgatgccgc atagttatat ggtgcactct cagtacaatc tgctctgatg    4140
ccgcatagtt aagccagccc cgacacccgc caacacagcc agccccgaca cccgccaaca    4200
cccgctgacg cgccctgacg ggcttgtctg ctcccggcat ccgcttacag acaagctgtg    4260
accgtctccg ggagctgcat gtgtcagagg ttttcaccgt catcaccgaa acgcgcgaga    4320
cgaaagggcc tcgtgatacg cctatttta taggttaatg tcatgataat aatggtttct    4380
tagacgtcag gtggcacttt tcggggaaat gtgcgcggaa cccctatttg tttattttc    4440 taaatacatt caaatatgta tccgctcatg agacaataac cctgataaat gctcaataat    4500
attgaaaaag gaagagtatg agtattcaac atttccgtgt cgcccttatt ccctttttg     4560 cggcattttg ccttcctgtt tttgctcacc cagaaacgct ggtgaaagta aaagatgctg    4620
aagatcagtt gggtgcacga gtgggttaca tcgaactgga tctcaacagc ggtaagatcc    4680
ttgagagttt cgccccgaa gaacgttttc caatgatgag cacttttaaa gttctgctat     4740
gtggcgcggt attatcccgt attgacgccg gcaagagca actcggtcgc cgcatacact    4800
attctcagaa tgacttggtt gagtactcac cagtcacaga aaagcatctt acggatggca    4860
tgacagtaag agaattatgc agtgctgcca taaccgagt tgataacact gcggccaact    4920
tacttctgac aacgatcgga ggaccgaagg agctaaccgc tttttttgcac aacatggggg    4980
```

```
atcatgtaac tcgccttgat cgttgggaac cggagctgaa tgaagccata ccaaacgacg    5040
agcgtgacac cacgatgcct gtagcaatgg caacaacgtt gcgcaaacta ttaactggcg    5100
aactacttac tctagcttcc cggcaacaat taatagactg gatggaggcg gataaagttg    5160
caggaccact tctgcgctcg gcccttccgg ctggctggtt tattgctgat aaatctggag    5220
ccggtgagcg tgggtctcgc ggtatcattg cagcactggg gccagatggt aagccctccc    5280
gtatcgtagt tatctacacg acggggagtc aggcaactat ggatgaacga atagacaga    5340 tcgctgagat aggtgcctca ctgattaagc attggtaact gtcagaccaa gtttactcat    5400
atatacttta gattgattta aaacttcatt tttaatttaa aaggatctag gtgaagatcc    5460 ttttttgataa tctcatgacc aaaatccctt aacgtgagtt ttcgttccac tgagcgtcag    5520
accccgtaga aaagatcaaa ggatcttctt gagatccttt ttttctgcgc gtaatctgct    5580
gcttgcaaac aaaaaaacca ccgctaccag cggtggtttg tttgccggat caagagctac    5640
caactctttt tccgaaggta actggcttca gcagagcgca gataccaaat actgtccttc    5700
tagtgtagcc gtagttaggc caccacttca agaactctgt agcaccgcct acatacctcg    5760
ctctgctaat cctgttacca gtggctgctg ccagtggcga taagtcgtgt cttaccgggt    5820
tggactcaag acgatagtta ccggataagg cgcagcggtc gggctgaacg gggggttcgt    5880
gcacacagcc cagcttggag cgaacgacct acaccgaact gagatacct a cagcgtgagc    5940 tatgagaaag cgccacgctt cccgaaggga gaaaggcgga caggtatccg gtaagcggca    6000
gggtcggaac aggagagcgc acgagggagc ttccaggggg aaacgcctgg tatctttata    6060
gtcctgtcgg gtttcgccac ctctgacttg agcgtcgatt tttgtgatgc tcgtcagggg    6120
ggcggagcct atggaaaaac gccagcaacg cggccttttt acggttcctg ccttttgct    6180 ggcctttgc tcacatgttc tttcctgcgt tatccctga ttctgtggat aaccgtatta    6240
ccgcctttga gtgagctgat accgctcgcc gcagccgaac gaccgagcgc agcgagtcag    6300
tgagcgagga agcggaagag cgcccaatac gcaaaccgcc tctccccgcg cgttggccga    6360
ttcattaatg                                                          6370
```

<210> SEQ ID NO 3
<211> LENGTH: 6228
<212> TYPE: DNA
<213> ORGANISM: Artificial Sequence
<220> FEATURE:
<223> OTHER INFORMATION: pAAVsc-TTRe-TTRm-MVM-co-FIX-R338L-BGHpA

<400> SEQUENCE: 3

```
agctggcgta atagcgaaga ggcccgcacc gatcgccctt cccaacagtt gcgcagcctg      60
aatggcgaat ggcgattccg ttgcaatggc tggcggtaat attgttctgg atattaccag    120
caaggccgat agtttgagtt cttctactca ggcaagtgat gttattacta atcaaagaag    180
tattgcgaca cggttaatt tgcgtgatgg acagactctt ttactcggtg gcctcactga    240
ttataaaaac acttctcagg attctggcgt accgttcctg tctaaaatcc ctttaatcgg    300
cctcctgttt agctcccgct ctgattctaa cgaggaaagc acgttatacg tgctcgtcaa    360
agcaaccata gtacgcgccc tgtagcgcg cattaagcgc ggcgggtgtg gtggttacgc    420
gcagcgtgac cgctacactt gccagcgccc tagcgcccgc tcctttcgct ttcttccctt    480
cctttctcgc cacgttcgcc ggctttcccc gtcaagctct aaatcggggg ctccctttag    540
ggttccgatt tagtgcttta cggcacctcg accccaaaaa acttgattag ggtgatggtt    600
```

```
cacgtagtgg gccatcgccc tgatagacgg ttttccgccc tttgacgttg gagtccacgt    660
tctttaatag tggactcttg ttccaaactg gaacaacact caaccctatc tcggtctatt    720
cttttgattt ataagggatt tgccgatttc ggcctattg gttaaaaaat gagctgattt     780
aacaaaaatt taacgcgaac tttaacaaaa tattaacgtt tacaatttaa atatttgctt    840
atacaatctt cctgttttg gggcttttct gattatcaac cggggtacat atgattgaca    900
tgctagtttt acgattaccg ttcatcgccc tgcgcgctcg ctcgctcact gaggccgccc    960
gggcaaagcc cgggcgtcgg gcgacctttg gtcgcccggc ctcagtgagc gagcgagcgc    1020
gcagagaggg agtggaattc acgcgtggat ctgaattcaa ttcacgcgtg gtacggccgc    1080
ggtacccact gggaggatgt tgagtaagat ggaaaactac tgatgaccct tgcagagaca    1140
gagtattagg acatgtttga acaggggccg ggcgatcagc aggtagctct agaggatccc    1200
cgtctgtctg cacatttcgt agagcgagtg ttccgatact ctaatctccc taggcaaggt    1260
tcatatttgt gtaggttact tattctcctt ttgttgacta agtcaataat cagaatcagc    1320
aggtttggag tcagcttggc agggatcagc agcctgggtt ggaaggaggg ggtataaaag    1380
cccccttcacc aggagaagcc gtcacacaga tccacaagct cctggctaga aagaggtaag    1440
ggtttaaggg atggttggtt ggtggggtat taatgtttaa ttacctggag cacctgcctg    1500
aaatcacttt ttttcaggtt gggctagccc accatgcagc gcgtgaacat gatcatggcc    1560
gagagccccg gcctgatcac catctgcctg ctgggctacc tgctgagcgc cgagtgcacc    1620
gtgttcctgg accacgagaa cgccaacaag atcctgaacc gccccaagcg ctacaacagc    1680
ggcaagctgg aggagttcgt gcagggcaac ctggagcgcg agtgcatgga ggagaagtgc    1740
agcttcgagg aggcccgcga ggtgttcgag aacaccgagc gcaccaccga gttctggaag    1800
cagtacgtgg acggcgacca gtgcgagagc aaccccctgcc tgaacggcgg cagctgcaag    1860
gacgacatca acagctacga gtgctggtgc cccttcggct tcgagggcaa gaactgcgag    1920
ctggacgtga cctgcaacat caagaacggc cgctgcgagc agttctgcaa gaacagcgcc    1980
gacaacaagg tggtgtgcag ctgcaccgag ggctaccgcc tggccgagaa ccagaagagc    2040
tgcgagcccg ccgtgccctt cccctgcggc cgcgtgagcg tgagccagac cagcaagctg    2100
acccgcgccg aggccgtgtt ccccgacgtg gactacgtga acagcaccga ggccgagacc    2160
atcctggaca catcacccca gagcacccag agcttcaacg acttcacccg cgtggtgggc    2220
ggcgaggacg ccaagcccgg ccagttcccc tggcaggtgg tgctgaacgg caaggtggac    2280
gccttctgcg gcggcagcat cgtgaacgag aagtggatcg tgaccgccgc ccactgcgtg    2340
gagaccggcg tgaagatcac cgtggtggcc ggcgagcaca acatcgagga gaccgagcac    2400
accgagcaga gcgcaacgt gatccgcatc atcccccacc acaactacaa cgccgccatc    2460
aacaagtaca ccacgacat cgccctgctg gagctggacg agcccctggt gctgaacagc    2520
tacgtgaccc ccatctgcat cgccgacaag gagtacacca acatcttcct gaagttcggc    2580
agcggctacg tgagcggctg gggccgcgtg ttccacaagg gccgcagcgc cctggtgctg    2640
cagtacctgc gcgtgccct ggtggaccgc gccacctgcc tgctgagcac caagttcacc    2700
atctacaaca catgttctg cgccggcttc cacgagggcg gccgcgacag ctgccagggc    2760
gacagcggcg gcccccacgt gaccgaggtg gagggcacca gcttcctgac cggcatcatc    2820
agctggggcg aggagtgcgc catgaagggc aagtacggca tctacaccaa ggtgagccgc    2880
tacgtgaact ggatcaagga gaagaccaag ctgacctaat gaaagatgga tttccaaggt    2940
taattcattg gaattgaaaa ttaacagccc ccccccccc cccctgcag atctgagccg    3000
```

```
aattcctgca gcccggggga tcagcctcga ctgtgccttc tagttgccag ccatctgttg    3060
tttgcccctc ccccgtgcct tccttgaccc tggaaggtgc cactcccact gtcctttcct    3120
aataaaatga ggaaattgca tcgcattgtc tgagtaggtg tcattctatt ctgggggtg     3180
gggtggggca ggacagcaag ggggaggatt gggaagacaa tagcaggcat gctgggatg     3240
cggtgggctc tatggcttct gaggcggaaa gaaccagctg ggaccggtg gatctcgata    3300
gcaggcatgc tggggagaga tcgatctgag gaaccctag tgatggagtt ggccactccc    3360
tctctgcgcg ctcgctcgct cactgaggcc gcccgggcaa agcccgggcg tcgggcgacc    3420
tttggtcgcc cggcctcagt gagcgagcga gcgcgcagag agggagtggc caaccccccc    3480
cccccccccc cccggcgatt ctcttgtttg ctccagactc tcaggcaatg acctgatagc    3540
ctttgtagag acctctcaaa aatagctacc ctctccggca tgaatttatc agctagaacg    3600
gttgaatatc atattgatgg tgatttgact gtctccggcc tttctcaccc gtttgaatct    3660
ttacctacac attactcagg cattgcattt aaaatatatg agggttctaa aaatttttat    3720
ccttgcgttg aaataaaggc ttctcccgca aaagtattac agggtcataa tgttttggt    3780
acaaccgatt tagctttatg ctctgaggct ttattgctta attttgctaa ttctttgcct    3840
tgcctgtatg atttattgga tgttggaatc gcctgatgcg gtattttctc cttacgcatc    3900
tgtgcggtat ttcacaccgc atatggtgca ctctcagtac aatctgctct gatgccgcat    3960
agttatatgg tgcactctca gtacaatctg ctctgatgcc gcatagttaa ccagccccg     4020
acaccgccca acagccag ccccgacacc cgccaacacc cgctgacgcg ccctgacggg      4080
cttgtctgct cccggcatcc gcttacagac aagctgtgac cgtctccggg agctgcatgt    4140
gtcagaggtt ttcaccgtca tcaccgaaac gcgcgagacg aaagggcctc gtgatacgcc    4200
tatttttata ggttaatgtc atgataataa tggtttctta gacgtcaggt ggcacttttc    4260
ggggaaatgt gcgcggaacc cctatttgtt tatttttcta aatacattca aatatgtatc    4320
cgctcatgag acaataaccc tgataaatgc tcaataatat tgaaaaagga agagtatgag    4380
tattcaacat ttccgtgtcg cccttattcc cttttttgcg gcattttgcc ttcctgtttt    4440
tgctcaccca gaaacgctgg tgaaagtaaa agatgctgaa gatcagttgg gtgcacgagt    4500
gggttacatc gaactggatc tcaacagcgg taagatcctt gagagttttc gccccgaaga    4560
acgttttcca atgatgagca cttttaaagt tctgctatgt ggcgcggtat tatcccgtat    4620
tgacgccggg caagagcaac tcggtcgccg catacactat tctcagaatg acttggttga    4680
gtactcacca gtcacagaaa agcatcttac ggatggcatg acagtaagag aattatgcag    4740
tgctgccata accatgagtg ataacactgc ggccaactta cttctgacaa cgatcggagg    4800
accgaaggag ctaaccgctt ttttgcacaa catgggggat catgtaactc gccttgatcg    4860
ttgggaaccg gagctgaatg aagccatacc aaacgacgag cgtgacacca cgatgcctgt    4920
agcaatggca acaacgttgc gcaaactatt aactggcgaa ctacttactc tagcttcccg    4980
gcaacaatta atagactgga tggaggcgga taaagttgca ggaccacttc tgcgctcggc    5040
ccttccggct ggctggttta ttgctgataa atctggagcc ggtgagcgtg ggtctcgcgg    5100
tatcattgca gcactgggc cagatggtaa gccctcccgt atcgtagtta tctacacgac    5160
ggggagtcag gcaactatgg atgaacgaaa tagacagatc gctgagatag gtgcctcact    5220
gattaagcat tggtaactgt cagaccaagt ttactcatat atactttaga ttgatttaaa    5280
acttcatttt taatttaaaa ggatctaggt gaagatcctt tttgataatc tcatgaccaa    5340
```

| | | |
|---|---|---|
| aatcccttaa cgtgagtttt cgttccactg agcgtcagac cccgtagaaa agatcaaagg | 5400 | |
| atcttcttga gatccttttt ttctgcgcgt aatctgctgc ttgcaaacaa aaaaaccacc | 5460 | |
| gctaccagcg gtggtttgtt tgccggatca agagctacca actcttttc cgaaggtaac | 5520 | |
| tggcttcagc agagcgcaga taccaaatac tgtccttcta gtgtagccgt agttaggcca | 5580 | |
| ccacttcaag aactctgtag caccgcctac atacctcgct ctgctaatcc tgttaccagt | 5640 | |
| ggctgctgcc agtggcgata gtcgtgtct taccggggttg gactcaagac gatagttacc | 5700 | |
| ggataaggcg cagcggtcgg gctgaacggg gggttcgtgc acacagccca gcttggagcg | 5760 | |
| aacgacctac accgaactga gatacctaca gcgtgagcta tgagaaagcg ccacgcttcc | 5820 | |
| cgaagggaga aaggcggaca ggtatccggt aagcggcagg gtcggaacag gagagcgcac | 5880 | |
| gagggagctt ccaggggaa acgcctggta tctttatagt cctgtcgggt ttcgccacct | 5940 | |
| ctgacttgag cgtcgatttt tgtgatgctc gtcaggggg cggagcctat ggaaaaacgc | 6000 | |
| cagcaacgcg gcctttttac ggttcctggc cttttgctgg ccttttgctc acatgttctt | 6060 | |
| tcctgcgtta tcccctgatt ctgtggataa ccgtattacc gcctttgagt gagctgatac | 6120 | |
| cgctcgccgc agccgaacga ccgagcgcag cgagtcagtg agcgaggaag cggaagagcg | 6180 | |
| cccaatacgc aaaccgcctc tccccgcgcg ttggccgatt cattaatg | 6228 | |

<210> SEQ ID NO 4
<211> LENGTH: 6448
<212> TYPE: DNA
<213> ORGANISM: Artificial Sequence
<220> FEATURE:
<223> OTHER INFORMATION: pAAVsc-3xSerpEnh-TTRe-TTRm-MVM-co-FIX-R338L-
  BGHpA

<400> SEQUENCE: 4

| | | |
|---|---|---|
| agctggcgta atagcgaaga ggcccgcacc gatcgccctt cccaacagtt gcgcagcctg | 60 | |
| aatggcgaat ggcgattccg ttgcaatggc tggcggtaat attgttctgg atattaccag | 120 | |
| caaggccgat agtttgagtt cttctactca ggcaagtgat gttattacta atcaaagaag | 180 | |
| tattgcgaca acggttaatt tgcgtgatgg acagactctt ttactcggtg gcctcactga | 240 | |
| ttataaaaac acttctcagg attctggcgt accgttcctg tctaaaatcc ctttaatcgg | 300 | |
| cctcctgttt agctcccgct ctgattctaa cgaggaaagc acgttatacg tgctcgtcaa | 360 | |
| agcaaccata gtacgcgccc tgtagcgcgc cattaagcgc ggcgggtgtg gtggttacgc | 420 | |
| gcagcgtgac cgctacactt gccagcgccc tagcgcccgc tcctttcgct ttcttccctt | 480 | |
| cctttctcgc cacgttcgcc ggctttcccc gtcaagctct aaatcggggg ctcccttta g | 540 | |
| ggttccgatt tagtgcttta cggcacctcg accccaaaaa acttgattag ggtgatggtt | 600 | |
| cacgtagtgg gccatcgccc tgatagacgg ttttcgccc tttgacgttg gagtccacgt | 660 | |
| tctttaatag tggactcttg ttccaaactg gaacaacact caaccctatc tcggtctatt | 720 | |
| cttttgattt ataagggatt tgccgatttc ggcctattgg ttaaaaaat gagctgattt | 780 | |
| aacaaaaatt taacgcgaac tttaacaaaa tattaacgtt tacaatttaa atatttgctt | 840 | |
| atacaatctt cctgtttttg gggcttttct gattatcaac cggggtacat atgattgaca | 900 | |
| tgctagtttt acgattaccg ttcatcgccc tgcgcgtcg ctcgctcact gaggccgccc | 960 | |
| gggcaaagcc cggcgtcgg gcgacctttg gtcgcccggc ctcagtgagc gagcgagcgc | 1020 | |
| gcagagaggg agtggaattc acgcgtggat ctgaattcaa ttcacgcgtg gtacggccgc | 1080 | |
| ggggggagg ctgctggtga atattaacca aggtcacccc agttatcgga ggagcaaaca | 1140 | |

-continued

```
ggggctaagt ccaccggggg aggctgctgg tgaatattaa ccaaggtcac cccagttatc      1200
ggaggagcaa acaggggcta agtccaccgg gggaggctgc tggtgaatat taaccaaggt      1260
caccccagtt atcggaggag caaacagggg ctaagtccac ggtacccact gggaggatgt      1320
tgagtaagat ggaaaactac tgatgaccct gcagagaca gagtattagg acatgtttga       1380
acaggggccg ggcgatcagc aggtagctct agaggatccc cgtctgtctg cacatttcgt     1440
agagcgagtg ttccgatact ctaatctccc taggcaaggt tcatatttgt gtaggttact     1500
tattctcctt ttgttgacta agtcaataat cagaatcagc aggtttggag tcagcttggc     1560
agggatcagc agcctgggtt ggaaggaggg ggtataaaag ccccttcacc aggagaagcc     1620
gtcacacaga tccacaagct cctggctaga aagaggtaag ggtttaaggg atggttggtt     1680
ggtggggtat taatgtttaa ttacctggag cacctgcctg aaatcacttt ttttcaggtt     1740
gggctagccc accatgcagc gcgtgaacat gatcatggcc gagagccccg gcctgatcac     1800
catctgcctg ctgggctacc tgctgagcgc cgagtgcacc gtgttcctgg accacgagaa     1860
cgccaacaag atcctgaacc gccccaagcg ctacaacagc ggcaagctgg aggagttcgt     1920
gcagggcaac ctggagcgcg agtgcatgga ggagaagtgc agcttcgagg aggcccgcga     1980
ggtgttcgag aacaccgagc gcaccaccga gttctggaag cagtacgtgg acggcgacca     2040
gtgcgagagc aaccccctgcc tgaacggcgg cagctgcaag gacgacatca cagctacga     2100 gtgctggtgc cccttcggct tcgagggcaa gaactgcgag ctggacgtga cctgcaacat     2160
caagaacggc cgctgcgagc agttctgcaa gaacagcgcc gacaacaagg tggtgtgcag     2220
ctgcaccgag ggctaccgcc tggccgagaa ccagaagagc tgcgagcccg ccgtgccctt     2280
cccctgcggc cgcgtgagcg tgagccagac cagcaagctg acccgcgccg aggccgtgtt     2340
ccccgacgtg gactacgtga acagcaccga ggccgagacc atcctggaca acatcaccca     2400
gagcacccag agcttcaacg acttcacccg cgtggtgggc ggcgaggacg ccaagcccgg     2460
ccagttcccc tggcaggtgg tgctgaacgg caaggtggac gccttctgcg gcggcagcat     2520
cgtgaacgag aagtggatcg tgaccgccgc ccactgcgtg gagaccggcg tgaagatcac     2580
cgtggtggcc ggcgagcaca acatcgagga gaccgagcac accgagcaga gcgcaacgt      2640 gatccgcatc atcccccacc acaactacaa cgccgccatc aacaagtaca ccacgacat      2700 cgccctgctg gagctggacg agccctggt gctgaacagc tacgtgaccc ccatctgcat      2760
cgccgacaag gagtacacca acatcttcct gaagttcggc agcggctacg tgagcggctg     2820
gggccgcgtg ttccacaagg gccgcagcgc cctggtgctg cagtacctgc gcgtgccct      2880 ggtggaccgc gccacctgcc tgctgagcac caagttcacc atctacaaca acatgttctg     2940
cgccggcttc cacagggcg ccgcgacag ctgccaggc gacagcggcg ccccacgt          3000 gaccgaggtg gagggcacca gcttcctgac cggcatcatc agctggggcg aggagtgcgc     3060
catgaagggc aagtacggca tctacaccaa ggtgagccgc tacgtgaact ggatcaagga     3120
gaagaccaag ctgacctaat gaaagatgga tttccaaggt taattcattg gaattgaaaa     3180
ttaacagccc cccccccccc ccccctgcag atctgagccg aattcctgca gcccggggga     3240
tcagcctcga ctgtgccttc tagttgccag ccatctgttg tttgccctc cccgtgcct       3300 tccttgaccc tggaaggtgc cactcccact gtcctttcct aataaatga ggaaattgca      3360 tcgcattgtc tgagtaggtg tcattctatt ctgggggtg ggtgggggca ggacagcaag      3420
ggggaggatt gggaagacaa tagcaggcat gctgggatg cggtgggctc tatggcttct     3480
gaggcggaaa gaaccagctg ggaccggtg atctcgata gcaggcatgc tggggagaga       3540
```

```
tcgatctgag gaacccctag tgatggagtt ggccactccc tctctgcgcg ctcgctcgct    3600
cactgaggcc gcccgggcaa agcccgggcg tcgggcgacc tttggtcgcc cggcctcagt    3660
gagcgagcga gcgcgcagag agggagtggc caaccccccc ccccccccccc cccggcgatt    3720 ctcttgtttg ctccagactc tcaggcaatg acctgatagc ctttgtagag acctctcaaa    3780
aatagctacc ctctccggca tgaatttatc agctagaacg gttgaatatc atattgatgg    3840
tgatttgact gtctccggcc tttctcaccc gtttgaatct ttacctacac attactcagg    3900
cattgcattt aaaatatatg agggttctaa aaattttat ccttgcgttg aaataaaggc    3960
ttctcccgca aaagtattac agggtcataa tgttttggt acaaccgatt tagctttatg    4020
ctctgaggct ttattgctta attttgctaa ttctttgcct tgcctgtatg atttattgga    4080
tgttggaatc gcctgatgcg gtattttctc cttacgcatc tgtgcggtat ttcacaccgc    4140
atatggtgca ctctcagtac aatctgctct gatgccgcat agttatatgg tgcactctca    4200
gtacaatctg ctctgatgcc gcatagttaa gccagcccg acaccgcca acacagccag    4260 ccccgacacc cgccaacacc cgctgacgcg ccctgacggg cttgtctgct cccggcatcc    4320
gcttacagac aagctgtgac cgtctccggg agctgcatgt gtcagaggtt ttcaccgtca    4380
tcaccgaaac gcgcgagacg aaagggcctc gtgatacgcc tatttttata ggttaatgtc    4440
atgataataa tggtttctta gacgtcaggt ggcactttc ggggaaatgt gcgcggaacc    4500
cctatttgtt tatttttcta aatacattca aatatgtatc cgctcatgag acaataaccc    4560
tgataaatgc tcaataatat tgaaaaagga agagtatgag tattcaacat ttccgtgtcg    4620
cccttattcc cttttttgcg gcattttgcc ttcctgtttt tgctcaccca gaaacgctgg    4680
tgaaagtaaa agatgctgaa gatcagttgg gtgcacgagt gggttacatc gaactggatc    4740
tcaacagcgg taagatcctt gagagttttc gccccgaaga acgttttcca atgatgagca    4800
cttttaaagt tctgctatgt ggcgcggtat tatcccgtat tgacgccggg caagagcaac    4860
tcggtcgccg catacactat tctcagaatg acttggttga gtactcacca gtcacagaaa    4920
agcatcttac ggatggcatg acagtaagag aattatgcag tgctgccata accatgagtg    4980
ataacactgc ggccaactta cttctgacaa cgatcggagg accgaaggag ctaaccgctt    5040
ttttgcacaa catgggggat catgtaactc gccttgatcg ttgggaaccg gagctgaatg    5100
aagccatacc aaacgacgag cgtgacacca cgatgcctgt agcaatggca acaacgttgc    5160
gcaaactatt aactggcgaa ctacttactc tagcttcccg gcaacaatta atagactgga    5220
tggaggcgga taaagttgca ggaccacttc tgcgctcggc ccttccggct ggctggttta    5280
ttgctgataa atctggagcc ggtgagcgtg ggtctcgcgg tatcattgca gcactggggc    5340
cagatggtaa gccctcccgt atcgtagtta tctacacgac ggggagtcag gcaactatgg    5400
atgaacgaaa tagacagatc gctgagatag gtgcctcact gattaagcat tggtaactgt    5460
cagaccaagt ttactcatat atactttaga ttgatttaaa acttcatttt taatttaaaa    5520
ggatctaggt gaagatcctt tttgataatc tcatgaccaa aatcccttaa cgtgagtttt    5580
cgttccactg agcgtcagac cccgtagaaa agatcaaagg atcttcttga tccttttt    5640 ttctgcgcgt aatctgctgc ttgcaaacaa aaaaaccacc gctaccagcg gtggtttgtt    5700
tgccggatca agagctacca actctttttc cgaaggtaac tggcttcagc agagcgcaga    5760
taccaaatac tgtccttcta gtgtagccgt agttaggcca ccacttcaag aactctgtag    5820
caccgcctac atacctcgct ctgctaatcc tgttaccagt ggctgctgcc agtggcgata    5880
```

| | |
|---|---:|
| agtcgtgtct taccgggttg gactcaagac gatagttacc ggataaggcg cagcggtcgg | 5940 |
| gctgaacggg gggttcgtgc acacagccca gcttggagcg aacgacctac accgaactga | 6000 |
| gatacctaca gcgtgagcta tgagaaagcg ccacgcttcc cgaagggaga aaggcggaca | 6060 |
| ggtatccggt aagcggcagg gtcggaacag gagagcgcac gagggagctt ccaggggggaa | 6120 |
| acgcctggta tctttatagt cctgtcgggt ttcgccacct ctgacttgag cgtcgatttt | 6180 |
| tgtgatgctc gtcaggggg cggagcctat ggaaaaacgc cagcaacgcg gcctttttac | 6240 |
| ggttcctggc cttttgctgg ccttttgctc acatgttctt tcctgcgtta tcccctgatt | 6300 |
| ctgtggataa ccgtattacc gcctttgagt gagctgatac cgctcgccgc agccgaacga | 6360 |
| ccgagcgcag cgagtcagtg agcgaggaag cggaagagcg cccaatacgc aaaccgcctc | 6420 |
| tccccgcgcg ttggccgatt cattaatg | 6448 |

<210> SEQ ID NO 5
<211> LENGTH: 72
<212> TYPE: DNA
<213> ORGANISM: Artificial Sequence
<220> FEATURE:
<223> OTHER INFORMATION: SerpEnh

<400> SEQUENCE: 5

| | |
|---|---:|
| ggggaggct gctggtgaat attaaccaag gtcaccccag ttatcggagg agcaaacagg | 60 |
| ggctaagtcc ac | 72 |

<210> SEQ ID NO 6
<211> LENGTH: 202
<212> TYPE: DNA
<213> ORGANISM: Artificial Sequence
<220> FEATURE:
<223> OTHER INFORMATION: TTRm

<400> SEQUENCE: 6

| | |
|---|---:|
| gtctgtctgc acatttcgta gagcgagtgt tccgatactc taatctccct aggcaaggtt | 60 |
| catatttgtg taggttactt attctccttt tgttgactaa gtcaataatc agaatcagca | 120 |
| ggtttggagt cagcttggca gggatcagca gcctgggttg aaggaggggg gtataaaagc | 180 |
| cccttcacca ggagaagccg tc | 202 |

<210> SEQ ID NO 7
<211> LENGTH: 21
<212> TYPE: DNA
<213> ORGANISM: Artificial Sequence
<220> FEATURE:
<223> OTHER INFORMATION: TTRm5'UTR

<400> SEQUENCE: 7

| | |
|---|---:|
| acacagatcc acaagctcct g | 21 |

<210> SEQ ID NO 8
<211> LENGTH: 92
<212> TYPE: DNA
<213> ORGANISM: Artificial Sequence
<220> FEATURE:
<223> OTHER INFORMATION: MVM intron

<400> SEQUENCE: 8

| | |
|---|---:|
| aagaggtaag ggtttaaggg atggttggtt ggtgggtat taatgtttaa ttacctggag | 60 |
| cacctgcctg aaatcacttt ttttcaggtt gg | 92 |

<210> SEQ ID NO 9
<211> LENGTH: 1389
<212> TYPE: DNA
<213> ORGANISM: Artificial Sequence
<220> FEATURE:
<223> OTHER INFORMATION: Co-FIX-R338L

<400> SEQUENCE: 9

```
atgcagcgcg tgaacatgat catggccgag agccccggcc tgatcaccat ctgcctgctg      60
ggctacctgc tgagcgccga gtgcaccgtg ttcctggacc acgagaacgc caacaagatc     120
ctgaaccgcc ccaagcgcta caacagcggc aagctggagg agttcgtgca gggcaacctg     180
gagcgcgagt gcatggagga aagtgcagc ttcgaggagg cccgcgaggt gttcgagaac      240
accgagcgca ccaccgagtt ctggaagcag tacgtggacg gcgaccagtg cgagagcaac     300
ccctgcctga cgcggcag ctgcaaggac gacatcaaca gctacgagtg ctggtgcccc       360
ttcggcttcg agggcaagaa ctgcgagctg gacgtgacct gcaacatcaa gaacggccgc     420
tgcgagcagt tctgcaagaa cagcgccgac aacaaggtgg tgtgcagctg caccgagggc     480
taccgcctgg ccgagaacca gaagagctgc gagcccgccg tgcccttccc ctgcggccgc     540
gtgagcgtga ccagaccag caagctgacc cgcgccgagg ccgtgttccc cgacgtggac      600
tacgtgaaca gcaccgaggc cgagaccatc ctggacaaca tcacccagag cacccagagc     660
ttcaacgact tcacccgcgt ggtgggcggc gaggacgcca agcccggcca gttcccctgg     720
caggtggtgc tgaacggcaa ggtggacgcc ttctgcggcg gcagcatcgt gaacgagaag     780
tggatcgtga ccgccgccca ctgcgtggag accggcgtga agatcaccgt ggtggccggc     840
gagcacaaca tcgaggagac cgagcacacc gagcagaagc gcaacgtgat ccgcatcatc     900
ccccaccaca actacaacgc cgccatcaac aagtacaacc acgacatcgc cctgctggag     960
ctggacgagc ccctggtgct gaacagctac gtgacccca tctgcatcgc cgacaaggag     1020
tacaccaaca tcttcctgaa gttcggcagc ggctacgtga gcggctgggg ccgcgtgttc    1080
cacaagggcc gcagcgccct ggtgctgcag tacctgcgcg tgcccctggt ggaccgcgcc    1140
acctgcctgc tgagcaccaa gttcaccatc tacaacaaca tgttctgcgc cggcttccac    1200
gagggcggcc gcgacagctg ccagggcgac agcggcggcc ccacgtgac cgaggtggag     1260
ggcaccagct tcctgaccgg catcatcagc tggggcgagg agtgcgccat gaagggcaag    1320
tacggcatct acaccaaggt gagccgctac gtgaactgga tcaaggagaa gaccaagctg    1380
acctaatga                                                            1389
```

<210> SEQ ID NO 10
<211> LENGTH: 295
<212> TYPE: DNA
<213> ORGANISM: Artificial Sequence
<220> FEATURE:
<223> OTHER INFORMATION: BGHpolyA

<400> SEQUENCE: 10

```
gatctgagcc gaattcctgc agcccggggg atcagcctcg actgtgcctt ctagttgcca     60
gccatctgtt gtttgcccct cccccgtgcc ttccttgacc ctggaaggtg ccactcccac    120
tgtcctttcc taataaaatg aggaaattgc atcgcattgt ctgagtaggt gtcattctat    180
tctggggggt ggggtggggc aggacagcaa gggggaggat tgggaagaca atagcaggca    240
tgctggggat gcggtgggct ctatggcttc tgaggcggaa agaaccagct gggga         295
```

<210> SEQ ID NO 11

<211> LENGTH: 218
<212> TYPE: DNA
<213> ORGANISM: Artificial Sequence
<220> FEATURE:
<223> OTHER INFORMATION: 3xSERP

<400> SEQUENCE: 11

```
gggggaggct gctggtgaat attaaccaag gtcaccccag ttatcggagg agcaaacagg      60
ggctaagtcc accggggagg ctgctggtg aatattaacc aaggtcaccc cagttatcgg     120
aggagcaaac aggggctaag tccaccgggg gaggctgctg gtgaatatta accaaggtca    180
ccccagttat cggaggagca acaggggct aagtccac                              218
```

<210> SEQ ID NO 12
<211> LENGTH: 100
<212> TYPE: DNA
<213> ORGANISM: Artificial Sequence
<220> FEATURE:
<223> OTHER INFORMATION: TTRe

<400> SEQUENCE: 12

```
cactgggagg atgttgagta agatggaaaa ctactgatga cccttgcaga gacagagtat     60
taggacatgt ttgaacaggg gccgggcgat cagcaggtag                         100
```

<210> SEQ ID NO 13
<211> LENGTH: 324
<212> TYPE: DNA
<213> ORGANISM: Artificial Sequence
<220> FEATURE:
<223> OTHER INFORMATION: 3xSERP-Flank-TTRe

<400> SEQUENCE: 13

```
gggggaggct gctggtgaat attaaccaag gtcaccccag ttatcggagg agcaaacagg      60
ggctaagtcc accggggag gctgctggtg aatattaacc aaggtcaccc cagttatcgg     120
aggagcaaac aggggctaag tccaccgggg gaggctgctg gtgaatatta accaaggtca    180
ccccagttat cggaggagca acaggggct aagtccacgg tacccactgg gaggatgttg     240
agtaagatgg aaaactactg atgacccttg cagagacaga gtattaggac atgtttgaac    300
aggggccggg cgatcagcag gtag                                          324
```

<210> SEQ ID NO 14
<211> LENGTH: 7757
<212> TYPE: DNA
<213> ORGANISM: Artificial Sequence
<220> FEATURE:
<223> OTHER INFORMATION: pAAVss-TTRm-MVM-CoFVIIIdeltaB-Sv40pA

<400> SEQUENCE: 14

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca    120
actccatcac taggggttcc tgcggccgcg gtaccgtctg tctgcacatt tcgtagagcg    180
agtgttccga tactctaatc tccctaggca aggttcatat ttgtgtaggt tacttattct    240
ccttttgttg actaagtcaa taatcagaat cagcaggttt ggagtcagct tggcagggat    300
cagcagcctg ggttggaagg aggggtata aaagccccctt caccaggaga agccgtcaca    360
cagatccaca agctcctgaa gaggtaaggg tttaagggat ggttggttgg tggggtatta    420
atgtttaatt acctggagca cctgcctgaa atcacttttt ttcaggttgg ctagtatgca    480
gatcgagctg tccacctgct ttttctgtg cctgctgcgg ttctgcttca gcgccacccg    540
```

```
gcggtactac ctgggcgccg tggagctgtc ctgggactac atgcagagcg acctgggcga   600
gctgcccgtg gacgcccggt tccccccag agtgcccaag agcttcccct tcaacaccag    660
cgtggtgtac aagaaaaccc tgttcgtgga gttcaccgac cacctgttca atatcgccaa   720
gcccaggccc ccctggatgg gcctgctggg ccccaccatc caggccgagg tgtacgacac   780
cgtggtgatc accctgaaga acatggccag ccaccccgtg agcctgcacg ccgtgggcgt   840
gagctactgg aaggccagcg agggcgccga gtacgacgac cagaccagcc agcgggagaa   900
agaagatgac aaggtgttcc ctggcggcag ccacacctac gtgtggcagg tgctgaaaga   960
aaacggcccc atggcctccg accccctgtg cctgacctac agctacctga ccacgtggat  1020
cctggtgaag gacctgaaca gcggcctgat cggcgctctg ctcgtctgcc gggagggcag  1080
cctggccaaa gagaaaaccc agaccctgca caagttcatc ctgctgttcg ccgtgttcga  1140
cgagggcaag agctggcaca gcgagacaaa gaacagcctg atgcaggacc gggacgccgc  1200
ctctgccaga gcctggccca agatgcacac cgtgaacggc tacgtgaaca agagcctgcc  1260
cggcctgatt ggctgccacc ggaagagcgt gtactggcac gtgatcggca tgggcaccac  1320
acccgaggtg cacagcatct ttctggaagg gcacaccttt ctggtccgga ccaccggca   1380
ggccagcctg gaaatcagcc ctatcacctt cctgaccgcc cagacactgc tgatggacct  1440
gggccagttc ctgctgtttt gccacatcag ctctcaccag cacgacggca tggaagccta  1500
cgtgaaggtg gactcttgcc ccgaggaacc ccagctgcgg atgaagaaca cgaggaagc   1560
cgaggactac gacgacgacc tgaccgcacg cgagatggac gtggtgcggt tcgacgacga  1620
caacagcccc agcttcatcc agatcagaag cgtggccaag aagcacccca gacctgggt   1680
gcactatatc gccgccgagg aagaggactg ggactacgcc cccctggtgc tggcccccga  1740
cgacagaagc tacaagagcc agtacctgaa caatggcccc agcggatcg gccggaagta   1800
caagaaagtg cggttcatgg cctacaccga cgagacattc aagacccggg aggccatcca  1860
gcacgagagc ggcatcctgg gccccctgct gtacggcgaa gtgggcgaca cactgctgat  1920
catcttcaag aaccaggcta gccgcccta caacatctac ccccacggca tcaccgacgt   1980
gcggcccctg tacagcaggc ggctgcccaa gggcgtgaag cacctgaagg acttccccat  2040
cctgcccggc gagatcttca gtacaagtg gaccgtgacc gtggaggacg gccccaccaa   2100
gagcgacccc agatgcctga cccggtacta cagcagcttc gtgaacatgg aacgggacct  2160
ggcctccggg ctgatcggac ctctgctgat ctgctacaaa gaaagcgtgg accagcgggg  2220
caaccagatc atgagcgaca gcggaacgt gatcctgttc agcgtgttcg atgagaaccg   2280
gtcctggtat ctgaccgaga acatccagcg gtttctgccc aaccctgccg gcgtgcagct  2340
ggaagatccc gagttccagg ccagcaacat catgcactcc atcaatggct acgtgttcga  2400
ctctctgcag ctctccgtgt gtctgcacga ggtggcctac tggtacatcc tgagcatcgg  2460
cgcccagacc gacttcctga gcgtgttctt cagcggctac accttcaagc acaagatggt  2520
gtacgaggac accctgaccc tgttcccttt cagcggcgag acagtgttca tgagcatgga  2580
aaacccggc ctgtggattc tgggctgcca caacagcgac ttccggaacc ggggcatgac   2640
cgccctgctg aaggtgtcca gctgcgacaa gaacaccggc gactactacg aggacagcta  2700
cgaggatatc agcgcctacc tgctgtccaa gaacaacgcc atcgaacccc ggagcttcag  2760
ccagaacccc cccgtgctga cgcgtcacca gcgggagatc acccggacaa ccctgcagtc  2820
cgaccaggaa gagatcgatt acgacgacac catcagcgtg gagatgaaga agaggatttt  2880
```

```
cgatatctac gacgaggacg agaaccagag ccccagaagc ttccagaaga aaacccggca    2940
ctacttcatt gccgccgtgg agaggctgtg ggactacggc atgagttcta gcccccacgt    3000
gctgcggaac cgggcccaga gcggcagcgt gccccagttc aagaaagtgg tgttccagga    3060
attcacagac ggcagcttca cccagcctct gtatagaggc gagctgaacg agcacctggg    3120
gctgctgggg ccctacatca gggccgaagt ggaggacaac atcatggtga ccttccggaa    3180
tcaggccagc agaccctact ccttctacag cagcctgatc agctacgaag aggaccagcg    3240
gcagggcgcc gaaccccgga agaacttcgt gaagcccaac gaaaccaaga cctacttctg    3300
gaaagtgcag caccacatgg cccccaccaa ggacgagttc gactgcaagg cctgggccta    3360
cttcagcgac gtggatctgg aaaaggacgt gcactctgga ctgattggcc cactcctggt    3420
ctgccacact aacaccctca accccgccca cggccgccag gtgaccgtgc aggaattcgc    3480
cctgttcttc accatcttcg acgagacaaa gtcctggtac ttcaccgaga atatggaacg    3540
gaactgcaga gcccctgca acatccagat ggaagatcct accttcaaag agaactaccg    3600
gttccacgcc atcaacggct acatcatgga caccctgcct ggcctggtga tgcccagga    3660 ccagagaatc cggtggtatc tgctgtccat gggcagcaac gagaatatcc acagcatcca    3720
cttcagcggc cacgtgttca ccgtgcgaa gaaagaagag tacaagatgg ccctgtacaa    3780
cctgtacccc ggcgtgttcg agacagtgga tgctgccc agcaaggccg gcatctggcg    3840
ggtggagtgt ctgatcggcg agcacctgca cgctggcatg agcaccctgt ttctggtgta    3900
cagcaacaag tgccagaccc cactgggcat ggcctctggc cacatccggg acttccagat    3960
caccgcctcc ggccagtacg gccagtgggc cccaagctg ccagactgc actacagcgg    4020 cagcatcaac gcctggtcca ccaaagagcc cttcagctgg atcaaggtgg acctgctggc    4080
ccctatgatc atccacggca ttaagaccca gggcgccagg cagaagttca gcagcctgta    4140
catcagccag ttcatcatca tgtacagcct ggacggcaag aagtggcaga cctaccgggg    4200
caacagcacc ggcaccctga tggtgttctt cggcaatgtg gacagcagcg gcatcaagca    4260
caacatcttc aaccccccca tcattgcccg gtacatccgg ctgcacccca cccactacag    4320
cattagatcc acactgagaa tggaactgat gggctgcgac ctgaactcct gcagcatgcc    4380
tctgggcatg gaaagcaagg ccatcagcga cgcccagatc acagccagca gctacttcac    4440
caacatgttc gccacctggt ccccctccaa ggcaggctg cacctgcagg ccggtccaa    4500 cgcctggcgg cctcaggtca caaccccaa agaatggctg caggtggact ttcagaaaac    4560
catgaaggtg accggcgtga ccacccaggg cgtgaaaagc ctgctgacca gcatgtacgt    4620
gaaagagttt ctgatcagca gctctcagga tggccaccag tggaccctgt tctttcagaa    4680
cggcaaggtg aaagtgttcc agggcaacca ggactccttc acccccgtgg tgaactccct    4740
ggaccccccc ctgctgaccc gctacctgag aatccacccc cagtcttggg tgcaccagat    4800
cgccctcagg atggaagtcc tgggatgtga ggcccaggat ctgtactgat gaggatctag    4860
gctcgacatg ctttatttgt gaaatttgtg atgctattgc tttatttgta accattataa    4920
gctgcaataa acaagttaac aacaacaatt gcattcattt tatgtttcag gttcaggggg    4980
aggtgtggga ggttttttaa actcgagatc cacggccgca ggaacccta gtgatggagt    5040 tggccactcc ctctctgcgc gctcgctcgc tcactgaggc cgggcgacca aggtcgccc    5100 gacgcccggg ctttgcccgg gcggcctcag tgagcgagcg agcgcgcagc tgcctgcagg    5160
ggcgcctgat gcggtatttt ctccttacgc atctgtgcgg tatttcacac cgcatacgtc    5220
aaagcaacca tagtacgcgc cctgtagcgg cgcattaagc gcggcgggtg tggtggttac    5280
```

```
gcgcagcgtg accgctacac ttgccagcgc cctagcgccc gctcctttcg ctttcttccc    5340
ttcctttctc gccacgttcg ccggcttccc ccgtcaagct ctaaatcggg ggctcccttt    5400
agggttccga tttagtgctt tacggcacct cgaccccaaa aaacttgatt tgggtgatgg    5460
ttcacgtagt gggccatcgc cctgatagac ggttttttcgc cctttgacgt tggagtccac    5520
gttctttaat agtggactct tgttccaaac tggaacaaca ctcaacccta tctcgggcta    5580
ttcttttgat ttataaggga ttttgccgat ttcggcctat tggttaaaaa atgagctgat    5640
ttaacaaaaa tttaacgcga attttaacaa aatattaacg tttacaattt tatggtgcac    5700
tctcagtaca atctgctctg atgccgcata gttaagccag ccccgacacc cgccaacacc    5760
cgctgacgcg ccctgacggg cttgtctgct cccggcatcc gcttacagac aagctgtgac    5820
cgtctccggg agctgcatgt gtcagaggtt ttcaccgtca tcaccgaaac gcgcgagacg    5880
aaagggcctc gtgatacgcc tatttttata ggttaatgtc atgataataa tggtttctta    5940
gacgtcaggt ggcactttc ggggaaatgt gcgcggaacc cctatttgtt tatttttcta    6000
aatacattca aatatgtatc cgctcatgag acaataaccc tgataaatgc ttcaataata    6060
ttgaaaaagg aagagtatga gtattcaaca tttccgtgtc gcccttattc ccttttttgc    6120
ggcattttgc cttcctgttt ttgctcaccc agaaacgctg gtgaaagtaa aagatgctga    6180
agatcagttg ggtgcacgag tgggttacat cgaactggat ctcaacagcg gtaagatcct    6240
tgagagtttt cgccccgaag aacgttttcc aatgatgagc acttttaaag ttctgctatg    6300
tggcgcggta ttatcccgta ttgacgccgg gcaagagcaa ctcggtcgcc gcatacacta    6360
ttctcagaat gacttggttg agtactcacc agtcacagaa aagcatctta cggatggcat    6420
gacagtaaga gaattatgca gtgctgccat aaccatgagt gataacactg cggccaactt    6480
acttctgaca acgatcggag gaccgaagga gctaaccgct ttttttgcaca acatggggga    6540 tcatgtaact cgccttgatc gttgggaacc ggagctgaat gaagccatac caaacgacga    6600
gcgtgacacc acgatgcctg tagcaatggc aacaacgttg cgcaaactat taactggcga    6660
actacttact ctagcttccc ggcaacaatt aatagactgg atggaggcgg ataaagttgc    6720
aggaccactt ctgcgctcgg cccttccggc tggctggttt attgctgata aatctggagc    6780
cggtgagcgt gggtctcgcg gtatcattgc agcactgggg ccagatggta agccctcccg    6840
tatcgtagtt atctacacga cggggagtca ggcaactatg gatgaacgaa atagacagat    6900
cgctgagata ggtgcctcac tgattaagca ttggtaactg tcagaccaag tttactcata    6960
tatactttag attgatttaa aacttcattt ttaatttaaa aggatctagg tgaagatcct    7020
ttttgataat ctcatgacca aaatccctta acgtgagttt tcgttccact gagcgtcaga    7080
ccccgtagaa aagatcaaag gatcttcttg agatccttt tttctgcgcg taatctgctg    7140
cttgcaaaca aaaaaaccac cgctaccagc ggtggtttgt ttgccggatc aagagctacc    7200
aactcttttt ccgaaggtaa ctggcttcag cagagcgcag ataccaaata ctgtccttct    7260
agtgtagccg tagttaggcc accacttcaa gaactctgta gcaccgccta catacctcgc    7320
tctgctaatc ctgttaccag tggctgctgc cagtggcgat aagtcgtgtc ttaccgggtt    7380
ggactcaaga cgatagttac cggataaggc gcagcggtcg gctgaacgg ggggttcgtg    7440 cacacagccc agcttggagc gaacgaccta caccgaactg agatacctac agcgtgagct    7500
atgagaaagc gccacgcttc ccgaagggag aaaggcggac aggtatccgg taagcggcag    7560
ggtcggaaca ggagagcgca cgagggagct tccaggggga aacgcctggt atctttatag    7620
```
tcctgtcggg tttcgccacc tctgacttga gcgtcgattt ttgtgatgct cgtcagggggg   7680 gcggagccta tggaaaaacg ccagcaacgc ggccttttta cggttcctgg ccttttgctg   7740
gccttttgct cacatgt                                                  7757

<210> SEQ ID NO 15
<211> LENGTH: 7849
<212> TYPE: DNA
<213> ORGANISM: Artificial Sequence
<220> FEATURE:
<223> OTHER INFORMATION: pAAVss-SerpEnh-TTRm-MVM-CoFVIIIdeltaB-Sv40pA

<400> SEQUENCE: 15
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac tagggggttcc tgcggccgcg gtaccggcgc gccgggggag gctgctggtg    180
aatattaacc aaggtcaccc cagttatcgg aggagcaaac aggggctaag tccacacgcg    240
tggtaccgtc tgtctgcaca tttcgtagag cgagtgttcc gatactctaa tctccctagg    300
caaggttcat atttgtgtag gttacttatt ctccttttgt tgactaagtc aataatcaga    360
atcagcaggt ttggagtcag cttggcaggg atcagcagcc tgggttggaa ggagggggta    420
taaaagcccc ttcaccagga gaagccgtca cacagatcca caagctcctg aagaggtaag    480
ggtttaaggg atggttggtt ggtgggtat taatgtttaa ttacctggag cacctgcctg    540
aaatcacttt ttttcaggtt ggctagtatg cagatcgagc tgtccacctg ctttttttctg    600 tgcctgctgc ggttctgctt cagcgccacc cggcggtact acctgggcgc cgtggagctg    660
tcctgggact acatgcagag cgacctgggc gagctgcccg tggacgcccg gttcccccccc    720 agagtgccca gagagcttccc cttcaacacc agcgtggtgt acaagaaaac cctgttcgtg    780
gagttcaccg accacctgtt caatatcgcc aagcccaggc ccccctggat gggcctgctg    840 ggcccccacca tccaggccga ggtgtacgac accgtggtga tcaccctgaa gaacatggcc    900 agccacccccg tgagcctgca cgccgtgggc gtgagctact ggaaggccag cgagggcgcc    960
gagtacgacg accagaccag ccagcgggag aaagaagatg acaaggtgtt ccctggcggc   1020
agccacacct acgtgtggca ggtgctgaaa gaaaacggcc ccatggcctc cgacccctg   1080 tgcctgacct acagctacct gagccacgtg gacctggtga aggacctgaa cagcggcctg   1140
atcggcgctc tgctcgtctg ccgggagggc agcctggcca agagaaaaac ccagacctg   1200 cacaagttca tcctgctgtt cgccgtgttc gacgagggca gagctggca cagcgagaca   1260 aagaacagcc tgatgcagga ccgggacgcc gcctctgcca gagcctggcc caagatgcac   1320
accgtgaacg gctacgtgaa cagaagcctg cccggcctga ttggctgcca ccggaagagc   1380
gtgtactggc acgtgatcgg catgggcacc acacccgagg tgcacagcat ctttctggaa   1440
gggcacacct ttctggtccg gaaccaccgg caggccagcc tggaaatcag ccctatcacc   1500
ttcctgaccg cccagacact gctgatggac ctgggccagt cctgctgtt ttgccacatc   1560 agctctcacc agcacgacgg catggaagcc tacgtgaagg tggactcttg ccccgaggaa   1620
ccccagctgc ggatgaagaa caacgaggaa gccgaggact acgacgacga cctgaccgac   1680
agcgagatgg acgtggtgcg gttcgacgac gacaacagcc cagcttcat ccagatcaga   1740 agcgtggcca gaagcaccc caagacctgg gtgcactata tcgccgccga ggaagaggac   1800
tgggactacg cccccctggt gctggccccc gacgacagaa gctacaagag ccagtacctg   1860
aacaatggcc cccagcggat cggccggaag tacaagaaag tgcggttcat ggcctacacc   1920

```
gacgagacat tcaagacccg ggaggccatc agcacgaga gcggcatcct gggcccctg      1980 ctgtacggcg aagtgggcga cacactgctg atcatcttca agaaccaggc tagccggccc      2040
tacaacatct accccacgg catcaccgac gtgcggcccc tgtacagcag gcggctgccc      2100
aagggcgtga agcacctgaa ggacttcccc atcctgcccg gcgagatctt caagtacaag      2160
tggaccgtga ccgtggagga cggcccacc aagagcgacc ccagatgcct gacccggtac      2220
tacagcagct tcgtgaacat ggaacgggac ctggcctccg ggctgatcgg acctctgctg      2280
atctgctaca agaaagcgt ggaccagcgg ggcaaccaga tcatgagcga caagcggaac      2340
gtgatcctgt tcagcgtgtt cgatgagaac cggtcctggt atctgaccga aacatccag      2400 cggtttctgc ccaaccctgc cggcgtgcag ctggaagatc ccgagttcca ggccagcaac      2460
atcatgcact ccatcaatgg ctacgtgttc gactctctgc agctctccgt gtgtctgcac      2520
gaggtggcct actggtacat cctgagcatc ggcgcccaga ccgacttcct gagcgtgttc      2580
ttcagcggct acaccttcaa gcacaagatg gtgtacgagg acaccctgac cctgttccct      2640
ttcagcggcg agacagtgtt catgagcatg gaaaaccccg gcctgtggat tctgggctgc      2700
cacaacagcg acttccggaa ccggggcatg accgccctgc tgaaggtgtc cagctgcgac      2760
aagaacaccg gcgactacta cgaggacagc tacgaggata tcagcgccta cctgctgtcc      2820
aagaacaacg ccatcgaacc ccggagcttc agccagaacc ccccgtgct gacgcgtcac      2880 cagcgggaga tcacccggac aaccctgcag tccgaccagg aagagatcga ttacgacgac      2940
accatcagcg tggagatgaa gaaagaggat ttcgatatct acgacgagga cgagaaccag      3000
agccccagaa gcttccagaa gaaaacccgg cactacttca ttgccgccgt ggagaggctg      3060
tgggactacg gcatgagttc tagccccac gtgctgcgga accgggccca gagcggcagc      3120
gtgccccagt tcaagaaagt ggtgttccag gaattcacag acggcagctt cacccagcct      3180
ctgtatagag gcgagctgaa cgagcacctg gggctgctgg ggcctacat cagggccgaa      3240 gtggaggaca acatcatggt gaccttccgg aatcaggcca gcagaccta ctccttctac      3300 agcagcctga tcagctacga agaggaccag cggcagggcg ccgaacccg gaagaacttc      3360 gtgaagccca acgaaaccaa gacctacttc tggaaagtgc agcaccacat ggcccccacc      3420
aaggacgagt cgactgcaa ggcctgggcc tacttcagcg acgtggatct ggaaaaggac      3480
gtgcactctg gactgattgg cccactcctg gtctgccaca ctaacaccct caaccccgcc      3540
cacggccgcc aggtgaccgt gcaggaattc gccctgttct tcaccatctt gacgagaca      3600 aagtcctggt acttcaccga gaatatggaa cggaactgca gagcccctg caacatccag      3660 atggaagatc ctaccttcaa agagaactac cggttccacg ccatcaacgg ctacatcatg      3720
gacaccctgc ctggctggt gatggcccag gaccagaga tccggtggta tctgctgtcc      3780
atgggcagca acgagaatat ccacagcatc cacttcagcg gccacgtgtt caccgtgcgg      3840
aagaaagaag agtacaagat ggcccctgtac aacctgtacc ccggcgtgtt cgagacagtg      3900
gagatgctgc ccagcaaggc cggcatctgg cgggtggagt gtctgatcgg cgagcacctg      3960
cacgctggca tgagcaccct gtttctggtg tacagcaaca agtgccagac cccactgggc      4020
atggcctctg gccacatccg ggacttccag atcaccgcct ccggccagta cggccagtgg      4080
gcccccaagc tggccagact gcactacagc ggcagcatca acgcctggtc caccaaagag      4140
cccttcagct ggatcaaggt ggacctgctg gcccctatga tcatccacgg cattaagacc      4200
cagggcgcca ggcagaagtt cagcagcctg tacatcagcc agttcatcat catgtacagc      4260
```

```
ctggacggca agaagtggca gacctaccgg ggcaacagca ccggcaccct gatggtgttc    4320
ttcggcaatg tggacagcag cggcatcaag cacaacatct tcaaccccc catcattgcc     4380 cggtacatcc ggctgcaccc cacccactac agcattgat ccacactgag aatggaactg     4440
atgggctgcg acctgaactc ctgcagcatg cctctgggca tggaaagcaa ggccatcagc    4500
gacgcccaga tcacagccag cagctacttc accaacatgt tcgccacctg gtcccctcc    4560 aaggccaggc tgcacctgca gggccggtcc aacgcctggc ggcctcaggt caacaaccc    4620 aaagaatggc tgcaggtgga cttttcagaaa accatgaagg tgaccggcgt gaccacccag    4680
ggcgtgaaaa gcctgctgac cagcatgtac gtgaaagagt ttctgatcag cagctctcag    4740
gatggccacc agtggaccct gttctttcag aacggcaagg tgaaagtgtt ccagggcaac    4800
caggactcct tcacccccgt ggtgaactcc ctggaccccc ccctgctgac ccgctacctg    4860
agaatccacc cccagtcttg ggtgcaccag atcgccctca ggatggaagt cctgggatgt    4920
gaggcccagg atctgtactg atgaggatct aggctcgaca tgctttattt gtgaaatttg    4980
tgatgctatt gctttatttg taaccattat aagctgcaat aaacaagtta caacaacaa    5040 ttgcattcat tttatgtttc aggttcaggg ggaggtgtgg gaggtttttt aaactcgaga    5100
tccacggccg caggaaccc tagtgatgga gttggccact ccctctctgc gcgctcgctc    5160
gctcactgag gccgggcgac caaaggtcgc ccgacgcccg gctttgccc gggcggcctc    5220 agtgagcgag cgagcgcgca gctgcctgca ggggcgcctg atgcggtatt ttctccttac    5280
gcatctgtgc ggtatttcac accgcatacg tcaaagcaac catagtacgc gccctgtagc    5340
ggcgcattaa gcgcggcggg tgtggtggtt acgcgcagcg tgaccgctac acttgccagc    5400
gccctagcgc ccgctccttt cgctttcttc ccttcctttc tcgccacgtt cgccggcttt    5460
ccccgtcaag ctctaaatcg ggggctccct ttagggttcc gatttagtgc tttacggcac    5520
ctcgacccca aaaaacttga tttgggtgat ggttcacgta gtgggccatc gccctgatag    5580
acggtttttc gccctttgac gttggagtcc acgttcttta atagtggact cttgttccaa    5640
actggaacaa cactcaaccc tatctcgggc tattcttttg atttataagg gattttgccg    5700
atttcggcct attggttaaa aaatgagctg atttaacaaa aatttaacgc gaattttaac    5760
aaaatattaa cgtttacaat tttatggtgc actctcagta caatctgctc tgatgccgca    5820
tagttaagcc agccccgaca cccgccaaca cccgctgacg cgccctgacg gcttgtctg    5880 ctcccggcat ccgcttacag acaagctgtg accgtctccg ggagctgcat gtgtcagagg    5940
ttttcaccgt catcaccgaa acgcgcgaga cgaaagggcc tcgtgatacg cctattttta    6000
taggttaatg tcatgataat aatggtttct tagacgtcag gtggcacttt tcggggaaat    6060
gtgcgcggaa cccctatttg tttattttc taaatacatt caaatatgta tccgctcatg    6120
agacaataac cctgataaat gcttcaataa tattgaaaaa ggaagagtat gagtattcaa    6180
catttccgtg tcgcccttat cccttttttt gcggcatttt gccttcctgt ttttgctcac    6240
ccagaaacgc tggtgaaagt aaaagatgct gaagatcagt tgggtgcacg agtgggttac    6300
atcgaactgg atctcaacag cggtaagatc cttgagagtt ttcgccccga agaacgtttt    6360
ccaatgatga gcacttttaa agttctgcta tgtggcgcgg tattatcccg tattgacgcc    6420
gggcaagagc aactcggtcg ccgcatacac tattctcaga atgacttggt tgagtactca    6480
ccagtcacag aaaagcatct tacggatggc atgacagtaa gagaattatg cagtgctgcc    6540
ataaccatga gtgataacac tgcggccaac ttacttctga caacgatcgg aggaccgaag    6600
gagctaaccg cttttttgca acatggggg gatcatgtaa ctcgccttga tcgttgggaa    6660
```

```
ccggagctga atgaagccat accaaacgac gagcgtgaca ccacgatgcc tgtagcaatg    6720
gcaacaacgt tgcgcaaact attaactggc gaactactta ctctagcttc ccggcaacaa    6780
ttaatagact ggatggaggc ggataaagtt gcaggaccac ttctgcgctc ggcccttccg    6840
gctggctggt ttattgctga taaatctgga gccggtgagc gtgggtctcg cggtatcatt    6900
gcagcactgg ggccagatgg taagccctcc cgtatcgtag ttatctacac gacggggagt    6960
caggcaacta tggatgaacg aaatagacag atcgctgaga taggtgcctc actgattaag    7020
cattggtaac tgtcagacca agtttactca tatatacttt agattgattt aaaacttcat    7080
ttttaattta aaaggatcta ggtgaagatc ctttttgata atctcatgac caaaatccct    7140
taacgtgagt tttcgttcca ctgagcgtca gaccccgtag aaaagatcaa aggatcttct    7200
tgagatcctt tttttctgcg cgtaatctgc tgcttgcaaa caaaaaaacc accgctacca    7260
gcggtggttt gtttgccgga tcaagagcta ccaactcttt ttccgaaggt aactggcttc    7320
agcagagcgc agataccaaa tactgtcctt ctagtgtagc cgtagttagg ccaccacttc    7380
aagaactctg tagcaccgcc tacatacctc gctctgctaa tcctgttacc agtggctgct    7440
gccagtggcg ataagtcgtg tcttaccggg ttggactcaa gacgatagtt accggataag    7500
gcgcagcggt cgggctgaac ggggggttcg tgcacacagc ccagcttgga gcgaacgacc    7560
tacaccgaac tgagatacct acagcgtgag ctatgagaaa gcgccacgct tcccgaaggg    7620
agaaaggcgg acaggtatcc ggtaagcggc agggtcggaa caggagagcg cacgagggag    7680
cttccagggg gaaacgcctg gtatctttat agtcctgtcg ggtttcgcca cctctgactt    7740
gagcgtcgat ttttgtgatg ctcgtcaggg gggcggagcc tatggaaaaa cgccagcaac    7800
gcggcctttt tacggttcct ggccttttgc tggccttttg ctcacatgt             7849
```

<210> SEQ ID NO 16
<211> LENGTH: 8007
<212> TYPE: DNA
<213> ORGANISM: Artificial Sequence
<220> FEATURE:
<223> OTHER INFORMATION: pAAVss-3xSerpEnh-TTRm-MVM-CoFVIIIdeltaB-Sv40pA

<400> SEQUENCE: 16

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggggttcc tgcggccgcg gtacgcgggg gaggctgctg gtgaatatta     180
accaaggtca ccccagttat cggaggagca aacagggggct aagtccaccg ggggaggctg     240
ctggtgaata ttaaccaagg tcaccccagt tatcggagga gcaaacaggg gctaagtcca     300 ccggggggagg ctgctggtga atattaacca aggtcacccc agttatcgga ggagcaaaca     360
ggggctaagt ccactgtaca acgcgtgaat tcgctagcgt ctgtctgcac atttcgtaga     420
gcgagtgttc cgatactcta atctcccctag gcaaggttca tatttgtgta ggttacttat     480
tctccttttg ttgactaagt caataatcag aatcagcagg tttggagtca gcttggcagg     540
gatcagcagc ctgggttgga aggagggggt ataaaagccc cttcaccagg agaagccgtc     600
acacagatcc acaagctcct gtctagaaag aggtaagggg ttaagggatg gttggttggt     660
ggggtattaa tgtttaatta cctggagcac ctgcctgaaa tcacttttttt tcaggttggg     720 ctagcatgca gatcgagctg tccacctgct tttttctgtg cctgctgcgg ttctgcttca     780
gcgccacccg gcggtactac ctgggcgccg tggagctgtc ctgggactac atgcagagcg     840
```

```
acctgggcga gctgcccgtg gacgcccggt tcccccccag agtgcccaag agcttcccct    900
tcaacaccag cgtggtgtac aagaaaaccc tgttcgtgga gttcaccgac cacctgttca    960
atatcgccaa gcccaggccc ccctggatgg gcctgctggg ccccaccatc caggccgagg   1020
tgtacgacac cgtggtgatc accctgaaga acatggccag ccaccccgtg agcctgcacg   1080
ccgtgggcgt gagctactgg aaggccagcg agggcgccga gtacgacgac cagaccagcc   1140
agcgggagaa agaagatgac aaggtgttcc ctggcggcag ccacacctac gtgtggcagg   1200
tgctgaaaga aaacggcccc atggcctccg accccctgtg cctgacctac agctacctga   1260
gccacgtgga cctggtgaag gacctgaaca cggcctgat cggcgctctg ctcgtctgcc    1320
gggagggcag cctggccaaa gagaaaaccc agaccctgca caagttcatc ctgctgttcg   1380
ccgtgttcga cgagggcaag agctggcaca gcgagacaaa gaacagcctg atgcaggacc   1440
gggacgccgc ctctgccaga gcctggccca agatgcacac cgtgaacggc tacgtgaaca   1500
gaagcctgcc cggcctgatt ggctgccacc ggaagagcgt gtactggcac gtgatcggca   1560
tgggcaccac acccgaggtg cacagcatct ttctggaagg gcacacctt ctggtccgga    1620 accaccggca ggccagcctg gaaatcagcc ctatcacctt cctgaccgcc cagacactgc   1680
tgatggacct gggccagttc ctgctgtttt gccacatcag ctctcaccag cacgacggca   1740
tggaagccta cgtgaaggtg gactcttgcc ccgaggaacc ccagctgcgg atgaagaaca   1800
acgaggaagc cgaggactac gacgacgacc tgaccgacag cgagatggac gtggtgcggt   1860
tcgacgacga caacagcccc agcttcatcc agatcagaag cgtggccaag aagcacccca   1920
agacctgggt gcactatatc gccgccgagg aagaggactg ggactacgcc cccctggtgc   1980
tggcccccga cgacagaagc tacaagagcc agtacctgaa caatggcccc cagcggatcg   2040
gccggaagta caagaaagtg cggttcatgg cctacaccga cgagacattc aagacccggg   2100
aggccatcca gcacgagagc ggcatcctgg ccccctgct gtacggcgaa gtgggcgaca   2160
cactgctgat catcttcaag aaccaggcta gccggcccta acatctac ccccacggca    2220 tcaccgacgt gcggcccctg tacagcaggc ggctgcccaa gggcgtgaag cacctgaagg   2280 acttcccat cctgccggc gagatcttca agtacaagtg gaccgtgacc gtggaggacg    2340
gccccaccaa gagcgacccc agatgcctga cccggtacta cagcagcttc gtgaacatgg   2400
aacgggacct ggcctccggg ctgatcggac ctctgctgat ctgctacaaa gaaagcgtgg   2460
accagcgggg caaccagatc atgagcgaca gcggaacgt gatcctgttc agcgtgttcg    2520
atgagaaccg gtcctggtat ctgaccgaga acatccagcg gtttctgccc aaccctgccg   2580
gcgtgcagct ggaagatccc gagttccagg ccagcaacat catgcactcc atcaatggct   2640
acgtgttcga ctctctgcag ctctccgtgt gtctgcacga ggtggcctac tggtacatcc   2700
tgagcatcgg cgcccagacc gacttcctga gcgtgttctt cagcggctac accttcaagc   2760
acaagatggt gtacgaggac accctgaccc tgttcccttt cagcggcgag acagtgttca   2820
tgagcatgga aaaccccggc ctgtggattc tgggctgcca aacagcgac ttccggaacc    2880 ggggcatgac cgccctgctg aaggtgtcca gctgcgacaa gaacaccggc gactactacg   2940
aggacagcta cgaggatatc agcgcctacc tgctgtccaa gaacaacgcc atcgaacccc   3000
ggagcttcag ccagaacccc ccgtgctga cgcgtcacca gcgggagatc acccggacaa    3060
ccctgcagtc cgaccaggaa gagatcgatt acgacgacac catcagcgtg gagatgaaga   3120 agaggatt cgatatctac gacgaggacg agaaccagag ccccagaagc ttccagaaga    3180
aaacccggca ctacttcatt gccgccgtgg agaggctgtg ggactacggc atgagttcta   3240
```

```
gccccccacgt gctgcggaac cgggcccaga gcggcagcgt gccccagttc aagaaagtgg   3300
tgttccagga attcacagac ggcagcttca cccagcctct gtatagaggc gagctgaacg   3360
agcacctggg gctgctgggg ccctacatca gggccgaagt ggaggacaac atcatggtga   3420
ccttccggaa tcaggccagc agaccctact ccttctacag cagcctgatc agctacgaag   3480
aggaccagcg gcagggcgcc gaaccccgga gaacttcgt gaagcccaac gaaaccaaga   3540
cctacttctg gaaagtgcag caccacatgg cccccaccaa ggacgagttc gactgcaagg   3600
cctgggccta cttcagcgac gtggatctgg aaaaggacgt gcactctgga ctgattggcc   3660
cactcctggt ctgccacact aacaccctca accccgccca cggccgccag gtgaccgtgc   3720
aggaattcgc cctgttcttc accatcttcg acgagacaaa gtcctggtac ttcaccgaga   3780
atatggaacg gaactgcaga gcccctgca acatccagat ggaagatcct accttcaaag   3840
agaactaccg gttccacgcc atcaacggct acatcatgga caccctgcct ggcctggtga   3900
tggcccagga ccagagaatc cggtggtatc tgctgtccat gggcagcaac gagaatatcc   3960
acagcatcca cttcagcggc cacgtgttca ccgtgcggaa gaaagaagag tacaagatgg   4020
ccctgtacaa cctgtacccc ggcgtgttcg agacagtgga gatgctgccc agcaaggccg   4080
gcatctggcg ggtggagtgt ctgatcggcg agcacctgca cgctggcatg agcaccctgt   4140
ttctggtgta cagcaacaag tgccagaccc cactgggcat ggcctctggc cacatccggg   4200
acttccagat caccgcctcc ggccagtacg ccagtgggc cccaagctg ccagactgc    4260 actacagcgg cagcatcaac gcctggtcca ccaaagagcc cttcagctgg atcaaggtgg   4320
acctgctggc ccctatgatc atccacggca ttaagaccca gggcgccagg cagaagttca   4380
gcagcctgta catcagccag ttcatcatca tgtacagcct ggacggcaag aagtggcaga   4440
cctaccgggg caacagcacc ggcaccctga tggtgttctt cggcaatgtg gacagcagcg   4500
gcatcaagca acacatcttc aacccccca tcattgcccg gtacatccgg ctgcacccca   4560
cccactacag cattagatcc acactgagaa tggaactgat gggctgcgac ctgaactcct   4620
gcagcatgcc tctgggcatg gaaagcaagg ccatcagcga cgcccagatc acagccagca   4680
gctacttcac caacatgttc gccacctggt cccctccaa ggccaggctg cacctgcagg   4740
gccggtccaa cgcctggcgg cctcaggtca caaccccaa agaatggctg caggtggact   4800
ttcagaaaac catgaaggtg accggcgtga ccacccaggg cgtgaaaagc ctgctgacca   4860
gcatgtacgt gaaagagttt ctgatcagca gctctcagga tggccaccag tggacccgt   4920 tctttcagaa cggcaaggtg aaagtgttcc agggcaacca ggactccttc accccgtgg   4980 tgaactccct ggacccccc ctgctgaccc gctacctgag aatccacccc cagtcttggg   5040
tgcaccagat cgccctcagg atggaagtcc tgggatgtga ggcccaggat ctgtactgat   5100
gaggatctag gctcgacatg ctttatttgt gaaatttgtg atgctattgc tttatttgta   5160
accattataa gctgcaataa acaagttaac aacaacaatt gcattcattt tatgtttcag   5220 gttcagggg aggtgtggga ggtttttttaa actcgagatc cacggccgca ggaaccccta   5280
gtgatggagt tggccactcc ctctctgcgc gctcgctcgc tcactgaggc cgggcgacca   5340
aaggtcgccc gacgcccggg ctttgcccgg cggcctcag tgagcgagcg agcgcgcagc   5400
tgcctgcagg ggcgcctgat gcggtatttt ctccttacgc atctgtgcgg tatttcacac   5460
cgcatacgtc aaagcaacca tagtacgcgc cctgtagcgg cgcattaagc gcggcgggtg   5520
tggtggttac gcgcagcgtg accgctacac ttgccagcgc cctagcgccc gctcctttcg   5580
```

```
ctttcttccc ttcctttctc gccacgttcg ccggctttcc ccgtcaagct ctaaatcggg    5640
ggctcccttt agggttccga tttagtgctt tacggcacct cgaccccaaa aaacttgatt    5700
tgggtgatgg ttcacgtagt gggccatcgc cctgatagac ggttttttcgc cctttgacgt   5760 tggagtccac gttctttaat agtggactct tgttccaaac tggaacaaca ctcaacccta    5820
tctcgggcta ttcttttgat ttataaggga ttttgccgat ttcggcctat tggttaaaaa    5880
atgagctgat ttaacaaaaa tttaacgcga attttaacaa aatattaacg tttacaattt    5940
tatggtgcac tctcagtaca atctgctctg atgccgcata gttaagccag ccccgacacc    6000
cgccaacacc cgctgacgcg ccctgacggg cttgtctgct cccggcatcc gcttacagac    6060
aagctgtgac cgtctccggg agctgcatgt gtcagaggtt ttcaccgtca tcaccgaaac    6120
gcgcgagacg aaagggcctc gtgatacgcc tatttttata ggttaatgtc atgataataa    6180
tggtttctta gacgtcaggt ggcactttc ggggaaatgt gcgcggaacc cctatttgtt    6240 tattttcta aatacattca aatatgtatc cgctcatgag acaataaccc tgataaatgc     6300
ttcaataata ttgaaaaagg aagagtatga gtattcaaca tttccgtgtc gcccttattc    6360
ccttttttgc ggcattttgc cttcctgttt ttgctcaccc agaaacgctg gtgaaagtaa    6420
aagatgctga agatcagttg ggtgcacgag tgggttacat cgaactggat ctcaacagcg    6480
gtaagatcct tgagagtttt cgccccgaag aacgttttcc aatgatgagc acttttaaag    6540
ttctgctatg tggcgcggta ttatcccgta ttgacgccgg gcaagagcaa ctcggtcgcc    6600
gcatacacta ttctcagaat gacttggttg agtactcacc agtcacagaa aagcatctta    6660
cggatggcat gacagtaaga gaattatgca gtgctgccat aaccatgagt gataacactg    6720
cggccaactt acttctgaca acgatcggag gaccgaagga gctaaccgct tttttgcaca    6780
acatggggga tcatgtaact cgccttgatc gttgggaacc ggagctgaat gaagccatac    6840
caaacgacga gcgtgacacc acgatgcctg tagcaatggc aacaacgttg cgcaaactat    6900
taactggcga actacttact ctagcttccc ggcaacaatt aatagactgg atggaggcgg    6960
ataaagttgc aggaccactt ctgcgctcgg cccttccggc tggctggttt attgctgata    7020
aatctggagc cggtgagcgt gggtctcgcg gtatcattgc agcactgggg ccagatggta    7080
agccctcccg tatcgtagtt atctacacga cggggagtca ggcaactatg gatgaacgaa    7140
atagacagat cgctgagata ggtgcctcac tgattaagca ttggtaactg tcagaccaag    7200
tttactcata tatactttag attgatttaa aacttcattt ttaatttaaa aggatctagg    7260
tgaagatcct ttttgataat ctcatgacca aaatccctta acgtgagttt tcgttccact    7320
gagcgtcaga ccccgtagaa aagatcaaag gatcttcttg agatcctttt tttctgcgcg    7380
taatctgctg cttgcaaaca aaaaaaccac cgctaccagc ggtggtttgt ttgccggatc    7440
aagagctacc aactcttttt ccgaaggtaa ctggcttcag cagagcgcag ataccaaata    7500
ctgtccttct agtgtagccg tagttaggcc accacttcaa gaactctgta gcaccgccta    7560
catacctcgc tctgctaatc ctgttaccag tggctgctgc cagtggcgat aagtcgtgtc    7620
ttaccgggtt ggactcaaga cgatagttac cggataaggc gcagcggtcg ggctgaacgg    7680
ggggttcgtg cacacagccc agcttggagc gaacgaccta caccgaactg agatacctac    7740
agcgtgagct atgagaaagc gccacgcttc ccgaagggag aaaggcggac aggtatccgg    7800
taagcggcag ggtcggaaca ggagagcgca cgagggagct tccaggggga aacgcctggt    7860
atctttatag tcctgtcggg tttcgccacc tctgacttga gcgtcgattt ttgtgatgct    7920
cgtcaggggg gcggagccta tggaaaaacg ccagcaacgc ggcctttta cggttcctgg    7980
```

<210> SEQ ID NO 17
<211> LENGTH: 7872
<212> TYPE: DNA
<213> ORGANISM: Artificial Sequence
<220> FEATURE:
<223> OTHER INFORMATION: pAAVss-TTRe-TTRm-MVM-CoFVIIIdeltaB-Sv40pA

<400> SEQUENCE: 17

```
cctttttgctg gccttttgct cacatgt                                    8007 cctgcaggca gctgcgcgct cgctcgctca ctgaggccgc ccgggcaaag cccgggcgtc   60
gggcgacctt tggtcgcccg gcctcagtga gcgagcgagc gcgcagagag ggagtggcca  120
actccatcac taggggttcc tgcggccgcg gtacccactg ggaggatgtt gagtaagatg  180
gaaaactact gatgacccct tgcagagacag agtattagga catgtttgaa caggggccgg  240
gcgatcagca ggtagctcta gaggatcccc gtctgtctgc acatttcgta gagcgagtgt  300
tccgatactc taatctccct aggcaaggtt catatttgtg taggttactt attctccttt  360
tgttgactaa gtcaataatc agaatcagca ggtttggagt cagcttggca gggatcagca  420
gcctgggttg aaggaggggg gtataaaagc cccttcacca ggagaagccg tcacacagat  480
ccacaagctc ctgaagaggt aagggtttaa gggatggttg gttggtgggg tattaatgtt  540
taattacctg gagcacctgc ctgaaatcac tttttttcag gttggctagt atgcagatcg  600
agctgtccac ctgctttttt ctgtgcctgc tgcggttctg cttcagcgcc acccggcggt  660
actacctggg cgccgtggag ctgtcctggg actacatgca gagcgacctg ggcgagctgc  720
ccgtggacgc ccggttcccc ccagagtgc caagagctt ccccttcaac accagcgtgg  780
tgtacaagaa aaccctgttc gtggagttca ccgaccacct gttcaatatc gccaagccca  840
ggcccccctg gatgggcctg ctgggcccca ccatccaggc cgaggtgtac gacaccgtgg  900
tgatcaccct gaagaacatg gccagccacc ccgtgagcct gcacgccgtg ggcgtgagct  960
actggaaggc cagcgagggc gccgagtacg acgaccagca cagccagcgg gagaaagaag 1020
atgacaaggt gttccctggc ggcagccaca cctacgtgtg gcaggtgctg aaagaaaacg 1080
gccccatggc ctccgacccc ctgtgcctga cctacagcta cctgagccac gtggacctgg 1140
tgaaggacct gaacagcggc ctgatcggcg ctctgctcgt ctgccgggag ggcagcctgg 1200
ccaaagagaa aacccagacc ctgcacaagt tcatcctgct gttcgccgtg ttcgacgagg 1260
gcaagagctg gcacagcgag acaaagaaca gcctgatgca ggaccgggac gccgcctctg 1320
ccagagcctg gccaagatg cacaccgtga acggctacgt gaacagaagc ctgcccggcc 1380
tgattggctg ccaccggaag agcgtgtact ggcacgtgat cggcatgggc accacacccg 1440
aggtgcacag catctttctg gaagggcaca cctttctggt ccggaaccac cggcaggcca 1500
gcctggaaat cagccctatc accttcctga ccgcccagac actgctgatg gacctgggcc 1560
agttcctgct gttttgccac atcagctctc caccagcacga cggcatggaa gcctacgtga 1620
aggtggactc ttgccccgag aaccccagc tgcggatgaa gaacaacgag gaagccgagg 1680
actacgacga cgacctgacc gacagcgaga tggacgtggt gcggttcgac gacgacaaca 1740
gccccagctt catccagatc agaagcgtgg ccaagaagca cccaagacc tgggtgcact 1800
atatcgccgc cgaggaagag gactgggact acgccccct ggtgctggcc cccgacgaca 1860
gaagctacaa gagccagtac ctgaacaatg gcccccagcg gatcggccgg aagtacaaga 1920
aagtgcggtt catggcctac accgacgaga cattcaagac ccgggaggcc atccagcacg 1980
```

-continued

| | |
|---|---|
| agagcggcat cctgggcccc ctgctgtacg gcgaagtggg cgacacactg ctgatcatct | 2040 |
| tcaagaacca ggctagccgg ccctacaaca tctaccccca cggcatcacc gacgtgcggc | 2100 |
| ccctgtacag caggcggctg cccaagggcg tgaagcacct gaaggacttc cccatcctgc | 2160 |
| ccggcgagat cttcaagtac aagtggaccg tgaccgtgga ggacggcccc accaagagcg | 2220 |
| accccagatg cctgacccgg tactacagca gcttcgtgaa catggaacgg gacctggcct | 2280 |
| ccgggctgat cggacctctg ctgatctgct acaaagaaag cgtggaccag cggggcaacc | 2340 |
| agatcatgag cgacaagcgg aacgtgatcc tgttcagcgt gttcgatgag aaccggtcct | 2400 |
| ggtatctgac cgagaacatc cagcggtttc tgcccaaccc tgccggcgtg cagctggaag | 2460 |
| atcccgagtt ccaggccagc aacatcatgc actccatcaa tggctacgtg ttcgactctc | 2520 |
| tgcagctctc cgtgtgtctg cacgaggtgg cctactggta catcctgagc atcgcgccc | 2580 |
| agaccgactt cctgagcgtg ttcttcagcg gctacaccct caagcacaag atggtgtacg | 2640 |
| aggacaccct gacctgttc cctttcagcg gcgagacagt gttcatgagc atggaaaacc | 2700 |
| ccggcctgtg gattctgggc tgccacaaca gcgacttccg gaaccggggc atgaccgccc | 2760 |
| tgctgaaggt gtccagctgc gacaagaaca ccggcgacta ctacgaggac agctacgagg | 2820 |
| atatcagcgc ctacctgctg tccaagaaca acgccatcga accccggagc ttcagccaga | 2880 |
| acccccccgt gctgacgcgt caccagcggg agatcacccg gacaaccctg cagtccgacc | 2940 |
| aggaagagat cgattacgac gacaccatca gcgtggagat gaagaaagag gatttcgata | 3000 |
| tctacgacga ggacgagaac cagagcccca gaagcttcca gaagaaaacc cggcactact | 3060 |
| tcattgccgc cgtggagagg ctgtgggact acggcatgag ttctagcccc cacgtgctgc | 3120 |
| ggaaccgggc ccagagcggc agcgtgcccc agttcaagaa agtggtgttc caggaattca | 3180 |
| cagacggcag cttcacccag cctctgtata gaggcgagct gaacgagcac ctggggctgc | 3240 |
| tggggcccta catcagggcc gaagtggagg acaacatcat ggtgaccttc cggaatcagg | 3300 |
| ccagcagacc ctactccttc tacagcagcc tgatcagcta cgaagaggac cagcggcagg | 3360 |
| gcgccgaacc ccggaagaac ttcgtgaagc ccaacgaaac caagacctac ttctggaaag | 3420 |
| tgcagcacca catggcccc accaaggacg agttcgactg caaggcctgg gcctacttca | 3480 |
| gcgacgtgga tctggaaaag gacgtgcact ctggactgat tggcccactc ctggtctgcc | 3540 |
| acactaacac cctcaacccc gcccacggcc gccaggtgac cgtgcaggaa ttcgccctgt | 3600 |
| tcttcaccat cttcgacgag acaaagtcct ggtacttcac cgagaatatg gaacggaact | 3660 |
| gcagagcccc ctgcaacatc cagatggaag atcctacctt caaagagaac taccggttcc | 3720 |
| acgccatcaa cggctacatc atggacaccc tgcctggcct ggtgatggcc caggaccaga | 3780 |
| gaatccggtg gtatctgctg tccatgggca gcaacgagaa tatccacagc atccacttca | 3840 |
| gcggccacgt gttcaccgtg cggaagaaag aagagtacaa gatggccctg tacaacctgt | 3900 |
| accccggcgt gttcgagaca gtggagatgc tgcccagcaa ggccggcatc tggcgggtgg | 3960 |
| agtgtctgat cggcgagcac ctgcacgctg gcatgagcac cctgtttctg gtgtacagca | 4020 |
| acaagtgcca gaccccactg ggcatggcct ctggccacat ccgggacttc cagatcaccg | 4080 |
| cctccggcca gtacgccag tgggccccca gctggccag actgcactac agcggcagca | 4140 |
| tcaacgcctg gtccaccaaa gagcccttca gctggatcaa ggtggacctg ctggccccta | 4200 |
| tgatcatcca cggcattaag acccagggcg ccaggcagaa gttcagcagc ctgtacatca | 4260 |
| gccagttcat catcatgtac agcctggacg gcaagaagtg gcagacctac cggggcaaca | 4320 |
| gcaccggcac cctgatggtg ttcttcggca atgtggacag cagcggcatc aagcacaaca | 4380 |

```
tcttcaaccc ccccatcatt gcccggtaca tccggctgca ccccacccac tacagcatta      4440
gatccacact gagaatggaa ctgatgggct gcgacctgaa ctcctgcagc atgcctctgg      4500
gcatggaaag caaggccatc agcgacgccc agatcacagc cagcagctac ttcaccaaca      4560
tgttcgccac ctggtccccc tccaaggcca ggctgcacct gcagggccgg tccaacgcct      4620
ggcggcctca ggtcaacaac cccaaagaat ggctgcaggt ggactttcag aaaaccatga      4680
aggtgaccgg cgtgaccacc cagggcgtga aaagcctgct gaccagcatg tacgtgaaag      4740
agtttctgat cagcagctct caggatggcc accagtggac cctgttcttt cagaacggca      4800
aggtgaaagt gttccagggc aaccaggact ccttcacccc cgtggtgaac tccctggacc      4860
cccccctgct gacccgctac ctgagaatcc accccagtc ttgggtgcac cagatcgccc       4920
tcaggatgga agtcctggga tgtgaggccc aggatctgta ctgatgagga tctaggctcg      4980
acatgcttta tttgtgaaat ttgtgatgct attgctttat ttgtaaccat tataagctgc      5040
aataaacaag ttaacaacaa caattgcatt cattttatgt ttcaggttca ggggaggtg       5100 tgggaggttt tttaaactcg agatccacgg ccgcaggaac ccctagtgat ggagttggcc      5160
actccctctc tgcgcgctcg ctcgctcact gaggccgggc gaccaaaggt cgcccgacgc      5220
ccgggctttg cccgggcggc ctcagtgagc gagcgagcgc gcagctgcct gcagggcgc       5280 ctgatgcggt attttctcct tacgcatctg tgcggtattt cacaccgcat acgtcaaagc      5340
aaccatagta cgcgccctgt agcggcgcat taagcgcggc gggtgtggtg gttacgcgca      5400
gcgtgaccgc tacacttgcc agcgccctag cgcccgctcc tttcgctttc ttcccttcct      5460
ttctcgccac gttcgccggc tttccccgtc aagctctaaa tcggggctc cctttagggt       5520 tccgatttag tgctttacgg cacctcgacc ccaaaaaact tgatttgggt gatggttcac      5580
gtagtgggcc atcgccctga tagacggttt ttcgcccttt gacgttggag tccacgttct      5640
ttaatagtgg actcttgttc caaactggaa caacactcaa ccctatctcg gctattctt       5700 ttgatttata agggattttg ccgatttcgg cctattggtt aaaaaatgag ctgatttaac      5760
aaaaatttaa cgcgaatttt aacaaaatat taacgtttac aatttatgg tgcactctca       5820 gtacaatctg ctctgatgcc gcatagttaa gccagccccg acacccgcca acaccgctg       5880 acgcgccctg acgggcttgt ctgctcccgg catccgctta cagacaagct gtgaccgtct      5940
ccgggagctg catgtgtcag aggttttcac cgtcatcacc gaaacgcgcg agacgaaagg      6000
gcctcgtgat acgcctattt ttataggtta atgtcatgat aataatggtt tcttagacgt      6060
caggtggcac ttttcgggga atgtgcgcg gaaccctat tgtttattt ttctaaatac         6120 attcaaatat gtatccgctc atgagacaat aaccctgata aatgcttcaa taatattgaa      6180
aaaggaagag tatgagtatt caacatttcc gtgtcgccct tattcccttt tttgcggcat      6240
tttgccttcc tgttttgct cacccagaaa cgctggtgaa agtaaaagat gctgaagatc       6300
agttgggtgc acgagtgggt tacatcgaac tggatctcaa cagcggtaag atccttgaga      6360
gttttcgccc cgaagaacgt tttccaatga tgagcacttt taaagttctg ctatgtggcg      6420
cggtattatc ccgtattgac gccgggcaag agcaactcgg tcgccgcata cactattctc      6480
agaatgactt ggttgagtac tcaccagtca cagaaaagca tcttacggat ggcatgacag      6540
taagagaatt atgcagtgct gccataacca tgagtgataa cactgcggcc aacttacttc      6600
tgacaacgat cggaggaccg aaggagctaa ccgcttttt gcacaacatg ggggatcatg       6660
taactcgcct tgatcgttgg gaaccggagc tgaatgaagc cataccaaac gacgagcgtg      6720
```

```
acaccacgat gcctgtagca atggcaacaa cgttgcgcaa actattaact ggcgaactac    6780
ttactctagc ttcccggcaa caattaatag actggatgga ggcggataaa gttgcaggac    6840
cacttctgcg ctcggccctt ccggctggct ggtttattgc tgataaatct ggagccggtg    6900
agcgtgggtc tcgcggtatc attgcagcac tggggccaga tggtaagccc tcccgtatcg    6960
tagttatcta cacgacgggg agtcaggcaa ctatggatga acgaaataga cagatcgctg    7020
agataggtgc ctcactgatt aagcattggt aactgtcaga ccaagtttac tcatatatac    7080
tttagattga tttaaaactt cattttttaat ttaaaaggat ctaggtgaag atccttttttg   7140 ataatctcat gaccaaaatc ccttaacgtg agttttcgtt ccactgagcg tcagaccccg    7200
tagaaaagat caaaggatct tcttgagatc ctttttttct gcgcgtaatc tgctgcttgc    7260
aaacaaaaaa accaccgcta ccagcggtgg tttgtttgcc ggatcaagag ctaccaactc    7320
tttttccgaa ggtaactggc ttcagcagag cgcagatacc aaatactgtc cttctagtgt    7380
agccgtagtt aggccaccac ttcaagaact ctgtagcacc gcctacatac ctcgctctgc    7440
taatcctgtt accagtggct gctgccagtg gcgataagtc gtgtcttacc gggttggact    7500
caagacgata gttaccggat aaggcgcagc ggtcgggctg aacggggggt tcgtgcacac    7560
agcccagctt ggagcgaacg acctacaccg aactgagata cctacagcgt gagctatgag    7620
aaagcgccac gcttcccgaa gggagaaagg cggacaggta tccggtaagc ggcagggtcg    7680
gaacaggaga gcgcacgagg gagcttccag ggggaaacgc ctggtatctt tatagtcctg    7740
tcgggtttcg ccacctctga cttgagcgtc gatttttgtg atgctcgtca gggggggcgga    7800 gcctatggaa aaacgccagc aacgcggcct ttttacggtt cctggccttt tgctggcctt    7860
ttgctcacat gt    7872
```

<210> SEQ ID NO 18
<211> LENGTH: 4377
<212> TYPE: DNA
<213> ORGANISM: Artificial Sequence
<220> FEATURE:
<223> OTHER INFORMATION: CoFVIIIdeltaB

<400> SEQUENCE: 18

```
atgcagatcg agctgtccac ctgctttttt ctgtgcctgc tgcggttctg cttcagcgcc      60
acccggcggt actacctggg cgccgtggag ctgtcctggg actacatgca gagcgacctg     120
ggcgagctgc ccgtggacgc ccggttcccc ccagagtgc ccaagagctt ccccttcaac      180
accagcgtgg tgtacaagaa aaccctgttc gtggagttca cgaccacct gttcaatatc      240 gccaagccca ggcccccctg gatgggcctg ctgggcccca ccatccaggc cgaggtgtac     300
gacaccgtgg tgatcaccct gaagaacatg gccagccacc ccgtgagcct gcacgccgtg     360
ggcgtgagct actggaaggc cagcgagggc gccgagtacg acgaccagac cagccagcgg     420
gagaaagaag atgacaaggt gttccctggc ggcagccaca cctacgtgtg gcaggtgctg     480
aaagaaaacg gccccatggc ctccgacccc ctgtgcctga cctacagcta cctgagccac     540
gtggacctgg tgaaggacct gaacagcggc ctgatcggcg ctctgctcgt ctgccgggag     600
ggcagcctgg ccaaagagaa aacccagacc tgcacaagt tcatcctgct gttcgccgtg     660
ttcgacgagg gcaagagctg gcacagcgag acaaagaaca gcctgatgca ggaccgggac     720
gccgcctctg ccagagcctg gcccaagatg cacaccgtga acggctacgt gaacagaagc     780
ctgcccggcc tgattggctg ccaccggaag agcgtgtact ggcacgtgat cggcatgggc     840
accacacccg aggtgcacag catctttctg gaagggcaca cctttctggt ccggaaccac    900
```

```
cggcaggcca gcctggaaat cagccctatc accttcctga ccgcccagac actgctgatg      960
gacctgggcc agttcctgct gttttgccac atcagctctc accagcacga cggcatggaa     1020
gcctacgtga aggtggactc ttgccccgag aaccccagc tgcggatgaa gaacaacgag      1080
gaagccgagg actacgacga cgacctgacc gacagcgaga tggacgtggt gcggttcgac     1140
gacgacaaca gccccagctt catccagatc agaagcgtgg ccaagaagca ccccaagacc     1200
tgggtgcact atatcgccgc cgaggaagag gactgggact acgcccccct ggtgctggcc     1260
cccgacgaca aagctacaa gagccagtac ctgaacaatg ccccccagcg gatcggccgg      1320
aagtacaaga agtgcggtt catggcctac accgacgaga cattcaagac ccgggaggcc     1380
atccagcacg agagcggcat cctgggcccc ctgctgtacg cgaagtggg cgacacactg      1440 ctgatcatct tcaagaacca ggctagccgg ccctacaaca tctacccca cggcatcacc     1500 gacgtgcggc ccctgtacag caggcggctg cccaagggcg tgaagcacct gaaggacttc     1560
cccatcctgc ccggcgagat cttcaagtac aagtggaccg tgaccgtgga ggacggcccc     1620
accaagagcg accccagatg cctgacccgg tactacagca gcttcgtgaa catggaacgg     1680
gacctggcct ccgggctgat cggacctctg ctgatctgct acaaagaaag cgtgaccag     1740 cggggcaacc agatcatgag cgacaagcgg aacgtgatcc tgttcagcgt gttcgatgag     1800
aaccggtcct ggtatctgac cgagaacatc cagcggtttc tgcccaaccc tgccggcgtg     1860
cagctggaag atcccgagtt ccaggccagc aacatcatgc actccatcaa tggctacgtg     1920
ttcgactctc tgcagctctc cgtgtgtctg cacgaggtgg cctactggta catcctgagc     1980
atcggcgccc agaccgactt cctgagcgtg ttcttcagcg gctacaccct caagcacaag     2040
atggtgtacg aggacaccct gaccctgttc cctttcagcg cgagacagt gttcatgagc     2100 atggaaaacc ccggcctgtg gattctgggc tgccacaaca gcgacttccg gaaccggggc     2160
atgaccgccc tgctgaaggt gtccagctgc gacaagaaca ccggcgacta ctacgaggac     2220
agctacgagg atatcagcgc ctacctgctg tccaagaaca acgccatcga accccggagc     2280
ttcagccaga ccccccccgt gctgacgcgt caccagcggg agatcacccg gacaaccctg     2340
cagtccgacc aggaagagat cgattacgac gacaccatca gcgtggagat gaagaaagag     2400
gatttcgata tctacgacga ggacgagaac cagagcccca aagcttcca aagaaaacc      2460 cggcactact tcattgccgc cgtggagagg ctgtgggact acggcatgag ttctagcccc     2520
cacgtgctgc ggaaccgggc ccagagcggc agcgtgcccc agttcaagaa agtggtgttc     2580
caggaattca cagacggcag cttcacccag cctctgtata gaggcgagct gaacgagcac     2640
ctggggctgc tgggggccta catcagggcc gaagtggagg acaacatcat ggtgaccttc     2700
cggaatcagg ccagcagacc ctactccttc tacagcagcc tgatcagcta cgaagaggac     2760
cagcggcagg gcgccgaacc ccggaagaac ttcgtgaagc ccaacgaaac caagacctac     2820
ttctggaaag tgcagcacca catggccccc accaaggacg agttcgactg caaggcctgg     2880
gcctacttca gcgacgtgga tctggaaaag gacgtgcact ctggactgat ggcccactc      2940 ctggtctgcc acactaacac cctcaacccc gcccacggcc gccaggtgac cgtgcaggaa     3000
ttcgccctgt tcttcaccat cttcgacgag acaaagtcct ggtacttcac cgagaatatg     3060
gaacggaact gcagagcccc ctgcaacatc cagatggaag atcctacctt caagagaaac     3120
taccggttcc acgccatcaa cggctacatc atggacaccc tgcctggcct ggtgatggcc     3180
caggaccaga gaatccggtg gtatctgctg tccatgggca gcaacgagaa tatccacagc     3240
```

| | |
|---|---:|
| atccacttca gcggccacgt gttcaccgtg cggaagaaag aagagtacaa gatggccctg | 3300 |
| tacaacctgt accccggcgt gttcgagaca gtggagatgc tgcccagcaa ggccggcatc | 3360 |
| tggcgggtgg agtgtctgat cggcgagcac ctgcacgctg gcatgagcac cctgtttctg | 3420 |
| gtgtacagca acaagtgcca gaccccactg ggcatggcct ctggccacat ccgggacttc | 3480 |
| cagatcaccg cctccggcca gtacggccag tgggccccca gctggccag actgcactac | 3540 |
| agcggcagca tcaacgcctg gtccaccaaa gagcccttca gctggatcaa ggtgacctg | 3600 |
| ctggccccta tgatcatcca cggcattaag acccagggcg ccaggcagaa gttcagcagc | 3660 |
| ctgtacatca gccagttcat catcatgtac agcctggacg gcaagaagtg gcagacctac | 3720 |
| cggggcaaca gcaccggcac cctgatggtg ttcttcggca atgtggacag cagcggcatc | 3780 |
| aagcacaaca tcttcaaccc ccccatcatt gcccggtaca tccggctgca ccccacccac | 3840 |
| tacagcatta gatccacact gagaatggaa ctgatgggct gcgacctgaa ctcctgcagc | 3900 |
| atgcctctgg gcatggaaag caaggccatc agcgacgccc agatcacagc cagcagctac | 3960 |
| ttcaccaaca tgttcgccac ctggtccccc tccaaggcca ggctgcacct gcagggccgg | 4020 |
| tccaacgcct ggcggcctca ggtcaacaac cccaagaat ggctgcaggt ggactttcag | 4080 |
| aaaaccatga aggtgaccgg cgtgaccacc cagggcgtga aaagcctgct gaccagcatg | 4140 |
| tacgtgaaag agtttctgat cagcagctct caggatggcc accagtggac cctgttctt | 4200 |
| cagaacggca aggtgaaagt gttccagggc aaccaggact ccttcacccc cgtggtgaac | 4260 |
| tccctggacc ccccctgct gacccgctac ctgagaatcc accccagtc ttgggtgcac | 4320 |
| cagatcgccc tcaggatgga agtcctggga tgtgaggccc aggatctgta ctgatga | 4377 |

<210> SEQ ID NO 19
<211> LENGTH: 134
<212> TYPE: DNA
<213> ORGANISM: Artificial Sequence
<220> FEATURE:
<223> OTHER INFORMATION: SV40polyA

<400> SEQUENCE: 19

| | |
|---|---:|
| atgctttatt tgtgaaattt gtgatgctat tgctttattt gtaaccatta taagctgcaa | 60 |
| taaacaagtt aacaacaaca attgcattca ttttatgttt caggttcagg ggaggtgtg | 120 |
| ggaggttttt taaa | 134 |

<210> SEQ ID NO 20
<211> LENGTH: 7922
<212> TYPE: DNA
<213> ORGANISM: Artificial Sequence
<220> FEATURE:
<223> OTHER INFORMATION: pAAVss-3xSerpEnh-TTRm-MVM-coFVIIIdeltaB-Synt-pA

<400> SEQUENCE: 20

| | |
|---|---:|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac taggggttcc tgcggccgcg gtacgcgggg gaggctgctg gtgaatatta | 180 |
| accaaggtca ccccagttat cggaggagca acagggct aagtccaccg ggggaggctg | 240 |
| ctggtgaata ttaaccaagg tcaccccagt tatcggagga gcaaacaggg gctaagtcca | 300 |
| ccggggagg ctgctggtga atattaacca aggtcacccc agttatcgga ggagcaaaca | 360 |
| ggggctaagt ccactgtaca acgcgtgaat tcgctagcgt ctgtctgcac atttcgtaga | 420 |
| gcgagtgttc cgatactcta atctccctag gcaaggttca tatttgtgta ggttacttat | 480 |

-continued

| | |
|---|---|
| tctccttttg ttgactaagt caataatcag aatcagcagg tttggagtca gcttggcagg | 540 |
| gatcagcagc ctgggttgga aggaggggt ataaaagccc cttcaccagg agaagccgtc | 600 |
| acacagatcc acaagctcct gtctagaaag aggtaagggt ttaagggatg gttggttggt | 660 |
| ggggtattaa tgtttaatta cctggagcac ctgcctgaaa tcactttttt tcaggttggg | 720 |
| ctagcatgca gatcgagctg tccacctgct ttttctgtg cctgctgcgg ttctgcttca | 780 |
| gcgccacccg gcggtactac ctgggcgccg tggagctgtc ctgggactac atgcagagcg | 840 |
| acctgggcga gctgcccgtg gacgcccggt cccccccag agtgcccaag agcttcccct | 900 |
| tcaacaccag cgtggtgtac aagaaaaccc tgttcgtgga gttcaccgac cacctgttca | 960 |
| atatcgccaa gcccaggccc cctggatgg gcctgctggg ccccaccatc caggccgagg | 1020 |
| tgtacgacac cgtggtgatc accctgaaga acatggccag ccaccccgtg agcctgcacg | 1080 |
| ccgtgggcgt gagctactgg aaggccagcg agggcgccga gtacgacgac cagaccagcc | 1140 |
| agcgggagaa agaagatgac aaggtgttcc ctggcggcag ccacacctac gtgtggcagg | 1200 |
| tgctgaaaga aaacggcccc atggcctccg accccctgtg cctgacctac agctacctga | 1260 |
| gccacgtgga cctggtgaag gacctgaaca cggcctgat cggcgctctg ctcgtctgcc | 1320 |
| gggagggcag cctggccaaa gagaaaaccc agaccctgca aagttcatc ctgctgttcg | 1380 |
| ccgtgttcga cgagggcaag agctggcaca gcgagacaaa gaacagcctg atgcaggacc | 1440 |
| gggacgccgc ctctgccaga gcctggccca agatgcacac cgtgaacggc tacgtgaaca | 1500 |
| gaagcctgcc cggcctgatt ggctgccacc ggaagagcgt gtactggcac gtgatcggca | 1560 |
| tgggcaccac acccgaggtg cacagcatct ttctggaagg gcacacctt ctggtccgga | 1620 |
| accaccggca ggccagcctg gaaatcagcc ctatcacctt cctgaccgcc agacactgc | 1680 |
| tgatggacct gggccagttc ctgctgtttt gccacatcag ctctcaccag cacgacggca | 1740 |
| tggaagccta cgtgaaggtg gactcttgcc ccgaggaacc ccagctgcgg atgaagaaca | 1800 |
| acgaggaagc cgaggactac gacgacgacc tgaccgacag cgagatggac gtggtgcggt | 1860 |
| tcgacgacga caacagcccc agcttcatcc agatcagaag cgtggccaag aagcacccca | 1920 |
| agacctgggt gcactatatc gccgccgagg aagaggactg gactacgcc ccctggtgc | 1980 |
| tggcccccga cgacagaagc tacaagagc agtacctgaa caatggcccc cagcggatcg | 2040 |
| gccggaagta caagaaagtg cggttcatgg cctacaccga cgagacattc aagacccggg | 2100 |
| aggccatcca gcacgagagc ggcatcctgg ccccctgct gtacggcgaa gtgggcgaca | 2160 |
| cactgctgat catcttcaag aaccaggcta gccggcccta acatctac ccccacggca | 2220 |
| tcaccgacgt gcggcccctg tacagcaggc ggctgcccaa gggcgtgaag cacctgaagg | 2280 |
| acttcccat cctgcccggc gagatcttca gtacaagtg accgtgacc gtggaggacg | 2340 |
| gccccaccaa gagcgacccc agatgcctga cccggtacta cagcagcttc gtgaacatgg | 2400 |
| aacgggacct ggcctccggg ctgatcggac ctctgctgat ctgctacaaa gaaagcgtgg | 2460 |
| accagcgggg caaccagatc atgagcgaca gcggaacgt gatcctgttc agcgtgttcg | 2520 |
| atgagaaccg gtcctggtat ctgaccgaga acatccagcg gtttctgccc aaccctgccg | 2580 |
| gcgtgcagct ggaagatccc gagttccagg ccagcaacat catgcactcc atcaatggct | 2640 |
| acgtgttcga ctctctgcag ctctccgtgt gtctgcacga ggtggcctac tggtacatcc | 2700 |
| tgagcatcgg cgcccagacc gacttcctga gcgtgttctt cagcggctac accttcaagc | 2760 |
| acaagatggt gtacgaggac accctgaccc tgttccctt cagcggcgag acagtgttca | 2820 |

-continued

```
tgagcatgga aaacccggc ctgtggattc tgggctgcca acagcgac ttccggaacc      2880
ggggcatgac cgccctgctg aaggtgtcca gctgcgacaa gaacaccggc gactactacg   2940
aggacagcta cgaggatatc agcgcctacc tgctgtccaa gaacaacgcc atcgaacccc   3000
ggagcttcag ccagaacccc ccgtgctga cgcgtcacca gcgggagatc acccggacaa   3060
ccctgcagtc cgaccaggaa gagatcgatt acgacgacac catcagcgtg gagatgaaga   3120
aagaggattt cgatatctac gacgaggacg agaaccagag ccccagaagc ttccagaaga   3180
aaacccggca ctacttcatt gccgccgtgg agaggctgtg ggactacggc atgagttcta   3240
gcccccacgt gctgcggaac cgggcccaga gcggcagcgt gccccagttc aagaaagtgg   3300
tgttccagga attcacagac ggcagcttca cccagcctct gtatagaggc gagctgaacg   3360
agcacctggg gctgctgggg ccctacatca gggccgaagt ggaggacaac atcatggtga   3420
ccttccggaa tcaggccagc agaccctact ccttctacag cagcctgatc agctacgaag   3480
aggaccagcg gcagggcgcc gaaccccgga agaacttcgt gaagcccaac gaaaccaaga   3540
cctacttctg gaaagtgcag caccacatgg cccccaccaa ggacgagttc gactgcaagg   3600
cctgggccta cttcagcgac gtggatctgg aaaaggacgt gcactctgga ctgattggcc   3660
cactcctggt ctgccacact aacacccctca accccgccca cggccgccag gtgaccgtgc   3720
aggaattcgc cctgttcttc accatcttcg acgagacaaa gtcctggtac ttcaccgaga   3780
atatggaacg gaactgcaga gccccctgca acatccagat ggaagatcct accttcaaag   3840
agaactaccg gttccacgcc atcaacggct acatcatgga caccctgcct ggcctggtga   3900
tggcccagga ccagagaatc cggtggtatc tgctgtccat gggcagcaac gagaatatcc   3960
acagcatcca cttcagcggc cacgtgttca ccgtgcggaa gaaagaagag tacaagatgg   4020
ccctgtacaa cctgtacccc ggcgtgttcg agacagtgga gatgctgccc agcaaggccg   4080
gcatctggcg ggtggagtgt ctgatcggcg agcacctgca cgctggcatg agcaccctgt   4140
ttctggtgta cagcaacaag tgccagaccc cactgggcat ggcctctggc cacatccggg   4200
acttccagat caccgcctcc ggccagtacg gccagtgggc cccaagctg gccagactgc   4260
actacagcgg cagcatcaac gcctggtcca ccaaagagcc cttcagctgg atcaaggtgg   4320
acctgctggc ccctatgatc atccacggca ttaagaccca gggcgccagg cagaagttca   4380
gcagcctgta catcagccag ttcatcatca tgtacagcct ggacggcaag aagtggcaga   4440
cctaccgggg caacagcacc ggcaccctga tggtgttctt cggcaatgtg gacagcagcg   4500
gcatcaagca acacatcttc aaccccccca tcattgcccg gtacatccgg ctgcaccccca  4560
cccactacag cattagatcc acactgagaa tggaactgat gggctgcgac ctgaactcct   4620
gcagcatgcc tctgggcatg gaagcaagg ccatcagcga cgcccagatc acagccagca   4680
gctacttcac caacatgttc gccacctggt ccccctccaa ggccaggctg cacctgcagg   4740
gccggtccaa cgcctggcgg cctcaggtca acaaccccaa agaatggctg caggtggact   4800
ttcagaaaac catgaaggtg accggcgtga ccacccaggg cgtgaaaagc ctgctgacca   4860
gcatgtacgt gaaagagttt ctgatcagca gctctcagga tggccaccag tggacccctgt  4920
tctttcagaa cggcaaggtg aaagtgttcc agggcaacca ggactccttc accccccgtgg  4980
tgaactccct ggacccccc ctgctgaccc gctacctgag aatccacccc cagtcttggg   5040
tgcaccagat cgcccctcag atggaagtcc tgggatgtga ggcccaggat ctgtactgat   5100
gaggatctag gctcgacaat aaaagatctt tattttcatt agatctgtgt gttggttttt   5160
tgtgtgctcg agatccacgg ccgcaggaac ccctagtgat ggagttggcc actccctctc   5220
```

```
tgcgcgctcg ctcgctcact gaggccgggc gaccaaaggt cgcccgacgc ccgggctttg      5280
cccgggcggc ctcagtgagc gagcgagcgc gcagctgcct gcaggggcgc ctgatgcggt      5340
attttctcct tacgcatctg tgcggtattt cacaccgcat acgtcaaagc aaccatagta      5400
cgcgccctgt agcggcgcat taagcgcggc gggtgtggtg gttacgcgca gcgtgaccgc      5460
tacacttgcc agcgccctag cgcccgctcc tttcgctttc ttcccttcct ttctcgccac      5520
gttcgccggc tttccccgtc aagctctaaa tcggggggctc cctttagggt tccgatttag      5580
tgctttacgg cacctcgacc ccaaaaaact tgatttgggt gatggttcac gtagtgggcc      5640
atcgccctga tagacggttt ttcgcccttt gacgttggag tccacgttct ttaatagtgg      5700
actcttgttc caaactggaa caacactcaa ccctatctcg gctattctt ttgatttata       5760 agggattttg ccgatttcgg cctattggtt aaaaaatgag ctgatttaac aaaaatttaa      5820
cgcgaatttt aacaaaatat taacgtttac aatttttatgg tgcactctca gtacaatctg     5880
ctctgatgcc gcatagttaa gccagccccg acacccgcca acaccgctg acgcgccctg       5940 acgggcttgt ctgctcccgg catccgctta cagacaagct gtgaccgtct ccgggagctg      6000
catgtgtcag aggttttcac cgtcatcacc gaaacgcgcg agacgaaagg gcctcgtgat     6060
acgcctattt ttataggtta atgtcatgat aataatggtt tcttagacgt caggtggcac     6120
ttttcgggga atgtgcgcg gaaccccct attgtttattt ttctaaatac attcaaatat       6180
gtatccgctc atgagacaat aaccctgata aatgcttcaa taatattgaa aaggaagag     6240 tatgagtatt caacatttcc gtgtcgccct tattccctt tttgcggcat tttgccttcc        6300 tgttttttgct cacccagaaa cgctggtgaa agtaaaagat gctgaagatc agttgggtgc    6360
acgagtgggt tacatcgaac tggatctcaa cagcggtaag atccttgaga gttttcgccc    6420
cgaagaacgt tttccaatga tgagcacttt taaagttctg ctatgtggcg cggtattatc    6480
ccgtattgac gccgggcaag agcaactcgg tcgccgcata cactattctc agaatgactt    6540
ggttgagtac tcaccagtca cagaaaagca tcttacggat ggcatgacag taagagaatt    6600
atgcagtgct gccataacca tgagtgataa cactgcggcc aacttacttc tgacaacgat    6660
cggaggaccg aaggagctaa ccgctttttt gcacaacatg ggggatcatg taactcgcct    6720
tgatcgttgg gaaccggagc tgaatgaagc cataccaaac gacgagcgtg acaccacgat    6780
gcctgtagca atggcaacaa cgttgcgcaa actattaact ggcgaactac ttactctagc    6840
ttcccggcaa caattaatag actggatgga ggcggataaa gttgcaggac cacttctgcg    6900
ctcggccctt ccggctggct ggtttattgc tgataaatct ggagccggtg agcgtgggtc    6960
tcgcggtatc attgcagcac tggggccaga tggtaagccc tcccgtatcg tagttatcta    7020
cacgacgggg agtcaggcaa ctatggatga acgaaataga cagatcgctg agataggtgc    7080
ctcactgatt aagcattggt aactgtcaga ccaagtttac tcatatatac tttagattga    7140
tttaaaactt catttttaat ttaaaaggat ctaggtgaag atccttttg ataatctcat      7200 gaccaaaatc ccttaacgtg agttttcgtt ccactgagcg tcagaccccg tagaaaagat    7260
caaaggatct tcttgagatc ctttttttct gcgcgtaatc tgctgcttgc aaacaaaaaa    7320
accaccgcta ccagcggtgg tttgtttgcc ggatcaagag ctaccaactc ttttttccgaa   7380 ggtaactggc ttcagcagag cgcagatacc aaatactgtc cttctagtgt agccgtagtt    7440
aggccaccac ttcaagaact ctgtagcacc gcctacatac ctcgctctgc taatcctgtt    7500
accagtggct gctgccagtg gcgataagtc gtgtcttacc gggttggact caagacgata    7560
```

```
gttaccggat aaggcgcagc ggtcgggctg aacgggggt tcgtgcacac agcccagctt    7620
ggagcgaacg acctacaccg aactgagata cctacagcgt gagctatgag aaagcgccac   7680
gcttcccgaa gggagaaagg cggacaggta tccggtaagc ggcagggtcg aacaggaga    7740
gcgcacgagg gagcttccag ggggaaacgc ctggtatctt tatagtcctg tcgggtttcg   7800
ccacctctga cttgagcgtc gattttgtg atgctcgtca ggggggcgga gcctatggaa    7860
aaacgccagc aacgcggcct ttttacggtt cctggccttt tgctggcctt ttgctcacat   7920
gt                                                                 7922

<210> SEQ ID NO 21
<211> LENGTH: 7814
<212> TYPE: DNA
<213> ORGANISM: Artificial Sequence
<220> FEATURE:
<223> OTHER INFORMATION: pAAVss-3xSerpEnh-TTRm-coFVIIIdeltaB-Synt-pA

<400> SEQUENCE: 21
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccgcg gtacgcgggg gaggctgctg gtgaatatta    180
accaaggtca ccccagttat cggaggagca acaggggct aagtccaccg ggggaggctg     240
ctggtgaata ttaaccaagg tcaccccagt tatcggagga gcaaacaggg gctaagtcca    300
ccggggagg ctgctggtga atattaacca aggtcacccc agttatcgga ggagcaaaca     360
ggggctaagt ccactgtaca acgcgtgaat tcgctagcgt ctgtctgcac atttcgtaga    420
gcgagtgttc cgatactcta atctccctag gcaaggttca tatttgtgta ggttacttat    480
tctccttttg ttgactaagt caataatcag aatcagcagg tttggagtca gcttggcagg    540
gatcagcagc ctgggttgga aggagggggt ataaaagccc cttcaccagg agaagccgtc    600
acacagatcc acaagctcct gctagtatgc agatcgagct gtccacctgc ttttttctgt    660
gcctgctgcg gttctgcttc agcgccaccc ggcggtacta cctgggcgcc gtggagctgt    720
cctgggacta catgcagagc gacctgggcg agctgcccgt ggacgcccgg ttcccccca     780
gagtgcccaa gagcttcccc ttcaacacca gcgtggtgta caagaaaacc ctgttcgtgg    840
agttcaccga ccacctgttc aatatcgcca agcccaggcc ccctggatg ggcctgctgg     900
gccccaccat ccaggccgag gtgtacgaca ccgtggtgat caccctgaag aacatggcca    960
gccacccgt gagcctgcac gccgtgggcg tgagctactg gaaggccagc gagggcgccg    1020
agtacgacga ccagaccagc cagcgggaga agaagatga caaggtgttc cctggcggca   1080
gccacaccta cgtgtggcag gtgctgaaag aaaacggccc catggcctcc gacccctgt    1140
gcctgaccta cagctacctg agccacgtgg acctggtgaa ggacctgaac agcggcctga   1200
tcggcgctct gctcgtctgc cgggagggca gcctggccaa agagaaaacc cagaccctgc   1260
acaagttcat cctgctgttc gccgtgttcg acgagggcaa gagctggcac agcgagacaa   1320
agaacagcct gatgcaggac cgggacgccg cctctgccag agcctggccc aagatgcaca   1380
ccgtgaacgg ctacgtgaac aggaagccctg ccggcctgat ggctgccac cggaagagcg   1440
tgtactggca cgtgatcggc atgggcacca cacccgaggt gcacagcatc tttctggaag   1500
ggcacacctt tctggtccgg aaccaccggc aggccagcct ggaaatcagc cctatcacct   1560
tcctgaccgc ccagacactg ctgatggacc tgggccagtt cctgctgttt tgccacatca   1620
gctctcacca gcacgacggc atggaagcct acgtgaaggt ggactcttgc cccgaggaac   1680
```

```
cccagctgcg gatgaagaac aacgaggaag ccgaggacta cgacgacgac ctgaccgaca      1740
gcgagatgga cgtggtgcgg ttcgacgacg acaacagccc cagcttcatc cagatcagaa      1800
gcgtggccaa gaagcacccc aagacctggg tgcactatat cgccgccgag aagaggact       1860
gggactacgc ccccctggtg ctggcccccg acgacagaag ctacaagagc cagtacctga      1920
acaatggccc ccagcggatc ggccggaagt acaagaaagt gcggttcatg gcctacaccg      1980
acgagacatt caagacccgg gaggccatcc agcacgagag cggcatcctg ggcccctgc       2040
tgtacggcga agtgggcgac acactgctga tcatcttcaa gaaccaggct agccggccct      2100
acaacatcta ccccacggc atcaccgacg tgcggcccct gtacagcagg cggctgccca       2160
agggcgtgaa gcacctgaag gacttcccca tcctgcccgg cgagatcttc aagtacaagt      2220
ggaccgtgac cgtggaggac ggccccacca gagcgaccc cagatgcctg acccggtact       2280
acagcagctt cgtgaacatg aacgggaccc tggcctccgg gctgatcgga cctctgctga      2340
tctgctacaa agaaagcgtg gaccagcggg gcaaccagat catgagcgac aagcggaacg      2400
tgatcctgtt cagcgtgttc gatgagaacc ggtcctggta tctgaccgag aacatccagc      2460
ggtttctgcc caaccctgcc ggcgtgcagc tggaagatcc cgagttccag gccagcaaca      2520
tcatgcactc catcaatggc tacgtgttcg actctctgca gctctccgtg tgtctgcacg      2580
aggtggccta ctggtacatc ctgagcatcg gcgcccagac cgacttcctg agcgtgttct      2640
tcagcggcta caccttcaag cacaagatgg tgtacgagga caccctgacc ctgttccctt      2700
tcagcggcga cagtgttc atgagcatgg aaaaccccgg cctgtggatt ctgggctgcc        2760
acaacagcga cttccggaac cggggcatga ccgccctgct gaaggtgtcc agctgcgaca      2820
agaacaccgg cgactactac gaggacagct acgaggatat cagcgcctac ctgctgtcca      2880
agaacaacgc catcgaaccc cggagcttca gccagaaccc ccccgtgctg acgcgtcacc      2940
agcgggagat caccccggaca accctgcagt ccgaccagga agatcgat tacgacgaca       3000
ccatcagcgt ggagatgaag aaagaggatt tcgatatcta cgacgaggac gagaaccaga     3060
gccccagaag cttccagaag aaaacccggc actacttcat tgccgccgtg gagaggctgt      3120
gggactacgg catgagttct agcccccacg tgctgcggaa ccgggcccag agcggcagcg      3180
tgccccagtt caagaaagtg gtgttccagg aattcacaga cggcagcttc acccagcctc      3240
tgtatagagg cgagctgaac gagcacctgg ggctgctggg gccctacatc agggccgaag      3300
tggaggacaa catcatggtg accttccgga atcaggccag cagaccctac tccttctaca      3360
gcagcctgat cagctacgaa gaggaccagc ggcagggcgc cgaaccccgg aagaacttcg      3420
tgaagcccaa cgaaaccaag acctacttct ggaaagtgca gcaccacatg gccccccacca     3480
aggacgagtt cgactgcaag gcctgggcct acttcagcga cgtggatctg aaaaggacg       3540
tgcactctgg actgattggc ccactcctgg tctgccacac taacaccctc aaccccgccc      3600
acggccgcca ggtgaccgtg caggaattcg ccctgttctt caccatcttc gacgagacaa      3660
agtcctggta cttcaccgag aatatggaac ggaactgcag agcccctgc aacatccaga       3720
tggaagatcc taccttcaaa gagaactacc ggttccacgc catcaacggc tacatcatgg      3780
acaccctgcc tggcctggtg atggcccagg accagagaat ccgtggtat ctgctgtcca       3840
tgggcagcaa cgagaatatc cacagcatcc acttcagcgg ccacgtgttc accgtgcgga      3900
agaaagaaga gtacaagatg gccctgtaca acctgtaccc cggcgtgttc gagacagtgg      3960
agatgctgcc cagcaaggcc ggcatctggc gggtggagtg tctgatcggc gagcacctgc      4020
```

```
acgctggcat gagcaccctg tttctggtgt acagcaacaa gtgccagacc ccactgggca      4080
tggcctctgg ccacatccgg gacttccaga tcaccgcctc cggccagtac ggccagtggg      4140
cccccaagct ggccagactg cactacagcg gcagcatcaa cgcctggtcc accaaagagc      4200
ccttcagctg gatcaaggtg gacctgctgg cccctatgat catccacggc attaagaccc      4260
agggcgccag gcagaagttc agcagcctgt acatcagcca gttcatcatc atgtacagcc      4320
tggacggcaa gaagtggcag acctaccggg caacagcac cggcaccctg atggtgttct       4380
tcggcaatgt ggacagcagc ggcatcaagc acaacatctt caacccccc atcattgccc       4440 ggtacatccg gctgcacccc acccactaca gcattagatc cacactgaga atggaactga      4500
tgggctgcga cctgaactcc tgcagcatgc ctctgggcat ggaaagcaag gccatcagcg      4560
acgcccagat cacagccagc agctacttca ccaacatgtt cgccacctgg tcccctccca     4620
aggccaggct gcacctgcag ggccggtcca acgcctggcg gcctcaggtc aacaacccca      4680
aagaatggct gcaggtggac tttcagaaaa ccatgaaggt gaccggcgtg accacccagg      4740
gcgtgaaaag cctgctgacc agcatgtacg tgaaagagtt tctgatcagc agctctcagg      4800
atggccacca gtggaccctg ttctttcaga acggcaaggt gaaagtgttc cagggcaacc      4860
aggactcctt caccccgtg gtgaactccc tggacccccc cctgctgacc cgctacctga      4920
gaatccaccc ccagtcttgg gtgcaccaga tcgccctcag gatggaagtc ctgggatgtg      4980
aggcccagga tctgtactga tgaggatcca ataaagatc tttatttca ttagatctgt        5040 gtgttggttt tttgtgtgct cgagatccac ggccgcagga acccctagtg atggagttgg      5100
ccactccctc tctgcgcgct cgctcgctca ctgaggccgg gcgaccaaag gtcgcccgac      5160
gcccgggctt tgcccgggcg gcctcagtga gcgagcgagc gcgcagctgc ctgcagggc      5220 gcctgatgcg gtattttctc cttacgcatc tgtgcggtat ttcacaccgc atacgtcaaa      5280
gcaaccatag tacgcgccct gtagcggcgc attaagcgcg gcgggtgtgg tggttacgcg      5340
cagcgtgacc gctacacttg ccagcgccct agcgcccgct cctttcgctt tcttcccttc      5400
ctttctcgcc acgttcgccg gctttccccg tcaagctcta aatcggggc tcccttttagg      5460 gttccgattt agtgctttac ggcacctcga ccccaaaaaa cttgatttgg gtgatggttc      5520
acgtagtggg ccatcgccct gatagacggt ttttcgccct ttgacgttgg agtccacgtt      5580
ctttaatagt ggactcttgt tccaaactgg aacaacactc aaccctatct cgggctattc      5640
ttttgattta agggatttt tgccgatttc ggcctattgg ttaaaaatg agctgattta       5700 acaaaatt aacgcgaatt ttaacaaaat attaacgtt acaatttat ggtgcactct          5760 cagtacaatc tgctctgatg ccgcatagtt aagccagccc cgacaccgc caacacccgc       5820 tgacgcgccc tgacgggctt gtctgctccc ggcatccgct tacagacaag ctgtgaccgt      5880
ctccgggagc tgcatgtgtc agaggttttc accgtcatca ccgaaacgcg cgagacgaaa      5940
gggcctcgtg atacgcctat ttttataggt taatgtcatg ataataatgg tttcttagac      6000
gtcaggtggc acttttcggg gaaatgtgcg cggaacccct atttgtttat ttttctaaat      6060
acattcaaat atgtatccgc tcatgagaca ataaccctga taaatgcttc aataatattg      6120
aaaaaggaag agtatgagta ttcaacattt ccgtgtcgcc cttattccct ttttgcggc       6180 attttgcctt cctgttttg ctcacccaga aacgctggtg aaagtaaaag atgctgaaga       6240
tcagttgggt gcacgagtgg gttacatcga actggatctc aacagcggta agatccttga     6300
gagttttcgc cccgaagaac gttttccaat gatgagcact ttaaagttc tgctatgtgg      6360 cgcggtatta tcccgtattg acgccgggca agagcaactc ggtcgccgca tacactattc     6420
```

```
tcagaatgac ttggttgagt actcaccagt cacagaaaag catcttacgg atggcatgac      6480
agtaagagaa ttatgcagtg ctgccataac catgagtgat aacactgcgg ccaacttact      6540
tctgacaacg atcggaggac cgaaggagct aaccgctttt ttgcacaaca tgggggatca      6600
tgtaactcgc cttgatcgtt gggaaccgga gctgaatgaa gccataccaa cgacgagcg      6660 tgacaccacg atgcctgtag caatggcaac aacgttgcgc aaactattaa ctggcgaact      6720
acttactcta gcttcccggc aacaattaat agactggatg gaggcggata agttgcagg      6780 accacttctg cgctcggccc ttccggctgg ctggtttatt gctgataaat ctggagccgg      6840
tgagcgtggg tctcgcggta tcattgcagc actggggcca gatggtaagc cctcccgtat      6900
cgtagttatc tacacgacgg ggagtcaggc aactatggat gaacgaaata gacagatcgc      6960
tgagataggt gcctcactga ttaagcattg gtaactgtca gaccaagttt actcatatat      7020
actttagatt gatttaaaac ttcattttta atttaaaagg atctaggtga agatcctttt      7080
tgataatctc atgaccaaaa tcccttaacg tgagttttcg ttccactgag cgtcagaccc      7140
cgtagaaaag atcaaaggat cttcttgaga tcctttttt ctgcgcgtaa tctgctgctt      7200
gcaaacaaaa aaaccaccgc taccagcggt ggtttgtttg ccggatcaag agctaccaac      7260
tctttttccg aaggtaactg gcttcagcag agcgcagata ccaaatactg tccttctagt      7320
gtagccgtag ttaggccacc acttcaagaa ctctgtagca ccgcctacat acctcgctct      7380
gctaatcctg ttaccagtgg ctgctgccag tggcgataag tcgtgtctta ccgggttgga      7440
ctcaagacga tagttaccgg ataaggcgca gcggtcgggc tgaacggggg gttcgtgcac      7500
acagcccagc ttggagcgaa cgacctacac cgaactgaga tacctacagc gtgagctatg      7560
agaaagcgcc acgcttcccg aagggagaaa ggcggacagg tatccggtaa gcggcagggt      7620
cggaacagga gagcgcacga gggagcttcc agggggaaac gcctggtatc tttatagtcc      7680
tgtcgggttt cgccacctct gacttgagcg tcgatttttg tgatgctcgt caggggggcg      7740
gagcctatgg aaaaacgcca gcaacgcggc ctttttacgg ttcctggcct tttgctggcc      7800
ttttgctcac atgt                                                       7814
```

<210> SEQ ID NO 22
<211> LENGTH: 8090
<212> TYPE: DNA
<213> ORGANISM: Artificial Sequence
<220> FEATURE:
<223> OTHER INFORMATION: pAAVss-3xSerpEnh-TTRe-TTRm-MVM-coFVIIIdeltaB-
      Sv40pA

<400> SEQUENCE: 22

```
cctgcaggca gctgcgcgct cgctcgctca ctgaggccgc ccgggcaaag cccgggcgtc       60
gggcgacctt tggtcgcccg gcctcagtga gcgagcgagc gcgcagagag ggagtggcca      120
actccatcac tagggttcc tgcggccgcg ggggaggctg ctggtgaata ttaaccaagg      180
tcaccccagt tatcggagga gcaaacaggg gctaagtcca ccggggggagg ctgctggtga      240 atattaacca aggtcacccc agttatcgga ggagcaaaca ggggctaagt ccaccggggg      300
aggctgctgg tgaatattaa ccaaggtcac cccagttatc ggaggagcaa acaggggcta      360
agtccacggt acccactggg aggatgttga gtaagatgga aaactactga tgacccttgc      420
agagacagag tattaggaca tgtttgaaca ggggccgggc gatcagcagg tagctctaga      480
ggatccccgt ctgtctgcac atttcgtaga gcgagtgttc cgatactcta atctccctag      540
gcaaggttca tatttgtgta ggttacttat tctcctttg ttgactaagt caataatcag      600
```

```
aatcagcagg tttggagtca gcttggcagg gatcagcagc ctgggttgga aggaggggt    660
ataaaagccc cttcaccagg agaagccgtc acacagatcc acaagctcct gaagaggtaa    720
gggtttaagg gatggttggt tggtggggta ttaatgttta attacctgga gcacctgcct    780
gaaatcactt tttttcaggt tggctagtat gcagatcgag ctgtccacct gcttttttct    840
gtgcctgctg cggttctgct tcagcgccac ccggcggtac tacctgggcg ccgtggagct    900
gtcctgggac tacatgcaga gcgacctggg cgagctgccc gtggacgccc ggttcccccc    960
cagagtgccc aagagcttcc ccttcaacac cagcgtggtg tacaagaaaa ccctgttcgt   1020
ggagttcacc gaccacctgt tcaatatcgc caagcccagg ccccctgga tgggcctgct   1080
gggcccacc atccaggccg aggtgtacga caccgtggtg atcaccctga agaacatggc   1140
cagccacccc gtgagcctgc acgccgtggg cgtgagctac tggaaggcca gcgagggcgc   1200
cgagtacgac gaccagacca gccagcggga gaaagaagat gacaaggtgt ccctggcgg   1260
cagccacacc tacgtgtggc aggtgctgaa agaaaacggc cccatggcct ccgaccccct   1320
gtgcctgacc tacagctacc tgagccacgt ggacctggtg aaggacctga acagcggcct   1380
gatcggcgct ctgctcgtct gccgggaggg cagcctggcc aaagagaaaa cccagaccct   1440
gcacaagttc atcctgctgt tcgccgtgtt cgacgagggc aagagctggc acagcgagac   1500
aaagaacagc ctgatgcagg accgggacgc cgcctctgcc agagcctggc caagatgca   1560
caccgtgaac ggctacgtga acagaagcct gcccggcctg attggctgcc accggaagag   1620
cgtgtactgg cacgtgatcg gcatgggcac cacacccgag gtgcacagca tctttctgga   1680
agggcacacc tttctggtcc ggaaccaccg gcaggccagc ctggaaatca gccctatcac   1740
cttcctgacc gcccagacac tgctgatgga cctgggccag ttcctgctgt tttgccacat   1800
cagctctcac cagcacgacg gcatggaagc ctacgtgaag gtggactctt gccccgagga   1860
accccagctg cggatgaaga caacgagga agccgaggac tacgacgacg acctgaccga   1920
cagcgagatg gacgtggtgc ggttcgacga cgacaacagc cccagcttca tccagatcag   1980
aagcgtggcc aagaagcacc ccaagacctg ggtgcactat atcgccgccg aggaagagga   2040
ctgggactac gccccctgg tgctggcccc cgacgacaga agctacaaga gccagtacct   2100
gaacaatggc ccccagcgga tcggccggaa gtacaagaaa gtgcggttca tggcctacac   2160
cgacgagaca ttcaagaccc gggaggcat ccagcacgag agcggcatcc tgggccccct   2220
gctgtacggc gaagtgggcg acacactgct gatcatcttc aagaaccagg ctagccggcc   2280
ctacaacatc taccccacg gcatcaccga cgtgcgccc ctgtacagca ggcggctgcc   2340
caagggcgtg aagcacctga aggacttccc catcctgccc ggcgagatct tcaagtacaa   2400
gtggaccgtg accgtggagg acggccccac caagagcgac cccagatgcc tgacccggta   2460
ctacagcagc ttcgtgaaca tggaacggga cctggcctcc gggctgatcg gacctctgct   2520
gatctgctac aaagaaagcg tggaccagcg gggcaaccag atcatgagcg acaagcggaa   2580
cgtgatcctg ttcagcgtgt tcgatgagaa ccggtcctgg tatctgaccg agaacatcca   2640
gcggtttctg cccaaccctg ccggcgtgca gctggaagat cccgagttcc aggccagcaa   2700
catcatgcac tccatcaatg gctacgtgtt cgactctctg cagctctccg tgtgtctgca   2760
cgaggtggcc tactggtaca tcctgagcat cggcgcccag accgacttcc tgagcgtgtt   2820
cttcagcggc tacaccttca gcacaagat ggtgtacgag gacaccctga cctgttccc   2880
tttcagcggc gagacagtgt tcatgagcat ggaaaacccc ggcctgtgga ttctgggctg   2940
```

```
ccacaacagc gacttccgga accggggcat gaccgccctg ctgaaggtgt ccagctgcga    3000
caagaacacc ggcgactact acgaggacag ctacgaggat atcagcgcct acctgctgtc    3060
caagaacaac gccatcgaac cccggagctt cagccagaac ccccccgtgc tgacgcgtca    3120
ccagcgggag atcaccccga caaccctgca gtccgaccag gaagagatcg attacgacga    3180
caccatcagc gtggagatga agaaagagga tttcgatatc tacgacgagg acgagaacca    3240
gagccccaga agcttccaga agaaaacccg gcactacttc attgccgccg tggagaggct    3300
gtgggactac ggcatgagtt ctagccccca cgtgctgcgg aaccgggccc agagcggcag    3360
cgtgccccag ttcaagaaag tggtgttcca ggaattcaca gacggcagct tcacccagcc    3420
tctgtataga ggcgagctga acgagcacct ggggctgctg gggccctaca tcagggccga    3480
agtggaggac aacatcatgg tgaccttccg gaatcaggcc agcagaccct actccttcta    3540
cagcagcctg atcagctacg aagaggacca gcggcagggc gccgaacccc ggaagaactt    3600
cgtgaagccc aacgaaacca agacctactt ctggaaagtg cagcaccaca tggcccccac    3660
caaggacgag ttcgactgca aggcctgggc ctacttcagc gacgtggatc tggaaaagga    3720
cgtgcactct ggactgattg gcccactcct ggtctgccac actaacaccc tcaacccgc     3780 ccacggccgc caggtgaccg tgcaggaatt cgccctgttc ttcaccatct cgacgagac     3840 aaagtcctgg tacttcaccg agaatatgga acggaactgc agagcccct gcaacatcca     3900 gatggaagat cctaccttca agagaactac cggttccac gccatcaacg ctacatcat     3960 ggacaccctg cctggcctgg tgatggccca ggaccagaga atccggtggt atctgctgtc    4020
catgggcagc aacgagaata tccacagcat ccacttcagc ggccacgtgt tcaccgtgcg    4080
gaagaaagaa gagtacaaga tggccctgta acctgtac cccggcgtgt tcgagacagt      4140
ggagatgctg cccagcaagg ccggcatctg gcgggtggga tgtctgatcg gcgagcacct    4200
gcacgctggc atgagcaccc tgtttctggt gtacagcaac aagtgccaga ccccactggg    4260
catggcctct ggccacatcc gggacttcca gatcaccgcc tccggccagt acggccagtg    4320
ggcccccaag ctggccagac tgcactacag cggcagcatc aacgcctggt ccaccaaaga    4380
gcccttcagc tggatcaagg tggacctgct ggcccctatg atcatccacg gcattaagac    4440
ccagggcgcc aggcagaagt tcagcagcct gtacatcagc cagttcatca tcatgtacag    4500 cctgacggc aagaagtggc agacctaccg gggcaacagc accggcaccc tgatggtgtt    4560
cttcggcaat gtggacagca gcggcatcaa gcacaacatc ttcaaccccc ccatcattgc    4620
ccggtacatc cggctgcacc ccacccacta cagcattaga tccacactga gaatggaact    4680
gatgggctgc gacctgaact cctgcagcat gcctctgggc atggaaagca aggccatcag    4740
cgacgcccag atcacagcca gcagctactt caccaacatg ttcgccacct ggtccccctc    4800
caaggccagg ctgcacctgc agggccggtc caacgcctgg cggcctcagg tcaacaaccc    4860
caaagaatgg ctgcaggtgg actttcagaa aaccatgaag gtgaccggcg tgaccaccca    4920
gggcgtgaaa agcctgctga ccagcatgta cgtgaaagag tttctgatca gcagctctca    4980
ggatggccac cagtggaccc tgttcttca gaacggcaag gtgaaagtgt tccagggcaa    5040
ccaggactcc ttcaccccg tggtgaactc cctggacccc ccctgctga cccgctacct      5100 gagaatccac ccccagtctt gggtgcacca gatcgccctc aggatggaag tcctgggatg    5160
tgaggcccag gatctgtact gatgaggatc taggctcgac atgctttatt tgtgaaattt    5220
gtgatgctat tgctttattt gtaaccatta taagctgcaa taaacaagtt aacaacaaca    5280
attgcattca ttttatgttt caggttcagg gggaggtgtg ggaggttttt taaactcgag    5340
```

```
atccacggcc gcaggaaccc ctagtgatgg agttggccac tccctctctg cgcgctcgct   5400
cgctcactga ggccgggcga ccaaaggtcg cccgacgccc gggctttgcc cgggcggcct   5460
cagtgagcga gcgagcgcgc agctgcctgc aggggcgcct gatgcggtat tttctcctta   5520
cgcatctgtg cggtatttca caccgcatac gtcaaagcaa ccatagtacg cgccctgtag   5580
cggcgcatta agcgcggcgg gtgtggtggt tacgcgcagc gtgaccgcta cacttgccag   5640
cgccctagcg cccgctcctt tcgctttctt cccttccttt ctcgccacgt tcgccggctt   5700
tccccgtcaa gctctaaatc gggggctccc tttagggttc cgatttagtg ctttacggca   5760
cctcgacccc aaaaaacttg atttgggtga tggttcacgt agtgggccat cgccctgata   5820
gacggttttt cgccctttga cgttggagtc cacgttcttt aatagtggac tcttgttcca   5880
aactggaaca cactcaacc ctatctcggg ctattctttt gatttataag gattttgcc    5940
gatttcggcc tattggttaa aaatgagct gatttaacaa aaatttaacg cgaattttaa    6000
caaaatatta cgttacaa ttttatggtg cactctcagt acaatctgct ctgatgccgc     6060
atagttaagc cagccccgac acccgccaac acccgctgac gcgccctgac gggcttgtct   6120
gctcccggca tccgcttaca gacaagctgt gaccgtctcc gggagctgca tgtgtcagag   6180
gttttcaccg tcatcaccga aacgcgcgag acgaaagggc ctcgtgatac gcctattttt   6240
ataggttaat gtcatgataa taatggtttc ttagacgtca ggtggcactt ttcggggaaa   6300
tgtgcgcgga acccctattt gtttattttt ctaaatacat tcaaatatgt atccgctcat   6360
gagacaataa ccctgataaa tgcttcaata atattgaaaa aggaagagta tgagtattca   6420
acatttccgt gtcgccctta ttcccttttt tgcggcattt tgccttcctg tttttgctca   6480
cccagaaacg ctggtgaaag taaaagatgc tgaagatcag ttgggtgcac gagtgggtta   6540
catcgaactg gatctcaaca gcggtaagat ccttgagagt tttcgccccg aagaacgttt   6600
tccaatgatg agcactttta agttctgct atgtggcgcg gtattatccc gtattgacgc    6660
cgggcaagag caactcggtc gccgcataca ctattctcag aatgacttgg ttgagtactc   6720
accagtcaca gaaaagcatc ttacggatgg catgacagta agagaattat gcagtgctgc   6780
cataaccatg agtgataaca ctgcggccaa cttacttctg acaacgatcg gaggaccgaa   6840
ggagctaacc gcttttttgc acaacatggg ggatcatgta actcgccttg atcgttggga   6900
accggagctg aatgaagcca taccaaacga cgagcgtgac accacgatgc ctgtagcaat   6960
ggcaacaacg ttgcgcaaac tattaactgg cgaactactt actctagctt cccggcaaca   7020
attaatagac tggatggagg cggataaagt tgcaggacca cttctgcgct cggcccttcc   7080
ggctggctgg tttattgctg ataaatctgg agccggtgag cgtgggtctc gcggtatcat   7140
tgcagcactg gggccagatg gtaagccctc ccgtatcgta gttatctaca cgacggggag   7200
tcaggcaact atggatgaac gaaatagaca gatcgctgag ataggtgcct cactgattaa   7260
gcattggtaa ctgtcagacc aagtttactc atatatactt tagattgatt taaaacttca   7320
ttttaatttt aaaaggatct aggtgaagat ccttttttgat aatctcatga ccaaaatccc   7380
ttaacgtgag ttttcgttcc actgagcgtc agacccgta gaaaagatca aggatcttc     7440
ttgagatcct ttttttctgc gcgtaatctg ctgcttgcaa acaaaaaaac caccgctacc   7500
agcggtggtt tgtttgccgg atcaagagct accaactctt tttccgaagg taactggctt   7560
cagcagagcg cagataccaa atactgtcct tctagtgtag ccgtagttag gccaccactt   7620
caagaactct gtagcaccgc ctacatacct cgctctgcta atcctgttac cagtggctgc   7680
```

| | |
|---|---|
| tgccagtggc gataagtcgt gtcttaccgg gttggactca agacgatagt taccggataa | 7740 |
| ggcgcagcgg tcgggctgaa cggggggttc gtgcacacag cccagcttgg agcgaacgac | 7800 |
| ctacaccgaa ctgagatacc tacagcgtga gctatgagaa agcgccacgc ttcccgaagg | 7860 |
| gagaaaggcg gacaggtatc cggtaagcgg cagggtcgga acaggagagc gcacgaggga | 7920 |
| gcttccaggg ggaaacgcct ggtatcttta tagtcctgtc gggtttcgcc acctctgact | 7980 |
| tgagcgtcga ttttgtgat gctcgtcagg ggggcgagc ctatggaaaa acgccagcaa | 8040 |
| cgcggccttt ttacggttcc tggccttttg ctggccttttt gctcacatgt | 8090 |

```
<210> SEQ ID NO 23
<211> LENGTH: 7904
<212> TYPE: DNA
<213> ORGANISM: Artificial Sequence
<220> FEATURE:
<223> OTHER INFORMATION: pAAVss-3xSerpEnh-TTRe-TTRm-coFVIIIdeltaB-Synt-
      pA

<400> SEQUENCE: 23
```

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac taggggttcc tgcggccgcg ggggaggctg ctggtgaata ttaaccaagg | 180 |
| tcacccagt tatcggagga gcaaacaggg gctaagtcca ccgggggag ctgctggtga | 240 |
| atattaacca aggtcacccc agttatcgga ggagcaaaca ggggctaagt ccaccggggg | 300 |
| aggctgctgg tgaatattaa ccaaggtcac cccagttatc ggaggagcaa acaggggcta | 360 |
| agtccacggt acccactggg aggatgttga gtaagatgga aaactactga tgacccttgc | 420 |
| agagacagag tattaggaca tgtttgaaca ggggccgggc gatcagcagg tagctctaga | 480 |
| ggatccccgt ctgtctgcac atttcgtaga gcgagtgttc cgatactcta atctccctag | 540 |
| gcaaggttca tatttgtgta ggttacttat tctccttttg ttgactaagt caataatcag | 600 |
| aatcagcagg tttggagtca gcttggcagg gatcagcagc ctgggttgga aggagggggt | 660 |
| ataaaagccc cttcaccagg agaagccgtc acacagatcc acaagctcct gctagtatgc | 720 |
| agatcgagct gtccacctgc ttttttctgt gcctgctgcg gttctgcttc agcgccaccc | 780 |
| ggcggtacta cctgggcgcc gtggagctgt cctgggacta catgcagagc gacctgggcg | 840 |
| agctgccgt ggacgcccgg ttcccccca gagtgcccaa gagcttcccc ttcaacacca | 900 |
| gcgtggtgta caagaaaacc ctgttcgtgg agttcaccga ccacctgttc aatatcgcca | 960 |
| agcccaggcc ccctggatg ggcctgctgg gccccaccat ccaggccgag gtgtacgaca | 1020 |
| ccgtggtgat caccctgaag aacatggcca gccaccccgt gagcctgcac gccgtgggcg | 1080 |
| tgagctactg gaaggccagc gagggcgccg agtacgacga ccagaccagc cagcgggaga | 1140 |
| agaagatga aaggtgttc cctggcggca gccacaccta cgtgtggcag gtgctgaaag | 1200 |
| aaaacgccc catggcctcc gacccccgt gcctgaccta cagctacctg agccacgtgg | 1260 |
| acctggtgaa ggacctgaac agcggcctga tcggcgctct gctcgtctgc cgggagggca | 1320 |
| gcctggccaa agagaaaacc cagacccgc acaagttcat cctgctgttc gccgtgttcg | 1380 |
| acgagggcaa gagctggcac agcgagacaa agaacagcct gatgcaggac cgggacgccg | 1440 |
| cctctgccag agcctggccc aagatgcaca ccgtgaacgg ctacgtgaac agaagcctgc | 1500 |
| ccggcctgat tggctgccac cggaagagcg tgtactggca cgtgatcggc atgggcacca | 1560 |
| cacccgaggt gcacagcatc tttctggaag ggcacacctt tctggtccgg aaccaccggc | 1620 |

-continued

```
aggccagcct ggaaatcagc cctatcacct tcctgaccgc ccagacactg ctgatggacc    1680
tgggccagtt cctgctgttt tgccacatca gctctcacca gcacgacggc atggaagcct    1740
acgtgaaggt ggactcttgc cccgaggaac cccagctgcg gatgaagaac aacgaggaag    1800
ccgaggacta cgacgacgac ctgaccgaca gcgagatgga cgtggtgcgg ttcgacgacg    1860
acaacagccc cagcttcatc cagatcagaa gcgtggccaa gaagcacccc aagacctggg    1920
tgcactatat cgccgccgag gaagaggact gggactacgc cccctggtg ctggcccccg    1980 acgacagaag ctacaagagc cagtacctga caatggccc ccagcggatc ggccggaagt    2040
acaagaaagt gcggttcatg gcctacaccg acgagacatt caagacccgg gaggccatcc    2100
agcacgagag cggcatcctg ggccccctgc tgtacggcga agtgggcgac acactgctga    2160
tcatcttcaa gaaccaggct agccggccct acaacatcta cccccacggc atcaccgacg    2220
tgcggcccct gtacagcagg cggctgccca agggcgtgaa gcacctgaag gacttcccca    2280
tcctgcccgg cgagatcttc aagtacaagt ggaccgtgac cgtggaggac ggccccacca    2340
agagcgaccc cagatgcctg acccggtact acagcagctt cgtgaacatg aacgggacc    2400 tggcctccgg gctgatcgga cctctgctga tctgctacaa agaaagcgtg gaccagcggg    2460
gcaaccagat catgagcgac aagcggaacg tgatcctgtt cagcgtgttc gatgagaacc    2520
ggtcctggta tctgaccgag aacatccagc ggtttctgcc caaccctgcc ggcgtgcagc    2580
tggaagatcc cgagttccag gccagcaaca tcatgcactc catcaatggc tacgtgttcg    2640
actctctgca gctctccgtg tgtctgcacg aggtggccta ctggtacatc ctgagcatcg    2700
gcgcccagac cgacttcctg agcgtgttct tcagcggcta caccttcaag cacaagatgg    2760
tgtacgagga caccctgacc ctgttcctt tcagcggcga cagtgttc atgagcatgg    2820 aaaaccccgg cctgtggatt ctgggctgcc acaacagcca cttccggaac cggggcatga    2880
ccgccctgct gaaggtgtcc agctgcgaca agaacaccgg cgactactac gaggacagct    2940
acgaggatat cagcgcctac ctgctgtcca agaacaacgc catcgaaccc cggagcttca    3000
gccagaaccc cccgtgctg acgcgtcacc agcgggagat caccccggaca accctgcagt    3060 ccgaccagga agagatcgat tacgacgaca ccatcagcgt ggagatgaag aaagaggatt    3120
tcgatatcta cgacgaggac gagaaccaga gccccagaag cttccagaag aaaacccggc    3180
actacttcat tgccgccgtg gagaggctgt gggactacgg catgagttct agcccccacg    3240
tgctgcggaa ccgggcccag agcggcagcg tgccccagtt caagaaagtg gtgttccagg    3300
aattcacaga cggcagcttc acccagcctc tgtatagagg cgagctgaac gagcacctgg    3360
ggctgctggg gccctacatc agggccgaag tggaggacaa catcatggtg accttccgga    3420
atcaggccag cagaccctac tccttctaca gcagcctgat cagctacgaa gaggaccagc    3480
ggcagggcgc cgaaccccgg aagaacttcg tgaagcccaa cgaaaccaag acctacttct    3540
ggaaagtgca gcaccatatg gccccccacca aggacgagtt cgactgcaag gcctgggcct    3600
acttcagcga cgtggatctg aaaaggacg tgcactctgg actgattggc ccactcctgg    3660
tctgccacac taacaccctc aaccccgccc acggccgcca ggtgaccgtg caggaattcg    3720
ccctgttctt caccatcttc gacgagacaa agtcctggta cttcaccgag aatatggaac    3780
ggaactgcag agcccctgc aacatccaga tggaagatcc taccttcaaa gagaactacc    3840
ggttccacgc catcaacggc tacatcatgg acaccctgcc tggcctggtg atggcccagg    3900
accagagaat ccggtggtat ctgctgtcca tgggcagcaa cgagaatatc cacagcatcc    3960
acttcagcgg ccacgtgttc accgtgcgga agaaagaaga gtacaagatg gccctgtaca    4020
```

```
acctgtaccc cggcgtgttc gagacagtgg agatgctgcc cagcaaggcc ggcatctggc    4080
gggtggagtg tctgatcggc gagcacctgc acgctggcat gagcaccctg tttctggtgt    4140
acagcaacaa gtgccagacc ccactgggca tggcctctgg ccacatccgg gacttccaga    4200
tcaccgcctc cggccagtac ggccagtggg cccccaagct ggccagactg cactacagcg    4260
gcagcatcaa cgcctggtcc accaaagagc ccttcagctg gatcaaggtg gacctgctgg    4320
cccctatgat catccacggc attaagaccc agggcgccag gcagaagttc agcagcctgt    4380
acatcagcca gttcatcatc atgtacagcc tggacggcaa gaagtggcag acctaccggg    4440
gcaacagcac cggcaccctg atggtgttct tcggcaatgt ggacagcagc ggcatcaagc    4500
acaacatctt caacccccc atcattgccc ggtacatccg gctgcacccc acccactaca    4560
gcattagatc cacactgaga atggaactga tgggctgcga cctgaactcc tgcagcatgc    4620
ctctgggcat ggaaagcaag gccatcagcg acgcccagat cacagccagc agctacttca    4680
ccaacatgtt cgccacctgg tcccctcca aggccaggct gcacctgcag gccggtcca    4740
acgcctggcg gcctcaggtc aacaacccca agaatggct gcaggtggac tttcagaaaa    4800
ccatgaaggt gaccggcgtg accacccagg gcgtgaaaag cctgctgacc agcatgtacg    4860
tgaaagagtt tctgatcagc agctctcagg atggccacca gtggaccctg ttctttcaga    4920
acggcaaggt gaaagtgttc cagggcaacc aggactcctt cacccccgtg gtgaactccc    4980
tggacccccc cctgctgacc cgctacctga gaatccaccc ccagtcttgg gtgcaccaga    5040
tcgccctcag gatggaagtc ctgggatgtg aggcccagga tctgtactga tgaggatcca    5100
ataaaagatc tttatttca ttagatctgt gtgttggttt tttgtgtgct cgagatccac    5160
ggccgcagga ccccctagtg atggagttgg ccactccctc tctgcgcgct cgctcgctca    5220
ctgaggccgg gcgaccaaag gtcgcccgac gcccgggctt gcccgggcg gcctcagtga    5280
gcgagcgagc gcgcagctgc ctgcaggggc gcctgatgcg gtattttctc cttacgcatc    5340
tgtgcggtat ttcacaccgc atacgtcaaa gcaaccatag tacgcgccct gtagcggcgc    5400
attaagcgcg gcgggtgtgg tggttacgcg cagcgtgacc gctacacttg ccagcgccct    5460
agcgcccgct cctttcgctt tcttcccttc ctttctcgcc acgttcgccg ctttccccg    5520
tcaagctcta atcgggggc tcccttaagg gttccgattt agtgctttac ggcacctcga    5580
ccccaaaaaa cttgatttgg gtgatggttc acgtagtggg ccatcgccct gatagacggt    5640
ttttcgccct tgacgttgg agtccacgtt ctttaatagt ggactcttgt tccaaactgg    5700
aacaacactc aaccctatct cgggctattc ttttgattta agggatttt gccgatttc    5760
ggcctattgg ttaaaaaatg agctgattta caaaaattt aacgcgaatt ttaacaaaat    5820
attaacgttt acaattttat ggtgcactct cagtacaatc tgctctgatg ccgcatagtt    5880
aagccagccc cgacacccgc caacacccgc tgacgcgccc tgacgggctt gtctgctccc    5940
ggcatccgct tacagacaag ctgtgaccgt ctccgggagc tgcatgtgtc agaggttttc    6000
accgtcatca ccgaaacgcg cgagacgaaa gggcctcgtg atacgcctat ttttataggt    6060
taatgtcatg ataataatgg tttcttagac gtcaggtggc acttttcggg gaaatgtgcg    6120
cggaacccct atttgtttat ttttctaaat acattcaaat atgtatccgc tcatgagaca    6180
ataaccctga taaatgcttc aataatattg aaaaaggaag agtatgagta ttcaacattt    6240
ccgtgtcgcc cttattccct tttttgcggc attttgcctt cctgttttg ctcacccaga    6300
aacgctggtg aaagtaaaag atgctgaaga tcagttgggt gcacgagtgg gttacatcga    6360
```

```
actggatctc aacagcggta agatccttga gagttttcgc cccgaagaac gttttccaat    6420
gatgagcact tttaaagttc tgctatgtgg cgcggtatta tcccgtattg acgccgggca    6480
agagcaactc ggtcgccgca tacactattc tcagaatgac ttggttgagt actcaccagt    6540
cacagaaaag catcttacgg atggcatgac agtaagagaa ttatgcagtg ctgccataac    6600
catgagtgat aacactgcgg ccaacttact tctgacaacg atcggaggac cgaaggagct    6660
aaccgctttt ttgcacaaca tgggggatca tgtaactcgc cttgatcgtt gggaaccgga    6720
gctgaatgaa gccataccaa acgacgagcg tgacaccacg atgcctgtag caatggcaac    6780
aacgttgcgc aaactattaa ctggcgaact acttactcta gcttcccggc aacaattaat    6840
agactggatg gaggcggata agttgcagg accacttctg cgctcggccc ttccggctgg    6900
ctggtttatt gctgataaat ctggagccgg tgagcgtggg tctcgcggta tcattgcagc    6960
actggggcca gatggtaagc cctcccgtat cgtagttatc tacacgacgg ggagtcaggc    7020
aactatggat gaacgaaata gacagatcgc tgagataggt gcctcactga ttaagcattg    7080
gtaactgtca gaccaagttt actcatatat actttagatt gatttaaaac ttcattttta    7140
atttaaaagg atctaggtga agatcctttt tgataatctc atgaccaaaa tcccttaacg    7200
tgagttttcg ttccactgag cgtcagaccc cgtagaaaag atcaaggat cttcttgaga    7260 tcctttttttt ctgcgcgtaa tctgctgctt gcaaacaaaa aaaccaccgc taccagcggt    7320
ggtttgtttg ccggatcaag agctaccaac tcttttccg aaggtaactg gcttcagcag    7380
agcgcagata ccaaatactg tccttctagt gtagccgtag ttaggccacc acttcaagaa    7440
ctctgtagca ccgcctacat acctcgctct gctaatcctg ttaccagtgg ctgctgccag    7500
tggcgataag tcgtgtctta ccgggttgga ctcaagacga tagttaccgg ataaggcgca    7560
gcggtcgggc tgaacggggg gttcgtgcac acagcccagc ttggagcgaa cgacctacac    7620
cgaactgaga tacctacagc gtgagctatg agaaagcgcc acgcttcccg aagggagaaa    7680
ggcggacagg tatccggtaa gcggcagggt cggaacagga gagcgcacga gggagcttcc    7740
agggggaaac gcctggtatc tttatagtcc tgtcgggttt cgccacctct gacttgagcg    7800
tcgatttttg tgatgctcgt caggggggcg gagcctatgg aaaaacgcca gcaacgcggc    7860 cttttttacgg ttcctggcct tttgctggcc ttttgctcac atgt                    7904
```

<210> SEQ ID NO 24
<211> LENGTH: 7683
<212> TYPE: DNA
<213> ORGANISM: Artificial Sequence
<220> FEATURE:
<223> OTHER INFORMATION: pAAVss-TTRe-TTRm-coFVIIIdeltaB-Synt-pA

<400> SEQUENCE: 24

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccgta cccactggga ggatgttgag taagatggaa    180
aactactgat gacccttgca gagacagagt attaggacat gtttgaacag gggccgggcg    240
atcagcaggt agctctagag gatccccgtc tgtctgcaca tttcgtagag cgagtgttcc    300
gatactctaa tctccctagg caaggttcat atttgtgtag gttacttatt ctcctttttgt    360 tgactaagtc aataatcaga atcagcaggt ttggagtcag cttggcaggg atcagcagcc    420
tgggttggaa ggagggggta taaaagcccc ttcaccagga gaagccgtca cacagatcca    480
caagctcctg ctagtatgca gatcgagctg tccacctgct tttttctgtg cctgctgcgg    540
```

```
ttctgcttca gcgccacccg gcggtactac ctgggcgccg tggagctgtc ctgggactac    600
atgcagagcg acctgggcga gctgccgtg dacgcccggt tcccccccag agtgcccaag     660
agcttcccct tcaacaccag cgtggtgtac aagaaaaccc tgttcgtgga gttcaccgac   720
cacctgttca atatcgccaa gcccaggccc cctggatgg gctgctggg ccccaccatc      780 caggccgagg tgtacgacac cgtggtgatc accctgaaga acatggccag ccaccccgtg   840
agcctgcacg ccgtgggcgt gagctactgg aaggccagcg agggcgccga gtacgacgac   900
cagaccagcc agcgggagaa agaagatgac aaggtgttcc ctggcggcag ccacacctac   960
gtgtggcagg tgctgaaaga aaacggcccc atggcctccg accccctgtg cctgacctac   1020
agctacctga gccacgtgga cctggtgaag gacctgaaca gcggcctgat cggcgctctg   1080
ctcgtctgcc gggagggcag cctggccaaa gagaaaaccc agaccctgca caagttcatc   1140
ctgctgttcg ccgtgttcga cgagggcaag agctggcaca gcgagacaaa gaacagcctg   1200
atgcaggacc gggacgccgc ctctgccaga gcctggccca agatgcacac cgtgaacggc   1260
tacgtgaaca gaagcctgcc cggcctgatt ggctgccacc ggaagagcgt gtactggcac   1320
gtgatcggca tgggcaccac acccgaggtg cacagcatct ttctggaagg cacacctt    1380 ctggtccgga ccaccggca ggccagcctg gaaatcagcc ctatcacctt cctgaccgcc   1440
cagacactgc tgatggacct gggccagttc ctgctgtttt gccacatcag ctctcaccag   1500
cacgacggca tggaagccta cgtgaaggtg gactcttgcc ccgaggaacc ccagctgcgg   1560
atgaagaaca cgaggaagc cgaggactac gacgacgacc tgaccgacag cgagatggac   1620
gtggtgcggt tcgacgacga caacagcccc agcttcatcc agatcagaag cgtggccaag   1680
aagcacccca gacctgggt gcactatatc gccgccgagg aagaggactg ggactacgcc   1740
cccctggtgc tggcccccga cgacagaagc tacaagagcc agtacctgaa caatggcccc   1800
cagcggatcg gccggaagta caagaaagtg cggttcatgg cctacaccga cgagacattc   1860
aagacccggg aggccatcca gcacgagagc ggcatcctgg gcccctgct gtacggcgaa   1920 gtgggcgaca cactgctgat catcttcaag aaccaggcta gccggcccta caacatctac   1980
ccccacggca tcaccgacgt gcgggcccctg tacagcaggg gctgcccaa gggcgtgaag   2040 cacctgaagg acttcccat cctgcccggc gagatcttca gtacaagtg daccgtgacc   2100 gtggaggacg gccccaccaa gagcgacccc agatgcctga cccggtacta cagcagcttc   2160
gtgaacatgg aacgggacct ggcctccggg ctgatcggac ctctgctgat ctgctacaaa   2220
gaaagcgtgg accagcgggg caaccagatc atgagcgaca gcggaacgt gatcctgttc   2280 agcgtgttcg atgagaaccg gtcctggtat ctgaccgaga acatccagcg gttttctgccc   2340 aaccctgccg gcgtgcagct ggaagatccc gagttccagg ccagcaacat catgcactcc   2400
atcaatggct acgtgttcga ctctctgcag ctctccgtgt gtctgcacga ggtggcctac   2460
tggtacatcc tgagcatcgg cgcccagacc gacttcctga gcgtgttctt cagcggctac   2520
accttcaagc acaagatggt gtacgaggac accctgaccc tgttcccttt cagcggcgag   2580
acagtgttca tgagcatgga aaaccccggc ctgtggatt tgggctgcca caacagcgac   2640
ttccggaacc ggggcatgac cgccctgctg aaggtgccaa gctgcgacaa gaacaccggc   2700
gactactacg aggacagcta cgaggatatc agcgcctacc tgctgtccaa gaacaacgcc   2760
atcgaacccc ggagcttcag ccagaacccc cccgtgctga cgcgtcacca gcgggagatc   2820
acccggacaa ccctgcagtc cgaccaggaa gagatcgatt acgacgacac catcagcgtg   2880
```

```
gagatgaaga aagaggattt cgatatctac gacgaggacg agaaccagag ccccagaagc    2940
ttccagaaga aaacccggca ctacttcatt gccgccgtgg agaggctgtg ggactacggc    3000
atgagttcta gcccccacgt gctgcggaac cgggcccaga gcggcagcgt gccccagttc    3060
aagaaagtgg tgttccagga attcacagac ggcagcttca cccagcctct gtatagaggc    3120
gagctgaacg agcacctggg gctgctgggg ccctacatca gggccgaagt ggaggacaac    3180
atcatggtga ccttccggaa tcaggccagc agaccctact ccttctacag cagcctgatc    3240
agctacgaag aggaccagcg gcagggcgcc gaaccccgga agaacttcgt gaagcccaac    3300
gaaaccaaga cctacttctg gaaagtgcag caccacatgg cccccaccaa ggacgagttc    3360
gactgcaagg cctgggccta cttcagcgac gtggatctgg aaaaggacgt gcactctgga    3420
ctgattggcc cactcctggt ctgccacact aacaccctca accccgccca cggccgccag    3480
gtgaccgtgc aggaattcgc cctgttcttc accatcttcg acgagacaaa gtcctggtac    3540
ttcaccgaga atatggaacg gaactgcaga gcccctgca acatccagat ggaagatcct    3600
accttcaaag agaactaccg gttccacgcc atcaacggct acatcatgga cacactgcct    3660
ggcctggtga tggcccagga ccagagaatc cggtggtatc tgctgtccat gggcagcaac    3720
gagaatatcc acagcatcca cttcagcggc cacgtgttca ccgtgcggaa gaagaagag    3780 tacaagatgg ccctgtacaa cctgtacccc ggcgtgttcg agacagtgga tgctgccc    3840 agcaaggccg gcatctggcg ggtggagtgt ctgatcggcg agcacctgca cgctggcatg    3900
agcaccctgt ttctggtgta cagcaacaag tgccagaccc cactgggcat ggcctctggc    3960
cacatccggg acttccagat caccgcctcc ggccagtacg ccagtgggc ccccaagctg    4020 gccagactgc actacagcgg cagcatcaac gcctggtcca ccaaagagcc cttcagctgg    4080
atcaaggtgg acctgctggc ccctatgatc atccacggca ttaagaccca gggcgccagg    4140
cagaagttca gcagcctgta catcagccag ttcatcatca tgtacagcct ggacggcaag    4200
aagtggcaga cctaccgggg caacagcacc ggcaccctga tggtgttctt cggcaatgtg    4260
gacagcagcg gcatcaagca caacatcttc aaccccccca tcattgcccg gtacatccgg    4320
ctgcacccca cccactacag cattagatcc acactgagaa tggaactgat gggctgcgac    4380
ctgaactcct gcagcatgcc tctgggcatg gaaagcaagg ccatcagcga cgcccagatc    4440
acagccagca gctacttcac caacatgttc gccacctggt cccctccaa ggccaggctg    4500 cacctgcagg gccggtccaa cgcctggcgg cctcaggtca acaaccccaa agaatggctg    4560
caggtggact tcagaaaaac catgaaggtg accggcgtga ccaccagggg cgtgaaaagc    4620
ctgctgacca gcatgtacgt gaaagagttt ctgatcagca gctctcagga tggccaccag    4680 tggacctgt tctttcagaa cggcaaggtg aaagtgttcc agggcaacca ggactccttc    4740
acccccgtgg tgaactccct ggacccccc ctgctgaccc gctacctgag aatccacccc    4800
cagtcttggg tgcaccagat cgccctcagg atggaagtcc tgggatgtga ggcccaggat    4860
ctgtactgat gaggatccaa taaaagatct ttatttcat tagatctgtg tgttggtttt    4920
ttgtgtgctc gagatccacg gccgcaggaa ccctagtga tggagttggc cactccctct    4980
ctgcgcgctc gctcgctcac tgaggccggg cgaccaaagg tcgcccgacg cccgggcttt    5040
gcccgggcgg cctcagtgag cgagcgagcg cgcagctgcc tgcaggggcg cctgatgcgg    5100 tatttttctcc ttacgcatct gtgcggtatt tcacaccgca tacgtcaaag caaccatagt    5160
acgcgccctg tagcggcgca ttaagcgcgg cgggtgtggt ggttacgcgc agcgtgaccg    5220
ctacacttgc cagcgcccta gcgcccgctc ctttcgcttt cttcccttcc tttctcgcca    5280
```

```
cgttcgccgg ctttccccgt caagctctaa atcgggggct ccctttaggg ttccgattta    5340
gtgctttacg gcacctcgac cccaaaaaac ttgatttggg tgatggttca cgtagtgggc    5400
catcgccctg atagacggtt tttcgccctt tgacgttgga gtccacgttc tttaatagtg    5460
gactcttgtt ccaaactgga acaacactca accctatctc gggctattct tttgatttat    5520
aagggatttt gccgatttcg gcctattggt taaaaatga gctgatttaa caaaaattta     5580
acgcgaattt taacaaaata ttaacgttta caattttatg gtgcactctc agtcaatct    5640
gctctgatgc cgcatagtta agccagcccc gacacccgcc aacacccgct gacgcgccct    5700
gacgggcttg tctgctcccg gcatccgctt acagacaagc tgtgaccgtc tccgggagct    5760
gcatgtgtca gaggttttca ccgtcatcac cgaaacgcgc gagacgaaag gcctcgtga    5820
tacgcctatt tttataggtt aatgtcatga taataatggt tcttagacg tcaggtggca     5880
cttttcgggg aaatgtgcgc ggaaccccta tttgtttatt tttctaaata cattcaaata    5940
tgtatccgct catgagacaa taaccctgat aaatgcttca ataatattga aaaggaaga    6000
gtatgagtat tcaacatttc cgtgtcgccc ttattcccct ttttgcggca ttttgccttc    6060
ctgttttgc tcacccagaa acgctggtga agtaaaaga tgctgaagat cagttgggtg    6120
cacgagtggg ttacatcgaa ctggatctca acagcggtaa gatccttgag agttttcgcc    6180
ccgaagaacg ttttccaatg atgagcactt taaagttct gctatgtggc gcggtattat     6240
cccgtattga cgccgggcaa gagcaactcg gtcgccgcat acactattct cagaatgact    6300
tggttgagta ctcaccagtc acagaaaagc atcttacgga tggcatgaca gtaagagaat    6360
tatgcagtgc tgccataacc atgagtgata acactgcggc caacttactt ctgacaacga    6420
tcggaggacc gaaggagcta accgcttttt tgcacaacat ggggggatcat gtaactcgcc    6480
ttgatcgttg ggaaccggag ctgaatgaag ccataccaaa cgacgagcgt gacaccacga    6540
tgcctgtagc aatggcaaca acgttgcgca aactattaac tggcgaacta cttactctag    6600
cttcccggca acaattaata gactggatgg aggcggataa agttgcagga ccacttctgc    6660
gctcggccct tccggctggc tggtttattg ctgataaatc tggagccggt gagcgtgggt    6720
ctcgcggtat cattgcagca ctggggccag atggtaagcc ctcccgtatc gtagttatct    6780
acacgacggg gagtcaggca actatggatg aacgaaatag acagatcgct gagataggtg    6840
cctcactgat taagcattgg taactgtcag accaagttta ctcatatata ctttagattg    6900
atttaaaact tcatttttaa tttaaaagga tctaggtgaa gatcctttt gataatctca    6960
tgaccaaaat cccttaacgt gagttttcgt tccactgagc gtcagacccc gtagaaaaga    7020
tcaaaggatc ttcttgagat cctttttttc tgcgcgtaat ctgctgcttg caaacaaaaa    7080
aaccaccgct accagcggtg gtttgtttgc cggatcaaga gctaccaact cttttttccga    7140
aggtaactgg cttcagcaga gcgcagatac caaatactgt ccttctagtg tagccgtagt    7200
taggccacca cttcaagaac tctgtagcac cgcctacata cctcgctctg ctaatcctgt    7260
taccagtggc tgctgccagt ggcgataagt cgtgtcttac cgggttggac tcaagacgat    7320
agttaccgga taaggcgcag cggtcgggct gaacggggggg ttcgtgcaca cagcccagct    7380
tggagcgaac gacctacacc gaactgagat acctacagcg tgagctatga gaaagcgcca    7440
cgcttcccga agggagaaag gcggacaggt atccggtaag cggcagggtc ggaacaggag    7500
agcgcacgag ggagcttcca gggggaaacg cctggtatct ttatagtcct gtcgggtttc    7560
gccacctctg acttgagcgt cgatttttgt gatgctcgtc aggggggcgg agcctatgga    7620
```

```
aaaacgccag caacgcggcc ttttttacggt tcctggcctt tgctggcct tttgctcaca    7680 tgt                                                                 7683
```

<210> SEQ ID NO 25
<211> LENGTH: 6207
<212> TYPE: DNA
<213> ORGANISM: Artificial Sequence
<220> FEATURE:
<223> OTHER INFORMATION: pAAVsc-3xSerpEnh-TTREnh-TTRm-MVM-co-FIX-R338L-
      Synt-pA

<400> SEQUENCE: 25

```
agctggcgta atagcgaaga ggcccgcacc gatcgccctt cccaacagtt gcgcagcctg      60
aatggcgaat ggcgattccg ttgcaatggc tggcggtaat attgttctgg atattaccag     120
caaggccgat agtttgagtt cttctactca ggcaagtgat gttattacta atcaaagaag     180
tattgcgaca acggttaatt tgcgtgatgg acagactctt ttactcggtg gcctcactga     240
ttataaaaac acttctcagg attctggcgt accgttcctg tctaaaatcc ctttaatcgg     300
cctcctgttt agctcccgct ctgattctaa cgaggaaagc acgttatacg tgctcgtcaa     360
agcaaccata gtacgcgccc gtagcggcg cattaagcgc ggcgggtgtg gtggttacgc      420
gcagcgtgac cgctacactt gccagcgccc tagcgcccgc tcctttcgct ttcttccctt     480
cctttctcgc cacgttcgcc ggctttcccc gtcaagctct aaatcggggg ctccctttag     540
ggttccgatt tagtgcttta cggcacctcg accccaaaaa acttgattag ggtgatggtt     600
cacgtagtgg gccatcgccc tgatagacgg ttttttcgcc ctttgacgttg gagtccacgt     660 tctttaatag tggactcttg ttccaaactg gaacaacact caaccctatc tcggtctatt     720
cttttgattt ataagggatt ttgccgattt cggcctattg gttaaaaaat gagctgattt     780
aacaaaaatt taacgcgaac tttaacaaaa tattaacgtt tacaatttaa atatttgctt     840
atacaatctt cctgtttttg gggcttttct gattatcaac cggggtacat atgattgaca     900
tgctagtttt acgattaccg ttcatcgccc tgcgcgctcg ctcgctcact gaggccgccc     960
gggcaaagcc cgggcgtcgg gcgaccttg gtcgcccggc ctcagtgagc gagcgagcgc    1020
gcagagaggg agtggaattc acgcgtggat ctgaattcaa ttcacgcgtg gtacggccgc    1080
gggggggagg ctgctggtga atattaacca aggtcacccc agttatcgga ggagcaaaca    1140
ggggctaagt ccaccggggg aggctgctgg tgaatattaa ccaaggtcac ccagttatc    1200 ggaggagcaa acaggggcta agtccaccgg gggaggctgc tggtgaatat taaccaaggt    1260
caccccagtt atcggaggag caaacagggg ctaagtccac ggtacccact gggaggatgt    1320
tgagtaagat ggaaaactac tgatgaccct gcagagaca gagtattagg acatgtttga    1380
acaggggccg ggcgatcagc aggtagctct agaggatccc cgtctgtctg cacatttcgt    1440
agagcgagtg ttccgatact ctaatctccc taggcaaggt tcatatttgt gtaggttact    1500
tattctcctt tgttgactaa gtcaataat cagaatcagc aggtttggag tcagcttggc    1560
agggatcagc agcctgggtt ggaaggaggg ggtataaaag cccccttcacc aggagaagcc    1620 gtcacacaga tccacaagct cctggctaga aagaggtaag ggtttaaggg atggttggtt    1680
ggtggggtat taatgtttaa ttacctggag cacctgcctg aaatcacttt ttttcaggtt    1740
gggctagccc accatgcagc gcgtgaacat gatcatggcc gagagccccg gcctgatcac    1800
catctgcctg ctgggctacc tgctgagcgc cgagtgcacc gtgttcctgg accacgagaa    1860
cgccaacaag atcctgaacc gccccaagcg ctacaacagc ggcaagctgg aggagttcgt    1920
```

```
gcagggcaac ctggagcgcg agtgcatgga ggagaagtgc agcttcgagg aggcccgcga    1980
ggtgttcgag aacaccgagc gcaccaccga gttctggaag cagtacgtgg acggcgacca    2040
gtgcgagagc aaccctgcc tgaacggcgg cagctgcaag gacgacatca acagctacga    2100
gtgctggtgc cccttcggct tcagggcaa gaactgcgag ctggacgtga cctgcaacat    2160
caagaacggc cgctgcgagc agttctgcaa gaacagcgcc gacaacaagg tggtgtgcag    2220
ctgcaccgag ggctaccgcc tggccgaaa ccagaagagc tgcgagcccg ccgtgccctt    2280
cccctgcggc cgcgtgagcg tgagccagac cagcaagctg acccgcgccg aggccgtgtt    2340
ccccgacgtg gactacgtga acagcaccga ggccgagacc atcctggaca acatcaccca    2400
gagcacccag agcttcaacg acttcacccg cgtggtgggc ggcgaggacg ccaagcccgg    2460
ccagttcccc tggcaggtgg tgctgaacgg caaggtggac gccttctgcg gcggcagcat    2520
cgtgaacgag aagtggatcg tgaccgccgc ccactgcgtg gagaccggcg tgaagatcac    2580
cgtggtggcc ggcgagcaca acatcgagga gaccgagcac accgagcaga gcgcaacgt    2640 gatccgcatc atcccccacc acaactacaa cgccgccatc aacaagtaca accacgacat    2700
cgccctgctg gagctggacg agcccctggt gctgaacagc tacgtgaccc ccatctgcat    2760
cgccgacaag gagtacacca acatcttcct gaagttcggc agcggctacg tgagcggctg    2820
gggccgcgtg ttccacaagg gccgcagcgc cctggtgctg cagtacctgc gcgtgcccct    2880
ggtggaccgc gccacctgcc tgctgagcac caagttcacc atctacaaca catgttctg    2940 cgccggcttc cacgagggcg gccgcgacag ctgccagggc gacagcggcg gccccacgt    3000 gaccgaggtg gagggcacca gcttcctgac cggcatcatc agctggggcg aggagtgcgc    3060
catgaagggc aagtacggca tctacaccaa ggtgagccgc tacgtgaact ggatcaagga    3120
gaagaccaag ctgacctaat gaaagatgga tttccaaggt taattcattg gaattgaaaa    3180
ttaacagccc cccccccccc ccccctgcag atctaataaa agatctttat tttcattaga    3240
tctgtgtgtt ggttttttgt gtgccggtgg atctcgatag caggcatgct ggggagagat    3300
cgatctgagg aaccctagt gatggagttg gccactccct ctctgcgcgc tcgctcgctc    3360
actgaggccg cccgggcaaa gcccgggcgt cgggcgacct ttggtcgccc ggcctcagtg    3420
agcgagcgag cgcgcagaga gggagtggcc aaccccccc cccccccccc ccggcgattc    3480
tcttgtttgc tccagactct caggcaatga cctgatagcc tttgtagaga cctctcaaaa    3540
atagctaccc tctccggcat gaatttatca gctagaacgg ttgaatatca tattgatggt    3600
gatttgactg tctccggcct ttctcacccg tttgaatctt tacctacaca ttactcaggc    3660
attgcattta aaatatatga gggttctaaa aattttatc cttgcgttga ataaaggct    3720 tctcccgcaa aagtattaca gggtcataat gttttggta caaccgattt agctttatgc    3780
tctgaggctt tattgcttaa ttttgctaat tctttgcctt gcctgtatga tttattggat    3840
gttggaatcg cctgatgcgg tatttttctcc ttacgcatct gtgcggtatt tcacaccgca    3900
tatggtgcac tctcagtaca atctgctctg atgccgcata gttatatggt gcactctcag    3960
tacaatctgc tctgatgccg catagttaag ccagccccga cacccgccaa cacagccagc    4020
cccgacaccc gccaacaccc gctgacgcgc cctgacgggc ttgtctgctc ccggcatccg    4080
cttacagaca agctgtgacc gtctccggga gctgcatgtg tcagaggttt tcaccgtcat    4140
caccgaaacg cgcgagacga aagggcctcg tgatacgcct atttttatag gttaatgtca    4200
tgataataat ggtttcttag acgtcaggtg gcacttttcg gggaaatgtg cgcggaaccc    4260
ctatttgttt attttctaa atacattcaa atatgtatcc gctcatgaga caataaccct    4320
```

```
gataaatgct caataatatt gaaaaaggaa gagtatgagt attcaacatt tccgtgtcgc    4380
ccttattccc tttttgcgg cattttgcct tcctgttttt gctcacccag aaacgctggt    4440
gaaagtaaaa gatgctgaag atcagttggg tgcacgagtg ggttacatcg aactggatct    4500
caacagcggt aagatccttg agagttttcg ccccgaagaa cgttttccaa tgatgagcac    4560
ttttaaagtt ctgctatgtg gcgcggtatt atcccgtatt gacgccgggc aagagcaact    4620
cggtcgccgc atacactatt ctcagaatga cttggttgag tactcaccag tcacagaaaa    4680
gcatcttacg gatggcatga cagtaagaga attatgcagt gctgccataa ccatgagtga    4740
taacactgcg gccaacttac ttctgacaac gatcggagga ccgaaggagc taaccgcttt    4800
tttgcacaac atgggggatc atgtaactcg ccttgatcgt tgggaaccgg agctgaatga    4860
agccatacca aacgacgagc gtgacaccac gatgcctgta gcaatggcaa caacgttgcg    4920
caaactatta actggcgaac tacttactct agcttcccgg caacaattaa tagactggat    4980
ggaggcggat aaagttgcag gaccacttct gcgctcggcc cttccggctg gctggtttat    5040
tgctgataaa tctggagccg gtgagcgtgg gtctcgcggt atcattgcag cactggggcc    5100
agatggtaag ccctcccgta tcgtagttat ctacacgacg gggagtcagg caactatgga    5160
tgaacgaaat agacagatcg ctgagatagg tgcctcactg attaagcatt ggtaactgtc    5220
agaccaagtt tactcatata ctttagat tgatttaaaa cttcattttt aatttaaaag    5280
gatctaggtg aagatccttt tgataatct catgaccaaa atcccttaac gtgagttttc    5340
gttccactga gcgtcagacc ccgtagaaaa gatcaaagga tcttcttgag atcctttttt    5400
tctgcgcgta atctgctgct tgcaaacaaa aaaaccaccg ctaccagcgg tggtttgttt    5460
gccggatcaa gagctaccaa ctctttttcc gaaggtaact ggcttcagca gagcgcagat    5520
accaaatact gtccttctag tgtagccgta gttaggccac cacttcaaga actctgtagc    5580
accgcctaca tacctcgctc tgctaatcct gttaccagtg gctgctgcca gtggcgataa    5640
gtcgtgtctt accgggttgg actcaagacg atagttaccg gataaggcgc agcggtcggg    5700
ctgaacgggg ggttcgtgca cacagcccag cttggagcga acgacctaca ccgaactgag    5760
atacctacag cgtgagctat gagaaagcgc cacgcttccc gaagggagaa aggcggacag    5820
gtatccggta agcggcaggg tcggaacagg agagcgcacg agggagcttc caggggggaaa    5880 cgcctggtat ctttatagtc ctgtcgggtt tcgccacctc tgacttgagc gtcgattttt    5940
gtgatgctcg tcaggggggc ggagcctatg gaaaaacgcc agcaacgcgg cctttttacg    6000
gttcctggcc ttttgctggc cttttgctca catgttcttt cctgcgttat cccctgattc    6060
tgtggataac cgtattaccg cctttgagtg agctgatacc gctcgccgca gccgaacgac    6120
cgagcgcagc gagtcagtga gcgaggaagc ggaagagcgc ccaatacgca aaccgcctct    6180
ccccgcgcgt tggccgattc attaatg    6207
```

<210> SEQ ID NO 26
<211> LENGTH: 371
<212> TYPE: DNA
<213> ORGANISM: Artificial Sequence
<220> FEATURE:
<223> OTHER INFORMATION: Flank-3xSERP-Flank-TTRe

<400> SEQUENCE: 26

```
aattcacgcg tggatctgaa ttcaattcac gcgtggtacg gccgcggggg ggaggctgct      60
ggtgaatatt aaccaaggtc accccagtta tcggaggagc aaacaggggc taagtccacc     120
```

| | |
|---|---|
| gggggaggct gctggtgaat attaaccaag gtcaccccag ttatcggagg agcaaacagg | 180 |
| ggctaagtcc accggggag gctgctggtg aatattaacc aaggtcaccc cagttatcgg | 240 |
| aggagcaaac aggggctaag tccacggtac ccactgggag gatgttgagt aagatggaaa | 300 |
| actactgatg acccttgcag agacagagta ttaggacatg tttgaacagg ggccgggcga | 360 |
| tcagcaggta g | 371 |

<210> SEQ ID NO 27
<211> LENGTH: 386
<212> TYPE: DNA
<213> ORGANISM: Artificial Sequence
<220> FEATURE:
<223> OTHER INFORMATION: Flank-3xSERP-Flank-TTRe-Flank

<400> SEQUENCE: 27

| | |
|---|---|
| aattcacgcg tggatctgaa ttcaattcac gcgtggtacg gccgcggggg ggaggctgct | 60 |
| ggtgaatatt aaccaaggtc accccagtta tcggaggagc aaacaggggc taagtccacc | 120 |
| gggggaggct gctggtgaat attaaccaag gtcaccccag ttatcggagg agcaaacagg | 180 |
| ggctaagtcc accggggag gctgctggtg aatattaacc aaggtcaccc cagttatcgg | 240 |
| aggagcaaac aggggctaag tccacggtac ccactgggag gatgttgagt aagatggaaa | 300 |
| actactgatg acccttgcag agacagagta ttaggacatg tttgaacagg ggccgggcga | 360 |
| tcagcaggta gctctagagg atcccc | 386 |

<210> SEQ ID NO 28
<211> LENGTH: 588
<212> TYPE: DNA
<213> ORGANISM: Artificial Sequence
<220> FEATURE:
<223> OTHER INFORMATION: Flank-3xSERP-Flank-TTRe-Flank-TTRm

<400> SEQUENCE: 28

| | |
|---|---|
| aattcacgcg tggatctgaa ttcaattcac gcgtggtacg gccgcggggg ggaggctgct | 60 |
| ggtgaatatt aaccaaggtc accccagtta tcggaggagc aaacaggggc taagtccacc | 120 |
| gggggaggct gctggtgaat attaaccaag gtcaccccag ttatcggagg agcaaacagg | 180 |
| ggctaagtcc accggggag gctgctggtg aatattaacc aaggtcaccc cagttatcgg | 240 |
| aggagcaaac aggggctaag tccacggtac ccactgggag gatgttgagt aagatggaaa | 300 |
| actactgatg acccttgcag agacagagta ttaggacatg tttgaacagg ggccgggcga | 360 |
| tcagcaggta gctctagagg atcccgtct gtctgcacat ttcgtagagc gagtgttccg | 420 |
| atactctaat ctccctaggc aaggttcata tttgtgtagg ttacttattc tccttttgtt | 480 |
| gactaagtca ataatcagaa tcagcaggtt tggagtcagc ttggcaggga tcagcagcct | 540 |
| gggttggaag gaggggtat aaaagcccct tcaccaggag aagccgtc | 588 |

<210> SEQ ID NO 29
<211> LENGTH: 615
<212> TYPE: DNA
<213> ORGANISM: Artificial Sequence
<220> FEATURE:
<223> OTHER INFORMATION: Flank-3xSERP-Flank-TTRe-Flank-TTRm-Flank

<400> SEQUENCE: 29

| | |
|---|---|
| aattcacgcg tggatctgaa ttcaattcac gcgtggtacg gccgcggggg ggaggctgct | 60 |
| ggtgaatatt aaccaaggtc accccagtta tcggaggagc aaacaggggc taagtccacc | 120 |
| gggggaggct gctggtgaat attaaccaag gtcaccccag ttatcggagg agcaaacagg | 180 |

```
ggctaagtcc accggggggag gctgctggtg aatattaacc aaggtcaccc cagttatcgg      240
aggagcaaac aggggctaag tccacggtac ccactgggag gatgttgagt aagatggaaa      300
actactgatg acccttgcag agacagagta ttaggacatg tttgaacagg ggccgggcga      360
tcagcaggta gctctagagg atccccgtct gtctgcacat ttcgtagagc gagtgttccg      420
atactctaat ctccctaggc aaggttcata tttgtgtagg ttacttattc tccttttgtt      480
gactaagtca ataatcagaa tcagcaggtt tggagtcagc ttggcaggga tcagcagcct      540
gggttggaag gaggggtat aaaagcccct tcaccaggag aagccgtcac acagatccac       600
aagctcctgg ctaga                                                       615
```

<210> SEQ ID NO 30
<211> LENGTH: 707
<212> TYPE: DNA
<213> ORGANISM: Artificial Sequence
<220> FEATURE:
<223> OTHER INFORMATION: Flank-3xSERP-Flank-TTRe-Flank-TTRm-Flank-MVM

<400> SEQUENCE: 30

```
aattcacgcg tggatctgaa ttcaattcac gcgtggtacg gccgcggggg ggaggctgct       60
ggtgaatatt aaccaaggtc accccagtta tcggaggagc aaacaggggc taagtccacc      120
gggggaggct gctggtgaat attaaccaag gtcaccccag ttatcggagg agcaaacagg      180
ggctaagtcc accggggggag gctgctggtg aatattaacc aaggtcaccc cagttatcgg      240
aggagcaaac aggggctaag tccacggtac ccactgggag gatgttgagt aagatggaaa      300
actactgatg acccttgcag agacagagta ttaggacatg tttgaacagg ggccgggcga      360
tcagcaggta gctctagagg atccccgtct gtctgcacat ttcgtagagc gagtgttccg      420
atactctaat ctccctaggc aaggttcata tttgtgtagg ttacttattc tccttttgtt      480
gactaagtca ataatcagaa tcagcaggtt tggagtcagc ttggcaggga tcagcagcct      540
gggttggaag gaggggtat aaaagcccct tcaccaggag aagccgtcac acagatccac       600
aagctcctgg ctagaaagag gtaagggttt aagggatggt tggttggtgg ggtattaatg      660
tttaattacc tggagcacct gcctgaaatc acttttttc aggttgg                    707
```

<210> SEQ ID NO 31
<211> LENGTH: 718
<212> TYPE: DNA
<213> ORGANISM: Artificial Sequence
<220> FEATURE:
<223> OTHER INFORMATION: Flank-3xSERP-Flank-TTRe-Flank-TTRm-Flank-MVM-
      Flank

<400> SEQUENCE: 31

```
aattcacgcg tggatctgaa ttcaattcac gcgtggtacg gccgcggggg ggaggctgct       60
ggtgaatatt aaccaaggtc accccagtta tcggaggagc aaacaggggc taagtccacc      120
gggggaggct gctggtgaat attaaccaag gtcaccccag ttatcggagg agcaaacagg      180
ggctaagtcc accggggggag gctgctggtg aatattaacc aaggtcaccc cagttatcgg      240
aggagcaaac aggggctaag tccacggtac ccactgggag gatgttgagt aagatggaaa      300
actactgatg acccttgcag agacagagta ttaggacatg tttgaacagg ggccgggcga      360
tcagcaggta gctctagagg atccccgtct gtctgcacat ttcgtagagc gagtgttccg      420
atactctaat ctccctaggc aaggttcata tttgtgtagg ttacttattc tccttttgtt      480
gactaagtca ataatcagaa tcagcaggtt tggagtcagc ttggcaggga tcagcagcct      540
```

```
gggttggaag gagggggtat aaaagcccct tcaccaggag aagccgtcac acagatccac    600
aagctcctgg ctagaaagag gtaagggttt aagggatggt tggttggtgg ggtattaatg    660
tttaattacc tggagcacct gcctgaaatc acttttttc aggttgggct agcccacc      718
```

<210> SEQ ID NO 32
<211> LENGTH: 2107
<212> TYPE: DNA
<213> ORGANISM: Artificial Sequence
<220> FEATURE:
<223> OTHER INFORMATION: Flank-3xSERP-Flank-TTRe-Flank-TTRm-Flank-MVM-
      Flank-co-FIX-R338L

<400> SEQUENCE: 32

```
aattcacgcg tggatctgaa ttcaattcac gcgtggtacg gccgcggggg ggaggctgct     60
ggtgaatatt aaccaaggtc accccagtta tcggaggagc aaacaggggc taagtccacc    120
gggggaggct gctggtgaat attaaccaag gtcaccccag ttatcggagg agcaaacagg    180
ggctaagtcc accggggag gctgctggtg aatattaacc aaggtcaccc cagttatcgg    240
aggagcaaac aggggctaag tccacggtac ccactgggag gatgttgagt aagatggaaa    300
actactgatg acccttgcag agacagagta ttaggacatg tttgaacagg ggccgggcga    360
tcagcaggta gctctagagg atccccgtct gtctgcacat tcgtagagc gagtgttccg     420 atactctaat ctccctaggc aaggttcata tttgtgtagg ttacttattc tccttttgtt    480
gactaagtca ataatcagaa tcagcaggtt tggagtcagc ttggcaggga tcagcagcct    540
gggttggaag gagggggtat aaaagcccct tcaccaggag aagccgtcac acagatccac    600
aagctcctgg ctagaaagag gtaagggttt aagggatggt tggttggtgg ggtattaatg    660
tttaattacc tggagcacct gcctgaaatc acttttttc aggttgggct agcccaccat    720
gcagcgcgtg aacatgatca tggccgagag ccccggcctg atcaccatct gcctgctggg    780
ctacctgctg agcgccgagt gcaccgtgtt cctggaccac gagaacgcca acaagatcct    840
gaaccgcccc aagcgctaca cagcggcaa gctggaggag ttcgtgcagg gcaacctgga    900
gcgcgagtgc atggaggaga agtgcagctt cgaggaggcc cgcgaggtgt tcgagaacac    960
cgagcgcacc accgagttct ggaagcagta cgtggacggc gaccagtgcg agagcaaccc   1020
ctgcctgaac ggcggcagct gcaaggacga catcaacagc tacgagtgct ggtgcccctt   1080
cggcttcgag ggcaagaact gcgagctgga cgtgacctgc aacatcaaga acggccgctg   1140
cgagcagttc tgcaagaaca cgccgacaa caaggtggtg tgcagctgca ccgagggcta   1200
ccgcctggcc gagaaccaga gagctgcga gcccgccgtg ccctcccct cggccgcgt    1260 gagcgtgagc cagaccagca agctgacccg cgccgaggcc gtgttccccg acgtggacta   1320
cgtgaacagc accgaggccg agaccatcct ggacaacatc acccagagca cccagagctt   1380
caacgacttc acccgcgtgg tgggcggcga ggacgccaag cccggccagt tcccctggca   1440
ggtggtgctg aacggcaagg tggacgcctt ctgcggcggc agcatcgtga acgagaagtg   1500
gatcgtgacc gccgcccact gcgtggagac cggcgtgaag atcaccgtgg tggccggcga   1560
gcacaacatc gaggagaccg agcacaccga gcagaagcgc aacgtgatcc gcatcatccc   1620
ccaccacaac tacaacgccg ccatcaacaa gtacaaccac gacatcgccc tgctggagct   1680
ggacgagccc ctggtgctga acagctacgt gaccccatc tgcatcgccg acaaggagta   1740
caccaacatc ttcctgaagt tcggcagcgg ctacgtgagc ggctgggggc gcgtgttcca   1800
caagggccgc agcgccctgg tgctgcagta cctgcgcgtg cccctggtgg accgcgccac   1860
```

```
ctgcctgctg agcaccaagt tcaccatcta caacaacatg ttctgcgccg gcttccacga    1920
gggcggccgc gacagctgcc agggcgacag cggcggcccc cacgtgaccg aggtggaggg    1980
caccagcttc ctgaccggca tcatcagctg gggcgaggag tgcgccatga agggcaagta    2040
cggcatctac accaaggtga ccgctacgt gaactggatc aaggagaaga ccaagctgac    2100
ctaatga                                                               2107
```

<210> SEQ ID NO 33
<211> LENGTH: 2174
<212> TYPE: DNA
<213> ORGANISM: Artificial Sequence
<220> FEATURE:
<223> OTHER INFORMATION: Flank-3xSERP-Flank-TTRe-Flank-TTRm-Flank-MVM-
      Flank-co-FIX-R338L-F lank

<400> SEQUENCE: 33

```
aattcacgcg tggatctgaa ttcaattcac gcgtggtacg gccgcggggg ggaggctgct      60
ggtgaatatt aaccaaggtc accccagtta tcggaggagc aaacaggggc taagtccacc     120
gggggaggct gctggtgaat attaaccaag gtcaccccag ttatcggagg agcaaacagg     180
ggctaagtcc accgggggag gctgctggtg aatattaacc aaggtcaccc cagttatcgg     240
aggagcaaac aggggctaag tccacggtac ccactgggag gatgttgagt aagatggaaa     300
actactgatg acccttgcag agacagagta ttaggacatg tttgaacagg ggccgggcga     360
tcagcaggta gctctagagg atccccgtct gtctgcacat tcgtagagc gagtgttccg     420 atactctaat ctccctaggc aaggttcata tttgtgtagg ttacttattc tccttttgtt     480
gactaagtca ataatcagaa tcagcaggtt tggagtcagc ttggcaggga tcagcagcct     540
gggttggaag gaggggtat aaaagcccct tcaccaggag aagccgtcac acagatccac     600
aagctcctgg ctagaaagag gtaagggttt aagggatggt tggttggtgg ggtattaatg     660
tttaattacc tggagcacct gcctgaaatc acttttttc aggttgggct agcccaccat     720
gcagcgcgtg aacatgatca tggccgagag ccccggcctg atcaccatct gcctgctggg     780
ctacctgctg agcgccgagt gcaccgtgtt cctggaccac gagaacgcca acaagatcct     840
gaaccgcccc aagcgctaca cagcggcaa gctggaggag ttcgtgcagg gcaacctgga     900
gcgcgagtgc atgaaggaga agtgcagctt cgaggaggcc cgcgaggtgt tcgagaacac     960
cgagcgcacc accgagttct ggaagcagta cgtggacggc gaccagtgcg agagcaaccc    1020
ctgcctgaac ggcggcagct gcaaggacga catcaacagc tacgagtgct ggtgcccctt    1080
cggcttcgag ggcaagaact gcgagctgga cgtgacctgc aacatcaaga acggccgctg    1140
cgagcagttc tgcaagaaca cgccgacaa caaggtggtg tgcagctgca ccagggcta    1200 ccgcctggcc gagaaccaga gagctgcga gcccgccgtg cccttcccct gcggccgcgt    1260
gagcgtgagc cagaccagca agctgacccg cgccgaggcc gtgttcccg acgtggacta    1320 cgtgaacagc accgaggccg agaccatcct ggacaacatc acccagagca cccagagctt    1380
caacgacttc acccgcgtgg tgggcggcga ggacgccaag cccggccagt tccctggca    1440 ggtggtgctg aacggcaagg tggacgcctt ctgcggcggc agcatcgtga acgagaagtg    1500
gatcgtgacc gccgcccact gcgtggagac cggcgtgaag atcaccgtgg tggccggcga    1560
gcacaacatc gaggagaccg agcacaccga gcagaagcgc aacgtgatcc gcatcatccc    1620
ccaccacaac tacaacgccg ccatcaacaa gtacaaccac gacatcgccc tgctggagct    1680
ggacgagccc ctggtgctga acagctacgt gaccccatc tgcatcgccg acaaggagta    1740
```

```
caccaacatc ttcctgaagt tcggcagcgg ctacgtgagc ggctgggggcc gcgtgttcca      1800 caagggccgc agcgccctgg tgctgcagta cctgcgcgtg ccctggtgg accgcgccac       1860 ctgcctgctg agcaccaagt tcaccatcta caacaacatg ttctgcgccg gcttccacga     1920
gggcggccgc gacagctgcc agggcgacag cggcggcccc cacgtgaccg aggtggaggg     1980
caccagcttc ctgaccggca tcatcagctg gggcgaggag tgcgccatga agggcaagta     2040
cggcatctac accaaggtga ccgctacgt gaactggatc aaggagaaga ccaagctgac      2100
ctaatgaaag atggatttcc aaggttaatt cattggaatt gaaaattaac agccccccc      2160 cccccccccc tgca                                                       2174

<210> SEQ ID NO 34
<211> LENGTH: 2469
<212> TYPE: DNA
<213> ORGANISM: Artificial Sequence
<220> FEATURE:
<223> OTHER INFORMATION: Flank-3xSERP-Flank-TTRe-Flank-TTRm-Flank-MVM-
      Flank-co-FIX-R338L-F lank-BGHpA

<400> SEQUENCE: 34
aattcacgcg tggatctgaa ttcaattcac gcgtggtacg gccgcggggg ggaggctgct      60
ggtgaatatt aaccaaggtc accccagtta tcggaggagc aaacagggc taagtccacc     120 gggggaggct gctggtgaat attaaccaag gtcaccccag ttatcggagg agcaaacagg     180
ggctaagtcc accgggggag gctgctggtg aatattaacc aaggtcaccc cagttatcgg     240
aggagcaaac aggggctaag tccacggtac ccactgggag gatgttgagt aagatggaaa     300
actactgatg acccttgcag agacagagta ttaggacatg tttgaacagg ggccgggcga     360
tcagcaggta gctctagagg atccccgtct gtctgcacat tcgtagagc gagtgttccg      420 atactctaat ctccctaggc aaggttcata tttgtgtagg ttacttattc tccttttgtt     480
gactaagtca ataatcagaa tcagcaggtt tggagtcagc ttggcaggga tcagcagcct     540
gggttggaag gaggggtat aaaagcccct tcaccaggag aagccgtcac acagatccac      600
aagctcctgg ctagaaagag gtaagggttt aagggatggt tggttggtgg ggtattaatg    660
tttaattacc tggagcacct gcctgaaatc actttttttc aggttgggct agcccaccat    720
gcagcgcgtg aacatgatca tggccgagag ccccggcctg atcaccatct gcctgctggg   780
ctacctgctg agcgccgagt gcaccgtgtt cctggaccac gagaacgcca acaagatcct    840
gaaccgcccc aagcgctaca cagcggcaa gctggaggag ttcgtgcagg caacctgga     900 gcgcgagtgc atggaggaga agtgcagctt cgaggaggcc cgcgaggtgt tcgagaacac    960
cgagcgcacc accgagttct ggaagcagta cgtggacggc gaccagtgcg agagcaaccc    1020
ctgcctgaac ggcggcagct gcaaggacga catcaacagc tacgagtgct ggtgccccctt   1080 cggcttcgag ggcaagaact gcgagctgga cgtgacctgc aacatcaaga acggccgctg    1140
cgagcagttc tgcaagaaca cgccgacaa caaggtggtg tgcagctgca ccgagggcta     1200
ccgcctggcc gagaaccaga gagctgcga gccgccgtg cccttcccct cggccgcgt      1260 gagcgtgagc cagaccagca gctgacccg cgccgaggcc gtgttcccg acgtggacta     1320 cgtgaacagc accgaggccg agaccatcct ggacaacatc cccagagca cccagagctt    1380 caacgacttc acccgcgtgg tgggcggcga ggacgccaag cccggccagt tccctggca    1440 ggtggtgctg aacggcaagg tggacgcctt ctgcggcggc agcatcgtga acgagaagtg   1500
gatcgtgacc gccgccact gcgtggagac cggcgtgaag atcaccgtgg tggccggcga   1560
```

```
gcacaacatc gaggagaccg agcacaccga gcagaagcgc aacgtgatcc gcatcatccc    1620
ccaccacaac tacaacgccg ccatcaacaa gtacaaccac gacatcgccc tgctggagct    1680
ggacgagccc ctggtgctga acagctacgt gaccccatc tgcatcgccg acaaggagta     1740
caccaacatc ttcctgaagt tcggcagcgg ctacgtgagc ggctgggcc gcgtgttcca     1800 caagggccgc agcgccctgg tgctgcagta cctgcgcgtg ccctggtgg accgcgccac     1860 ctgcctgctg agcaccaagt tcaccatcta acaacatg ttctgcgccg cttccacga      1920 gggcggccgc gacagctgcc agggcgacag cggcggcccc cacgtgaccg aggtggaggg    1980
caccagcttc ctgaccggca tcatcagctg ggcgaggag tgcgccatga agggcaagta    2040
cggcatctac accaaggtga gccgctacgt gaactggatc aaggagaaga ccaagctgac    2100
ctaatgaaag atggattcc aaggttaatt cattggaatt gaaaattaac agcccccccc    2160
cccccccccc tgcagatctg agccgaattc ctgcagcccg ggggatcagc ctcgactgtg    2220
ccttctagtt gccagccatc tgttgtttgc ccctccccg tgccttcctt gaccctggaa    2280
ggtgccactc ccactgtcct ttcctaataa aatgaggaaa ttgcatcgca ttgtctgagt    2340
aggtgtcatt ctattctggg gggtggggtg ggcaggaca gcaaggggga ggattgggaa    2400
gacaatagca ggcatgctgg ggatgcggtg gctctatgg cttctgaggc ggaaagaacc    2460
agctgggga                                                           2469

<210> SEQ ID NO 35
<211> LENGTH: 2508
<212> TYPE: DNA
<213> ORGANISM: Artificial Sequence
<220> FEATURE:
<223> OTHER INFORMATION: Flank-3xSERP-Flank-TTRe-Flank-TTRm-Flank-MVM-
      Flank-co-FIX-R338L-F lank-BGHpA-Flank

<400> SEQUENCE: 35
aattcacgcg tggatctgaa ttcaattcac gcgtggtacg gccgcggggg ggaggctgct      60
ggtgaatatt aaccaaggtc accccagtta tcggaggagc aaacaggggc taagtccacc     120
gggggaggct gctggtgaat attaaccaag gtcacccag ttatcggagg agcaaacagg     180
ggctaagtcc accgggggag gctgctggtg aatattaacc aaggtcaccc cagttatcgg    240
aggagcaaac aggggctaag tccacggtac ccactgggag gatgttgagt aagatggaaa    300
actactgatg acccttgcag agacagagta ttaggacatg tttgaacagg ggccgggcga    360
tcagcaggta gctctagagg atccccgtct gtctgcacat ttcgtagagc gagtgttccg    420
atactctaat ctccctaggc aaggttcata tttgtgtagg ttacttattc tccttttgtt    480
gactaagtca ataatcagaa tcagcaggtt tggagtcagc ttggcaggga tcagcagcct    540
gggttggaag gaggggtat aaaagcccct tcaccaggag aagccgtcac acagatccac    600
aagctcctgg ctagaaagag gtaagggttt aagggatggt tggttggtgg gtattaatg    660 tttaattacc tggagcacct gcctgaaatc acttttttc aggttgggct agcccaccat    720
gcagcgcgtg aacatgatca tggccgagag ccccggcctg atcaccatct gcctgctggg    780
ctacctgctg agcgccgagt gcaccgtgtt cctggaccac gagaacgcca acaagatcct    840
gaaccgcccc aagcgctaca cagcggcaa gctggaggag ttcgtgcagg gcaacctgga    900
gcgcgagtgc atggaggaga agtgcagctt cgaggaggcc cgcgaggtgt tcgaaacac    960 cgagcgcacc accgagttct ggaagcagta cgtggacggc gaccagtgcg agagcaaccc    1020
ctgcctgaac ggcggcagct gcaaggacga catcaacagc tacgagtgct ggtgccctt    1080
```

```
cggcttcgag ggcaagaact gcgagctgga cgtgacctgc aacatcaaga acggccgctg   1140
cgagcagttc tgcaagaaca cgccgacaa caaggtggtg tgcagctgca ccgagggcta    1200
ccgcctggcc gagaaccaga gagctgcga gcccgccgtg cccttcccct gcggccgcgt    1260
gagcgtgagc cagaccagca agctgacccg cgccgaggcc gtgttccccg acgtggacta   1320
cgtgaacagc accgaggccg agaccatcct ggacaacatc acccagagca cccagagctt   1380
caacgacttc acccgcgtgg tgggcggcga ggacgccaag cccggccagt cccctggca    1440 ggtggtgctg aacggcaagg tggacgcctt ctgcggcggc agcatcgtga cgagaagtg    1500 gatcgtgacc gccgcccact gcgtggagac cggcgtgaag atcaccgtgg tggccggcga   1560
gcacaacatc gaggagaccg agcacaccga gcagaagcgc aacgtgatcc gcatcatccc   1620
ccaccacaac tacaacgccg ccatcaacaa gtacaaccac gacatcgccc tgctggagct   1680
ggacgagccc ctggtgctga acagctacgt gaccccccatc tgcatcgccg acaaggagta  1740
caccaacatc ttcctgaagt tcggcagcgg ctacgtgagc ggctggggcc gcgtgttcca   1800
caagggccgc agcgccctgg tgctgcagta cctgcgcgtg cccctggtgg accgcgccac   1860
ctgcctgctg agcaccaagt tcaccatcta caacaacatg ttctgcgccg gcttccacga   1920
gggcggccgc gacagctgcc agggcgacag cggcggcccc cacgtgaccg aggtggaggg   1980
caccagcttc ctgaccggca tcatcagctg gggcgaggag tgcgccatga gggcaagta    2040 cggcatctac accaaggtga gccgctacgt gaactggatc aaggagaaga ccaagctgac   2100
ctaatgaaag atggatttcc aaggttaatt cattggaatt gaaaattaac agccccccc    2160 ccccccccc tgcagatctg agccgaattc ctgcagcccg ggggatcagc ctcgactgtg    2220
ccttctagtt gccagccatc tgttgtttgc cctcccccg tgccttcctt gaccctggaa    2280
ggtgccactc ccactgtcct ttcctaataa aatgaggaaa ttgcatcgca ttgtctgagt   2340
aggtgtcatt ctattctggg gggtggggtg gggcaggaca gcaagggga ggattgggaa    2400 gacaatagca ggcatgctgg ggatgcggtg ggctctatgg cttctgaggc ggaaagaacc   2460
agctggggac cggtggatct cgatagcagg catgctgggg agagatcg               2508
```

<210> SEQ ID NO 36
<211> LENGTH: 2223
<212> TYPE: DNA
<213> ORGANISM: Artificial Sequence
<220> FEATURE:
<223> OTHER INFORMATION: Flank-3xSERP-Flank-TTRe-Flank-TTRm-Flank-MVM-
      Flank-co-FIX-R338L-Flank-Synt-pA

<400> SEQUENCE: 36

```
aattcacgcg tggatctgaa ttcaattcac gcgtggtacg gccgcggggg ggaggctgct     60
ggtgaatatt aaccaaggtc acccccagtta tcggaggagc aaacaggggc taagtccacc   120
gggggaggct gctggtgaat attaaccaag gtcaccccag ttatcggagg agcaaacagg   180
ggctaagtcc accgggggag gctgctggtg aatattaacc aaggtcaccc cagttatcgg   240
aggagcaaac aggggctaag tccacggtac ccactgggag gatgttgagt aagatggaaa   300
actactgatg acccttgcag agacagagta ttaggacatg tttgaacagg gccgggcga    360 tcagcaggta gctctagagg atccccgtct gtctgcacat ttcgtagagc gagtgttccg   420
atactctaat ctcccctaggc aaggttcata tttgtgtagg ttacttattc tccttttgtt   480
gactaagtca ataatcagaa tcagcaggtt tggagtcagc ttggcaggga tcagcagcct   540
gggttggaag gagggggtat aaaagcccct tcaccaggag aagccgtcac acagatccac   600
```

```
aagctcctgg ctagaaagag gtaagggttt aagggatggt tggttggtgg ggtattaatg    660
tttaattacc tggagcacct gcctgaaatc acttttttc aggttgggct agcccaccat     720
gcagcgcgtg aacatgatca tggccgagag ccccggcctg atcaccatct gcctgctggg    780
ctacctgctg agcgccgagt gcaccgtgtt cctggaccac gagaacgcca acaagatcct    840
gaaccgcccc aagcgctaca cagcggcaa gctggaggag ttcgtgcagg caacctgga     900 gcgcgagtgc atggaggaga agtgcagctt cgaggaggcc cgcgaggtgt tcgagaacac    960
cgagcgcacc accgagttct ggaagcagta cgtggacggc gaccagtgcg agagcaaccc    1020
ctgcctgaac ggcggcagct gcaaggacga catcaacagc tacgagtgct ggtgccccttt  1080 cggcttcgag ggcaagaact gcgagctgga cgtgacctgc aacatcaaga acggccgctg    1140
cgagcagttc tgcaagaaca cgccgacaa caaggtggtg tgcagctgca ccgagggcta    1200
ccgcctggcc gagaaccaga gagctgcga gcccgccgtg cccttcccct cggccgcgt    1260 gagcgtgagc cagaccagca agctgacccg cgccgaggcc gtgttccccg acgtggacta    1320
cgtgaacagc accgaggccg agaccatcct ggacaacatc cccagagca cccagagctt    1380 caacgacttc acccgcgtgg tgggcggcga ggacgccaag cccggccagt ccccctggca    1440
ggtggtgctg aacggcaagg tggacgcctt ctgcggcggc agcatcgtga acgagaagtg    1500
gatcgtgacc gccgcccact gcgtggagac cggcgtgaag atcaccgtgg tggccggcga    1560
gcacaacatc gaggagaccg agcacaccga gcagaagcgc aacgtgatcc gcatcatccc    1620
ccaccacaac tacaacgccg ccatcaacaa gtacaaccac gacatcgccc tgctggagct    1680
ggacgagccc ctggtgctga acagctacgt gacccccatc tgcatcgccg acaaggagta    1740
caccaacatc ttcctgaagt tcggcagcgg ctacgtgagc ggctgggcc gcgtgttcca    1800 caagggccgc agcgccctgg tgctgcagta cctgcgcgtg ccccctggtgg accgcgccac    1860 ctgcctgctg agcaccaagt tcaccatcta caacaacatg ttctgcgccg gcttccacga    1920
gggcggccgc gacagctgcc agggcgacag cggcggcccc cacgtgaccg aggtggaggg    1980
caccagcttc ctgaccggca tcatcagctg gggcgaggag tgcgccatga agggcaagta    2040
cggcatctac accaaggtga gccgctacgt gaactggatc aaggagaaga ccaagctgac    2100
ctaatgaaag atggatttcc aaggttaatt cattggaatt gaaaattaac agcccccccc    2160
cccccccccc tgcaaataaa agatctttat tttcattaga tctgtgtgtt ggttttttgt    2220
gtg                                                                  2223
```

<210> SEQ ID NO 37
<211> LENGTH: 2262
<212> TYPE: DNA
<213> ORGANISM: Artificial Sequence
<220> FEATURE:
<223> OTHER INFORMATION: Flank-3xSERP-Flank-TTRe-Flank-TTRm-Flank-MVM-
      Flank-co-FIX-R338L-F lank-Synt.pA-Flank

<400> SEQUENCE: 37

```
aattcacgcg tggatctgaa ttcaattcac gcgtggtacg gccgcggggg ggaggctgct    60
ggtgaatatt aaccaaggtc accccagtta tcggaggagc aaacagggc taagtccacc     120 gggggaggct gctggtgaat attaaccaag gtcaccccag ttatcggagg agcaaacagg    180
ggctaagtcc accgggggag gctgctggtg aatattaacc aaggtcaccc cagttatcgg    240
aggagcaaac aggggctaag tccacggtac ccactgggag gatgttgagt aagatggaaa    300
actactgatg acccttgcag agacagagta ttaggacatg tttgaacagg ggccgggcga    360
```

```
tcagcaggta gctctagagg atccccgtct gtctgcacat ttcgtagagc gagtgttccg      420
atactctaat ctccctaggc aaggttcata tttgtgtagg ttacttattc tcctttttgtt    480 gactaagtca ataatcagaa tcagcaggtt tggagtcagc ttggcaggga tcagcagcct     540
gggttggaag gaggggtat aaaagcccct tcaccaggaa aagccgtcac acagatccac     600
aagctcctgg ctagaaagag gtaagggttt aagggatggt tggttggtgg ggtattaatg    660
tttaattacc tggagcacct gcctgaaatc acttttttc aggttgggct agcccaccat     720
gcagcgcgtg aacatgatca tggccgagag ccccggcctg atcaccatct gcctgctggg    780
ctacctgctg agcgccgagt gcaccgtgtt cctggaccac gagaacgcca acaagatcct    840
gaaccgcccc aagcgctaca cagcggcaa gctggaggag ttcgtgcagg gcaacctgga    900
gcgcgagtgc atggaggaga agtgcagctt cgaggaggcc cgcgaggtgt tcgagaacac    960
cgagcgcacc accgagttct ggaagcagta cgtggacggc gaccagtgcg agagcaaccc   1020
ctgcctgaac ggcggcagct gcaaggacga catcaacagc tacgagtgct ggtgcccctt   1080
cggcttcgag ggcaagaact gcgagctgga cgtgacctgc aacatcaaga acggccgctg   1140
cgagcagttc tgcaagaaca cgccgacaa caaggtggtg tgcagctgca ccgagggcta   1200
ccgcctggcc gagaaccaga gagctgcga gcccgccgtg cccttcccct gcggccgcgt   1260
gagcgtgagc cagaccagca agctgacccg cgccgaggcc gtgttcccg acgtggacta   1320 cgtgaacagc accgaggccg agaccatcct ggacaacatc acccagagca cccagagctt   1380
caacgacttc acccgcgtgg tgggcggcga ggacgccaag cccggccagt tcccctggca   1440
ggtggtgctg aacggcaagg tggacgcctt ctgcggcggc agcatcgtga acgagaagtg   1500
gatcgtgacc gccgcccact gcgtggagac cggcgtgaag atcaccgtgg tggccggcga   1560
gcacaacatc gaggagaccg agcaccgaa gcagaagcgc aacgtgatcc gcatcatccc   1620
ccaccacaac tacaacgccg ccatcaacaa gtacaaccac gacatcgccc tgctggagct   1680
ggacgagccc ctggtgctga acagctacgt gacccccatc tgcatcgccg acaaggagta   1740
caccaacatc ttcctgaagt tcggcagcgg ctacgtgagc ggctgggccc gcgtgttcca   1800
caagggccgc agcgccctgg tgctgcagta cctgcgcgtg ccctggtgg accgcgccac   1860 ctgcctgctg agcaccaagt tcaccatcta caacaacatg ttctgcgccg gcttccacga   1920
gggcggccgc gacagctgcc agggcgacag cggcggcccc cacgtgaccg aggtggaggg   1980
caccagcttc ctgaccggca tcatcagctg gggcgaggag tgcgccatga agggcaagta   2040
cggcatctac accaaggtga ccgctacgt gaactgatc aaggagaaga ccaagctgac   2100
ctaatgaaag atggatttcc aaggttaatt cattggaatt gaaaattaac agccccccc    2160 cccccccccc tgcaaataaa agatctttat tttcattaga tctgtgtgtt ggttttttgt   2220
gtgccggtgg atctcgatag caggcatgct ggggagagat cg                      2262
```

<210> SEQ ID NO 38
<211> LENGTH: 239
<212> TYPE: DNA
<213> ORGANISM: Artificial Sequence
<220> FEATURE:
<223> OTHER INFORMATION: Flank-3xSERP-Flank

<400> SEQUENCE: 38

```
gcggccgcgg tacgcggggg aggctgctgg tgaatattaa ccaaggtcac cccagttatc       60
ggaggagcaa acaggggcta agtccaccgg gggaggctgc tggtgaatat taaccaaggt     120
``` cacccccagtt atcggaggag caaacagggg ctaagtccac cggggggaggc tgctggtgaa    180 tattaaccaa ggtcaccccca gttatcggag gagcaaacag gggctaagtc cacggtacc     239

<210> SEQ ID NO 39
<211> LENGTH: 339
<212> TYPE: DNA
<213> ORGANISM: Artificial Sequence
<220> FEATURE:
<223> OTHER INFORMATION: Flank-3xSERP-Flank-TTRe

<400> SEQUENCE: 39
gcggccgcgg tacgcggggg aggctgctgg tgaatattaa ccaaggtcac cccagttatc      60
ggaggagcaa acaggggcta agtccaccgg gggaggctgc tggtgaatat taaccaaggt     120 cacccccagtt atcggaggag caaacagggg ctaagtccac cggggggaggc tgctggtgaa    180 tattaaccaa ggtcacccca gttatcggag gagcaaacag gggctaagtc cacggtaccc    240
actgggagga tgttgagtaa gatggaaaac tactgatgac ccttgcagag acagagtatt    300
aggacatgtt tgaacagggg ccgggcgatc agcaggtag                            339

<210> SEQ ID NO 40
<211> LENGTH: 354
<212> TYPE: DNA
<213> ORGANISM: Artificial Sequence
<220> FEATURE:
<223> OTHER INFORMATION: Flank-3xSERP-Flank-TTRe-Flank

<400> SEQUENCE: 40
gcggccgcgg tacgcggggg aggctgctgg tgaatattaa ccaaggtcac cccagttatc      60
ggaggagcaa acaggggcta agtccaccgg gggaggctgc tggtgaatat taaccaaggt     120 cacccccagtt atcggaggag caaacagggg ctaagtccac cggggggaggc tgctggtgaa    180 tattaaccaa ggtcacccca gttatcggag gagcaaacag gggctaagtc cacggtaccc    240
actgggagga tgttgagtaa gatggaaaac tactgatgac ccttgcagag acagagtatt    300
aggacatgtt tgaacagggg ccgggcgatc agcaggtagc tctagaggat cccc          354

<210> SEQ ID NO 41
<211> LENGTH: 556
<212> TYPE: DNA
<213> ORGANISM: Artificial Sequence
<220> FEATURE:
<223> OTHER INFORMATION: Flank-3xSERP-Flank-TTRe-Flank-TTRm

<400> SEQUENCE: 41
gcggccgcgg tacgcggggg aggctgctgg tgaatattaa ccaaggtcac cccagttatc      60
ggaggagcaa acaggggcta agtccaccgg gggaggctgc tggtgaatat taaccaaggt     120 cacccccagtt atcggaggag caaacagggg ctaagtccac cggggggaggc tgctggtgaa    180 tattaaccaa ggtcacccca gttatcggag gagcaaacag gggctaagtc cacggtaccc    240
actgggagga tgttgagtaa gatggaaaac tactgatgac ccttgcagag acagagtatt    300
aggacatgtt tgaacagggg ccgggcgatc agcaggtagc tctagaggat ccccgtctgt    360
ctgcacattt cgtagagcga gtgttccgat actctaatct ccctaggcaa ggttcatatt    420
tgtgtaggtt acttattctc cttttgttga ctaagtcaat aatcagaatc agcaggtttg    480
gagtcagctt ggcagggatc agcagcctgg gttggaagga gggggtataa agcccccttc    540
accaggagaa gccgtc                                                     556

<210> SEQ ID NO 42
<211> LENGTH: 561
<212> TYPE: DNA
<213> ORGANISM: Artificial Sequence
<220> FEATURE:
<223> OTHER INFORMATION: Flank-3xSERP-Flank-TTRe-Flank-TTRm-Flank

<400> SEQUENCE: 42

```
gcggccgcgg tacgcggggg aggctgctgg tgaatattaa ccaaggtcac cccagttatc      60
ggaggagcaa acaggggcta agtccaccgg gggaggctgc tggtgaatat taaccaaggt     120
caccccagtt atcggaggag caaacagggg ctaagtccac cggggaggc tgctggtgaa      180
tattaaccaa ggtcacccca gttatcggag gagcaaacag ggctaagtc cacggtaccc      240
actgggagga tgttgagtaa gatggaaaac tactgatgac ccttgcagag acagagtatt     300
aggacatgtt tgaacagggg ccgggcgatc agcaggtagc tctagaggat ccccgtctgt     360
ctgcacattt cgtagagcga gtgttccgat actctaatct ccctaggcaa ggttcatatt     420
tgtgtaggtt acttattctc cttttgttga ctaagtcaat aatcagaatc agcaggtttg     480
gagtcagctt ggcagggatc agcagcctgg gttggaagga gggggtataa agccccttc     540
accaggagaa gccgtcctag t                                               561
```

<210> SEQ ID NO 43
<211> LENGTH: 4938
<212> TYPE: DNA
<213> ORGANISM: Artificial Sequence
<220> FEATURE:
<223> OTHER INFORMATION: Flank-3xSERP-Flank-TTRe-Flank-TTRm-Flank-
      coFVIIIdeltaB

<400> SEQUENCE: 43

```
gcggccgcgg tacgcggggg aggctgctgg tgaatattaa ccaaggtcac cccagttatc      60
ggaggagcaa acaggggcta agtccaccgg gggaggctgc tggtgaatat taaccaaggt     120
caccccagtt atcggaggag caaacagggg ctaagtccac cggggaggc tgctggtgaa      180
tattaaccaa ggtcacccca gttatcggag gagcaaacag ggctaagtc cacggtaccc      240
actgggagga tgttgagtaa gatggaaaac tactgatgac ccttgcagag acagagtatt     300
aggacatgtt tgaacagggg ccgggcgatc agcaggtagc tctagaggat ccccgtctgt     360
ctgcacattt cgtagagcga gtgttccgat actctaatct ccctaggcaa ggttcatatt     420
tgtgtaggtt acttattctc cttttgttga ctaagtcaat aatcagaatc agcaggtttg     480
gagtcagctt ggcagggatc agcagcctgg gttggaagga gggggtataa agccccttc     540
accaggagaa gccgtcctag tatgcagatc gagctgtcca cctgcttttt tctgtgcctg     600
ctgcggttct gcttcagcgc cacccggcgg tactacctgg gcgccgtgga gctgtcctgg     660
gactacatgc agagcgacct gggcgagctg cccgtggacg cccggttccc cccagagtg     720
cccaagagct ccccttcaa caccagcgtg gtgtacaaga aaccctgtt cgtggagttc     780
accgaccacc tgttcaatat cgccaagccc aggccccct ggatgggcct gctgggcccc     840
accatccagg ccgaggtgta cgacaccgtg gtgatcaccc tgaagaacat ggccagccac     900
cccgtgagcc tgcacgccgt gggcgtgagc tactggaagg ccagcgaggg cgccgagtac     960
gacgaccaga ccagccagcg ggagaaagaa gatgacaagg tgttccctgg cggcagccac    1020
acctacgtgt ggcaggtgct gaaagaaaac ggccccatgg cctccgaccc cctgtgcctg    1080
acctacagct acctgagcca cgtggacctg gtgaaggacc tgaacagcgg cctgatcggc    1140
gctctgctcg tctgccggga gggcagcctg gccaaagaga aaacccagac cctgcacaag    1200
```

```
ttcatcctgc tgttcgccgt gttcgacgag ggcaagagct ggcacagcga gacaagaac      1260 agcctgatgc aggaccggga cgccgcctct gccagagcct ggcccaagat gcacaccgtg      1320
aacggctacg tgaacagaag cctgcccggc ctgattggct gccaccggaa gagcgtgtac      1380
tggcacgtga tcggcatggg caccacaccc gaggtgcaca gcatctttct ggaagggcac      1440
acctttctgg tccggaacca ccggcaggcc agcctggaaa tcagccctat caccttcctg      1500
accgcccaga cactgctgat ggacctgggc cagttcctgc tgttttgcca catcagctct      1560
caccagcacg acggcatgga agcctacgtg aaggtggact cttgccccga ggaaccccag      1620
ctgcggatga agaacaacga ggaagccgag gactacgacg acgacctgac cgacagcgag      1680
atggacgtgg tgcggttcga cgacgacaac agccccagct tcatccagat cagaagcgtg      1740
gccaagaagc accccaagac ctgggtgcac tatatcgccg ccgaggaaga ggactgggac      1800 tacgccccc tggtgctggc ccccgacgac agaagctaca agagccagta cctgaacaat      1860
ggcccccagc ggatcggccg gaagtacaag aaagtgcggt tcatggccta caccgacgag      1920
acattcaaga cccgggaggc catccagcac gagagcggca tcctgggccc cctgctgtac      1980
ggcgaagtgg cgacacact gctgatcatc ttcaagaacc aggctagccg gccctacaac      2040
atctaccccc acggcatcac cgacgtgcgg cccctgtaca gcaggcggct gcccaagggc      2100
gtgaagcacc tgaaggactt ccccatcctg cccggcgaga tcttcaagta caagtggacc      2160
gtgaccgtgg aggacggccc caccaagagc gaccccagat gcctgacccg gtactacagc      2220
agcttcgtga acatggaacg ggacctggcc tccgggctga tcggacctct gctgatctgc      2280
tacaaagaaa gcgtggacca gcggggcaac cagatcatga gcgacaagcg gaacgtgatc      2340
ctgttcagcg tgttcgatga aaccggtcc tggtatctga ccgagaacat ccagcggttt      2400
ctgcccaacc ctgccggcgt gcagctggaa gatcccgagt tccaggccag caacatcatg      2460
cactccatca atggctacgt gttcgactct ctgcagctct ccgtgtgtct gcacgaggtg      2520
gcctactggt acatcctgag catcggcgcc cagaccgact tcctgagcgt gttcttcagc      2580
ggctacacct tcaagcacaa gatggtgtac gaggacaccc tgaccctgtt ccctttcagc      2640
ggcgagacag tgttcatgag catggaaaac cccggcctgt ggattctggg ctgccacaac      2700
agcgacttcc ggaaccgggg catgaccgcc ctgctgaagg tgtccagctg cgacaagaac      2760
accggcgact actacgagga cagctacgag gatatcagcg cctacctgct gtccaagaac      2820
aacgccatcg aaccccggag cttcagccag aaccccccg tgctgacgcg tcaccagcgg      2880
gagatcaccc ggacaaccct gcagtccgac caggaagaga tcgattacga cgacaccatc      2940
agcgtggaga tgaagaaaga ggatttcgat atctacgacg aggacgagaa ccagagcccc      3000
agaagcttcc agaagaaaac ccggcactac ttcattgccg ccgtggagag gctgtgggac      3060
tacggcatga gttctagccc ccacgtgctg cggaaccggg cccagagcgg cagcgtgccc      3120
cagttcaaga aagtggtgtt ccaggaattc acagacggca gcttcaccca gcctctgtat      3180
agaggcgagc tgaacgagca cctggggctg ctggggccct acatcagggc cgaagtggag      3240
gacaacatca tggtgacctt ccggaatcag gccagcagac cctactcctt ctacagcagc      3300
ctgatcagct acgaagagga ccagcggcag ggcgccgaac cccggaagaa cttcgtgaag      3360
cccaacgaaa ccaagaccta cttctggaaa gtgcagcacc acatggcccc caccaaggac      3420
gagttcgact gcaaggcctg ggcctacttc agcgacgtgg atctggaaaa ggacgtgcac      3480
tctggactga ttggcccact cctggtctgc cacactaaca ccctcaaccc cgcccacggc      3540
```

| | | |
|---|---|---|
| cgccaggtga ccgtgcagga attcgccctg ttcttcacca tcttcgacga gacaaagtcc | 3600 |
| tggtacttca ccgagaatat ggaacggaac tgcagagccc cctgcaacat ccagatggaa | 3660 |
| gatcctacct tcaaagagaa ctaccggttc cacgccatca acggctacat catggacacc | 3720 |
| ctgcctggcc tggtgatggc ccaggaccag agaatccggt ggtatctgct gtccatgggc | 3780 |
| agcaacgaga atatccacag catccacttc agcggccacg tgttcaccgt gcggaagaaa | 3840 |
| gaagagtaca agatggccct gtacaacctg taccccggcg tgttcgagac agtggagatg | 3900 |
| ctgcccagca aggccggcat ctggcgggtg gagtgtctga tcggcgagca cctgcacgct | 3960 |
| ggcatgagca ccctgtttct ggtgtacagc aacaagtgcc agacccccact gggcatggcc | 4020 |
| tctggccaca tccgggactt ccagatcacc gcctccggcc agtacggcca gtgggccccc | 4080 |
| aagctggcca gactgcacta cagcggcagc atcaacgcct ggtccaccaa agagcccttc | 4140 |
| agctggatca aggtggacct gctggcccct atgatcatcc acggcattaa gacccagggc | 4200 |
| gccaggcaga agttcagcag cctgtacatc agccagttca tcatcatgta cagcctggac | 4260 |
| ggcaagaagt ggcagaccta ccggggcaac agcaccggca ccctgatggt gttcttcggc | 4320 |
| aatgtggaca gcagcggcat caagcacaac atcttcaacc ccccatcat gcccggtac | 4380 |
| atccggctgc accccaccca ctacagcatt agatccacac tgagaatgga actgatgggc | 4440 |
| tgcgacctga actcctgcag catgcctctg gcatggaaaa gcaaggccat cagcgacgcc | 4500 |
| cagatcacag ccagcagcta cttcaccaac atgttcgcca cctggtcccc ctccaaggcc | 4560 |
| aggctgcacc tgcagggccg gtccaacgcc tggcggcctc aggtcaacaa ccccaaagaa | 4620 |
| tggctgcagg tggactttca gaaaaccatg aaggtgaccg gcgtgaccac ccagggcgtg | 4680 |
| aaaagcctgc tgaccagcat gtacgtgaaa gagtttctga tcagcagctc tcaggatggc | 4740 |
| caccagtgga ccctgttctt tcagaacggc aaggtgaaag tgttccaggg caaccaggac | 4800 |
| tccttcaccc ccgtggtgaa ctccctggac ccccccctgc tgacccgcta cctgagaatc | 4860 |
| caccccagt cttgggtgca ccagatcgcc ctcaggatgg aagtcctggg atgtgaggcc | 4920 |
| caggatctgt actgatga | 4938 |

<210> SEQ ID NO 44
<211> LENGTH: 4944
<212> TYPE: DNA
<213> ORGANISM: Artificial Sequence
<220> FEATURE:
<223> OTHER INFORMATION: Flank-3xSERP-Flank-TTRe-Flank-TTRm-Flank-
      coFVIIIdeltaB-Flank

<400> SEQUENCE: 44

| | | |
|---|---|---|
| gcggccgcgg tacgcggggg aggctgctgg tgaatattaa ccaaggtcac cccagttatc | 60 |
| ggaggagcaa acaggggcta agtccaccgg gggaggctgc tggtgaatat taaccaaggt | 120 |
| caccccagtt atcggaggag caaacagggg ctaagtccac cggggaggc tgctggtgaa | 180 |
| tattaaccaa ggtcaccca gttatcggag gagcaaacag gggctaagtc cacggtaccc | 240 |
| actgggagga tgttgagtaa gatggaaaac tactgatgac ccttgcagag acagagtatt | 300 |
| aggacatgtt tgaacagggg ccgggcgatc agcaggtagc tctagaggat ccccgtctgt | 360 |
| ctgcacattt cgtagagcga gtgttccgat actctaatct ccctaggcaa ggttcatatt | 420 |
| tgtgtaggtt acttattctc cttttgttga ctaagtcaat aatcagaatc agcaggtttg | 480 |
| gagtcagctt ggcagggatc agcagcctgg gttggaagga gggggtataa aagccccttc | 540 |
| accaggagaa gccgtcctag tatgcagatc gagctgtcca cctgcttttt tctgtgcctg | 600 |

-continued

| | |
|---|---|
| ctgcggttct gcttcagcgc cacccggcgg tactacctgg gcgccgtgga gctgtcctgg | 660 |
| gactacatgc agagcgacct gggcgagctg cccgtggacg cccggttccc ccccagagtg | 720 |
| cccaagagct tccccttcaa caccagcgtg gtgtacaaga aaaccctgtt cgtggagttc | 780 |
| accgaccacc tgttcaatat cgccaagccc aggccccct ggatgggcct gctgggcccc | 840 |
| accatccagg ccgaggtgta cgacaccgtg gtgatcaccc tgaagaacat ggccagccac | 900 |
| cccgtgagcc tgcacgccgt gggcgtgagc tactggaagg ccagcgaggg cgccgagtac | 960 |
| gacgaccaga ccagccagcg ggagaaagaa gatgacaagg tgttccctgg cggcagccac | 1020 |
| acctacgtgt ggcaggtgct gaaagaaaac ggccccatgg cctccgaccc cctgtgcctg | 1080 |
| acctacagct acctgagcca cgtggacctg gtgaaggacc tgaacagcgg cctgatcggc | 1140 |
| gctctgctcg tctgccggga gggcagcctg gccaaagaga aaacccagac cctgcacaag | 1200 |
| ttcatcctgc tgttcgccgt gttcgacgag ggcaagagct ggcacagcga gacaaagaac | 1260 |
| agcctgatgc aggaccggga cgccgcctct gccagagcct ggcccaagat gcacaccgtg | 1320 |
| aacggctacg tgaacagaag cctgcccggc ctgattggct gccaccggaa gagcgtgtac | 1380 |
| tggcacgtga tcggcatggg caccacaccc gaggtgcaca gcatctttct ggaagggcac | 1440 |
| acctttctgg tccggaacca ccggcaggcc agcctggaaa tcagccctat caccttcctg | 1500 |
| accgcccaga cactgctgat ggacctgggc cagttcctgc tgttttgcca catcagctct | 1560 |
| caccagcacg acggcatgga agcctacgtg aaggtggact cttgccccga ggaaccccag | 1620 |
| ctgcggatga agaacaacga ggaagccgag gactacgacg acgacctgac cgacagcgag | 1680 |
| atggacgtgg tgcggttcga cgacgacaac agccccagct tcatccagat cagaagcgtg | 1740 |
| gccaagaagc accccaagac ctgggtgcac tatatcgccg ccgaggaaga ggactgggac | 1800 |
| tacgccccc tggtgctggc ccccgacgac agaagctaca agagccagta cctgaacaat | 1860 |
| ggcccccagc ggatcggccg gaagtacaag aaagtgcggt tcatggccta caccgacgag | 1920 |
| acattcaaga cccgggaggc catccagcac gagagcggca tcctgggccc cctgctgtac | 1980 |
| ggcgaagtgg gcgacacact gctgatcatc ttcaagaacc aggctagccg gccctacaac | 2040 |
| atctacccc acggcatcac cgacgtgcgg cccctgtaca gcaggcggct gcccaagggc | 2100 |
| gtgaagcacc tgaaggactt ccccatcctg cccggcgaga tcttcaagta caagtggacc | 2160 |
| gtgaccgtgg aggacggccc caccaagagc gaccccagat gcctgacccg gtactacagc | 2220 |
| agcttcgtga acatggaacg ggacctggcc tccgggctga tcggacctct gctgatctgc | 2280 |
| tacaaagaaa gcgtggacca gcggggcaac cagatcatga gcgacaagcg gaacgtgatc | 2340 |
| ctgttcagcg tgttcgatga aaccggtcc tggtatctga ccgagaacat ccagcggttt | 2400 |
| ctgcccaacc tgccggcgt gcagctggaa gatcccgagt ccaggccag caacatcatg | 2460 |
| cactccatca atggctacgt gttcgactct ctgcagctct ccgtgtgtct gcacgaggtg | 2520 |
| gcctactggt acatcctgag catcggcgcc cagaccgact tcctgagcgt gttcttcagc | 2580 |
| ggctacacct tcaagcacaa gatggtgtac gaggacaccc tgaccctgtt ccctttcagc | 2640 |
| ggcgagacag tgttcatgag catggaaaac cccggcctgt ggattctggg ctgccacaac | 2700 |
| agcgacttcc ggaaccgggg catgaccgcc ctgctgaagg tgtccagctg cgacaagaac | 2760 |
| accggcgact actacgagga cagctacgag gatatcagcg cctacctgct gtccaagaac | 2820 |
| aacgccatcg aaccccggag cttcagccag aaccccccg tgctgacgcg tcaccagcgg | 2880 |
| gagatcaccc ggacaacccct gcagtccgac caggaagaga tcgattacga cgacaccatc | 2940 |
| agcgtggaga tgaagaaaga ggatttcgat atctacgacg aggacgagaa ccagagcccc | 3000 |

```
agaagcttcc agaagaaaac ccggcactac ttcattgccg ccgtggagag gctgtgggac    3060
tacggcatga gttctagccc ccacgtgctg cggaaccggg cccagagcgg cagcgtgccc    3120
cagttcaaga aagtggtgtt ccaggaattc acagacggca gcttcaccca gcctctgtat    3180
agaggcgagc tgaacgagca cctggggctg ctggggccct acatcagggc cgaagtggag    3240
gacaacatca tggtgacctt ccggaatcag gccagcagac cctactcctt ctacagcagc    3300
ctgatcagct acgaagagga ccagcggcag ggcgccgaac cccggaagaa cttcgtgaag    3360
cccaacgaaa ccaagaccta cttctggaaa gtgcagcacc acatggcccc caccaaggac    3420
gagttcgact gcaaggcctg ggcctacttc agcgacgtgg atctggaaaa ggacgtgcac    3480
tctggactga ttggcccact cctggtctgc cacactaaca ccctcaaccc cgcccacggc    3540
cgccaggtga ccgtgcagga attcgccctg ttcttcacca tcttcgacga gacaaagtcc    3600
tggtacttca ccgagaatat ggaacggaac tgcagagccc cctgcaacat ccagatggaa    3660
gatcctacct tcaaagagaa ctaccggttc cacgccatca acggctacat catggacacc    3720
ctgcctggcc tggtgatggc ccaggaccag agaatccggt ggtatctgct gtccatgggc    3780
agcaacgaga atatccacag catccacttc agcggccacg tgttcaccgt gcggaagaaa    3840
gaagagtaca gatggcccct gtacaacctg taccccggcg tgttcgagac agtggagatg    3900
ctgcccagca aggccggcat ctggcgggtg gagtgtctga tcggcgagca cctgcacgct    3960
ggcatgagca ccctgtttct ggtgtacagc aacaagtgcc agacccact gggcatggcc    4020 tctggccaca tccgggactt ccagatcacc gcctccggcc agtacggcca gtgggccccc    4080
aagctggcca gactgcacta cagcggcagc atcaacgcct ggtccaccaa agagcccttc    4140
agctggatca aggtggacct gctggcccct atgatcatcc acggcattaa gacccagggc    4200
gccaggcaga agttcagcag cctgtacatc agccagttca tcatcatgta cagcctggac    4260
ggcaagaagt ggcagaccta ccggggcaac agcaccggca ccctgatggt gttcttcggc    4320
aatgtggaca gcagcggcat caagcacaac atcttcaacc ccccatcat tgcccggtac    4380 atccggctgc accccaccca ctacagcatt agatccacac tgagaatgga actgatgggc    4440
tgcgacctga actcctgcag catgcctctg ggcatggaaa gcaaggccat cagcgacgcc    4500
cagatcacag ccagcagcta cttcaccaac atgttcgcca cctggtcccc ctccaaggcc    4560
aggctgcacc tgcagggccg gtccaacgcc tggcggcctc aggtcaacaa ccccaaagaa    4620
tggctgcagg tggactttca gaaaaccatg aaggtgaccg gcgtgaccac ccagggcgtg    4680
aaaagcctgc tgaccagcat gtacgtgaaa gagtttctga tcagcagctc tcaggatggc    4740
caccagtgga cgctgttctt tcagaacggc aaggtgaaag tgttccaggg caaccaggac    4800
tccttcaccc ccgtggtgaa ctccctggac cccccctgc tgacccgcta cctgagaatc    4860 caccccagt cttgggtgca ccagatcgcc ctcaggatgg aagtcctggg atgtgaggcc    4920
caggatctgt actgatgagg atcc                                           4944
```

<210> SEQ ID NO 45
<211> LENGTH: 5078
<212> TYPE: DNA
<213> ORGANISM: Artificial Sequence
<220> FEATURE:
<223> OTHER INFORMATION: Flank-3xSERP-Flank-TTRe-Flank-TTRm-Flank-coFVIIIdeltaB-Flank-SV40 pA

<400> SEQUENCE: 45

```
gcggccgcgg tacgcggggg aggctgctgg tgaatattaa ccaaggtcac cccagttatc      60
```

```
ggaggagcaa acagggcta agtccaccgg gggaggctgc tggtgaatat taaccaaggt    120 cacccagtt atcggaggag caaacagggg ctaagtccac cggggaggc tgctggtgaa     180 tattaaccaa ggtcacccca gttatcggag gagcaaacag ggctaagtc cacggtaccc    240 actggagga tgttgagtaa gatgaaaac tactgatgac ccttgcagag acagagtatt     300
aggacatgtt tgaacagggg ccgggcgatc agcaggtagc tctagaggat ccccgtctgt   360
ctgcacattt cgtagagcga gtgttccgat actctaatct ccctaggcaa ggttcatatt   420
tgtgtaggtt acttattctc cttttgttga ctaagtcaat aatcagaatc agcaggtttg   480
gagtcagctt ggcagggatc agcagcctgg gttggaagga gggggtataa aagcccttc    540 accaggagaa gccgtcctag tatgcagatc gagctgtcca cctgcttttt tctgtgcctg   600
ctgcggttct gcttcagcgc cacccggcgg tactacctgg gcgccgtgga gctgtcctgg   660
gactacatgc agagcgacct gggcgagctg cccgtggacg cccggttccc ccccagagtg   720
cccaagagct ccccttcaa caccagcgtg gtgtacaaga aaaccctgtt cgtggagttc    780
accgaccacc tgttcaatat cgccaagccc aggcccccct ggatgggcct gctgggcccc   840
accatccagg ccgaggtgta cgacaccgtg gtgatcaccc tgaagaacat ggccagccac   900
cccgtgagcc tgcacgccgt gggcgtgagc tactggaagg ccagcgaggg cgccgagtac   960
gacgaccaga ccagccagcg ggagaaagaa gatgacaagg tgttccctgg cggcagccac   1020
acctacgtgt ggcaggtgct gaaagaaaac ggccccatgg cctccgaccc cctgtgcctg   1080
acctacagct acctgagcca cgtggacctg gtgaaggacc tgaacagcgg cctgatcggc   1140
gctctgctcg tctgccggga gggcagcctg gccaaagaga aacccagac cctgcacaag    1200 ttcatcctgc tgttcgccgt gttcgacgag ggcaagagct ggcacagcga dacaaagaac   1260
agcctgatgc aggaccggga cgccgcctct gccagagcct ggcccaagat gcacaccgtg   1320
aacggctacg tgaacagaag cctgcccggc ctgattggct gccaccggaa gagcgtgtac   1380
tggcacgtga tcggcatggg caccacaccc gaggtgcaca gcatctttct ggaagggcac   1440
acctttctgg tccggaacca ccggcaggcc agcctggaaa tcagccctat caccttcctg   1500
accgcccaga cactgctgat ggacctgggc cagttcctgc tgttttgcca catcagctct   1560
caccagcacg acggcatgga agcctacgtg aaggtggact cttgccccga ggaaccccag   1620
ctgcggatga agaacaacga ggaagccgag gactacgacg acgacctgac cgacagcgag   1680
atggacgtgg tgcggttcga cgacgacaac agccccagct tcatccagat cagaagcgtg   1740
gccaagaagc accccaagac ctgggtgcac tatatcgccg ccgaggaaga ggactgggac   1800
tacgcccccc tggtgctggc ccccgacgac agaagctaca agagccagta cctgaacaat   1860 ggccccagc ggatcggccg gaagtacaag aaagtgcggt tcatggccta caccgacgag    1920
acattcaaga cccgggaggc catccagcac gagagcggca tcctgggccc cctgctgtac   1980
ggcgaagtgg gcgacacact gctgatcatc ttcaagaacc aggctagccg gccctacaac   2040
atctaccccc acggcatcac cgacgtgcgg ccctgtaca gcaggcggct gcccaagggc    2100
gtgaagcacc tgaaggactt ccccatcctg cccggcgaga tcttcaagta caagtggacc   2160
gtgaccgtgg aggacggccc caccaagagc gaccccgat gcctgacccg gtactacagc    2220
agcttcgtga acatggaacg ggacctggcc tccgggctga tcggacctct gctgatctgc   2280
tacaaagaaa gcgtggacca gcggggcaac cagatcatga cgacaagcg gaacgtgatc    2340 ctgttcagcg tgttcgatga gaaccggtcc tggtatctga ccgagaacat ccagcggttt   2400
```

```
ctgcccaacc ctgccggcgt gcagctggaa gatcccgagt tccaggccag caacatcatg    2460
cactccatca atggctacgt gttcgactct ctgcagctct ccgtgtgtct gcacgaggtg    2520
gcctactggt acatcctgag catcggcgcc cagaccgact tcctgagcgt gttcttcagc    2580
ggctacacct tcaagcacaa gatggtgtac gaggacaccc tgaccctgtt ccctttcagc    2640
ggcgagacag tgttcatgag catggaaaac cccggcctgt ggattctggg ctgccacaac    2700
agcgacttcc ggaaccgggg catgaccgcc ctgctgaagg tgtccagctg cgacaagaac    2760
accggcgact actacgagga cagctacgag gatatcagcg cctacctgct gtccaagaac    2820
aacgccatcg aacccggag cttcagccag aacccccccg tgctgacgcg tcaccagcgg    2880
gagatcaccc ggacaaccct gcagtccgac caggaagaga tcgattacga cgacaccatc    2940
agcgtggaga tgaagaaaga ggatttcgat atctacgacg aggacgagaa ccagagcccc    3000
agaagcttcc agaagaaaac ccggcactac ttcattgccg ccgtggagag gctgtgggac    3060
tacggcatga gttctagccc ccacgtgctg cggaaccggg cccagagcgg cagcgtgccc    3120
cagttcaaga aagtggtgtt ccaggaattc acagacggca gcttcaccca gcctctgtat    3180
agaggcgagc tgaacgagca cctggggctg ctggggccct acatcagggc cgaagtggag    3240
gacaacatca tggtgacctt ccggaatcag gccagcagac cctactcctt ctacagcagc    3300
ctgatcagct acgaagagga ccagcggcag ggcgccgaac cccggaagaa cttcgtgaag    3360
cccaacgaaa ccaagaccta cttctggaaa gtgcagcacc acatggcccc caccaaggac    3420
gagttcgact gcaaggcctg gcctacttc agcgacgtgg atctggaaaa ggacgtgcac    3480
tctggactga ttggcccact cctggtctgc cacactaaca ccctcaaccc cgcccacggc    3540
cgccaggtga ccgtgcagga attcgccctg ttcttcacca tcttcgacga gacaaagtcc    3600
tggtacttca ccgagaatat ggaacggaac tgcagagccc cctgcaacat ccagatggaa    3660
gatcctacct tcaaagagaa ctaccggttc cacgccatca acggctacat catggacacc    3720
ctgcctggcc tggtgatggc ccaggaccag agaatccggt ggtatctgct gtccatgggc    3780
agcaacgaga atatccacag catccacttc agcggccacg tgttcaccgt gcggaagaaa    3840
gaagagtaca gatggccct gtacaacctg taccccggcg tgttcgagac agtggagatg    3900
ctgcccagca aggccggcat ctggcgggtg gagtgtctga tcggcgagca cctgcacgct    3960
ggcatgagca ccctgtttct ggtgtacagc aacaagtgcc agacccccact gggcatggcc    4020 tctggccaca tccgggactt ccagatcacc gcctccggcc agtacggcca gtgggcccc    4080 aagctggcca gactgcacta cagcggcagc atcaacgcct ggtccaccaa agagcccttc    4140
agctggatca aggtggacct gctggcccct atgatcatcc acggcattaa gacccagggc    4200
gccaggcaga agttcagcag cctgtacatc agccagttca tcatcatgta cagcctggac    4260
ggcaagaagt ggcagaccta ccggggcaac agcaccggca ccctgatggt gttcttcggc    4320
aatgtggaca gcagcggcat caagcacaac atcttcaacc cccccatcat tgcccggtac    4380
atccggctgc accccacca ctacagcatt agatccacac tgagaatgga actgatgggc    4440
tgcgacctga actcctgcag catgcctctg ggcatggaaa gcaaggccat cagcgacgcc    4500
cagatcacag ccagcagcta cttcaccaac atgttcgcca cctggtcccc ctccaaggcc    4560
aggctgcacc tgcagggccg gtccaacgcc tggcggcctc aggtcaacaa ccccaaagaa    4620
tggctgcagg tggactttca gaaaaccatg aaggtgaccg gcgtgaccac ccagggcgtg    4680
aaaagcctgc tgaccagcat gtacgtgaaa gagtttctga tcagcagctc tcaggatggc    4740
caccagtgga ccctgttctt tcagaacggc aaggtgaaag tgttccaggg caaccaggac    4800
```

```
tccttcaccc ccgtggtgaa ctccctggac ccccccctgc tgaccgccta cctgagaatc    4860
cacccccagt cttgggtgca ccagatcgcc ctcaggatgg aagtcctggg atgtgaggcc    4920
caggatctgt actgatgagg atccatgctt tatttgtgaa atttgtgatg ctattgcttt    4980
atttgtaacc attataagct gcaataaaca agttaacaac aacaattgca ttcattttat    5040
gtttcaggtt caggggagg tgtgggaggt tttttaaa                             5078
```

<210> SEQ ID NO 46
<211> LENGTH: 5096
<212> TYPE: DNA
<213> ORGANISM: Artificial Sequence
<220> FEATURE:
<223> OTHER INFORMATION: Flank-3xSERP-Flank-TTRe-Flank-TTRm-Flank-
      coFVIIIdeltaB-Flank-SV40 pA-Flank

<400> SEQUENCE: 46

```
gcggccgcgg tacgcggggg aggctgctgg tgaatattaa ccaaggtcac cccagttatc      60
ggaggagcaa acagggcta agtccaccgg gggaggctgc tggtgaatat taaccaaggt     120 cacccccagtt atcggaggag caaacagggg ctaagtccac cggggaggc tgctggtgaa     180 tattaaccaa ggtcaccca gttatcggag gagcaaacag gggctaagtc cacggtaccc     240
actgggagga tgttgagtaa gatgaaaaac tactgatgac ccttgcagag acagagtatt     300
aggacatgtt tgaacagggg ccgggcgatc agcaggtagc tctagaggat ccccgtctgt     360
ctgcacattt cgtagagcga gtgttccgat actctaatct ccctaggcaa ggttcatatt     420
tgtgtaggtt acttattctc cttttgttga ctaagtcaat aatcagaatc agcaggtttg     480
gagtcagctt ggcagggatc agcagcctgg gttggaagga gggggtataa agcccccttc     540
accaggagaa gccgtcctag tatgcagatc gagctgtcca cctgcttttt tctgtgcctg     600
ctgcggttct gcttcagcgc cacccggcgg tactacctgg gcgccgtgga gctgtcctgg     660
gactacatgc agagcgacct gggcgagctg cccgtggacg cccggttccc ccccagagtg     720
cccaagagct tccccttcaa caccagcgtg gtgtacaaga aaaccctgtt cgtggagttc     780
accgaccacc tgttcaatat cgccaagccc aggccccccct ggatgggcct gctgggcccc     840
accatccagg ccgaggtgta cgacaccgtg gtgatcaccc tgaagaacat ggccagccac     900
cccgtgagcc tgcacgccgt gggcgtgagc tactggaagg ccagcgaggg cgccgagtac     960
gacgaccaga ccagccagcg ggagaaagaa gatgacaagg tgttccctgg cggcagccac    1020
acctacgtgt ggcaggtgct gaaagaaaac ggccccatgg cctccgaccc cctgtgcctg    1080
acctacagct acctgagcca cgtggacctg gtgaaggacc tgaacagcgg cctgatcggc    1140
gctctgctcg tctgccggga gggcagcctg gccaaagaga aaacccagac cctgcacaag    1200
ttcatcctgc tgttcgccgt gttcgacgag ggcaagagct ggcacagcga gacaaagaac    1260
agcctgatgc aggaccggga cgccgcctct gccagagcct ggcccaagat gcacaccgtg    1320
aacggctacg tgaacagaag cctgcccggc ctgattggct gccaccggaa gagcgtgtac    1380
tggcacgtga tcggcatggg caccacaccc gaggtgcaca gcatctttct ggaagggcac    1440 accttctctgg tccggaacca ccggcaggcc agcctggaaa tcagcccta caccttcctg    1500 accgcccaga cactgctgat ggacctgggc cagttcctgc tgttttgcca catcagctct    1560
caccagcacg acggcatgga agcctacgtg aaggtggact cttgccccga ggaaccccag    1620
ctgcggatga agaacaacga ggaagccgag gactacgacg acgacctgac cgacagcgag    1680
atggacgtgg tgcggttcga cgacgacaac agccccagct tcatccagat cagaagcgtg    1740
```

```
gccaagaagc accccaagac ctgggtgcac tatatcgccg ccgaggaaga ggactgggac    1800
tacgccccc  tggtgctggc ccccgacgac agaagctaca agagccagta cctgaacaat    1860
ggcccccagc ggatcggccg gaagtacaag aaagtgcggt tcatggccta caccgacgag    1920
acattcaaga cccgggaggc catccagcac gagagcggca tcctgggccc cctgctgtac    1980
ggcgaagtgg gcgacacact gctgatcatc ttcaagaacc aggctagccg gccctacaac    2040
atctaccccc acggcatcac cgacgtgcgg ccctgtaca gcaggcggct gcccaagggc     2100
gtgaagcacc tgaaggactt ccccatcctg cccggcgaga tcttcaagta caagtggacc    2160
gtgaccgtgg aggacggccc caccaagagc accccagat gcctgacccg gtactacagc     2220
agcttcgtga acatggaacg ggacctggcc tccgggctga tcggacctct gctgatctgc    2280
tacaaagaaa gcgtggacca gcggggcaac cagatcatga gcgacaagcg gaacgtgatc    2340
ctgttcagcg tgttcgatga gaaccggtcc tggtatctga ccgagaacat ccagcggttt    2400
ctgcccaacc tgccggcgt gcagctggaa gatcccgagt tccaggccag caacatcatg     2460
cactccatca atggctacgt gttcgactct ctgcagctct ccgtgtgtct gcacgaggtg    2520
gcctactggt acatcctgag catcggcgcc cagaccgact tcctgagcgt gttcttcagc    2580
ggctacacct tcaagcacaa gatggtgtac gaggacaccc tgaccctgtt ccctttcagc    2640
ggcgagacag tgttcatgag catggaaaac cccggcctgt ggattctggg ctgccacaac    2700
agcgacttcc ggaaccgggg catgaccgcc ctgctgaagg tgtccagctg cgacaagaac    2760
accggcgact actacgagga cagctacgag gatatcagcg cctacctgct gtccaagaac    2820
aacgccatcg aaccccggag cttcagccag aaccccccg tgctgacgcg tcaccagcgg     2880
gagatcaccc ggacaaccct gcagtccgac caggaagaga tcgattacga cgacaccatc    2940
agcgtggaga tgaagaaaga ggatttcgat atctacgacg aggacgagaa ccagagcccc    3000
agaagcttcc agaagaaaac ccggcactac ttcattgccg ccgtggagag gctgtgggac    3060
tacggcatga gttctagccc ccacgtgctg cggaaccggg cccagagcgg cagcgtgccc    3120
cagttcaaga agtggtgtt ccaggaattc acagacggca gcttcaccca gcctctgtat     3180
agaggcgagc tgaacgagca cctggggctg ctggggccct acatcagggc cgaagtggag    3240
gacaacatca tggtgacctt ccggaatcag gccagcagac cctactcctt ctacagcagc    3300
ctgatcagct acgaagagga ccagcggcag ggcgccgaac cccggaagaa cttcgtgaag    3360
cccaacgaaa ccaagaccta cttctggaaa gtgcagcacc acatggcccc caccaaggac    3420
gagttcgact gcaaggcctg gcctacttc agcgacgtgg atctggaaaa ggacgtgcac     3480
tctggactga ttggcccact cctggtctgc cacactaaca ccctcaaccc cgcccacggc    3540
cgccaggtga ccgtgcagga attcgccctg ttcttcacca tcttcgacga acaaagtcc    3600
tggtacttca ccgagaatat ggaacggaac tgcagagccc cctgcaacat ccagatggaa    3660
gatcctacct tcaaagagaa ctaccggttc acgccatca acggctacat catggacacc    3720
ctgcctggcc tggtgatggc ccaggaccag agaatccggt ggtatctgct gtccatgggc    3780
agcaacgaga atatccacag catccacttc agcggccacg tgttcaccgt gcggaagaaa    3840
gaagagtaca agatggccct gtacaacctg taccccggcg tgttcgagac agtggagatg    3900
ctgcccagca aggccggcat ctggcgggtg gagtgtctga tcggcgagca cctgcacgct    3960
ggcatgagca cctgtttct ggtgtacagc aacaagtgcc agaccccact gggcatggcc    4020
tctggccaca tccgggactt ccagatcacc gcctccggcc agtacggcca gtgggcccc    4080
```

```
aagctggcca gactgcacta cagcggcagc atcaacgcct ggtccaccaa agagcccttc    4140
agctggatca aggtggacct gctggcccct atgatcatcc acggcattaa gacccagggc    4200
gccaggcaga agttcagcag cctgtacatc agccagttca tcatcatgta cagcctggac    4260
ggcaagaagt ggcagaccta ccggggcaac agcaccggca ccctgatggt gttcttcggc    4320
aatgtggaca gcagcggcat caagcacaac atcttcaacc ccccatcat tgcccggtac     4380 atccggctgc acccccaccca ctacagcatt agatccacac tgagaatgga actgatgggc   4440
tgcgacctga actcctgcag catgcctctg ggcatggaaa gcaaggccat cagcgacgcc    4500
cagatcacag ccagcagcta cttcaccaac atgttcgcca cctggtcccc ctccaaggcc    4560
aggctgcacc tgcagggccg gtccaacgcc tggcggcctc aggtcaacaa ccccaaagaa    4620
tggctgcagg tggactttca gaaaaccatg aaggtgaccg cgtgaccac ccagggcgtg     4680 aaaagcctgc tgaccagcat gtacgtgaaa gagtttctga tcagcagctc tcaggatggc    4740
caccagtgga ccctgttctt tcagaacggc aaggtgaaag tgttccaggg caaccaggac    4800
tccttcaccc ccgtggtgaa ctccctggac cccccctgc tgacccgcta cctgagaatc     4860
cacccccagt cttgggtgca ccagatcgcc ctcaggatgg aagtcctggg atgtgaggcc    4920
caggatctgt actgatgagg atccatgctt tatttgtgaa atttgtgatg ctattgcttt    4980
atttgtaacc attataagct gcaataaaca agttaacaac aacaattgca ttcatttat     5040 gtttcaggtt caggggaagg tgtgggaggt tttttaaact cgagatccac ggccgc        5096
```

<210> SEQ ID NO 47
<211> LENGTH: 4993
<212> TYPE: DNA
<213> ORGANISM: Artificial Sequence
<220> FEATURE:
<223> OTHER INFORMATION: Flank-3xSERP-Flank-TTRe-Flank-TTRm-Flank-
      coFVIIIdeltaB-Flank-Synt .pA

<400> SEQUENCE: 47

```
gcggccgcgg tacgcggggg aggctgctgg tgaatattaa ccaaggtcac cccagttatc      60
ggaggagcaa acaggggcta agtccaccgg gggaggctgc tggtgaatat taaccaaggt    120
caccccagtt atcggaggag caaacagggg ctaagtccac cggggaggc tgctggtgaa     180 tattaaccaa ggtcacccca gttatcggag gagcaaacag gggctaagtc cacggtaccc    240
actgggagga tgttgagtaa gatggaaaac tactgatgac ccttgcagag acagagtatt    300
aggacatgtt tgaacagggg ccgggcgatc agcaggtagc tctagaggat ccccgtctgt    360
ctgcacattt cgtagagcga gtgttccgat actctaatct ccctaggcaa ggttcatatt    420
tgtgtaggtt acttattctc cttttgttga ctaagtcaat aatcagaatc agcaggtttg    480
gagtcagctt gcagggatc agcagcctgg gttggaagga gggggtataa agcccttc      540 accaggagaa gccgtcctag tatgcagatc gagctgtcca cctgctttt tctgtgcctg    600 ctgcggttct gcttcagcgc caccggcgg tactacctgg gcgccgtgga gctgtcctgg    660
gactacatgc agagcgacct gggcgagctg cccgtggacg cccggttccc ccccagagtg    720
cccaagagct tccccttcaa caccagcgtg gtgtacaaga aaccctgtt cgtggagttc    780 accgaccacc tgttcaatat cgccaagccc aggcccccct ggatgggcct gctgggcccc    840
accatccagg ccgaggtgta cgacaccgtg gtgatcaccc tgaagaacat ggccagccac    900
cccgtgagcc tgcacgccgt gggcgtgagc tactggaagg ccagcgaggg cgccgagtac    960
gacgaccaga ccagccagcg ggagaaagaa gatgacaagg tgttccctgg cggcagccac   1020
```

```
acctacgtgt ggcaggtgct gaaagaaaac ggccccatgg cctccgaccc cctgtgcctg    1080
acctacagct acctgagcca cgtggacctg gtgaaggacc tgaacagcgg cctgatcggc    1140
gctctgctcg tctgccggga gggcagcctg gccaaagaga aacccagac cctgcacaag    1200 ttcatcctgc tgttcgccgt gttcgacgag ggcaagagct ggcacagcga dacaaagaac    1260
agcctgatgc aggaccggga cgccgcctct gccagagcct ggcccaagat gcacaccgtg    1320
aacggctacg tgaacagaag cctgcccggc ctgattggct gccaccggaa gagcgtgtac    1380
tggcacgtga tcggcatggg caccacaccc gaggtgcaca gcatctttct ggaagggcac    1440
acctttctgg tccggaacca ccggcaggcc agcctggaaa tcagcccat caccttcctg    1500 accgcccaga cactgctgat ggacctgggc cagttcctgc tgttttgcca catcagctct    1560
caccagcacg acggcatgga agcctacgtg aaggtggact cttgccccga ggaaccccag    1620
ctgcggatga agaacaacga ggaagccgag gactacgacg acgacctgac cgacagcgag    1680
atggacgtgg tgcggttcga cgacgacaac agccccagct tcatccagat cagaagcgtg    1740
gccaagaagc accccaagac ctgggtgcac tatatcgccg ccgaggaaga ggactgggac    1800 tacgccccc tggtgctggc ccccgacgac agaagctaca agagccagta cctgaacaat    1860 ggccccagc ggatcggccg gaagtacaag aaagtgcggt tcatggccta caccgacgag    1920
acattcaaga cccgggaggc catccagcac gagagcggca tcctgggccc cctgctgtac    1980
ggcgaagtgg gcgacacact gctgatcatc ttcaagaacc aggctagccg gccctacaac    2040
atctaccccc acggcatcac cgacgtgcgg cccctgtaca gcaggcggct gcccaagggc    2100
gtgaagcacc tgaaggactt ccccatcctg cccggcgaga tcttcaagta caagtggacc    2160
gtgaccgtgg aggacggccc caccaagagc gaccccagat gcctgacccg gtactacagc    2220
agcttcgtga acatggaacg ggacctggcc tccgggctga tcggacctct gctgatctgc    2280
tacaaagaaa gcgtggacca gcggggcaac cagatcatga gcgacaagcg gaacgtgatc    2340
ctgttcagcg tgttcgatga aaccggtcc tggtatctga ccgagaacat ccagcggttt    2400
ctgcccaacc ctgccggcgt gcagctggaa gatcccgagt tccaggccag caacatcatg    2460
cactccatca atggctacgt gttcgactct ctgcagctct ccgtgtgtct gcacgaggtg    2520
gcctactggt acatcctgag catcggcgcc cagaccgact tcctgagcgt gttcttcagc    2580
ggctacacct tcaagcacaa gatggtgtac gaggacaccc tgaccctgtt cccttttcagc    2640 ggcgagacag tgttcatgag catggaaaac cccggcctgt ggattctggg ctgccacaac    2700
agcgacttcc ggaaccgggg catgaccgcc ctgctgaagg tgtccagctg cgacaagaac    2760
accggcgact actacgagga cagctacgag gatatcagcg cctacctgct gtccaagaac    2820
aacgccatcg aacccggag cttcagccag aaccccccg tgctgacgcg tcaccagcgg    2880
gagatcaccc ggacaaccct gcagtccgac caggaagaga tcgattacga cgacaccatc    2940
agcgtgggag tgaagaaaga ggatttcgat atctacgacg aggacgagaa ccagagcccc    3000
agaagcttcc agaagaaaac ccggcactac ttcattgccg ccgtggagag ctgtgggac    3060 tacggcatga gttctagccc ccacgtgctg cggaaccggg cccagagcgg cagcgtgccc    3120
cagttcaaga aagtggtgtt ccaggaattc acagacggca gcttcaccca gcctctgtat    3180
agaggcgagc tgaacgagca cctggggctg ctggggccct acatcagggc cgaagtggag    3240
gacaacatca tggtgacctt ccggaatcag gccagcagac cctactcctt ctacagcagc    3300
ctgatcagct acgaagagga ccagcggcag ggcgccgaac cccggaagaa cttcgtgaag    3360
cccaacgaaa ccaagaccta cttctggaaa gtgcagcacc acatggcccc caccaaggac    3420
```

-continued

```
gagttcgact gcaaggcctg ggcctacttc agcgacgtgg atctggaaaa ggacgtgcac     3480
tctggactga ttggcccact cctggtctgc cacactaaca ccctcaaccc cgcccacggc     3540
cgccaggtga ccgtgcagga attcgccctg ttcttcacca tcttcgacga gacaaagtcc     3600
tggtacttca ccgagaatat ggaacggaac tgcagagccc cctgcaacat ccagatggaa     3660
gatcctacct tcaaagagaa ctaccggttc cacgccatca acggctacat catggacacc     3720
ctgcctggcc tggtgatggc ccaggaccag agaatccggt ggtatctgct gtccatgggc     3780
agcaacgaga atatccacag catccacttc agcggccacg tgttcaccgt gcggaagaaa     3840
gaagagtaca gatggcccct gtacaacctg taccccggcg tgttcgagac agtggagatg     3900
ctgcccagca aggccggcat ctggcgggtg gagtgtctga tcggcgagca cctgcacgct     3960
ggcatgagca ccctgtttct ggtgtacagc aacaagtgcc agaccccact gggcatggcc     4020
tctggccaca tccgggactt ccagatcacc gcctccggcc agtacggcca gtgggccccc     4080
aagctggcca gactgcacta cagcggcagc atcaacgcct ggtccaccaa agagcccttc     4140
agctggatca aggtggacct gctggcccct atgatcatcc acggcattaa gacccagggc     4200
gccaggcaga agttcagcag cctgtacatc agccagttca tcatcatgta cagcctggac     4260
ggcaagaagt ggcagaccta ccggggcaac agcaccggca ccctgatggt gttcttcggc     4320
aatgtggaca gcagcggcat caagcacaac atcttcaacc cccccatcat gcccggtac      4380 atccggctgc accccaccca ctacagcatt agatccacac tgagaatgga actgatgggc     4440
tgcgacctga actcctgcag catgcctctg gcatggaaa gcaaggccat cagcgacgcc      4500
cagatcacag ccagcagcta cttcaccaac atgttcgcca cctggtcccc ctccaaggcc     4560
aggctgcacc tgcagggccg gtccaacgcc tggcggcctc aggtcaacaa ccccaaagaa     4620
tggctgcagg tggactttca gaaaaccatg aaggtgaccg cgtgaccac ccagggcgtg      4680 aaaagcctgc tgaccagcat gtacgtgaaa gagtttctga tcagcagctc tcaggatggc     4740
caccagtgga ccctgttctt tcagaacggc aaggtgaaag tgttccaggg caaccaggac     4800
tccttcaccc ccgtggtgaa ctccctggac cccccctgc tgacccgcta cctgagaatc      4860
cacccccagt cttgggtgca ccagatcgcc ctcaggatgg aagtcctggg atgtgaggcc     4920
caggatctgt actgatgagg atccaataaa agatctttat tttcattaga tctgtgtgtt     4980
ggttttttgt gtg                                                        4993
```

<210> SEQ ID NO 48
<211> LENGTH: 5011
<212> TYPE: DNA
<213> ORGANISM: Artificial Sequence
<220> FEATURE:
<223> OTHER INFORMATION: Flank-3xSERP-Flank-TTRe-Flank-TTRm-Flank-
     coFVIIIdeltaB-Flank- SyntpA-Flank

<400> SEQUENCE: 48

```
gcggccgcgg tacgcggggg aggctgctgg tgaatattaa ccaaggtcac cccagttatc       60
ggaggagcaa acaggggcta agtccaccgg gggaggctgc tggtgaatat taaccaaggt      120
caccccagtt atcggaggag caaacagggg ctaagtccac cggggaggc tgctggtgaa       180 tattaaccaa ggtcaccccca gttatcggag gagcaaacag gggctaagtc cacggtaccc     240
actgggagga tgttgagtaa gatggaaaac tactgatgac ccttgcagag acagagtatt     300
aggacatgtt tgaacagggg ccgggcgatc agcaggtagc tctagaggat ccccgtctgt      360
ctgcacattt cgtagagcga gtgttccgat actctaatct ccctaggcaa ggttcatatt     420
```

-continued

```
tgtgtaggtt acttattctc cttttgttga ctaagtcaat aatcagaatc agcaggtttg      480
gagtcagctt ggcagggatc agcagcctgg gttggaagga gggggtataa aagccccttc      540
accaggagaa gccgtcctag tatgcagatc gagctgtcca cctgcttttt tctgtgcctg      600
ctgcggttct gcttcagcgc cacccggcgg tactacctgg gcgccgtgga gctgtcctgg      660
gactacatgc agagcgacct gggcgagctg cccgtggacg cccggttccc ccccagagtg      720
cccaagagct tccccttcaa caccagcgtg gtgtacaaga aaccctgtt cgtggagttc       780 accgaccacc tgttcaatat cgccaagccc aggcccccct ggatgggcct gctgggcccc      840
accatccagg ccgaggtgta cgacaccgtg gtgatcaccc tgaagaacat ggccagccac      900
cccgtgagcc tgcacgccgt gggcgtgagc tactggaagg ccagcgaggg cgccgagtac      960
gacgaccaga ccagccagcg ggagaaagaa gatgacaagg tgttccctgg cggcagccac     1020
acctacgtgt ggcaggtgct gaaagaaaac ggccccatgg cctccgaccc cctgtgcctg     1080
acctacagct acctgagcca cgtggacctg gtgaaggacc tgaacagcgg cctgatcggc     1140
gctctgctcg tctgccggga gggcagcctg gccaagagaa aacccagac cctgcacaag      1200 ttcatcctgc tgttcgccgt gttcgacgag ggcaagagct ggcacagcga gacaaagaac     1260
agcctgatgc aggaccggga cgccgcctct gccagagcct ggcccaagat gcacaccgtg     1320
aacggctacg tgaacagaag cctgcccggc ctgattggct gccaccggaa gagcgtgtac     1380
tggcacgtga tcggcatggg caccacaccc gaggtgcaca gcatctttct ggaagggcac     1440
acctttctgg tccggaacca ccggcaggcc agcctggaaa tcagccctat caccttcctg     1500
accgcccaga cactgctgat ggacctgggc cagttcctgc tgttttgcca catcagctct     1560
caccagcacg acggcatgga agcctacgtg aaggtggact cttgccccga ggaaccccag     1620
ctgcggatga agaacaacga ggaagccgag gactacgacg acgacctgac cgacagcgag     1680
atggacgtgg tgcggttcga cgacgacaac agccccagct tcatccagat cagaagcgtg     1740
gccaagaagc accccaagac ctgggtgcac tatatcgccg ccgaggaaga ggactgggac     1800
tacgcccccc tggtgctggc ccccgacgac agaagctaca agagccagta cctgaacaat     1860
ggcccccagc ggatcggccg gaagtacaag aaagtgcggt tcatggccta caccgacgag     1920
acattcaaga cccggaggc catccagcac gagagcggca tcctgggccc cctgctgtac     1980
ggcgaagtgg gcgacacact gctgatcatc ttcaagaacc aggctagccg gccctacaac     2040 atctacccc acggcatcac cgacgtgcgg cccctgtaca gcaggcggct gcccaagggc     2100
gtgaagcacc tgaaggactt ccccatcctg cccggcgaga tcttcaagta caagtggacc     2160
gtgaccgtgg aggacggccc caccaagagc gaccccagat gcctgacccg gtactacagc     2220
agcttcgtga acatggaacg ggacctggcc tccgggctga tcggacctct gctgatctgc     2280
tacaaagaaa gcgtggacca gcggggcaac cagatcatga gcgacaagcg gaacgtgatc     2340
ctgttcagcg tgttcgatga gaaccggtcc tggtatctga ccgagaacat ccagcggttt     2400
ctgcccaacc ctgccggcgt gcagctggaa gatcccgagt ccaggccag caacatcatg      2460 cactccatca atggctacgt gttcgactct ctgcagctct ccgtgtgtct gcacgaggtg     2520
gcctactggt acatcctgag catcggcgcc cagaccgact tcctgagcgt gttcttcagc     2580
ggctacacct tcaagcacaa gatggtgtac gaggacaccc tgaccctgtt ccctttcagc     2640
ggcgagacag tgttcatgag catggaaaac cccggcctgt ggattctggg ctgccacaac     2700
agcgacttcc ggaaccgggg catgaccgcc ctgctgaagg tgtccagctg cgacaagaac     2760
```

| | |
|---|---|
| accggcgact actacgagga cagctacgag gatatcagcg cctacctgct gtccaagaac | 2820 |
| aacgccatcg aacccggag cttcagccag aaccccccg tgctgacgcg tcaccagcgg | 2880 |
| gagatcaccc ggacaaccct gcagtccgac caggaagaga tcgattacga cgacaccatc | 2940 |
| agcgtggaga tgaagaaaga ggatttcgat atctacgacg aggacgagaa ccagagcccc | 3000 |
| agaagcttcc agaagaaaac ccggcactac ttcattgccg ccgtggagag gctgtgggac | 3060 |
| tacggcatga gttctagccc ccacgtgctg cggaaccggg cccagagcgg cagcgtgccc | 3120 |
| cagttcaaga agtggtgtt ccaggaattc acagacggca gcttcaccca gcctctgtat | 3180 |
| agaggcgagc tgaacgagca cctggggctg ctggggccct acatcagggc cgaagtggag | 3240 |
| gacaacatca tggtgacctt ccggaatcag gccagcagac cctactcctt ctacagcagc | 3300 |
| ctgatcagct acgaagagga ccagcggcag ggcgccgaac cccggaagaa cttcgtgaag | 3360 |
| cccaacgaaa ccaagaccta cttctggaaa gtgcagcacc acatggcccc caccaaggac | 3420 |
| gagttcgact gcaaggcctg gcctacttc agcgacgtgg atctggaaaa ggacgtgcac | 3480 |
| tctggactga ttggcccact cctggtctgc cacactaaca ccctcaaccc cgcccacggc | 3540 |
| cgccaggtga ccgtgcagga attcgccctg ttcttcacca tcttcgacga gacaaagtcc | 3600 |
| tggtacttca ccgagaatat ggaacggaac tgcagagccc cctgcaacat ccagatggaa | 3660 |
| gatcctacct tcaaagagaa ctaccggttc cacgccatca acggctacat catggacacc | 3720 |
| ctgcctggcc tggtgatggc ccaggaccag agaatccggt ggtatctgct gtccatgggc | 3780 |
| agcaacgaga atatccacag catccacttc agcggccacg tgttcaccgt gcggaagaaa | 3840 |
| gaagagtaca gatggcct gtacaacctg taccccggcg tgttcgagac agtggagatg | 3900 |
| ctgcccagca aggccggcat ctggcgggtg gagtgtctga tcggcgagca cctgcacgct | 3960 |
| ggcatgagca ccctgtttct ggtgtacagc aacaagtgcc agaccccact gggcatggcc | 4020 |
| tctggccaca tccgggactt ccagatcacc gcctccggcc agtacggcca gtgggccccc | 4080 |
| aagctggcca gactgcacta cagcggcagc atcaacgcct ggtccaccaa agagcccttc | 4140 |
| agctggatca aggtggacct gctggcccct atgatcatcc acggcattaa gacccagggc | 4200 |
| gccaggcaga agttcagcag cctgtacatc agccagttca tcatcatgta cagcctggac | 4260 |
| ggcaagaagt ggcagaccta ccggggcaac agcaccggca ccctgatggt gttcttcggc | 4320 |
| aatgtggaca gcagcggcat caagcacaac atcttcaacc cccccatcat tgcccggtac | 4380 |
| atccggctgc acccaccca ctacagcatt agatccacac tgagaatgga actgatgggc | 4440 |
| tgcgacctga actcctgcag catgcctctg ggcatggaaa gcaaggccat cagcgacgcc | 4500 |
| cagatcacag ccagcagcta cttcaccaac atgttcgcca cctggtcccc ctccaaggcc | 4560 |
| aggctgcacc tgcagggccg gtccaacgcc tggcggcctc aggtcaacaa ccccaaagaa | 4620 |
| tggctgcagg tggactttca gaaaaccatg aaggtgaccg cgtgaccac ccagggcgtg | 4680 |
| aaaagcctgc tgaccagcat gtacgtgaaa gagtttctga tcagcagctc tcaggatggc | 4740 |
| caccagtgga ccctgttctt tcagaacggc aaggtgaaag tgttccaggg caaccaggac | 4800 |
| tccttcaccc ccgtggtgaa ctccctggac cccccctgc tgaccgcta cctgagaatc | 4860 |
| cacccccagt cttgggtgca ccagatcgcc ctcaggatgg aagtcctggg atgtgaggcc | 4920 |
| caggatctgt actgatgagg atccaataaa agatctttat tttcattaga tctgtgtgtt | 4980 |
| ggttttttgt gtgctcgaga tccacggccg c | 5011 |

<210> SEQ ID NO 49
<211> LENGTH: 653

<212> TYPE: DNA
<213> ORGANISM: Artificial Sequence
<220> FEATURE:
<223> OTHER INFORMATION: Flank-3xSERP-Flank-TTRe-Flank-TTRm-MVM-Flank

<400> SEQUENCE: 49

```
gcggccgcgg tacgcggggg aggctgctgg tgaatattaa ccaaggtcac cccagttatc      60
ggaggagcaa acaggggcta agtccaccgg gggaggctgc tggtgaatat taaccaaggt     120
cacccccagtt atcggaggag caaacagggg ctaagtccac cggggaggc tgctggtgaa     180
tattaaccaa ggtcaccccca gttatcggag gagcaaacag gggctaagtc cacggtaccc     240
actggggagga tgttgagtaa gatgaaaaac tactgatgac ccttgcagag acagagtatt     300
aggacatgtt tgaacagggg ccgggcgatc agcaggtagc tctagaggat ccccgtctgt     360
ctgcacatttt cgtagagcga gtgttccgat actctaatct ccctaggcaa ggttcatatt     420
tgtgtaggtt acttattctc cttttgttga ctaagtcaat aatcagaatc agcaggtttg     480
gagtcagctt ggcagggatc agcagcctgg gttggaagga gggggtataa aagccccttc     540
accaggagaa gccgtcaaga ggtaagggtt taagggatgg ttggttggtg gggtattaat     600
gtttaattac ctggagcacc tgcctgaaat cacttttttt caggttggct agt             653
```

<210> SEQ ID NO 50
<211> LENGTH: 5030
<212> TYPE: DNA
<213> ORGANISM: Artificial Sequence
<220> FEATURE:
<223> OTHER INFORMATION: Flank-3xSERP-Flank-TTRe-Flank-TTRm-MVM-Flank-coFVIIIdeltaB

<400> SEQUENCE: 50

```
gcggccgcgg tacgcggggg aggctgctgg tgaatattaa ccaaggtcac cccagttatc      60
ggaggagcaa acaggggcta agtccaccgg gggaggctgc tggtgaatat taaccaaggt     120
cacccccagtt atcggaggag caaacagggg ctaagtccac cggggaggc tgctggtgaa     180
tattaaccaa ggtcaccccca gttatcggag gagcaaacag gggctaagtc cacggtaccc     240
actggggagga tgttgagtaa gatgaaaaac tactgatgac ccttgcagag acagagtatt     300
aggacatgtt tgaacagggg ccgggcgatc agcaggtagc tctagaggat ccccgtctgt     360
ctgcacatttt cgtagagcga gtgttccgat actctaatct ccctaggcaa ggttcatatt     420
tgtgtaggtt acttattctc cttttgttga ctaagtcaat aatcagaatc agcaggtttg     480
gagtcagctt ggcagggatc agcagcctgg gttggaagga gggggtataa aagccccttc     540
accaggagaa gccgtcaaga ggtaagggtt taagggatgg ttggttggtg gggtattaat     600
gtttaattac ctggagcacc tgcctgaaat cacttttttt caggttggct agtatgcaga     660
tcgagctgtc cacctgctttt tttctgtgcc tgctgcggtt ctgcttcagc gccacccggc     720
ggtactacct gggcgccgtg gagctgtcct gggactacat gcagagcgac ctgggcgagc     780
tgcccgtgga cgcccggttc ccccccagag tgcccaagag cttccccttc aacaccagcg     840
tggtgtacaa gaaaaccctg ttcgtggagt tcaccgacca cctgttcaat atcgccaagc     900
ccaggccccc ctggatgggc ctgctgggcc ccaccatcca ggccgaggtg tacgacaccg     960
tggtgatcac cctgaagaac atggccagcc accccgtgag cctgcacgcc gtgggcgtga    1020
gctactggaa ggcagcgag ggcgccgagt acgacgacca gaccagccag cgggagaaag    1080
aagatgacaa ggtgttccct ggcggcagcc acacctacgt gtggcaggtg ctgaaagaaa    1140
acggccccat ggcctccgac ccctgtgcc tgacctacag ctacctgagc cacgtggacc    1200
```

```
tggtgaagga cctgaacagc ggcctgatcg gcgctctgct cgtctgccgg gagggcagcc    1260
tggccaaaga gaaaacccag accctgcaca agttcatcct gctgttcgcc gtgttcgacg    1320
agggcaagag ctggcacagc gagacaaaga acagcctgat gcaggaccgg gacgccgcct    1380
ctgccagagc ctggcccaag atgcacaccg tgaacggcta cgtgaacaga agcctgcccg    1440
gcctgattgg ctgccaccgg aagagcgtgt actggcacgt gatcggcatg ggcaccacac    1500
ccgaggtgca cagcatcttt ctggaagggc acacctttct ggtccggaac caccggcagg    1560
ccagcctgga aatcagccct atcaccttcc tgaccgccca gacactgctg atggacctgg    1620
gccagttcct gctgttttgc cacatcagct ctcaccagca cgacggcatg gaagcctacg    1680
tgaaggtgga ctcttgcccc gaggaacccc agctgcggat gaagaacaac gaggaagccg    1740
aggactacga cgacgacctg accgacagcg agatggacgt ggtgcggttc gacgacgaca    1800
acagccccag cttcatccag atcagaagcg tggccaagaa gcaccccaag acctgggtgc    1860
actatatcgc cgccgaggaa gaggactggg actacgcccc cctggtgctg gcccccgacg    1920
acagaagcta caagagccag tacctgaaca atggccccca gcggatcggc cggaagtaca    1980
agaaagtgcg gttcatggcc tacaccgacg agacattcaa gacccgggag gccatccagc    2040
acgagagcgg catcctgggc cccctgctgt acggcgaagt gggcgacaca ctgctgatca    2100
tcttcaagaa ccaggctagc cggccctaca acatctaccc ccacggcatc accgacgtgc    2160 ggccccctgta cagcaggcgg ctgcccaagg gcgtgaagca cctgaaggac ttccccatcc    2220
tgcccggcga gatcttcaag tacaagtgga ccgtgaccgt ggaggacggc cccaccaaga    2280 gcgacccccag atgcctgacc cggtactaca gcagcttcgt gaacatggaa cgggacctgg    2340
cctccgggct gatcggacct ctgctgatct gctacaaaga aagcgtggac cagcggggca    2400
accagatcat gagcgacaag cggaacgtga tcctgttcag cgtgttcgat gagaaccggt    2460
cctggtatct gaccgagaac atccagcggt tctgcccaa ccctgccggc gtgcagctgg    2520
aagatcccga gttccaggcc agcaacatca tgcactccat caatggctac gtgttcgact    2580
ctctgcagct ctccgtgtgt ctgcacgagg tggcctactg gtacatcctg agcatcggcg    2640
cccagaccga cttcctgagc gtgttcttca gcggctacac cttcaagcac aagatggtgt    2700
acgaggacac cctgaccctg ttccctttca gcggcgagac agtgttcatg agcatggaaa    2760
accccggcct gtggattctg ggctgccaca acagcgactt ccggaaccgg gcatgaccg    2820 ccctgctgaa ggtgtccagc tgcgacaaga caccggcga ctactacgag acagctacg    2880 aggatatcag cgcctacctg ctgtccaaga caacgccat cgaaccccgg agcttcagcc    2940 agaaccccc cgtgctgacg cgtcaccagc gggagatcac ccggacaacc ctgcagtccg    3000
accaggaaga gatcgattac gacgacacca tcagcgtgga gatgaagaaa gaggatttcg    3060
atatctacga cgaggacgag aaccagagcc ccagaagctt ccagaagaaa cccggcact    3120 acttcattgc cgccgtggag aggctgtggg actacgcat gagttctagc ccccacgtgc    3180
tgcggaaccg ggcccagagc ggcagcgtgc cccagttcaa gaaagtggtg ttccaggaat    3240
tcacagacgg cagcttcacc cagcctctgt atagaggcga gctgaacgag cacctggggc    3300
tgctggggcc ctacatcagg gccgaagtgg aggacaaacat catggtgacc ttccggaatc    3360
aggccagcag accctactcc ttctacagca gcctgatcag ctacgaagag accagcggc    3420 agggcgccga accccggaag aacttcgtga agcccaacga aaccaagacc tacttctgga    3480
aagtgcagca ccacatggcc cccaccaagg acgagttcga ctgcaaggcc tgggcctact    3540
```

```
tcagcgacgt ggatctggaa aaggacgtgc actctggact gattggccca ctcctggtct    3600
gccacactaa caccctcaac cccgcccacg gccgccaggt gaccgtgcag gaattcgccc    3660
tgttcttcac catcttcgac gagacaaagt cctggtactt caccgagaat atggaacgga    3720
actgcagagc ccctgcaac atccagatgg aagatcctac cttcaaagag aactaccggt    3780
tccacgccat caacggctac atcatggaca ccctgcctgg cctggtgatg gcccaggacc    3840
agagaatccg gtggtatctg ctgtccatgg gcagcaacga gaatatccac agcatccact    3900
tcagcggcca cgtgttcacc gtgcggaaga agaagagta caagatggcc ctgtacaacc    3960
tgtaccccgg cgtgttcgag acagtggaga tgctgcccag caaggccggc atctggcggg    4020
tggagtgtct gatcggcgag cacctgcacg ctggcatgag caccctgttt ctggtgtaca    4080
gcaacaagtg ccagacccca ctgggcatgg cctctggcca catccgggac ttccagatca    4140
ccgcctccgg ccagtacggc cagtgggccc ccaagctggc cagactgcac tacagcggca    4200
gcatcaacgc ctggtccacc aaagagccct cagctggat caaggtggac ctgctggccc    4260
ctatgatcat ccacggcatt aagacccagg gcgccaggga gaagttcagc agcctgtaca    4320
tcagccagtt catcatcatg tacagcctgg acggcaagaa gtggcagacc taccggggca    4380
acagcaccgg caccctgatg gtgttcttcg gcaatgtgga cagcagcggc atcaagcaca    4440
acatcttcaa ccccccccatc attgcccggt acatccggct gcaccccacc cactacagca    4500
ttagatccac actgagaatg gaactgatgg gctgcgacct gaactcctgc agcatgcctc    4560
tgggcatgga aagcaaggcc atcagcgacg cccagatcac agccagcagc tacttccacc a    4620
acatgttcgc cacctggtcc ccctccaagg ccaggctgca cctgcagggc cggtccaacg    4680
cctggcggcc tcaggtcaac aaccccaaag aatggctgca ggtggacttt cagaaaacca    4740
tgaaggtgac cggcgtgacc acccagggcg tgaaaagcct gctgaccagc atgtacgtga    4800
aagagtttct gatcagcagc tctcaggatg gccaccagtg gaccctgttc tttcagaacg    4860
gcaaggtgaa agtgttccag ggcaaccagg actccttcac ccccgtggtg aactccctgg    4920
accccccccct gctgacccgc tacctgagaa tccacccca gtcttgggtg caccagatcg    4980
ccctcaggat ggaagtcctg ggatgtgagg cccaggatct gtactgatga    5030
```

<210> SEQ ID NO 51
<211> LENGTH: 5036
<212> TYPE: DNA
<213> ORGANISM: Artificial Sequence
<220> FEATURE:
<223> OTHER INFORMATION: Flank-3xSERP-Flank-TTRe-Flank-TTRm-MVM-Flank-
      coFVIIIdeltaB-Flank

<400> SEQUENCE: 51

```
gcggccgcgg tacgcggggg aggctgctgg tgaatattaa ccaaggtcac cccagttatc      60
ggaggagcaa acaggggcta agtccaccgg gggaggctgc tggtgaatat taaccaaggt    120
cacccccagtt atcggaggag caaacagggg ctaagtccac cggggaggc tgctggtgaa    180
tattaaccaa ggtcaccccca gttatcggag gagcaaacag gggctaagtc acggtaccc    240
actgggagga tgttgagtaa gatggaaaac tactgatgac ccttgcagag acagagtatt    300
aggacatgtt tgaacagggg ccgggcgatc agcaggtagc tctagaggat cccgtctgt    360
ctgcacattt cgtagagcga gtgttccgat actctaatct ccctaggcaa ggttcatatt    420
tgtgtaggtt acttattctc cttttgttga ctaagtcaat aatcagaatc agcaggtttg    480
gagtcagctt ggcagggatc agcagcctgg gttggaagga gggggtataa aagccccttc    540
```

| | |
|---|---|
| accaggagaa gccgtcaaga ggtaagggtt taagggatgg ttggttggtg gggtattaat | 600 |
| gtttaattac ctggagcacc tgcctgaaat cacttttttt caggttggct agtatgcaga | 660 |
| tcgagctgtc cacctgcttt tttctgtgcc tgctgcggtt ctgcttcagc gccacccggc | 720 |
| ggtactacct gggcgccgtg gagctgtcct gggactacat gcagagcgac ctgggcgagc | 780 |
| tgcccgtgga cgcccggttc ccccccagag tgcccaagag cttccccttc aacaccagcg | 840 |
| tggtgtacaa gaaaaccctg ttcgtggagt tcaccgacca cctgttcaat atcgccaagc | 900 |
| ccaggccccc ctggatgggc ctgctgggcc ccaccatcca ggccgaggtg tacgacaccg | 960 |
| tggtgatcac cctgaagaac atggccagcc accccgtgag cctgcacgcc gtgggcgtga | 1020 |
| gctactggaa ggccagcgag ggcgccgagt acgacgacca gaccagccag cgggagaaag | 1080 |
| aagatgacaa ggtgttccct ggcggcagcc acacctacgt gtggcaggtg ctgaaagaaa | 1140 |
| acggccccat ggcctccgac cccctgtgcc tgacctacag ctacctgagc cacgtggacc | 1200 |
| tggtgaagga cctgaacagc ggcctgatcg gcgctctgct cgtctgccgg gagggcagcc | 1260 |
| tggccaaaga gaaaacccag accctgcaca gttcatcct gctgttcgcc gtgttcgacg | 1320 |
| agggcaagag ctggcacagc gagacaaaga acagcctgat gcaggaccgg gacgccgcct | 1380 |
| ctgccagagc ctggccaaag atgcacaccg tgaacggcta cgtgaacaga gcctgcccg | 1440 |
| gcctgattgg ctgccaccgg aagagcgtgt actggcacgt gatcggcatg ggcaccacac | 1500 |
| ccgaggtgca cagcatcttt ctggaagggc acacctttct ggtccggaac caccggcagg | 1560 |
| ccagcctgga aatcagccct atcaccttcc tgaccgccca gacactgctg atggacctgg | 1620 |
| gccagttcct gctgttttgc cacatcagct ctcaccagca cgacggcatg gaagcctacg | 1680 |
| tgaaggtgga ctcttgcccc gaggaacccc agctgcggat gaagaacaac gaggaagccg | 1740 |
| aggactacga cgacgacctg accgacacgc agatggacgt ggtgcggttc gacgacgaca | 1800 |
| acagccccag cttcatccag atcagaagcg tggccaagaa gcaccccaag acctgggtgc | 1860 |
| actatatcgc cgccgaggaa gaggactggg actacgcccc cctggtgctg gcccccgacg | 1920 |
| acagaagcta caagagccag tacctgaaca atggccccca gcggatcggc cggaagtaca | 1980 |
| agaaagtgcg gttcatggcc tacaccgacg agacattcaa gacccgggag gccatccagc | 2040 |
| acgagagcgg catcctgggc cccctgctgt acggcgaagt gggcgacaca ctgctgatca | 2100 |
| tcttcaagaa ccaggctagc cggccctaca acatctaccc ccacggcatc accgacgtgc | 2160 |
| ggccccctgta cagcaggcgg ctgcccaagg gcgtgaagca cctgaaggac ttccccatcc | 2220 |
| tgcccggcga gatcttcaag tacaagtgga ccgtgaccgt ggaggacggc cccaccaaga | 2280 |
| gcgacccag atgcctgacc cggtactaca gcagcttcgt gaacatggaa cgggacctgg | 2340 |
| cctccgggct gatcggacct ctgctgatct gctacaaaga aagcgtggac cagcggggca | 2400 |
| accagatcat gagcgacaag cggaacgtga tcctgttcag cgtgttcgat gagaaccggt | 2460 |
| cctggtatct gaccgagaac atccagcggt tcctgcccaa ccctgccggc gtgcagctgg | 2520 |
| aagatcccga gttccaggcc agcaacatca tgcactccat caatggctac gtgttcgact | 2580 |
| ctctgcagct ctccgtgtgt ctgcacgagg tggcctactg gtacatcctg agcatcggcg | 2640 |
| cccagaccga cttcctgagc gtgttcttca gcggctacac cttcaagcac aagatggtgt | 2700 |
| acgaggacac cctgacccctg ttccctttca gcggcgagac agtgttcatg agcatggaaa | 2760 |
| accccggcct gtggattctg ggctgccaca cagcgactt ccggaaccgg gcatgaccg | 2820 |
| ccctgctgaa ggtgtccagc tgcgacaaga caccggcga ctactacgag acagctacg | 2880 |
| aggatatcag cgcctacctg ctgtccaaga caacgccat cgaaccccgg agcttcagcc | 2940 |

```
agaaccccc cgtgctgacg cgtcaccagc gggagatcac ccggacaacc ctgcagtccg    3000
accaggaaga gatcgattac gacgacacca tcagcgtgga gatgaagaaa gaggatttcg    3060
atatctacga cgaggacgag aaccagagcc ccagaagctt ccagaagaaa acccggcact    3120
acttcattgc cgccgtggag aggctgtggg actacggcat gagttctagc ccccacgtgc    3180
tgcggaaccg ggcccagagc ggcagcgtgc cccagttcaa gaaagtggtg ttccaggaat    3240
tcacagacgg cagcttcacc cagcctctgt atagaggcga gctgaacgag cacctggggc    3300
tgctggggcc ctacatcagg gccgaagtgg aggacaacat catggtgacc ttccggaatc    3360
aggccagcag accctactcc ttctacagca gcctgatcag ctacgaagag accagcggcc    3420
agggcgccga accccggaag aacttcgtga agcccaacga aaccaagacc tacttctgga    3480
aagtgcagca ccacatggcc cccaccaagg acgagttcga ctgcaaggcc tgggcctact    3540
tcagcgacgt ggatctggaa aaggacgtgc actctggact gattggccca ctcctggtct    3600
gccacactaa caccctcaac cccgccacg ccgccaggt gaccgtgcag gaattcgccc    3660
tgttcttcac catcttcgac gagacaaagt cctggtactt caccgagaat atggaacgga    3720
actgcagagc cccctgcaac atccagatgg aagatcctac cttcaaagag aactaccggt    3780
tccacgccat caacggctac atcatggaca ccctgcctgg cctggtgatg gcccaggacc    3840
agagaatccg gtggtatctg ctgtccatgg gcagcaacga gaatatccac agcatccact    3900
tcagcggcca cgtgttcacc gtgcggaaga aagaagagta caagatggcc ctgtacaacc    3960
tgtaccccgg cgtgttcgag acagtggaga tgctgcccag caaggccggc atctggcggg    4020
tggagtgtct gatcggcgag cacctgcacg ctggcatgag caccctgttt ctggtgtaca    4080
gcaacaagtg ccagaccca ctgggcatgg cctctggcca catccgggac ttccagatca    4140
ccgcctccgg ccagtacggc cagtgggccc ccaagctggc cagactgcac tacagcggca    4200
gcatcaacgc ctggtccacc aaagagccct cagctggat caaggtggac ctgctggccc    4260
ctatgatcat ccacggcatt aagacccagg gcgccaggca gaagttcagc agcctgtaca    4320
tcagccagtt catcatcatg tacagcctgg acggcaagaa gtggcagacc taccggggca    4380
acagcaccgg caccctgatg gtgttcttcg gcaatgtgga cagcagcggc atcaagcaca    4440
acatcttcaa cccccccatc attgcccggt acatccggct gcaccccacc cactacagca    4500
ttagatccac actgagaatg gaactgatgg gctgcgacct gaactcctgc agcatgcctc    4560
tgggcatgga aagcaaggcc atcagcgacg cccagatcac agccagcagc tacttcacca    4620
acatgttcgc cacctggtcc ccctccaagg ccaggctgca cctgcagggc cggtccaacg    4680
cctggcggcc tcaggtcaac aaccccaaag aatggctgca ggtggacttt cagaaaacca    4740
tgaaggtgac cggcgtgacc acccagggcg tgaaaagcct gctgaccagc atgtacgtga    4800
aagagtttct gatcagcagc tctcaggatg gccaccagtg gaccctgttc tttcagaacg    4860
gcaaggtgaa agtgttccag ggcaaccagg actccttcac ccccgtggtg aactccctgg    4920 accccccct gctgacccgc tacctgagaa tccacccca gtcttgggtg caccagatcg    4980
ccctcaggat ggaagtcctg ggatgtgagg cccaggatct gtactgatga ggatcc       5036
```

<210> SEQ ID NO 52
<211> LENGTH: 5170
<212> TYPE: DNA
<213> ORGANISM: Artificial Sequence
<220> FEATURE:
<223> OTHER INFORMATION: Flank-3xSERP-Flank-TTRe-Flank-TTRm-MVM-Flank-
      coFVIIIdeltaB-Flank- SV40pA

<400> SEQUENCE: 52

```
gcggccgcgg tacgcggggg aggctgctgg tgaatattaa ccaaggtcac cccagttatc        60
ggaggagcaa acagggctaa gtccaccgg gggaggctgc tggtgaatat taaccaaggt       120
cacccccagtt atcggaggag caaacagggg ctaagtccac cggggaggc tgctggtgaa       180
tattaaccaa ggtcacccca gttatcggag gagcaaacag gggctaagtc cacggtaccc       240
actgggagga tgttgagtaa gatggaaaac tactgatgac ccttgcagag acagagtatt       300
aggacatgtt tgaacagggg ccggcgatc agcaggtagc tctagaggat ccccgtctgt       360
ctgcacattt cgtagagcga gtgttccgat actctaatct ccctaggcaa ggttcatatt       420
tgtgtaggtt acttattctc cttttgttga ctaagtcaat aatcagaatc agcaggtttg       480
gagtcagctt ggcagggatc agcagcctgg gttggaagga gggggtataa aagcccttc        540
accaggagaa gccgtcaaga ggtaagggtt taagggatgg ttggttggtg gggtattaat       600
gtttaattac ctggagcacc tgcctgaaat cactttttt caggttggct agtatgcaga        660
tcgagctgtc cacctgcttt tttctgtgcc tgctgcggtt ctgcttcagc gccacccggc       720
ggtactacct gggcgccgtg gagctgtcct gggactacat gcagagcgac ctgggcgagc       780
tgcccgtgga cgcccggttc ccccccagag tgcccaagag cttccccttc aacaccagcg       840
tggtgtacaa gaaaccctg ttcgtggagt tcaccgacca cctgttcaat atcgccaagc        900
ccaggccccc ctggatgggc ctgctgggcc ccaccatcca ggccgaggtg tacgacaccg       960
tggtgatcac cctgaagaac atggccagca cccgtgag cctgcacgcc gtgggcgtga        1020
gctactggaa ggccagcgag ggcgccgagt acgacgacca gaccagccag cgggagaaag      1080
aagatgacaa ggtgttccct ggcggcagcc acacctacgt gtggcaggtg ctgaaagaaa      1140
acggccccat ggcctccgac cccctgtgcc tgacctacag ctacctgagc cacgtggacc      1200
tggtgaagga cctgaacagc ggcctgatcg gcgctctgct cgtctgccgg gagggcagcc      1260
tggccaaaga gaaaacccag accctgcaca agttcatcct gctgttcgcc gtgttcgacg      1320
agggcaagag ctggcacagc gagacaaaga acagcctgat gcaggaccgg gacgccgcct      1380
ctgccagagc ctggccaag atgcacaccg tgaacggcta cgtgaacaga agcctgcccg      1440
gcctgattgg ctgccaccgg aagagcgtgt actggcacgt gatcggcatg ggcaccacac      1500
ccgaggtgca cagcatctt ctggaagggc acacctttct ggtccggaac caccggcagg      1560
ccagcctgga aatcagccct atcaccttcc tgaccgccca gacactgctg atggacctgg      1620
gccagttcct gctgttttgc cacatcagct ctcaccagca cgacggcatg gaagcctacg      1680
tgaaggtgga ctcttgcccc gaggaacccc agctgcggat gaagaacaac gaggaagccg      1740
aggactacga cgacgacctg accgacgcg agatggacgt ggtgcggttc gacgacgaca       1800
acagccccag cttcatccag atcagaagcg tggccaagaa gcaccccaag acctgggtgc      1860
actatatcgc cgccgaggaa gaggactggg actacgcccc cctggtgctg gccccgacg      1920
acagaagcta caagagccag tacctgaaca atggcccca gcggatcggc cggaagtaca      1980
agaaagtgcg gttcatggcc tacaccgacg agacattcaa gacccgggag gccatccagc      2040
acgagagcgg catcctgggc ccctgctgt acggcgaagt gggcgacaca ctgctgatca      2100
tcttcaagaa ccaggctagc cggccctaca acatctaccc ccacggcatc accgacgtgc      2160
ggcccctgta cagcaggcgg ctgcccaagg gcgtgaagca cctgaaggac ttccccatcc      2220
tgcccggcga gatcttcaag tacaagtgga ccgtgaccgt ggaggacggc cccaccaaga      2280
```

```
gcgaccccag atgcctgacc cggtactaca gcagcttcgt gaacatggaa cgggacctgg    2340
cctccgggct gatcggacct ctgctgatct gctacaaaga aagcgtggac cagcggggca    2400
accagatcat gagcgacaag cggaacgtga tcctgttcag cgtgttcgat gagaaccggt    2460
cctggtatct gaccgagaac atccagcggt ttctgcccaa ccctgccggc gtgcagctgg    2520
aagatcccga gttccaggcc agcaacatca tgcactccat caatggctac gtgttcgact    2580
ctctgcagct ctccgtgtgt ctgcacgagg tggcctactg gtacatcctg agcatcggcg    2640
cccagaccga cttcctgagc gtgttcttca gcggctacac cttcaagcac aagatggtgt    2700
acgaggacac cctgaccctg ttcccttca gcggcgagac agtgttcatg agcatggaaa    2760
accccggcct gtggattctg ggctgccaca acagcgactt ccggaaccgg ggcatgaccg    2820
ccctgctgaa ggtgtccagc tgcgacaaga acaccggcga ctactacgag acagctacg    2880 aggatatcag cgcctacctg ctgtccaaga caacgccat cgaacccgg agcttcagcc    2940 agaaccccc cgtgctgacg cgtcaccagc gggagatcac ccggacaacc ctgcagtccg    3000
accaggaaga gatcgattac gacgacacca tcagcgtgga gatgaagaaa gaggatttcg    3060
atatctacga cgaggacgag aaccagagcc ccagaagctt ccagaagaaa acccggcact    3120
acttcattgc cgccgtggag aggctgtggg actacgcat gagttctagc ccccacgtgc    3180
tgcggaaccg ggcccagagc ggcagcgtgc cccagttcaa gaaagtggtg ttccaggaat    3240
tcacagacgg cagcttcacc cagcctctgt atagaggcga gctgaacgag cacctggggc    3300
tgctggggcc ctacatcagg gccgaagtgg aggacaacat catggtgacc ttccggaatc    3360
aggccagcag accctactcc ttctacagca gcctgatcag ctacgaagag gaccagcggc    3420
agggcgccga accccggaag aacttcgtga gcccaacga aaccaagacc tacttctgga    3480
aagtgcagca ccacatggcc cccaccaagg acgagttcga ctgcaaggcc tgggcctact    3540
tcagcgacgt ggatctggaa aaggacgtgc actctggact gattggccca ctcctggtct    3600
gccacactaa cacccctcaac cccgcccacg ccgccaggt gaccgtgcag gaattcgccc    3660
tgttcttcac catcttcgac gagacaaagt cctggtactt caccgagaat atggaacgga    3720
actgcagagc cccctgcaac atccagatgg aagatcctac cttcaaagag aactaccggt    3780
tccacgccat caacggctac atcatggaca ccctgcctgg cctggtgatg gcccaggacc    3840
agagaatccg gtggtatctg ctgtccatgg gcagcaacga aatatccac agcatccact    3900 tcagcggcca cgtgttcacc gtgcggaaga agaagagta caagatggcc ctgtacaacc    3960
tgtaccccgg cgtgttcgag acagtggaga tgctgcccag caaggccggc atctggcggg    4020
tggagtgtct gatcggcgag cacctgcacg ctggcatgag cacccctgttt ctggtgtaca    4080 gcaacaagtg ccagacccca ctgggcatgg cctctggcca catccgggac ttccagatca    4140
ccgcctccgg ccagtacggc cagtgggccc ccaagctggc cagactgcac tacagcggca    4200
gcatcaacgc ctggtccacc aaagagcccct cagctggat caaggtggac ctgctggccc    4260
ctatgatcat ccacggcatt aagacccagg gcgccaggca gaagttcagc agcctgtaca    4320
tcagccagtt catcatcatg tacagcctgg acggcaagaa gtggcagacc taccgggggca    4380 acagcaccgg caccctgatg gtgttcttcg gcaatgtgga cagcagcggc atcaagcaca    4440
acatcttcaa cccccccatc attgcccggt acatccggct gcaccccacc cactacagca    4500
ttagatccac actgagaatg gaactgatgg gctgcgacct gaactcctgc agcatgcctc    4560
tgggcatgga aagcaaggcc atcagcgacg cccagatcac agccagcagc tacttccacca    4620 acatgttcgc cacctggtcc ccctccaagg ccaggctgca cctgcagggc cggtccaacg    4680
```

```
cctggcggcc tcaggtcaac aaccccaaag aatggctgca ggtggacttt cagaaaacca    4740
tgaaggtgac cggcgtgacc acccagggcg tgaaaagcct gctgaccagc atgtacgtga    4800
aagagtttct gatcagcagc tctcaggatg ccaccagtg  gaccctgttc tttcagaacg    4860
gcaaggtgaa agtgttccag ggcaaccagg actccttcac ccccgtggtg aactccctgg    4920 accccccccct gctgacccgc tacctgagaa tccaccccca gtcttgggtg caccagatcg    4980
ccctcaggat ggaagtcctg ggatgtgagg cccaggatct gtactgatga ggatccatgc    5040
tttatttgtg aaatttgtga tgctattgct ttatttgtaa ccattataag ctgcaataaa    5100
caagttaaca acaacaattg cattcatttt atgtttcagg ttcagggga  ggtgtgggag    5160 gttttttaaa                                                           5170
```

<210> SEQ ID NO 53
<211> LENGTH: 5188
<212> TYPE: DNA
<213> ORGANISM: Artificial Sequence
<220> FEATURE:
<223> OTHER INFORMATION: Flank-3xSERP-Flank-TTRe-Flank-TTRm-MVM-Flank-
      coFVIIIdeltaB-Flank- SV40pA-Flank

<400> SEQUENCE: 53

```
gcggccgcgg tacgcggggg aggctgctgg tgaatattaa ccaaggtcac cccagttatc      60
ggaggagcaa acaggggcta agtccaccgg gggaggctgc tggtgaatat taaccaaggt     120
caccccagtt atcggaggag caaacagggg ctaagtccac cggggaggc  tgctggtgaa     180 tattaaccaa ggtcacccca gttatcggag gagcaaacag gggctaagtc cacggtaccc     240
actgggagga tgttgagtaa gatggaaaac tactgatgac ccttgcagag acagagtatt     300
aggacatgtt tgaacagggg ccgggcgatc agcaggtagc tctagaggat ccccgtctgt     360
ctgcacattt cgtagagcga gtgttccgat actctaatct ccctaggcaa ggttcatatt     420
tgtgtaggtt acttattctc cttttgttga ctaagtcaat aatcagaatc agcaggtttg     480
gagtcagctt ggcagggatc agcagcctgg gttggaagga gggggtataa aagccccttc     540
accaggagaa gccgtcaaga ggtaagggtt taagggatgg ttggttggtg gggtattaat     600
gtttaattac ctggagcacc tgcctgaaat cacttttttt caggttggct agtatgcaga     660
tcgagctgtc cacctgcttt tttctgtgcc tgctgcggtt ctgcttcagc gccaccggc      720 ggtactacct gggcgccgtg gagctgtcct gggactacat gcagagcgac ctgggcgagc     780 tgccccgtgga cgcccggttc ccccccagag tgcccaagag cttccccttc aacaccagcg     840
tggtgtacaa gaaaaccctg ttcgtggagt tcaccgacca cctgttcaat atcgccaagc     900
ccaggccccc ctggatgggc ctgctgggcc ccaccatcca ggccgaggtg tacgacaccg     960
tggtgatcac cctgaagaac atggccagcc accccgtgag cctgcacgcc gtgggcgtga    1020
gctactggaa ggccagcgag ggcgccgagt acgacgacca gaccagccag cgggagaaag    1080
aagatgacaa ggtgttccct ggcggcagcc acacctacgt gtggcaggtg ctgaaagaaa    1140
acggccccat ggcctccgac ccctgtgcc  tgacctacag ctacctgagc cacgtggacc    1200
tggtgaagga cctgaacagc ggcctgatcg gcgctctgct cgtctgccgg gagggcagcc    1260
tggccaaaga gaaaacccag accctgcaca gttcatcct  gctgttcgcc gtgttcgacg    1320
agggcaagag ctggcacagc gagacaaaga acagcctgat gcaggaccgg gacgccgcct    1380
ctgccagagc ctggccaaag atgcacaccg tgaacggcta cgtgaacaga agcctgcccg    1440
gcctgattgg ctgccaccgg aagagcgtgt actggcacgt gatcggcatg ggcaccacac    1500
```

```
ccgaggtgca cagcatcttt ctggaagggc acacctttct ggtccggaac caccggcagg    1560
ccagcctgga aatcagccct atcaccttcc tgaccgccca cactgctg atggacctgg      1620 gccagttcct gctgttttgc cacatcagct ctcaccagca cgacggcatg aagcctacg     1680 tgaaggtgga ctcttgcccc gaggaacccc agctgcggat aagaacaac gaggaagccg    1740 aggactacga cgacgacctg accgacagcg agatggacgt ggtgcggttc gacgacgaca    1800
acagccccag cttcatccag atcagaagcg tggccaagaa gcaccccaag acctgggtgc    1860
actatatcgc cgccgaggaa gaggactggg actacgcccc cctggtgctg gcccccgacg    1920
acagaagcta caagagccag tacctgaaca atggcccca gcggatcggc cggaagtaca     1980
agaaagtgcg gttcatggcc tacaccgacg agacattcaa gacccgggag gccatccagc    2040
acgagagcgg catcctgggc cccctgctgt acggcgaagt gggcgacaca ctgctgatca    2100
tcttcaagaa ccaggctagc cggccctaca acatctaccc ccacggcatc accgacgtgc    2160 ggccctgta cagcaggcgg ctgcccaagg gcgtgaagca cctgaaggac ttccccatcc    2220
tgcccggcga gatcttcaag tacaagtgga ccgtgaccgt ggaggacggc cccaccaaga    2280
gcgaccccag atgcctgacc cggtactaca gcagcttcgt gaacatggaa cgggacctgg    2340
cctccgggct gatcggacct ctgctgatct gctacaaaga aagcgtggac cagcggggca    2400
accagatcat gagcgacaag cggaacgtga tcctgttcag cgtgttcgat gagaaccggt    2460
cctggtatct gaccgagaac atccagcggt ttctgcccaa ccctgccggc gtgcagctgg    2520
aagatcccga gttccaggcc agcaacatca tgcactccat caatggctac gtgttcgact    2580
ctctgcagct ctccgtgtgt ctgcacgagg tggcctactg gtacatcctg agcatcggcg    2640
cccagaccga cttcctgagc gtgttcttca gcggctacac cttcaagcac aagatggtgt    2700
acgaggacac cctgacccctg ttcccttttca gcggcgagac agtgttcatg agcatggaaa    2760
acccccgcct gtggattctg gctgccaca acagcgactt ccggaaccgg gcatgaccg    2820 ccctgctgaa ggtgtccagc tgcgacaaga acaccggcga ctactacgag acagctacg     2880 aggatatcag cgcctacctg ctgtccaaga acaacgccat cgaaccccgg agcttcagcc    2940 agaaccccc cgtgctgacg cgtcaccagc gggagatcac ccgacaacc ctgcagtccg     3000 accaggaaga gatcgattac gacgacacca tcagcgtgga gatgaagaaa gaggatttcg    3060
atatctacga cgaggacgag aaccagagcc cagaagctt ccagaagaaa cccggcact    3120 acttcattgc cgccgtggag aggctgtggg actacggcat gagttctagc ccccacgtgc    3180
tgcggaaccg ggcccagagc ggcagcgtgc cccagttcaa gaaagtggtg ttccaggaat    3240
tcacagacgg cagcttcacc cagcctctgt atagaggcga gctgaacgag cacctggggc    3300
tgctggggcc ctcatcagg gccgaagtgg aggacaacat catggtgacc ttccggaatc    3360
aggccagcag accctactcc ttctacagca gcctgatcag ctacgaagag gaccagcggc    3420
agggcgccga accccggaag aacttcgtga gcccaacga accaagacc tacttctgga    3480 aagtgcagca ccacatggcc cccaccaagg acagttcga ctgcaaggcc tgggcctact    3540
tcagcgacgt ggatctggaa aaggacgtgc actctggact gattggccca ctcctggtct    3600
gccacactaa caccctcaac cccgcccacg gcgccaggt gaccgtgcag gaattcgccc    3660
tgttcttcac catcttcgac gagacaaagt cctggtactt caccgagaat atggaacgga    3720
actgcagagc ccctgcaac atccagatgg aagatcctac cttcaaagag aactaccggt    3780
tccacgccat caacggctac atcatggaca ccctgcctgg cctggtgatg gcccaggacc    3840
```

| agagaatccg gtggtatctg ctgtccatgg gcagcaacga gaatatccac agcatccact | 3900 |
| tcagcggcca cgtgttcacc gtgcggaaga agaagagta caagatggcc ctgtacaacc | 3960 |
| tgtaccccgg cgtgttcgag acagtggaga tgctgcccag caaggccggc atctggcggg | 4020 |
| tggagtgtct gatcggcgag cacctgcacg ctggcatgag caccctgttt ctggtgtaca | 4080 |
| gcaacaagtg ccagacccca ctgggcatgg cctctggcca catccgggac ttccagatca | 4140 |
| ccgcctccgg ccagtacggc cagtgggccc ccaagctggc cagactgcac tacagcggca | 4200 |
| gcatcaacgc ctggtccacc aaagagccct cagctggat caaggtggac ctgctggccc | 4260 |
| ctatgatcat ccacggcatt aagacccagg gcgccaggca gaagttcagc agcctgtaca | 4320 |
| tcagccagtt catcatcatg tacagcctgg acggcaagaa gtggcagacc taccggggca | 4380 |
| acagcaccgg caccctgatg gtgttcttcg gcaatgtgga cagcagcggc atcaagcaca | 4440 |
| acatcttcaa ccccccatc attgcccggt acatccggct gcaccccacc cactacagca | 4500 |
| ttagatccac actgagaatg gaactgatgg gctgcgacct gaactcctgc agcatgcctc | 4560 |
| tgggcatgga aagcaaggcc atcagcgacg cccagatcac agccagcagc tacttcacca | 4620 |
| acatgttcgc cacctggtcc ccctccaagg ccaggctgca cctgcagggc cggtccaacg | 4680 |
| cctggcggcc tcaggtcaac aaccccaaag aatggctgca ggtggacttt cagaaaacca | 4740 |
| tgaaggtgac cggcgtgacc acccagggcg tgaaaagcct gctgaccagc atgtacgtga | 4800 |
| aagagtttct gatcagcagc tctcaggatg ccaccagtg acccctgttc tttcagaacg | 4860 |
| gcaaggtgaa agtgttccag ggcaaccagg actccttcac ccccgtggtg aactccctgg | 4920 |
| accccccct gctgacccgc tacctgagaa tccacccca gtcttgggtg caccagatcg | 4980 |
| ccctcaggat ggaagtcctg ggatgtgagg cccaggatct gtactgatga ggatccatgc | 5040 |
| tttatttgtg aaatttgtga tgctattgct ttatttgtaa ccattataag ctgcaataaa | 5100 |
| caagttaaca acaacaattg cattcatttt atgtttcagg ttcaggggga ggtgtgggag | 5160 |
| gtttttaaa ctcgagatcc acggccgc | 5188 |

<210> SEQ ID NO 54
<211> LENGTH: 5085
<212> TYPE: DNA
<213> ORGANISM: Artificial Sequence
<220> FEATURE:
<223> OTHER INFORMATION: Flank-3xSERP-Flank-TTRe-Flank-TTRm-MVM-Flank-
 coFVIIIdeltaB-Flank- Synt-pA

<400> SEQUENCE: 54

| gcggccgcgg tacgcggggg aggctgctgg tgaatattaa ccaaggtcac cccagttatc | 60 |
| ggaggagcaa acaggggcta agtccaccgg gggaggctgc tggtgaatat taaccaaggt | 120 |
| caccccagtt atcggaggag caaacagggg ctaagtccac cggggaggc tgctggtgaa | 180 |
| tattaaccaa ggtcaccca gttatcggag gagcaaacag ggctaagtc cacggtaccc | 240 |
| actgggagga tgttgagtaa gatgaaaac tactgatgac ccttgcagag acagagtatt | 300 |
| aggacatgtt tgaacagggg ccgggcgatc agcaggtagc tctagaggat ccccgtctgt | 360 |
| ctgcacattt cgtagagcga gtgttccgat actctaatct ccctaggcaa ggttcatatt | 420 |
| tgtgtaggtt acttattctc cttttgttga ctaagtcaat aatcagaatc agcaggtttg | 480 |
| gagtcagctt ggcagggatc agcagcctgg gttggaagga ggggtataa agcccttc | 540 |
| accaggagaa gccgtcaaga ggtaagggtt taagggatgg ttggttggtg gggtattaat | 600 |
| gtttaattac ctgagcacc tgcctgaaat cactttttt caggttggct agtatgcaga | 660 |

```
tcgagctgtc cacctgcttt tttctgtgcc tgctgcggtt ctgcttcagc gccacccggc    720
ggtactacct gggcgccgtg gagctgtcct gggactacat gcagagcgac ctgggcgagc    780
tgcccgtgga cgcccggttc ccccccagag tgcccaagag cttccccttc aacaccagcg    840
tggtgtacaa gaaaaccctg ttcgtggagt tcaccgacca cctgttcaat atcgccaagc    900
ccaggccccc ctggatgggc ctgctgggcc ccaccatcca ggccgaggtg tacgacaccg    960
tggtgatcac cctgaagaac atggccagcc acccgtgag cctgcacgcc gtgggcgtga    1020
gctactggaa ggccagcgag ggcgccgagt acgacgacca gaccagccag cgggagaaag    1080
aagatgacaa ggtgttccct ggcggcagcc acacctacgt gtggcaggtg ctgaaagaaa    1140
acggccccat ggcctccgac cccctgtgcc tgacctacag ctacctgagc cacgtggacc    1200
tggtgaagga cctgaacagc ggcctgatcg gcgctctgct cgtctgccgg agggcagcc    1260 tggccaaaga gaaaacccag accctgcaca agttcatcct gctgttcgcc gtgttcgacg    1320
agggcaagag ctggcacagc gagacaaaga acagcctgat gcaggaccgg gacgccgcct    1380
ctgccagagc ctggcccaag atgcacaccg tgaacggcta cgtgaacaga agcctgcccg    1440
gcctgattgg ctgccaccgg aagagcgtgt actggcacgt gatcggcatg ggcaccacac    1500
ccgaggtgca cagcatcttt ctggaagggc acacctttct ggtccggaac caccggcagg    1560
ccagcctgga aatcagccct atcaccttcc tgaccgccca gacactgctg atggacctgg    1620
gccagttcct gctgttttgc cacatcagct ctcaccagca cgacggcatg gaagcctacg    1680
tgaaggtgga ctcttgcccc gaggaacccc agctgcggat gaagaacaac gaggaagccg    1740
aggactacga cgacgacctg accgacagcg agatggacgt ggtgcggttc gacgacgaca    1800
acagccccag cttcatccag atcagaagcg tggccaagaa gcaccccaag acctgggtgc    1860
actatatcgc cgccgaggaa gaggactggg actacgcccc cctggtgctg gcccccgacg    1920
acagaagcta caagagccag tacctgaaca atggcccca gcggatcggc cggaagtaca    1980
agaaagtgcg gttcatggcc tacaccgacg agacattcaa gacccgggag gccatccagc    2040
acgagagcgg catcctgggc cccctgctgt acggcgaagt gggcgacaca ctgctgatca    2100
tcttcaagaa ccaggctagc cggccctaca acatctaccc ccacggcatc accgacgtgc    2160 ggccctgta cagcaggcgg ctgcccaagg gcgtgaagca cctgaaggac ttccccatcc    2220
tgcccggcga gatcttcaag tacaagtgga ccgtgaccgt ggaggacggc ccaccaagga    2280
gcgaccccag atgcctgacc cggtactaca gcagcttcgt gaacatggaa cgggacctgg    2340
cctccgggct gatcggacct ctgctgatct gctacaaaga aagcgtggac cagcggggca    2400
accagatcat gagcgacaag cggaacgtga tcctgttcag cgtgttcgat gagaaccggt    2460
cctggtatct gaccgagaac atccagcggt ttctgcccaa ccctgccggc gtgcagctgg    2520
aagatcccga gttccaggcc agcaacatca tgcactccat caatggctac gtgttcgact    2580
ctctgcagct ctccgtgtgt ctgcacgagg tggcctactg gtacatcctg agcatcggcg    2640
cccagaccga cttcctgagc gtgttcttca gcggctacac cttcaagcac aagatggtgt    2700
acgaggacac cctgaccctg ttccctttca gcggcgagac agtgttcatg agcatggaaa    2760
accccggcct gtggattctg ggctgccaca acagcgactt ccggaaccgg gcatgaccg    2820 ccctgctgaa ggtgtccagc tgcgacaaga caccggcga ctactacgag acagctacg    2880 aggatatcag cgcctacctg ctgtccaaga caacgccat cgaacccgg agcttcagcc    2940 agaaccccc cgtgctgacg cgtcaccagc gggagatcac ccggacaacc ctgcagtccg    3000
accaggaaga gatcgattac gacgacacca tcagcgtgga gatgaagaaa gaggatttcg    3060
```

```
atatctacga cgaggacgag aaccagagcc ccagaagctt ccagaagaaa acccggcact    3120
acttcattgc cgccgtggag aggctgtggg actacggcat gagttctagc ccccacgtgc    3180
tgcggaaccg ggcccagagc ggcagcgtgc cccagttcaa gaaagtggtg ttccaggaat    3240
tcacagacgg cagcttcacc cagcctctgt atagaggcga gctgaacgag cacctggggc    3300
tgctggggcc ctacatcagg gccgaagtgg aggacaacat catggtgacc ttccggaatc    3360
aggccagcag accctactcc ttctacagca gcctgatcag ctacgaagag gaccagcggc    3420
agggcgccga accccggaag aacttcgtga agcccaacga aaccaagacc tacttctgga    3480
aagtgcagca ccacatggcc cccaccaagg acgagttcga ctgcaaggcc tgggcctact    3540
tcagcgacgt ggatctggaa aaggacgtgc actctggact gattggccca ctcctggtct    3600
gccacactaa caccctcaac cccgcccacg gcgccaggt gaccgtgcag gaattcgccc     3660
tgttcttcac catcttcgac gagacaaagt cctggtactt caccgagaat atggaacgga    3720
actgcagagc cccctgcaac atccagatgg aagatcctac cttcaaagag aactaccggt    3780
tccacgccat caacggctac atcatggaca ccctgcctgg cctggtgatg gcccaggacc    3840
agagaatccg gtggtatctg ctgtccatgg gcagcaacga gaatatccac agcatccact    3900
tcagcggcca cgtgttcacc gtgcggaaga agaagagta agatggcc ctgtacaacc       3960 tgtaccccgg cgtgttcgag acagtggaga tgctgcccag caaggccggc atctggcggg    4020
tggagtgtct gatcggcgag cacctgcacg ctggcatgag caccctgttt ctggtgtaca    4080
gcaacaagtg ccagacccca ctgggcatgg cctctggcca catccgggac ttccagatca    4140
ccgcctccgg ccagtacggc cagtgggccc ccaagctggc cagactgcac tacagcggca    4200
gcatcaacgc ctggtccacc aaagagccct cagctggat caaggtggac ctgctggccc    4260
ctatgatcat ccacggcatt aagacccagg gcgccaggca gaagttcagc agcctgtaca    4320
tcagccagtt catcatcatg tacagcctgg acggcaagaa gtggcagacc taccgggggca   4380 acagcaccgg caccctgatg gtgttcttcg gcaatgtgga cagcagcggc atcaagcaca    4440
acatcttcaa ccccccatc attgcccggt acatccggct gcaccccacc cactacagca    4500
ttagatccac actgagaatg gaactgatgg gctgcgacct gaactcctgc agcatgcctc    4560
tgggcatgga aagcaaggcc atcagcgacg cccagatcac agccagcagc tacttccacca    4620 acatgttcgc cacctggtcc ccctccaagg ccaggctgca cctgcagggc cggtccaacg    4680
cctggcggcc tcaggtcaac aaccccaaag aatggctgca ggtggacttt cagaaaacca    4740
tgaaggtgac cggcgtgacc acccagggcg tgaaaagcct gctgaccagc atgtacgtga    4800
aagagtttct gatcagcagc tctcaggatg gccaccagtg accctgttc tttcagaacg    4860 gcaaggtgaa agtgttccag ggcaaccagg actccttcac ccccgtggtg aactccctgg    4920 accccccct gctgacccgc tacctgagaa tccacccca gtcttgggtg caccagatcg    4980
ccctcaggat ggaagtcctg ggatgtgagg cccaggatct gtactgatga ggatccaata    5040
aaagatcttt attttcatta gatctgtgtg ttggttttt gtgtg                      5085
```

<210> SEQ ID NO 55
<211> LENGTH: 5103
<212> TYPE: DNA
<213> ORGANISM: Artificial Sequence
<220> FEATURE:
<223> OTHER INFORMATION: Flank-3xSERP-Flank-TTRe-Flank-TTRm-MVM-Flank-
      coFVIIIdeltaB-Flank- Synt.pA-Flank

<400> SEQUENCE: 55

-continued

```
gcggccgcgg tacgcggggg aggctgctgg tgaatattaa ccaaggtcac cccagttatc      60
ggaggagcaa acaggggcta agtccaccgg gggaggctgc tggtgaatat taaccaaggt     120 cacccccagtt atcggaggag caaacagggg ctaagtccac cggggggaggc tgctggtgaa    180 tattaaccaa ggtcaccccca gttatcggag gagcaaacag gggctaagtc cacggtaccc    240
actgggagga tgttgagtaa gatggaaaac tactgatgac ccttgcagag acagagtatt    300
aggacatgtt tgaacagggg ccgggcgatc agcaggtagc tctagaggat ccccgtctgt    360
ctgcacattt cgtagagcga gtgttccgat actctaatct ccctaggcaa ggttcatatt    420
tgtgtaggtt acttattctc cttttgttga ctaagtcaat aatcagaatc agcaggtttg    480
gagtcagctt ggcagggatc agcagcctgg gttggaagga gggggtataa aagccccttc    540
accaggagaa gccgtcaaga ggtaagggtt taagggatgg ttggttggtg gggtattaat    600
gtttaattac ctggagcacc tgcctgaaat cacttttttt caggttggct agtatgcaga    660
tcgagctgtc cacctgcttt tttctgtgcc tgctgcggtt ctgcttcagc gccacccggc    720
ggtactacct gggcgccgtg gagctgtcct gggactacat gcagagcgac ctgggcgagc    780
tgcccgtgga cgcccggttc ccccccagag tgcccaagag cttccccttc aacaccagcg    840
tggtgtacaa gaaaaccctg ttcgtggagt tcaccgacca cctgttcaat atcgccaagc    900
ccaggccccc ctggatgggc ctgctgggcc ccaccatcca ggccgaggtg tacgacaccg    960
tggtgatcac cctgaagaac atggccagcc accccgtgag cctgcacgcc gtgggcgtga   1020
gctactggaa ggccagcgag ggcgccgagt acgaccacca gaccagccag cgggagaaag   1080
aagatgacaa ggtgttccct gcggcagcc acacctacgt gtggcaggtg ctgaaagaaa   1140
acggccccat ggcctccgac cccctgtgcc tgacctacag ctacctgagc cacgtggacc   1200
tggtgaagga cctgaacagc ggcctgatcg gcgctctgct cgtctgccgg gagggcagcc   1260
tggccaaaga gaaacccag accctgcaca agttcatcct gctgttcgcc gtgttcgacg   1320
agggcaagag ctggcacagc gagacaaaga acagcctgat gcaggaccgg gacgccgcct   1380
ctgccagagc ctggcccaag atgcacaccg tgaacggcta cgtgaacaga agcctgcccg   1440
gcctgattgg ctgccaccgg aagagcgtgt actggcacgt gatcggcatg ggcaccacac   1500
ccgaggtgca cagcatcttt ctggaagggc acacctttct ggtccggaac caccggcagg   1560
ccagcctgga aatcagccct atcaccttcc tgaccgccca gacactgctg atggacctgg   1620
gccagttcct gctgttttgc cacatcagct ctcaccagca cgacggcatg gaagcctacg   1680
tgaaggtgga ctcttgcccc gaggaacccc agctgcggat gaagaacaac gaggaagccg   1740
aggactacga cgacgacctg accgacagcg agatggacgt ggtgcggttc gacgacgaca   1800
acagccccag cttcatccag atcagaagcg tggccaagaa gcaccccaag acctgggtgc   1860
actatatcgc cgccgaggaa gaggactggg actacgcccc cctggtgctg gcccccgacg   1920
acagaagcta caagagccag tacctgaaca atggccccca gcggatcggc cggaagtaca   1980
agaaagtgcg gttcatggcc tacaccgacg agacattcaa gacccgggag gccatccagc   2040
acgagagcgg catcctgggc cccctgctgt acggcgaagt gggcgacaca ctgctgatca   2100
tcttcaagaa ccaggctagc cggccctaca acatctaccc ccacgcgatc accgacgtgc   2160
ggcccctgta cagcaggcgg ctgcccaagg gcgtgaagca cctgaaggac ttccccatcc   2220
tgcccggcga gatcttcaag tacaagtgga ccgtgaccgt ggaggacggc cccaccaaga   2280 gcgacccag atgcctgacc cggtactaca gcagcttcgt gaacatggaa cgggacctgg   2340
```

-continued

```
cctccgggct gatcggacct ctgctgatct gctacaaaga aagcgtggac cagcggggca      2400
accagatcat gagcgacaag cggaacgtga tcctgttcag cgtgttcgat gagaaccggt      2460
cctggtatct gaccgagaac atccagcggt ttctgcccaa ccctgccggc gtgcagctgg      2520
aagatcccga gttccaggcc agcaacatca tgcactccat caatggctac gtgttcgact      2580
ctctgcagct ctccgtgtgt ctgcacgagg tggcctactg gtacatcctg agcatcggcg      2640
cccagaccga cttcctgagc gtgttcttca gcggctacac cttcaagcac aagatggtgt      2700
acgaggacac cctgaccctg ttcccttcca gcggcgagac agtgttcatg agcatggaaa      2760
accccggcct gtggattctg gctgccaca acagcgactt ccggaaccgg ggcatgaccg      2820
ccctgctgaa ggtgtccagc tgcgacaaga caccggcga ctactacgag acagctacg      2880 aggatatcag cgcctacctg ctgtccaaga caacgccat cgaacccgg agcttcagcc      2940 agaaccccc cgtgctgacg cgtcaccagc gggagatcac ccggacaacc ctgcagtccg      3000
accaggaaga gatcgattac gacgacacca tcagcgtgga gatgaagaaa gaggatttcg      3060
atatctacga cgaggacgag aaccagagcc ccagaagctt ccagaagaaa acccggcact      3120
acttcattgc cgccgtggag aggctgtggg actacggcat gagttctagc ccccacgtgc      3180
tgcggaaccg ggcccagagc ggcagcgtgc cccagttcaa gaaagtggtg ttccaggaat      3240
tcacagacgg cagcttcacc cagcctctgt atagaggcga gctgaacgag cacctggggc      3300
tgctggggcc ctacatcagg gccgaagtgg aggacaacat catggtgacc ttccggaatc      3360
aggccagcag accctactcc ttctacagca gcctgatcag ctacgaagag gaccagcggc      3420
agggcgccga accccggaag aacttcgtga agcccaacga aaccaagacc tacttctgga      3480
aagtgcagca ccacatggcc cccaccaagg acgagttcga ctgcaaggcc tgggcctact      3540
tcagcgacgt ggatctggaa aaggacgtgc actctggact gattggccca ctcctggtct      3600
gccacactaa caccctcaac cccgcccacg ccgccaggt gaccgtgcag gaattcgccc      3660
tgttcttcac catcttcgac gagacaaagt cctggtactt caccgagaat atggaacgga      3720
actgcagagc cccctgcaac atccagatgg aagatcctac cttcaaagag aactaccggt      3780
tccacgccat caacggctac atcatggaca ccctgcctgg cctggtgatg gcccaggacc      3840
agagaatccg gtggtatctg ctgtccatgg gcagcaacga aatatccac agcatccact      3900 tcagcggcca cgtgttcacc gtgcggaaga agaagagta caagatggcc ctgtacaacc      3960
tgtaccccgg cgtgttcgag acagtggaga tgctgcccag caaggccggc atctggcggg      4020
tggagtgtct gatcggcgag cacctgcacg ctggcatgag caccctgttt ctggtgtaca      4080
gcaacaagtg ccagacccca ctgggcatgg cctctggcca catccgggac ttccagatca      4140
ccgcctccgg ccagtacggc cagtgggccc caagctggcc cagactgcac tacagcggca      4200
gcatcaacgc ctggtccacc aaagagccct tcagctggat caaggtggac ctgctggccc      4260
ctatgatcat ccacggcatt aagacccagg gcgccaggca gaagttcagc agcctgtaca      4320
tcagccagtt catcatcatg tacagcctgg acggcaagaa gtggcagacc taccggggca      4380
acagcaccgg caccctgatg gtgttcttcg gcaatgtgga cagcagcggc atcaagcaca      4440
acatcttcaa ccccccatc attgcccggt acatccggct gcaccccacc cactacagca      4500
ttagatccac actgagaatg gaactgatgg gctgcgacct gaactcctgc agcatgcctc      4560
tgggcatgga aagcaaggcc atcagcgacg cccagatcac agccagcagc tacttccacc      4620
acatgttcgc cacctggtcc ccctccaagg ccaggctgca cctgcagggc cggtccaacg      4680
cctggcggcc tcaggtcaac aaccccaaag aatggctgca ggtggacttt cagaaaacca      4740
```

```
tgaaggtgac cggcgtgacc acccagggcg tgaaaagcct gctgaccagc atgtacgtga    4800
aagagtttct gatcagcagc tctcaggatg gccaccagtg gaccctgttc tttcagaacg    4860
gcaaggtgaa agtgttccag ggcaaccagg actccttcac ccccgtggtg aactccctgg    4920 accccccccct gctgacccgc tacctgagaa tccaccccca gtcttgggtg caccagatcg    4980
```

(Note: line above as printed: `accccccccct gctgacccgc tacctgagaa tccaccccca gtcttgggtg caccagatcg`)

```
ccctcaggat ggaagtcctg ggatgtgagg cccaggatct gtactgatga ggatccaata    5040
aaagatcttt attttcatta gatctgtgtg ttggtttttt gtgtgctcga gatccacggc    5100
cgc                                                                  5103
```

<210> SEQ ID NO 56
<211> LENGTH: 49
<212> TYPE: DNA
<213> ORGANISM: Artificial Sequence
<220> FEATURE:
<223> OTHER INFORMATION: synthetic polyadenylation signal (Synt-pA)

<400> SEQUENCE: 56

```
aataaaagat ctttatttc attagatctg tgtgttggtt ttttgtgtg                   49
```

<210> SEQ ID NO 57
<211> LENGTH: 339
<212> TYPE: DNA
<213> ORGANISM: Artificial Sequence
<220> FEATURE:
<223> OTHER INFORMATION: 3xSERP-Flank-TTRe-Flank

<400> SEQUENCE: 57

```
gggggaggct gctggtgaat attaaccaag gtcaccccag ttatcggagg agcaaacagg     60
ggctaagtcc accgggggag gctgctggtg aatattaacc aaggtcaccc cagttatcgg    120
aggagcaaac aggggctaag tccaccgggg gaggctgctg gtgaatatta accaaggtca    180
ccccagttat cggaggagca acagggggct aagtccacgg tacccactgg aggatgttg     240 agtaagatgg aaaactactg atgacccttg cagagacaga gtattaggac atgtttgaac    300
aggggccggg cgatcagcag gtagctctag aggatcccc                           339
```

<210> SEQ ID NO 58
<211> LENGTH: 541
<212> TYPE: DNA
<213> ORGANISM: Artificial Sequence
<220> FEATURE:
<223> OTHER INFORMATION: 3xSERP-Flank-TTRe-Flank-TTRm

<400> SEQUENCE: 58

```
gggggaggct gctggtgaat attaaccaag gtcaccccag ttatcggagg agcaaacagg     60
ggctaagtcc accgggggag gctgctggtg aatattaacc aaggtcaccc cagttatcgg    120
aggagcaaac aggggctaag tccaccgggg gaggctgctg gtgaatatta accaaggtca    180
ccccagttat cggaggagca acagggggct aagtccacgg tacccactgg aggatgttg     240 agtaagatgg aaaactactg atgacccttg cagagacaga gtattaggac atgtttgaac    300
aggggccggg cgatcagcag gtagctctag aggatccccg tctgtctgca catttcgtag    360
agcgagtgtt ccgatactct aatctcccta ggcaaggttc atatttgtgt aggttactta    420
ttctcctttt gttgactaag tcaataatca gaatcagcag gtttggagtc agcttggcag    480
ggatcagcag cctgggttgg aaggaggggg tataaaagcc ccttcaccag gagaagccgt    540
c                                                                    541
```

```
<210> SEQ ID NO 59
<211> LENGTH: 14
<212> TYPE: PRT
<213> ORGANISM: Artificial Sequence
<220> FEATURE:
<223> OTHER INFORMATION: linker

<400> SEQUENCE: 59

Ser Phe Ser Gln Asn Pro Pro Val Leu Thr Arg His Gln Arg
1               5                   10

<210> SEQ ID NO 60
<211> LENGTH: 20
<212> TYPE: DNA
<213> ORGANISM: Artificial Sequence
<220> FEATURE:
<223> OTHER INFORMATION: primer

<400> SEQUENCE: 60
gccttctagt tgccagccat                                              20

<210> SEQ ID NO 61
<211> LENGTH: 19
<212> TYPE: DNA
<213> ORGANISM: Artificial Sequence
<220> FEATURE:
<223> OTHER INFORMATION: primer

<400> SEQUENCE: 61
ggcaccttcc agggtcaag                                               19

<210> SEQ ID NO 62
<211> LENGTH: 20
<212> TYPE: DNA
<213> ORGANISM: Artificial Sequence
<220> FEATURE:
<223> OTHER INFORMATION: primer

<400> SEQUENCE: 62
aacggctacg tgaacagaag                                              20

<210> SEQ ID NO 63
<211> LENGTH: 20
<212> TYPE: DNA
<213> ORGANISM: Artificial Sequence
<220> FEATURE:
<223> OTHER INFORMATION: primer

<400> SEQUENCE: 63
gatagggctg atttccaggc                                              20

<210> SEQ ID NO 64
<211> LENGTH: 418
<212> TYPE: DNA
<213> ORGANISM: Homo sapiens

<400> SEQUENCE: 64
ggatcttgct accagtggaa cagccactaa ggattctgca gtgagagcag agggccagct    60
aagtggtact ctcccagaga ctgtctgact cacgccaccc cctccacctt ggacacagga   120
cgctgtggtt tctgagccag gtacaatgac tcctttcggt aagtgcagtg gaagctgtac   180
actgcccagg caaagcgtcc gggcagcgta ggcgggcgac tcagatccca gccagtggac   240
ttagcccctg tttgctcctc cgataactgg ggtgaccttg gttaatattc accagcagcc   300
```

```
tcccccgttg ccctctgga tccactgctt aaatacggac gaggacaggg ccctgtctcc    360
tcagcttcag gcaccaccac tgacctggga cagtgaatga tcccctgat ctgcggcc    418

<210> SEQ ID NO 65
<211> LENGTH: 6601
<212> TYPE: DNA
<213> ORGANISM: Artificial Sequence
<220> FEATURE:
<223> OTHER INFORMATION: pAAVsc-3xSerpEnh-TTRe-AAT-FIX-co-R338L-BGHpA

<400> SEQUENCE: 65
agctggcgta atagcgaaga ggcccgcacc gatcgccctt cccaacagtt gcgcagcctg    60
aatggcgaat ggcgattccg ttgcaatggc tggcggtaat attgttctgg atattaccag    120
caaggccgat agtttgagtt cttctactca ggcaagtgat gttattacta atcaaagaag    180
tattgcgaca acggttaatt tgcgtgatgg acagactctt ttactcggtg gcctcactga    240
ttataaaaac acttctcagg attctggcgt accgttcctg tctaaaatcc ctttaatcgg    300
cctcctgttt agctcccgct ctgattctaa cgaggaaagc acgttatacg tgctcgtcaa    360
agcaaccata gtacgcgccc tgtagcggcg cattaagcgc ggcgggtgtg gtggttacgc    420
gcagcgtgac cgctacactt gccagcgccc tagcgcccgc tcctttcgct ttcttccctt    480
cctttctcgc cacgttcgcc ggctttcccc gtcaagctct aaatcggggg ctccctttag    540
ggttccgatt tagtgcttta cggcacctcg accccaaaaa acttgattag ggtgatggtt    600
cacgtagtgg gccatcgccc tgatagacgg ttttttcgccc tttgacgttg gagtccacgt    660
tctttaatag tggactcttg ttccaaactg gaacaacact caaccctatc tcggtctatt    720
cttttgattt ataagggatt tgccgatttc ggcctattg gttaaaaaat gagctgattt    780
aacaaaaatt taacgcgaac tttaacaaaa tattaacgtt tacaatttaa atatttgctt    840
atacaatctt cctgttttg gggctttttct gattatcaac cggggtacat atgattgaca    900
tgctagtttt acgattaccg ttcatcgccc tgcgcgctcg ctcgctcact gaggccgccc    960
gggcaaagcc cggcgtcgg cgacctttg tcgcccggc ctcagtgagc gagcgagcgc    1020
gcagagaggg agtggaattc acgcgtcggg ggaggctgct ggtgaatatt aaccaaggtc    1080
accccagtta tcggaggagc aaacagggc taagtccacc gggggaggct gctggtgaat    1140
attaaccaag gtcaccccag ttatcggagg agcaaacagg ggctaagtcc accgggggag    1200
gctgctggtg aatattaacc aaggtcaccc cagttatcgg aggagcaaac aggggctaag    1260
tccacggcgc gcccactggg aggatgttga gtaagatgaa aaactactga tgaccccttgc    1320 agagacagag tattaggaca tgtttgaaca ggggccgggc gatcagcagg tagggtaccg    1380
gatcttgcta ccagtggaac agccactaag gattctgcag tgagagcaga gggccagcta    1440
agtggtactc tcccagagac tgtctgactc acgccacccc ctccaccttg gacacaggac    1500
gctgtggttt ctgagccagg tacaatgact cctttcggta agtgcagtgg aagctgtaca    1560
ctgcccaggc aaagcgtccg ggcagcgtag gcgggcgact cagatcccag ccagtggact    1620
tagcccctgt ttgctcctcc gataactggg gtgaccttgg ttaatattca ccagcagcct    1680
cccccgttgc ccctctggat ccactgctta aatacggacg aggacagggc ctgtctcct    1740 cagcttcagg caccaccact gacctggac agtgaatgat cccctgatc tgcggcctct    1800 agaaagaggt aagggtttaa gggatggttg gttggtgggg tattaatgtt taattacctg    1860
gagcacctgc ctgaaatcac tttttttcag gttgggctag cccaccatgc agcgcgtgaa    1920
catgatcatg gccgagagcc ccggcctgat caccatctgc ctgctgggct acctgctgag    1980
```

```
cgccgagtgc accgtgttcc tggaccacga gaacgccaac aagatcctga accgccccaa    2040
gcgctacaac agcggcaagc tggaggagtt cgtgcagggc aacctggagc gcagtgcat     2100 ggaggagaag tgcagcttcg aggaggcccg cgaggtgttc gagaacaccg agcgcaccac    2160
cgagttctgg aagcagtacg tggacggcga ccagtgcgag agcaaccct gcctgaacgg     2220 cggcagctgc aaggacgaca tcaacagcta cgagtgctgg tgccccttcg cttcgaggg     2280 caagaactgc gagctggacg tgacctgcaa catcaagaac ggccgctgcg agcagttctg    2340
caagaacagc gccgacaaca aggtggtgtg cagctgcacc gagggctacc gcctggccga    2400
gaaccagaag agctgcgagc ccgccgtgcc cttcccctgc ggccgcgtga gcgtgagcca    2460
gaccagcaag ctgacccgcg ccgaggccgt gttccccgac gtggactacg tgaacagcac    2520
cgaggccgag accatcctgg acaacatcac ccagagcacc cagagcttca cgacttcac    2580 ccgcgtggtg ggcggcgagg acgccaagcc cggccagttc ccctggcagg tggtgctgaa    2640
cggcaaggtg gacgccttct gcggcggcag catcgtgaac gagaagtgga tcgtgaccgc    2700
cgcccactgc gtggagaccg gcgtgaagat caccgtggtg gccggcgagc acaacatcga    2760
ggagaccgag cacaccgagc agaagcgcaa cgtgatccgc atcatccccc accacaacta    2820
caacgccgcc atcaacaagt acaaccacga catcgccctg ctggagctgg acgagcccct    2880
ggtgctgaac agctacgtga ccccccatctg catcgccgac aaggagtaca ccaacatctt    2940
cctgaagttc ggcagcggct acgtgagcgg ctggggccgc gtgttccaca agggccgcag    3000
cgccctggtg ctgcagtacc tgcgcgtgcc cctggtggac cgcgccacct gcctgctgag    3060
caccaagttc accatctaca caacatgtt ctgcgccggc ttccacgagg cggccgcga    3120 cagctgccag ggcgacagcg gcggccccca cgtgaccgag gtggagggca ccagcttcct    3180
gaccggcatc atcagctggg gcgaggagtg cgccatgaag ggcaagtacg gcatctacac    3240
caaggtgagc cgctacgtga actggatcaa ggagaagacc aagctgacct aatgaaagat    3300
ggatttccaa ggttaattca ttggaattga aaattaacag ccccccccc cccccctg      3360 cagatctgag ccgaattcct gcagcccggg ggatcagcct cgactgtgcc ttctagttgc    3420
cagccatctg ttgtttgccc ctcccccgtg ccttccttga ccctgaaagg tgccactccc    3480
actgtccttt cctaataaaa tgaggaaatt gcatcgcatt gtctgagtag gtgtcattct    3540
attctggggg gtgggggtggg gcaggacagc aaggggggagg attgggaaga caatagcagg    3600
catgctgggg atgcggtggg ctctatggct tctgaggcgg aaagaaccag ctggggaccg    3660
gtggatctcg atagcaggca tgctggggag agatcgatct gaggaacccc tagtgatgga    3720
gttggccact ccctctctgc gcgctcgctc gctcactgag gccgcccggg caaagcccgg    3780
gcgtcgggcg acctttggtc gcccggcctc agtgagcgag cgagcgcgca gagagggagt    3840
ggccaacccc cccccccccc cccccggcg attctcttgt tgctccaga ctctcaggca     3900 atgacctgat agcctttgta gagacctctc aaaaatagct accctctccg gcatgaattt    3960
atcagctaga acggttgaat atcatattga tggtgatttg actgtctccg gcctttctca    4020
cccgtttgaa tctttaccta cacattactc aggcattgca tttaaaatat atgagggttc    4080
taaaaatttt tatccttgcg ttgaaataaa ggcttctccc gcaaaagtat tacagggtca    4140
taatgttttt ggtacaaccg atttagcttt atgctctgag gctttattgc ttaattttgc    4200
taattctttg ccttgcctgt atgatttatt ggatgttgga atcgcctgat gcggtatttt    4260
ctccttacgc atctgtgcgg tatttcacac cgcatatggt gcactctcag tacaatctgc    4320
```

```
tctgatgccg catagttata tggtgcactc tcagtacaat ctgctctgat gccgcatagt    4380
taagccagcc ccgacacccg ccaacacagc cagccccgac acccgccaac acccgctgac    4440
gcgccctgac gggcttgtct gctcccggca tccgcttaca gacaagctgt gaccgtctcc    4500
gggagctgca tgtgtcagag gttttcaccg tcatcaccga aacgcgcgag acgaaagggc    4560
ctcgtgatac gcctattttt ataggttaat gtcatgataa taatggtttc ttagacgtca    4620
ggtggcactt tcggggaaa tgtgcgcgga acccctattt gtttattttt ctaaatacat     4680
tcaaatatgt atccgctcat gagacaataa ccctgataaa tgctcaataa tattgaaaaa    4740
ggaagagtat gagtattcaa catttccgtg tcgcccttat tcccttttt gcggcatttt     4800
gccttcctgt ttttgctcac ccagaaacgc tggtgaaagt aaaagatgct gaagatcagt    4860
tgggtgcacg agtgggttac atcgaactgg atctcaacag cggtaagatc cttgagagtt    4920
ttcgccccga agaacgtttt ccaatgatga gcacttttaa agttctgcta tgtggcgcgg    4980
tattatcccg tattgacgcc gggcaagagc aactcggtcg ccgcatacac tattctcaga    5040
atgacttggt tgagtactca ccagtcacag aaaagcatct tacggatggc atgacagtaa    5100
gagaattatg cagtgctgcc ataaccatga gtgataacac tgcggccaac ttacttctga    5160
caacgatcgg aggaccgaag gagctaaccg ctttttttgca caacatgggg gatcatgtaa    5220
ctcgccttga tcgttgggaa ccggagctga atgaagccat accaaacgac gagcgtgaca    5280
ccacgatgcc tgtagcaatg gcaacaacgt tgcgcaaact attaactggc gaactactta    5340
ctctagcttc ccggcaacaa ttaatagact ggatggaggc ggataaagtt gcaggaccac    5400
ttctgcgctc ggcccttccg gctggctggt ttattgctga taaatctgga gccggtgagc    5460
gtgggtctcg cggtatcatt gcagcactgg ggccagatgg taagccctcc cgtatcgtag    5520
ttatctacac gacggggagt caggcaacta tggatgaacg aaatagacag atcgctgaga    5580
taggtgcctc actgattaag cattggtaac tgtcagacca agtttactca tatatacttt    5640
agattgattt aaaacttcat ttttaattta aaaggatcta ggtgaagatc ctttttgata    5700
atctcatgac caaaatccct taacgtgagt tttcgttcca ctgagcgtca gaccccgtag    5760
aaaagatcaa aggatcttct tgagatcctt ttttctgcg cgtaatctgc tgcttgcaaa     5820
caaaaaaacc accgctacca gcggtggttt gtttgccgga tcaagagcta ccaactcttt    5880
ttccgaaggt aactggcttc agcagagcgc agataccaaa tactgtcctt ctagtgtagc    5940
cgtagttagg ccaccacttc aagaactctg tagcaccgcc tacatacctc gctctgctaa    6000
tcctgttacc agtggctgct gccagtggcg ataagtcgtg tcttaccggg ttggactcaa    6060
gacgatagtt accggataag gcgcagcggt cgggctgaac ggggggttcg tgcacacagc    6120
ccagcttgga gcgaacgacc tacaccgaac tgagatacct acagcgtgag ctatgagaaa    6180
gcgccacgct tcccgaaggg agaaaggcgg acaggtatcc ggtaagcggc agggtcggaa    6240
caggagagcg cacgagggag cttccagggg gaaacgcctg gtatctttat agtcctgtcg    6300
ggtttcgcca cctctgactt gagcgtcgat ttttgtgatg ctcgtcaggg ggcggagcc     6360
tatggaaaaa cgccagcaac gcggcctttt tacggttcct ggccttttgc tggccttttg    6420
ctcacatgtt ctttcctgcg ttatcccctg attctgtgga taaccgtatt accgcctttg    6480
agtgagctga taccgctcgc cgcagccgaa cgaccgagcg cagcgagtca gtgagcgagg    6540
aagcggaaga gcgcccaata cgcaaaccgc ctctccccgc gcgttggccg attcattaat    6600
g                                                                   6601
```

<210> SEQ ID NO 66
<211> LENGTH: 6494
<212> TYPE: DNA
<213> ORGANISM: Artificial Sequence
<220> FEATURE:
<223> OTHER INFORMATION: pAAVsc-3xSerpEnh-AAT-FIX-co-R338L-BGHpA

<400> SEQUENCE: 66

```
agctggcgta atagcgaaga ggcccgcacc gatcgccctt cccaacagtt gcgcagcctg      60
aatggcgaat ggcgattccg ttgcaatggc tggcggtaat attgttctgg atattaccag     120
caaggccgat agtttgagtt cttctactca ggcaagtgat gttattacta atcaaagaag     180
tattgcgaca acggttaatt tgcgtgatgg acagactctt ttactcggtg cctcactga     240
ttataaaaac acttctcagg attctggcgt accgttcctg tctaaaatcc ctttaatcgg     300
cctcctgttt agctcccgct ctgattctaa cgaggaaagc acgttatacg tgctcgtcaa     360
agcaaccata gtacgcgccc tgtagcggcg cattaagcgc ggcgggtgtg gtggttacgc     420
gcagcgtgac cgctacactt gccagcgccc tagcgcccgc tcctttcgct ttcttccctt     480
cctttctcgc cacgttcgcc ggctttcccc gtcaagctct aaatcggggg ctccctttag     540
ggttccgatt tagtgcttta cggcacctcg accccaaaaa acttgattag ggtgatggtt     600
cacgtagtgg gccatcgccc tgatagacgg ttttttcgcc tttgacgttg gagtccacgt     660
tctttaatag tggactcttg ttccaaactg gaacaacact caaccctatc tcggtctatt     720
cttttgattt ataagggatt tgccgatttc ggcctattgg ttaaaaaat gagctgattt     780
aacaaaaatt taacgcgaac tttaacaaaa tattaacgtt tacaatttaa atatttgctt     840
atacaatctt cctgttttg gggcttttct gattatcaac cggggtacat atgattgaca     900
tgctagtttt acgattaccg ttcatcgccc tgcgcgctcg ctcgctcact gaggccgccc     960
gggcaaagcc cgggcgtcgg gcgacctttg gtcgcccggc ctcagtgagc gagcgagcgc    1020
gcagagaggg agtggaattc acgcgcccgg gggaggctgc tggtgaatat taaccaaggt    1080
cacccccagtt atcggaggag caaacagggg ctaagtccac cggggaggc tgctggtgaa    1140
tattaaccaa ggtcaccccca gttatcggag gagcaaacag gggctaagtc caccgggga    1200
ggctgctggt gaatattaac caaggtcacc ccagttatcg gaggagcaaa caggggctaa    1260
gtccacggta ccggatcttg ctaccagtgg aacagccact aaggattctg cagtgagagc    1320
agagggccag ctaagtggta ctctcccaga gactgtctga ctcacgccac ccctccacc    1380
ttggacacag gacgctgtgg tttctgagcc aggtacaatg actcctttcg gtaagtgcag    1440
tggaagctgt acactgccca ggcaaagcgt ccgggcagcg taggcgggcg actcagatcc    1500
cagccagtgg acttagcccc tgtttgctcc tccgataact ggggtgacct tggttaatat    1560
tcaccagcag cctcccccgt tgcccctctg gatccactgc ttaaatacgg acgaggacag    1620
ggccctgtct cctcagcttc aggcaccacc actgacctgg gacagtgaat gatccccctg    1680
atctgcggcc tctagaaaga ggtaagggtt taagggatgg ttggttggtg ggtattaat    1740
gtttaattac ctggagcacc tgcctgaaat cactttttt caggttgggc tagcccacca    1800
tgcagcgcgt gaacatgatc atggccgaga gccccggcct gatcaccatc tgcctgctgg    1860
gctacctgct gagcgccgag tgcaccgtgt tcctggacca cgagaacgcc aacaagatcc    1920
tgaaccgccc caagcgctac aacagcggca agctggagga gttcgtgcag ggcaacctgg    1980
agcgcgagtg catggaggag aagtgcagct cgaggaggc ccgcgaggtg ttcgagaaca    2040
ccgagcgcac caccgagttc tggaagcagt acgtggacgg cgaccagtgc gagagcaacc    2100
```

```
cctgcctgaa cggcggcagc tgcaaggacg acatcaacag ctacgagtgc tggtgcccct    2160
tcggcttcga gggcaagaac tgcgagctgg acgtgacctg caacatcaag aacggccgct    2220
gcgagcagtt ctgcaagaac agcgccgaca caaggtggt gtgcagctgc accgagggct     2280
accgcctggc cgagaaccag aagagctgcg agcccgccgt gcccttcccc tgcggccgcg    2340
tgagcgtgag ccagaccagc aagctgaccc gcgccgaggc cgtgttcccc gacgtggact    2400
acgtgaacag caccgaggcc gagaccatcc tggacaacat cacccagagc acccagagct    2460
tcaacgactt cacccgcgtg gtgggcggcg aggacgccaa gcccggccag ttcccctggc    2520
aggtggtgct gaacggcaag gtggacgcct ctgcggcgg cagcatcgtg aacgagaagt     2580
ggatcgtgac cgccgcccac tgcgtggaga ccggcgtgaa gatcaccgtg gtggccggcg    2640
agcacaacat cgaggagacc gagcacaccg agcagaagcg caacgtgatc cgcatcatcc    2700
cccaccacaa ctacaacgcc gccatcaaca agtacaacca cgacatcgcc ctgctggagc    2760
tggacgagcc cctggtgctg aacagctacg tgacccccat ctgcatcgcc gacaaggagt    2820
acaccaacat cttcctgaag ttcggcagcg gctacgtgag cggctgggc cgcgtgttcc     2880 acaagggccg cagcgccctg gtgctgcagt acctgcgcgt gccctggtg gaccgcgcca     2940 cctgcctgct gagcaccaag ttcaccatct acaacaat gttctgcgcc ggcttccacg      3000
agggcggccg cgacagctgc cagggcgaca cggcggccc ccacgtgacc gaggtggagg     3060
gcaccagctt cctgaccggc atcatcagct ggggcgagga gtgcgccatg aagggcaagt    3120
acggcatcta caccaaggtg agccgctacg tgaactggat caaggagaag accaagctga    3180
cctaatgaaa gatggatttc caaggttaat tcattggaat tgaaaattaa cagccccccc    3240 ccccccccc ctgcagatct gagccgaatt cctgcagccc gggggatcag cctcgactgt    3300
gccttctagt tgccagccat ctgttgtttg cccctcccc gtgccttcct tgaccctgga     3360
aggtgccact cccactgtcc tttcctaata aaatgaggaa attgcatcgc attgtctgag    3420
taggtgtcat tctattctgg ggggtggggt ggggcaggac agcaagggg aggattggga     3480 agacaatagc aggcatgctg gggatgcggt gggctctatg gcttctgagg cggaaagaac    3540
cagctgggga ccggtggatc tcgatagcag gcatgctggg gagagatcga tctgaggaac    3600
ccctagtgat ggagttggcc actccctctc tgcgcgctcg ctcgctcact gaggccgccc    3660
gggcaaagcc cggcgtcgg gcgacctttg gtcgcccggc ctcagtgagc gagcgagcgc     3720
gcagagaggg agtggccaac ccccccccc cccccccg gcgattctct tgtttgctcc       3780
agactctcag gcaatgacct gatagccttt gtagagacct ctcaaaaata gctaccctct    3840
ccggcatgaa tttatcagct agaacggttg aatatcatat tgatggtgat ttgactgtct    3900
ccggcctttc tcacccgttt gaatctttac ctacacatta tcaggcatt gcatttaaaa     3960 tatatgaggg ttctaaaaat ttttatcctt gcgttgaaat aaaggcttct cccgcaaaag    4020
tattacaggg tcataatgtt tttggtacaa ccgatttagc tttatgctct gaggctttat    4080
tgcttaattt tgctaattct ttgccttgcc tgtatgattt attggatgtt ggaatcgcct    4140
gatgcggtat tttctcctta cgcatctgtg cggtatttca caccgcatat ggtgcactct    4200
cagtacaatc tgctctgatg ccgcatagtt atatggtgca ctctcagtac aatctgctct    4260
gatgccgcat agttaagcca gccccgacac ccgccaacac agccagcccc gacacccgcc    4320
aacacccgct gacgcgccct gacgggcttg tctgctcccg gcatccgctt acagacaagc    4380
tgtgaccgtc tccgggagct gcatgtgtca gaggttttca ccgtcatcac cgaaacgcgc    4440
gagacgaaag ggcctcgtga tacgcctatt tttataggtt aatgtcatga taataatggt    4500
```

```
ttcttagacg tcaggtggca ctttcgggg aaatgtgcgc ggaaccccta tttgtttatt      4560
tttctaaata cattcaaata tgtatccgct catgagacaa taaccctgat aaatgctcaa      4620
taatattgaa aaaggaagag tatgagtatt caacatttcc gtgtcgccct tattcccttt      4680
tttgcggcat tttgccttcc tgttttgct cacccagaaa cgctggtgaa agtaaaagat      4740
gctgaagatc agttgggtgc acgagtgggt tacatcgaac tggatctcaa cagcggtaag      4800
atccttgaga gttttcgccc cgaagaacgt tttccaatga tgagcacttt taaagttctg      4860
ctatgtggcg cggtattatc ccgtattgac gccgggcaag agcaactcgg tcgccgcata      4920
cactattctc agaatgactt ggttgagtac tcaccagtca cagaaaagca tcttacggat      4980
ggcatgacag taagagaatt atgcagtgct gccataacca tgagtgataa cactgcggcc      5040
aacttacttc tgacaacgat cggaggaccg aaggagctaa ccgcttttt gcacaacatg      5100 ggggatcatg taactcgcct tgatcgttgg gaaccggagc tgaatgaagc cataccaaac      5160
gacgagcgtg acaccacgat gcctgtagca atggcaacaa cgttgcgcaa actattaact      5220
ggcgaactac ttactctagc ttcccggcaa caattaatag actggatgga ggcggataaa      5280
gttgcaggac cacttctgcg ctcggccctt ccggctggct ggtttattgc tgataaatct      5340
ggagccggtg agcgtgggtc tcgcggtatc attgcagcac tggggccaga tggtaagccc      5400
tcccgtatcg tagttatcta cacgacgggg agtcaggcaa ctatggatga acgaaataga      5460
cagatcgctg agataggtgc ctcactgatt aagcattggt aactgtcaga ccaagtttac      5520
tcatatatac tttagattga tttaaaactt catttttaat ttaaaaggat ctaggtgaag      5580
atcctttttg ataatctcat gaccaaaatc ccttaacgtg agttttcgtt ccactgagcg      5640
tcagaccccg tagaaaagat caaaggatct tcttgagatc ctttttttct gcgcgtaatc      5700
tgctgcttgc aaacaaaaaa accaccgcta ccagcggtgg tttgtttgcc ggatcaagag      5760
ctaccaactc tttttccgaa ggtaactggc ttcagcagag cgcagatacc aaatactgtc      5820
cttctagtgt agccgtagtt aggccaccac ttcaagaact ctgtagcacc gcctacatac      5880
ctcgctctgc taatcctgtt accagtggct gctgccagtg gcgataagtc gtgtcttacc      5940
gggttggact caagacgata gttaccggat aaggcgcagc ggtcgggctg aacggggggt      6000
tcgtgcacac agcccagctt ggagcgaacg acctacaccg aactgagata cctacagcgt      6060
gagctatgag aaagcgccac gcttcccgaa gggagaaagg cggacaggta tccggtaagc      6120
ggcagggtcg gaacaggaga gcgcacgagg gagcttccag ggggaaacgc ctggtatctt      6180
tatagtcctg tcgggtttcg ccacctctga cttgagcgtc gatttttgtg atgctcgtca      6240
ggggggcgga gcctatggaa aaacgccagc aacgcggcct ttttacggtt cctggccttt      6300
tgctggcctt ttgctcacat gttctttcct gcgttatccc ctgattctgt ggataaccgt      6360
attaccgcct ttgagtgagc tgataccgct cgccgcagcc gaacgaccga gcgcagcgag      6420
tcagtgagcg aggaagcgga agagcgccca atacgcaaac cgcctctccc cgcgcgttgg      6480
ccgattcatt aatg                                                       6494
```

<210> SEQ ID NO 67
<211> LENGTH: 6375
<212> TYPE: DNA
<213> ORGANISM: Artificial Sequence
<220> FEATURE:
<223> OTHER INFORMATION: pAAVsc-TTRe-AAT-FIX-co-R338L-BGHpA

<400> SEQUENCE: 67

-continued

```
agctggcgta atagcgaaga ggcccgcacc gatcgccctt cccaacagtt gcgcagcctg      60
aatggcgaat ggcgattccg ttgcaatggc tggcggtaat attgttctgg atattaccag     120
caaggccgat agtttgagtt cttctactca ggcaagtgat gttattacta atcaaagaag     180
tattgcgaca acggttaatt tgcgtgatgg acagactctt ttactcggtg gcctcactga     240
ttataaaaac acttctcagg attctggcgt accgttcctg tctaaaatcc ctttaatcgg     300
cctcctgttt agctcccgct ctgattctaa cgaggaaagc acgttatacg tgctcgtcaa     360
agcaaccata gtacgcgccc tgtagcggcg cattaagcgc ggcgggtgtg gtggttacgc     420
gcagcgtgac cgctacactt gccagcgccc tagcgcccgc tcctttcgct ttcttccctt     480
cctttctcgc cacgttcgcc ggctttcccc gtcaagctct aaatcggggg ctcccttag     540 ggttccgatt tagtgcttta cggcacctcg accccaaaaa acttgattag ggtgatggtt     600
cacgtagtgg gccatcgccc tgatagacgg ttttcgccc tttgacgttg gagtccacgt      660
tctttaatag tggactcttg ttccaaactg gaacaacact caaccctatc tcggtctatt     720
cttttgattt ataagggatt tgccgatttc ggcctattg gttaaaaaat gagctgattt      780
aacaaaaatt taacgcgaac tttaacaaaa tattaacgtt tacaatttaa atatttgctt     840
atacaatctt cctgttttg gggcttttct gattatcaac cggggtacat atgattgaca     900
tgctagtttt acgattaccg ttcatcgccc tgcgcgctcg ctcgctcact gaggccgccc     960
gggcaaagcc cgggcgtcgg gcgacctttg gtcgcccggc ctcagtgagc gagcgagcgc    1020
gcagagaggg agtggaattc acgcgcccac tgggaggatg ttgagtaaga tggaaaacta    1080
ctgatgaccc ttgcagagac agagtattag gacatgtttg aacaggggcc gggcgatcag    1140
caggtagggt accggatctt gctaccagtg gaacagccac taaggattct gcagtgagag    1200
cagagggcca gctaagtggt actctcccag agactgtctg actcacgcca cccctccac     1260 cttggacaca ggacgctgtg gtttctgagc caggtacaat gactcctttc ggtaagtgca    1320
gtggaagctg tacactgccc aggcaaagcg tccgggcagc gtaggcgggc gactcagatc    1380
ccagccagtg gacttagccc ctgtttgctc ctccgataac tggggtgacc ttggttaata    1440
ttcaccagca gcctccccg ttgcccctct ggatccactg cttaaatacg gacgaggaca     1500
gggccctgtc tcctcagctt caggcaccac cactgacctg ggacagtgaa tgatccccct    1560
gatctgcggc ctctagaaag aggtaagggt ttaagggatg gttggttggt ggggtattaa    1620
tgtttaatta cctggagcac ctgcctgaaa tcactttttt tcaggttggg ctagcccacc    1680
atgcagcgcg tgaacatgat catggccgag agccccggcc tgatcaccat ctgcctgctg    1740
ggctacctgc tgagcgccga gtgcaccgtg ttcctggacc acgagaacgc caacaagatc    1800
ctgaaccgcc caagcgcta acagcggc aagctggagg agttcgtgca gggcaacctg       1860
gagcgcgagt gcatggagga gaagtgcagc ttcgaggagg cccgcgaggt gttcgagaac    1920
accgagcgca ccaccgagtt ctggaagcag tacgtggacg gcgaccagtg cgagagcaac    1980
ccctgcctga acggcggcag ctgcaaggac gacatcaaca gctacgagtg ctggtgcccc    2040
ttcggcttcg agggcaagaa ctgcgagctg gacgtgacct gcaacatcaa gaacggccgc    2100
tgcgagcagt tctgcaagaa cagcgccgac aacaaggtgg tgtgcagctg caccgagggc    2160
taccgcctgg ccgagaacca aaagagctgc gagcccgccg tgcccttccc ctgcggccgc    2220
gtgagcgtga gccagaccag caagctgacc cgcgccgagg ccgtgttccc cgacgtggac    2280
tacgtgaaca gcaccgaggc cgagaccatc ctggacaaca tcacccagag cacccagagc    2340
ttcaacgact tcacccgcgt ggtgggcggc gaggacgcca agcccggcca gttcccctgg    2400
```

```
caggtggtgc tgaacggcaa ggtggacgcc ttctgcggcg gcagcatcgt gaacgagaag    2460
tggatcgtga ccgccgccca ctgcgtggag accggcgtga agatcaccgt ggtggccggc    2520
gagcacaaca tcgaggagac cgagcacacc gagcagaagc gcaacgtgat ccgcatcatc    2580
ccccaccaca actacaacgc cgccatcaac aagtacaacc acgacatcgc cctgctggag    2640
ctggacgagc ccctggtgct gaacagctac gtgaccccca tctgcatcgc cgacaaggag    2700
tacaccaaca tcttcctgaa gttcggcagc ggctacgtga gcggctgggg ccgcgtgttc    2760
cacaagggcc gcagcgccct ggtgctgcag tacctgcgcg tgcccctggt ggaccgcgcc    2820
acctgcctgc tgagcaccaa gttcaccatc tacaacaaca tgttctgcgc cggcttccac    2880
gagggcggcc gcgacagctg ccagggcgac agcggcggcc ccacgtgacc gaggtggag    2940 ggcaccagct tcctgaccgg catcatcagc tggggcgagg agtgcgccat gaagggcaag    3000
tacggcatct acaccaaggt gagccgctac gtgaactgga tcaaggagaa gaccaagctg    3060
acctaatgaa agatggattt ccaaggttaa ttcattggaa ttgaaaatta acagcccccc    3120
cccccccccc cctgcagatc tgagccgaat tcctgcagcc cggggatca gcctcgactg    3180 tgccttctag ttgccagcca tctgttgttt gcccctcccc cgtgccttcc ttgaccctgg    3240
aaggtgccac tcccactgtc ctttcctaat aaaatgagga aattgcatcg cattgtctga    3300
gtaggtgtca ttctattctg ggggtgggg tggggcagga cagcaagggg gaggattggg    3360
aagacaatag caggcatgct ggggatgcgg tgggctctat ggcttctgag gcggaaagaa    3420
ccagctgggg accggtggat ctcgatagca ggcatgctgg ggagagatcg atctgaggaa    3480
cccctagtga tggagttggc cactccctct ctgcgcgctc gctcgctcac tgaggccgcc    3540
cgggcaaagc ccgggcgtcg ggcgacccttt ggtcgcccgg cctcagtgag cgagcgagcg    3600
cgcagagagg gagtggccaa ccccccccc cccccccc ggcgattctc ttgtttgctc    3660
cagactctca ggcaatgacc tgatagcctt tgtagagacc tctcaaaat agctaccctc    3720 tccggcatga atttatcagc tagaacggtt gaatatcata ttgatggtga tttgactgtc    3780
tccggccttt ctcacccgtt tgaatcttta cctacacatt actcaggcat tgcatttaaa    3840
atatatgagg gttctaaaaa tttttatcct tgcgttgaaa taaaggcttc tcccgcaaaa    3900
gtattacagg gtcataatgt ttttggtaca accgatttag ctttatgctc tgaggcttta    3960
ttgcttaatt ttgctaattc tttgccttgc ctgtatgatt tattgatgt tggaatcgcc    4020 tgatgcggta ttttctcctt acgcatctgt gcggtatttc acaccgcata tggtgcactc    4080
tcagtacaat ctgctctgat gccgcatagt tatatggtgc actctcagta caatctgctc    4140
tgatgccgca tagttaagcc agccccgaca cccgccaaca cagccagccc cgacacccgc    4200
caacacccgc tgacgcgccc tgacgggctt gtctgctccc ggcatccgct tacagacaag    4260
ctgtgaccgt ctccgggagc tgcatgtgtc agaggttttc accgtcatca ccgaaacgcg    4320
cgagacgaaa gggcctcgtg atacgcctat ttttataggt taatgtcatg ataataatgg    4380
tttcttagac gtcaggtggc acttttcggg gaaatgtgcg cggaacccct atttgtttat    4440
ttttctaaat acattcaaat atgtatccgc tcatgagaca ataaccctga taaatgctca    4500
ataatattga aaaggaaga gtatgagtat tcaacatttc cgtgtcgccc ttattcccgt    4560
ttttgcggca ttttgccttc ctgtttttgc tcacccagaa acgctggtga agtaaaaga    4620 tgctgaagat cagttgggtg cacgagtggg ttacatcgaa ctggatctca acagcggtaa    4680
gatccttgag agttttcgcc ccgaagaacg ttttccaatg atgagcactt ttaaagttct    4740
```

-continued

| | |
|---|---|
| gctatgtggc gcggtattat cccgtattga cgccgggcaa gagcaactcg gtcgccgcat | 4800 |
| acactattct cagaatgact tggttgagta ctcaccagtc acagaaaagc atcttacgga | 4860 |
| tggcatgaca gtaagagaat tatgcagtgc tgccataacc atgagtgata acactgcggc | 4920 |
| caacttactt ctgacaacga tcggaggacc gaaggagcta accgcttttt tgcacaacat | 4980 |
| gggggatcat gtaactcgcc ttgatcgttg ggaaccggag ctgaatgaag ccataccaaa | 5040 |
| cgacgagcgt gacaccacga tgcctgtagc aatggcaaca acgttgcgca aactattaac | 5100 |
| tggcgaacta cttactctag cttcccggca acaattaata gactggatgg aggcggataa | 5160 |
| agttgcagga ccacttctgc gctcggccct tccggctggc tggtttattg ctgataaatc | 5220 |
| tggagccggt gagcgtgggt ctcgcggtat cattgcagca ctggggccag atggtaagcc | 5280 |
| ctcccgtatc gtagttatct acacgacggg gagtcaggca actatggatg aacgaaatag | 5340 |
| acagatcgct gagataggtg cctcactgat taagcattgg taactgtcag accaagttta | 5400 |
| ctcatatata ctttagattg atttaaaact tcatttttaa tttaaaagga tctaggtgaa | 5460 |
| gatccttttt gataatctca tgaccaaaat cccttaacgt gagttttcgt tccactgagc | 5520 |
| gtcagacccc gtagaaaaga tcaaaggatc ttcttgagat cctttttttc tgcgcgtaat | 5580 |
| ctgctgcttg caaacaaaaa aaccaccgct accagcggtg gtttgtttgc cggatcaaga | 5640 |
| gctaccaact cttttccga aggtaactgg cttcagcaga gcgcagatac caaatactgt | 5700 |
| ccttctagtg tagccgtagt taggccacca cttcaagaac tctgtagcac cgcctacata | 5760 |
| cctcgctctg ctaatcctgt taccagtggc tgctgccagt ggcgataagt cgtgtcttac | 5820 |
| cgggttggac tcaagacgat agttaccgga taaggcgcag cggtcgggct gaacggggggg | 5880 |
| ttcgtgcaca cagcccagct tggagcgaac gacctacacc gaactgagat acctacagcg | 5940 |
| tgagctatga gaaagcgcca cgcttcccga agggagaaag gcggacaggt atccggtaag | 6000 |
| cggcagggtc ggaacaggag agcgcacgag ggagcttcca gggggaaacg cctggtatct | 6060 |
| ttatagtcct gtcgggtttc gccacctctg acttgagcgt cgatttttgt gatgctcgtc | 6120 |
| agggggggcgg agcctatgga aaaacgccag caacgcggcc tttttacggt tcctggcctt | 6180 |
| ttgctggcct tttgctcaca tgttctttcc tgcgttatcc cctgattctg tggataaccg | 6240 |
| tattaccgcc tttgagtgag ctgataccgc tcgccgcagc cgaacgaccg agcgcagcga | 6300 |
| gtcagtgagc gaggaagcgg aagagcgccc aatacgcaaa ccgcctctcc ccgcgcgttg | 6360 |
| gccgattcat taatg | 6375 |

<210> SEQ ID NO 68
<211> LENGTH: 6601
<212> TYPE: DNA
<213> ORGANISM: Artificial Sequence
<220> FEATURE:
<223> OTHER INFORMATION: pAAVsc-TTRe-3xSerpEnh-AAT-FIX-co-R338L-BGHpA

<400> SEQUENCE: 68

| | |
|---|---|
| agctggcgta atagcgaaga ggcccgcacc gatcgccctt cccaacagtt gcgcagcctg | 60 |
| aatggcgaat ggcgattccg ttgcaatggc tggcggtaat attgttctgg atattaccag | 120 |
| caaggccgat agtttgagtt cttctactca ggcaagtgat gttattacta atcaaagaag | 180 |
| tattgcgaca acggttaatt tgcgtgatgg acagactctt ttactcggtg gcctcactga | 240 |
| ttataaaaac acttctcagg attctggcgt accgttcctg tctaaaatcc ctttaatcgg | 300 |
| cctcctgttt agctcccgct ctgattctaa cgaggaaagc acgttatacg tgctcgtcaa | 360 |
| agcaaccata gtacgcgccc tgtagcggcg cattaagcgc ggcgggtgtg gtggttacgc | 420 |

```
gcagcgtgac cgctacactt gccagcgccc tagcgcccgc tcctttcgct ttcttcccft     480 cctttctcgc cacgttcgcc ggcttccccc gtcaagctct aaatcggggg ctccctttag     540
ggttccgatt tagtgcttta cggcacctcg accccaaaaa acttgattag ggtgatggtt     600
cacgtagtgg gccatcgccc tgatagacgg ttttcgccc tttgacgttg gagtccacgt     660
tctttaatag tggactcttg ttccaaactg aacaacact caaccctatc tcggtctatt     720
cttttgattt ataagggatt ttgccgattt cggcctattg gttaaaaaat gagctgattt     780
aacaaaaatt taacgcgaac tttaacaaaa tattaacgtt tacaatttaa atatttgctt     840
atacaatctt cctgtttttg gggcttttct gattatcaac cggggtacat atgattgaca     900
tgctagtttt acgattaccg ttcatcgccc tgcgcgctcg ctcgctcact gaggccgccc     960
gggcaaagcc cgggcgtcgg gcgacctttg gtcgcccggc ctcagtgagc gagcgagcgc    1020
gcagagaggg agtggaattc acgcgtcact gggaggatgt tgagtaagat ggaaaactac    1080
tgatgaccct tgcagagaca gagtattagg acatgtttga acaggggccg ggcgatcagc    1140
aggtagggcg cgcccggggg aggctgctgg tgaatattaa ccaaggtcac cccagttatc    1200
ggaggagcaa acaggggcta agtccaccgg gggaggctgc tggtgaatat taaccaaggt    1260
caccccagtt atcggaggag caaacagggg ctaagtccac cggggaggc tgctggtgaa    1320 tattaaccaa ggtcacccca gttatcggag gagcaaacag gggctaagtc cacggtaccg    1380
gatcttgcta ccagtggaac agccactaag gattctgcag tgagagcaga gggccagcta    1440
agtggtactc tcccagagac tgtctgactc acgccacccc ctccacccttg gacacaggac    1500 gctgtggttt ctgagccagg tacaatgact cctttcggta agtgcagtgg aagctgtaca    1560
ctgcccaggc aaagcgtccg ggcagcgtag gcgggcgact cagatcccag ccagtggact    1620
tagcccctgt ttgctcctcc gataactggg gtgaccttgg ttaatattca ccagcagcct    1680 ccccccgttgc ccctctggat ccactgctta aatacggacg aggacagggc cctgtctcct    1740
cagcttcagg caccaccact gacctgggac agtgaatgat cccctgatc tgcggcctct    1800 agaaagaggt aagggtttaa gggatggttg gttggtgggg tattaatgtt taattacctg    1860
gagcacctgc ctgaaatcac ttttttttcag gttgggctag cccaccatgc agcgcgtgaa    1920
catgatcatg gccgagagcc ccggcctgat caccatctgc ctgctgggct acctgctgag    1980
cgccgagtgc accgtgttcc tggaccacga gaacgccaac aagatcctga accgccccaa    2040
gcgctacaac agcggcaagc tggaggagtt cgtgcagggc aacctggagc gcgagtgcat    2100
ggaggagaag tgcagcttcg aggaggcccg cgaggtgttc gagaacaccg agcgcaccac    2160
cgagttctgg aagcagtacg tggacggcga ccagtgcgag agcaacccct gcctgaacgg    2220
cggcagctgc aaggacgaca tcaacagcta cgagtgctgg tgccccttcg gcttcgaggg    2280
caagaactgc gagctggacg tgacctgcaa catcaagaac ggccgctgcg agcagttctg    2340
caagaacagc gccgacaaca aggtggtgtg cagctgcacc gagggctacc gcctggccga    2400
gaaccagaag agctgcgagc cgccgtgcc cttcccctgc ggccgcgtga gcgtgagcca    2460
gaccagcaag ctgacccgcg ccgaggccgt gttccccgac gtggactacg tgaacagcac    2520
cgaggccgag accatcctgg acaacatcac ccagagcacc cagagcttca acgacttcac    2580
ccgcgtggtg ggcggcgagg acgccaagcc cggccagttc ccctggcagg tggtgctgaa    2640
cggcaaggtg gacgccttct gcggcggcag catcgtgaac gagaagtgga tcgtgaccgc    2700
cgcccactgc gtggagaccg gcgtgaagat caccgtggtg gccggcgagc acaacatcga    2760
```

```
ggagaccgag cacaccgagc agaagcgcaa cgtgatccgc atcatccccc accacaacta    2820
caacgccgcc atcaacaagt acaaccacga catcgccctg ctggagctgg acgagcccct    2880
ggtgctgaac agctacgtga cccccatctg catcgccgac aaggagtaca ccaacatctt    2940
cctgaagttc ggcagcggct acgtgagcgg ctggggccgc gtgttccaca agggccgcag    3000
cgccctggtg ctgcagtacc tgcgcgtgcc cctggtggac cgcgccacct gcctgctgag    3060
caccaagttc accatctaca acaacatgtt ctgcgccggc ttccacgagg gcggccgcga    3120
cagctgccag ggcgacagcg gcggccccca cgtgaccgag gtggagggca ccagcttcct    3180
gaccggcatc atcagctggg gcgaggagtg cgccatgaag ggcaagtacg gcatctacac    3240
caaggtgagc cgctacgtga actggatcaa ggagaagacc aagctgacct aatgaaagat    3300
ggatttccaa ggttaattca ttggaattga aaattaacag cccccccccc cccccccctg    3360
cagatctgag ccgaattcct gcagcccggg ggatcagcct cgactgtgcc ttctagttgc    3420
cagccatctg ttgtttgccc ctcccccgtg ccttccttga ccctggaagg tgccactccc    3480
actgtccttt cctaataaaa tgaggaaatt gcatcgcatt gtctgagtag gtgtcattct    3540
attctggggg gtggggtggg gcaggacagc aaggggggagg attgggaaga caatagcagg    3600
catgctgggg atgcggtggg ctctatggct tctgaggcgg aaagaaccag ctggggaccg    3660
gtggatctcg atagcaggca tgctggggag agatcgatct gaggaacccc tagtgatgga    3720
gttggccact ccctctctgc gcgctcgctc gctcactgag gccgcccggg caaagcccgg    3780
gcgtcgggcg acctttggtc gcccggcctc agtgagcgag cgagcgcgca gagagggagt    3840 ggccaaccc cccccccccc ccccccggcg attctcttgt ttgctccaga ctctcaggca    3900
atgacctgat agcctttgta gagacctctc aaaaatagct accctctccg gcatgaattt    3960
atcagctaga acgttgaat atcatattga tggtgatttg actgtctccg gcctttctca    4020
cccgtttgaa tctttaccta cacattactc aggcattgca tttaaaatat atgagggttc    4080
taaaaatttt tatccttgcg ttgaaataaa ggcttctccc gcaaaagtat tacagggtca    4140
taatgttttt ggtacaaccg atttagcttt atgctctgag gctttattgc ttaattttgc    4200
taattctttg ccttgcctgt atgatttatt ggatgttgga atcgcctgat gcggtatttt    4260
ctccttacgc atctgtgcgg tatttcacac cgcatatggt gcactctcag tacaatctgc    4320
tctgatgccg catagttata tggtgcactc tcagtacaat ctgctctgat gccgcatagt    4380
taagccagcc ccgacacccg ccaacacagc cagccccgac acccgccaac acccgctgac    4440
gcgccctgac gggcttgtct gctcccggca tccgcttaca caagctgt gaccgtctcc    4500 gggagctgca tgtgtcagag gttttcaccg tcatcaccga aacgcgcgag acgaaagggc    4560
ctcgtgatac gcctattttt ataggttaat gtcatgataa taatggtttc ttagacgtca    4620
ggtggcactt ttcggggaaa tgtgcgcgga acccctattt gtttattttt ctaaatacat    4680
tcaaatatgt atccgctcat gagacaataa ccctgataaa tgcttcaataa tattgaaaaa    4740 ggaagagtat gagtattcaa catttccgtg tcgcccttat tcccttttt gcggcatttt    4800 gccttcctgt ttttgctcac ccagaaacgc tggtgaaagt aaaagatgct gaagatcagt    4860
tgggtgcacg agtgggttac atcgaactgg atctcaacag cggtaagatc cttgagagtt    4920
ttcgccccga agaacgtttt ccaatgatga gcactttta agttctgcta tgtggcgcgg    4980
tattatcccg tattgacgcc gggcaagagc aactcggtcg ccgcatacac tattctcaga    5040
atgacttggt tgagtactca ccagtcacag aaaagcatct tacgatggc atgacagtaa    5100 gagaattatg cagtgctgcc ataaccatga gtgataacac tgcggccaac ttacttctga    5160
```

```
caacgatcgg aggaccgaag gagctaaccg cttttttgca caacatgggg gatcatgtaa      5220
ctcgccttga tcgttgggaa ccggagctga atgaagccat accaaacgac gagcgtgaca      5280
ccacgatgcc tgtagcaatg gcaacaacgt tgcgcaaact attaactggc gaactactta      5340
ctctagcttc ccggcaacaa ttaatagact ggatggaggc ggataaagtt gcaggaccac      5400
ttctgcgctc ggcccttccg gctggctggt ttattgctga taaatctgga gccggtgagc      5460
gtgggtctcg cggtatcatt gcagcactgg ggccagatgg taagccctcc cgtatcgtag      5520
ttatctacac gacggggagt caggcaacta tggatgaacg aaatagacag atcgctgaga      5580
taggtgcctc actgattaag cattggtaac tgtcagacca agtttactca tatatacttt      5640
agattgattt aaaacttcat ttttaattta aaaggatcta ggtgaagatc ctttttgata      5700
atctcatgac caaaatccct aacgtgagt tttcgttcca ctgagcgtca gaccccgtag      5760
aaaagatcaa aggatcttct tgagatcctt ttttttctgcg cgtaatctgc tgcttgcaaa      5820
caaaaaaacc accgctacca gcggtggttt gtttgccgga tcaagagcta ccaactcttt      5880
ttccgaaggt aactggcttc agcagagcgc agataccaaa tactgtcctt ctagtgtagc      5940
cgtagttagg ccaccacttc aagaactctg tagcaccgcc tacataccctc gctctgctaa      6000 tcctgttacc agtggctgct gccagtggcg ataagtcgtg tcttaccggg ttggactcaa      6060
gacgatagtt accggataag gcgcagcggt cgggctgaac ggggggttcg tgcacacagc      6120
ccagcttgga gcgaacgacc tacaccgaac tgagatacct acagcgtgag ctatgagaaa      6180
gcgccacgct tcccgaaggg agaaaggcgg acaggtatcc ggtaagcggc agggtcggaa      6240
caggagagcg cacgagggag cttccagggg gaaacgcctg gtatctttat agtcctgtcg      6300
ggtttcgcca cctctgactt gagcgtcgat ttttgtgatg ctcgtcaggg gggcggagcc      6360 tatgaaaaa cgccagcaac gcggcctttt tacggttcct ggccttttgc tggccttttg      6420
ctcacatgtt ctttcctgcg ttatcccctg attctgtgga taaccgtatt accgcctttg      6480
agtgagctga taccgctcgc cgcagccgaa cgaccgagcg cagcgagtca gtgagcgagg      6540
aagcggaaga gcgcccaata cgcaaaccgc ctctccccgc gcgttggccg attcattaat      6600
g                                                                     6601
```

<210> SEQ ID NO 69
<211> LENGTH: 317
<212> TYPE: DNA
<213> ORGANISM: Artificial Sequence
<220> FEATURE:
<223> OTHER INFORMATION: TTRe-TTRm

<400> SEQUENCE: 69

```
cactgggagg atgttgagta agatggaaaa ctactgatga cccttgcaga gacagagtat        60
taggacatgt ttgaacaggg gccgggcgat cagcaggtag ctctagagga tccccgtctg       120
tctgcacatt tcgtagagcg agtgttccga tactctaatc tccctaggca aggttcatat       180
ttgtgtaggt tacttattct ccttttgttg actaagtcaa taatcagaat cagcaggttt       240
ggagtcagct tggcagggat cagcagcctg ggttggaagg agggggtata aaagccccctt      300 caccaggaga agccgtc                                                     317
```

<210> SEQ ID NO 70
<211> LENGTH: 59
<212> TYPE: DNA
<213> ORGANISM: Artificial Sequence
<220> FEATURE:

<223> OTHER INFORMATION: flanking sequence

<400> SEQUENCE: 70
aattcacgcg tggatctgaa ttcaattcac gcgtggtacg gccgcggtac cggcgcgcc    59

<210> SEQ ID NO 71
<211> LENGTH: 12
<212> TYPE: DNA
<213> ORGANISM: Artificial Sequence
<220> FEATURE:
<223> OTHER INFORMATION: flanking sequence

<400> SEQUENCE: 71
acgcgtggta cc    12

<210> SEQ ID NO 72
<211> LENGTH: 10
<212> TYPE: DNA
<213> ORGANISM: Artificial Sequence
<220> FEATURE:
<223> OTHER INFORMATION: flanking sequence

<400> SEQUENCE: 72
ctagcccacc    10

<210> SEQ ID NO 73
<211> LENGTH: 67
<212> TYPE: DNA
<213> ORGANISM: Artificial Sequence
<220> FEATURE:
<223> OTHER INFORMATION: flanking sequence

<400> SEQUENCE: 73
aagatggatt tccaaggtta attcattgga attgaaaatt aacagccccc cccccccccc    60
ccctgca    67

<210> SEQ ID NO 74
<211> LENGTH: 39
<212> TYPE: DNA
<213> ORGANISM: Artificial Sequence
<220> FEATURE:
<223> OTHER INFORMATION: flanking sequence

<400> SEQUENCE: 74
ccggtggatc tcgatagcag gcatgctggg gagagatcg    39

<210> SEQ ID NO 75
<211> LENGTH: 66
<212> TYPE: DNA
<213> ORGANISM: Artificial Sequence
<220> FEATURE:
<223> OTHER INFORMATION: flanking sequence

<400> SEQUENCE: 75
aattcacgcg tggatctgaa ttcaattcac gcgtggtacg gccgcggtac cggcgcgccc    60
gtacgc    66

<210> SEQ ID NO 76
<211> LENGTH: 24
<212> TYPE: DNA
<213> ORGANISM: Artificial Sequence
<220> FEATURE:
<223> OTHER INFORMATION: flanking sequence

<400> SEQUENCE: 76

```
tgtacaacgc gtgaattcgc tagc                                          24

<210> SEQ ID NO 77
<211> LENGTH: 51
<212> TYPE: DNA
<213> ORGANISM: Artificial Sequence
<220> FEATURE:
<223> OTHER INFORMATION: flanking sequence

<400> SEQUENCE: 77
aattcacgcg tggatctgaa ttcaattcac gcgtggtacg gccgcggtac c            51

<210> SEQ ID NO 78
<211> LENGTH: 15
<212> TYPE: DNA
<213> ORGANISM: Artificial Sequence
<220> FEATURE:
<223> OTHER INFORMATION: flanking sequence

<400> SEQUENCE: 78
ctctagagga tcccc                                                    15

<210> SEQ ID NO 79
<211> LENGTH: 47
<212> TYPE: DNA
<213> ORGANISM: Artificial Sequence
<220> FEATURE:
<223> OTHER INFORMATION: flanking sequence

<400> SEQUENCE: 79
aattcacgcg tggatctgaa ttcaattcac gcgtggtacg gccgcgg                 47

<210> SEQ ID NO 80
<211> LENGTH: 14
<212> TYPE: DNA
<213> ORGANISM: Artificial Sequence
<220> FEATURE:
<223> OTHER INFORMATION: flanking sequence

<400> SEQUENCE: 80
gcggccgcgg tacc                                                     14

<210> SEQ ID NO 81
<211> LENGTH: 15
<212> TYPE: DNA
<213> ORGANISM: Artificial Sequence
<220> FEATURE:
<223> OTHER INFORMATION: flanking sequence

<400> SEQUENCE: 81
ggatctaggc tcgac                                                    15

<210> SEQ ID NO 82
<211> LENGTH: 18
<212> TYPE: DNA
<213> ORGANISM: Artificial Sequence
<220> FEATURE:
<223> OTHER INFORMATION: flanking sequence

<400> SEQUENCE: 82
ctcgagatcc acggccgc                                                 18

<210> SEQ ID NO 83
<211> LENGTH: 22
<212> TYPE: DNA
```

```
<213> ORGANISM: Artificial Sequence
<220> FEATURE:
<223> OTHER INFORMATION: flanking sequence

<400> SEQUENCE: 83
gcggccgcgg taccggcgcg cc                                                 22

<210> SEQ ID NO 84
<211> LENGTH: 15
<212> TYPE: DNA
<213> ORGANISM: Artificial Sequence
<220> FEATURE:
<223> OTHER INFORMATION: flanking sequence

<400> SEQUENCE: 84
gcggccgcgg tacgc                                                         15

<210> SEQ ID NO 85
<211> LENGTH: 11
<212> TYPE: DNA
<213> ORGANISM: Artificial Sequence
<220> FEATURE:
<223> OTHER INFORMATION: flanking sequence

<400> SEQUENCE: 85
gcggccgtac c                                                             11
```